US012159718B2

(12) United States Patent
Ono et al.

(10) Patent No.: US 12,159,718 B2
(45) Date of Patent: Dec. 3, 2024

(54) METHOD FOR EVALUATING PANCREATIC CANCER, PANCREATIC CANCER EVALUATING APPARATUS, PANCREATIC CANCER EVALUATING METHOD, PANCREATIC CANCER EVALUATING PROGRAM PRODUCT, PANCREATIC CANCER EVALUATING SYSTEM AND INFORMATION COMMUNICATION TERMINAL APPARATUS

(71) Applicant: Ajinomoto Co., Inc., Tokyo (JP)

(72) Inventors: Nobukazu Ono, Kanagawa (JP); Atsuko Shinhara, Kanagawa (JP); Takahiko Muramatsu, Kanagawa (JP); Shinya Kikuchi, Kanagawa (JP); Hiroshi Yamamoto, Kanagawa (JP); Koichi Shiraishi, Kanagawa (JP); Kazuhiro Katayama, Osaka (JP); Nobuyasu Fukutake, Osaka (JP); Masahiko Higashiyama, Osaka (JP); Shinichi Ohkawa, Osaka (JP); Makoto Ueno, Kanagawa (JP); Yohei Miyagi, Kanagawa (JP); Naoyuki Okamoto, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 511 days.

(21) Appl. No.: 17/307,644

(22) Filed: May 4, 2021

(65) Prior Publication Data
US 2021/0287802 A1 Sep. 16, 2021

Related U.S. Application Data

(63) Continuation of application No. 14/721,439, filed on May 26, 2015, now abandoned, which is a continuation of application No. PCT/JP2013/081981, filed on Nov. 27, 2013.

(51) Int. Cl.
G01N 33/48 (2006.01)
G01N 33/574 (2006.01)
G01N 33/68 (2006.01)
G16B 20/00 (2019.01)
G16B 99/00 (2019.01)
G16H 50/20 (2018.01)

(52) U.S. Cl.
CPC ....... *G16H 50/20* (2018.01); *G01N 33/57438* (2013.01); *G01N 33/6806* (2013.01); *G16B 20/00* (2019.02); *G16B 99/00* (2019.02)

(58) Field of Classification Search
None
See application file for complete search history.

(56) References Cited

U.S. PATENT DOCUMENTS

| 7,148,069 | B2 | 12/2006 | Miyano et al. | |
| 7,494,815 | B2 | 2/2009 | Shimbo et al. | |
| 8,234,075 | B2 | 7/2012 | Kimura et al. | |
| 2006/0286673 | A1 | 12/2006 | Miyano et al. | |
| 2007/0134156 | A1 | 6/2007 | Mizuno et al. | |
| 2007/0269899 | A1 | 11/2007 | Shimbo et al. | |
| 2008/0147368 | A1 | 6/2008 | Sugimoto et al. | |
| 2010/0009401 | A1 | 1/2010 | Imaizumi et al. | |
| 2010/0009402 | A1 | 1/2010 | Imaizumi et al. | |
| 2010/0017144 | A1 | 1/2010 | Imaizumi et al. | |
| 2010/0017145 | A1 | 1/2010 | Imaizumi et al. | |
| 2010/0280809 | A1 | 11/2010 | Takahashi et al. | |
| 2011/0035156 | A1* | 2/2011 | Imaizumi | G16B 40/20 |
| | | | | 702/19 |
| 2011/0091924 | A1 | 4/2011 | Imaizumi et al. | |
| 2011/0138889 | A1 | 6/2011 | Okamoto et al. | |
| 2011/0143444 | A1 | 6/2011 | Muramatsu et al. | |

(Continued)

FOREIGN PATENT DOCUMENTS

| JP | 2008-164517 A | 7/2008 |
| JP | 2011-247869 A | 12/2011 |

(Continued)

OTHER PUBLICATIONS

Ueno, Hideki, et al. "Multicenter phase II study of gemcitabine and S-1 combination therapy (GS Therapy) in patients with metastatic pancreatic cancer." Japanese journal of clinical oncology 41.8 (2011): 953-958.*

Zhang, Lin, et al. "Distinguishing pancreatic cancer from chronic pancreatitis and healthy individuals by 1H nuclear magnetic resonance-based metabonomic profiles." Clinical biochemistry 45.13-14 (2012): 1064-1069.*

Kazuhiko et al., "Metabolome analysis as liquid biopsy in colorectal cancer," G.I. Research, Aug. 1, 2016, 24(4):260-265, with partial English translation.

Office Action dated Aug. 2, 2022 in JP Appeal 2022-1620, with English translation.

(Continued)

*Primary Examiner* — Anna Skibinsky
(74) *Attorney, Agent, or Firm* — Foley & Lardner LLP

(57) ABSTRACT

A method of evaluating pancreatic cancer includes (I) an obtaining step of obtaining amino acid concentration data on a concentration value of an amino acid in blood collected from a subject to be evaluated, and (II) an evaluating step of evaluating a state of pancreatic cancer in the subject by calculating a value of a formula using the amino acid concentration data of the subject obtained at the obtaining step and the formula previously established for evaluating the state of pancreatic cancer, including an explanatory variable to be substituted with the concentration value of the amino acid. The amino acid concentration data includes the concentration values of at least two amino acids of Asn, His, Thr, Ala, Cit, Arg, Tyr, Val, Met, Lys, Trp, Gly, Pro, Orn, Ile, Leu, Phe, Ser, and Gln, and the formula includes at least two explanatory variables to be substituted with the concentration values of at least two amino acids of Asn, His, Thr, Ala, Cit, Arg, Tyr, Val, Met, Lys, Trp, Gly, Pro, Orn, Ile, Leu, Phe, Ser, and Gln.

3 Claims, 15 Drawing Sheets

(56) References Cited

U.S. PATENT DOCUMENTS

| | | |
|---|---|---|
| 2012/0239366 A1 | 9/2012 | Kimura et al. |
| 2013/0140452 A1 | 6/2013 | Kamlage et al. |
| 2014/0323352 A1 | 10/2014 | Reszka et al. |
| 2015/0344969 A1 | 12/2015 | Manna et al. |

FOREIGN PATENT DOCUMENTS

| | | |
|---|---|---|
| JP | 2014-106114 A | 6/2014 |
| WO | WO-03/069328 A1 | 8/2003 |
| WO | WO-2004/052191 A1 | 6/2004 |
| WO | WO-2005/116629 A1 | 12/2005 |
| WO | WO-2006/098192 A1 | 9/2006 |
| WO | WO-2008/016111 A1 | 2/2008 |
| WO | WO-2008/075662 A1 | 6/2008 |
| WO | WO-2008/075663 A1 | 6/2008 |
| WO | WO-2008/075664 A1 | 6/2008 |
| WO | WO-2009/054351 A1 | 4/2009 |
| WO | WO-2009/099005 A1 | 8/2009 |
| WO | WO-2009/110517 A1 | 9/2009 |
| WO | WO-2009/154296 A1 | 12/2009 |
| WO | WO-2009/154297 A1 | 12/2009 |
| WO | WO-2011/096210 A1 | 8/2011 |
| WO | WO-2013/146621 A1 | 10/2013 |
| WO | WO-2015/109263 A2 | 7/2015 |

OTHER PUBLICATIONS

Suga et al., "Studies on the Utilization of Infused Amino Acids in Patients with Advanced Gastric Cancer, from the View-Point of Both Plasma and Urine Aminograms," Use of Infusion Amino Acids in Gastric Cancer Patients, Medical Treatment, 1980, 45(5):49-53, with English abstract.
Nishiumi et al., "A Novel Serum Metabolomics-Based Diagnostic Approach for Colorectal Cancer," PLoS ONE, 2012, 7(7):e40459, 10 pages.
Office Action dated Jul. 26, 2022 in JP 2021-128537, with English translation.
Bergstrom et al., "Intracellular free amino acid concentration in human muscle tissue," J. Appl. Physiol., 1974, 36(6):693-697.
Caballero et al., "Plasma amino acid concentrations in healthy elderly men and women," Am. J. Clin. Nutr., 1991, 53(5):1249-1252.
Cynober, Luc A., Ed., Metabolic and Therapeutic Aspects of Amino Acids in Clinical Nutrition, 2nd Ed., 2004, 339-354.
Dempo et al., "Demonstration of Gamma-Glutamyl Transferase, Alkaline Phosphatase, CEA and HCG in human lung cancer," Oncodevelopmental Biology and Medicine, 1981, 2:21-37.
Ehrmeyer et al., "A Cancer-associated, Fast, Homoarginine-sensitive Electrophoretic Form of Serum Alkaline Phosphatase," Cancer Research, Mar. 1978, 38:599-601.
Explanation of relevance of JP 2011-247869 A, published Dec. 8, 2011, 1 page.
Kaur et al., "Metabolomic profiling for biomarker discovery in pancreatic cancer," International Journal of Mass Spectrometry, 2012, 310:44-51.
McMenamy et al., "Unbound amino acid concentrations in human blood plasmas," J. Clin. Invest., 1957, 36(12):1672-1679.
Ouyang et al., "Metabolomic Profiling of Serum from Human Pancreatic Cancer Patients Using 1H Nmr Spectoscopy and Principal Component Analysis," Appl. Biochem. Biotechnol., 2011, 165:148-154.
Schrader et al., "Amino Acid Malnutrition in Patients with Chronic Pancreatitis and Pancreatic Carcinoma," Pancreas, May 2009, 38(4):416-421.
Stein et al., "The free amino acids of human blood plasma," J. Biol. Chem., 1954, 211(2):915-926.
Vissers et al., "Plasma arginine concentrations are reduced in cancer patients: evidence for arginine deficiency?" Am. J. Clin. Nutr., 2005, 81:1142-1146.
Yoshida et al., "The challenge of disease diagnosis by metabolomics," Fukuoka Acta Medica, Nov. 25, 2010, 101(11):231-237, with partial English translation of indication portions.
Kobayashi et al., "A Novel Serum Metabolomics-Based Diagnostic Approach to Pancreatic Cancer," Cancer Epidemiology, Biomarkers & Prevention, Apr. 2, 2013, 22(4):571-579.
Office Action dated Sep. 7, 2021 in KR 10-2019-7009532, with English translation.
Non-Final Office Action in U.S. Appl. No. 16/373,193 dated Aug. 17, 2023.
Non-Final Office Action in U.S. Appl. No. 16/373,427 dated Jul. 6, 2023.
Non-Final Office Action dated Sep. 4, 2024 in U.S. Appl. No. 16/373,427.

\* cited by examiner (BASIC PRINCIPLE OF THE INVENTION)

(BASIC PRINCIPLE OF THE INVENTION)

| USER ID | USER PASSWORD | NAME | ORGANI-ZATION ID | DEPART-MENT ID | DEPART-MENT NAME | E-MAIL ADDRESS | ... |
|---------|---------------|------|------------------|----------------|------------------|----------------|-----|
| ⋮ | ⋮ | ⋮ | ⋮ | ⋮ | ⋮ | ⋮ | ⋮ |

| INDIVIDUAL (SAMPLE) NO. | AMINO ACID CONCENTRATION DATA | | | | | |
|---|---|---|---|---|---|---|
| | Gly | Leu | Val | Ile | Phe | ... |
| U-1 | 9.5 | 11.2 | 2.7 | 8.5 | 4.9 | ... |
| U-2 | 8.5 | 10.5 | 3.9 | 9.8 | 6.1 | ... |
| ⋮ | ⋮ | ⋮ | ⋮ | ⋮ | ⋮ | ⋮ |

FIG.9

| INDIVIDUAL (SAMPLE) NO. | PANCREATIC CANCER STATE INDEX DATA (T) | | | | AMINO ACID CONCENTRATION DATA | | | | | | 106c |
|---|---|---|---|---|---|---|---|---|---|---|---|
| | $T_1$ | $T_2$ | $T_3$ | ... | Gly | Leu | Val | Ile | Phe | ... | |
| A-1 | 23.4 | 62.5 | 37.1 | ... | 9.5 | 11.2 | 2.7 | 8.5 | 4.9 | ... | |
| A-2 | 27.5 | 66.1 | 39.5 | ... | 8.5 | 10.5 | 3.9 | 9.8 | 6.1 | ... | |
| ... | ... | ... | ... | ... | ... | ... | ... | ... | ... | ... | |

FIG.10

| INDIVIDUAL (SAMPLE) NO. | PANCREATIC CANCER STATE INDEX DATA (T) | AMINO ACID CONCENTRATION DATA | | | |
|---|---|---|---|---|---|
| | $T_2$ | Gly | Leu | Phe | ... |
| A-1 | 62.5 | 9.5 | 11.2 | 4.9 | ... |
| A-2 | 66.1 | 8.5 | 10.5 | 6.1 | ... |
| ⋮ | ⋮ | ⋮ | ⋮ | ⋮ | ⋮ |

| RANK | CANDIDATE FORMULA |
|---|---|
| 1 | $F_1$(Gly,Leu,Phe,...) |
| 2 | $F_2$(Gly,Leu,Phe,...) |
| 3 | $F_3$(Gly,Leu,Phe,...) |
| ⋮ | ⋮ |

| RANK | EVALUATION FORMULA | THRESH-OLD VALUE | VERIFICA-TION RESULT |
|---|---|---|---|
| 1 | $F_p(Phe,\cdots)$ | 0.23 | 0.62 |
| 2 | $F_p(Gly,Leu,Phe)$ | -2.12 | 1.02 |
| 3 | $F_k(Gly,Leu,Phe,\cdots)$ | 1.23 | 1.22 |
| ⋮ | ⋮ | ⋮ | ⋮ |

| INDIVIDUAL (SAMPLE) NO. | AMINO ACID CONCENTRATION DATA | | | | EVALUATION RESULT |
|---|---|---|---|---|---|
| | Gly | Leu | Phe | ⋯ | |
| U-1 | 9.5 | 11.2 | 4.9 | ⋯ | |
| U-2 | 8.5 | 10.5 | 6.1 | ⋯ | |
| ⋮ | ⋮ | ⋮ | ⋮ | | |

106f

METHOD FOR EVALUATING PANCREATIC CANCER, PANCREATIC CANCER EVALUATING APPARATUS, PANCREATIC CANCER EVALUATING METHOD, PANCREATIC CANCER EVALUATING PROGRAM PRODUCT, PANCREATIC CANCER EVALUATING SYSTEM AND INFORMATION COMMUNICATION TERMINAL APPARATUS

CROSS-REFERENCE TO RELATED APPLICATION

This application is based upon and claims the benefit of priority from PCT Application PCT/JP2013/081981, filed Nov. 27, 2013, which claims priority from Japanese Patent Application No. 2012-259167, filed Nov. 27, 2012, the entire contents of which are incorporated herein by reference.

BACKGROUND OF THE INVENTION

1. Field of the Invention

The present invention relates to a method of evaluating pancreatic cancer, a pancreatic cancer-evaluating apparatus, a pancreatic cancer-evaluating method, a pancreatic cancer-evaluating program product, a pancreatic cancer-evaluating system, and an information communication terminal apparatus.

2. Description of the Related Art

In Japan, the number of male deaths from pancreatic cancer in 2009 is 14094, which ranks fifth in the total number of male deaths from cancer and the number of female deaths from pancreatic cancer in 2009 is 12697, which ranks fourth in the total number of female deaths from cancer. The lifetime incidence rate of pancreatic cancer is 2%.

Pancreatic cancer has few symptoms in some cancer sites and is often found at an advanced stage. Even when detected at a size of 2 cm or smaller using image diagnosis, pancreatic cancer has often spread to adjacent tissues outside the pancreas and has an extremely poor prognosis. It is desired that pancreatic cancer should be found at an operable earlier stage.

Pancreatic cancer is diagnosed using abdominal ultrasonography, CT (computed tomography), or MRI (magnetic resonance imaging), in all of which the detection rate is not high.

Serum tumor markers include CA19-9, CEA, SPan-1, DUPAN-2, and the like. These markers have relatively high sensitivity and specificity for advanced cancer but have a low positive rate for early cancer and may be positive even in cancers other than pancreatic cancer.

Image diagnosis using an endoscopy, such as ERCP (endoscopic retrograde cholangiopancreatography) and EUS (endoscopic ultrasonography), is known to be effective with a high detection rate for pancreatic cancer but increases the patient's physical burden and is unsuitable for population screening and may have a risk of bleeding. Histologic diagnosis by biopsy provides a definite diagnosis, but is a highly invasive test. Performing a biopsy at the screening is not practical.

It is therefore desirable from the viewpoints of a physical burden imposed on patients and of cost-benefit performance to narrow down the target range of subjects with a high possibility of onset of pancreatic cancer and to subject those people to treatment. Specifically, it is desirable to narrow the target range of subjects by selecting subjects in accordance with a less invasive method and subjecting the selected subjects to image diagnosis, and to treat the subjects who are definitively diagnosed as having pancreatic cancer.

It is known that the concentrations of amino acids in blood change as a result of onset of cancer. For example, Cynober ("Cynober, L. ed., Metabolic and therapeutic aspects of amino acids in clinical nutrition. 2nd ed., CRC Press") has reported that the amount of consumption increases in cancer cells, for glutamine mainly as an oxidation energy source, for arginine as a precursor of nitrogen oxide and polyamine, and for methionine through the activation of the ability of cancer cells to take in methionine. Schrader et al. ("Schrader H, Menge B A, Belyaev O, Uhl W, Schmidt W E, Meier J J., Amino acid malnutrition in patients with chronic pancreatitis and pancreatic carcinoma. Pancreas. 2009 May; 38 (4):416-21.") and Vissers et al. ("Vissers Y L, Dejong C H, Luiking Y C, Fearon K C, von Meyenfeldt M F, Deutz N E. Plasma arginine concentrations are reduced in cancer patients: evidence for arginine deficiency? Am J Clin Nutr. 2005 May; 81(5):1142-6.") have reported that the amino acid composition in plasma in pancreatic cancer patients is different from that of healthy subjects.

JP-A-2011-247869 discloses that "of biogenic substances in a sample collected from a subject, a specified finite number of analysis object substances are selected, the quantity is determined, a multivariate analysis is performed to perform metabolome analysis, and the analysis result is compared with the analysis results of a healthy subject group and a disease patient group obtained beforehand. Thus, the inspections of specific diseases, such as early diagnosis, determination of therapeutic effect and prognosis for instance, can be easily performed." The example described in JP-A-2011-247869 describes that "a multivariate analysis using 61 components is performed using SIMCA-P+ (Umetrics). The difference is examined using the score plot of principal component analysis (PCA). Of, in total, 61 analyzed biomoleculars, PC1(t[1]), PC2(t[2]), and PC3(t[3]) are of 20 (32.3%), 15 (24.7%), and 7 (12.0%), respectively, in the 61 components (A=3, R2X=0.69). It is thus confirmed that the distributions of analyzed biomoleculars in pancreatic cancer patients and healthy subjects are different," on data of serum metabolomes measured by GCMS (gas chromatography and mass spectroscopy) for healthy subjects and pancreatic cancer.

WO 2004/052191, WO 2006/098192, and WO 2009/054351 related to a method of relating an amino acid concentration and a biological state are disclosed as previous patents. WO 2008/016111 related to a method of evaluating a state of lung cancer using an amino acid concentration, WO 2008/075662 related to a method of evaluating a state of breast cancer using an amino acid concentration, WO 2008/075663 related to a method of evaluating a state of colorectal cancer using an amino acid concentration, WO 2008/075664 related to a method of evaluating a state of cancer using an amino acid concentration, WO 2009/099005 related to a method of evaluating a state of gastric cancer using an amino acid concentration, WO 2009/110517 related to a method of evaluating a cancer type using an amino acid concentration, WO 2009/154296 related to a method of evaluating a state of female genital cancer using an amino acid concentration, and WO 2009/154297 related to a method of evaluating a state of prostatic disease including at least one of prostatic cancer and prostatic hypertrophy using an amino acid concentration are disclosed as previous patents.

However, neither "Schrader H, Menge B A, Belyaev O, Uhl W, Schmidt W E, Meier J J., Amino acid malnutrition in patients with chronic pancreatitis and pancreatic carcinoma. Pancreas. 2009 May; 38(4):416-21." nor "Vissers Y L, Dejong C H, Luiking Y C, Fearon K C, von Meyenfeldt M F, Deutz N E. Plasma arginine concentrations are reduced in cancer patients: evidence for arginine deficiency? Am J Clin Nutr. 2005 May; 81(5):1142-6." search for a combination of biomoleculars or an index formula using multivariate analysis optimum for evaluating a state of pancreatic cancer.

The example described in JP-A-2011-247869 merely shows the tendency of general components of a large number of analyzed biomolecular components using the principal component analysis, which is one of multivariate analyses, and does not search for a combination of biomoleculars or an index formula using multivariate analysis optimum for evaluating a state of pancreatic cancer.

Even when the index formulae disclosed in WO 2004/052191, WO 2006/098192, WO 2009/054351, WO 2008/016111, WO 2008/075662, WO 2008/075663, WO 2008/075664, WO 2009/099005, WO 2009/110517, WO 2009/154296, and WO 2009/154297 are used for evaluating a state of pancreatic cancer, evaluation results having sufficient reliability cannot be obtained because diseases to be evaluated are different. In particular, WO 2009/110517 describes a method of evaluating a cancer type but does not describe a blood marker or an index formula specifically suitable for classification into subjects with a high possibility of being affected with pancreatic cancer and subjects with a high possibility of being affected with cancers other than pancreatic cancer. WO 2009/110517 does not describe an index formula that accurately classifies subjects into subjects with a high possibility of being affected with pancreatic cancer and subjects with a low possibility of being affected with pancreatic cancer and that is suitable for classification into subjects with a high possibility of being affected with pancreatic cancer and subjects with a high possibility of being affected with cancers other than pancreatic cancer.

No blood marker has been reported for classification into subjects with a high possibility of being affected with pancreatic cancer and subjects with a high possibility of being affected with cancers other than pancreatic cancer, such as colorectal cancer, lung cancer, breast cancer, prostatic cancer, gastric cancer, uterine cancer (cervical cancer, endometrial cancer), and ovarian cancer.

There is a problem that a method of evaluating a state of pancreatic cancer using a formula including at least two explanatory variables to be substituted with the concentration values of at least two amino acids has not been developed nor put into practice.

SUMMARY OF THE INVENTION

It is an object of the present invention to at least partially solve the problems in the conventional technology.

The present invention has been made in view of the problems described above, and an object of the present invention is to provide a method of evaluating pancreatic cancer, a pancreatic cancer-evaluating apparatus, a pancreatic cancer-evaluating method, a pancreatic cancer-evaluating program product, a pancreatic cancer-evaluating system, and an information communication terminal apparatus, which can provide reliable information that may be helpful in knowing a state of pancreatic cancer.

To solve the problem and achieve the object described above, a method of evaluating pancreatic cancer according to one aspect of the present invention includes an obtaining step of obtaining amino acid concentration data on a concentration value of an amino acid in blood collected from a subject to be evaluated, and an evaluating step of evaluating a state of pancreatic cancer in the subject by calculating a value of a formula (hereinafter referred sometimes as the value of the evaluation formula or the evaluation value) using the amino acid concentration data of the subject obtained at the obtaining step and the formula (hereinafter referred sometimes as the evaluation formula) previously established for evaluating the state of pancreatic cancer, including an explanatory variable to be substituted with the concentration value of the amino acid, wherein the amino acid concentration data includes the concentration values of at least two amino acids of Asn, His, Thr, Ala, Cit, Arg, Tyr, Val, Met, Lys, Trp, Gly, Pro, Orn, Ile, Leu, Phe, Ser, and Gln, and the formula includes at least two explanatory variables to be substituted with the concentration values of at least two amino acids of Asn, His, Thr, Ala, Cit, Arg, Tyr, Val, Met, Lys, Trp, Gly, Pro, Orn, Ile, Leu, Phe, Ser, and Gln.

In the present specification, various amino acids are mainly written in abbreviations, the formal names of these are as follows.

(Abbreviation) (Formal Name)

Ala Alanine
Arg Arginine
Asn Asparagine
Cit Citrulline
Gln Glutamine
Gly Glycine
His Histidine
Ile Isoleucine
Leu Leucine
Lys Lysine
Met Methionine
Orn Ornithine
Phe Phenylalanine
Pro Proline
Ser Serine
Thr Threonine
Trp Tryptophan
Tyr Tyrosine
Val Valine The method of evaluating pancreatic cancer according to another aspect of the present invention is the method of evaluating pancreatic cancer, wherein the state of pancreatic cancer is the degree of the possibility of being affected with pancreatic cancer, and evaluating the state of pancreatic cancer in the subject is evaluating the degree of the possibility that the subject is affected with pancreatic cancer.

In the present specification, as an example of the state of pancreatic cancer, for example, the degree of progress of pancreatic cancer is included in addition to the degree of the possibility being affected with pancreatic cancer.

The method of evaluating pancreatic cancer according to still another aspect of the present invention is the method of evaluating pancreatic cancer, wherein a plurality of categories defined considering at least the degree of the possibility of being affected with pancreatic cancer, and one or more thresholds are previously established, and evaluating the degree of the possibility that the subject is affected with pancreatic cancer is classifying the subject into any one of the categories using the value of the formula and the threshold.

The method of evaluating pancreatic cancer according to still another aspect of the present invention is the method of evaluating pancreatic cancer, wherein the categories include at least one category defined considering at least the degree of the possibility of being affected with pancreatic cancer and the degree of the possibility of being affected with a cancer other than pancreatic cancer.

The method of evaluating pancreatic cancer according to still another aspect of the present invention is the method of evaluating pancreatic cancer, wherein the categories include a category (hereinafter, also referred to as the category X) to which a subject with a high possibility of being affected with pancreatic cancer (for example, a subject assumed to be affected with pancreatic cancer) belongs and a category (hereinafter, also referred to as the category Y) to which a subject with a low possibility of being affected with pancreatic cancer (for example, a subject assumed to be not affected with pancreatic cancer) belongs.

The method of evaluating pancreatic cancer according to still another aspect of the present invention is the method of evaluating pancreatic cancer, wherein the category to which a subject with a low possibility of being affected with pancreatic cancer belongs, includes a healthy category to which a subject with a high possibility of being healthy (for example, a subject assumed to be healthy) belongs, other cancer category to which a subject with a high possibility of being affected with a cancer other than pancreatic cancer (for example, a subject assumed to be affected with a cancer other than pancreatic cancer) belongs, or a healthy/other cancer category to which a subject with a high possibility of being healthy and a subject with a high possibility of being affected with a cancer other than pancreatic cancer belong.

The method of evaluating pancreatic cancer according to still another aspect of the present invention is the method of evaluating pancreatic cancer, wherein the category to which a subject with a low possibility of being affected with pancreatic cancer belongs includes the healthy category to which a subject with a high possibility of being healthy belongs and the other cancer category to which a subject with a high possibility of being affected with a cancer other than pancreatic cancer belongs.

The method of evaluating pancreatic cancer according to still another aspect of the present invention is the method of evaluating pancreatic cancer, wherein the formula is any one of a logistic regression equation, a fractional expression, a linear discriminant, a multiple regression equation, a formula prepared by a support vector machine, a formula prepared by a Mahalanobis' generalized distance method, a formula prepared by canonical discriminant analysis, and a formula prepared by a decision tree.

The method of evaluating pancreatic cancer according to still another aspect of the present invention may be the method of evaluating pancreatic cancer, wherein evaluating the state of pancreatic cancer in the subject is deciding that the value of the formula reflects the state of pancreatic cancer in the subject.

The method of evaluating pancreatic cancer according to still another aspect of the present invention may be the method of evaluating pancreatic cancer, wherein at the evaluating step, the value of the formula is converted by a predetermined method, and it is decided that the converted value reflects the state of pancreatic cancer in the subject.

The method of evaluating pancreatic cancer according to still another aspect of the present invention may be the method of evaluating pancreatic cancer, wherein at the evaluating step, a positional information about a position of a predetermined mark corresponding to the value of the formula or the converted value is generated on a predetermined scale visually presented on a display device such as a monitor or a physical medium such as paper for evaluating the state of pancreatic cancer, using the value of the formula or the converted value, and it is decided that the generated positional information reflects the state of pancreatic cancer in the subject.

The method of evaluating pancreatic cancer according to still another aspect of the present invention may be the method of evaluating pancreatic cancer, wherein at the evaluating step, the value of the formula is converted by a predetermined method, and the subject is classified into any one of the categories using the converted value.

The method of evaluating pancreatic cancer according to still another aspect of the present invention may be the method of evaluating pancreatic cancer, wherein the categories are the category X and the category Y, and at the evaluating step, the subject is classified into one of the category X and the category Y. When the classification is executed, the category X may be written as for example, a pancreatic cancer category, and the category Y may be written as for example, a pancreatic cancer-free category.

The method of evaluating pancreatic cancer according to still another aspect of the present invention may be the method of evaluating pancreatic cancer, wherein (I) the formula is named as a first formula, a second formula that is different from the first formula and includes at least two explanatory variables to be substituted with the concentration values of at least two amino acids of Asn, His, Thr, Ala, Cit, Arg, Tyr, Val, Met, Lys, Trp, Gly, Pro, Orn, Ile, Leu, Phe, Ser, Gln is previously established, and (II) at the evaluating step, the value of the first formula and the value of the second formula are calculated, and the subject is classified into one of the category X and the category Y using the calculated values of the first formula and the second formula.

The method of evaluating pancreatic cancer according to still another aspect of the present invention may be the method of evaluating pancreatic cancer, wherein (I) the category Y includes the healthy category to which a subject with a high possibility of being healthy belongs and the other cancer category to which a subject with a high possibility of being affected with a cancer other than pancreatic cancer belongs, the first formula is a formula for classifying a subject into one of the category X and the healthy category, the second formula is a formula for classifying a subject into one of the category X and the other cancer category, and (II) at the evaluating step, (i) the value of the first formula is first calculated, (ii) the subject is classified into one of the category X and the healthy category using the calculated value of the first formula, (iii) then if the classification result is the category X, the value of the second formula is calculated, (iv) the subject classified in the category X using the value of the first formula is further classified into one of the category X and the other cancer category using the calculated value of the second formula, and then (v) the subject classified in the healthy category and the subject classified in the other cancer category is finally classified into the category Y.

The method of evaluating pancreatic cancer according to still another aspect of the present invention may be the method of evaluating pancreatic cancer, wherein at the evaluating step, the subject is classified into one of the category X and the healthy category. When the classification is executed, the category X may be written as for example, the pancreatic cancer category.

The method of evaluating pancreatic cancer according to still another aspect of the present invention may be the method of evaluating pancreatic cancer, wherein at the evaluating step, the subject is classified into one of the category X and the other cancer category. When the classification is executed, the category X may be written as for example, the pancreatic cancer category.

The method of evaluating pancreatic cancer according to still another aspect of the present invention may be the method of evaluating pancreatic cancer, wherein at the evaluating step, the subject is classified into one of the category X and the healthy/other cancer category. When the classification is executed, the category X may be written as for example, the pancreatic cancer category.

The method of evaluating pancreatic cancer according to still another aspect of the present invention may be the method of evaluating pancreatic cancer, wherein at the evaluating step, the subject is classified into any one of the category X, the healthy category, and the other cancer category. When the classification is executed, the category X may be written as for example, the pancreatic cancer category.

The method of evaluating pancreatic cancer according to still another aspect of the present invention may be the method of evaluating pancreatic cancer, wherein (I) the formula is named as a first formula, a second formula that is different from the first formula and includes at least two explanatory variables to be substituted with the concentration values of at least two amino acids of Asn, His, Thr, Ala, Cit, Arg, Tyr, Val, Met, Lys, Trp, Gly, Pro, Orn, Ile, Leu, Phe, Ser, Gln is previously established, and (II) at the evaluating step, the value of the first formula and the value of the second formula are calculated, and the subject is classified into any one of the category X, the healthy category, and the other cancer category using the calculated values of the first formula and the second formula.

The method of evaluating pancreatic cancer according to still another aspect of the present invention may be the method of evaluating pancreatic cancer, wherein (I) the first formula is a formula for classifying a subject into one of the category X and the healthy category, the second formula is a formula for classifying a subject into one of the category X and the other cancer category, and (II) at the evaluating step, (i) the value of the first formula is first calculated, (ii) the subject is classified into one of the category X and the healthy category using the calculated value of the first formula, (iii) then if the classification result is the category X, the value of the second formula is calculated, (iv) the subject classified in the category X using the value of the first formula is further classified into one of the category X and the other cancer category using the calculated value of the second formula, and then (v) the subject classified in the category X using the value of the first formula and classified in the other cancer category using the value of the second formula is finally classified into the other cancer category.

A pancreatic cancer-evaluating apparatus according to one aspect of the present invention includes a control unit and a memory unit to evaluate a state of pancreatic cancer in a subject to be evaluated, wherein the control unit includes an evaluating unit that evaluates the state of pancreatic cancer in the subject by calculating a value of a formula using previously obtained amino acid concentration data of the subject on a concentration value of an amino acid and the formula previously stored in the memory unit for evaluating the state of pancreatic cancer, including an explanatory variable to be substituted with the concentration value of the amino acid, wherein the amino acid concentration data includes the concentration values of at least two amino acids of Asn, His, Thr, Ala, Cit, Arg, Tyr, Val, Met, Lys, Trp, Gly, Pro, Orn, Ile, Leu, Phe, Ser, and Gln, and the formula includes at least two explanatory variables to be substituted with the concentration values of at least two amino acids of Asn, His, Thr, Ala, Cit, Arg, Tyr, Val, Met, Lys, Trp, Gly, Pro, Orn, Ile, Leu, Phe, Ser, and Gln.

The pancreatic cancer-evaluating apparatus according to another aspect of the present invention may be the pancreatic cancer-evaluating apparatus, wherein (I) the control unit further includes an evaluation formula-preparing unit that prepares the evaluation formula stored in the memory unit, based on prostatic cancer state information stored in the memory unit, including the amino acid concentration data and prostatic cancer state index data on an index for indicating the state of prostatic cancer, wherein (II) the evaluation formula-preparing unit further includes (i) a candidate formula-preparing unit that prepares a candidate formula that is a candidate of the evaluation formula, based on a predetermined formula-preparing method from the pancreatic cancer state information, (ii) a candidate formula-verifying unit that verifies the candidate formula prepared by the candidate formula-preparing unit, based on a predetermined verifying method, and (iii) an explanatory variable-selecting unit that selects the explanatory variable of the candidate formula based on a predetermined explanatory variable-selecting method thereby selecting a combination of the amino acid concentration data included in the pancreatic cancer state information used in preparing the candidate formula, and (iv) the evaluation formula-preparing unit prepares the evaluation formula by selecting the candidate formula used as the evaluation formula, from a plurality of the candidate formulae, based on the verification results accumulated by repeatedly executing the candidate formula-preparing unit, the candidate formula-verifying unit, and the explanatory variable-selecting unit.

A pancreatic cancer-evaluating method according to one aspect of the present invention is a method of evaluating a state of pancreatic cancer in a subject to be evaluated, which method is carried out with an information processing apparatus including a control unit and a memory unit, wherein the method includes an evaluating step of evaluating the state of pancreatic cancer in the subject by calculating a value of a formula using previously obtained amino acid concentration data of the subject on a concentration value of an amino acid and the formula previously stored in the memory unit for evaluating the state of pancreatic cancer, including an explanatory variable to be substituted with the concentration value of the amino acid, wherein the amino acid concentration data includes the concentration values of at least two amino acids of Asn, His, Thr, Ala, Cit, Arg, Tyr, Val, Met, Lys, Trp, Gly, Pro, Orn, Ile, Leu, Phe, Ser, and Gln, the formula includes at least two explanatory variables to be substituted with the concentration values of at least two amino acids of Asn, His, Thr, Ala, Cit, Arg, Tyr, Val, Met, Lys, Trp, Gly, Pro, Orn, Ile, Leu, Phe, Ser, and Gln, and the evaluating step is executed by the control unit.

A pancreatic cancer-evaluating program product according to one aspect of the present invention has a non-transitory computer readable medium including programmed instructions for making an information processing apparatus including a control unit and a memory unit execute a method of evaluating a state of pancreatic cancer in a subject to be evaluated, wherein the method includes an evaluating step of evaluating the state of pancreatic cancer in the subject by calculating a value of a formula using previously obtained amino acid concentration data of the subject on a concentration value of an amino acid and the formula previously stored in the memory unit for evaluating the state of pancreatic cancer, including an explanatory variable to be substituted with the concentration value of the amino acid, wherein the amino acid concentration data includes the concentration values of at least two amino acids of Asn, His, Thr, Ala, Cit, Arg, Tyr, Val, Met, Lys, Trp, Gly, Pro, Orn, Ile, Leu, Phe, Ser, and Gln, the formula includes at least two explanatory variables to be substituted with the concentration values of at least two amino acids of Asn, His, Thr, Ala, Cit, Arg, Tyr, Val, Met, Lys, Trp, Gly, Pro, Orn, Ile, Leu, Phe, Ser, and Gln, and the evaluating step is executed by the control unit.

A non-transitory computer-readable recording medium according to one aspect of the present invention includes the programmed instructions for making an information processing apparatus execute the pancreatic cancer-evaluating method.

A pancreatic cancer-evaluating system according to one aspect of the present invention includes (I) a pancreatic cancer-evaluating apparatus including a control unit and a memory unit to evaluate a state of pancreatic cancer in a subject to be evaluated and (II) an information communication terminal apparatus including a control unit to provide amino acid concentration data of the subject on a concentration value of an amino acid that are connected to each other communicatively via a network, wherein (III) the control unit of the information communication terminal apparatus includes an amino acid concentration data-sending unit that transmits the amino acid concentration data of the subject to the pancreatic cancer-evaluating apparatus and an evaluation result-receiving unit that receives an evaluation result on the state of pancreatic cancer in the subject, transmitted from the pancreatic cancer-evaluating apparatus, and (IV) the control unit of the pancreatic cancer-evaluating apparatus includes an amino acid concentration data-receiving unit that receives the amino acid concentration data of the subject transmitted from the information communication terminal apparatus, an evaluating unit that evaluates the state of pancreatic cancer in the subject by calculating a value of a formula using the amino acid concentration data of the subject received by the amino acid concentration data-receiving unit and the formula previously stored in the memory unit for evaluating the state of pancreatic cancer, including an explanatory variable to be substituted with the concentration value of the amino acid, and an evaluation result-sending unit that transmits the evaluation result of the subject obtained by the evaluating unit to the information communication terminal apparatus, wherein (V) the amino acid concentration data includes the concentration values of at least two amino acids of Asn, His, Thr, Ala, Cit, Arg, Tyr, Val, Met, Lys, Trp, Gly, Pro, Orn, Ile, Leu, Phe, Ser, and Gln, and the formula includes at least two explanatory variables to be substituted with the concentration values of at least two amino acids of Asn, His, Thr, Ala, Cit, Arg, Tyr, Val, Met, Lys, Trp, Gly, Pro, Orn, Ile, Leu, Phe, Ser, and Gln.

An information communication terminal apparatus according to one aspect of the present invention includes a control unit to provide amino acid concentration data of a subject to be evaluated on a concentration value of an amino acid, being connected communicatively via a network to a pancreatic cancer-evaluating apparatus that evaluates a state of pancreatic cancer in the subject, wherein the control unit includes an amino acid concentration data-sending unit that transmits the amino acid concentration data of the subject to the pancreatic cancer-evaluating apparatus, and an evaluation result-receiving unit that receives an evaluation result on the state of pancreatic cancer in the subject, transmitted from the pancreatic cancer-evaluating apparatus, wherein the evaluation result is the result of (I) receiving the amino acid concentration data of the subject transmitted from the information communication terminal apparatus and (II) evaluating the state of pancreatic cancer in the subject by calculating a value of a formula using the received amino acid concentration data of the subject and the formula previously stored in the pancreatic cancer-evaluating apparatus for evaluating the state of pancreatic cancer, including an explanatory variable to be substituted with the concentration value of the amino acid, wherein the (I) and (II) are executed by the pancreatic cancer-evaluating apparatus, wherein the amino acid concentration data includes the concentration values of at least two amino acids of Asn, His, Thr, Ala, Cit, Arg, Tyr, Val, Met, Lys, Trp, Gly, Pro, Orn, Ile, Leu, Phe, Ser, and Gln, and the formula includes at least two explanatory variables to be substituted with the concentration values of at least two amino acids of Asn, His, Thr, Ala, Cit, Arg, Tyr, Val, Met, Lys, Trp, Gly, Pro, Orn, Ile, Leu, Phe, Ser, and Gln. An information communication terminal apparatus according to one aspect of the present invention includes a control unit to provide amino acid concentration data of a subject to be evaluated on a concentration value of an amino acid, wherein the control unit includes an evaluation result-receiving unit that receives an evaluation result on a state of pancreatic cancer in the subject, wherein the evaluation result is the result of evaluating the state of pancreatic cancer in the subject by calculating a value of a formula using the amino acid concentration data of the subject and the formula for evaluating the state of pancreatic cancer, including an explanatory variable to be substituted with the concentration value of the amino acid, wherein the amino acid concentration data includes the concentration values of at least two amino acids of Asn, His, Thr, Ala, Cit, Arg, Tyr, Val, Met, Lys, Trp, Gly, Pro, Orn, Ile, Leu, Phe, Ser, and Gln, and the formula includes at least two explanatory variables to be substituted with the concentration values of at least two amino acids of Asn, His, Thr, Ala, Cit, Arg, Tyr, Val, Met, Lys, Trp, Gly, Pro, Orn, Ile, Leu, Phe, Ser, and Gln.

A pancreatic cancer-evaluating apparatus according to one aspect of the present invention includes a control unit and a memory unit to evaluate a state of pancreatic cancer in a subject to be evaluated, being connected communicatively via a network to an information communication terminal apparatus that provides amino acid concentration data of the subject on a concentration value of an amino acid, wherein the control unit includes an amino acid concentration data-receiving unit that receives the amino acid concentration data of the subject transmitted from the information communication terminal apparatus, an evaluating unit that evaluates the state of pancreatic cancer in the subject by calculating a value of a formula using the amino acid concentration data of the subject received by the amino acid concentration data-receiving unit and the formula previously stored in the memory unit for evaluating the state of pancreatic cancer, including an explanatory variable to be substituted with the concentration value of the amino acid, and an evaluation result-sending unit that transmits an evaluation result on the state of pancreatic cancer in the subject obtained by the evaluating unit to the information communication terminal apparatus, wherein the amino acid concentration data includes the concentration values of at least two amino acids of Asn, His, Thr, Ala, Cit, Arg, Tyr, Val, Met, Lys, Trp, Gly, Pro, Orn, Ile, Leu, Phe, Ser, and Gln, and the formula includes at least two explanatory variables to be substituted with the concentration values of at least two amino acids of Asn, His, Thr, Ala, Cit, Arg, Tyr, Val, Met, Lys, Trp, Gly, Pro, Orn, Ile, Leu, Phe, Ser, and Gln.

A method of searching for preventing/ameliorating substance for pancreatic cancer according to one aspect of the present invention includes (I) an obtaining step of obtaining amino acid concentration data on a concentration value of an amino acid in blood collected from a subject to be evaluated to which a desired substance group consisting of one or more substances has been administered, (II) an evaluating step of evaluating a state of pancreatic cancer in the subject by calculating a value of a formula using the amino acid concentration data of the subject obtained at the obtaining step and the formula previously established for evaluating the state of pancreatic cancer, including an explanatory variable to be substituted with the concentration value of the amino acid, and (III) a judging step of judging whether or not the desired substance group prevents pancreatic cancer or ameliorates the state of pancreatic cancer, using an evaluation result obtained at the evaluating step, wherein the amino acid concentration data includes the concentration values of at least two amino acids of Asn, His, Thr, Ala, Cit, Arg, Tyr, Val, Met, Lys, Trp, Gly, Pro, Orn, Ile, Leu, Phe, Ser, and Gln, and the formula includes at least two explanatory variables to be substituted with the concentration values of at least two amino acids of Asn, His, Thr, Ala, Cit, Arg, Tyr, Val, Met, Lys, Trp, Gly, Pro, Orn, Ile, Leu, Phe, Ser, and Gln.

According to the present invention, (I) the amino acid concentration data on the concentration value of the amino acid in blood collected from the subject (the one including the concentration values of at least two amino acids of the 19 kinds of amino acids composed of Asn, His, Thr, Ala, Cit, Arg, Tyr, Val, Met, Lys, Trp, Gly, Pro, Orn, Ile, Leu, Phe, Ser, and Gln) is obtained, and (II) the state of pancreatic cancer in the subject is evaluated by calculating the value of the formula using the obtained amino acid concentration data of the subject and the formula previously established for evaluating the state of pancreatic cancer, including the explanatory variable to be substituted with the concentration value of the amino acid (the one including at least two explanatory variables to be substituted with the concentration values of at least two amino acids of the 19 kinds of amino acids). Hence, reliable information that may be helpful in knowing the state of pancreatic cancer can be provided. Both improvement in reliability of the information and reduction in various burdens imposed on users (for example, mental, physical, temporal, financial, or other burdens) can be achieved.

According to the present invention, the state of pancreatic cancer is the degree of the possibility of being affected with pancreatic cancer, and evaluating the state of pancreatic cancer in the subject is evaluating the degree of the possibility that the subject is affected with pancreatic cancer. Hence, reliable information that may be helpful in knowing the degree of the possibility of being affected with pancreatic cancer can be provided.

According to the present invention, the categories defined considering at least the degree of the possibility of being affected with pancreatic cancer, and one or more thresholds are previously established, and evaluating the degree of the possibility that the subject is affected with pancreatic cancer is classifying the subject into any one of the categories using the value of the formula and the threshold. Hence, reliable information that may be helpful in knowing the degree of the possibility of being affected with pancreatic cancer can be provided in easily understandable form.

According to the present invention, the categories include at least one category defined considering at least the degree of the possibility of being affected with pancreatic cancer and the degree of the possibility of being affected with a cancer other than pancreatic cancer. Hence, reliable information can be provided in easily understandable form, which may be helpful in knowing not only the degree of the possibility of being affected with pancreatic cancer but also the degree of the possibility of being affected with a cancer other than pancreatic cancer.

According to the present invention, the categories include the category X and the category Y. Hence, reliable information that may be helpful in knowing whether the possibility of being affected with pancreatic cancer is high or low can be provided in easily understandable form.

According to the present invention, the category Y includes the healthy category to which a subject with a high possibility of being healthy belongs, the other cancer category to which a subject with a high possibility of being affected with a cancer other than pancreatic cancer (for example, lung cancer, colorectal cancer, prostatic cancer, breast cancer, gastric cancer, uterine cancer (cervical cancer, endometrial cancer), ovarian cancer, or the like) belongs, or the healthy/other cancer category to which a subject with a high possibility of being healthy and a subject with a high possibility of being affected with a cancer other than pancreatic cancer belong. Hence, reliable information can be provided in easily understandable form, which may be helpful in knowing not only whether the possibility of being affected with pancreatic cancer is high but also whether the possibility of being healthy is high, whether the possibility of being affected with a cancer other than pancreatic cancer is high, or whether the possibility of being healthy or being affected with a cancer other than pancreatic cancer is high.

According to the present invention, the category Y includes the healthy category to which a subject with a high possibility of being healthy belongs and the other cancer category to which a subject with a high possibility of being affected with a cancer other than pancreatic cancer belongs. Hence, reliable information can be provided in easily understandable form, which may be helpful in knowing not only whether the possibility of being affected with pancreatic cancer is high but also whether the possibility of being healthy is high and whether the possibility of being affected with a cancer other than pancreatic cancer is high.

According to the present invention, the formula is any one of a logistic regression equation, a fractional expression, a linear discriminant, a multiple regression equation, a formula prepared by a support vector machine, a formula prepared by a Mahalanobis' generalized distance method, a formula prepared by canonical discriminant analysis, and a formula prepared by a decision tree. Hence, further improvement in reliability of information that may be helpful in knowing the state of pancreatic cancer can be achieved.

According to the present invention, evaluating the state of pancreatic cancer in the subject may be deciding that the value of the formula reflects the state of pancreatic cancer in the subject. Hence, reliable information that may be helpful in knowing the state of pancreatic cancer can be provided.

According to the present invention, the value of the formula may be converted by the predetermined method, and it may be decided that the converted value reflects the state of pancreatic cancer in the subject. Hence, reliable information that may be helpful in knowing the state of pancreatic cancer can be provided.

According to the present invention, the positional information about the position of the predetermined mark (for example, a circle sign or a star sign) corresponding to the value of the formula or the converted value may be generated on the predetermined scale (for example, a graduated scale at least marked with graduations corresponding to the upper limit value and the lower limit value in the possible range of the value of the formula or the converted value, or part of the range) visually presented on the display device such as a monitor or the physical medium such as paper for evaluating the state of pancreatic cancer, using the value of the formula or the converted value, and it may be decided that the generated positional information reflects the state of pancreatic cancer in the subject. Hence, reliable information that may be helpful in knowing the state of pancreatic cancer can be provided.

According to the present invention, the value of the formula may be converted by the predetermined method, and the subject may be classified into any one of the categories using the converted value. Hence, reliable information that may be helpful in knowing the state of pancreatic cancer can be provided.

According to the present invention, the categories may be the category X and the category Y, and the subject may be classified into one of the category X and the category Y. Hence, reliable information that may be helpful in knowing whether the possibility of being affected with pancreatic cancer is high or low can be provided in easily understandable form.

According to the present invention, (I) the formula may be named as the first formula, the second formula that is different from the first formula and includes at least two explanatory variables to be substituted with the concentration values of at least two amino acids of the 19 kinds of amino acids may be previously established, and (II) the value of the first formula and the value of the second formula may be calculated, and the subject may be classified into one of the category X and the category Y using the calculated values of the first formula and the second formula. Hence, further improvement in reliability of information that may be helpful in knowing whether the possibility of being affected with pancreatic cancer is high or low can be achieved.

According to the present invention, (I) the category Y may include the healthy category and the other cancer category, the first formula may be a formula for classifying a subject into one of the category X and the healthy category, the second formula may be a formula for classifying a subject into one of the category X and the other cancer category, and (II) (i) the value of the first formula may be first calculated, (ii) the subject may be classified into one of the category X and the healthy category using the calculated value of the first formula, (iii) then if the classification result is the category X, the value of the second formula may be calculated, (iv) the subject classified in the category X using the value of the first formula may be further classified into one of the category X and the other cancer category using the calculated value of the second formula, and then (v) the subject classified in the healthy category and the subject classified in the other cancer category may be finally classified into the category Y. Hence, further improvement in reliability of information that may be helpful in knowing whether the possibility of being affected with pancreatic cancer is high or low can be achieved.

According to the present invention, the subject may be classified into one of the category X and the healthy category. Hence, reliable information that may be helpful in knowing whether the possibility of being affected with pancreatic cancer is high or the possibility of being healthy is high can be provided in easily understandable form.

According to the present invention, the subject may be classified into one of the category X and the other cancer category. Hence, reliable information that may be helpful in knowing whether the possibility of being affected with pancreatic cancer is high or whether the possibility of being affected with a cancer other than pancreatic cancer is high can be provided in easily understandable form.

According to the present invention, the subject may be classified into one of the category X and the healthy/other cancer category. Hence, reliable information that may be helpful in knowing whether the possibility of being affected with pancreatic cancer is high or whether the possibility of being healthy or being affected with a cancer other than pancreatic cancer is high can be provided in easily understandable form.

According to the present invention, the category Y may include the healthy category and the other cancer category, and the subject may be classified into any one of the category X, the healthy category, and the other cancer category. Hence, reliable information that may be helpful in knowing whether the possibility of being affected with pancreatic cancer is high, whether the possibility of being healthy is high, or whether the possibility of being affected with a cancer other than pancreatic cancer is high can be provided in easily understandable form.

According to the present invention, (I) the formula may be named as the first formula, the second formula that is different from the first formula and includes at least two explanatory variables to be substituted with the concentration values of at least two amino acids of the 19 kinds of amino acids may be previously established, and (II) the value of the first formula and the value of the second formula may be calculated, and the subject may be classified into any one of the category X, the healthy category, and the other cancer category using the calculated values of the first formula and the second formula. This leads to further improvement in reliability of information that may be helpful in knowing whether the possibility of being affected with pancreatic cancer is high, whether the possibility of being healthy is high, or whether the possibility of being affected with a cancer other than pancreatic cancer is high.

According to the present invention, (I) the first formula may be a formula for classifying a subject into one of the category X and the healthy category, the second formula may be a formula for classifying a subject into one of the category X and the other cancer category, and (II) (i) the value of the first formula may be first calculated, (ii) the subject may be classified into one of the category X and the healthy category using the calculated value of the first formula, (iii) then if the classification result is the category X, the value of the second formula may be calculated, (iv) the subject classified in the category X using the value of the first formula may be further classified into one of the category X and the other cancer category using the calculated value of the second formula, and then (v) the subject classified in the category X using the value of the first formula and classified in the other cancer category using the value of the second formula may be finally classified into the other cancer category. This leads to further improvement in reliability of information that may be helpful in knowing whether the possibility of being affected with pancreatic cancer is high, whether the possibility of being healthy is high, or whether the possibility of being affected with a cancer other than pancreatic cancer is high.

According to the present invention, the evaluation formula may be prepared based on the pancreatic cancer state information previously stored in the memory unit including the amino acid concentration data and the pancreatic cancer state index data on the index for indicating the state of pancreatic cancer. Specifically, (I) the candidate formula may be prepared based on the predetermined formula-preparing method from the pancreatic cancer state information, (II) the prepared candidate formula may be verified based on the predetermined verifying method, (III) the explanatory variables of the candidate formula may be selected based on the predetermined explanatory variable-selecting method, thereby selecting the combination of the amino acid concentration data contained in the pancreatic cancer state information used in preparing of the candidate formula, and (IV) the candidate formula used as the evaluation formula may be selected from a plurality of the candidate formulae based on the verification results accumulated by repeatedly executing the (I), (II) and (III), thereby preparing the evaluation formula. Hence, the evaluation formula most appropriate for evaluating the state of pancreatic cancer can be prepared.

According to the present invention, (I) the amino acid concentration data on the concentration value of the amino acid in blood collected from the subject to which the desired substance group consisting of one or more substances has been administered (the one including the concentration values of at least two amino acids of the 19 kinds of amino acids) may be obtained, (II) the state of pancreatic cancer in the subject may be evaluated by calculating the value of the formula using the obtained amino acid concentration data of the subject and the formula previously established for evaluating the state of pancreatic cancer, including the explanatory variable to be substituted with the concentration value of the amino acid (the one including at least two explanatory variables to be substituted with the concentration values of at least two amino acids of the 19 kinds of amino acids), and (III) whether or not the desired substance group prevents pancreatic cancer or ameliorates the state of pancreatic cancer may be judged using the obtained evaluation result. Hence, reliable information on a substance preventing pancreatic cancer or a substance ameliorating the state of pancreatic cancer can be provided by applying the method of evaluating pancreatic cancer which can provide reliable information that may be helpful in knowing the state of pancreatic cancer. Both improvement in reliability of the information and reduction in various burdens imposed on users can be achieved. An existing animal model partially reflecting the state of progress of pancreatic cancer or a clinically effective chemical at an early stage can be selected by using typical data on variation patterns of the concentration values of amino acids of an individual being affected with pancreatic cancer and the formula appropriate for evaluating the state of pancreatic cancer.

In the present invention, when the state of pancreatic cancer is evaluated, the concentration value of an amino acid other than the 19 kinds of amino acids may be additionally used. In the present invention, when the state of pancreatic cancer is evaluated, a value of other biological information (for example, the values listed in 1. through 5. below) may be used in addition to the concentration values of amino acids. In the present invention, the formula described above may additionally include one or more explanatory variables to be substituted with the concentration value of an amino acid other than the 19 kinds of amino acids. In the present invention, the formula described above may additionally include one or more explanatory variables to be substituted with the value of other biological information (for example, the values listed in 1. through 5. below), in addition to the explanatory variables to be substituted with the concentration values of amino acids.

1. the concentration values of metabolites in blood other than amino acids (amino acid metabolites, carbohydrates, lipids, and the like), proteins, peptides, minerals, hormones, and the like
2. the values of tumor markers in blood (CA19-9, CEA, CA125, SPan-1, DUPAN-2, SLX, SCC, CYFRA, ProGRP, p53, elastase, and the like)
3. blood test values such as albumin, total protein, triglyceride, HbA1c, LDL cholesterol, HDL cholesterol, amylase, total bilirubin, and uric acid
4. the values obtained from image information of ultrasonography, X rays, CT, MRI, and the like
5. the values of biological indices such as age, height, weight, BMI, blood pressure, gender, smoking information, dietary information, drinking information, exercise information, stress information, sleeping information, family medical history, disease history information (diabetes, pancreatitis, and the like)

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7 is a chart showing an example of information stored in a user information file 106*a*;

FIG. 8 is a chart showing an example of information stored in an amino acid concentration data file 106*b*;

FIG. 9 is a chart showing an example of information stored in a pancreatic cancer state information file 106*c*;

FIG. 10 is a chart showing an example of information stored in a designated pancreatic cancer state information file 106*d*;

FIG. 11 is a chart showing an example of information stored in a candidate formula file 106*e*1;

FIG. 14 is a chart showing an example of information stored in an evaluation formula file 106*e*4;

FIG. 15 is a chart showing an example of information stored in an evaluation result file 106*f*;

DETAILED DESCRIPTION OF THE PREFERRED EMBODIMENTS

Hereinafter, an embodiment (first embodiment) of the method of evaluating pancreatic cancer according to the present invention and an embodiment (second embodiment) of the pancreatic cancer-evaluating apparatus, the pancreatic cancer-evaluating method, the pancreatic cancer-evaluating program, the recording medium, the pancreatic cancer-evaluating system, and the information communication terminal apparatus according to the present invention are described in detail with reference to the drawings. The present invention is not limited to these embodiments.

First Embodiment

1-1. Outline of First Embodiment

Figure 1:
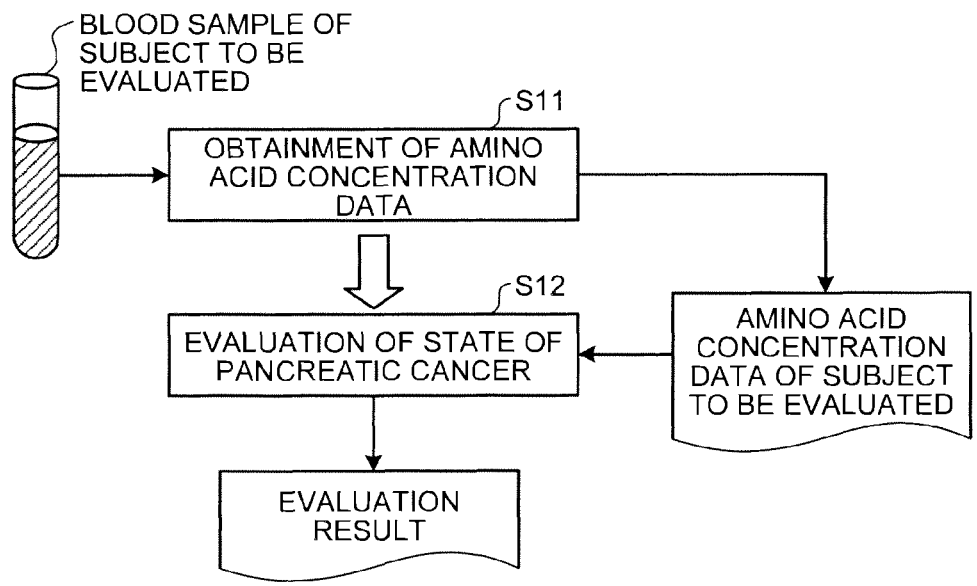
FIG. 1 is a principle configurational diagram showing a basic principle of a first embodiment.

Here, an outline of the first embodiment will be described with reference to FIG. 1. FIG. 1 is a principle configurational diagram showing a basic principle of the first embodiment.

Amino acid concentration data on a concentration value of an amino acid (the one including concentration values of at least two amino acids of the 19 kinds of amino acids composed of Asn, His, Thr, Ala, Cit, Arg, Tyr, Val, Met, Lys, Trp, Gly, Pro, Orn, Ile, Leu, Phe, Ser, and Gln) in blood (including, for example, plasma or serum) collected from a subject to be evaluated (for example, an individual such as animal or human) is obtained (step S11).

In step S11, for example, the amino acid concentration data determined by a company or the like that performs amino acid concentration value measurements may be obtained, or the amino acid concentration data may be obtained by determining the concentration value of the amino acid by a measurement method such as, for example, the following method (A) or (B) from blood collected from the subject. Here, the unit of the concentration value of the amino acid may be, for example, a molar concentration, a weight concentration, or one obtained by addition, subtraction, multiplication, and division of any constant with these concentrations.

(A) Plasma is separated from blood by centrifuging a collected blood sample. All plasma samples are frozen and stored at −80° C. until an amino acid concentration value is measured. At the time of measuring an amino acid concentration value, acetonitrile is added to perform a protein removal treatment, pre-column derivatization is then performed using a labeled reagent (3-aminopyridyl-N-hydroxysuccinimidyl carbamate), and an amino acid concentration value is analyzed by liquid chromatograph mass spectrometer (LC/MS) (see International Publication WO 2003/069328 and International Publication WO 2005/116629).

(B) Plasma is separated from blood by centrifuging a collected blood sample. All plasma samples are frozen and stored at −80° C. until an amino acid concentration value is measured. At the time of measuring an amino acid concentration value, sulfosalicylic acid is added to perform a protein removal treatment, and an amino acid concentration value is analyzed by an amino acid analyzer based on post-column derivatization using a ninhydrin reagent.

A state of pancreatic cancer in the subject is evaluated using, as evaluation values for evaluating a state of pancreatic cancer, the concentration values of at least two amino acids of the 19 kinds of amino acids included in the amino acid concentration data obtained in step S11 (step S12). Before step S12 is executed, data such as defective and outliers may be removed from the amino acid concentration data obtained in step S11.

According to the first embodiment described above, in step S11, the amino acid concentration data of the subject is obtained, and in step S12, the state of pancreatic cancer in the subject is evaluated using, as the evaluation values, the concentration values of at least two amino acids of the 19 kinds of amino acids included in the amino acid concentration data of the subject obtained in step S11. Hence, reliable information that may be helpful in knowing the state of pancreatic cancer can be provided. Both improvement in reliability of the information and reduction in various burdens imposed on users (for example, mental burden, physical burden, temporal burden, or financial burden) can be achieved.

The state of pancreatic cancer may be the degree of the possibility of being affected with pancreatic cancer. Evaluating the state of pancreatic cancer in the subject may be evaluating the degree of the possibility that the subject is affected with pancreatic cancer. Hence, reliable information that may be helpful in knowing the degree of the possibility of being affected with pancreatic cancer can be provided.

In step S12, it may be decided that the concentration values of at least two amino acids of the 19 kinds of amino acids included in the amino acid concentration data of the subject obtained at step S11 reflect the state of pancreatic cancer in the subject. The concentration values may be converted, for example, by the methods listed below, and it may be decided that the converted values reflect the state of pancreatic cancer in the subject. In other words, in step S12, the concentration values or the converted values may be treated per se as the evaluation result on the state of pancreatic cancer in the subject. Hence, reliable information that may be helpful in knowing the state of pancreatic cancer can be provided.

The concentration value may be converted such that the possible range of the concentration value falls within a predetermined range (for example, the range from 0.0 to 1.0, the range from 0.0 to 10.0, the range from 0.0 to 100.0, or the range from −10.0 to 10.0), for example, by addition, subtraction, multiplication, and division of any given value with the concentration value, by conversion of the concentration value by a predetermined conversion method (for example, index transformation, logarithm transformation, angular transformation, square root transformation, probit transformation, or reciprocal transformation), or by performing a combination of these computations on the concentration value. For example, the value of an exponential function with the concentration value as an exponent and Napier constant as the base (specifically, the value of $p/(1-p)$ where a natural logarithm $\ln(p/(1-p))$ is equal to the concentration value when the probability p of being affected with pancreatic cancer is defined) may be further calculated, and a value (specifically, the value of probability p) may be further calculated by dividing the calculated value of exponential function by the sum of 1 and the value of exponential function.

The concentration value may be converted such that the converted value is particular value when a particular condition is met. For example, the concentration value may be converted such that the converted value is 5.0 when the specificity is 80% and the converted value is 8.0 when the specificity is 95%.

In step S12, the positional information about the position of a predetermined mark (for example, a circle sign or a star sign) corresponding to the concentration value or the converted value may be generated on a predetermined scale (for example, a graduated scale at least marked with graduations corresponding to the upper limit value and the lower limit value in the possible range of the concentration value or the converted value, or part of the range) visually presented on a display device such as a monitor or a physical medium such as paper for evaluating the state of pancreatic cancer, using the concentration values of at least two amino acids of the 19 kinds of amino acids included in the amino acid concentration data of the subject obtained in step S11 or, if the concentration values are converted, the converted values. Then it may be decided that the generated positional information reflects the state of pancreatic cancer. Hence, reliable information that may be helpful in knowing the state of pancreatic cancer can be provided.

In step S12, the state of pancreatic cancer in the subject may be evaluated by calculating the value of the evaluation formula using the amino acid concentration data of the subject and the previously established formula for evaluating the state of pancreatic cancer, including the explanatory variable to be substituted with the concentration value of the amino acid (the one including at least two explanatory variables to be substituted with the concentration values of at least two amino acids of the 19 kinds of amino acids). Hence, reliable information that may be helpful in knowing the state of pancreatic cancer can be provided.

In step S12, it may be decided that the calculated value of the formula reflects the state of pancreatic cancer in the subject. The value of the formula may be converted, for example, by the methods listed below, and it may be decided that the converted value reflects the state of pancreatic cancer in the subject. In other words, in step S12, the value of the formula or the converted value may be treated per se as the evaluation result on the state of pancreatic cancer in the subject. Hence, reliable information that may be helpful in knowing the state of pancreatic cancer can be provided.

The value of the evaluation formula may be converted such that the possible range of the value of the evaluation formula falls within a predetermined range (for example, the range from 0.0 to 1.0, the range from 0.0 to 10.0, the range from 0.0 to 100.0, or the range from −10.0 to 10.0), for example, by addition, subtraction, multiplication, and division of any given number with the value of the evaluation formula, by conversion of the value of the evaluation formula by a predetermined conversion method (for example, index transformation, logarithm transformation, angular transformation, square root transformation, probit transformation, or reciprocal transformation), or by performing a combination of these computations on the value of the evaluation formula. For example, the value of an exponential function with the value of the evaluation formula as an exponent and Napier constant as the base (specifically, the value of $p/(1-p)$ where a natural logarithm $\ln(p/(1-p))$ is equal to the value of the evaluation formula when the probability p of being affected with pancreatic cancer is defined) may be further calculated, and a value (specifically, the value of probability p) may be calculated by dividing the calculated value of exponential function by the sum of 1 and the value of exponential function.

The value of the evaluation formula may be converted such that the converted value is a particular value when a particular condition is met. For example, the value of the evaluation formula may be converted such that the converted value is 5.0 when the specificity is 80% and the converted value is 8.0 when the specificity is 95%.

In step S12, the positional information about the position of a predetermined mark (for example, a circle sign or a star sign) corresponding to the value of the formula or the converted value may be generated on a predetermined scale (for example, a graduated scale at least marked with graduations corresponding to the upper limit value and the lower limit value in the possible range of the value of the formula or the converted value, or part of the range) visually presented on a display device such as a monitor or a physical medium such as paper for evaluating the state of pancreatic cancer, using the value of the formula or, if the value of the formula is converted, the converted value. Then it may be decided that the generated positional information reflects the state of pancreatic cancer in the subject. Hence, reliable information that may be helpful in knowing the state of pancreatic cancer can be provided.

When a plurality of categories defined considering at least the degree of the possibility of being affected with pancreatic cancer, and one or more thresholds are previously established, in step S12, the subject may be classified into any one of the categories using the concentration values of at least two amino acids of the 19 kinds of amino acids or, if the concentration values are converted, the converted values, and a threshold. Alternatively, the subject may be classified into any one of the categories using the value of the formula or, if the value of the formula is converted, the converted value, and a threshold. Hence, reliable information that may be helpful in knowing the degree of the possibility of being affected with pancreatic cancer can be provided in easily understandable form.

The categories may include at least one category defined considering at least the degree of the possibility of being affected with pancreatic cancer and the degree of the possibility of being affected with a cancer other than pancreatic cancer (for example, lung cancer, colorectal cancer, prostatic cancer, breast cancer, gastric cancer, uterine cancer (cervical cancer, endometrial cancer), or ovarian cancer). Hence, reliable information that may be helpful in knowing not only the degree of the possibility of being affected with pancreatic cancer but also the degree of the possibility of being affected with a cancer other than pancreatic cancer can be provided.

In a set of the concentration values of at least two amino acids of the 19 kinds of amino acids included in the amino acid concentration data of a plurality of test subjects proved to be not affected with pancreatic cancer (for example, to be healthy), the boundary value when the specificity is a predetermined value (for example 80 or 95) may be established as a threshold. In a set of a plurality of values of the evaluation formula calculated for each test subject using the amino acid concentration data and the evaluation formula, the boundary value when the specificity is a predetermined value may be established as a threshold.

In a set of the concentration values of at least two amino acids of the 19 kinds of amino acids included in the amino acid concentration data of a plurality of test subjects proved to be affected with pancreatic cancer, the boundary value when the sensitivity is a predetermined value (for example, 80 or 95) may be established as a threshold. In a set of a plurality of values of the evaluation formula calculated for each test subject using the amino acid concentration data and the evaluation formula, the boundary value when the sensitivity is a predetermined value may be established as a threshold.

The categories may include a category X to which a subject with a high possibility of being affected with pancreatic cancer belongs and a category Y to which a subject with a low possibility of being affected with pancreatic cancer belongs. Hence, reliable information that may be helpful in knowing whether the possibility of being affected with pancreatic cancer is high or low can be provided in easily understandable form.

The category Y may include a healthy category to which a subject with a high possibility of being healthy belongs, other cancer category to which a subject with a high possibility of being affected with a cancer other than pancreatic cancer belongs, or a healthy/other cancer category to which a subject with a high possibility of being healthy and a subject with a high possibility of being affected with a cancer other than pancreatic cancer belong. Hence, reliable information can be provided in easily understandable form, which may be helpful in knowing not only whether the possibility of being affected with pancreatic cancer is high but also whether the possibility of being healthy is high, whether the possibility of being affected with a cancer other than pancreatic cancer is high, or whether the possibility of being healthy or being affected with a cancer other than pancreatic cancer is high.

The category Y may include the healthy category and the other cancer category. Hence, reliable information can be provided in easily understandable form, which may be helpful in knowing not only whether the possibility of being affected with pancreatic cancer is high but also whether the possibility of being healthy is high and whether the possibility of being affected with a cancer other than pancreatic cancer is high.

When the categories are the category X and the category Y, in step S12, the subject may be classified into one of the category X and the category Y, using the concentration values of at least two amino acids of the 19 kinds of amino acids or, if the concentration values are converted, the converted values, and a threshold. Alternatively, the subject may be classified into one of the category X and the category Y, using the value of the formula or, if the value of the formula is converted, the converted value, and a threshold. Hence, reliable information that may be helpful in knowing whether the possibility of being affected with pancreatic cancer is high or low can be provided in easily understandable form.

When a first formula and a second formula that are different from each other and each include at least two explanatory variables to be substituted with the concentration values of at least two amino acids of the 19 kinds of amino acids are previously established as evaluation formulae, in step S12, the value of the first formula and the value of the second formula may be calculated, and the subject may be classified into one of the category X and the category Y using the calculated values of the first formula and the second formula. This leads to further improvement in reliability of information that may be helpful in knowing whether the possibility of being affected with pancreatic cancer is high or low.

Specifically, when the healthy category and the other cancer category are previously established as the category Y, a formula for classifying a subject into one of the category X and the healthy category is previously established as the first formula, and a formula for classifying a subject into one of the category X and the other cancer category is previously established as the second formula, in step S12, the value of the first formula may be first calculated, and the subject may be classified into one of the category X and the healthy category using the calculated value of the first formula. Then if the classification result is the category X, the value of the second formula may be calculated, and the subject classified in the category X using the value of the first formula may be further classified into one of the category X and the other cancer category using the calculated value of the second formula. Then the subject classified in the healthy category and the subject classified in the other cancer category may be finally classified into the category Y.

When the healthy category is previously established as the category Y, in step S12, the subject may be classified into one of the category X and the healthy category, using the concentration values of at least two amino acids of the 19 kinds of amino acids or, if the concentration values are converted, the converted values, and a threshold. Alternatively, the subject may be classified into one of the category X and the healthy category using the value of the formula or, if the value of the formula is converted, the converted value, and a threshold. Hence, reliable information that may be helpful in knowing whether the possibility of being affected with pancreatic cancer is high or whether the possibility of being healthy is high can be provided in easily understandable form.

When the other cancer category is previously established as the category Y, in step S12, the subject may be classified into one of the category X and the other cancer category using the concentration values of at least two amino acids of the 19 kinds of amino acids or, if the concentration values are converted, the converted values, and a threshold. Alternatively, the subject may be classified into one of the category X and the other cancer category using the value of the formula or, if the value of the formula is converted, the converted value, and a threshold. Hence, reliable information that may be helpful in knowing whether the possibility of being affected with pancreatic cancer is high or whether the possibility of being affected with a cancer other than pancreatic cancer is high can be provided in easily understandable form.

When the healthy/other cancer category is previously established as the category Y, in step S12, the subject may be classified into one of the category X and the healthy/other cancer category using the concentration values of at least two amino acids of the 19 kinds of amino acids or, if the concentration values are converted, the converted values, and a threshold. Alternatively, the subject may be classified into one of the category X and the healthy/other cancer category using the value of the formula or, if the value of the formula is converted, the converted value, and a threshold. Hence, reliable information that may be helpful in knowing whether the possibility of being affected with pancreatic cancer is high or whether the possibility of being healthy or being affected with a cancer other than pancreatic cancer is high can be provided in easily understandable form.

When the healthy category and the other cancer category are previously established as the category Y, in step S12, the subject may be classified into any one of the category X, the healthy category, and the other cancer category using the concentration values of at least two amino acids of the 19 kinds of amino acids or, if the concentration values are converted, the converted values, and a threshold. Alternatively, the subject may be classified into any one of the category X, the healthy category, and the other cancer category using the value of the formula or, if the value of the formula is converted, the converted value, and a threshold. Hence, reliable information that may be helpful in knowing whether the possibility of being affected with pancreatic cancer is high, whether the possibility of being healthy is high, or whether the possibility of being affected with a cancer other than pancreatic cancer is high can be provided in easily understandable form.

When the first formula and the second formula that are different from each other and each include at least two explanatory variables to be substituted with the concentration values of at least two amino acids of the 19 kinds of amino acids are previously established as evaluation formulae, in step S12, the value of the first formula and the value of the second formula may be calculated, and the subject may be classified into any one of the category X, the healthy category, and the other cancer category using the calculated values of the first formula and the second formula. This leads to further improvement in reliability of information that may be helpful in knowing whether the possibility of being affected with pancreatic cancer is high, whether the possibility of being healthy is high, or whether the possibility of being affected with a cancer other than pancreatic cancer is high.

Specifically, when a formula for classifying a subject into one of the category X and the healthy category is previously established as the first formula, and a formula for classifying a subject into one of the category X and the other cancer category is previously established as the second formula, in step S12, the value of the first formula may be first calculated, and the subject may be classified into one of the category X and the healthy category using the calculated value of the first formula. Then if the classification result is the category X, the value of the second formula may be calculated, and the subject classified in the category X using the value of the first formula may be further classified into one of the category X and the other cancer category using the calculated value of the second formula. Then the subject classified in the category X using the value of the first formula and classified in the other cancer category using the value of the second formula may be finally classified into the other cancer category.

The evaluation formula may be any one of the logistic regression equation, the fractional expression, the linear discriminant, the multiple regression equation, the formula prepared by the support vector machine, the formula prepared by the Mahalanobis' generalized distance method, the formula prepared by the canonical discriminant analysis, and the formula prepared by the decision tree. This leads to further improvement in reliability of information that may be helpful in knowing the state of pancreatic cancer.

In addition to the formulae described in the present specification, the formulae described in the international patent applications, filed by the present applicant, WO 2008/016111, WO 2008/075662, WO 2008/075663, WO 2009/099005, WO 2009/154296, and WO 2009/154297 can be additionally employed as evaluation formulae to evaluate the state of pancreatic cancer.

The formula employed as the evaluation formula may be prepared by a method described in WO 2004/052191 that is an international application filed by the present applicant or by a method described in WO 2006/098192 that is an international application filed by the present applicant. Any formulae obtained by these methods can be preferably used in the evaluation of the state of pancreatic cancer, regardless of the unit of the amino acid concentration value in the amino acid concentration data as input data.

The formula employed as the evaluation formula refers to a form of equation used generally in multivariate analysis and includes, for example, fractional expression, multiple regression equation, multiple logistic regression equation, linear discriminant function, Mahalanobis' generalized distance, canonical discriminant function, support vector machine, decision tree, and an equation shown by the sum of different forms of equations. In the multiple regression equation, the multiple logistic regression equation, and the canonical discriminant function, a coefficient and a constant term are added to each explanatory variable, and the coefficient and the constant term may be preferably real numbers, more preferably values in the range of 99% confidence interval for the coefficient and the constant term obtained from data for the various kinds of classifications described above, more preferably in the range of 95% confidence interval for the coefficient and the constant term obtained from data for the various kinds of classifications described above. The value of each coefficient and the confidence interval thereof may be those multiplied by a real number, and the value of the constant term and the confidence interval thereof may be those having an arbitrary actual constant added or subtracted or those multiplied or divided by an arbitrary actual constant. When an expression such as a logistic regression, a linear discriminant, and a multiple regression analysis is used as an evaluation formula, a linear transformation of the expression (addition of a constant and multiplication by a constant) and a monotonic increasing (decreasing) transformation (for example, a logit transformation) of the expression do not alter evaluation performance and thus are equivalent to before transformation. Therefore, the expression includes an expression that is subjected to a linear transformation and a monotonic increasing (decreasing) transformation.

In the fractional expression, the numerator of the fractional expression is expressed by the sum of the amino acids A, B, C etc. and the denominator of the fractional expression is expressed by the sum of the amino acids a, b, c etc. The fractional expression also includes the sum of the fractional expressions $\alpha$, $\beta$, $\gamma$ etc. (for example, $\alpha+\beta$) having such constitution. The fractional expression also includes divided fractional expressions. The amino acids used in the numerator or denominator may have suitable coefficients respectively. The amino acids used in the numerator or denominator may appear repeatedly. Each fractional expression may have a suitable coefficient. A value of a coefficient for each explanatory variable and a value for a constant term may be any real numbers. In a fractional expression and the one in which explanatory variables in the numerator and explanatory variables in the denominator in the fractional expression are switched with each other, the positive and negative signs are generally reversed in correlation with objective explanatory variables, but because their correlation is maintained, the evaluation performance can be assumed to be equivalent. The fractional expression therefore also includes the one in which explanatory variables in the numerator and explanatory variables in the denominator in the fractional expression are switched with each other.

In the first embodiment, when the state of pancreatic cancer is evaluated, the concentration value of an amino acid other than the 19 kinds of amino acids may be additionally used. In the first embodiment, when the state of pancreatic cancer is evaluated, a value of other biological information (for example, the values listed in 1. through 5. below) may be used in addition to the concentration values of amino acids. In the first embodiment, the formula employed as the evaluation formula may additionally include one or more explanatory variables to be substituted with the concentration value of an amino acid other than the 19 kinds of amino acids. In the first embodiment, the formula employed as the evaluation formula may additionally include one or more explanatory variables to be substituted with the value of other biological information (for example, the values listed in 1. through 5. below), in addition to the explanatory variables to be substituted with the concentration values of amino acids.

1. the concentration values of metabolites in blood other than amino acids (amino acid metabolites, carbohydrates, lipids, and the like), proteins, peptides, minerals, hormones, and the like
2. the values of tumor markers in blood (CA19-9, CEA, CA125, SPan-1, DUPAN-2, SLX, SCC, CYFRA, ProGRP, p53, elastase, and the like)
3. blood test values such as albumin, total protein, triglyceride, HbA1c, LDL cholesterol, HDL cholesterol, amylase, total bilirubin, and uric acid
4. the values obtained from image information of ultrasonography, X rays, CT, MRI, and the like
5. the values of biological indices such as age, height, weight, BMI, blood pressure, gender, smoking information, dietary information, drinking information, exercise information, stress information, sleeping information, family medical history, disease history information (diabetes, pancreatitis, and the like)

When, before step S11 is executed, a desired substance group consisting of one or more substances is administered to the subject, and then blood is collected from the subject, and in step S11, the amino acid concentration data of the subject is obtained, a substance preventing pancreatic cancer or a substance ameliorating the state of pancreatic cancer may be searched by judging whether or not the administered substance group prevents pancreatic cancer or ameliorates the state of pancreatic cancer, using the evaluation result obtained in step S12. Hence, reliable information on a substance preventing pancreatic cancer or a substance ameliorating the state of pancreatic cancer can be provided by applying the method of evaluating pancreatic cancer which can provide reliable information that may be helpful in knowing the state of pancreatic cancer.

Before step S11 is executed, a suitable combination of an existing drug, amino acid, food and supplement capable of administration to humans (for example, a suitable combination of drugs known to be effective in prevention or amelioration of pancreatic cancer (for example, gemcitabine, erlotinib, and TS-1)) may be administered over a predetermined period (for example in the range of 1 day to 12 months) in a predetermined amount at predetermined frequency and timing (for example 3 times per day, after food) by a predetermined administration method (for example, oral administration). The administration method, dose, and dosage form may be suitably combined depending on the condition of a patient. The dosage form may be determined based on known techniques. The dose is not particularly limited, and for example, a drug containing 1 μg to 100 g active ingredient may be given.

When the judgement result that the administered substance group prevents pancreatic cancer or ameliorates the state of pancreatic cancer is obtained, the administered substance group may be searched as a substance preventing pancreatic cancer or a substance ameliorating the state of pancreatic cancer. The substance group searched by the searching method includes, for example, the amino acid group including at least two amino acids of the 19 kinds of amino acids.

Substances that restore normal value to the concentration values of the amino acid group including at least two amino acids of the 19 kinds of amino acids or the value of the evaluation formula can be selected using the method of evaluating pancreatic cancer in the first embodiment or the pancreatic cancer-evaluating apparatus in the second embodiment.

Searching for a substance preventing pancreatic cancer or a substance ameliorating the state of pancreatic cancer includes not only discovery of a novel substance effective in preventing and ameliorating pancreatic cancer, but also (i) new discovery of use of a known substance in preventing and ameliorating pancreatic cancer, (ii) discovery of a novel composition consisting of a combination of existing drugs, supplements etc. having efficacy expectable for prevention and amelioration of pancreatic cancer, (iii) discovery of the suitable usage, dose and combination described above to form them into a kit, (iv) presentation of a preventing and therapeutic menu including a diet, exercise etc., and (v) presentation of a necessary change in menu for each individual by monitoring the effect of the preventing and therapeutic menu.

1-2. Specific Example of the First Embodiment

Figure 2:
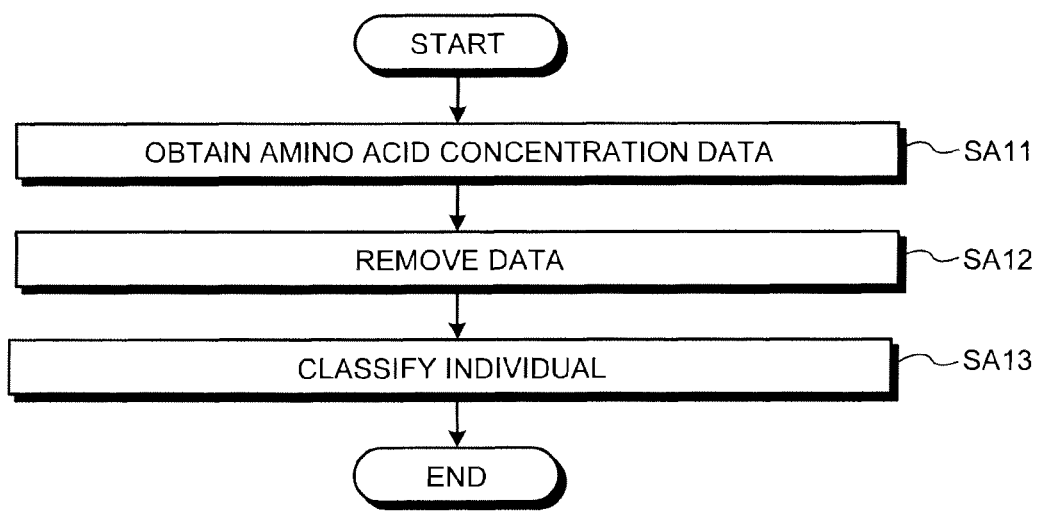
FIG. 2 is a flowchart showing an example of a method of evaluating pancreatic cancer according to the first embodiment.

Here, a specific example of the first embodiment will be described with reference to FIG. 2. FIG. 2 is a flowchart showing the specific example of the first embodiment.

The amino acid concentration data on the concentration values of the amino acids in blood collected from an individual such as animal or human (the one including the concentration values of at least two amino acids of the 19 kinds of amino acids) is obtained (step SA11). In step SA11, for example, the amino acid concentration data determined by a company or the like that performs amino acid concentration value measurements may be obtained, or the amino acid concentration data may be obtained by determining the concentration values of the amino acids by the measurement method such as, for example, the above described (A) or (B) from blood collected from the individual.

Data such as defective and outliers is then removed from the amino acid concentration data of the individual obtained in step SA11 (step SA12).

The value of the formula is calculated using (i) the amino acid concentration data of the individual from which the data such as the defective and the outliers have been removed in step SA12 and (ii) the formula previously established as an evaluation formula, including at least two explanatory variables to be substituted with the concentration values of at least two amino acids of the 19 kinds of amino acids. Any one of the classifications of 1. through 6. below is then executed using the calculated value of the formula (evaluation value) and a previously established threshold (step SA13).

1. When a plurality of categories defined considering at least the degree of the possibility that a subject is affected with pancreatic cancer (the categories may include at least one category defined considering at least the degree of the possibility that a subject is affected with pancreatic cancer and the degree of the possibility that a subject is affected with a cancer other than pancreatic cancer), and one or more thresholds are previously established, the individual is classified into any one of the categories using the evaluation value and the threshold(s).

2. When the pancreatic cancer category and the pancreatic cancer-free category, and a threshold are previously established, the individual is classified into one of the pancreatic cancer category and the pancreatic cancer-free category using the evaluation value and the threshold.

When the first formula and the second formula different from each other are previously established as evaluation formulae, the value of the first formula and the value of the second formula may be calculated, and the individual may be classified into one of the pancreatic cancer category and the pancreatic cancer-free category using the calculated values of the first formula and the second formula.

When the healthy category and the other cancer category are previously established as the pancreatic cancer-free category, a formula for classifying a subject into one of the pancreatic cancer category and the healthy category is previously established as the first formula, and a formula for classifying a subject into one of the pancreatic cancer category and the other cancer category is previously established as the second formula, the value of the first formula may be first calculated, and the individual may be classified into one of the pancreatic cancer category and the healthy category using the calculated value of the first formula. Then if the classification result is the pancreatic cancer category, the value of the second formula may be calculated, and the individual classified in the pancreatic cancer category using the value of the first formula may be further classified into one of the pancreatic cancer category and the other cancer category using the calculated value of the second formula. Then the individual classified in the healthy category and the individual classified in the other cancer category may be finally classified into the pancreatic cancer-free category. The individual classified into the pancreatic cancer category using the value of the first formula and classified into the pancreatic cancer category using the value of the second formula is finally classified into the pancreatic cancer category, as a matter of course.

3. When the pancreatic cancer category and the healthy category, and a threshold are previously established, the individual is classified into one of the pancreatic cancer category and the healthy category using the evaluation value and the threshold.

4. When the pancreatic cancer category and the other cancer category, and a threshold are previously established, the individual is classified into one of the pancreatic cancer category and the other cancer category using the evaluation value and the threshold.

5. When the pancreatic cancer category and the healthy/other cancer category, and a threshold are previously established, the individual is classified into one of the pancreatic cancer category and the healthy/other cancer category using the evaluation value and the threshold.

6. When the pancreatic cancer category, the healthy category, and the other cancer category, and a threshold are previously established, the individual is classified into any one of the pancreatic cancer category, the healthy category, and the other cancer category using the evaluation values and the threshold.

When the first formula and the second formula that are different from each other are previously established as evaluation formulae, the value of the first formula and the value of the second formula may be calculated, and the individual may be classified into any one of the pancreatic cancer category, the healthy category, and the other cancer category using the calculated values of the first formula and the second formula.

when a formula for classifying a subject into one of the pancreatic cancer category and the healthy category is previously established as the first formula, and a formula for classifying a subject into one of the pancreatic cancer category and the other cancer category is previously established as the second formula, the value of the first formula may be first calculated, and the individual may be classified into one of the pancreatic cancer category and the healthy category using the calculated value of the first formula. Then if the classification result is the pancreatic cancer category, the value of the second formula may be calculated, and the individual classified in the pancreatic cancer category using the value of the first formula may be further classified into one of the pancreatic cancer category and the other cancer category using the calculated value of the second formula. Then the individual classified in the pancreatic cancer category using the value of the first formula and classified in the other cancer category using the value of the second formula may be finally classified into the other cancer category. The individual classified in the healthy category using the value of the first formula is finally classified into the healthy category, as a matter of course, and the individual classified in the pancreatic cancer category using the value of the first formula and classified in the pancreatic cancer category using the value of the second formula is finally classified into the pancreatic cancer category, as a matter of course.

Second Embodiment 2-1. Outline of the Second Embodiment

Figure 3:
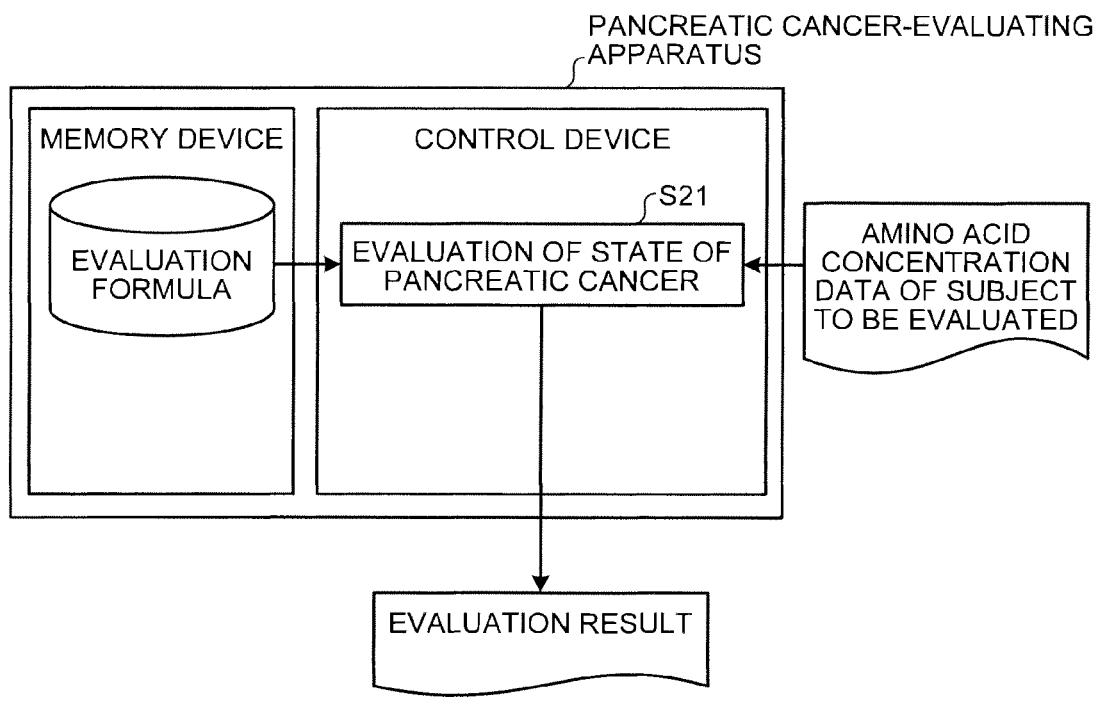
FIG. 3 is a principle configurational diagram showing a basic principle of a second embodiment.

Here, outlines of the second embodiment will be described in detail with reference to FIG. 3. FIG. 3 is a principle configurational diagram showing a basic principle of the second embodiment.

A control device evaluates a state of pancreatic cancer in a subject to be evaluated (for example, an individual such as animal or human) by calculating a value of a formula using (i) the concentration values of at least two amino acids of the 19 kinds of amino acids composed of Asn, His, Thr, Ala, Cit, Arg, Tyr, Val, Met, Lys, Trp, Gly, Pro, Orn, Ile, Leu, Phe, Ser, and Gln, including previously obtained amino acid concentration data of the subject on the concentration value of an amino acid and (ii) the formula previously stored in a memory device for evaluating the state of pancreatic cancer, including an explanatory variable to be substituted with the concentration value of the amino acid (the one including at least two explanatory variables to be substituted with the concentration values of at least two amino acids of the 19 kinds of amino acids) (step S21).

According to the second embodiment described above, in step S21, the state of pancreatic cancer in the subject is evaluated by calculating the value of the evaluation formula using the amino acid concentration data of the subject and the formula stored in the memory device as the evaluation formula. Hence, reliable information that may be helpful in knowing the state of pancreatic cancer can be provided. Both improvement in reliability of the information and reduction in various burdens imposed on users (for example, mental burden, physical burden, temporal burden, or financial burden) can be achieved.

The state of pancreatic cancer may be the degree of the possibility of being affected with pancreatic cancer. Evaluating the state of pancreatic cancer in the subject may be evaluating the degree of the possibility that the subject is affected with pancreatic cancer. Hence, reliable information that may be helpful in knowing the degree of the possibility of being affected with pancreatic cancer can be provided.

In step S21, it may be decided that the calculated value of the formula reflects the state of pancreatic cancer in the subject. The value of the formula may be converted, for example, by the methods listed below, and it may be decided that the converted value reflects the state of pancreatic cancer in the subject. In other words, in step S21, the value of the formula or the converted value may be treated per se as the evaluation result on the state of pancreatic cancer in the subject. Hence, reliable information that may be helpful in knowing the state of pancreatic cancer can be provided.

The value of the evaluation formula may be converted such that the possible range of the value of the evaluation formula falls within a predetermined range (for example, the range from 0.0 to 1.0, the range from 0.0 to 10.0, the range from 0.0 to 100.0, or the range from −10.0 to 10.0), for example, by addition, subtraction, multiplication, and division of any given number with the value of the evaluation formula, by conversion of the value of the evaluation formula by a predetermined conversion method (for example, index transformation, logarithm transformation, angular transformation, square root transformation, probit transformation, or reciprocal transformation), or by performing a combination of these computations on the value of the evaluation formula. For example, the value of an exponential function with the value of the evaluation formula as an exponent and Napier constant as the base (specifically, the value of $p/(1-p)$ where a natural logarithm $\ln(p/(1-p))$ is equal to the value of the evaluation formula when the probability p of being affected with pancreatic cancer is defined) may be further calculated, and a value (specifically, the value of probability p) may be calculated by dividing the calculated value of exponential function by the sum of 1 and the value of exponential function.

The value of the evaluation formula may be converted such that the converted value is a particular value when a particular condition is met. For example, the value of the evaluation formula may be converted such that the converted value is 5.0 when the specificity is 80% and the converted value is 8.0 when the specificity is 95%.

In step S21, the positional information about the position of a predetermined mark (for example, a circle sign or a star sign) corresponding to the value of the formula or the converted value may be generated on a predetermined scale (for example, a graduated scale at least marked with graduations corresponding to the upper limit value and the lower limit value in the possible range of the value of the formula or the converted value, or part of the range) visually presented on a display device such as a monitor or a physical medium such as paper for evaluating the state of pancreatic cancer, using the value of the formula or, if the value of the formula is converted, the converted value. Then it may be decided that the generated positional information reflects the state of pancreatic cancer in the subject. Hence, reliable information that may be helpful in knowing the state of pancreatic cancer can be provided.

When a plurality of categories defined considering at least the degree of the possibility of being affected with pancreatic cancer, and one or more thresholds are previously established, in step S21, the subject may be classified into any one of the categories using the value of the formula or, if the value of the formula is converted, the converted value, and a threshold. Hence, reliable information that may be helpful in knowing the degree of the possibility of being affected with pancreatic cancer can be provided in easily understandable form.

The categories may include at least one category defined considering at least the degree of the possibility of being affected with pancreatic cancer and the degree of the possibility of being affected with a cancer other than pancreatic cancer (for example, lung cancer, colorectal cancer, prostatic cancer, breast cancer, gastric cancer, uterine cancer (cervical cancer, endometrial cancer), or ovarian cancer). Hence, reliable information that may be helpful in knowing not only the degree of the possibility of being affected with pancreatic cancer but also the degree of the possibility of being affected with a cancer other than pancreatic cancer can be provided.

In a set of a plurality of values of the evaluation formula calculated for each test subject using the amino acid concentration data of the plurality of test subjects proved to be not affected with pancreatic cancer (for example, to be healthy) and the evaluation formula, the boundary value when the specificity is a predetermined value (for example 80 or 95) may be established as a threshold.

In a set of a plurality of values of the evaluation formula calculated for each test subject using the amino acid concentration data of the plurality of test subjects proved to be affected with pancreatic cancer and the evaluation formula, the boundary value when the sensitivity is a predetermined value (for example, 80 or 95) may be established as a threshold.

The categories may include a category X to which a subject with a high possibility of being affected with pancreatic cancer belongs and a category Y to which a subject with a low possibility of being affected with pancreatic cancer belongs. Hence, reliable information that may be helpful in knowing whether the possibility of being affected with pancreatic cancer is high or low can be provided in easily understandable form.

The category Y may include a healthy category to which a subject with a high possibility of being healthy belongs, other cancer category to which a subject with a high possibility of being affected with a cancer other than pancreatic cancer belongs, or a healthy/other cancer category to which a subject with a high possibility of being healthy and a subject with a high possibility of being affected with a cancer other than pancreatic cancer belong. Hence, reliable information can be provided in easily understandable form, which may be helpful in knowing not only whether the possibility of being affected with pancreatic cancer is high but also whether the possibility of being healthy is high, whether the possibility of being affected with a cancer other than pancreatic cancer is high, or whether the possibility of being healthy or being affected with a cancer other than pancreatic cancer is high.

The category Y may include the healthy category and the other cancer category. Hence, reliable information can be provided in easily understandable form, which may be helpful in knowing not only whether the possibility of being affected with pancreatic cancer is high but also whether the possibility of being healthy is high and whether the possibility of being affected with a cancer other than pancreatic cancer is high.

When the categories are the category X and the category Y, in step S21, the subject may be classified into one of the category X and the category Y, using the value of the formula or, if the value of the formula is converted, the converted value, and a threshold. Hence, reliable information that may be helpful in knowing whether the possibility of being affected with pancreatic cancer is high or low can be provided in easily understandable form.

When a first formula and a second formula that are different from each other and each include at least two explanatory variables to be substituted with the concentration values of at least two amino acids of the 19 kinds of amino acids are previously established as evaluation formulae, in step S21, the value of the first formula and the value of the second formula may be calculated, and the subject may be classified into one of the category X and the category Y using the calculated values of the first formula and the second formula. This leads to further improvement in reliability of information that may be helpful in knowing whether the possibility of being affected with pancreatic cancer is high or low.

Specifically, when the healthy category and the other cancer category are previously established as the category Y, a formula for classifying a subject into one of the category X and the healthy category is previously established as the first formula, and a formula for classifying a subject into one of the category X and the other cancer category is previously established as the second formula, in step S21, the value of the first formula may be first calculated, and the subject may be classified into one of the category X and the healthy category using the calculated value of the first formula. Then if the classification result is the category X, the value of the second formula may be calculated, and the subject classified in the category X using the value of the first formula may be further classified into one of the category X and the other cancer category using the calculated value of the second formula. Then the subject classified in the healthy category and the subject classified in the other cancer category may be finally classified into the category Y.

When the healthy category is previously established as the category Y, in step S21, the subject may be classified into one of the category X and the healthy category using the value of the formula or, if the value of the formula is converted, the converted value, and a threshold. Hence, reliable information that may be helpful in knowing whether the possibility of being affected with pancreatic cancer is high or whether the possibility of being healthy is high can be provided in easily understandable form.

When the other cancer category is previously established as the category Y, in step S21, the subject may be classified into one of the category X and the other cancer category using the value of the formula or, if the value of the formula is converted, the converted value, and a threshold. Hence, reliable information that may be helpful in knowing whether the possibility of being affected with pancreatic cancer is high or whether the possibility of being affected with a cancer other than pancreatic cancer is high can be provided in easily understandable form.

When the healthy/other cancer category is previously established as the category Y, in step S21, the subject may be classified into one of the category X and the healthy/other cancer category using the value of the formula or, if the value of the formula is converted, the converted value, and a threshold. Hence, reliable information that may be helpful in knowing whether the possibility of being affected with pancreatic cancer is high or whether the possibility of being healthy or being affected with a cancer other than pancreatic cancer is high can be provided in easily understandable form.

When the healthy category and the other cancer category are previously established as the category Y, in step S21, the subject may be classified into any one of the category X, the healthy category, and the other cancer category using the value of the formula or, if the value of the formula is converted, the converted value, and a threshold. Hence, reliable information that may be helpful in knowing whether the possibility of being affected with pancreatic cancer is high, whether the possibility of being healthy is high, or whether the possibility of being affected with a cancer other than pancreatic cancer is high can be provided in easily understandable form.

When the first formula and the second formula that are different from each other and each include at least two explanatory variables to be substituted with the concentration values of at least two amino acids of the 19 kinds of amino acids are previously established as evaluation formulae, in step S21, the value of the first formula and the value of the second formula may be calculated, and the subject may be classified into any one of the category X, the healthy category, and the other cancer category using the calculated values of the first formula and the second formula. This leads to further improvement in reliability of information that may be helpful in knowing whether the possibility of being affected with pancreatic cancer is high, whether the possibility of being healthy is high, or whether the possibility of being affected with a cancer other than pancreatic cancer is high.

Specifically, when a formula for classifying a subject into one of the category X and the healthy category is previously established as the first formula, and a formula for classifying a subject into one of the category X and the other cancer category is previously established as the second formula, in step S21, the value of the first formula may be first calculated, and the subject may be classified into one of the category X and the healthy category using the calculated value of the first formula. Then if the classification result is the category X, the value of the second formula may be calculated, and the subject classified in the category X using the value of the first formula may be further classified into one of the category X and the other cancer category using the calculated value of the second formula. Then the subject classified in the category X using the value of the first formula and classified in the other cancer category using the value of the second formula may be finally classified into the other cancer category.

The evaluation formula may be any one of the logistic regression equation, the fractional expression, the linear discriminant, the multiple regression equation, the formula prepared by the support vector machine, the formula prepared by the Mahalanobis' generalized distance method, the formula prepared by the canonical discriminant analysis, and the formula prepared by the decision tree. This leads to further improvement in reliability of information that may be helpful in knowing the state of pancreatic cancer.

In addition to the formulae described in the present specification, the formulae described in the international patent applications, filed by the present applicant, WO 2008/016111, WO 2008/075662, WO 2008/075663, WO 2009/099005, WO 2009/154296, and WO 2009/154297 can be additionally employed to evaluate the state of pancreatic cancer.

The formula employed as the evaluation formula may be prepared by a method described in WO 2004/052191 that is an international application filed by the present applicant or by a method described in WO 2006/098192 that is an international application filed by the present applicant. Any formulae obtained by these methods can be preferably used in the evaluation of the state of pancreatic cancer, regardless of the unit of the amino acid concentration value in the amino acid concentration data as input data.

The formula employed as the evaluation formula refers to a form of equation used generally in multivariate analysis and includes, for example, fractional expression, multiple regression equation, multiple logistic regression equation, linear discriminant function, Mahalanobis' generalized distance, canonical discriminant function, support vector machine, decision tree, and an equation shown by the sum of different forms of equations. In the multiple regression equation, the multiple logistic regression equation, and the canonical discriminant function, a coefficient and a constant term are added to each explanatory variable, and the coefficient and the constant term may be preferably real numbers, more preferably values in the range of 99% confidence interval for the coefficient and the constant term obtained from data for the various kinds of classifications described above, more preferably in the range of 95% confidence interval for the coefficient and the constant term obtained from data for the various kinds of classifications described above. The value of each coefficient and the confidence interval thereof may be those multiplied by a real number, and the value of the constant term and the confidence interval thereof may be those having an arbitrary actual constant added or subtracted or those multiplied or divided by an arbitrary actual constant. When an expression such as a logistic regression, a linear discriminant, and a multiple regression analysis is used as an evaluation formula, a linear transformation of the expression (addition of a constant and multiplication by a constant) and a monotonic increasing (decreasing) transformation (for example, a logit transformation) of the expression do not alter evaluation performance and thus are equivalent to before transformation. Therefore, the expression includes an expression that is subjected to a linear transformation and a monotonic increasing (decreasing) transformation.

In the fractional expression, the numerator of the fractional expression is expressed by the sum of the amino acids A, B, C etc. and the denominator of the fractional expression is expressed by the sum of the amino acids a, b, c etc. The fractional expression also includes the sum of the fractional expressions $\alpha$, $\beta$, $\gamma$ etc. (for example, $\alpha+\beta$) having such constitution. The fractional expression also includes divided fractional expressions. The amino acids used in the numerator or denominator may have suitable coefficients respectively. The amino acids used in the numerator or denominator may appear repeatedly. Each fractional expression may have a suitable coefficient. A value of a coefficient for each explanatory variable and a value for a constant term may be any real numbers. In a fractional expression and the one in which explanatory variables in the numerator and explanatory variables in the denominator in the fractional expression are switched with each other, the positive and negative signs are generally reversed in correlation with objective explanatory variables, but because their correlation is maintained, the evaluation performance can be assumed to be equivalent. The fractional expression therefore also includes the one in which explanatory variables in the numerator and explanatory variables in the denominator in the fractional expression are switched with each other.

In the second embodiment, when the state of pancreatic cancer is evaluated, the concentration value of an amino acid other than the 19 kinds of amino acids may be additionally used. In the second embodiment, when the state of pancreatic cancer is evaluated, a value of other biological information (for example, the values listed in 1. through 5. below) may be used in addition to the concentration values of amino acids. In the second embodiment, the formula employed as the evaluation formula may additionally include one or more explanatory variables to be substituted with the concentration value of an amino acid other than the 19 kinds of amino acids. In the second embodiment, the formula employed as the evaluation formula may additionally include one or more explanatory variables to be substituted with the value of other biological information (for example, the values listed in 1. through 5. below), in addition to the explanatory variables to be substituted with the concentration values of amino acids.

1. the concentration values of metabolites in blood other than amino acids (amino acid metabolites, carbohydrates, lipids, and the like), proteins, peptides, minerals, hormones, and the like
2. the values of tumor markers in blood (CA19-9, CEA, CA125, SPan-1, DUPAN-2, SLX, SCC, CYFRA, Pro-GRP, p53, elastase, and the like)
3. blood test values such as albumin, total protein, triglyceride, HbA1c, LDL cholesterol, HDL cholesterol, amylase, total bilirubin, and uric acid
4. the values obtained from image information of ultrasonography, X rays, CT, MRI, and the like
5. the values of biological indices such as age, height, weight, BMI, blood pressure, gender, smoking information, dietary information, drinking information, exercise information, stress information, sleeping information, family medical history, disease history information (diabetes, pancreatitis, and the like)

Here, the summary of the evaluation formula-preparing processing (steps 1 to 4) is described in detail. The processing described below is merely one example, and the method of preparing the evaluation formula is not limited thereto.

First, the control device prepares a candidate formula (e.g., $y=a_1x_1+a_2x_2+\ldots+a_nx_n$, y: pancreatic cancer state index data, $x_i$: amino acid concentration data, $a_i$: constant, $i=1, 2, \ldots, n$) that is a candidate for the evaluation formula, based on a predetermined formula-preparing method from pancreatic cancer state information previously stored in the memory device containing the amino acid concentration data and pancreatic cancer state index data on an index for indicating the state of pancreatic cancer (step 1). Data containing defective and outliers may be removed in advance from the pancreatic cancer state information.

In step 1, a plurality of the candidate formulae may be prepared from the pancreatic cancer state information by using a plurality of the different formula-preparing methods (including those for multivariate analysis such as principal component analysis, discriminant analysis, support vector machine, multiple regression analysis, logistic regression analysis, k-means method, cluster analysis, and decision tree). Specifically, a plurality of the candidate formulae may be prepared simultaneously and concurrently by using a plurality of different algorithms with the pancreatic cancer state information which is multivariate data composed of the amino acid concentration data and the pancreatic cancer state index data obtained by analyzing blood obtained from a large number of healthy groups and pancreatic cancer groups. For example, the two different candidate formulae may be formed by performing discriminant analysis and logistic regression analysis simultaneously with the different algorithms. Alternatively, the candidate formula may be formed by converting the pancreatic cancer state information with the candidate formula prepared by performing principal component analysis and then performing discriminant analysis of the converted pancreatic cancer state information. In this way, it is possible to finally prepare the most suitable evaluation formula.

The candidate formula prepared by principal component analysis is a linear expression including each amino acid explanatory variable maximizing the variance of all amino acid concentration data. The candidate formula prepared by discriminant analysis is a high-powered expression (including exponential and logarithmic expressions) including each amino acid explanatory variable minimizing the ratio of the sum of the variances in respective groups to the variance of all amino acid concentration data. The candidate formula prepared by using support vector machine is a high-powered expression (including kernel function) including each amino acid explanatory variable maximizing the boundary between groups. The candidate formula prepared by multiple regression analysis is a high-powered expression including each amino acid explanatory variable minimizing the sum of the distances from all amino acid concentration data. The candidate formula prepared by logistic regression analysis is a linear model expressing logarithmic odds of probability, and a linear expression including each amino acid explanatory variable maximizing the likelihood of the probability. The k-means method is a method of searching k pieces of neighboring amino acid concentration data in various groups, designating the group containing the greatest number of the neighboring points as its data-belonging group, and selecting the amino acid explanatory variable that makes the group to which input amino acid concentration data belong agree well with the designated group. The cluster analysis is a method of clustering (grouping) the points closest in entire amino acid concentration data. The decision tree is a method of ordering amino acid explanatory variables and predicting the group of amino acid concentration data from the pattern possibly held by the higher-ordered amino acid explanatory variable.

Returning to the description of the evaluation formula-preparing processing, the control device verifies the candidate formula prepared in step 1 based on a particular verifying method (step 2). The verification of the candidate formula is performed on each other to each candidate formula prepared in step 1.

In step 2, at least one of discrimination rate, sensitivity, specificity, information criterion, ROC_AUC (area under the curve in a receiver operating characteristic curve), and the like of the candidate formula may be verified by at least one of the bootstrap method, holdout method, N-fold method, leave-one-out method, and the like. In this way, it is possible to prepare the candidate formula higher in predictability or reliability, by taking the pancreatic cancer state information and the evaluation condition into consideration.

The discrimination rate is the rate of the states of pancreatic cancer judged correct according to the present embodiment in all input data. The sensitivity is the rate of the states of pancreatic cancer judged correct according to the present embodiment in the states of pancreatic cancer declared pancreatic cancer in the input data. The specificity is the rate of the states of pancreatic cancer judged correct according to the present embodiment in the states of pancreatic cancer declared healthy in the input data. The information criterion is the sum of the number of the amino acid explanatory variables in the candidate formula prepared in step 1 and the difference in number between the states of pancreatic cancer evaluated according to the present embodiment and those declared in input data. ROC_AUC (area under the curve in a receiver operating characteristic curve) is defined as an area under the curve in a receiver operating characteristic curve (ROC) which is a curve prepared by plotting (x,y)=(1−specificity, sensitivity) on a two-dimensional coordinate, the value of ROC_AUC is equal to 1 for perfect discrimination, and discrimination performance becomes higher as the value becomes closer to 1. The predictability is the average of the discrimination rate, sensitivity, or specificity obtained by repeating verification of the candidate formula. Alternatively, the reliability is the variance of the discrimination rate, sensitivity, or specificity obtained by repeating verification of the candidate formula.

Returning to the description of the evaluation formula-preparing processing, the control device selects a combination of the amino acid concentration data contained in the pancreatic cancer state information used in preparing the candidate formula, by selecting the explanatory variable of the candidate formula based on a predetermined explanatory variable-selecting method (step 3). The selection of the amino acid explanatory variable may be performed on each candidate formula prepared in step 1. In this way, it is possible to select the amino acid explanatory variable of the candidate formula properly. The step 1 is executed once again by using the pancreatic cancer state information including the amino acid concentration data selected in step 3.

In step 3, the amino acid explanatory variable of the candidate formula may be selected based on at least one of the stepwise method, best path method, local search method, and genetic algorithm from the verification result obtained in step 2.

The best path method is a method of selecting an amino acid explanatory variable by optimizing an evaluation index of the candidate formula while eliminating the amino acid explanatory variables contained in the candidate formula one by one.

Returning to the description of the evaluation formula-preparing processing, the control device prepares the evaluation formula by repeatedly performing the steps 1, 2 and 3, and based on verification results thus accumulated, selecting the candidate formula used as the evaluation formula from a plurality of the candidate formulae (step 4). In the selection of the candidate formula, there are cases where the optimum formula is selected from the candidate formulae prepared in the same formula-preparing method or the optimum formula is selected from all candidate formulae.

As described above, in the evaluation formula-preparing processing, the processing for the preparation of the candidate formulae, the verification of the candidate formulae, and the selection of the explanatory variables in the candidate formulae are performed based on the pancreatic cancer state information in a series of operations in a systematized manner, whereby the evaluation formula most appropriate for evaluating the state of pancreatic cancer can be prepared. In other words, in the evaluation formula-preparing processing, the amino acid concentration is used in multivariate statistical analysis, and for selecting the optimum and robust combination of the explanatory variables, the explanatory variable-selecting method is combined with cross-validation to extract the evaluation formula having high evaluation performance. Logistic regression equation, linear discriminant, support vector machine, Mahalanobis' generalized distance method, multiple regression analysis, cluster analysis, Cox proportional-hazards model, and the like can be used as the evaluation formula.

2-2. System Configuration

Hereinafter, the configuration of the pancreatic cancer-evaluating system according to the second embodiment (hereinafter referred to sometimes as the present system) will be described with reference to FIGS. 4 to 19. This system is merely one example, and the present invention is not limited thereto.

Figure 4:
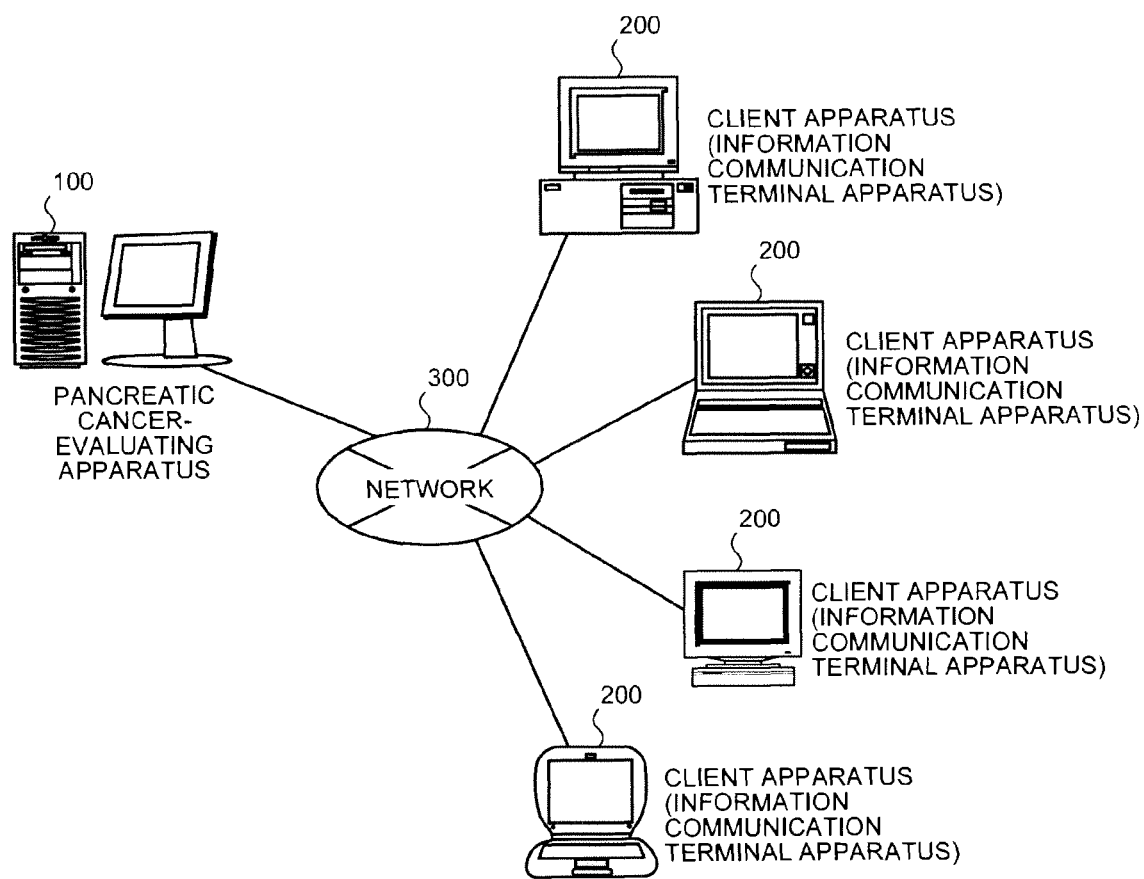
FIG. 4 is a diagram showing an example of an entire configuration of a present system.
Figure 5:
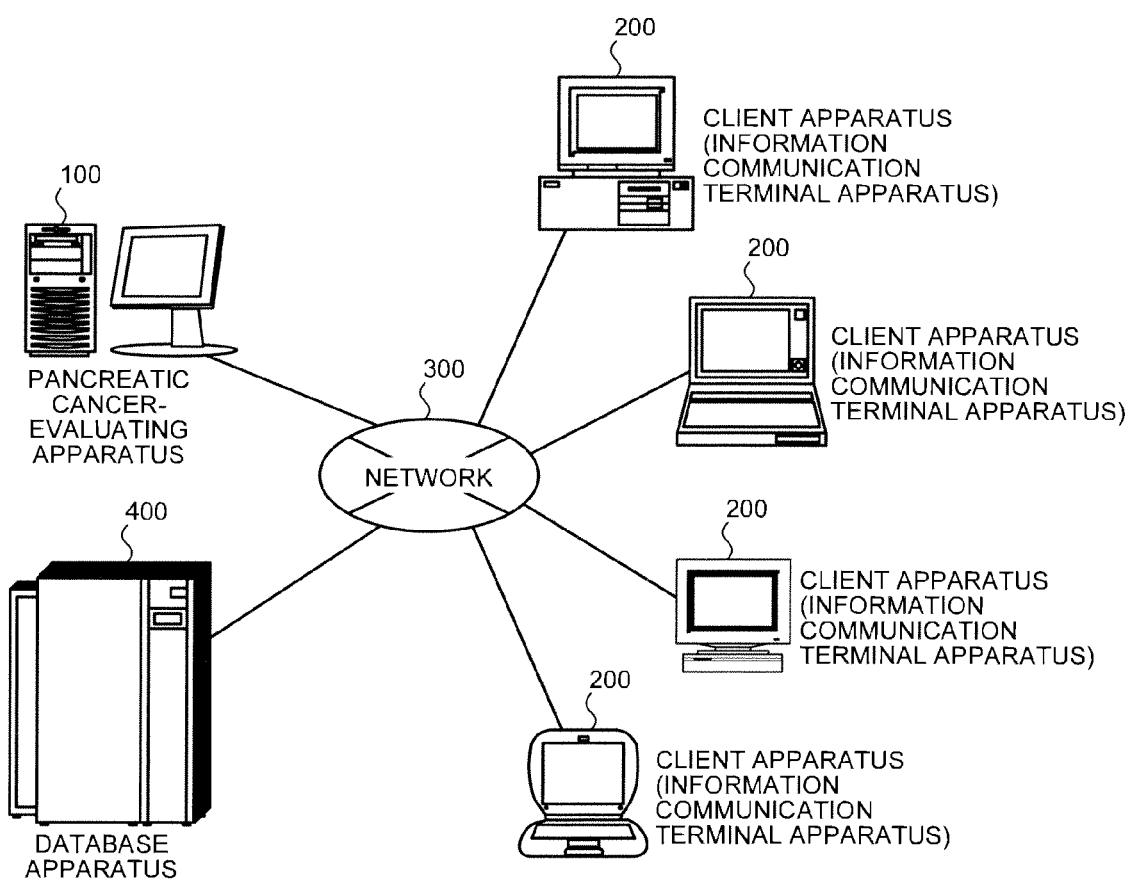
FIG. 5 is a diagram showing another example of an entire configuration of the present system.

First, an entire configuration of the present system will be described with reference to FIGS. 4 and 5. FIG. 4 is a diagram showing an example of the entire configuration of the present system. FIG. 5 is a diagram showing another example of the entire configuration of the present system. As shown in FIG. 4, the present system is constituted in which the pancreatic cancer-evaluating apparatus 100 that evaluates the state of pancreatic cancer in the individual as the subject, and the client apparatus 200 (corresponding to the information communication terminal apparatus of the present invention) that provides the amino acid concentration data of the individual on the concentration values of amino acids, are communicatively connected to each other via a network 300.

In the present system as shown in FIG. 5, in addition to the pancreatic cancer-evaluating apparatus 100 and the client apparatus 200, the database apparatus 400 storing, for example, the pancreatic cancer state information used in preparing the evaluation formula and the evaluation formula used in evaluating the state of pancreatic cancer in the pancreatic cancer-evaluating apparatus 100, may be communicatively connected via the network 300. In this configuration, reliable information that may be helpful in knowing the state of pancreatic cancer, or the like is provided via the network 300 from the pancreatic cancer-evaluating apparatus 100 to the client apparatuses 200 and the database apparatus 400, or from the client apparatuses 200 and the database apparatus 400 to the pancreatic cancer-evaluating apparatus 100. The reliable information that may be helpful in knowing the state of pancreatic cancer is, for example, information on the measured values of particular items as to the state of pancreatic cancer of organisms including human. The reliable information that may be helpful in knowing the state of pancreatic cancer is generated in the pancreatic cancer-evaluating apparatus 100, client apparatus 200, or other apparatuses (e.g., various measuring apparatuses) and stored mainly in the database apparatus 400.

Figure 6:
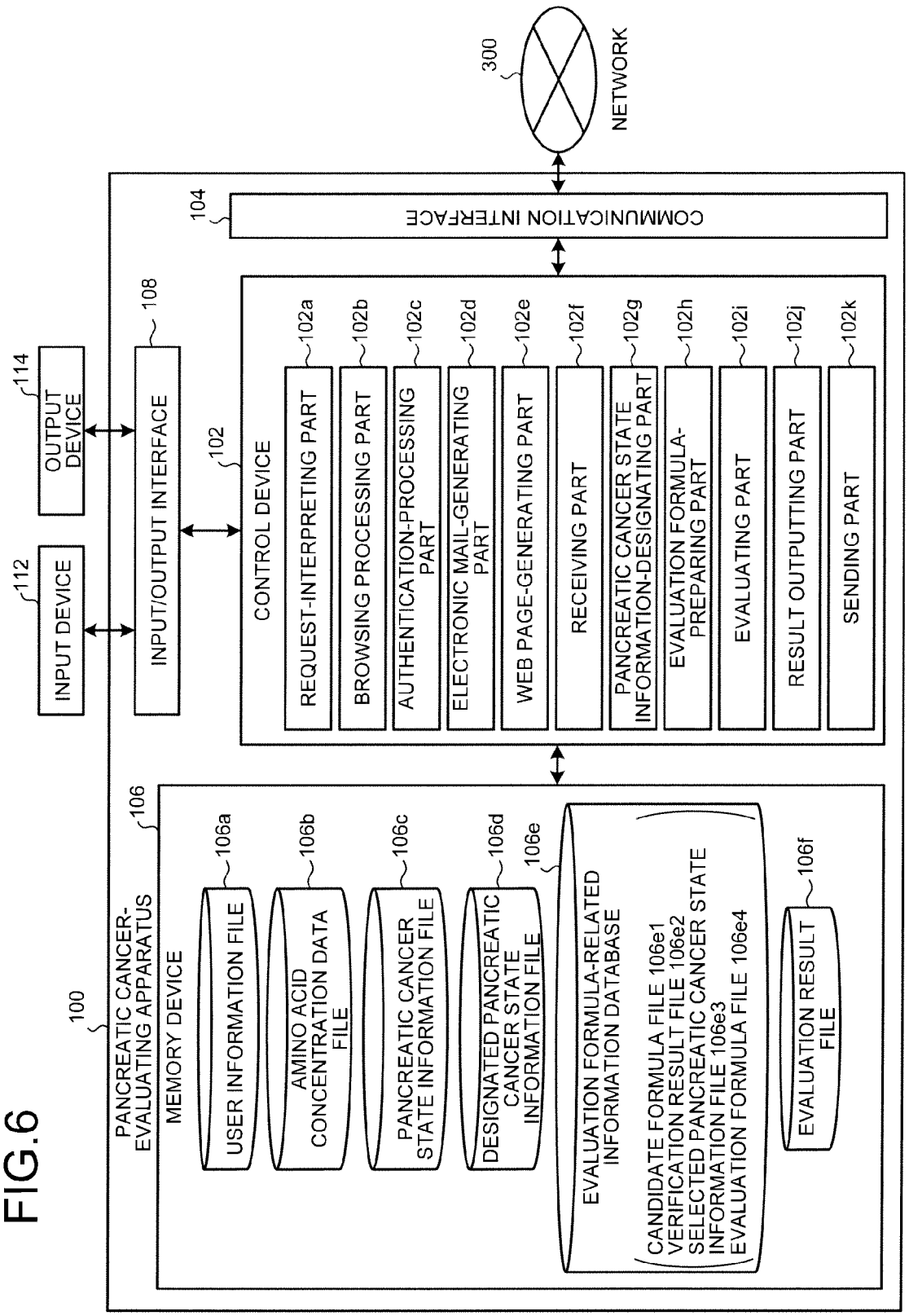
FIG. 6 is a block diagram showing an example of a configuration of a pancreatic cancer-evaluating apparatus 100 in the present system.

Now, the configuration of the pancreatic cancer-evaluating apparatus 100 in the present system will be described with reference to FIGS. 6 to 17. FIG. 6 is a block diagram showing an example of the configuration of the pancreatic cancer-evaluating apparatus 100 in the present system, showing conceptually only the region relevant to the present invention.

The pancreatic cancer-evaluating apparatus 100 includes (I) a control device 102, such as CPU (Central Processing Unit), that integrally controls the pancreatic cancer-evaluating apparatus, (II) a communication interface 104 that connects the pancreatic cancer-evaluating apparatus to the network 300 communicatively via communication apparatuses such as a router and wired or wireless communication lines such as a private line, (III) a memory device 106 that stores various databases, tables, files and others, and (IV) an input/output interface 108 connected to an input device 112 and an output device 114, and these parts are connected to each other communicatively via any communication channel. The pancreatic cancer-evaluating apparatus 100 may be present together with various analyzers (e.g., amino acid analyzer) in a same housing.

The memory device 106 is a storage means, and examples thereof include memory apparatuses such as RAM (Random Access Memory) and ROM (Read Only Memory), fixed disk drives such as a hard disk, a flexible disk, an optical disk, and the like. The memory device 106 stores computer programs giving instructions to the CPU for various processings, together with OS (Operating System). As shown in the figure, the memory device 106 stores the user information file 106*a*, the amino acid concentration data file 106*b*, the pancreatic cancer state information file 106*c*, the designated pancreatic cancer state information file 106*d*, an evaluation formula-related information database 106*e*, and the evaluation result file 106*f*.

The user information file 106*a* stores user information on users. FIG. 7 is a chart showing an example of information stored in the user information file 106*a*. As shown in FIG. 7, the information stored in the user information file 106*a* includes user ID (identification) for identifying a user uniquely, user password for authentication of the user, user name, organization ID for uniquely identifying an organization of the user, department ID for uniquely identifying a department of the user organization, department name, and electronic mail address of the user that are correlated to one another.

Returning to FIG. 6, the amino acid concentration data file 106*b* stores the amino acid concentration data on the concentration values of amino acids. FIG. 8 is a chart showing an example of information stored in the amino acid concentration data file 106*b*. As shown in FIG. 8, the information stored in the amino acid concentration data file 106*b* includes individual number for uniquely identifying an individual (sample) as a subject to be evaluated and amino acid concentration data that are correlated to one another. In FIG. 8, the amino acid concentration data is assumed to be numerical values, i.e., on a continuous scale, but the amino acid concentration data may be expressed on a nominal scale or an ordinal scale. In the case of the nominal or ordinal scale, any number may be allocated to each state for analysis. The amino acid concentration data may be combined with the concentration value of an amino acid other than the 19 kinds of amino acids or the value of other biological information (for example, the values listed in 1. through 5. below).

1. the concentration values of metabolites in blood other than amino acids (amino acid metabolites, carbohydrates, lipids, and the like), proteins, peptides, minerals, hormones, and the like
2. the values of tumor markers in blood (CA19-9, CEA, CA125, SPan-1, DUPAN-2, SLX, SCC, CYFRA, Pro-GRP, p53, elastase, and the like)
3. blood test values such as albumin, total protein, triglyceride, HbA1c, LDL cholesterol, HDL cholesterol, amylase, total bilirubin, and uric acid
4. the values obtained from image information of ultrasonography, X rays, CT, MRI, and the like
5. the values of biological indices such as age, height, weight, BMI, blood pressure, gender, smoking information, dietary information, drinking information, exercise information, stress information, sleeping information, family medical history, disease history information (diabetes, pancreatitis, and the like)

Returning to FIG. 6, the pancreatic cancer state information file 106*c* stores the pancreatic cancer state information used in preparing the evaluation formula. FIG. 9 is a chart showing an example of information stored in the pancreatic cancer state information file 106*c*. As shown in FIG. 9, the information stored in the pancreatic cancer state information file 106*c* includes individual (sample) number, pancreatic cancer state index data (T) on index (index $T_1$, index $T_2$, index $T_3$ . . . ) for indicating the state of pancreatic cancer, and amino acid concentration data that are correlated to one another. In FIG. 9, the pancreatic cancer state index data and the amino acid concentration data are assumed to be numerical values, i.e., on a continuous scale, but the pancreatic cancer state index data and the amino acid concentration data may be expressed on a nominal scale or an ordinal scale. In the case of the nominal or ordinal scale, any number may be allocated to each state for analysis. The pancreatic cancer state index data is a single known condition index serving as a marker of the state of pancreatic cancer, and numerical data may be used.

Returning to FIG. 6, the designated pancreatic cancer state information file 106d stores the pancreatic cancer state information designated in a pancreatic cancer state information-designating part 102g described below. FIG. 10 is a chart showing an example of information stored in the designated pancreatic cancer state information file 106d. As shown in FIG. 10, the information stored in the designated pancreatic cancer state information file 106d includes individual number, designated pancreatic cancer state index data, and designated amino acid concentration data that are correlated to one another.

Returning to FIG. 6, the evaluation formula-related information database 106e is composed of (I) the candidate formula file 106e1 storing the candidate formula prepared in a candidate formula-preparing part 102h1 described below, (II) the verification result file 106e2 storing the verification results obtained in a candidate formula-verifying part 102h2 described below, (III) the selected pancreatic cancer state information file 106e3 storing the pancreatic cancer state information containing the combination of the amino acid concentration data selected in an explanatory variable-selecting part 102h3 described below, and (IV) the evaluation formula file 106e4 storing the evaluation formula prepared in the evaluation formula-preparing part 102h described below.

The candidate formula file 106e1 stores the candidate formulae prepared in the candidate formula-preparing part 102h1 described below. FIG. 11 is a chart showing an example of information stored in the candidate formula file 106e1. As shown in FIG. 11, the information stored in the candidate formula file 106e1 includes rank, and candidate formula (e.g., $F_1$ (Gly, Leu, Phe, . . . ), $F_2$ (Gly, Leu, Phe, . . . ), or $F_3$ (Gly, Leu, Phe, . . . ) in FIG. 11) that are correlated to each other.

Figure 12:
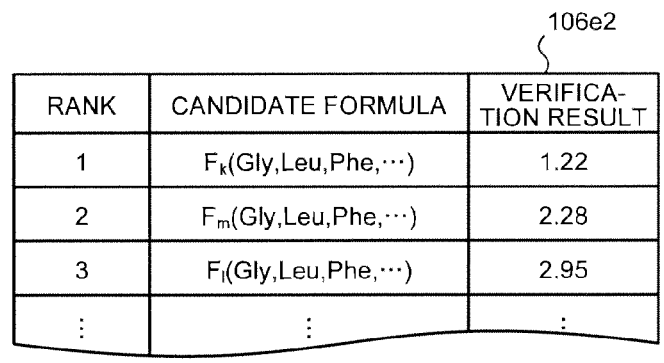
FIG. 12 is a chart showing an example of information stored in a verification result file 106*e*2.

Returning to FIG. 6, the verification result file 106e2 stores the verification results obtained in the candidate formula-verifying part 102h2 described below. FIG. 12 is a chart showing an example of information stored in the verification result file 106e2. As shown in FIG. 12, the information stored in the verification result file 106e2 includes rank, candidate formula (e.g., $F_k$ (Gly, Leu, Phe, . . . ), $F_m$ (Gly, Leu, Phe, . . . ), $F_l$ (Gly, Leu, Phe, . . . ) in FIG. 12), and verification result of each candidate formula (e.g., evaluation value of each candidate formula) that are correlated to one another.

Figure 13:
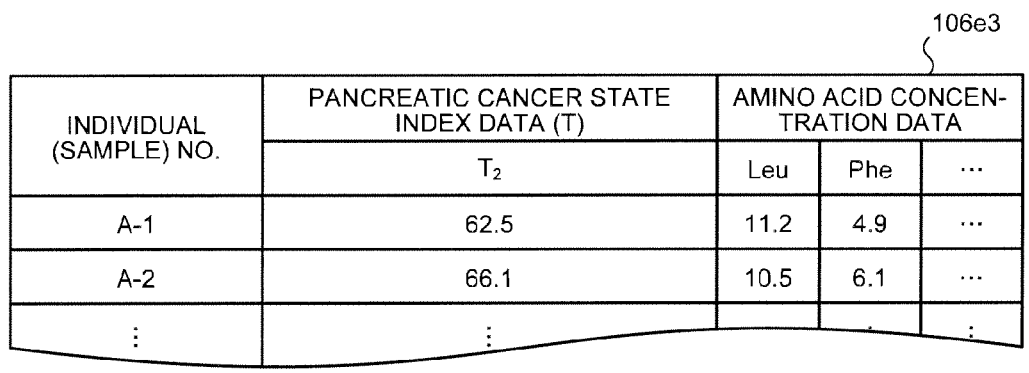
FIG. 13 is a chart showing an example of information stored in a selected pancreatic cancer state information file 106*e*3.

Returning to FIG. 6, the selected pancreatic cancer state information file 106e3 stores the pancreatic cancer state information including the combination of the amino acid concentration data corresponding to the explanatory variables selected in the explanatory variable-selecting part 102h3 described below. FIG. 13 is a chart showing an example of information stored in the selected pancreatic cancer state information file 106e3. As shown in FIG. 13, the information stored in the selected pancreatic cancer state information file 106e3 includes individual number, pancreatic cancer state index data designated in the pancreatic cancer state information-designating part 102g described below, and amino acid concentration data selected in the explanatory variable-selecting part 102h3 described below that are correlated to one another.

Returning to FIG. 6, the evaluation formula file 106e4 stores the evaluation formulae prepared in the evaluation formula-preparing part 102h described below. FIG. 14 is a chart showing an example of information stored in the evaluation formula file 106e4. As shown in FIG. 14, the information stored in the evaluation formula file 106e4 includes rank, evaluation formula (e.g., $F_p$ (Phe, . . . ), $F_p$ (Gly, Leu, Phe), $F_k$ (Gly, Leu, Phe, . . . ) in FIG. 14), a threshold corresponding to each formula-preparing method, and verification result of each evaluation formula (e.g., evaluation value of each evaluation formula) that are correlated to one another.

Returning to FIG. 6, the evaluation result file 106f stores the evaluation results obtained in the evaluating part 102i described below. FIG. 15 is a chart showing an example of information stored in the evaluation result file 106f. The information stored in the evaluation result file 106f includes individual number for uniquely identifying the individual (sample) as the subject, previously obtained amino acid concentration data of the individual, and evaluation result on the state of pancreatic cancer (for example, the value of the evaluation formula calculated by a calculating part 102i1 described below, the converted value of the evaluation formula by a converting part 102i2 described below, the positional information generated by a generating part 102i3 described below, or the classification result obtained by a classifying part 102i4 described below), that are correlated to one another.

Returning to FIG. 6, the memory device 106 stores various Web data for providing the client apparatuses 200 with web site information, CGI programs, and others as information other than the information described above. The Web data include data for displaying the Web pages described below and others, and the data are generated as, for example, a HTML (HyperText Markup Language) or XML (Extensible Markup Language) text file. Files for components and files for operation for generation of the Web data, and other temporary files, and the like are also stored in the memory device 106. In addition, the memory device 106 may store as needed sound files of sounds for transmission to the client apparatuses 200 in WAVE format or AIFF (Audio Interchange File Format) format and image files of still images or motion pictures in JPEG (Joint Photographic Experts Group) format or MPEG2 (Moving Picture Experts Group phase 2) format.

The communication interface 104 allows communication between the pancreatic cancer-evaluating apparatus 100 and the network 300 (or communication apparatus such as a router). Thus, the communication interface 104 has a function to communicate data via a communication line with other terminals.

The input/output interface 108 is connected to the input device 112 and the output device 114. A monitor (including a home television), a speaker, or a printer may be used as the output device 114 (hereinafter, the output device 114 may be described as a monitor 114). A keyboard, a mouse, a microphone, or a monitor functioning as a pointing device together with a mouse may be used as the input device 112.

The control device 102 has an internal memory storing control programs such as OS (Operating System), programs for various processing procedures, and other needed data, and performs various information processings according to these programs. As shown in the figure, the control device 102 includes mainly a request-interpreting part 102a, a browsing processing part 102b, an authentication-processing part 102c, an electronic mail-generating part 102d, a Web page-generating part 102e, a receiving part 102f, the pancreatic cancer state information-designating part 102g, the evaluation formula-preparing part 102h, the evaluating part 102i, a result outputting part 102j and a sending part 102*k*. The control device 102 performs data processings such as removal of data including defective, removal of data including many outliers, and removal of explanatory variables for the defective-including data in the pancreatic cancer state information transmitted from the database apparatus 400 and in the amino acid concentration data transmitted from the client apparatus 200.

The request-interpreting part 102*a* interprets the requests transmitted from the client apparatus 200 or the database apparatus 400 and sends the requests to other parts in the control device 102 according to results of interpreting the requests. Upon receiving browsing requests for various screens transmitted from the client apparatus 200, the browsing processing part 102*b* generates and transmits web data for these screens. Upon receiving authentication requests transmitted from the client apparatus 200 or the database apparatus 400, the authentication-processing part 102*c* performs authentication. The electronic mail-generating part 102*d* generates electronic mails including various kinds of information. The Web page-generating part 102*e* generates Web pages for users to browse with the client apparatus 200.

The receiving part 102*f* receives, via the network 300, information (specifically, the amino acid concentration data, the pancreatic cancer state information, the evaluation formula, etc.) transmitted from the client apparatus 200 and the database apparatus 400. The pancreatic cancer state information-designating part 102*g* designates objective pancreatic cancer state index data and objective amino acid concentration data in preparing the evaluation formula.

The evaluation formula-preparing part 102*h* generates the evaluation formula based on the pancreatic cancer state information received in the receiving part 102*f* and the pancreatic cancer state information designated in the pancreatic cancer state information-designating part 102*g*. Specifically, the evaluation formula-preparing part 102*h* generates the evaluation formula by selecting the candidate formula used as the evaluation formula from a plurality of the candidate formulae, based on verification results accumulated by repeating processings in the candidate formula-preparing part 102*h*1, the candidate formula-verifying part 102*h*2, and the explanatory variable-selecting part 102*h*3 from the pancreatic cancer state information.

If the evaluation formulae are stored previously in a predetermined region of the memory device 106, the evaluation formula-preparing part 102*h* may generate the evaluation formula by selecting the desired evaluation formula out of the memory device 106. Alternatively, the evaluation formula-preparing part 102*h* may generate the evaluation formula by selecting and downloading the desired evaluation formula from the evaluation formulae previously stored in another computer apparatus (e.g., the database apparatus 400).

Figure 16:
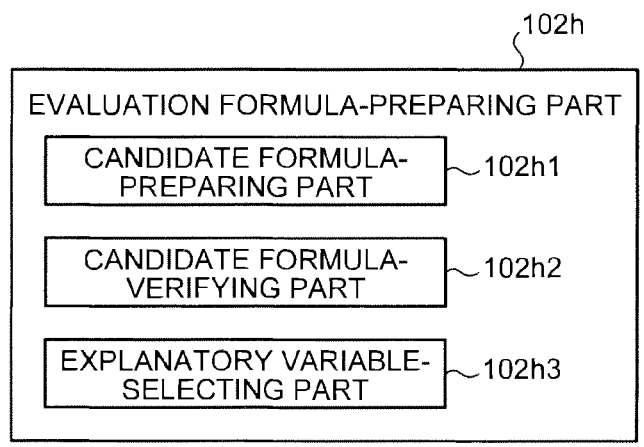
FIG. 16 is a block diagram showing a configuration of an evaluation formula-preparing part 102*h*.

Hereinafter, a configuration of the evaluation formula-preparing part 102*h* will be described with reference to FIG. 16. FIG. 16 is a block diagram showing the configuration of the evaluation formula-preparing part 102*h*, and only a part in the configuration related to the present invention is shown conceptually. The evaluation formula-preparing part 102*h* includes the candidate formula-preparing part 102*h*1, the candidate formula-verifying part 102*h*2, and the explanatory variable-selecting part 102*h*3, additionally. The candidate formula-preparing part 102*h*1 generates the candidate formula that is a candidate of the evaluation formula, from the pancreatic cancer state information based on a predetermined formula-preparing method. The candidate formula-preparing part 102*h*1 may generate a plurality of the candidate formulae from the pancreatic cancer state information, by using a plurality of the different formula-preparing methods. The candidate formula-verifying part 102*h*2 verifies the candidate formula prepared by the candidate formula-preparing part 102*h*1 based on a particular verifying method. The candidate formula-verifying part 102*h*2 may verify at least one of the discrimination rate, sensitivity, specificity, information criterion, and ROC_AUC (area under the curve in a receiver operating characteristic curve) of the candidate formulae based on at least one of the bootstrap method, holdout method, N-fold method, and leave-one-out method. The explanatory variable-selecting part 102*h*3 selects the combination of the amino acid concentration data contained in the pancreatic cancer state information used in preparing the candidate formula, by selecting the explanatory variables of the candidate formula based on a particular explanatory variable-selecting method. The explanatory variable-selecting part 102*h*3 may select the explanatory variables of the candidate formula based on at least one of the stepwise method, best path method, local search method, and genetic algorithm from the verification results.

Returning to FIG. 6, the evaluating part 102*i* evaluates the state of pancreatic cancer in the individual by calculating the value of the evaluation formula using the previously obtained formula (for example, the evaluation formula prepared by the evaluation formula-preparing part 102*h* or the evaluation formula received by the receiving part 102*f*) and the amino acid concentration data received by the receiving part 102*f*.

Figure 17:
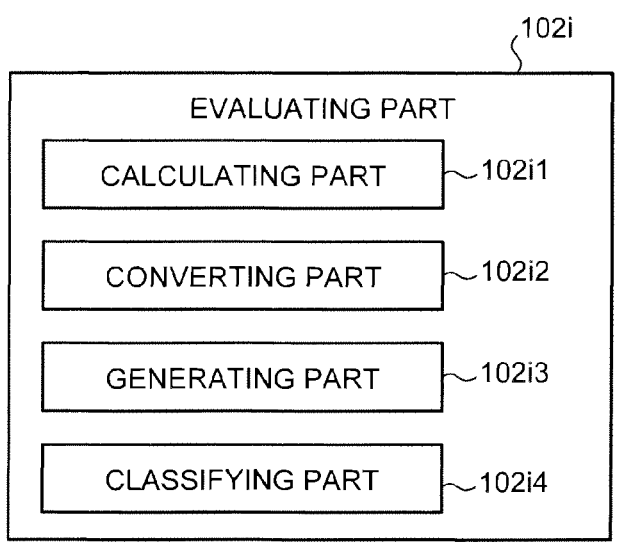
FIG. 17 is a block diagram showing a configuration of an evaluating part 102i.

Hereinafter, a configuration of the evaluating part 102*i* will be described with reference to FIG. 17. FIG. 17 is a block diagram showing the configuration of the evaluating part 102*i*, and only a part in the configuration related to the present invention is shown conceptually. The evaluating part 102*i* includes the calculating part 102*i*1, the converting part 102*i*2, the generating part 102*i*3, and the classifying part 102*i*4, additionally.

The calculating part 102*i*1 calculates the value of the evaluation formula using (i) the concentration values of at least two amino acids of the 19 kinds of amino acids, including the amino acid concentration data and (ii) the evaluation formula including at least two explanatory variables to be substituted with the concentration values of at least two amino acids of the 19 kinds of amino acids. The evaluating part 102*i* stores the value of the evaluation formula calculated by the calculating part 102*i*1 as an evaluation result in a predetermined region of the evaluation result file 106*f*. The evaluation formula may be any one of a logistic regression equation, a fractional expression, a linear discriminant, a multiple regression equation, a formula prepared by a support vector machine, a formula prepared by a Mahalanobis' generalized distance method, a formula prepared by canonical discriminant analysis, and a formula prepared by a decision tree.

The converting part 102*i*2 converts the value of the evaluation formula calculated by the calculating part 102*i*1, for example, by the conversion method described above. The evaluating part 102*i* stores the converted value by the converting part 102*i*2 as an evaluation result in a predetermined region of the evaluation result file 106*f*.

The generating part 102*i*3 generates the positional information about the position of a predetermined mark (for example, a circle sign or a star sign) corresponding to the value of the formula or the converted value on a predetermined scale (for example, a graduated scale at least marked with graduations corresponding to the upper limit value and the lower limit value in the possible range of the value of the formula or the converted value, or part of the range) visually presented on a display device such as a monitor or a physical medium such as paper for evaluating the state of pancreatic cancer, using the value of the formula calculated by the calculating part 102i1 or the converted value by the converting part 102i2. The evaluating part 102i stores the positional information generated by the generating part 102i3 as an evaluation result in a predetermined region of the evaluation result file 106f.

The classifying part 102i4 classifies the individual into any one of a plurality of categories previously defined considering at least the degree of the possibility of being affected with pancreatic cancer, using the value of the evaluation formula calculated by the calculating part 102i1 or the converted value by the converting part 102i2.

The categories may include at least one category defined considering at least the degree of the possibility that a subject is affected with pancreatic cancer and the degree of the possibility that a subject is affected with a cancer other than pancreatic cancer.

When the category X and the category Y are previously established as the categories, the classifying part 102i4 classifies the individual into one of the category X and the category Y using the evaluation value and a threshold. When the first formula and the second formula that are different from each other are previously established as evaluation formulae, the calculating part 102i1 may calculate the value of the first formula and the value of the second formula, and the classifying part 102i4 may classify the individual into one of the category X and the category Y using the values of the first formula and the second formula. When the healthy category and the other cancer category are previously established as the category Y, a formula for classifying a subject into one of the category X and the healthy category is previously established as the first formula, and a formula for classifying a subject into one of the category X and the other cancer category is previously established as the second formula, the calculating part 102i1 may first calculate the value of the first formula, and the classifying part 102i4 may classify the individual into one of the category X and the healthy category using the calculated value of the first formula. Then if the classification result is the category X, the calculating part 102i1 may calculate the value of the second formula, and the classifying part 102i4 may further classify the individual classified in the category X using the value of the first formula into one of the category X and the other cancer category, using the calculated value of the second formula. Then the classifying part 102i4 may finally classify the individual classified in the healthy category and the individual classified in the other cancer category into the category Y.

When the category X and the healthy category are previously established as the categories, the classifying part 102i4 classifies the individual into one of the category X and the healthy category using the evaluation value and a threshold.

When the category X and the other cancer category are previously established as the categories, the classifying part 102i4 classifies the individual into one of the category X and the other cancer category using the evaluation value and a threshold.

When the category X and the healthy/other cancer category are previously established as the categories, the classifying part 102i4 classifies the individual into one of the category X and the healthy/other cancer category using the evaluation value and a threshold.

When the category X, the healthy category, and the other cancer category are previously established as the categories, the classifying part 102i4 classifies the individual into any one of the category X, the healthy category, and the other cancer category, using the evaluation value and a threshold. When the first formula and the second formula that are different from each other are previously established as the evaluation formulae, the calculating part 102i1 may calculate the value of the first formula and the value of the second formula, and the classifying part 102i4 may classify the individual into any one of the category X, the healthy category, and the other cancer category, using the calculated values of the first formula and the second formula. When a formula for classifying a subject into one of the category X and the healthy category is previously established as the first formula, and a formula for classifying a subject into one of the category X and the other cancer category is previously established as the second formula, the calculating part 102i1 may first calculate the value of the first formula, and the classifying part 102i4 may classify the individual into one of the category X and the healthy category using the calculated value of the first formula. Then if the classification result is the category X, the calculating part 102i1 may calculate the value of the second formula, and the classifying part 102i4 may further classify the individual classified in the category X using the value of the first formula into one of the category X and the other cancer category, using the calculated value of the second formula. Then the classifying part 102i4 may finally classify the individual classified in the category X using the value of the first formula and classified in the other cancer category using the value of the second formula into the other cancer category.

Returning to FIG. 6, the result outputting part 102j outputs, into the output device 114, the processing results in each processing part in the control device 102 (including the evaluation results obtained by the evaluating part 102i) etc.

The sending part 102k transmits the evaluation results to the client apparatus 200 that is a sender of the amino acid concentration data of the individual, and transmits the evaluation formulae prepared in the pancreatic cancer-evaluating apparatus 100 and the evaluation results to the database apparatus 400.

Figure 18:
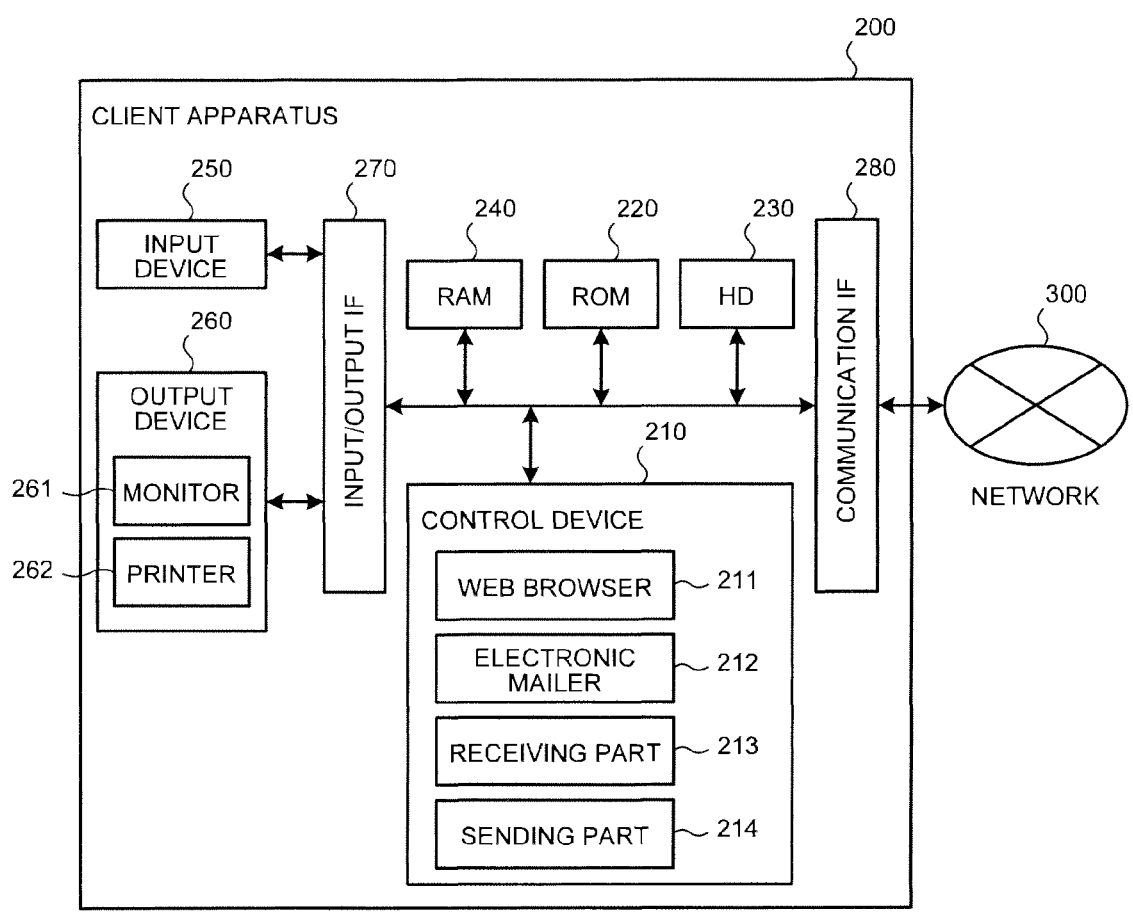
FIG. 18 is a block diagram showing an example of a configuration of a client apparatus 200 in the present system.

Hereinafter, a configuration of the client apparatus 200 in the present system will be described with reference to FIG. 18. FIG. 18 is a block diagram showing an example of the configuration of the client apparatus 200 in the present system, and only the part in the configuration relevant to the present invention is shown conceptually.

The client apparatus 200 includes a control device 210, ROM 220, HD (Hard Disk) 230, RAM 240, an input device 250, an output device 260, an input/output IF 270, and a communication IF 280 that are connected communicatively to one another through a communication channel.

The control device 210 has a Web browser 211, an electronic mailer 212, a receiving part 213, and a sending part 214. The Web browser 211 performs browsing processings of interpreting Web data and displaying the interpreted Web data on a monitor 261 described below. The Web browser 211 may have various plug-in softwares, such as stream player, having functions to receive, display and feedback streaming screen images. The electronic mailer 212 sends and receives electronic mails using a particular protocol (e.g., SMTP (Simple Mail Transfer Protocol) or POP3 (Post Office Protocol version 3)). The receiving part 213 receives various kinds of information, such as the evaluation results transmitted from the pancreatic cancer-evaluating apparatus 100, via the communication IF 280.

The sending part 214 sends various kinds of information such as the amino acid concentration data of the individual, via the communication IF 280, to the pancreatic cancer-evaluating apparatus 100.

The input device 250 is for example a keyboard, a mouse or a microphone. The monitor 261 described below also functions as a pointing device together with a mouse. The output device 260 is an output means for outputting information received via the communication IF 280, and includes the monitor 261 (including home television) and a printer 262. In addition, the output device 260 may have a speaker or the like additionally. The input/output IF 270 is connected to the input device 250 and the output device 260.

The communication IF 280 connects the client apparatus 200 to the network 300 (or communication apparatus such as a router) communicatively. In other words, the client apparatuses 200 are connected to the network 300 via a communication apparatus such as a modem, TA (Terminal Adapter) or a router, and a telephone line, or a private line. In this way, the client apparatuses 200 can access to the pancreatic cancer-evaluating apparatus 100 by using a particular protocol.

The client apparatus 200 may be realized by installing softwares (including programs, data and others) for a Web data-browsing function and an electronic mail-processing function to an information processing apparatus (for example, an information processing terminal such as a known personal computer, a workstation, a family computer, Internet TV (Television), PHS (Personal Handyphone System) terminal, a mobile phone terminal, a mobile unit communication terminal or PDA (Personal Digital Assistants)) connected as needed with peripheral devices such as a printer, a monitor, and an image scanner.

All or a part of processings of the control device 210 in the client apparatus 200 may be performed by CPU and programs read and executed by the CPU. Computer programs for giving instructions to the CPU and executing various processings together with the OS (Operating System) are recorded in the ROM 220 or HD 230. The computer programs, which are executed as they are loaded in the RAM 240, constitute the control device 210 with the CPU. The computer programs may be stored in application program servers connected via any network to the client apparatus 200, and the client apparatus 200 may download all or a part of them as needed. All or any part of processings of the control device 210 may be realized by hardware such as wired-logic.

The control device 210 may include an evaluating part 210a (including a calculating part 210a1, a converting part 210a2, a generating part 210a3, and a classifying part 210a4) having the same functions as the functions of the evaluating part 102i in the control device 102 of the pancreatic cancer-evaluating apparatus 100. When the control device 210 includes the evaluating part 210a, the evaluating part 210a may convert the value of the formula in the converting part 210a2, generate the positional information corresponding to the value of the formula or the converted value in the generating part 210a3, and classify the individual into any one of the categories using the value of the formula or the converted value in the classifying part 210a4, in accordance with information included in the evaluation result transmitted from the pancreatic cancer-evaluating apparatus 100.

Hereinafter, the network 300 in the present system will be described with reference to FIGS. 4 and 5. The network 300 has a function to connect the pancreatic cancer-evaluating apparatus 100, the client apparatuses 200, and the database apparatus 400 mutually, communicatively to one another, and is for example the Internet, an intranet, or LAN (Local Area Network (including both wired and wireless)). The network 300 may be VAN (Value Added Network), a personal computer communication network, a public telephone network (including both analog and digital), a leased line network (including both analog and digital), CATV (Community Antenna Television) network, a portable switched network or a portable packet-switched network (including IMT2000 (International Mobile Telecommunication 2000) system, GSM (registered trademark) (Global System for Mobile Communications) system, or PDC (Personal Digital Cellular)/PDC-P system), a wireless calling network, a local wireless network such as Bluetooth (registered trademark), PHS network, a satellite communication network (including CS (Communication Satellite), BS (Broadcasting Satellite), ISDB (Integrated Services Digital Broadcasting), and the like), or the like.

Figure 19:
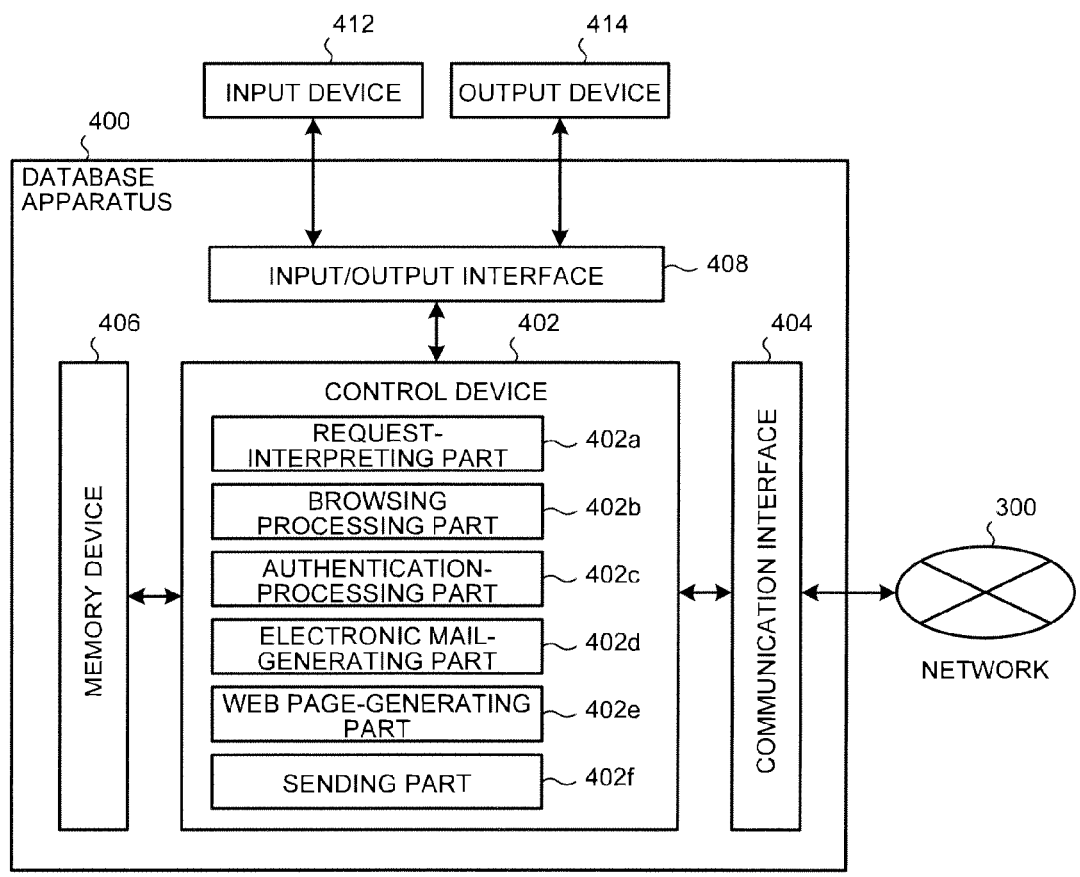
FIG. 19 is a block diagram showing an example of a configuration of a database apparatus 400 in the present system.

Hereinafter, the configuration of the database apparatus 400 in the present system will be described with reference to FIG. 19. FIG. 19 is a block diagram showing an example of the configuration of the database apparatus 400 in the present system, showing conceptually only the region relevant to the present invention.

The database apparatus 400 has functions to store, for example, the pancreatic cancer state information used in preparing the evaluation formulae in the pancreatic cancer-evaluating apparatus 100 or in the database apparatus, the evaluation formulae prepared in the pancreatic cancer-evaluating apparatus 100, and the evaluation results obtained in the pancreatic cancer-evaluating apparatus 100. As shown in FIG. 19, the database apparatus 400 includes (I) a control device 402, such as CPU, which integrally controls the entire database apparatus, (II) a communication interface 404 connecting the database apparatus to the network 300 communicatively via a communication apparatus such as a router and via wired or wireless communication circuits such as a private line, (III) a memory device 406 storing various databases, tables and files (for example, files for Web pages), and (IV) an input/output interface 408 connected to an input device 412 and an output device 414, and these parts are connected communicatively to each other via any communication channel.

The memory device 406 is a storage means, and may be, for example, memory apparatus such as RAM or ROM, a fixed disk drive such as a hard disk, a flexible disk, an optical disk, and the like. The memory device 406 stores, for example, various programs used in various processings. The communication interface 404 allows communication between the database apparatus 400 and the network 300 (or a communication apparatus such as a router). Thus, the communication interface 404 has a function to communicate data via a communication line with other terminals. The input/output interface 408 is connected to the input device 412 and the output device 414. A monitor (including a home television), a speaker, or a printer may be used as the output device 414 (hereinafter, the output device 414 may be described as a monitor 414). A keyboard, a mouse, a microphone, or a monitor functioning as a pointing device together with a mouse may be used as the input device 412.

The control device 402 has an internal memory storing control programs such as OS (Operating System), programs for various processing procedures, and other needed data, and performs various information processings according to these programs. As shown in the figure, the control device 402 includes mainly a request-interpreting part 402a, a browsing processing part 402b, an authentication-processing part 402c, an electronic mail-generating part 402d, a Web page-generating part 402e, and a sending part 402f.

The request-interpreting part 402a interprets the requests transmitted from the pancreatic cancer-evaluating apparatus 100 and sends the requests to other parts in the control device 402 according to results of interpreting the requests. Upon receiving browsing requests for various screens transmitted from the pancreatic cancer-evaluating apparatus 100, the browsing processing part 402b generates and transmits web data for these screens. Upon receiving authentication requests transmitted from the pancreatic cancer-evaluating apparatus 100, the authentication-processing part 402c performs authentication. The electronic mail-generating part 402d generates electronic mails including various kinds of information. The Web page-generating part 402e generates Web pages for users to browse with the client apparatus 200. The sending part 402f transmits various kinds of information such as the pancreatic cancer state information and the evaluation formulae to the pancreatic cancer-evaluating apparatus 100.

2-3. Specific Example of the Second Embodiment

Figure 20:
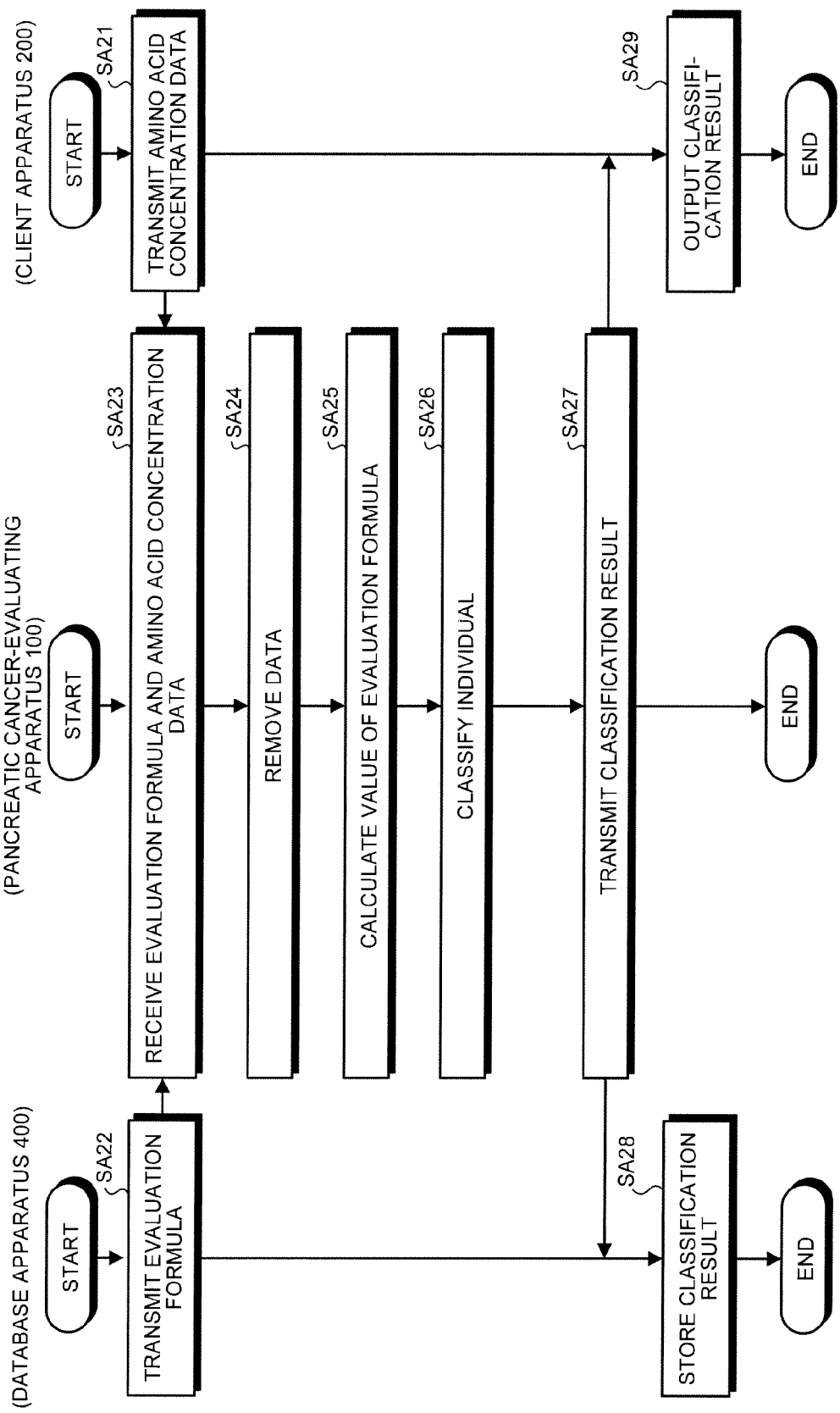
FIG. 20 is a flowchart showing an example of a pancreatic cancer evaluation service processing performed in the present system.

Here, a specific example of the second embodiment will be described with reference to FIG. 20. FIG. 20 is a flowchart showing the example of the pancreatic cancer evaluation service processing according to the second embodiment.

The amino acid concentration data used in the present processing is data concerning the concentration values of amino acids obtained by analyzing, by professionals or ourselves, blood (including, for example, plasma or serum) previously collected from an individual by the measurement method such as the following (A) or (B). Here, the unit of the amino acid concentration may be, for example, a molar concentration, a weight concentration, or one obtained by addition, subtraction, multiplication, and division of any constant with these concentrations.

(A) Plasma is separated from blood by centrifuging a collected blood sample. All plasma samples are frozen and stored at −80° C. until an amino acid concentration is measured. At the time of measuring an amino acid concentration, acetonitrile is added to perform a protein removal treatment, pre-column derivatization is then performed using a labeled reagent (3-aminopyridyl-N-hydroxysuccinimidyl carbamate), and an amino acid concentration is analyzed by liquid chromatograph mass spectrometer (LC/MS) (see International Publication WO 2003/069328 and International Publication WO 2005/116629).

(B) Plasma is separated from blood by centrifuging a collected blood sample. All plasma samples are frozen and stored at −80° C. until an amino acid concentration is measured. At the time of measuring an amino acid concentration, sulfosalicylic acid is added to perform a protein removal treatment, and an amino acid concentration is analyzed by an amino acid analyzer based on post-column derivatization using a ninhydrin reagent.

First, the client apparatus 200 accesses the pancreatic cancer-evaluating apparatus 100 when the user specifies the Web site address (such as URL) provided from the pancreatic cancer-evaluating apparatus 100, via the input device 250 on the screen displaying the Web browser 211. Specifically, when the user instructs update of the Web browser 211 screen on the client apparatus 200, the Web browser 211 sends the Web site address provided from the pancreatic cancer-evaluating apparatus 100 by a particular protocol to the pancreatic cancer-evaluating apparatus 100, thereby transmitting requests demanding a transmission of Web page corresponding to an amino acid concentration data transmission screen to the pancreatic cancer-evaluating apparatus 100 based on a routing of the address.

Then, upon receipt of the request transmitted from the client apparatus 200, the request-interpreting part 102a in the pancreatic cancer-evaluating apparatus 100 analyzes the transmitted requests and sends the requests to other parts in the control device 102 according to analytical results. Specifically, when the transmitted requests are requests to send the Web page corresponding to the amino acid concentration data transmission screen, mainly the browsing processing part 102b in the pancreatic cancer-evaluating apparatus 100 obtains the Web data for display of the Web page stored in a predetermined region of the memory device 106 and sends the obtained Web data to the client apparatus 200. More specifically, upon receiving the requests to transmit the Web page corresponding to the amino acid concentration data transmission screen by the user, the control device 102 in the pancreatic cancer-evaluating apparatus 100 demands inputs of user ID and user password from the user. If the user ID and password are input, the authentication-processing part 102c in the pancreatic cancer-evaluating apparatus 100 examines the input user ID and password by comparing them with the user ID and user password stored in the user information file 106a for authentication. Only when the user is authenticated, the browsing processing part 102b in the pancreatic cancer-evaluating apparatus 100 sends the Web data for displaying the Web page corresponding to the amino acid concentration data transmission screen to the client apparatus 200. The client apparatus 200 is identified with the IP (Internet Protocol) address transmitted from the client apparatus 200 together with the transmission requests.

Then, the client apparatus 200 receives, in the receiving part 213, the Web data (for displaying the Web page corresponding to the amino acid concentration data transmission screen) transmitted from the pancreatic cancer-evaluating apparatus 100, interprets the received Web data with the Web browser 211, and displays the amino acid concentration data transmission screen on the monitor 261.

When the user inputs and selects, via the input device 250, for example the amino acid concentration data of the individual on the amino acid concentration data transmission screen displayed on the monitor 261, the sending part 214 of the client apparatus 200 transmits an identifier for identifying input information and selected items to the pancreatic cancer-evaluating apparatus 100, thereby transmitting the amino acid concentration data of the individual to the pancreatic cancer-evaluating apparatus 100 (step SA21). In step SA21, the transmission of the amino acid concentration data may be realized for example by using an existing file transfer technology such as FTP (File Transfer Protocol).

Then, the request-interpreting part 102a of the pancreatic cancer-evaluating apparatus 100 interprets the identifier transmitted from the client apparatus 200 thereby interpreting the requests from the client apparatus 200, and requests the database apparatus 400 to send the evaluation formula.

Then, the request-interpreting part 402a in the database apparatus 400 interprets the transmission requests from the pancreatic cancer-evaluating apparatus 100 and transmits, to the pancreatic cancer-evaluating apparatus 100, the evaluation formula (for example, the updated newest evaluation formula) stored in a predetermined region of the memory device 406 (step SA22). Specifically, in step SA22, one or more evaluation formulae including at least two explanatory variables to be substituted with the concentration values of at least two amino acids of the 19 kinds of amino acids (for example, any one of a logistic regression equation, a fractional expression, a linear discriminant, a multiple regression equation, a formula prepared by a support vector machine, a formula prepared by a Mahalanobis' generalized distance method, a formula prepared by canonical discriminant analysis, and a formula prepared by a decision tree) are transmitted to the pancreatic cancer-evaluating apparatus 100.

Then, the pancreatic cancer-evaluating apparatus 100 receives, in the receiving part 102*f*, the amino acid concentration data of the individual transmitted from the client apparatuses 200 and the evaluation formula transmitted from the database apparatus 400, and stores the received amino acid concentration data in a predetermined memory region of the amino acid concentration data file 106*b* and the received evaluation formula in a predetermined memory region of the evaluation formula file 106*e*4 (step SA23).

Then, the control device 102 in the pancreatic cancer-evaluating apparatus 100 removes data such as defective and outliers from the amino acid concentration data of the individual received in step SA23 (step SA24).

The evaluating part 102*i* then uses the amino acid concentration data of the individual from which the data such as defective and outliers has been removed in step SA24 and one or more evaluation formulae received in step SA23 to calculate one or more values of the evaluation formula(e) in the calculating part 102*i*1 (step SA25).

When the first formula and the second formula different from each other are received as evaluation formulae in step SA23, the evaluating part 102*i* may calculate the value of the first formula and the value of the second formula in the calculating part 102*i*1.

When the first formula for classifying a subject into one of the pancreatic cancer category and the healthy category and the second formula for classifying a subject into one of the pancreatic cancer category and the other cancer category are received in step SA23, the evaluating part 102*i* may first calculate the value of the first formula in the calculating part 102*i*1, and, if the classification result obtained in the classifying part 102*i*4 is the pancreatic cancer category, may calculate the value of the second formula.

The evaluating part 102*i* then executes any one of the classifications of 1. through 6. below using the value of the evaluation formula (evaluation value) calculated in step SA25 and the previously established threshold in the classifying part 102*i*4 and stores the obtained classification result into a predetermined storage area of the evaluation result file 106*f* (step SA26).

1. When a plurality of categories defined considering at least the degree of the possibility that a subject is affected with pancreatic cancer (the categories may include at least one category defined considering the degree of the possibility that a subject is affected with pancreatic cancer and the degree of the possibility that a subject is affected with a cancer other than pancreatic cancer), and one or more thresholds are previously established, the evaluating part 102*i* classifies the individual into any one of the categories using the evaluation value and the threshold(s) in the classifying part 102*i*4.

2. When the pancreatic cancer category and the pancreatic cancer-free category, and a threshold are previously established, the evaluating part 102*i* classifies the individual into one of the pancreatic cancer category and the pancreatic cancer-free category using the evaluation value and the threshold in the classifying part 102*i*4.

When the first formula and the second formula different from each other are received as evaluation formulae in step SA23, the evaluating part 102*i* may classify the individual into one of the pancreatic cancer category and the pancreatic cancer-free category, using the value of the first formula and the value of the second formula calculated in the calculating part 102*i*1, in the classifying part 102*i*4.

When the healthy category and the other cancer category are previously established as the pancreatic cancer-free category, and the first formula for classifying a subject into one of the pancreatic cancer category and the healthy category and the second formula for classifying a subject into one of the pancreatic cancer category and the other cancer category are received in step SA23, the evaluating part 102*i* may classify the individual into one of the pancreatic cancer category and the healthy category using the value of the first formula calculated in the calculating part 102*i*1 in the classifying part 102*i*4. If the classification result is the pancreatic cancer category, the evaluating part 102*i* may further classify the individual classified in the pancreatic cancer category using the value of the first formula into one of the pancreatic cancer category and the other cancer category using the value of the second formula calculated in the calculating part 102*i* in the classifying part 102*i*4. The evaluating part 102*i* may finally classify the individual classified in the healthy category and the individual classified in the other cancer category into the pancreatic cancer-free category in the classifying part 102*i*4. The individual classified into the pancreatic cancer category using the value of the first formula and classified into the pancreatic cancer category using the value of the second formula is finally classified into the pancreatic cancer category, as a matter of course.

3. When the pancreatic cancer category and the healthy category, and a threshold are previously established, the evaluating part 102*i* classifies the individual into one of the pancreatic cancer category and the healthy category, using the evaluation value and the threshold in the classifying part 102*i*4.

4. When the pancreatic cancer category and the other cancer category, and a threshold are previously established, the evaluating part 102*i* classifies the individual into one of the pancreatic cancer category and the other cancer category, using the evaluation value and the threshold in the classifying part 102*i*4.

5. When the pancreatic cancer category and the healthy/other cancer category, and a threshold are previously established, the evaluating part 102*i* classifies the individual into one of the pancreatic cancer category and the healthy/other cancer category, using the evaluation value and the threshold in the classifying part 102*i*4.

6. When the pancreatic cancer category, the healthy category, and the other cancer category, and a threshold are previously established, the evaluating part 102*i* classifies the individual into one of the pancreatic cancer category, the healthy category, and the other cancer category, using the evaluation values and the threshold in the classifying part 102*i*4.

When the first formula and the second formula different from each other are received as evaluation formulae in step SA23, the evaluating part 102*i* may classify the individual into one of the pancreatic cancer category, the healthy category, and the other cancer category, using the value of the first formula and the value of the second formula calculated in the calculating part 102*i*1, in the classifying part 102*i*4.

When the first formula for classifying a subject into one of the pancreatic cancer category and the healthy category and the second formula for classifying a subject into one of the pancreatic cancer category and the other cancer category are received in step SA23, the evaluating part 102*i* may classify the individual into one of the pancreatic cancer category and the healthy category using the value of the first formula calculated in the calculating part 102*i*1, in the classifying part 102*i*4. If the classification result is the pancreatic cancer category, the evaluating part 102*i* may further classify the individual classified in the pancreatic cancer category using the value of the first formula into one of the pancreatic cancer category and the other cancer category, using the value of the second formula calculated in the calculating part 102*i*, in the classifying part 102*i*4. The evaluating part 102*i* may finally classify the individual classified in the pancreatic cancer category using the value of the first formula and classified in the other cancer category using the value of the second formula, into the other cancer category, in the classifying part 102*i*4. The individual classified in the healthy category using the value of the first formula is finally classified into the healthy category, as a matter of course, and the individual classified in the pancreatic cancer category using the value of the first formula and classified in the pancreatic cancer category using the value of the second formula is finally classified into the pancreatic cancer category, as a matter of course.

Returning to the description of FIG. 20, the sending part 102*k* in the pancreatic cancer-evaluating apparatus 100 sends, to the client apparatus 200 that has sent the amino acid concentration data and to the database apparatus 400, the classification results obtained in step SA26 (step SA27). Specifically, the pancreatic cancer-evaluating apparatus 100 first generates a Web page for displaying the classification results in the Web page-generating part 102*e* and stores the Web data corresponding to the generated Web page in a predetermined memory region of the memory device 106. Then, the user is authenticated as described above by inputting a predetermined URL (Uniform Resource Locator) into the Web browser 211 of the client apparatus 200 via the input device 250, and the client apparatus 200 sends a Web page browsing request to the pancreatic cancer-evaluating apparatus 100. The pancreatic cancer-evaluating apparatus 100 then interprets the browsing request transmitted from the client apparatus 200 in the browsing processing part 102*b* and reads the Web data corresponding to the Web page for displaying the classification results, out of the predetermined memory region of the memory device 106. The sending part 102*k* in the pancreatic cancer-evaluating apparatus 100 then sends the read-out Web data to the client apparatus 200 and simultaneously sends the Web data or the classification results to the database apparatus 400.

In step SA27, the control device 102 in the pancreatic cancer-evaluating apparatus 100 may notify the classification results to the user client apparatus 200 by electronic mail. Specifically, the electronic mail-generating part 102*d* in the pancreatic cancer-evaluating apparatus 100 first acquires the user electronic mail address by referencing the user information stored in the user information file 106*a* based on the user ID and the like at the transmission timing. The electronic mail-generating part 102*d* in the pancreatic cancer-evaluating apparatus 100 then generates electronic mail data with the acquired electronic mail address as its mail address, including the user name and the classification results. The sending part 102*k* in the pancreatic cancer-evaluating apparatus 100 then sends the generated electronic mail data to the user client apparatus 200.

Also in step SA27, the pancreatic cancer-evaluating apparatus 100 may send the classification results to the user client apparatus 200 by using, for example, an existing file transfer technology such as FTP.

Returning to the description of FIG. 20, the control device 402 in the database apparatus 400 receives the classification results or the Web data transmitted from the pancreatic cancer-evaluating apparatus 100 and stores (accumulates) the received classification results or the received Web data in a predetermined memory region of the memory device 406 (step SA28).

The receiving part 213 of the client apparatus 200 receives the Web data transmitted from the pancreatic cancer-evaluating apparatus 100, and the received Web data is interpreted with the Web browser 211, to display on the monitor 261 the Web page screen displaying the classification results of the individual (step SA29). When the classification results are sent from the pancreatic cancer-evaluating apparatus 100 by electronic mail, the electronic mail transmitted from the pancreatic cancer-evaluating apparatus 100 is received at any timing, and the received electronic mail is displayed on the monitor 261 with the known function of the electronic mailer 212 in the client apparatus 200.

In this way, the user can confirm the classification results by browsing the Web page displayed on the monitor 261. The user may print out the content of the Web page displayed on the monitor 261 by the printer 262.

When the classification results are transmitted by electronic mail from the pancreatic cancer-evaluating apparatus 100, the user reads the electronic mail displayed on the monitor 261, whereby the user can confirm the classification results. The user may print out the content of the electronic mail displayed on the monitor 261 by the printer 262.

As described in detail above, the client apparatus 200 transmits the amino acid concentration data of the individual to the pancreatic cancer-evaluating apparatus 100. Upon receiving a request from the pancreatic cancer-evaluating apparatus 100, the database apparatus 400 transmits the evaluation formula to the pancreatic cancer-evaluating apparatus 100. The pancreatic cancer-evaluating apparatus 100 (i) receives the amino acid concentration data from the client apparatus 200 and receives the evaluation formula from the database apparatus 400, (ii) calculates the evaluation value using the received amino acid concentration data and evaluation formula, (iii) executes any one of the classifications 1. through 6. using the calculated evaluation value and the threshold, and (iv) transmits the obtained classification result to the client apparatus 200 and the database apparatus 400. The client apparatus 200 then receives and displays the classification result transmitted from the pancreatic cancer-evaluating apparatus 100. The database apparatus 400 receives and stores the classification result transmitted from the pancreatic cancer-evaluating apparatus 100.

Hence, reliable information that may be helpful in knowing the degree of the possibility of being affected with pancreatic cancer can be provided in easily understandable form. Reliable information that may be helpful in knowing not only the degree of the possibility of being affected with pancreatic cancer but also the degree of the possibility of being affected with a cancer other than pancreatic cancer can be provided in easily understandable form.

Reliable information that may be helpful in knowing whether the possibility of being affected with pancreatic cancer is high or low can be provided in easily understandable form.

Reliable information that may be helpful in knowing whether the possibility of being affected with pancreatic cancer is high or whether the possibility of being healthy is high can be provided in easily understandable form.

Reliable information that may be helpful in knowing whether the possibility of being affected with pancreatic cancer is high or whether the possibility of being affected with a cancer other than pancreatic cancer is high can be provided in easily understandable form.

Reliable information that may be helpful in knowing whether the possibility of being affected with pancreatic cancer is high or whether the possibility of being healthy or being affected with a cancer other than pancreatic cancer is high can be provided in easily understandable form.

Reliable information that may be helpful in knowing whether the possibility of being affected with pancreatic cancer is high, whether the possibility of being healthy is high, or whether the possibility of being affected with a cancer other than pancreatic cancer is high can be provided in easily understandable form.

Given the foregoing description, the explanation of the pancreatic cancer evaluation service processing is finished.

In the present description, the pancreatic cancer-evaluating apparatus 100 executes the reception of the amino acid concentration data, the calculation of the value of the evaluation formula, the classification of the individual into the category, and the transmission of the classification result, and the client apparatus 200 executes the reception of the classification result, by way of example. However, when the client apparatus 200 includes the evaluating part 210a, the pancreatic cancer-evaluating apparatus 100 only has to execute the calculation of the value of the evaluation formula, and, for example, the execution of conversion of the value of the evaluation formula, the generation of the positional information, and the classification of the individual into the category, and the like may be appropriately shared between the pancreatic cancer-evaluating apparatus 100 and the client apparatus 200.

For example, when the client apparatus 200 receives the value of the formula from the pancreatic cancer-evaluating apparatus 100, the evaluating part 210a may convert the value of the formula in the converting part 210a2, generate the positional information corresponding to the value of the formula or the converted value in the generating part 210a3, and classify the individual into any one of the plurality of categories using the value of the formula or the converted value in the classifying part 210a4.

When the client apparatus 200 receives the converted value from the pancreatic cancer-evaluating apparatus 100, the evaluating part 210a may generate the positional information corresponding to the converted value in the generating part 210a3 and classify the individual into one of the plurality of categories using the converted value in the classifying part 210a4.

When the client apparatus 200 receives the value of the formula or the converted value and the positional information from the pancreatic cancer-evaluating apparatus 100, the evaluating part 210a may classify the individual into one of the plurality of categories using the value of the formula or the converted value in the classifying part 210a4.

2-4. Other Embodiments

In addition to the second embodiment described above, the pancreatic cancer-evaluating apparatus, the pancreatic cancer-evaluating method, the pancreatic cancer-evaluating program product, the pancreatic cancer-evaluating system, and the information communication terminal apparatus according to the present invention can be practiced in various different embodiments within the technological scope of the claims.

Of the processings described in the second embodiment, all or a part of the processings described as automatically performed ones may be manually performed, or all or a part of the processings described as manually performed ones may be also automatically performed by known methods.

In addition, the processing procedures, the control procedures, the specific names, the information including parameters such as registered data of various processings and retrieval conditions, the screen examples, and the database configuration shown in the description and the drawings may be arbitrarily modified unless otherwise specified.

The components of the pancreatic cancer-evaluating apparatus 100 shown in the figures are functionally conceptual and therefore not be physically configured as shown in the figures.

For example, for the operational functions provided in the pancreatic cancer-evaluating apparatus 100, in particular, for the operational functions performed in the control device 102, all or part thereof may be implemented by a CPU (Central Processing Unit) and programs interpreted and executed in the CPU, or may be implemented by wired-logic hardware. The program is recorded in a non-transitory computer-readable recording medium including programmed instructions for making an information processing apparatus execute the pancreatic cancer-evaluating method according to the present invention, and is mechanically read as needed by the pancreatic cancer-evaluating apparatus 100. More specifically, computer programs to give instructions to the CPU in cooperation with an OS (operating system) to perform various processes are recorded in the memory device 106 such as ROM or a HDD (hard disk drive). The computer programs are executed by being loaded to RAM, and form the control unit in cooperation with the CPU.

The computer programs may be stored in an application program server connected to the pancreatic cancer-evaluating apparatus 100 via an arbitrary network, and all or part thereof can be downloaded as necessary.

The pancreatic cancer-evaluating program according to the present invention may be stored in the non-transitory computer-readable recording medium, or can be configured as a program product. The "recording medium" mentioned here includes any "portable physical medium" such as a memory card, a USB (universal serial bus) memory, an SD (secure digital) card, a flexible disk, a magneto-optical disc, ROM, EPROM (erasable programmable read only memory), EEPROM (electronically erasable and programmable read only memory), CD-ROM (compact disk read only memory), MO (magneto-optical disk), DVD (digital versatile disk), and a Blu-ray Disc.

The "program" mentioned here is a data processing method described in an arbitrary language or description method, and therefore any form such as a source code and a binary code is acceptable. The "program" is not necessarily limited to a program configured as a single unit, and, therefore, includes those dispersively configured as a plurality of modules and libraries and those in which the function of the program is achieved in cooperation with separate programs represented as OS (operating system). Any known configuration and procedures can be used as a specific configuration and reading procedure to read a recording medium by each apparatus shown in the embodiments or as an installation procedure after the reading, or the like.

The various databases and the like stored in the memory device 106 is a storage unit which is a memory device such as RAM and ROM, a fixed disk drive such as a hard disk, a flexible disk, and an optical disc, or the like. The memory device 106 stores therein various programs, tables, databases, files for Web (World Wide Web) pages, and the like used to perform various processes and to provide Web sites.

The pancreatic cancer-evaluating apparatus 100 may be configured as an information processing apparatus such as known personal computer and work station, or may be configured as the information processing apparatus connected to an arbitrary peripheral device. The pancreatic cancer-evaluating apparatus 100 may be provided by installing software (including the programs and the data, etc.) to cause the information processing apparatus to implement the pancreatic cancer-evaluating method according to the present invention.

Furthermore, a specific configuration of dispersion or integration of the apparatuses is not limited to the shown one. The apparatuses can be configured by functionally or physically dispersing or integrating all or part of the apparatuses in arbitrary units according to various types of additions or the like or according to functional loads. In other words, the embodiments may be implemented in arbitrary combinations thereof or an embodiment may be selectively implemented.

Figure 21:
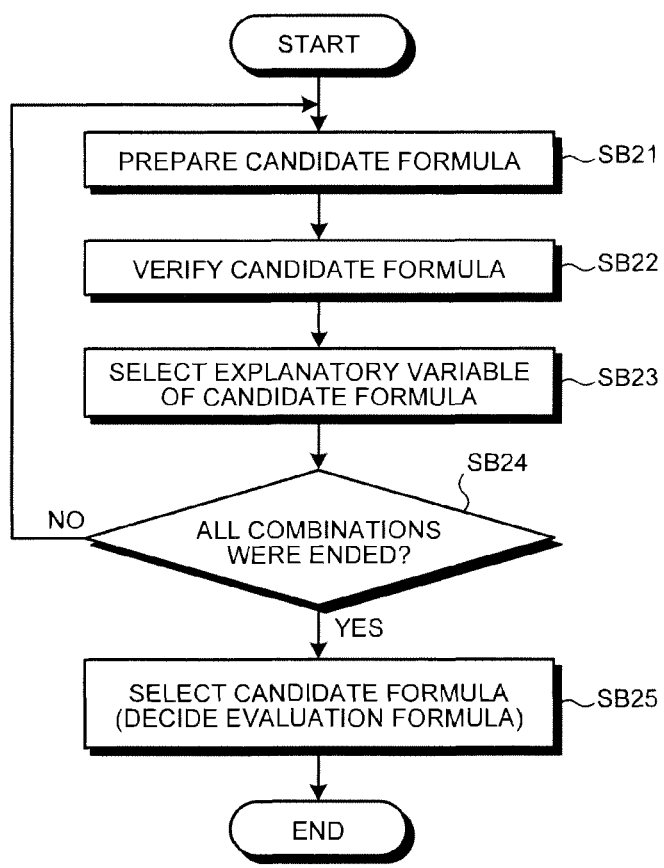
FIG. 21 is a flowchart showing an example of a evaluation formula-preparing processing performed in the pancreatic cancer-evaluating apparatus 100 in the present system.

Finally, an example of the evaluation formula-preparing processing performed in the pancreatic cancer-evaluating apparatus 100 is described in detail with reference to FIG. 21. The processing described below is merely one example, and the method of preparing evaluation formula is not limited thereto. FIG. 21 is a flowchart showing an example of the evaluation formula-preparing processing. The evaluation formula-preparing processing may be performed in the database apparatus 400 handling the pancreatic cancer state information.

In the present description, the pancreatic cancer-evaluating apparatus 100 stores the pancreatic cancer state information previously obtained from the database apparatus 400 in a predetermined memory region of the pancreatic cancer state information file 106c. The pancreatic cancer-evaluating apparatus 100 shall store, in a predetermined memory region of the designated pancreatic cancer state information file 106d, the pancreatic cancer state information including the pancreatic cancer state index data and the amino acid concentration data (the one including the concentration values of the 19 kinds of amino acids) designated previously in the pancreatic cancer state information-designating part 102g.

The candidate formula-preparing part 102h1 in the evaluation formula-preparing part 102h first prepares the candidate formulae based on a predetermined formula-preparing method from the pancreatic cancer state information stored in a predetermine memory region of the designated pancreatic cancer state information file 106d, and stores the prepared candidate formulae in a predetermined memory region of the candidate formula file 106e1 (step SB21). Specifically, the candidate formula-preparing part 102h1 in the evaluation formula-preparing part 102h first selects a desired method out of a plurality of different formula-preparing methods (including those for multivariate analysis such as principal component analysis, discriminant analysis, support vector machine, multiple regression analysis, logistic regression analysis, k-means method, cluster analysis, and decision tree) and determines the form of the candidate formula to be prepared (the form of formula) based on the selected formula-preparing method. The candidate formula-preparing part 102h1 in the evaluation formula-preparing part 102h then performs various calculation corresponding to the selected formula-selecting method (e.g., average or variance), based on the pancreatic cancer state information. The candidate formula-preparing part 102h1 in the evaluation formula-preparing part 102h then determines the parameters for the calculation result and the determined candidate formula. In this way, the candidate formula is generated based on the selected formula-preparing method. When the candidate formulae are generated simultaneously and concurrently (in parallel) by using a plurality of different formula-preparing methods in combination, the processings described above may be executed concurrently for each selected formula-preparing method. Alternatively when the candidate formulae are generated in series by using a plurality of different formula-preparing methods in combination, for example, the candidate formulae may be generated by converting the pancreatic cancer state information with the candidate formulae prepared by performing principal component analysis and performing discriminant analysis of the converted pancreatic cancer state information.

The candidate formula-verifying part 102h2 in the evaluation formula-preparing part 102h verifies (mutually verifies) the candidate formula prepared in step SB21 according to a particular verifying method and stores the verification result in a predetermined memory region of the verification result file 106e2 (step SB22). Specifically, the candidate formula-verifying part 102h2 in the evaluation formula-preparing part 102h first generates the verification data to be used in verification of the candidate formula, based on the pancreatic cancer state information stored in a predetermined memory region of the designated pancreatic cancer state information file 106d, and verifies the candidate formula according to the generated verification data. If a plurality of the candidate formulae is generated by using a plurality of different formula-preparing methods in step SB21, the candidate formula-verifying part 102h2 in the evaluation formula-preparing part 102h verifies each candidate formula corresponding to each formula-preparing method according to a particular verifying method. Here in step SB22, at least one of the discrimination rate, sensitivity, specificity, information criterion, ROC_AUC (area under the curve in a receiver operating characteristic curve), and the like of the candidate formula may be verified based on at least one method of the bootstrap method, holdout method, N-fold method, leave-one-out method, and the like. Thus, it is possible to select the candidate formula higher in predictability or reliability, by taking the pancreatic cancer state information and evaluation condition into consideration.

Then, the explanatory variable-selecting part 102h3 in the evaluation formula-preparing part 102h selects the combination of the amino acid concentration data contained in the pancreatic cancer state information used in preparing the candidate formula by selecting the explanatory variable of the candidate formula according to a predetermined explanatory variable-selecting method, and stores the pancreatic cancer state information including the selected combination of the amino acid concentration data in a predetermined memory region of the selected pancreatic cancer state information file 106e3 (step SB23). When a plurality of the candidate formulae is generated by using a plurality of different formula-preparing methods in step SB21 and each candidate formula corresponding to each formula-preparing method is verified according to a predetermined verifying method in step SB22, the explanatory variable-selecting part 102*h*3 in the evaluation formula-preparing part 102*h* may select the explanatory variable of the candidate formula for each candidate formula according to a predetermined explanatory variable-selecting method in step SB23. Here in step SB23, the explanatory variable of the candidate formula may be selected from the verification results according to at least one of the stepwise method, best path method, local search method, and genetic algorithm. The best path method is a method of selecting an explanatory variable by optimizing an evaluation index of the candidate formula while eliminating the explanatory variables contained in the candidate formula one by one. In step SB23, the explanatory variable-selecting part 102*h*3 in the evaluation formula-preparing part 102*h* may select the combination of the amino acid concentration data based on the pancreatic cancer state information stored in a predetermined memory region of the designated pancreatic cancer state information file 106*d*.

The evaluation formula-preparing part 102*h* then judges whether all combinations of the amino acid concentration data contained in the pancreatic cancer state information stored in a predetermined memory region of the designated pancreatic cancer state information file 106*d* are processed, and if the judgment result is "End" (Yes in step SB24), the processing advances to the next step (step SB25), and if the judgment result is not "End" (No in step SB24), it returns to step SB21. The evaluation formula-preparing part 102*h* may judge whether the processing is performed a predetermined number of times, and if the judgment result is "End" (Yes in step SB24), the processing may advance to the next step (step SB25), and if the judgment result is not "End" (No in step SB24), it may return to step SB21. The evaluation formula-preparing part 102*h* may judge whether the combination of the amino acid concentration data selected in step SB23 is the same as the combination of the amino acid concentration data contained in the pancreatic cancer state information stored in a predetermined memory region of the designated pancreatic cancer state information file 106*d* or the combination of the amino acid concentration data selected in the previous step SB23, and if the judgment result is "the same" (Yes in step SB24), the processing may advance to the next step (step SB25) and if the judgment result is not "the same" (No in step SB24), it may return to step SB21. If the verification result is specifically the evaluation value for each candidate formula, the evaluation formula-preparing part 102*h* may advance to step SB25 or return to step SB21, based on the comparison of the evaluation value with a particular threshold corresponding to each formula-preparing method.

Then, the evaluation formula-preparing part 102*h* determines the evaluation formula by selecting the candidate formula used as the evaluation formula based on the verification results from a plurality of the candidate formulae, and stores the determined formula (the selected candidate formula) in particular memory region of the evaluation formula file 106*e*4 (step SB25). Here, in step SB25, for example, there are cases where the optimal evaluation formula is selected from the candidate formulae prepared in the same formula-preparing method or the optimal evaluation formula is selected from all candidate formulae.

Given the foregoing description, the explanation of the evaluation formula-preparing processing is finished.

Example 1

In the present Example 1 and the following examples, data of the concentration values of amino acids (nmol/ml) in plasma measured using the amino acid analysis method from a blood sample in each of the groups below is used. Pancreatic cancer patients (51 people) with definite diagnosis of pancreatic cancer are divided into a pancreatic cancer group. Healthy individuals with no anamnesis or history of cancer are divided into a healthy group (255 people). The cancer patients with definite diagnosis of lung cancer, colorectal cancer, prostatic cancer, and breast cancer are divided into a lung cancer group (320 people), a colorectal cancer group (252 people), a prostatic cancer group (87 people), and a breast cancer group (121 people), respectively, and these four groups form the other cancers group (780 people).

The capability of discriminating between the pancreatic cancer group and the healthy group for each amino acid is evaluated with ROC_AUC (the area under the curve in a receiver operating characteristic curve). Amino acids with significant ROC_AUC (p<0.05) in examination with a null hypothesis of "ROC_AUC=0.5" under the assumption of non-parametric are Asn, His, Thr, Ala, Cit, Arg, Tyr, Val, Met, Lys, and Trp. These amino acids significantly decreased in the pancreatic cancer group. The concentration values of these amino acids are thought to be useful in evaluation of the state of pancreatic cancer with consideration of the healthy state, because ROC_AUC is significant.

Example 2

The sample data used in Example 1 is used. A multivariate discriminant (multivariate function) including an explanatory variable to be substituted with the concentration value of an amino acid in plasma is obtained for discriminating between two groups: the pancreatic cancer group and the healthy group. As for the obtained multivariate discriminant, the capability of discriminating between the pancreatic cancer group and the other cancers group, between the pancreatic cancer group and the lung cancer group, between the pancreatic cancer group and the colorectal cancer group, between the pancreatic cancer group and the prostatic cancer group, and between the pancreatic cancer group and the breast cancer group is also shown.

A logistic regression equation is used as a multivariate discriminant. The 19 kinds of amino acids (specifically, Asn, His, Thr, Ala, Cit, Arg, Tyr, Val, Met, Lys, Trp, Gly, Pro, Orn, Ile, Leu, Phe, Ser, and Gln) are searched for a combination of six or less explanatory variables to be included in the logistic regression equation. The Leave-One-Out method is employed as validation to explore a logistic regression equation having a good capability of discriminating between the pancreatic cancer group and the healthy group.

List of Logistic Regression Equations Searched in Example 2 (ROC_AUC value: 0.500 or greater) provided later shows (i) a list of logistic regression equations with two explanatory variables where the ROC_AUC value for the pancreatic cancer group and the healthy group with validation is equal to or greater than 0.500, (ii) a list of logistic regression equations with three explanatory variables where the ROC_AUC value for the pancreatic cancer group and the healthy group with validation is equal to or greater than 0.500, (iii) a list of logistic regression equations with four explanatory variables where the ROC_AUC value for the pancreatic cancer group and the healthy group with validation is equal to or greater than 0.500, (iv) a list of logistic regression equations with five explanatory variables where the ROC_AUC value for the pancreatic cancer group and the healthy group with validation is equal to or greater than 0.500, and (v) a list of logistic regression equations with six explanatory variables where the ROC_AUC value for the pancreatic cancer group and the healthy group with validation is equal to or greater than 0.500. These logistic regression equations are thought to be useful in the evaluation because the ROC_AUC value is high.

The logistic regression equations where the ROC_AUC value for the pancreatic cancer group and the healthy group with validation is equal to or greater than 0.750 are shown later in List (1) of Logistic Regression Equations Searched in Example 2. These logistic regression equations are thought to be useful in the evaluation because the ROC_AUC value is extremely high. When the amino acid explanatory variables included in these logistic regression equations are listed in the descending order of occurrence frequency from the highest to the tenth, they are arranged in the following order: Met, Phe, Trp, Ile, Ser, Val, His, Thr, Asn, Ala (see Table 1 below). These amino acids are thought to be useful in the evaluation as with the equations because they are explanatory variables included in the equations thought to be useful in the evaluation. For these logistic regression equations, the average value of the ROC_AUC values for the pancreatic cancer group and the lung cancer group, for the pancreatic cancer group and the colorectal cancer group, for the pancreatic cancer group and the prostatic cancer group, and for the pancreatic cancer group and the breast cancer group is equal to or greater than 0.775, and the capability of discriminating between the pancreatic cancer group and a variety of other cancer groups is good. These logistic regression equations are thought to be useful in evaluation of the state of pancreatic cancer with additional consideration of the state of cancers other than pancreatic cancer, because the ROC_AUC value is extremely high. Among these logistic regression equations, for example, the index formula 1 "(−1.3217)+(0.0545)Ser+(−0.0544)Val+(−0.3973)Met+(0.1922)Ile+(0.1506)Phe+(−0.1179)Trp" having a set of explanatory variables "Ser, Val, Met, Ile, Phe, Trp" (the multivariate discriminant including Ser, Val, Met, Ile, Phe, Trp as explanatory variables) has a good discriminating capability with ROC_AUC(Validation)=0.902, ROC_AUC(No Validation)=0.923, sensitivity=0.902, specificity=0.804. The sensitivity and the specificity are the values when the maximum discriminate point, where the average of sensitivity and specificity is highest, is a

TABLE 1

Pancreatic cancer group vs Healthy group

| Amino acid | Univariate | Logistic regression equation | | Linear discriminant | |
|---|---|---|---|---|---|
| | | Healthy group | Average of other cancers | Healthy group | Average of other cancers |
| Ser | | 66 | | 70 | |
| Asn | O | 13 | 75 | 23 | 79 |
| Gly | | | | | |
| Gln | | | 100 | | 98 |
| His | O | 45 | 24 | 46 | 28 |
| Thr | O | 38 | | 38 | |
| Ala | O | 11 | 36 | | 33 |
| Cit | O | | 52 | 10 | 58 |
| Arg | O | | | | |
| Pro | | | | | |
| Tyr | O | | 23 | | |
| Val | O | 54 | 23 | 47 | 28 |
| Met | O | 90 | 46 | 81 | 38 |
| Orn | | | | | |
| Lys | O | | | | 17 |
| Ile | | 66 | | 61 | 17 |
| Leu | | | | | |
| Phe | | 79 | 48 | 90 | 45 |
| Trp | O | 75 | 100 | 71 | 100 |

(O indicates the amino acid that varies significantly. The numeral indicates the frequency of occurrence of the amino acid explanatory variable.)

The value of the formula is calculated using the index formula 1 and the amino acid concentration values (µmol/L) of the pancreatic cancer group, and each case in the pancreatic cancer group is classified into any one of a plurality of categories established as shown below, using the calculated value of the formula and a previously established cutoff value. As candidates for the cutoff value, the value of the formula when the specificity is 80% and the value of the formula when the specificity is 95% are found to be −2.002 and −0.528, respectively. When these values are set as cutoff values, the sensitivities are 86% and 71%, respectively.

The amino acid concentration values of a case having the highest value of the formula are Ser: 166.3, Val: 149.9, Met: 18.5, Ile: 69.0, Phe: 44.1, Trp: 33.6, and the value of the formula in this case is 8.2. The relational expression "logarithm odds $\ln(p/(1-p))$=value of formula" (where p is the probability of cancer) is defined, and the odds $p/(1-p)$, calculated from the value 8.2 of this formula, are 3508.0. The probability p, calculated from the odds, is 1.0.

When the value −0.528 of the formula when the specificity is 95% is established as a cutoff value, and when the value of the formula higher than the cutoff value is defined positive (equivalent to the pancreatic cancer category), and when the value of the formula lower than the cutoff value is defined negative (equivalent to the healthy category), then the case in which the value of the formula is 8.2 is classified either as positive or as negative. This case is classified as positive because the value of the formula is higher than the cutoff value.

When the value −2.002 of the formula when the specificity is 80% is established as a first cutoff value, and the value −0.528 of the formula when the specificity is 95% is established as a second cutoff value, and when the value of the formula lower than the first cutoff value is defined rank A (the category meaning that the possibility (probability, risk) of pancreatic cancer is low), when the value of the formula higher than the first cutoff value and lower than the second cutoff value is defined rank B (the category that means the possibility of having pancreatic cancer is moderate), and when the value of the formula higher than the second cutoff value is defined rank C (the category meaning that the possibility of pancreatic cancer is high), then the case in which the value of the formula is 8.2 is classified into any one of the three ranks. This case is classified into the rank C because the value of the formula is higher than the second cutoff value.

A linear discriminant is used as a multivariate discriminant. The 19 kinds of amino acids are searched for a combination of six or less explanatory variables to be included in the linear discriminant, and the bootstrap method is employed as validation to explore a linear discriminant with a good capability of discriminating between the pancreatic cancer group and the healthy group.

A list of linear discriminants where the ROC_AUC value for the pancreatic cancer group and the healthy group with validation is equal to or greater than 0.750 is shown later in List (1) of Linear Discriminants Searched in Example 2. These linear discriminants are thought to be useful in evaluation of the state of pancreatic cancer with consideration of the healthy state, because the ROC_AUC value is extremely high. When the amino acid explanatory variables included in these linear discriminants are listed in the descending order of occurrence frequency from the highest to the tenth, they are arranged in the following order: Phe, Met, Trp, Ser, Ile, Val, His, Thr, Asn, Cit (see Table 1 above). The concentration values of these amino acids are thought to be useful in the evaluation as with the formula, because they are explanatory variables included in the formula thought to be useful in the evaluation. As for these linear discriminants, the average value of the ROC_AUC values for the pancreatic cancer group and the lung cancer group, for the pancreatic cancer group and the colorectal cancer group, for the pancreatic cancer group and the prostatic cancer group, and for the pancreatic cancer group and the breast cancer group is equal to or greater than 0.762, and the capability of discriminating between the pancreatic cancer group and a variety of other cancer groups is good. These linear discriminants are thought to be useful in evaluation of the state of pancreatic cancer with additional consideration of the state of cancers other than pancreatic cancer, because the ROC_AUC value is extremely high. Among these linear discriminants, for example, the index formula 2 "(−1.0207)+(0.0564)Ser+(−0.0410)Val+(−0.4144)Met+(0.1407)Ile+(0.1786)Phe+(−0.1154)Trp" having a set of explanatory variables "Ser, Val, Met, Ile, Phe, Trp" (the multivariate discriminant including Ser, Val, Met, Ile, Phe, Trp as explanatory variables) has a good discriminating capability with ROC_AUC(Validation)=0.912, ROC_AUC(No Validation)=0.926, sensitivity=0.800, and specificity=0.902. The sensitivity and the specificity are the values when the maximum discriminate point, where the average of sensitivity and specificity is the highest, is a cutoff value.

The value of the formula is calculated using the index formula 2 and the amino acid concentration values (μmol/L) of the pancreatic cancer group, and each case in the pancreatic cancer group is classified into any one of a plurality of categories established as shown below, using the calculated value of the formula and a previously established cutoff value. As candidates for the cutoff value, the value of the formula when the specificity is 80% and the value of the formula when the specificity is 95% are found to be −0.434 and 1.093, respectively. When these values are set as cutoff values, the sensitivities are 90% and 69%, respectively.

The amino acid concentration values in a case having the highest value of the formula are Ser: 166.3, Val: 149.9, Met: 18.5, Ile: 69.0, Phe: 44.1, Trp: 33.6, and the value of the formula in this case is 8.2.

When the value 1.093 of the formula when the specificity is 95% is established as a cutoff value, and when the value of the formula higher than the cutoff value is defined positive, and when the value of the formula lower than the cutoff value is defined negative, then the case in which the value of the formula is 8.2 is classified either as positive or negative. This case is classified as positive because the value of the formula is higher than the cutoff value.

In addition, when the value −0.434 of the formula when the specificity is 80% is established as a first cutoff value, and the value 1.093 of the formula when the specificity is 95% is established as a second cutoff value, and when the value of the formula lower than the first cutoff value is defined rank A, when the value of the formula higher than the first cutoff value and lower than the second cutoff value is defined rank B, and when the value of the formula higher than the second cutoff value is defined rank C, then the case in which the value of the formula is 8.2 is classified into any one of the three ranks. This case is classified into rank C because the value of the formula is higher than the second cutoff value.

List (2) of Logistic Regression Equations Searched in Example 2 provided later shows a list of logistic regression equations in which the ROC_AUC value for the pancreatic cancer group and the healthy group with validation is equal to or greater than 0.750 and the capability of discriminating between the pancreatic cancer group and a variety of other cancer groups is also good. These logistic regression equations are thought to be useful in evaluation of the state of pancreatic cancer with consideration of both the healthy state and the state of cancers other than pancreatic cancer, because the ROC_AUC value is extremely high. When the amino acid explanatory variables included in these logistic regression equations are listed in the descending order of occurrence frequency from the highest to the tenth, they are arranged in the following order: Trp, Gln, Asn, Cit, Phe, Met, Ala, His, Val, Tyr (see Table 1 above). The concentration values of these amino acids are thought to be useful in the evaluation as with the formula because they are explanatory variables included in the formula thought to be useful in the evaluation. Among these logistic regression equations, for example, the index formula 3 "(2.2508)+(0.0135)Gln+(−0.1156)His+(−0.0544)Cit+(−0.1821)Met+(0.1518)Phe+(−0.1151)Trp" having a set of explanatory variables "Gln, His, Cit, Met, Phe, Trp" (the multivariate discriminant including Gln, His, Cit, Met, Phe, Trp as explanatory variables) has a good discriminating capability with ROC_AUC (Validation)=0.862, ROC_AUC(No Validation)=0.894, sensitivity=0.831, and specificity=0.843. The sensitivity and the specificity are the values when the maximum discriminate point, where the average of sensitivity and specificity is the highest, is a cutoff value.

The value of the formula is calculated using the index formula 3 and the amino acid concentration values (μmol/L) of the pancreatic cancer group, and each case in the pancreatic cancer group is classified into any one of a plurality of categories established as shown below, using the calculated value of the formula and a previously established cutoff value. As candidates for the cutoff value, the value of the formula when the specificity is 80% and the value of the formula when the specificity is 95% are found to be −1.659 and −0.288, respectively. When these values are set as cutoff values, the sensitivities are 84% and 57%, respectively.

The amino acid concentration values of a case having the highest value of the formula are Gln: 484.6, His: 32.4, Cit: 17.7, Met: 18.4, Phe: 56.6, Trp: 30.4, and the value of the formula in this case is 5.8. The odds, calculated from the value 5.8 of this formula, are 341.5. The probability p, calculated from the odds, is 1.0.

When the value −0.288 of the formula when the specificity is 95% is established as a cutoff value, and when the value of the formula higher than the cutoff value is defined positive, and when the value of the formula lower than the cutoff value is defined negative, then the case in which the value of the formula is 5.8 is classified either as positive or negative. This case is classified into a positive because the value of the formula is higher than the cutoff value.

When classifying each case either as positive or negative using the amino acid concentration values of the other cancers group when the value −1.659 of the formula when the specificity is 80% is established as a cutoff value and when the value −0.288 of the formula when the specificity is 95% is established as a cutoff value, then the false positive rates for the other cancers group are 24% and 10%, respectively. These values are lower than the false positive rates of 40% and 22% for the other cancers group when the index formula 1 is used. The index formula 3 is therefore useful in evaluation of the state of pancreatic cancer with consideration of both the healthy state and the state of cancers other than pancreatic cancer.

When the value −1.659 of the formula when the specificity is 80% is established as a first cutoff value, and the value −0.288 of the formula when the specificity is 95% is established as a second cutoff value, and when the value of the formula lower than the first cutoff value is defined rank A, when the value of the formula higher than the first cutoff value and lower than the second cutoff value is defined rank B, and when the value of the formula higher than the second cutoff value is defined rank C, then the case in which the value of the formula is 5.8 is classified into any one of the three ranks. This case is classified into the rank C because the value of the formula is higher than the second cutoff value.

List (2) of Linear Discriminants Searched in Example 2 provided later shows a list of linear discriminants in which the ROC_AUC value for the pancreatic cancer group and the healthy group with validation is equal to or greater than 0.750 and the capability of discriminating between the pancreatic cancer group and a variety of other cancer groups is also good. These linear discriminants are thought to be useful in evaluation of the state of pancreatic cancer with consideration of both the healthy state and the state of cancers other than pancreatic cancer, because the ROC_AUC value is extremely high. When the amino acid explanatory variables included in these linear discriminants are listed in the descending order of occurrence frequency from the highest to the tenth, they are arranged in the following order: Trp, Gln, Asn, Cit, Phe, Met, Ala, Val, His, Ile, Lys, in total eleven (see Table 1 above). The concentration values of these amino acids are thought to be useful in the evaluation as with the formula because they are explanatory variables included in the formula thought to be useful in the evaluation. Among these linear discriminants, for example, the index formula 4 "(2.6773)+(0.0131)Gln+(−0.0833)His+(−0.0369)Cit+(−0.1942)Met+(0.1325)Phe+(−0.1189)Trp" having a set of explanatory variables "Gln, His, Cit, Met, Phe, Trp" (the multivariate discriminant including Gln, His, Cit, Met, Phe, Trp as explanatory variables) has a good discriminating capability with ROC_AUC(Validation)=0.876, ROC_AUC(No Validation)=0.897, sensitivity=0.831, specificity=0.804. The sensitivity and the specificity are the values when the maximum discriminate point, where the average of sensitivity and specificity is the highest, is a cutoff value.

The value of the formula is calculated using the index formula 4 and the amino acid concentration values (μmol/L) of the pancreatic cancer group, and each case in the pancreatic cancer group is classified into any one of a plurality of categories established as shown below, using the calculated value of the formula and a previously established cutoff value. As candidates for the cutoff value, the value of the formula when the specificity is 80% and the value of the formula when the specificity is 95% are found to be −0.092 and 1.103, respectively. When these values are set as cutoff values, the sensitivities are 80% and 55%, respectively.

The amino acid concentration values of a case with the highest value of the formula are Gln: 484.6, His: 32.4, Cit: 17.7, Met: 18.4, Phe: 56.6, Trp: 30.4, and the value of the formula in this case is 6.0.

When the value 1.103 of the formula when the specificity is 95% is established as a cutoff value, and when the value of the formula higher than the cutoff value is defined positive, and when the value of the formula lower than the cutoff value is defined negative, then the case in which the value of the formula is 6.0 is classified either as positive or negative. This case is classified as positive because the value of the formula is higher than the cutoff value.

When each case is classified either as positive or negative using the amino acid concentration values of the other cancers group when the value −0.092 of the formula when the specificity is 80% is established as a cutoff value and when the value 1.103 of the formula when the specificity is 95% is established as a cutoff value, then the false positive rates for the other cancers group are 23% and 10%, respectively. These values are lower than the false positive rates of 40% and 20% for the other cancers group when the index formula 2 is used. The index formula 4 is therefore useful in evaluation of the state of pancreatic cancer with consideration of both the healthy state and the state of cancers other than pancreatic cancer.

When the value −0.092 of the formula when the specificity is 80% is established as a first cutoff value, and the value 1.103 of the formula when the specificity is 95% is established as a second cutoff value, and when the value of the formula lower than the first cutoff value is defined rank A, when the value of the formula higher than the first cutoff value and lower than the second cutoff value is defined rank B, and when the value of the formula higher than the second cutoff value is defined rank C, then the case in which the value of the formula is 6.0 is classified into any one of the three ranks. This case is classified into the rank C because the value of the formula is higher than the second cutoff value.

Example 3

The sample data used in Example 1 is used. The capability of discriminating between the pancreatic cancer group and the other cancers group for each amino acid is evaluated with ROC_AUC. Amino acids with significant ROC_AUC ($p<0.05$) in examination with a null hypothesis of "ROC_AUC=0.5" under the assumption of non-parametric are Asn, Gly, His, Thr, Ala, Cit, Arg, Pro, Tyr, Val, Met, Orn, Lys, Ile, Leu, Phe, and Trp. These amino acids significantly decreased in the pancreatic cancer group. The concentration values of these amino acids are thought to be useful in evaluation of the state of pancreatic cancer with consideration of the state of cancers other than pancreatic cancer, because ROC_AUC is significant.

The capability of discriminating between the pancreatic cancer group and the lung cancer group for each amino acid is evaluated with ROC_AUC. Amino acids with significant ROC_AUC ($p<0.05$) in examination with a null hypothesis of "ROC_AUC=0.5" under the assumption of non-parametric are Ser, Asn, Gly, His, Thr, Ala, Cit, Arg, Pro, Tyr, Val, Met, Orn, Lys, Ile, Leu, Phe, and Trp. These amino acids significantly decreased in the pancreatic cancer group. The concentration values of these amino acids are thought to be useful in evaluation of the state of pancreatic cancer with consideration of the state of lung cancer, because ROC_AUC is significant.

The capability of discriminating between the pancreatic cancer group and the colorectal cancer group for each amino acid is evaluated with ROC_AUC. Amino acids with significant ROC_AUC (p<0.05) in examination with a null hypothesis of "ROC_AUC=0.5" under the assumption of non-parametric are Asn, Gly, Gln, His, Thr, Ala, Cit, Arg, Pro, Tyr, Val, Met, Lys, Ile, Leu, Phe, and Trp. These amino acids significantly decreased in the pancreatic cancer group. The concentration values of these amino acids are thought to be useful in evaluation of the state of pancreatic cancer with consideration of the state of colorectal cancer, because ROC_AUC is significant.

The capability of discriminating between the pancreatic cancer group and the prostatic cancer group for each amino acid is evaluated with ROC_AUC. Amino acids with significant ROC_AUC (p<0.05) in examination with a null hypothesis of "ROC_AUC=0.5" under the assumption of non-parametric are Asn, His, Thr, Ala, Cit, Arg, Pro, Tyr, Val, Met, Lys, Leu, Phe, and Trp. These amino acids significantly decreased in the pancreatic cancer group. The concentration values of these amino acids are thought to be useful in evaluation of the state of pancreatic cancer with consideration of the state of prostatic cancer, because ROC_AUC is significant.

The capability of discriminating between the pancreatic cancer group and the breast cancer group for each amino acid is evaluated with ROC_AUC. Amino acids with significant ROC_AUC (p<0.05) in examination with a null hypothesis of "ROC_AUC=0.5" under the assumption of non-parametric are Ser, Asn, Gly, His, Thr, Ala, Val, Met, Lys, Ile, and Trp. These amino acids significantly decreased in the pancreatic cancer group. The concentration values of these amino acids are thought to be useful in evaluation of the state of pancreatic cancer with consideration of the state of breast cancer, because ROC_AUC is significant.

Example 4

The sample data used in Example 1 is used. A multivariate discriminant (multivariate function) including an explanatory variable to be substituted with the concentration value of an amino acid in plasma is obtained for discriminating between two groups: the pancreatic cancer group and the other cancers group. As for the obtained multivariate discriminant, the capability of discriminating between the pancreatic cancer group and the healthy group is also shown.

A logistic regression equation is used as a multivariate discriminant. The 19 kinds of amino acids are searched for a combination of six or less explanatory variables to be included in the logistic regression equation. The Leave-One-Out method is employed as validation to explore a logistic regression equation having a good capability of discriminating between the pancreatic cancer group and the other cancers group.

The logistic regression equations where the ROC_AUC value for the pancreatic cancer group and the other cancers group with validation is equal to or greater than 0.750 are shown later in List (1) of Logistic Regression Equations Searched in Example 4. These logistic regression equations are thought to be useful in evaluation of the state of pancreatic cancer with consideration of the state of cancers other than pancreatic cancer because the ROC_AUC value is extremely high. When the amino acid explanatory variables included in these logistic regression equations are listed in the descending order of occurrence frequency from the highest to the tenth, they are arranged in the following order: Trp, Gln, Asn, Cit, Ala, Phe, Gly, Val, Met, Pro (see Table 2 below). These amino acids are thought to be useful in the evaluation as with the equations because they are explanatory variables included in the equations thought to be useful in the evaluation. For these logistic regression equations, the ROC_AUC value for the pancreatic cancer group and the healthy group is equal to or greater than 0.760, and the capability of discriminating between the pancreatic cancer group and the healthy group is good. These logistic regression equations are thought to be useful in evaluation of the state of pancreatic cancer with additional consideration of the healthy state, because the ROC_AUC value is extremely high. Among these logistic regression equations, for example, the index formula 5 "(1.7072)+(−0.0985)Asn+(0.0115)Gln+(−0.0063)Ala+(−0.0582)Cit+(0.0212)Phe+(−0.0792)Trp" having a set of explanatory variables "Asn, Gln, Ala, Cit, Phe, Trp" (the multivariate discriminant including Asn, Gln, Ala, Cit, Phe, Trp as explanatory variables) has a good discriminating capability with ROC_AUC (Validation)=0.854, ROC_AUC(No Validation)=0.873, sensitivity=0.740, specificity=0.882. The sensitivity and the specificity are the values when the maximum discriminate point, where the average of sensitivity and specificity is highest, is a

TABLE 2

Pancreatic cancer group vs Other cancers group

| Amino acid | Univariate | Logistic regression equation | | Linear discriminant | |
|---|---|---|---|---|---|
| | | Other cancers group | Healthy group | Other cancers group | Healthy group |
| Ser | | | | | 47 |
| Asn | O | 95 | 20 | 97 | 31 |
| Gly | O | 32 | | 41 | |
| Gln | | 100 | 84 | 100 | 38 |
| His | O | | 80 | | 61 |
| Thr | O | | | | |
| Ala | O | 39 | | 41 | |
| Cit | O | 54 | 27 | 48 | 23 |
| Arg | O | | | | |
| Pro | O | 18 | | 18 | |
| Tyr | O | | | | |
| Val | O | 29 | 26 | 27 | 20 |
| Met | O | 18 | 41 | 22 | 73 |
| Orn | O | | | | |
| Lys | O | | | | |
| Ile | O | | 37 | | 26 |
| Leu | O | | 23 | | |
| Phe | O | 37 | 78 | 36 | 99 |
| Trp | O | 100 | 100 | 100 | 99 |

(O indicates the amino acid that varies significantly. The numeral indicates the frequency of occurrence of the amino acid explanatory variable.)

The value of the formula is calculated using the index formula 5 and the amino acid concentration values (μmol/L) of the pancreatic cancer group, and each case in the pancreatic cancer group is classified into any one of a plurality of categories established as shown below, using the calculated value of the formula and a previously established cutoff value. As candidates for the cutoff value, the value of the formula when the specificity is 80% and the value of the formula when the specificity is 95% are found to be −2.650 and −1.316, respectively. When these values are set as cutoff values, the sensitivities are 76% and 39%, respectively.

The amino acid concentration values of a case having the highest value of the formula are Asn: 35.2, Gln: 697.3, Ala: 249.3, Cit: 26.0, Phe: 44.1, Trp: 33.6, and the value of the formula in this case is 1.5. The odds, calculated from the value 1.5 of this formula, are 4.3. The probability p, calculated from the odds, is 0.8.

When the value −1.316 of the formula when the specificity is 95% is established as a cutoff value, and when the value of the formula higher than the cutoff value is defined positive (equivalent to the pancreatic cancer category), and when the value of the formula lower than the cutoff value is defined negative (equivalent to the other cancer category), then the case in which the value of the formula is 1.5 is classified either as positive or as negative. This case is classified as positive because the value of the formula is higher than the cutoff value.

When the value −2.650 of the formula when the specificity is 80% is established as a first cutoff value, and the value −1.316 of the formula when the specificity is 95% is established as a second cutoff value, and when the value of the formula lower than the first cutoff value is defined rank A (the category meaning that the possibility of pancreatic cancer is low and the possibility of a cancer other than pancreatic cancer is high), when the value of the formula higher than the first cutoff value and lower than the second cutoff value is defined rank B (the category that means both the possibility of having pancreatic cancer and the possibility of having a cancer other than pancreatic cancer are moderate), and when the value of the formula higher than the second cutoff value is defined rank C (the category meaning that the possibility of pancreatic cancer is high and the possibility of a cancer other than pancreatic cancer is low), then the case in which the value of the formula is 1.5 is classified into any one of the three ranks. This case is classified into the rank C because the value of the formula is higher than the second cutoff value.

A linear discriminant is used as a multivariate discriminant. The 19 kinds of amino acids are searched for a combination of six or less explanatory variables to be included in the linear discriminant, and the bootstrap method is employed as validation to explore a linear discriminant with a good capability of discriminating between the pancreatic cancer group and the other cancers group.

A list of linear discriminants where the ROC_AUC value for the pancreatic cancer group and the other cancers group with validation is equal to or greater than 0.750 is shown later in List (1) of Linear Discriminants Searched in Example 4. These linear discriminants are thought to be useful in evaluation of the state of pancreatic cancer with consideration of the state of cancers other than pancreatic cancer, because the ROC_AUC value is extremely high. When the amino acid explanatory variables included in these linear discriminants are listed in the descending order of occurrence frequency from the highest to the tenth, they are arranged in the following order: Trp, Gln, Asn, Cit, Gly, Ala, Phe, Val, Met, Pro (see Table 2 above). The concentration values of these amino acids are thought to be useful in the evaluation as with the formula, because they are explanatory variables included in the formula thought to be useful in the evaluation. As for these linear discriminants, the ROC_AUC value for the pancreatic cancer group and the healthy group is equal to or greater than 0.784, and the capability of discriminating between the pancreatic cancer group and the healthy group is good. These linear discriminants are thought to be useful in evaluation of the state of pancreatic cancer with additional consideration of the healthy state, because the ROC_AUC value is extremely high. Among these linear discriminants, for example, the index formula 6 "(5.4468)+(−0.1111)Asn+(0.0122)Gln+(−0.0083)Ala+(−0.0524)Cit+(0.0345)Phe+(−0.1015)Trp" having a set of explanatory variables "Asn, Gln, Ala, Cit, Phe, Trp" (the multivariate discriminant including Asn, Gln, Ala, Cit, Phe, Trp as explanatory variables) has a good discriminating capability with ROC_AUC(Validation)=0.859, ROC_AUC (No Validation)=0.874, sensitivity=0.742, and specificity=0.902. The sensitivity and the specificity are the values when the maximum discriminate point, where the average of sensitivity and specificity is the highest, is a cutoff value.

The value of the formula is calculated using the index formula 6 and the amino acid concentration values (μmol/L) of the pancreatic cancer group, and each case in the pancreatic cancer group is classified into any one of a plurality of categories established as shown below, using the calculated value of the formula and a previously established cutoff value. As candidates for the cutoff value, the value of the formula when the specificity is 80% and the value of the formula when the specificity is 95% are found to be 0.109 and 1.780, respectively. When these values are set as cutoff values, the sensitivities are 73% and 37%, respectively.

The amino acid concentration values in a case having the highest value of the formula are Asn: 35.2, Gln: 697.3, Ala: 249.3, Cit: 26.0, Phe: 44.1, Trp: 33.6, and the value of the formula in this case is 4.7.

When the value 1.780 of the formula when the specificity is 95% is established as a cutoff value, and when the value of the formula higher than the cutoff value is defined positive, and when the value of the formula lower than the cutoff value is defined negative, then the case in which the value of the formula is 4.7 is classified either as positive or negative. This case is classified as positive because the value of the formula is higher than the cutoff value.

In addition, when the value 0.109 of the formula when the specificity is 80% is established as a first cutoff value, and the value 1.780 of the formula when the specificity is 95% is established as a second cutoff value, and when the value of the formula lower than the first cutoff value is defined rank A, when the value of the formula higher than the first cutoff value and lower than the second cutoff value is defined rank B, and when the value of the formula higher than the second cutoff value is defined rank C, then the case in which the value of the formula is 4.7 is classified into any one of the three ranks. This case is classified into rank C because the value of the formula is higher than the second cutoff value.

List (2) of Logistic Regression Equations Searched in Example 4 provided later shows a list of logistic regression equations in which the ROC_AUC value for the pancreatic cancer group and the other cancers group with validation is equal to or greater than 0.750 and the capability of discriminating between the pancreatic cancer group and the healthy group is also good. These logistic regression equations are thought to be useful in evaluation of the state of pancreatic cancer with consideration of both the healthy state and the state of cancers other than pancreatic cancer, because the ROC_AUC value is extremely high. When the amino acid explanatory variables included in these logistic regression equations are listed in the descending order of occurrence frequency from the highest to the tenth, they are arranged in the following order: Trp, Gln, His, Phe, Met, Ile, Cit, Val, Leu, Asn (see Table 2 above). The concentration values of these amino acids are thought to be useful in the evaluation as with the formula because they are explanatory variables included in the formula thought to be useful in the evaluation. Among these logistic regression equations, for example, the index formula 7 "(0.8883)+(0.0101)Gln+(−0.0453)His+(−0.1983)Met+(0.0032)Ile+(0.0304)Phe+(−0.0647)Trp" having a set of explanatory variables "Gln, His, Met, Ile, Phe, Trp" (the multivariate discriminant including Gln, His, Met, Ile, Phe, Trp as explanatory variables) has a good discriminating capability with ROC_AUC(Validation)=0.832, ROC_AUC(No Validation)= 0.854, sensitivity=0.690, and specificity=0.902. The sensitivity and the specificity are the values when the maximum discriminate point, where the average of sensitivity and specificity is the highest, is a cutoff value.

The value of the formula is calculated using the index formula 7 and the amino acid concentration values (μmol/L) of the pancreatic cancer group, and each case in the pancreatic cancer group is classified into any one of a plurality of categories established as shown below, using the calculated value of the formula and a previously established cutoff value. As candidates for the cutoff value, the value of the formula when the specificity is 80% and the value of the formula when the specificity is 95% are found to be −2.626 and −1.306, respectively. When these values are set as cutoff values, the sensitivities are 75% and 43%, respectively.

The amino acid concentration values of a case having the highest value of the formula are Gln: 697.3, His: 54.0, Met: 18.5, Ile: 69.0, Phe: 44.1, Trp: 33.6, and the value of the formula in this case is 1.2. The odds, calculated from the value 1.2 of this formula, are 3.3. The probability p, calculated from the odds, is 0.8.

When the value −1.306 of the formula when the specificity is 95% is established as a cutoff value, and when the value of the formula higher than the cutoff value is defined positive, and when the value of the formula lower than the cutoff value is defined negative, then the case in which the value of the formula is 1.2 is classified either as positive or negative. This case is classified into a positive because the value of the formula is higher than the cutoff value.

When classifying each case either as positive or negative using the amino acid concentration values of the healthy group when the value −2.626 of the formula when the specificity is 80% is established as a cutoff value and when the value −1.306 of the formula when the specificity is 95% is established as a cutoff value, then the false positive rates for the healthy group are 22% and 2%, respectively. These values are lower than the false positive rates of 28% and 5% for the healthy group when the index formula 5 is used. The index formula 7 is therefore useful in evaluation of the state of pancreatic cancer with consideration of both the healthy state and the state of cancers other than pancreatic cancer.

When the value −2.626 of the formula when the specificity is 80% is established as a first cutoff value, and the value −1.306 of the formula when the specificity is 95% is established as a second cutoff value, and when the value of the formula lower than the first cutoff value is defined rank A, when the value of the formula higher than the first cutoff value and lower than the second cutoff value is defined rank B, and when the value of the formula higher than the second cutoff value is defined rank C, then the case in which the value of the formula is 1.2 is classified into any one of the three ranks. This case is classified into the rank C because the value of the formula is higher than the second cutoff value.

List (2) of Linear Discriminants Searched in Example 4 provided later shows a list of linear discriminants in which the ROC_AUC value for the pancreatic cancer group and the other cancers group with validation is equal to or greater than 0.750 and the capability of discriminating between the pancreatic cancer group and the healthy group is also good.

These linear discriminants are thought to be useful in evaluation of the state of pancreatic cancer with consideration of both the healthy state and the state of cancers other than pancreatic cancer, because the ROC_AUC value is extremely high. When the amino acid explanatory variables included in these linear discriminants are listed in the descending order of occurrence frequency from the highest to the tenth, they are arranged in the following order: Trp, Phe, Met, His, Ser, Gln, Asn, Ile, Cit, Val (see Table 2 above). The concentration values of these amino acids are thought to be useful in the evaluation as with the formula because they are explanatory variables included in the formula thought to be useful in the evaluation. Among these linear discriminants, for example, the index formula 8 "(5.7313)+(0.0114)Ser+(−0.0226)Val+(−0.2232)Met+(0.0489)Ile+(0.0676)Phe+(−0.0795)Trp" having a set of explanatory variables "Ser, Val, Met, Ile, Phe, Trp" (the multivariate discriminant including Ser, Val, Met, Ile, Phe, Trp as explanatory variables) has a good discriminating capability with ROC_AUC(Validation)=0.833, ROC_AUC (No Validation)=0.849, sensitivity=0.837, specificity=0.784. The sensitivity and the specificity are the values when the maximum discriminate point, where the average of sensitivity and specificity is the highest, is a cutoff value.

The value of the formula is calculated using the index formula 8 and the amino acid concentration values (μmol/L) of the pancreatic cancer group, and each case in the pancreatic cancer group is classified into any one of a plurality of categories established as shown below, using the calculated value of the formula and a previously established cutoff value. As candidates for the cutoff value, the value of the formula when the specificity is 80% and the value of the formula when the specificity is 95% are found to be 0.019 and 1.739, respectively. When these values are set as cutoff values, the sensitivities are 78% and 31%, respectively.

The amino acid concentration values of a case with the highest value of the formula are Ser: 166.3, Gln: 697.3, Asn: 35.2, Ile: 69.0, Cit: 26.0, Val: 149.9, and the value of the formula in this case is 3.8.

When the value 1.739 of the formula when the specificity is 95% is established as a cutoff value, and when the value of the formula higher than the cutoff value is defined positive, and when the value of the formula lower than the cutoff value is defined negative, then the case in which the value of the formula is 3.8 is classified either as positive or negative. This case is classified as positive because the value of the formula is higher than the cutoff value.

When each case is classified either as positive or negative using the amino acid concentration values of the healthy group when the value 0.019 of the formula when the specificity is 80% is established as a cutoff value and when the value 1.739 of the formula when the specificity is 95% is established as a cutoff value, then the false positive rates for the healthy group are 17% and 1%, respectively. These values are lower than the false positive rates of 28% and 4% for the healthy group when the index formula 6 is used. The index formula 8 is therefore useful in evaluation of the state of pancreatic cancer with consideration of both the healthy state and the state of cancers other than pancreatic cancer.

When the value 0.019 of the formula when the specificity is 80% is established as a first cutoff value, and the value 1.739 of the formula when the specificity is 95% is established as a second cutoff value, and when the value of the formula lower than the first cutoff value is defined rank A, when the value of the formula higher than the first cutoff value and lower than the second cutoff value is defined rank B, and when the value of the formula higher than the second cutoff value is defined rank C, then the case in which the value of the formula is 3.8 is classified into any one of the three ranks. This case is classified into the rank C because the value of the formula is higher than the second cutoff value.

Example 5

The sample data used in Example 1 is used. A multivariate discriminant (multivariate function) including an explanatory variable to be substituted with the concentration value of an amino acid in plasma is obtained for discriminating between two groups: the pancreatic cancer group and the lung cancer group.

A logistic regression equation is used as a multivariate discriminant. The 19 kinds of amino acids are searched for a combination of six or less explanatory variables to be included in the logistic regression equation. The Leave-One-Out method is employed as validation to explore a logistic regression equation having a good capability of discriminating between the pancreatic cancer group and the lung cancer group.

The logistic regression equations where the ROC_AUC value for the pancreatic cancer group and the lung cancer group with validation is equal to or greater than 0.750 are shown later in List (1) of Logistic Regression Equations Searched in Example 5. These logistic regression equations are thought to be useful in evaluation of the state of pancreatic cancer with consideration of the state of lung cancer because the ROC_AUC value is extremely high. When the amino acid explanatory variables included in these logistic regression equations are listed in the descending order of occurrence frequency from the highest to the tenth, they are arranged in the following order: Gln, Asn, Trp, Val, Ala, Phe, Cit, Arg, Pro, Leu (see Table 3 below). These amino acids are thought to be useful in the evaluation as with the equations because they are explanatory variables included in the equations thought to be useful in the evaluation. For these logistic regression equations, the ROC_AUC value for the pancreatic cancer group and the healthy group is equal to or greater than 0.725, and the capability of discriminating between the pancreatic cancer group and the healthy group is good. These logistic regression equations are thought to be useful in evaluation of the state of pancreatic cancer with additional consideration of the healthy state, because the ROC_AUC value is extremely high. Among these logistic regression equations, for example, the index formula 9 "(2.5017)+(−0.1544)Asn+(0.0144)Gln+(−0.0136)Pro+(−0.0179)Val+(0.0647)Phe+(−0.0751)Trp" having a set of explanatory variables "Asn, Gln, Pro, Val, Phe, Trp" (the multivariate discriminant including Asn, Gln, Pro, Val, Phe, Trp as explanatory variables) has a good discriminating capability with ROC_AUC(Validation)=0.879, ROC_AUC(No Validation)=0.901, sensitivity=0.831, specificity=0.902. The sensitivity and the specificity are the values when the maximum discriminate point, where the average of sensitivity and specificity is highest, is a cutoff value.

TABLE 3

Pancreatic cancer group vs Lung cancer group

| Amino acid | Univariate | Logistic regression equation | | Linear discriminant | |
|---|---|---|---|---|---|
| | | Lung cancer group | Healthy group | Lung cancer group | Healthy group |
| Ser | O | | 44 | | 66 |
| Asn | O | 97 | 40 | 92 | 40 |
| Gly | O | | | | |
| Gln | | 100 | 43 | 100 | 32 |
| His | O | | 35 | | 38 |
| Thr | O | | | | |
| Ala | O | 46 | | 50 | |
| Cit | O | 23 | 42 | 18 | 29 |
| Arg | O | 22 | 12 | | |
| Pro | O | 21 | | 25 | |
| Tyr | O | | | | 14 |
| Val | O | 67 | | 65 | |
| Met | O | | 66 | 19 | 73 |
| Orn | O | | | | |
| Lys | O | | 16 | | 15 |
| Ile | O | | 12 | | |
| Leu | O | 15 | | 22 | |
| Phe | O | 31 | 98 | 28 | 98 |
| Trp | O | 96 | 100 | 98 | 100 |

(O indicates the amino acid that varies significantly. The numeral indicates the frequency of occurrence of the amino acid explanatory variable.)

The value of the formula can be calculated using the index formula 9 as with Example 4, and each case can be classified using the calculated value of the formula and a previously established cutoff value as with Example 4.

A linear discriminant is used as a multivariate discriminant. The 19 kinds of amino acids are searched for a combination of six or less explanatory variables to be included in the linear discriminant, and the bootstrap method is employed as validation to explore a linear discriminant with a good capability of discriminating between the pancreatic cancer group and the lung cancer group.

A list of linear discriminants where the ROC_AUC value for the pancreatic cancer group and the lung cancer group with validation is equal to or greater than 0.750 is shown later in List (1) of Linear Discriminants Searched in Example 5. These linear discriminants are thought to be useful in evaluation of the state of pancreatic cancer with consideration of the state of lung cancer, because the ROC_AUC value is extremely high. When the amino acid explanatory variables included in these linear discriminants are listed in the descending order of occurrence frequency from the highest to the tenth, they are arranged in the following order: Gln, Trp, Asn, Val, Ala, Phe, Pro, Leu, Met, Cit (see Table 3 above). The concentration values of these amino acids are thought to be useful in the evaluation as with the formula, because they are explanatory variables included in the formula thought to be useful in the evaluation. As for these linear discriminants, the ROC_AUC value for the pancreatic cancer group and the healthy group is equal to or greater than 0.727, and the capability of discriminating between the pancreatic cancer group and the healthy group is good. These linear discriminants are thought to be useful in evaluation of the state of pancreatic cancer with additional consideration of the healthy state, because the ROC_AUC value is extremely high. Among these linear discriminants, for example, the index formula 10 "(5.6262)+(−0.1579)Asn+(0.0147)Gln+(−0.0133)Pro+(−0.0175)Val+(0.0680)Phe+(−0.1047)Trp" having a set of explanatory variables "Asn, Gln, Pro, Val, Phe, Trp" (the multivariate discriminant including Asn, Gln, Pro, Val, Phe, Trp as explanatory variables) has a good discriminating capability with ROC_AUC(Validation)=0.889, ROC_AUC(No Validation)=0.900, sensitivity=0.828, and specificity=0.882. The sensitivity and the specificity are the values when the maximum discriminate point, where the average of sensitivity and specificity is the highest, is a cutoff value.

The value of the formula can be calculated using the index formula 10 as with Example 4, and each case can be classified using the calculated value of the formula and a previously established cutoff value as with Example 4.

List (2) of Logistic Regression Equations Searched in Example 5 provided later shows a list of logistic regression equations in which the ROC_AUC value for the pancreatic cancer group and the lung cancer group with validation is equal to or greater than 0.750 and the capability of discriminating between the pancreatic cancer group and the healthy group is also good. These logistic regression equations are thought to be useful in evaluation of the state of pancreatic cancer with consideration of both the healthy state and the state of lung cancer, because the ROC_AUC value is extremely high. When the amino acid explanatory variables included in these logistic regression equations are listed in the descending order of occurrence frequency from the highest to the tenth, they are arranged in the following order: Trp, Phe, Met, Ser, Gln, Cit, Asn, His, Lys, Ile, Arg, in total eleven (see Table 3 above). The concentration values of these amino acids are thought to be useful in the evaluation as with the formula because they are explanatory variables included in the formula thought to be useful in the evaluation. Among these logistic regression equations, for example, the index formula 11 "(0.7428)+(−0.0948)Asn+(0.0147)Gln+(−0.0250)His+(−0.1901)Met+(0.0579)Phe+(−0.0741)Trp" having a set of explanatory variables "Asn, Gln, His, Met, Phe, Trp" (the multivariate discriminant including Asn, Gln, His, Met, Phe, Trp as explanatory variables) has a good discriminating capability with ROC_AUC(Validation)=0.858, ROC_AUC(No Validation)=0.882, sensitivity=0.747, and specificity=0.902. The sensitivity and the specificity are the values when the maximum discriminate point, where the average of sensitivity and specificity is the highest, is a cutoff value.

The value of the formula can be calculated using the index formula 11 as with Example 4, and each case can be classified using the calculated value of the formula and a previously established cutoff value as with Example 4.

List (2) of Linear Discriminants Searched in Example 5 provided later shows a list of linear discriminants in which the ROC_AUC value for the pancreatic cancer group and the lung cancer group with validation is equal to or greater than 0.750 and the capability of discriminating between the pancreatic cancer group and the healthy group is also good. These linear discriminants are thought to be useful in evaluation of the state of pancreatic cancer with consideration of both the healthy state and the state of lung cancer, because the ROC_AUC value is extremely high. When the amino acid explanatory variables included in these linear discriminants are listed in the descending order of occurrence frequency from the highest to the tenth, they are arranged in the following order: Trp, Phe, Met, Ser, Asn, His, Gln, Cit, Lys, Tyr (see Table 3 above). The concentration values of these amino acids are thought to be useful in the evaluation as with the formula because they are explanatory variables included in the formula thought to be useful in the evaluation. Among these linear discriminants, for example, the index formula 12 "(6.6327)+(0.0159)Ser+(−0.0688)Asn+(−0.0166)Cit+(−0.1442)Met+(0.0618)Phe+(−0.0996)Trp" having a set of explanatory variables "Ser, Asn, Cit, Met, Phe, Trp" (the multivariate discriminant including Ser, Asn, Cit, Met, Phe, Trp as explanatory variables) has a good discriminating capability with ROC_AUC (Validation)=0.841, ROC_AUC(No Validation)=0.858, sensitivity=0.825, specificity=0.804. The sensitivity and the specificity are the values when the maximum discriminate point, where the average of sensitivity and specificity is the highest, is a cutoff value.

The value of the formula can be calculated using the index formula 12 as with Example 4, and each case can be classified using the calculated value of the formula and a previously established cutoff value as with Example 4.

Example 6

The sample data used in Example 1 is used. A multivariate discriminant (multivariate function) including an explanatory variable to be substituted with the concentration value of an amino acid in plasma is obtained for discriminating between two groups: the pancreatic cancer group and the colorectal cancer group.

A logistic regression equation is used as a multivariate discriminant. The 19 kinds of amino acids are searched for a combination of six or less explanatory variables to be included in the logistic regression equation. The Leave-One-Out method is employed as validation to explore a logistic regression equation having a good capability of discriminating between the pancreatic cancer group and the colorectal cancer group.

The logistic regression equations where the ROC_AUC value for the pancreatic cancer group and the colorectal cancer group with validation is equal to or greater than 0.750 are shown later in List (1) of Logistic Regression Equations Searched in Example 6. These logistic regression equations are thought to be useful in evaluation of the state of pancreatic cancer with consideration of the state of colorectal cancer because the ROC_AUC value is extremely high. When the amino acid explanatory variables included in these logistic regression equations are listed in the descending order of occurrence frequency from the highest to the tenth, they are arranged in the following order: Trp, Cit, Tyr, Met, Asn, Orn, Gln, Pro, Ala, Gly (see Table 4 below). These amino acids are thought to be useful in the evaluation as with the equations because they are explanatory variables included in the equations thought to be useful in the evaluation. For these logistic regression equations, the ROC_AUC value for the pancreatic cancer group and the healthy group is equal to or greater than 0.803, and the capability of discriminating between the pancreatic cancer group and the healthy group is good. These logistic regression equations are thought to be useful in evaluation of the state of pancreatic cancer with additional consideration of the healthy state, because the ROC_AUC value is extremely high. Among these logistic regression equations, for example, the index formula 13 "(5.6692)+(−0.0719)Asn+(0.0072)Gln+(−0.0715)Cit+(0.0674)Tyr+(−0.1878)Met+(−0.1103)Trp" having a set of explanatory variables "Asn, Gln, Cit, Tyr, Met, Trp" (the multivariate discriminant including Asn, Gln, Cit, Tyr, Met, Trp as explanatory variables) has a good discriminating capability with ROC_AUC(Validation)=0.851, ROC_AUC(No Validation)=0.874, sensitivity=0.889, specificity=0.804. The sensitivity and the specificity are the values when the maximum discriminate point, where the average of sensitivity and specificity is highest, is a

TABLE 4

Pancreatic cancer group vs Colorectal cancer group

| Amino acid | Univariate | Logistic regression equation | | Linear discriminant | |
|---|---|---|---|---|---|
| | | Colorectal cancer group | Healthy group | Colorectal cancer group | Healthy group |
| Ser | | | | 12 | 37 |
| Asn | O | 43 | 32 | 41 | 21 |
| Gly | O | 14 | | 13 | |
| Gln | O | 24 | 83 | 33 | 42 |
| His | O | | 89 | | 61 |
| Thr | O | | 22 | 12 | 40 |
| Ala | O | 14 | | | |
| Cit | O | 100 | 19 | 97 | 25 |
| Arg | O | | | | |
| Pro | O | 16 | | | |
| Tyr | O | 99 | | 96 | |
| Val | O | | | | |
| Met | O | 70 | 39 | 75 | 82 |
| Orn | | 27 | 19 | 21 | |
| Lys | O | | | | |
| Ile | O | | | | 16 |
| Leu | O | | 22 | | |
| Phe | O | | 77 | 20 | 97 |
| Trp | O | 100 | 100 | 100 | 100 |

(O indicates the amino acid that varies significantly. The numeral indicates the frequency of occurrence of the amino acid explanatory variable.)

The value of the formula can be calculated using the index formula 13 as with Example 4, and each case can be classified using the calculated value of the formula and a previously established cutoff value as with Example 4.

A linear discriminant is used as a multivariate discriminant. The 19 kinds of amino acids are searched for a combination of six or less explanatory variables to be included in the linear discriminant, and the bootstrap method is employed as validation to explore a linear discriminant with a good capability of discriminating between the pancreatic cancer group and the colorectal cancer group.

A list of linear discriminants where the ROC_AUC value for the pancreatic cancer group and the colorectal cancer group with validation is equal to or greater than 0.750 is shown later in List (1) of Linear Discriminants Searched in Example 6. These linear discriminants are thought to be useful in evaluation of the state of pancreatic cancer with consideration of the state of colorectal cancer, because the ROC_AUC value is extremely high. When the amino acid explanatory variables included in these linear discriminants are listed in the descending order of occurrence frequency from the highest to the tenth, they are arranged in the following order: Trp, Cit, Tyr, Met, Asn, Gln, Orn, Phe, Gly, Thr, Ser, in total eleven (see Table 4 above). The concentration values of these amino acids are thought to be useful in the evaluation as with the formula, because they are explanatory variables included in the formula thought to be useful in the evaluation. As for these linear discriminants, the ROC_AUC value for the pancreatic cancer group and the healthy group is equal to or greater than 0.793, and the capability of discriminating between the pancreatic cancer group and the healthy group is good. These linear discriminants are thought to be useful in evaluation of the state of pancreatic cancer with additional consideration of the healthy state, because the ROC_AUC value is extremely high. Among these linear discriminants, for example, the index formula 14 "(6.7413)+(−0.0941)Asn+(0.0093)Gln+(−0.0666)Cit+(0.0561)Tyr+(−0.1268)Met+(−0.1224)Trp" having a set of explanatory variables "Asn, Gln, Cit, Tyr, Met, Trp" (the multivariate discriminant including Asn, Gln, Cit, Tyr, Met, Trp as explanatory variables) has a good discriminating capability with ROC_AUC(Validation)=0.862, ROC_AUC(No Validation)=0.876, sensitivity=0.861, and specificity=0.824. The sensitivity and the specificity are the values when the maximum discriminate point, where the average of sensitivity and specificity is the highest, is a cutoff value.

The value of the formula can be calculated using the index formula 14 as with Example 4, and each case can be classified using the calculated value of the formula and a previously established cutoff value as with Example 4.

List (2) of Logistic Regression Equations Searched in Example 6 provided later shows a list of logistic regression equations in which the ROC_AUC value for the pancreatic cancer group and the colorectal cancer group with validation is equal to or greater than 0.750 and the capability of discriminating between the pancreatic cancer group and the healthy group is also good. These logistic regression equations are thought to be useful in evaluation of the state of pancreatic cancer with consideration of both the healthy state and the state of colorectal cancer, because the ROC_AUC value is extremely high. When the amino acid explanatory variables included in these logistic regression equations are listed in the descending order of occurrence frequency from the highest to the tenth, they are arranged in the following order: Trp, His, Gln, Phe, Met, Asn, Leu, Thr, Cit, Orn (see Table 4 above). The concentration values of these amino acids are thought to be useful in the evaluation as with the formula because they are explanatory variables included in the formula thought to be useful in the evaluation. Among these logistic regression equations, for example, the index formula 15 "(4.0457)+(0.0070)Gln+(−0.0515)His+(0.0059)Thr+(−0.1935)Met+(0.0373)Phe+(−0.0815)Trp" having a set of explanatory variables "Gln, His, Thr, Met, Phe, Trp" (the multivariate discriminant including Gln, His, Thr, Met, Phe, Trp as explanatory variables) has a good discriminating capability with ROC_AUC(Validation)=0.822, ROC_AUC(No Validation)=0.849, sensitivity=0.762, and specificity=0.843. The sensitivity and the specificity are the values when the maximum discriminate point, where the average of sensitivity and specificity is the highest, is a cutoff value.

The value of the formula can be calculated using the index formula 15 as with Example 4, and each case can be classified using the calculated value of the formula and a previously established cutoff value as with Example 4.

List (2) of Linear Discriminants Searched in Example 6 provided later shows a list of linear discriminants in which the ROC_AUC value for the pancreatic cancer group and the colorectal cancer group with validation is equal to or greater than 0.750 and the capability of discriminating between the pancreatic cancer group and the healthy group is also good. These linear discriminants are thought to be useful in evaluation of the state of pancreatic cancer with consideration of both the healthy state and the state of colorectal cancer, because the ROC_AUC value is extremely high. When the amino acid explanatory variables included in these linear discriminants are listed in the descending order of occurrence frequency from the highest to the tenth, they are arranged in the following order: Trp, Phe, Met, His, Gln, Thr, Ser, Cit, Asn, Ile (see Table 4 above). The concentration values of these amino acids are thought to be useful in the evaluation as with the formula because they are explanatory variables included in the formula thought to be useful in the evaluation. Among these linear discriminants, for example, the index formula 16 "(4.7750)+(0.0066)Gln+(−0.0466)

His+(0.0084)Thr+(−0.1967)Met+(0.0666)Phe+(−0.1057) Trp" having a set of explanatory variables "Gln, His, Thr, Met, Phe, Trp" (the multivariate discriminant including Gln, His, Thr, Met, Phe, Trp as explanatory variables) has a good discriminating capability with ROC_AUC(Validation)=0.835, ROC_AUC(No Validation)=0.856, sensitivity=0.730, specificity=0.882. The sensitivity and the specificity are the values when the maximum discriminate point, where the average of sensitivity and specificity is the highest, is a cutoff value.

The value of the formula can be calculated using the index formula 16 as with Example 4, and each case can be classified using the calculated value of the formula and a previously established cutoff value as with Example 4.

Example 7

Among the sample data used in Example 1, only the sample data of males is used. A multivariate discriminant (multivariate function) including an explanatory variable to be substituted with the concentration value of an amino acid in plasma is obtained for discriminating between two groups: the pancreatic cancer group and the prostatic cancer group.

A logistic regression equation is used as a multivariate discriminant. The 19 kinds of amino acids are searched for a combination of six or less explanatory variables to be included in the logistic regression equation. The Leave-One-Out method is employed as validation to explore a logistic regression equation having a good capability of discriminating between the pancreatic cancer group and the prostatic cancer group.

The logistic regression equations where the ROC_AUC value for the pancreatic cancer group and the prostatic cancer group with validation is equal to or greater than 0.750 are shown later in List (1) of Logistic Regression Equations Searched in Example 7. These logistic regression equations are thought to be useful in evaluation of the state of pancreatic cancer with consideration of the state of prostatic cancer because the ROC_AUC value is extremely high. When the amino acid explanatory variables included in these logistic regression equations are listed in the descending order of occurrence frequency from the highest to the tenth, they are arranged in the following order: Ile, Val, Ala, Ser, Met, Cit, Gln, Asn, Pro, Thr (see Table 5 below). These amino acids are thought to be useful in the evaluation as with the equations because they are explanatory variables included in the equations thought to be useful in the evaluation. For these logistic regression equations, the ROC_AUC value for the pancreatic cancer group and the healthy group is equal to or greater than 0.816, and the capability of discriminating between the pancreatic cancer group and the healthy group is good. These logistic regression equations are thought to be useful in evaluation of the state of pancreatic cancer with additional consideration of the healthy state, because the ROC_AUC value is extremely high. Among these logistic regression equations, for example, the index formula 17 "(3.0499)+(0.0406)Ser+(−0.0121)Ala+(−0.0402)Val+(−0.1789)Met+(0.1361)Ile" having a set of explanatory variables "Ser, Ala, Val, Met, Ile" (the multivariate discriminant including Ser, Ala, Val, Met, Ile as explanatory variables) has a good discriminating capability with ROC_AUC(Validation)=0.877, ROC_AUC (No Validation)=0.907, sensitivity=0.828, specificity=0.903. The sensitivity and the specificity are the values when the maximum discriminate point, where the average of sensitivity and specificity is highest, is a cutoff value.

TABLE 5

Pancreatic cancer group vs Prostatic cancer group

| Amino acid | Univariate | Logistic regression equation | | Linear discriminant | |
|---|---|---|---|---|---|
| | | Prostatic cancer group | Healthy group | Prostatic cancer group | Healthy group |
| Ser | | 61 | 100 | | 99 |
| Asn | O | 23 | | 15 | |
| Gly | | | | | |
| Gln | | 33 | | 20 | |
| His | O | | | | |
| Thr | O | 17 | 30 | | 15 |
| Ala | O | 81 | | 92 | |
| Cit | O | 41 | | 21 | |
| Arg | O | | 15 | 8 | 15 |
| Pro | O | 17 | | 25 | |
| Tyr | O | | 14 | 8 | 15 |
| Val | O | 91 | 45 | 96 | 32 |
| Met | O | 54 | 100 | 41 | 100 |
| Orn | | | | | 14 |
| Lys | O | | 19 | | |
| Ile | | 100 | 81 | 100 | 35 |
| Leu | O | | | 9 | 14 |
| Phe | O | | 43 | | 93 |
| Trp | O | | 65 | | 86 |

(O indicates the amino acid that varies significantly. The numeral indicates the frequency of occurrence of the amino acid explanatory variable.)

The value of the formula can be calculated using the index formula 17 as with Example 4, and each case can be classified using the calculated value of the formula and a previously established cutoff value as with Example 4.

A linear discriminant is used as a multivariate discriminant. The 19 kinds of amino acids are searched for a combination of six or less explanatory variables to be included in the linear discriminant, and the bootstrap method is employed as validation to explore a linear discriminant with a good capability of discriminating between the pancreatic cancer group and the prostatic cancer group.

A list of linear discriminants where the ROC_AUC value for the pancreatic cancer group and the prostatic cancer group with validation is equal to or greater than 0.750 is shown later in List (1) of Linear Discriminants Searched in Example 7. These linear discriminants are thought to be useful in evaluation of the state of pancreatic cancer with consideration of the state of prostatic cancer, because the ROC_AUC value is extremely high. When the amino acid explanatory variables included in these linear discriminants are listed in the descending order of occurrence frequency from the highest to the tenth, they are arranged in the following order: Ile, Val, Ala, Met, Pro, Cit, Gln, Asn, Leu, Arg, Tyr, in total eleven (see Table 5 above). The concentration values of these amino acids are thought to be useful in the evaluation as with the formula, because they are explanatory variables included in the formula thought to be useful in the evaluation. As for these linear discriminants, the ROC_AUC value for the pancreatic cancer group and the healthy group is equal to or greater than 0.818, and the capability of discriminating between the pancreatic cancer group and the healthy group is good. These linear discriminants are thought to be useful in evaluation of the state of pancreatic cancer with additional consideration of the healthy state, because the ROC_AUC value is extremely high. Among these linear discriminants, for example, the index formula 18 "(5.0859)+(0.0109)Gln+(−0.0171)Ala+(−0.0452)Cit+(−0.0389)Val+(−0.1548)Met+(0.1284)Ile"

having a set of explanatory variables "Gln, Ala, Cit, Val, Met, Ile" (the multivariate discriminant including Gln, Ala, Cit, Val, Met, Ile as explanatory variables) has a good discriminating capability with ROC_AUC(Validation)=0.889, ROC_AUC(No Validation)=0.914, sensitivity=0.862, and specificity=0.871. The sensitivity and the specificity are the values when the maximum discriminate point, where the average of sensitivity and specificity is the highest, is a cutoff value.

The value of the formula can be calculated using the index formula 18 as with Example 4, and each case can be classified using the calculated value of the formula and a previously established cutoff value as with Example 4.

List (2) of Logistic Regression Equations Searched in Example 7 provided later shows a list of logistic regression equations in which the ROC_AUC value for the pancreatic cancer group and the prostatic cancer group with validation is equal to or greater than 0.750 and the capability of discriminating between the pancreatic cancer group and the healthy group is also good. These logistic regression equations are thought to be useful in evaluation of the state of pancreatic cancer with consideration of both the healthy state and the state of prostatic cancer, because the ROC_AUC value is extremely high. When the amino acid explanatory variables included in these logistic regression equations are listed in the descending order of occurrence frequency from the highest to the tenth, they are arranged in the following order: Met, Ser, Ile, Trp, Val, Phe, Thr, Lys, Arg, Tyr (see Table 5 above). The concentration values of these amino acids are thought to be useful in the evaluation as with the formula because they are explanatory variables included in the formula thought to be useful in the evaluation. Among these logistic regression equations, for example, the index formula 19 "(−0.4061)+(0.0399)Ser+(−0.2141)Met+(0.1298)Ile+(−0.0658)Leu+(0.0402)Phe+(−0.0539)Trp" having a set of explanatory variables "Ser, Met, Ile, Leu, Phe, Trp" (the multivariate discriminant including Ser, Met, Ile, Leu, Phe, Trp as explanatory variables) has a good discriminating capability with ROC_AUC(Validation)=0.787, ROC_AUC(No Validation)=0.856, sensitivity=0.851, and specificity=0.774. The sensitivity and the specificity are the values when the maximum discriminate point, where the average of sensitivity and specificity is the highest, is a cutoff value.

The value of the formula can be calculated using the index formula 19 as with Example 4, and each case can be classified using the calculated value of the formula and a previously established cutoff value as with Example 4.

List (2) of Linear Discriminants Searched in Example 7 provided later shows a list of linear discriminants in which the ROC_AUC value for the pancreatic cancer group and the prostatic cancer group with validation is equal to or greater than 0.750 and the capability of discriminating between the pancreatic cancer group and the healthy group is also good. These linear discriminants are thought to be useful in evaluation of the state of pancreatic cancer with consideration of both the healthy state and the state of prostatic cancer, because the ROC_AUC value is extremely high. When the amino acid explanatory variables included in these linear discriminants are listed in the descending order of occurrence frequency from the highest to the tenth, they are arranged in the following order: Met, Ser, Phe, Trp, Ile, Val, Tyr, Arg, Thr, Orn, Leu, in total eleven (see Table 5 above). The concentration values of these amino acids are thought to be useful in the evaluation as with the formula because they are explanatory variables included in the formula thought to be useful in the evaluation. Among these linear discriminants, for example, the index formula 20 "(1.6394)+(0.0387)Ser+(−0.0455)Val+(−0.2545)Met+(0.1283)Ile+(0.0546)Phe+(−0.0299)Trp" having a set of explanatory variables "Ser, Val, Met, Ile, Phe, Trp" (the multivariate discriminant including Ser, Val, Met, Ile, Phe, Trp as explanatory variables) has a good discriminating capability with ROC_AUC(Validation)=0.859, ROC_AUC(No Validation)=0.885, sensitivity=0.908, specificity=0.742. The sensitivity and the specificity are the values when the maximum discriminate point, where the average of sensitivity and specificity is the highest, is a cutoff value.

The value of the formula can be calculated using the index formula 20 as with Example 4, and each case can be classified using the calculated value of the formula and a previously established cutoff value as with Example 4.

Example 8

Among the sample data used in Example 1, only the sample data of females is used. A multivariate discriminant (multivariate function) including an explanatory variable to be substituted with the concentration value of an amino acid in plasma is obtained for discriminating between two groups: the pancreatic cancer group and the breast cancer group.

A logistic regression equation is used as a multivariate discriminant. The 19 kinds of amino acids are searched for a combination of six or less explanatory variables to be included in the logistic regression equation. The Leave-One-Out method is employed as validation to explore a logistic regression equation having a good capability of discriminating between the pancreatic cancer group and the breast cancer group.

The logistic regression equations where the ROC_AUC value for the pancreatic cancer group and the breast cancer group with validation is equal to or greater than 0.750 are shown later in List (1) of Logistic Regression Equations Searched in Example 8. These logistic regression equations are thought to be useful in evaluation of the state of pancreatic cancer with consideration of the state of breast cancer because the ROC_AUC value is extremely high. When the amino acid explanatory variables included in these logistic regression equations are listed in the descending order of occurrence frequency from the highest to the tenth, they are arranged in the following order: Tyr, Trp, Gly, Ala, Asn, Lys, Met, Val, Orn, Leu (see Table 6 below). These amino acids are thought to be useful in the evaluation as with the equations because they are explanatory variables included in the equations thought to be useful in the evaluation. For these logistic regression equations, the ROC_AUC value for the pancreatic cancer group and the healthy group is equal to or greater than 0.796, and the capability of discriminating between the pancreatic cancer group and the healthy group is good. These logistic regression equations are thought to be useful in evaluation of the state of pancreatic cancer with additional consideration of the healthy state, because the ROC_AUC value is extremely high. Among these logistic regression equations, for example, the index formula 21 "(19.7721)+(−0.1860)Asn+(−0.0214)Gly+(−0.0294)Arg+(0.1519)Tyr+(−0.0325)Val+(−0.1932)Trp" having a set of explanatory variables "Asn, Gly, Arg, Tyr, Val, Trp" (the multivariate discriminant including Asn, Gly, Arg, Tyr, Val, Trp as explanatory variables) has a good discriminating capability with ROC_AUC(Validation)=0.945, ROC_AUC(No Validation)=0.965, sensitivity=0.851, specificity=1.000. The sensitivity and the specificity are the values when the maximum discriminate point, where the average of sensitivity and specificity is highest, is a cutoff value.

TABLE 6

Pancreatic cancer group vs Breast cancer group

| Amino acid | Univariate | Logistic regression equation Breast cancer group | Logistic regression equation Healthy | Linear discriminant Breast cancer group | Linear discriminant Healthy group |
|---|---|---|---|---|---|
| Ser | O | | | | |
| Asn | O | 48 | | 55 | |
| Gly | O | 84 | | 80 | 16 |
| Gln | | | 37 | | 28 |
| His | O | | 100 | 14 | 98 |
| Thr | O | | | | |
| Ala | O | 61 | | 63 | |
| Cit | | | 34 | | 31 |
| Arg | | | 60 | | 69 |
| Pro | | | | | |
| Tyr | | 100 | 33 | 100 | 23 |
| Val | O | 26 | | 26 | |
| Met | O | 30 | | 32 | |
| Orn | | 17 | | 18 | |
| Lys | O | 32 | 30 | 27 | 31 |
| Ile | O | | 69 | | 94 |
| Leu | | 16 | 34 | | 21 |
| Phe | | | 34 | | |
| Trp | O | 100 | 94 | 100 | 100 |

(O indicates the amino acid that varies significantly. The numeral indicates the frequency of occurrence of the amino acid explanatory variable.)

The value of the formula can be calculated using the index formula 21 as with Example 4, and each case can be classified using the calculated value of the formula and a previously established cutoff value as with Example 4.

A linear discriminant is used as a multivariate discriminant. The 19 kinds of amino acids are searched for a combination of six or less explanatory variables to be included in the linear discriminant, and the bootstrap method is employed as validation to explore a linear discriminant with a good capability of discriminating between the pancreatic cancer group and the breast cancer group.

A list of linear discriminants where the ROC_AUC value for the pancreatic cancer group and the breast cancer group with validation is equal to or greater than 0.750 is shown later in List (1) of Linear Discriminants Searched in Example 8. These linear discriminants are thought to be useful in evaluation of the state of pancreatic cancer with consideration of the state of breast cancer, because the ROC_AUC value is extremely high. When the amino acid explanatory variables included in these linear discriminants are listed in the descending order of occurrence frequency from the highest to the tenth, they are arranged in the following order: Tyr, Trp, Gly, Ala, Asn, Met, Lys, Val, Orn, His (see Table 6 above). The concentration values of these amino acids are thought to be useful in the evaluation as with the formula, because they are explanatory variables included in the formula thought to be useful in the evaluation. As for these linear discriminants, the ROC_AUC value for the pancreatic cancer group and the healthy group is equal to or greater than 0.800, and the capability of discriminating between the pancreatic cancer group and the healthy group is good. These linear discriminants are thought to be useful in evaluation of the state of pancreatic cancer with additional consideration of the healthy state, because the ROC_AUC value is extremely high. Among these linear discriminants, for example, the index formula 22 "(16.5080)+(−0.1847)Asn+(−0.0136)Gly+(0.1059)Tyr+(−0.0166)Val+(−0.0144)Lys+(−0.1261)Trp" having a set of explanatory variables "Asn, Gly, Tyr, Val, Lys, Trp" (the multivariate discriminant including Asn, Gly, Tyr, Val, Lys, Trp as explanatory variables) has a good discriminating capability with ROC_AUC (Validation)=0.947, ROC_AUC(No Validation)=0.963, sensitivity=0.851, and specificity=1.000. The sensitivity and the specificity are the values when the maximum discriminate point, where the average of sensitivity and specificity is the highest, is a cutoff value.

The value of the formula can be calculated using the index formula 22 as with Example 4, and each case can be classified using the calculated value of the formula and a previously established cutoff value as with Example 4.

List (2) of Logistic Regression Equations Searched in Example 8 provided later shows a list of logistic regression equations in which the ROC_AUC value for the pancreatic cancer group and the breast cancer group with validation is equal to or greater than 0.750 and the capability of discriminating between the pancreatic cancer group and the healthy group is also good. These logistic regression equations are thought to be useful in evaluation of the state of pancreatic cancer with consideration of both the healthy state and the state of breast cancer, because the ROC_AUC value is extremely high. When the amino acid explanatory variables included in these logistic regression equations are listed in the descending order of occurrence frequency from the highest to the tenth, they are arranged in the following order: His, Trp, Ile, Arg, Gln, Phe, Cit, Leu, Tyr, Lys (see Table 6 above). The concentration values of these amino acids are thought to be useful in the evaluation as with the formula because they are explanatory variables included in the formula thought to be useful in the evaluation. Among these logistic regression equations, for example, the index formula 23 "(9.6001)+(0.0010)Gln+(−0.1052)His+(−0.0386)Arg+(0.0762)Tyr+(0.0049)Ile+(−0.1257)Trp" having a set of explanatory variables "Gln, His, Arg, Tyr, Ile, Trp" (the multivariate discriminant including Gln, His, Arg, Tyr, Ile, Trp as explanatory variables) has a good discriminating capability with ROC_AUC(Validation)=0.878, ROC_AUC (No Validation)=0.923, sensitivity=0.876, and specificity=0.900. The sensitivity and the specificity are the values when the maximum discriminate point, where the average of sensitivity and specificity is the highest, is a cutoff value.

The value of the formula can be calculated using the index formula 23 as with Example 4, and each case can be classified using the calculated value of the formula and a previously established cutoff value as with Example 4.

List (2) of Linear Discriminants Searched in Example 8 provided later shows a list of linear discriminants in which the ROC_AUC value for the pancreatic cancer group and the breast cancer group with validation is equal to or greater than 0.750 and the capability of discriminating between the pancreatic cancer group and the healthy group is also good. These linear discriminants are thought to be useful in evaluation of the state of pancreatic cancer with consideration of both the healthy state and the state of breast cancer, because the ROC_AUC value is extremely high. When the amino acid explanatory variables included in these linear discriminants are listed in the descending order of occurrence frequency from the highest to the tenth, they are arranged in the following order: Trp, His, Ile, Arg, Lys, Cit, Gln, Tyr, Leu, Gly (see Table 6 above). The concentration values of these amino acids are thought to be useful in the evaluation as with the formula because they are explanatory variables included in the formula thought to be useful in the evaluation. Among these linear discriminants, for example, the index formula 24 "(10.5615)+(0.0037)Gln+(−0.1087)His+(−0.0445)Arg+(0.0653)Tyr+(0.0380)Ile+(−0.1489)Trp" having a set of explanatory variables "Gln, His, Arg, Tyr, Ile, Trp" (the multivariate discriminant including Gln, His, Arg, Tyr, Ile, Trp as explanatory variables) has a good discriminating capability with ROC_AUC(Validation)=0.896, ROC_AUC(No Validation)=0.924, sensitivity=0.843, specificity=0.950. The sensitivity and the specificity are the values when the maximum discriminate point, where the average of sensitivity and specificity is the highest, is a cutoff value.

The value of the formula can be calculated using the index formula 24 as with Example 4, and each case can be classified using the calculated value of the formula and a previously established cutoff value as with Example 4.

Example 9

The sample data used in Example 1 is used. First, the index formula 1 obtained in Example 2 is established as the first formula, and each case in each group is classified either as positive (equivalent to the pancreatic cancer category) or as negative (equivalent to the healthy category) using the amino acid concentration values of the pancreatic cancer group (51 cases), the healthy group (255 cases), and the other cancers group (780 cases), and the first formula. When the specificity (the percentage of cases in the healthy group correctly classified into the healthy category) is 95%, the positive rate for each group is as follows: 71% for the pancreatic cancer group (36 positive cases), 5% for the healthy group (13 positive cases), and 22% for the other cancers group (170 cases).

The index formula 5 obtained in Example 4 is established as the second formula, and each case in each group is classified either as positive (equivalent to the pancreatic cancer category) or as negative (equivalent to the other cancer category) using the amino acid concentration values of the cases in each group found positive with the index formula 1 (the pancreatic cancer group (36 cases), the healthy group (13 cases), the other cancers group (170 cases)) and the second formula. When the specificity (the percentage of cases in the other cancers group correctly classified into the other cancer category) is 95%, the positive rate for each group is as follows: 33% (17 positive cases) for the pancreatic cancer group, 2% (4 positive cases) for the healthy group, and 4% (32 cases) for the other cancers group. When the specificity is 80%, the positive rate for each group is as follows: 59% (30 positive cases) for the pancreatic cancer group, 4% (9 positive cases) for the healthy group, and 10% (78 cases) for the other cancers group.

As described above, a plurality of formulae can be used to reduce the false positive rate for the other cancers group without noticeably reducing the true positive rate for the pancreatic cancer group.

Based on the results described above, the cases that are positive with the first formula and also positive with the second formula may be classified into the pancreatic cancer category, and the other cases may be classified into the pancreatic cancer-free category.

The cases that are positive with the first formula and also positive with the second formula may be classified into the pancreatic cancer category, the cases that are positive with the first formula and negative with the second formula may be classified into the other cancer category, and the cases that are negative with the first formula may be classified into the healthy category. The case classified in the pancreatic cancer category may be established as rank C, which is a category meaning that the possibility of having pancreatic cancer is high (for example, a category meaning that the possibility of having pancreatic cancer is high and the possibility of having a cancer other than pancreatic cancer is not high), the case classified in the other cancer category may be established as rank B, which is a category meaning that the possibility of having pancreatic cancer is moderate (for example, a category meaning that the possibility of having pancreatic cancer is moderate and the possibility of having a cancer other than pancreatic cancer is not low), and the case classified in the healthy category may be established as rank A, which is a category meaning that the possibility of having pancreatic cancer is low.

With the index formula 1 established as the first formula, each case in each group may be classified either as positive (equivalent to the pancreatic cancer category) or as negative (equivalent to the healthy category), using the amino acid concentration values of the pancreatic cancer group (51 cases), the healthy group (255 cases), and the other cancers group (780 cases), and the first formula. In addition, with the index formula 5 established as the second formula, each case in each group may be classified either as positive (equivalent to the pancreatic cancer category) or as negative (equivalent to the other cancer category), using the amino acid concentration values of the pancreatic cancer group (51 cases), the healthy group (255 cases), and the other cancers group (780 cases), and the second formula. Those classification results may be comprehensively considered to make a final classification.

List (1) of Logistic Regression Equations Searched in Example 2

The logistic regression equations searched in Example 2 above are listed below. Before each equation, "the value of ROC_AUC for the pancreatic cancer group and the healthy group with validation", "the value of ROC_AUC for the pancreatic cancer group and the healthy group without validation", "the value of ROC_AUC for the pancreatic cancer group and the other cancers group", "the value of ROC_AUC for the pancreatic cancer group and the lung cancer group", "the value of ROC_AUC for the pancreatic cancer group and the colorectal cancer group", "the value of ROC_AUC for the pancreatic cancer group and the prostatic cancer group", "the value of ROC_AUC for the pancreatic cancer group and the breast cancer group", and "the average value of the value of ROC_AUC for the pancreatic cancer group and the lung cancer group, the value of ROC_AUC for the pancreatic cancer group and the colorectal cancer group, the value of ROC_AUC for the pancreatic cancer group and the prostatic cancer group, and the value of ROC_AUC for the pancreatic cancer group and the breast cancer group" obtained for the equation are additionally listed.

0.902, 0.923, 0.809, 0.790, 0.778, 0.870, 0.878, 0.829, (−1.3217)+(0.0545)Ser+(−0.0544)Val+(−0.3973)Met+(0.1922)Ile+(0.1506)Phe+(−0.1179)Trp; 0.900, 0.919, 0.800, 0.780, 0.815, 0.860, 0.777, 0.808, (1.1114)+(0.0530)Ser+(−0.1384)His+(0.0420)Thr+(−0.3641)Met+(0.1993)Phe+(−0.1237)Trp; 0.899, 0.917, 0.812, 0.798, 0.789, 0.854, 0.864, 0.826, (2.2454)+(0.0452)Thr+(−0.0612)Val+(−0.4741)Met+(0.2021)Ile+(0.1569)Phe+(−0.1267)Trp; 0.894, 0.918, 0.783, 0.749, 0.760, 0.870, 0.859, 0.810, (−1.8219)+(0.0622)Ser+(−0.1003)His+(−0.0447)Val+(−0.4105)Met+(0.1701)Ile+(0.1621)Phe; 0.891, 0.913, 0.825, 0.813, 0.822, 0.870, 0.830, 0.834, (−0.7646)+(0.0539)Ser+(0.0080)

Gln+(−0.1367)His+(−0.2716)Met+(0.1766)Phe+
(−0.1028)Trp; 0.891, 0.910, 0.793, 0.765, 0.776, 0.856,
0.858, 0.814, (2.3264)+(−0.0966)His+(0.0489)Thr+
(−0.0552)Val+(−0.4896)Met+(0.1897)Ile+(0.1580)
Phe; 0.890, 0.916, 0.807, 0.794, 0.791, 0.854, 0.841,
0.820, (−1.8334)+(0.0536)Ser+(−0.3463)Met+(0.173)
Ile+(−0.0820)Leu+(0.1380)Phe+(−0.1330)Trp; 0.890,
0.912, 0.785, 0.765, 0.749, 0.870, 0.849, 0.808,
(−3.2110)+(0.0409)Ser+(0.0284)Thr+(−0.0697)Val+
(−0.5814)Met+(0.2181)Ile+(0.1512)Phe; 0.890, 0.914,
0.791, 0.754, 0.794, 0.854, 0.836, 0.810, (−0.4856)+
(0.0659)Ser+(−0.1214)His+(−0.2902)Met+(0.0720)
Ile+(0.1503)Phe+(−0.1121)Trp; 0.889, 0.910, 0.831,
0.819, 0.840, 0.854, 0.829, 0.835, (2.1791)+(0.0103)
Gln+(−0.1446)His+(0.0467)Thr+(−0.3603)Met+
(0.1795)Phe+(−0.1251)Trp; 0.888, 0.909, 0.797, 0.783,
0.752, 0.872, 0.876, 0.821, (−2.0528)+(0.0623)Ser+
(−0.1191)Asn+(−0.0671)Val+(−0.3897)Met+(0.2086)
Ile+(0.1559) Phe; 0.887, 0.911, 0.794, 0.768, 0.802,
0.853, 0.801, 0.806, (0.2218)+(0.0663)Ser+(−0.1176)
His+(0.0128)Pro+(−0.2882)Met+(0.1713)Phe+
(−0.1063)Trp; 0.885, 0.906, 0.770, 0.736, 0.762, 0.850,
0.821, 0.792, (−2.1269)+(0.0641)Ser+(−0.1326)His+
(−0.3520)Met+(0.1518)Ile+(−0.0632)Leu+(0.1622)
Phe; 0.885, 0.904, 0.807, 0.790, 0.811, 0.859, 0.806,
0.816, (0.7826)+(0.0620)Ser+(−0.1170)His+(−0.2419)
Met+(0.1752)Phe+(−0.1023)Trp; 0.885, 0.908, 0.812,
0.789, 0.821, 0.865, 0.815, 0.822, (0.6585)+(0.0637)
Ser+(−0.1191)His+(0.0234)Tyr+(−0.2771)Met+
(0.1715)Phe+(−0.1085)Trp; 0.884, 0.906, 0.805, 0.777,
0.785, 0.883, 0.862, 0.827, (2.1234)+(0.0509)Ser+
(0.0590)Tyr+(−0.0488)Val+(−0.3619)Met+(0.1995)
Ile+(−0.1244)Trp; 0.884, 0.905, 0.810, 0.795, 0.815,
0.858, 0.807, 0.819, (1.0354)+(0.0642)Ser+(−0.0298)
Asn+(−0.1127)His+(−0.2223)Met+(0.1737)Phe+
(−0.1009)Trp; 0.884, 0.909, 0.795, 0.777, 0.745, 0.877,
0.887, 0.821, (−3.0328)+(0.0510)Ser+(−0.0050)Ala+
(−0.0625)Val+(−0.4487)Met+(0.2107)Ile+(0.1401)
Phe; 0.883, 0.907, 0.791, 0.769, 0.747, 0.865, 0.888,
0.817, (−3.0576)+(0.0592)Ser+(−0.0056)Gly+
(−0.0640)Val+(−0.4783)Met+(0.2055)Ile+(0.1405)
Phe; 0.882, 0.903, 0.805, 0.787, 0.810, 0.855, 0.804,
0.814, (0.7088)+(0.0622)Ser+(−0.1177)His+(0.0009)
Ala+(−0.2474)Met+(0.1748)Phe+(−0.1026)Trp; 0.882,
0.906, 0.804, 0.785, 0.812, 0.858, 0.803, 0.814,
(0.7718)+(0.0609)Ser+(−0.1195)His+(−0.2422)Met+
(0.0111)Orn+(0.1700)Phe+(−0.1017)Trp; 0.882, 0.905,
0.799, 0.771, 0.809, 0.852, 0.813, 0.811, (0.5016)+
(0.0636)Ser+(−0.1239)His+(−0.2582)Met+(0.0196)
Leu+(0.1610)Phe+(−0.1091)Trp; 0.881, 0.904, 0.787,
0.767, 0.743, 0.868, 0.870, 0.812, (−3.2208)+(0.0511)
Ser+(−0.0642)Val+(−0.4837)Met+(0.2047)Ile+
(0.1423)Phe; 0.881, 0.904, 0.802, 0.772, 0.819, 0.829,
0.825, 0.811, (4.6013)+(−0.1241)His+(0.0491)Thr+
(−0.3361)Met+(0.0575)Ile+(0.1484)Phe+(−0.1339)
Trp; 0.881, 0.904, 0.805, 0.787, 0.811, 0.852, 0.806,
0.814, (0.5622)+(0.0605)Ser+(−0.1208)His+(−0.2627)
Met+(0.0083)Lys+(0.1749)Phe+(−0.1088)Trp; 0.881,
0.906, 0.790, 0.769, 0.755, 0.871, 0.860, 0.814,
(−2.7772)+(0.0534)Ser+(−0.0583)Cit+(−0.0611)Val+
(−0.4725)Met+(0.2025)Ile+(0.1483)Phe; 0.881, 0.903,
0.805, 0.784, 0.812, 0.856, 0.807, 0.815, (0.7259)+
(0.0625)Ser+(−0.1217)His+(0.0048)Val+(−0.2448)
Met+(0.1692)Phe+(−0.1064)Trp; 0.881, 0.902, 0.798,
0.784, 0.760, 0.859, 0.869, 0.818, (1.4747)+(−0.0872)
Asn+(0.0451)Thr+(−0.0745)Val+(−0.4746)Met+
(0.2248)Ile+(0.1468)Phe; 0.880, 0.904, 0.810, 0.792,
0.812, 0.857, 0.817, 0.819, (0.8210)+(0.0648)Ser+
(−0.0022)Gly+(−0.1140)His+(−0.2398)Met+(0.1738)
Phe+(−0.1039)Trp; 0.880, 0.905, 0.809, 0.792, 0.817,
0.858, 0.800, 0.817, (0.8548)+(0.0627)Ser+(−0.1030)
His+(−0.0434)Cit+(−0.2268)Met+(0.1810)Phe+
(−0.1120)Trp; 0.880, 0.902, 0.804, 0.783, 0.783, 0.880,
0.849, 0.824, (3.5594)+(0.0437)Ser+(−0.0504)Cit+
(−0.0373)Val+(−0.2208)Met+(0.1758)Ile+(−0.1170)
Trp; 0.880, 0.901, 0.798, 0.783, 0.774, 0.878, 0.833,
0.817, (3.5083)+(0.0341)Ser+(0.0217)Thr+(−0.0447)
Val+(−0.3282)Met+(0.1883)Ile+(−0.1110)Trp; 0.880,
0.900, 0.831, 0.825, 0.800, 0.853, 0.898, 0.844,
(1.6131)+(0.0057)Gln+(−0.0525)Val+(−0.3431)Met+
(0.1808)Ile+(0.1304)Phe+(−0.1173)Trp; 0.880, 0.904,
0.789, 0.773, 0.750, 0.855, 0.866, 0.811, (1.3300)+
(0.0530)Ser+(−0.1787)Asn+(−0.0502)Val+(0.1586)
Ile+(0.1013)Phe+(−0.1205)Trp; 0.879, 0.903, 0.784,
0.768, 0.742, 0.863, 0.861, 0.808, (−3.3275)+(0.0510)
Ser+(−0.0566)Val+(−0.4745)Met+(0.2287)Ile+(−
0.0295)Leu+(0.1461)Phe; 0.879, 0.906, 0.789, 0.765,
0.751, 0.871, 0.874, 0.815, (−3.4771)+(0.0531)Ser+
(0.0228)Tyr+(−0.0672)Val+(−0.5232)Met+(0.2117)
Ile+(0.1378)Phe; 0.878, 0.897, 0.812, 0.796, 0.830,
0.832, 0.800, 0.815, (5.1467)+(−0.1179)His+(0.0505)
Thr+(−0.3103)Met+(0.1690)Phe+(−0.1253)Trp; 0.878,
0.903, 0.801, 0.777, 0.813, 0.835, 0.817, 0.811,
(−1.3020)+(0.0581)Ser+(−0.0917)Cit+(−0.3118)Met+
(0.0708)Ile+(0.1355)Phe+(−0.1702)Trp; 0.878, 0.905,
0.782, 0.763, 0.741, 0.862, 0.860, 0.807, (−3.2369)+
(0.0521)Ser+(0.0053)Pro+(−0.0643)Val+(−0.4981)
Met+(0.1980)Ile+(0.1419)Phe; 0.878, 0.904, 0.807,
0.792, 0.812, 0.857, 0.802, 0.816, (0.8772)+(0.0632)
Ser+(−0.1150)His+(−0.0075)Arg+(−0.2326)Met+
(0.1756)Phe+(−0.1014)Trp; 0.878, 0.898, 0.758, 0.725,
0.747, 0.823, 0.821, 0.779, (1.1231)+(0.0472)Ser+
(−0.1274)His+(0.1065)Ile+(−0.0390)Leu+(0.1044)
Phe+(−0.1281)Trp; 0.877, 0.903, 0.807, 0.797, 0.795,
0.855, 0.824, 0.818, (1.0488)+(0.0524)Ser+(−0.1170)
Asn+(0.0077)Gln+(−0.1332)His+(0.1277)Phe+(−
0.1078)Trp; 0.877, 0.900, 0.754, 0.707, 0.768, 0.840,
0.783, 0.775, (−1.3972)+(0.0567)Ser+(−0.1699)His+
(0.0295)Thr+(−0.4330)Met+(0.0672)Ile+(0.1506)Phe;
0.877, 0.904, 0.782, 0.761, 0.740, 0.865, 0.866, 0.808,
(−2.9436)+(0.0528)Ser+(−0.0012)Gln+(−0.0642)Val+
(−0.4767)Met+(0.2056)Ile+(0.1425)Phe; 0.877, 0.900,
0.812, 0.798, 0.791, 0.876, 0.848, 0.828, (6.5712)+
(0.0336)Thr+(−0.0519)Cit+(−0.0438)Val+(−0.2732)
Met+(0.1832)Ile+(−0.1144)Trp; 0.877, 0.903, 0.819,
0.801, 0.795, 0.849, 0.894, 0.835, (4.9139)+(−0.0543)
His+(−0.0452)Val+(−0.2526)Met+(0.1687)Ile+
(0.1312)Phe+(−0.0958)Trp; 0.877, 0.900, 0.797, 0.784,
0.755, 0.863, 0.875, 0.819, (0.3843)+(0.0393)Thr+
(−0.0042)Ala+(−0.0697)Val+(−0.5055)Met+(0.2222)
Ile+(0.1346)Phe; 0.877, 0.899, 0.803, 0.787, 0.768,
0.879, 0.865, 0.824, (3.2446)+(0.0417)Ser+(−0.0046)
Ala+(−0.0407)Val+(−0.2260)Met+(0.1885)Ile+(−
0.1079)Trp; 0.877, 0.896, 0.806, 0.783, 0.828, 0.827,
0.804, 0.811, (5.1385)+(−0.1262)His+(0.0512)Thr+
(−0.3199)Met+(0.0154)Leu+(0.1582)Phe+(−0.1315)
Trp; 0.877, 0.895, 0.811, 0.802, 0.778, 0.873, 0.862,
0.828, (6.3171)+(0.0318)Thr+(−0.0048)Ala+(−0.0466)
Val+(−0.2706)Met+(0.1948)Ile+(−0.1108)Trp; 0.877,
0.901, 0.770, 0.737, 0.753, 0.844, 0.841, 0.794,
(1.5645)+(0.0502)Ser+(−0.1331)His+(−0.0071)Ala+
(0.0682)Ile+(0.1022)Phe+(−0.1303)Trp; 0.877, 0.904,
0.787, 0.767, 0.744, 0.867, 0.870, 0.812, (−3.2265)+
(0.0513)Ser+(−0.0640)Val+(−0.4840)Met+(−0.0021)
Orn+(0.2050)Ile+(0.1430)Phe; 0.876, 0.899, 0.796, 0.776, 0.772, 0.871, 0.847, 0.817, (3.1391)+(0.0431) Ser+(0.0063)Pro+(−0.0420)Val+(−0.2707)Met+ (0.1750)Ile+(−0.1119)Trp; 0.876, 0.896, 0.800, 0.782, 0.782, 0.859, 0.843, 0.817, (7.1237)+(−0.0566)His+ (0.0346)Thr+(−0.0375)Val+(−0.2613)Met+(0.1722) Ile+(−0.0947)Trp; 0.876, 0.900, 0.789, 0.772, 0.802, 0.820, 0.788, 0.796, (−1.7780)+(0.0469)Ser+(0.0220) Thr+(−0.4185)Met+(0.0601)Ile+(0.1200)Phe+ (−0.1623)Trp; 0.876, 0.900, 0.814, 0.814, 0.828, 0.840, 0.768, 0.812, (0.3731)+(0.0463)Ser+(−0.0799)Asn+ (0.0272)Thr+(−0.3209)Met+(0.1461)Phe+(−0.1531) Trp; 0.876, 0.898, 0.813, 0.799, 0.830, 0.833, 0.801, 0.816, (5.1380)+(−0.1164)His+(0.0508)Thr+(−0.0016) Val+(−0.3109)Met+(0.1713)Phe+(−0.1240)Trp; 0.876, 0.898, 0.781, 0.748, 0.787, 0.859, 0.796, 0.798, (4.0210)+(0.0445)Ser+(−0.1021)His+(0.0220)Thr+ (−0.2402)Met+(0.0941)Ile+(−0.1075)Trp; 0.876, 0.898, 0.804, 0.786, 0.774, 0.882, 0.856, 0.824, (3.7945)+(0.0469)Ser+(−0.0611)Asn+(−0.0421)Val+ (−0.2051)Met+(0.1806)Ile+(−0.1024)Trp; 0.876, 0.899, 0.803, 0.783, 0.772, 0.871, 0.868, 0.824, (3.1847)+(0.0513)Ser+(−0.0059)Gly+(−0.0407)Val+ (−0.2496)Met+(0.1795)Ile+(−0.1110)Trp; 0.876, 0.898, 0.815, 0.806, 0.785, 0.847, 0.882, 0.830, (3.0411)+(0.0040)Gly+(−0.0542)Val+(−0.3097)Met+ (0.1869)Ile+(0.1305)Phe+(−0.1123)Trp; 0.876, 0.899, 0.777, 0.739, 0.777, 0.852, 0.825, 0.798, (−3.0222)+ (0.0578)Ser+(0.0068)Gln+(−0.1683)His+(−0.3616) Met+(0.0626)Ile+(0.1415)Phe; 0.876, 0.900, 0.792, 0.772, 0.765, 0.863, 0.851, 0.813, (0.6553)+(0.0436) Thr+(−0.0620)Cit+(−0.0694)Val+(−0.5305)Met+ (0.2201)Ile+(0.1426)Phe; 0.875, 0.898, 0.808, 0.802, 0.833, 0.838, 0.750, 0.806, (0.0690)+(0.0437)Ser+ (0.0320)Thr+(−0.0895)Cit+(−0.3650)Met+(0.1686) Phe+(−0.1704)Trp; 0.875, 0.896, 0.820, 0.810, 0.789, 0.844, 0.895, 0.835, (3.7150)+(−0.0537)Val+(−0.2954) Met+(0.1852)Ile+(0.1259)Phe+(−0.1109)Trp; 0.875, 0.895, 0.789, 0.774, 0.751, 0.853, 0.860, 0.810, (0.1159)+(0.0397)Thr+(−0.0717)Val+(−0.5387)Met+ (0.2196)Ile+(0.1380)Phe; 0.875, 0.898, 0.810, 0.795, 0.828, 0.831, 0.799, 0.813, (5.0416)+(0.0077)Asn+ (−0.1194)His+(0.0503)Thr+(−0.3161)Met+(0.1699) Phe+(−0.1255)Trp; 0.875, 0.899, 0.825, 0.817, 0.787, 0.854, 0.906, 0.841, (3.9291)+(−0.0044)Ala+(−0.0534) Val+(−0.2665)Met+(0.1920)Ile+(0.1248)Phe+ (−0.1088)Trp; 0.875, 0.897, 0.794, 0.778, 0.763, 0.875, 0.845, 0.815, (4.6063)+(0.0465)Ser+(−0.1092)Asn+ (−0.0635)Cit+(−0.0374)Val+(0.1596)Ile+(−0.1266) Trp; 0.875, 0.899, 0.781, 0.761, 0.783, 0.844, 0.786, 0.793, (2.7059)+(0.0543)Ser+(−0.1114)Asn+(−0.1258) His+(0.0185)Thr+(0.1304)Phe+(−0.1179)Trp; 0.875, 0.903, 0.785, 0.768, 0.746, 0.863, 0.855, 0.808, (−3.1220)+(0.0548)Ser+(−0.0162)Arg+(−0.0640)Val+ (−0.4578)Met+(0.2053)Ile+(0.1464)Phe; 0.875, 0.898, 0.806, 0.793, 0.824, 0.832, 0.786, 0.809, (4.7360)+ (0.0034)Gly+(−0.1236)His+(0.0487)Thr+(−0.3151) Met+(0.1724)Phe+(−0.1208)Trp; 0.875, 0.904, 0.786, 0.767, 0.743, 0.868, 0.870, 0.812, (−3.2133)+(0.0512) Ser+(−0.0641)Val+(−0.4828)Met+(−0.0003)Lys+ (0.2046)Ile+(0.1423)Phe; 0.875, 0.895, 0.798, 0.781, 0.770, 0.873, 0.849, 0.818, (3.1269)+(0.0422)Ser+ (−0.0412)Val+(−0.2543)Met+(0.1807)Ile+(−0.1110) Trp; 0.875, 0.895, 0.792, 0.776, 0.753, 0.867, 0.864, 0.815, (3.8125)+(0.0350)Ser+(−0.0086)Ala+(−0.0759) Cit+(−0.0342)Val+(0.1732)Ile+(−0.1444)Trp; 0.875, 0.898, 0.808, 0.792, 0.825, 0.827, 0.799, 0.811, (5.0167)+(−0.1163)His+(0.0493)Thr+(0.0042)Pro+ (−0.3173)Met+(0.1656)Phe+(−0.1257)Trp; 0.874, 0.892, 0.811, 0.795, 0.789, 0.870, 0.856, 0.827, (5.8798)+(0.0306)Thr+(0.0275)Tyr+(−0.0494)Val+ (−0.3312)Met+(0.1907)Ile+(−0.1191)Trp; 0.874, 0.898, 0.811, 0.797, 0.829, 0.831, 0.799, 0.814, (5.1472)+(−0.1179)His+(0.0507)Thr+(−0.0017)Tyr+ (−0.3085)Met+(0.1695)Phe+(−0.1249)Trp; 0.874, 0.898, 0.788, 0.761, 0.770, 0.865, 0.842, 0.810, (3.8623)+(0.0473)Ser+(−0.0629)His+(−0.0301)Val+ (−0.2091)Met+(0.1648)Ile+(−0.0919)Trp; 0.874, 0.898, 0.792, 0.790, 0.806, 0.814, 0.751, 0.790, (−1.0344)+(0.0456)Ser+(0.0230)Thr+(0.0098)Pro+ (−0.4138)Met+(0.1413)Phe+(−0.1577)Trp; 0.874, 0.895, 0.788, 0.774, 0.751, 0.854, 0.859, 0.809, (0.0531)+(0.0005)Gly+(0.0394)Thr+(−0.0716)Val+ (−0.5394) Met+(0.2193)Ile+(0.1383)Phe; 0.874, 0.897, 0.812, 0.798, 0.830, 0.831, 0.801, 0.815, (5.1552)+ (−0.1177)His+(0.0509)Thr+(−0.3113)Met+(−0.0016) Orn+(0.1700)Phe+(−0.1256)Trp; 0.874, 0.896, 0.754, 0.722, 0.735, 0.823, 0.828, 0.777, (1.3999)+(0.0456) Ser+(−0.1187)His+(−0.0254)Val+(0.1124)Ile+(0.1002) Phe+(−0.1271)Trp; 0.874, 0.895, 0.768, 0.727, 0.765, 0.852, 0.820, 0.791, (−1.5196)+(0.0660)Ser+(−0.1481) His+(−0.0042)Ala+(−0.3256)Met+(0.0732)Ile+ (0.1382)Phe; 0.873, 0.897, 0.812, 0.814, 0.827, 0.835, 0.756, 0.808, (−0.1619)+(0.0395)Ser+(0.0286)Thr+ (−0.0081)Val+(−0.3801)Met+(0.1583)Phe+(−0.1520) Trp; 0.873, 0.895, 0.802, 0.787, 0.773, 0.876, 0.850, 0.821, (3.6154)+(0.0371)Ser+(−0.0090)Ala+(−0.0871) Cit+(0.1770)Ile+(−0.0599)Leu+(−0.1475)Trp; 0.873, 0.897, 0.812, 0.798, 0.829, 0.832, 0.800, 0.815, (5.1575)+(−0.1177)His+(0.0505)Thr+(−0.0002)Ala+ (−0.3093)Met+(0.1691)Phe+(−0.1253)Trp; 0.873, 0.896, 0.799, 0.783, 0.771, 0.872, 0.851, 0.819, (3.0224)+(0.0410)Ser+(−0.0428)Val+(−0.2747)Met+ (0.0061)Lys+(0.1815)Ile+(−0.1138)Trp; 0.873, 0.891, 0.804, 0.793, 0.778, 0.865, 0.845, 0.820, (6.1068)+ (0.0314)Thr+(−0.0472)Val+(−0.2968)Met+(0.1870) Ile+(−0.1123)Trp; 0.873, 0.897, 0.810, 0.795, 0.829, 0.825, 0.801, 0.812, (4.9661)+(−0.1202)His+(0.0488) Thr+(−0.3182)Met+(0.0049)Lys+(0.1679)Phe+(− 0.1273)Trp; 0.873, 0.896, 0.821, 0.812, 0.790, 0.844, 0.896, 0.836, (3.8662)+(−0.0081)Asn+(−0.0538)Val+ (−0.2881)Met+(0.1849)Ile+(0.1257)Phe+(−0.1096) Trp; 0.873, 0.897, 0.811, 0.799, 0.833, 0.830, 0.787, 0.812, (5.5816)+(−0.1144)His+(0.0550)Thr+(−0.0157) Arg+(−0.3019)Met+(0.1705)Phe+(−0.1270)Trp; 0.873, 0.896, 0.801, 0.784, 0.773, 0.874, 0.851, 0.821, (2.9282)+(0.0409)Ser+(0.0009)Gln+(−0.0410)Val+ (−0.2589)Met+(0.1794)Ile+(−0.1121)Trp; 0.873, 0.898, 0.818, 0.808, 0.788, 0.842, 0.891, 0.832, (3.7193)+(0.0050)Pro+(−0.0540)Val+(−0.3080)Met+ (0.1806)Ile+(0.1269)Phe+(−0.1125)Trp; 0.873, 0.900, 0.837, 0.818, 0.833, 0.859, 0.882, 0.848, (2.0349)+ (0.0121)Gln+(−0.1284)His+(−0.2378)Met+(0.0584) Ile+(0.1200)Phe+(−0.1165)Trp; 0.873, 0.894, 0.802, 0.801, 0.821, 0.824, 0.749, 0.799, (−0.5508)+(0.0412) Ser+(0.0255)Thr+(−0.3787)Met+(0.1449)Phe+(− 0.1587)Trp; 0.873, 0.894, 0.796, 0.777, 0.771, 0.871, 0.843, 0.816, (3.1019)+(0.0405)Ser+(−0.0430)Val+ (−0.2624)Met+(0.0147)Orn+(0.1798)Ile+(−0.1110) Trp; 0.873, 0.898, 0.769, 0.735, 0.765, 0.837, 0.822, 0.790, (1.7038)+(0.0588)Ser+(−0.0844)Asn+ (−0.1247)His+(0.0537)Ile+(0.1038)Phe+(−0.1227) Trp; 0.872, 0.895, 0.789, 0.774, 0.751, 0.853, 0.860, 0.809, (0.1187)+(0.0392)Thr+(−0.0702)Val+(−0.5356) Met+(0.2227)Ile+(−0.0048)Leu+(0.1384)Phe; 0.872, 0.897, 0.808, 0.807, 0.808, 0.826, 0.795, 0.809, (−0.3872)+(0.0586)Ser+(−0.0695)Asn+(0.0110)Pro+ (−0.2845)Met+(0.1316)Phe+(−0.1409)Trp

List (1) of Linear Discriminants Searched in Example 2

The linear discriminants searched in Example 2 above are listed below. Before each equation, "the value of ROC_AUC for the pancreatic cancer group and the healthy group with validation", "the value of ROC_AUC for the pancreatic cancer group and the healthy group without validation", "the value of ROC_AUC for the pancreatic cancer group and the other cancers group", "the value of ROC_AUC for the pancreatic cancer group and the lung cancer group", "the value of ROC_AUC for the pancreatic cancer group and the colorectal cancer group", "the value of ROC_AUC for the pancreatic cancer group and the prostatic cancer group", "the value of ROC_AUC for the pancreatic cancer group and the breast cancer group", and "the average value of the value of ROC_AUC for the pancreatic cancer group and the lung cancer group, the value of ROC_AUC for the pancreatic cancer group and the colorectal cancer group, the value of ROC_AUC for the pancreatic cancer group and the prostatic cancer group, and the value of ROC_AUC for the pancreatic cancer group and the breast cancer group" obtained for the equation are additionally listed.

0.912, 0.926, 0.816, 0.798, 0.795, 0.864, 0.874, 0.833, (−1.0207)+(0.0564)Ser+(−0.0410)Val+(−0.4144)Met+(0.1407)Ile+(0.1786)Phe+(−0.1154)Trp; 0.910, 0.923, 0.800, 0.780, 0.816, 0.856, 0.776, 0.807, (1.2502)+(0.0519)Ser+(−0.1044)His+(0.0391)Thr+(−0.3808)Met+(0.2058)Phe+(−0.1332)Trp; 0.906, 0.919, 0.815, 0.803, 0.802, 0.853, 0.847, 0.826, (2.7689)+(0.0555)Thr+(−0.0511)Val+(−0.5140)Met+(0.1555)Ile+(0.1792)Phe+(−0.1223)Trp; 0.904, 0.920, 0.812, 0.798, 0.800, 0.846, 0.847, 0.823, (−1.2604)+(0.0530)Ser+(−0.3551)Met+(0.1373)Ile+(−0.0676)Leu+(0.1759)Phe+(−0.1399)Trp; 0.903, 0.919, 0.782, 0.749, 0.760, 0.870, 0.853, 0.808, (−1.6453)+(0.0604)Ser+(−0.0790)His+(−0.0373)Val+(−0.4011)Met+(0.1385)Ile+(0.1636)Phe; 0.902, 0.918, 0.796, 0.762, 0.801, 0.856, 0.831, 0.813, (−0.1304)+(0.0660)Ser+(−0.0940)His+(−0.3073)Met+(0.0543)Ile+(0.1677)Phe+(−0.1190)Trp; 0.901, 0.917, 0.781, 0.760, 0.753, 0.860, 0.839, 0.803, (−2.7861)+(0.0400)Ser+(0.0326)Thr+(−0.0608)Val+(−0.5850)Met+(0.1830)Ile+(0.1702)Phe; 0.900, 0.914, 0.824, 0.813, 0.821, 0.868, 0.828, 0.833, (−0.3399)+(0.0555)Ser+(0.0065)Gln+(−0.0993)His+(−0.2838)Met+(0.1822)Phe+(−0.1212)Trp; 0.898, 0.912, 0.789, 0.763, 0.776, 0.851, 0.839, 0.807, (2.3150)+(−0.0751)His+(0.0555)Thr+(−0.0488)Val+(−0.4979)Met+(0.1558)Ile+(0.1591)Phe; 0.897, 0.911, 0.828, 0.820, 0.837, 0.842, 0.822, 0.830, (2.6477)+(0.0093)Gln+(−0.1101)His+(0.0480)Thr+(−0.3592)Met+(0.1701)Phe+(−0.1325)Trp; 0.896, 0.909, 0.814, 0.800, 0.818, 0.858, 0.809, 0.821, (1.4707)+(0.0650)Ser+(−0.0399)Asn+(−0.0828)His+(−0.2276)Met+(0.1831)Phe+(−0.1217)Trp; 0.895, 0.908, 0.807, 0.791, 0.813, 0.856, 0.804, 0.816, (1.0068)+(0.0630)Ser+(−0.0875)His+(−0.2579)Met+(0.1830)Phe+(−0.1207)Trp; 0.895, 0.911, 0.813, 0.791, 0.824, 0.864, 0.814, 0.823, (0.7601)+(0.0642)Ser+(−0.0885)His+(0.0236)Tyr+(−0.2880)Met+(0.1795)Phe+(−0.1278)Trp; 0.895, 0.911, 0.812, 0.801, 0.783, 0.855, 0.870, 0.827, (2.8531)+(0.0444)Ser+(−0.1615)Asn+(−0.0336)Val+(0.0949)Ile+(0.1195)Phe+(−0.1303)Trp; 0.895, 0.910, 0.798, 0.781, 0.751, 0.878, 0.886, 0.824, (−2.2067)+(0.0513)Ser+(−0.0059)Ala+(−0.0514)Val+(−0.4276)Met+(0.1741)Ile+(0.1473)Phe; 0.895, 0.911, 0.801, 0.780, 0.808, 0.853, 0.805, 0.812, (0.6315)+(0.0639)Ser+(−0.0888)His+(0.0082)Pro+(−0.2857)Met+(0.1818)Phe+(−0.1202)Trp; 0.894, 0.912, 0.798, 0.783, 0.758, 0.867, 0.869, 0.819, (−1.5328)+(0.0563)Ser+(−0.0818)Asn+(−0.0541)Val+(−0.3937)Met+(0.1667)Ile+(0.1569)Phe; 0.894, 0.909, 0.811, 0.796, 0.817, 0.858, 0.802, 0.818, (1.1779)+(0.0634)Ser+(−0.0818)His+(−0.0228)Cit+(−0.2535)Met+(0.1837)Phe+(−0.1223)Trp; 0.894, 0.908, 0.808, 0.792, 0.813, 0.856, 0.804, 0.816, (1.0402)+(0.0632)Ser+(−0.0871)His+(−0.2558)Met+(−0.0009)Lys+(0.1834)Phe+(−0.1204)Trp; 0.893, 0.908, 0.806, 0.789, 0.813, 0.852, 0.800, 0.814, (0.9480)+(0.0631)Ser+(−0.0881)His+(0.0006)Ala+(−0.2617)Met+(0.1834)Phe+(−0.1213)Trp; 0.893, 0.909, 0.800, 0.777, 0.808, 0.853, 0.807, 0.811, (0.7256)+(0.0651)Ser+(−0.0952)His+(−0.2689)Met+(0.0129)Leu+(0.1735)Phe+(−0.1209)Trp; 0.893, 0.908, 0.806, 0.788, 0.813, 0.856, 0.804, 0.815, (0.9375)+(0.0634)Ser+(−0.0899)His+(0.0018)Val+(−0.2577)Met+(0.1809)Phe+(−0.1216)Trp; 0.893, 0.908, 0.811, 0.795, 0.815, 0.855, 0.815, 0.820, (1.1251)+(0.0658)Ser+(−0.0023)Gly+(−0.0856)His+(−0.2575)Met+(0.1816)Phe+(−0.1211)Trp; 0.892, 0.909, 0.791, 0.767, 0.752, 0.860, 0.887, 0.816, (−2.4043)+(0.0586)Ser+(−0.0057)Gly+(−0.0530)Val+(−0.4602)Met+(0.1686)Ile+(0.1487)Phe; 0.892, 0.908, 0.815, 0.804, 0.804, 0.854, 0.838, 0.825, (2.1627)+(0.0471)Ser+(−0.1168)Asn+(0.0059)Gln+(−0.0954)His+(0.1334)Phe+(−0.1287)Trp; 0.892, 0.907, 0.784, 0.762, 0.748, 0.860, 0.860, 0.807, (−2.7343)+(0.0512)Ser+(−0.0535)Val+(−0.4634)Met+(0.1686)Ile+(0.1515)Phe; 0.892, 0.908, 0.784, 0.764, 0.748, 0.860, 0.857, 0.807, (−2.7747)+(0.0506)Ser+(−0.0498)Val+(−0.4593)Met+(0.1763)Ile+(−0.0120)Leu+(0.1538)Phe; 0.892, 0.908, 0.808, 0.793, 0.814, 0.856, 0.801, 0.816, (1.0417)+(0.0637)Ser+(−0.0871)His+(−0.0031)Arg+(−0.2535)Met+(0.1829)Phe+(−0.1201)Trp; 0.891, 0.909, 0.805, 0.788, 0.811, 0.856, 0.802, 0.814, (0.8987)+(0.0622)Ser+(−0.0896)His+(−0.2581)Met+(0.0100)Orn+(0.1790)Phe+(−0.1200)Trp; 0.890, 0.908, 0.781, 0.760, 0.746, 0.858, 0.858, 0.805, (−2.7988)+(0.0513)Ser+(0.0023)Pro+(−0.0534)Val+(−0.4692)Met+(0.1662)Ile+(0.1516)Phe; 0.889, 0.908, 0.785, 0.761, 0.753, 0.863, 0.857, 0.809, (−2.4869)+(0.0531)Ser+(−0.0401)Cit+(−0.0510)Val+(−0.4534)Met+(0.1694)Ile+(0.1506)Phe; 0.889, 0.909, 0.785, 0.760, 0.752, 0.865, 0.865, 0.810, (−2.9300)+(0.0517)Ser+(0.0129)Tyr+(−0.0546)Val+(−0.4830)Met+(0.1714)Ile+(0.1491)Phe; 0.888, 0.906, 0.780, 0.758, 0.745, 0.858, 0.859, 0.805, (−2.4649)+(0.0528)Ser+(−0.0012)Gln+(−0.0535)Val+(−0.4582)Met+(0.1693)Ile+(0.1524)Phe; 0.888, 0.906, 0.785, 0.765, 0.747, 0.859, 0.862, 0.808, (−2.7176)+(0.0518)Ser+(−0.0532)Val+(−0.4646)Met+(−0.0055)Orn+(0.1704)Ile+(0.1529)Phe; 0.888, 0.903, 0.799, 0.788, 0.760, 0.864, 0.864, 0.819, (1.2361)+(0.0468)Thr+(−0.0057)Ala+(−0.0605)Val+(−0.5055)Met+(0.1871)Ile+(0.1435)Phe; 0.887, 0.903, 0.799, 0.785, 0.770, 0.856, 0.854, 0.816, (2.0233)+(−0.0687)Asn+(0.0503)Thr+(−0.0636)Val+(−0.4866)Met+(0.1810)Ile+(0.1515)Phe; 0.887, 0.903, 0.810, 0.804, 0.789, 0.834, 0.849, 0.819, (2.1560)+(0.0423)Ser+(−0.1386)Asn+(0.1029)Ile+(−0.0610)Leu+(0.1253)Phe+(−0.1484)Trp; 0.887, 0.904, 0.814, 0.790, 0.798, 0.885, 0.861, 0.834, (3.2556)+(0.0393)Ser+(0.0476)Tyr+(−0.0321)Val+(−0.3074)Met+(0.1395)Ile+(−0.0999)Trp; 0.887, 0.905, 0.802, 0.781, 0.813, 0.833, 0.812, 0.810, (−0.7602)+(0.0589)Ser+(−0.0644)Cit+(−0.3340)Met+(0.0567)Ile+(0.1461)Phe+(−0.1536)Trp; 0.887, 0.904, 0.766, 0.728, 0.761, 0.848, 0.817, 0.788, (−1.8629)+(0.0597)Ser+(−0.1027)His+(−0.3399)Met+(0.1177)

Ile+(−0.0470)Leu+(0.1542)Phe; 0.887, 0.907, 0.784, 0.763, 0.750, 0.861, 0.855, 0.807, (−2.5250)+(0.0533) Ser+(−0.0519)Val+(−0.4475)Met+(−0.0066)Lys+ (0.1685)Ile+(0.1528)Phe; 0.887, 0.903, 0.795, 0.767, 0.815, 0.822, 0.807, 0.803, (4.6094)+(−0.0974)His+ (0.0547)Thr+(−0.3593)Met+(0.0451)Ile+(0.1510) Phe+(−0.1313)Trp; 0.887, 0.901, 0.806, 0.803, 0.819, 0.831, 0.769, 0.806, (0.8909)+(0.0495)Ser+(−0.0804) Asn+(0.0274)Thr+(−0.3250)Met+(0.1731)Phe+ (−0.1660)Trp; 0.887, 0.902, 0.804, 0.791, 0.784, 0.886, 0.823, 0.821, (4.4196)+(0.0274)Ser+(0.0224)Thr+ (−0.0324)Val+(−0.3009)Met+(0.1397)Ile+(−0.0907) Trp; 0.886, 0.905, 0.844, 0.843, 0.816, 0.856, 0.897, 0.853, (2.0355)+(0.0066)Gln+(−0.0397)Val+(−0.3168) Met+(0.1284)Ile+(0.1311)Phe+(−0.1090)Trp; 0.886, 0.900, 0.804, 0.806, 0.818, 0.825, 0.758, 0.802, (0.4259)+(0.0430)Ser+(0.0297)Thr+(−0.0105)Val+ (−0.3931)Met+(0.1880)Phe+(−0.1582)Trp; 0.886, 0.899, 0.796, 0.778, 0.794, 0.846, 0.812, 0.808, (3.1351)+(0.0540)Ser+(−0.1002)Asn+(−0.0861)His+ (0.1369)Phe+(−0.1276)Trp; 0.886, 0.902, 0.809, 0.789, 0.793, 0.883, 0.841, 0.827, (4.2488)+(0.0388)Ser+ (−0.0459)Cit+(−0.0260)Val+(−0.2229)Met+(0.1326) Ile+(−0.0884)Trp; 0.885, 0.901, 0.787, 0.767, 0.767, 0.855, 0.831, 0.805, (1.0928)+(0.0508)Thr+(−0.0475) Cit+(−0.0603)Val+(−0.5411)Met+(0.1843)Ile+ (0.1481)Phe; 0.885, 0.902, 0.803, 0.795, 0.827, 0.833, 0.749, 0.801, (0.5012)+(0.0459)Ser+(0.0317)Thr+ (−0.0619)Cit+(−0.3861)Met+(0.1783)Phe+(−0.1682) Trp; 0.885, 0.903, 0.778, 0.748, 0.758, 0.852, 0.842, 0.800, (2.1169)+(0.0446)Ser+(−0.1004)His+(−0.0073) Ala+(0.0451)Ile+(0.1020)Phe+(−0.1174)Trp; 0.885, 0.898, 0.786, 0.772, 0.756, 0.849, 0.842, 0.805, (0.7111)+(0.0469)Thr+(−0.0625)Val+(−0.5409)Met+ (0.1818)Ile+(0.1477)Phe; 0.885, 0.905, 0.783, 0.764, 0.750, 0.858, 0.849, 0.805, (−2.5667)+(0.0542)Ser+ (−0.0117)Arg+(−0.0530)Val+(−0.4456)Met+(0.1685) Ile+(0.1517)Phe; 0.885, 0.902, 0.793, 0.775, 0.794, 0.844, 0.803, 0.804, (3.5394)+(0.0482)Ser+(−0.1125) Asn+(−0.0924)His+(0.0136)Thr+(0.1363)Phe+ (−0.1331)Trp; 0.885, 0.901, 0.813, 0.800, 0.800, 0.883, 0.826, 0.827, (6.9234)+(0.0383)Thr+(−0.0519)Cit+ (−0.0325)Val+(−0.2896)Met+(0.1428)Ile+(−0.0934) Trp; 0.885, 0.902, 0.787, 0.769, 0.803, 0.816, 0.782, 0.793, (−1.1723)+(0.0475)Ser+(0.0242)Thr+(−0.4228) Met+(0.0442)Ile+(0.1547)Phe+(−0.1668)Trp; 0.885, 0.900, 0.788, 0.782, 0.805, 0.809, 0.754, 0.788, (−0.4771)+(0.0461)Ser+(0.0245)Thr+(0.0063)Pro+ (−0.4030)Met+(0.1676)Phe+(−0.1663)Trp; 0.884, 0.898, 0.786, 0.772, 0.756, 0.850, 0.842, 0.805, (0.7556)+(−0.0003)Gly+(0.0471)Thr+(−0.0625)Val+ (−0.5408)Met+(0.1819)Ile+(0.1475)Phe; 0.884, 0.901, 0.762, 0.726, 0.760, 0.832, 0.808, 0.782, (2.0817)+ (0.0488)Ser+(−0.1010)His+(−0.0148)Lys+(0.0398) Ile+(0.1108)Phe+(−0.1212)Trp; 0.884, 0.901, 0.786, 0.772, 0.761, 0.849, 0.828, 0.803, (1.1646)+(0.0531) Thr+(−0.0168)Arg+(−0.0631)Val+(−0.5324)Met+ (0.1839)Ile+(0.1497)Phe; 0.884, 0.900, 0.785, 0.772, 0.756, 0.842, 0.843, 0.803, (0.8173)+(0.0536)Thr+ (−0.0628)Val+(−0.5701)Met+(−0.0240)Orn+(0.1923) Ile+(0.1576)Phe; 0.884, 0.900, 0.807, 0.800, 0.807, 0.814, 0.821, 0.811, (2.6359)+(0.0383)Thr+(−0.3763) Met+(0.1339)Ile+(−0.0707)Leu+(0.1592)Phe+(− 0.1470)Trp; 0.884, 0.901, 0.844, 0.832, 0.839, 0.854, 0.880, 0.851, (2.0499)+(0.0118)Gln+(−0.0940)His+ (−0.2274)Met+(0.0420)Ile+(0.1165)Phe+(−0.1146) Trp; 0.884, 0.900, 0.765, 0.736, 0.756, 0.822, 0.820, 0.783, (1.7752)+(0.0391)Ser+(−0.0937)His+(0.0719) Ile+(−0.0325)Leu+(0.1113)Phe+(−0.1251)

Trp; 0.884, 0.898, 0.804, 0.790, 0.826, 0.817, 0.786, 0.805, (5.3455)+(−0.0929)His+(0.0545)Thr+(−0.3233) Met+(0.1661)Phe+(−0.1329)Trp; 0.884, 0.899, 0.788, 0.775, 0.757, 0.849, 0.843, 0.806, (0.4472)+(0.0008) Gln+(0.0460)Thr+(−0.0623)Val+(−0.5433)Met+ (0.1812)Ile+(0.1473)Phe; 0.883, 0.899, 0.804, 0.789, 0.796, 0.857, 0.820, 0.816, (3.2583)+(0.0541)Ser+ (−0.0948)Asn+(−0.0836)His+(−0.0025)Ala+(0.1386) Phe+(−0.1244)Trp; 0.883, 0.901, 0.784, 0.757, 0.780, 0.839, 0.824, 0.800, (2.6411)+(0.0537)Ser+(−0.1017) Asn+(−0.0912)His+(0.0314)Ile+(0.1210)Phe+ (−0.1273)Trp; 0.883, 0.900, 0.797, 0.782, 0.795, 0.846, 0.809, 0.808, (3.2209)+(0.0557)Ser+(−0.0944)Asn+ (−0.0840)His+(−0.0055)Lys+(0.1410)Phe+(−0.1256) Trp; 0.883, 0.899, 0.798, 0.782, 0.794, 0.848, 0.812, 0.809, (3.1873)+(0.0539)Ser+(−0.1013)Asn+ (−0.0845)His+(−0.0011)Val+(0.1384)Phe+(−0.1271) Trp; 0.883, 0.899, 0.814, 0.800, 0.780, 0.890, 0.869, 0.835, (4.1970)+(0.0368)Ser+(−0.0056)Ala+(−0.0282) Val+(−0.2090)Met+(0.1393)Ile+(−0.0803)Trp; 0.883, 0.898, 0.794, 0.776, 0.791, 0.844, 0.811, 0.806, (3.0890)+(0.0538)Ser+(−0.1016)Asn+(−0.0866)His+ (0.0020)Pro+(0.1351)Phe+(−0.1277)Trp; 0.883, 0.898, 0.798, 0.782, 0.819, 0.815, 0.786, 0.800, (5.1658)+ (−0.0933)His+(0.0540)Thr+(0.0051)Pro+(−0.3376) Met+(0.1643)Phe+(−0.1324)Trp; 0.883, 0.900, 0.762, 0.729, 0.754, 0.826, 0.821, 0.782, (1.9680)+(0.0396) Ser+(−0.0956)His+(−0.0123)Val+(0.0554)Ile+ (0.1032)Phe+(−0.1204)Trp; 0.883, 0.898, 0.784, 0.757, 0.792, 0.862, 0.785, 0.799, (5.0116)+(0.0365)Ser+ (−0.0816)His+(0.0226)Thr+(−0.2202)Met+(0.0714) Ile+(−0.0924)Trp; 0.883, 0.901, 0.792, 0.773, 0.791, 0.847, 0.806, 0.804, (3.0109)+(0.0532)Ser+(−0.1029) Asn+(−0.0884)His+(0.0136)Orn+(0.1319)Phe+ (−0.1267)Trp; 0.883, 0.900, 0.786, 0.770, 0.757, 0.851, 0.841, 0.805, (1.0460)+(0.0493)Thr+(−0.0614)Val+ (−0.5303)Met+(−0.0066)Lys+(0.1825)Ile+(0.1493) Phe; 0.883, 0.903, 0.829, 0.818, 0.807, 0.849, 0.892, 0.842, (5.0397)+(−0.0326)His+(−0.0343)Val+ (−0.2336)Met+(0.1210)Ile+(0.1267)Phe+(−0.0933) Trp; 0.882, 0.899, 0.785, 0.773, 0.754, 0.849, 0.837, 0.803, (0.7801)+(0.0474)Thr+(−0.0075)Tyr+(−0.0620) Val+(−0.5326)Met+(0.1806)Ile+(0.1498)Phe; 0.882, 0.898, 0.786, 0.772, 0.756, 0.849, 0.842, 0.805, (0.7094)+(0.0469)Thr+(0.0001)Pro+(−0.0625)Val+ (−0.5411)Met+(0.1817)Ile+(0.1477)Phe; 0.882, 0.899, 0.786, 0.771, 0.756, 0.849, 0.842, 0.805, (0.7287)+ (0.0475)Thr+(−0.0642)Val+(−0.5450)Met+(0.1789) Ile+(0.0050)Leu+(0.1471)Phe; 0.882, 0.899, 0.805, 0.789, 0.807, 0.829, 0.823, 0.812, (−0.2954)+(0.0595) Ser+(−0.0653)Asn+(−0.2876)Met+(0.0433)Ile+ (0.1463)Phe+(−0.1537)Trp; 0.882, 0.900, 0.819, 0.814, 0.793, 0.847, 0.868, 0.830, (3.2539)+(0.0061)Gly+ (−0.0409)Val+(−0.2897)Met+(0.1335)Ile+(0.1368) Phe+(−0.1032)Trp; 0.882, 0.898, 0.798, 0.780, 0.795, 0.846, 0.817, 0.809, (3.2007)+(0.0557)Ser+(−0.0993) Asn+(−0.0015)Gly+(−0.0850)His+(0.1359)Phe+ (−0.1279)Trp; 0.882, 0.900, 0.741, 0.695, 0.759, 0.833, 0.763, 0.762, (−1.5427)+(0.0550)Ser+(−0.1392)His+ (0.0297)Thr+(−0.4182)Met+(0.0553)Ile+(0.1512)Phe; 0.882, 0.895, 0.805, 0.788, 0.782, 0.876, 0.844, 0.823, (3.9518)+(0.0364)Ser+(−0.0291)Val+(−0.2346)Met+ (0.1321)Ile+(−0.0863)Trp; 0.882, 0.896, 0.757, 0.720, 0.757, 0.824, 0.805, 0.776, (1.8875)+(0.0428)Ser+ (−0.1075)His+(0.0302)Ile+(0.1017)Phe+(−0.1267) Trp; 0.882, 0.897, 0.821, 0.819, 0.827, 0.839, 0.801, 0.821, (1.3070)+(0.0603)Ser+(−0.0728) Asn+(−0.0484)Cit+(−0.2247)Met+(0.1651)

Phe+(−0.1517)Trp; 0.882, 0.896, 0.808, 0.803, 0.811, 0.825, 0.804, 0.811, (0.4379)+(0.0587)Ser+(−0.0718)Asn+(0.0068)Pro+(−0.2643)Met+(0.1589)Phe+(−0.1529)Trp; 0.882, 0.898, 0.811, 0.798, 0.786, 0.876, 0.849, 0.827, (5.8199)+(0.0366)Ser+(−0.1098)Asn+(−0.0498)Cit+(−0.0238)Val+(0.1071)Ile+(−0.1023)Trp; 0.882, 0.896, 0.794, 0.791, 0.813, 0.811, 0.753, 0.792, (−0.1750)+(0.0452)Ser+(0.0255)Thr+(−0.3843)Met+(0.1693)Phe+(−0.1668)Trp; 0.882, 0.899, 0.797, 0.784, 0.820, 0.822, 0.766, 0.798, (4.7434)+(0.0043)Gly+(−0.0969)His+(0.0516)Thr+(−0.3247)Met+(0.1714)Phe+(−0.1316)Trp; 0.882, 0.899, 0.793, 0.774, 0.792, 0.844, 0.812, 0.805, (3.0641)+(0.0543)Ser+(−0.0998)Asn+(−0.0887)His+(0.0040)Leu+(0.1330)Phe+(−0.1277)Trp; 0.882, 0.898, 0.805, 0.791, 0.826, 0.821, 0.786, 0.806, (5.4643)+(−0.0922)His+(0.0554)Thr+(−0.3198)Met+(−0.0024)Lys+(0.1671)Phe+(−0.1324)Trp; 0.882, 0.896, 0.804, 0.790, 0.791, 0.865, 0.823, 0.817, (7.3957)+(−0.0482)His+(0.0382)Thr+(−0.0270)Val+(−0.2600)Met+(0.1258)Ile+(−0.0800)Trp; 0.881, 0.895, 0.817, 0.809, 0.786, 0.885, 0.853, 0.834, (6.6887)+(0.0341)Thr+(−0.0054)Ala+(−0.0345)Val+(−0.2668)Met+(0.1478)Ile+(−0.0845)Trp; 0.881, 0.897, 0.798, 0.794, 0.816, 0.823, 0.751, 0.796, (0.2587)+(0.0471)Ser+(0.0290)Thr+(−0.3706)Met+(−0.0105)Lys+(0.1761)Phe+(−0.1636)Trp; 0.881, 0.898, 0.805, 0.797, 0.817, 0.827, 0.786, 0.807, (−0.0129)+(0.0566)Ser+(−0.0507)Cit+(0.0079)Pro+(−0.3110)Met+(0.1611)Phe+(−0.1531)Trp; 0.881, 0.897, 0.806, 0.792, 0.828, 0.819, 0.789, 0.807, (5.5754)+(−0.0149)Asn+(−0.0911)His+(0.0549)Thr+(−0.3115)Met+(0.1657)Phe+(−0.1333)Trp; 0.881, 0.899, 0.834, 0.829, 0.808, 0.848, 0.894, 0.845, (4.9454)+(−0.0295)Asn+(−0.0406)Val+(−0.2362)Met+(0.1316)Ile+(0.1266)Phe+(−0.0995)Trp

List (2) of Logistic Regression Equations Searched in Example 2

The logistic regression equations searched in Example 2 above are listed below. Before each equation, "the value of ROC_AUC for the pancreatic cancer group and the healthy group with validation", "the value of ROC_AUC for the pancreatic cancer group and the healthy group without validation", "the value of ROC_AUC for the pancreatic cancer group and the other cancers group", "the value of ROC_AUC for the pancreatic cancer group and the lung cancer group", "the value of ROC_AUC for the pancreatic cancer group and the colorectal cancer group", "the value of ROC_AUC for the pancreatic cancer group and the prostatic cancer group", "the value of ROC_AUC for the pancreatic cancer group and the breast cancer group", and "the average value of the value of ROC_AUC for the pancreatic cancer group and the lung cancer group, the value of ROC_AUC for the pancreatic cancer group and the colorectal cancer group, the value of ROC_AUC for the pancreatic cancer group and the prostatic cancer group, and the value of ROC_AUC for the pancreatic cancer group and the breast cancer group" obtained for the equation are additionally listed.

0.862, 0.894, 0.855, 0.850, 0.855, 0.863, 0.864, 0.858, (2.2508)+(0.0135)Gln+(−0.1156)His+(−0.0544)Cit+(−0.1821)Met+(0.1518)Phe+(−0.1151)Trp; 0.809, 0.842, 0.860, 0.862, 0.869, 0.866, 0.830, 0.857, (5.7676)+(−0.0593)Asn+(0.0090)Gln+(−0.0683)Cit+(0.0235)Tyr+(−0.0892)Met+(−0.1426)Trp; 0.805, 0.839, 0.859, 0.866, 0.861, 0.867, 0.831, 0.856, (6.0629)+(−0.0739)Asn+(0.0084)Gln+(−0.0022)Ala+(−0.0714)Cit+(0.0130)Tyr+(−0.1421)Trp; 0.861, 0.892, 0.852, 0.845, 0.851, 0.860, 0.867, 0.856, (2.3965)+(0.0128)Gln+(−0.1297)His+(0.0154)Tyr+(−0.2172)Met+(0.1374)Phe+(−0.1094)Trp; 0.826, 0.858, 0.859, 0.874, 0.841, 0.836, 0.870, 0.855, (3.3210)+(−0.0919)Asn+(0.0062)Gln+(−0.0041)Ala+(−0.0060)Val+(0.0931)Phe+(−0.1458)Trp; 0.865, 0.892, 0.852, 0.849, 0.848, 0.857, 0.864, 0.854, (2.5117)+(−0.0105)Asn+(0.0128)Gln+(−0.1258)His+(−0.1885)Met+(0.1391)Phe+(−0.1051)Trp; 0.832, 0.863, 0.856, 0.865, 0.848, 0.848, 0.856, 0.854, (3.4918)+(−0.0812)Asn+(0.0083)Gln+(−0.0048)Ala+(−0.0926)Cit+(0.1044)Phe+(−0.1577)Trp; 0.838, 0.869, 0.859, 0.865, 0.865, 0.838, 0.846, 0.854, (2.2614)+(−0.0481)Asn+(0.0098)Gln+(−0.0872)Cit+(−0.1772)Met+(0.1247)Phe+(−0.1533)Trp; 0.859, 0.890, 0.851, 0.849, 0.847, 0.857, 0.859, 0.853, (2.4884)+(0.0134)Gln+(−0.1272)His+(−0.0096)Arg+(−0.1820)Met+(0.1400)Phe+(−0.1049)Trp; 0.867, 0.892, 0.850, 0.846, 0.846, 0.857, 0.862, 0.853, (2.4271)+(0.0126)Gln+(−0.1275)His+(−0.1955)Met+(0.1405)Phe+(−0.1055)Trp; 0.864, 0.892, 0.849, 0.846, 0.846, 0.856, 0.861, 0.852, (2.4120)+(0.0126)Gln+(−0.1277)His+(0.0002)Ala+(−0.1968)Met+(0.1405)Phe+(−0.1055)Trp; 0.863, 0.892, 0.849, 0.844, 0.846, 0.853, 0.863, 0.851, (2.4047)+(0.0126)Gln+(−0.1304)His+(0.0029)Val+(−0.1969)Met+(0.1366)Phe+(−0.1080)Trp; 0.835, 0.865, 0.859, 0.875, 0.857, 0.820, 0.854, 0.851, (2.1650)+(−0.0499)Asn+(0.0079)Gln+(−0.0068)Val+(−0.2042)Met+(0.1209)Phe+(−0.1369)Trp; 0.857, 0.889, 0.846, 0.840, 0.841, 0.860, 0.862, 0.851, (3.4876)+(−0.0572)Asn+(0.0125)Gln+(−0.1139)His+(−0.0612)Cit+(0.1171)Phe+(−0.1225)Trp; 0.865, 0.893, 0.845, 0.835, 0.844, 0.857, 0.867, 0.851, (2.3748)+(0.0127)Gln+(−0.1335)His+(−0.2057)Met+(0.0145)Leu+(0.1299)Phe+(−0.1120)Trp; 0.820, 0.855, 0.855, 0.869, 0.845, 0.833, 0.855, 0.850, (3.1828)+(−0.0751)Asn+(0.0067)Gln+(−0.0048)Ala+(−0.0135)Arg+(0.0888)Phe+(−0.1544)Trp; 0.805, 0.839, 0.853, 0.857, 0.860, 0.863, 0.821, 0.850, (5.3506)+(0.0073)Gln+(−0.0019)Ala+(−0.0665)Cit+(0.0274)Tyr+(−0.1208)Met+(−0.1440)Trp; 0.805, 0.839, 0.854, 0.866, 0.852, 0.861, 0.821, 0.850, (6.1032)+(−0.0730)Asn+(0.0085)Gln+(−0.0017)Ala+(−0.0706)Cit+(0.0030)Arg+(−0.1376)Trp; 0.810, 0.839, 0.854, 0.867, 0.853, 0.861, 0.819, 0.850, (6.1036)+(−0.0709)Asn+(0.0086)Gln+(−0.0016)Ala+(−0.0689)Cit+(−0.1374)Trp; 0.810, 0.839, 0.855, 0.868, 0.854, 0.861, 0.817, 0.850, (5.9973)+(−0.0607)Asn+(0.0090)Gln+(−0.0008)Ala+(−0.0658)Cit+(−0.0447)Met+(−0.1345)Trp; 0.825, 0.853, 0.852, 0.864, 0.838, 0.830, 0.865, 0.849, (3.1978)+(−0.0869)Asn+(0.0061)Gln+(−0.0051)Ala+(0.0844)Phe+(−0.1536)Trp; 0.826, 0.862, 0.855, 0.868, 0.850, 0.823, 0.855, 0.849, (2.1377)+(−0.0445)Asn+(0.0075)Gln+(−0.0022)Ala+(−0.1950)Met+(0.1113)Phe+(−0.1437)Trp; 0.827, 0.863, 0.857, 0.872, 0.855, 0.823, 0.847, 0.849, (3.2812)+(−0.0886)Asn+(0.0069)Gln+(−0.0139)Arg+(−0.0078)Val+(0.0929)Phe+(−0.1487)Trp; 0.817, 0.853, 0.852, 0.864, 0.838, 0.829, 0.865, 0.849, (3.1937)+(−0.0876)Asn+(0.0060)Gln+(−0.0051)Ala+(0.0004)Lys+(0.0841)Phe+(−0.1538)Trp; 0.862, 0.892, 0.846, 0.841, 0.843, 0.853, 0.858, 0.849, (2.4961)+(0.0121)Gln+(−0.1282)His+(−0.1947)Met+(0.0089)Orn+(0.1359)Phe+(−0.1050)Trp; 0.808, 0.840, 0.853, 0.865, 0.854, 0.859, 0.816, 0.849, (5.9367)+(−0.0631)Asn+(0.0089)Gln+(−0.0682)Cit+(0.0039)Arg+(−0.0539)Met+(−0.1360)Trp; 0.842, 0.868, 0.838, 0.828, 0.823, 0.866, 0.876, 0.848, (4.8214)+(−0.0550)Asn+(0.0081)Gln+(−0.0076)Ala+

(−0.0880)Cit+(0.0799)Ile+(−0.1627)Trp; 0.828, 0.856, 0.846, 0.845, 0.844, 0.866, 0.837, 0.848, (6.2674)+ (−0.0542)Asn+(0.0120)Gln+(−0.0952)His+(−0.0395) Cit+(0.0220)Tyr+(−0.1092)Trp; 0.858, 0.885, 0.843, 0.841, 0.829, 0.856, 0.866, 0.848, (3.7749)+(−0.0504) Asn+(0.0112)Gln+(−0.1257)His+(−0.0027)Ala+ (0.1070)Phe+(−0.1122)Trp; 0.813, 0.839, 0.853, 0.866, 0.853, 0.859, 0.814, 0.848, (5.9487)+(−0.0612)Asn+ (0.0091)Gln+(−0.0660)Cit+(−0.0511)Met+(−0.1357) Trp; 0.873, 0.900, 0.837, 0.818, 0.833, 0.859, 0.882, 0.848, (2.0349)+(0.0121)Gln+(−0.1284)His+(−0.2378) Met+(0.0584)Ile+(0.1200)Phe+(−0.1165)Trp; 0.818, 0.853, 0.851, 0.863, 0.836, 0.828, 0.865, 0.848, (3.1849)+(−0.0865)Asn+(0.0060)Gln+(−0.0052)Ala+ (0.0017)Leu+(0.0830)Phe+(−0.1548)Trp; 0.807, 0.836, 0.852, 0.864, 0.850, 0.858, 0.819, 0.848, (5.9789)+(−0.0773)Asn+(0.0083)Gln+(−0.0018)Ala+ (−0.0686)Cit+(0.0044)Lys+(−0.1405)Trp; 0.834, 0.865, 0.852, 0.858, 0.855, 0.835, 0.843, 0.848, (2.0349)+(0.0082)Gln+(−0.0027)Ala+(−0.0866)Cit+ (−0.1904)Met+(0.1300)Phe+(−0.1549)Trp; 0.823, 0.855, 0.845, 0.841, 0.845, 0.870, 0.834, 0.848, (5.8022)+(0.0115)Gln+(−0.0987)His+(−0.0345)Cit+ (0.0344)Tyr+(−0.0969)Met+(−0.1080)Trp; 0.832, 0.863, 0.852, 0.860, 0.850, 0.835, 0.845, 0.848, (3.5427)+(−0.0934)Asn+(0.0083)Gln+(−0.0913)Cit+ (−0.0035)Val+(0.0985)Phe+(−0.1588)Trp; 0.832, 0.863, 0.854, 0.868, 0.847, 0.820, 0.856, 0.848, (3.3020)+(−0.1020)Asn+(0.0061)Gln+(−0.0083)Val+ (0.0893)Phe+(−0.1476)Trp; 0.809, 0.835, 0.852, 0.860, 0.857, 0.854, 0.818, 0.848, (5.9745)+(−0.0783)Asn+ (0.0085)Gln+(−0.0724)Cit+(0.0081)Tyr+(−0.1447) Trp; 0.795, 0.830, 0.852, 0.866, 0.845, 0.852, 0.827, 0.848, (5.1777)+(−0.0531)Asn+(0.0075)Gln+ (−0.0015)Ala+(0.0202)Tyr+(−0.1137)Met+(−0.1356) Trp; 0.864, 0.892, 0.844, 0.840, 0.841, 0.848, 0.860, 0.847, (2.0904)+(0.0121)Gln+(−0.1342)His+(−0.2275) Met+(0.0111)Lys+(0.1425)Phe+(−0.1118)Trp; 0.802, 0.835, 0.852, 0.860, 0.856, 0.854, 0.819, 0.847, (5.9724)+(−0.0793)Asn+(0.0084)Gln+(−0.0731)Cit+ (0.0014)Arg+(0.0078)Tyr+(−0.1447)Trp; 0.821, 0.854, 0.850, 0.862, 0.836, 0.831, 0.861, 0.847, (3.0860)+ (−0.0887)Asn+(0.0010)Gly+(0.0059)Gln+(−0.0051) Ala+(0.0855)Phe+(−0.1536)Trp; 0.809, 0.852, 0.849, 0.861, 0.834, 0.831, 0.861, 0.847, (3.2964)+(−0.0890) Asn+(0.0057)Gln+(−0.0053)Ala+(0.0094)Orn+ (0.0792)Phe+(−0.1521)Trp; 0.825, 0.855, 0.846, 0.851, 0.839, 0.868, 0.829, 0.847, (6.3495)+(−0.0438)Asn+ (0.0121)Gln+(−0.0878)His+(−0.0359)Cit+(−0.0188) Met+(−0.0982)Trp; 0.807, 0.836, 0.851, 0.859, 0.852, 0.856, 0.819, 0.847, (5.8630)+(−0.0663)Asn+(0.0085) Gln+(−0.0027)Ala+(−0.0747)Cit+(0.0053)Val+ (−0.1459)Trp; 0.832, 0.862, 0.850, 0.856, 0.852, 0.836, 0.843, 0.847, (3.5137)+(−0.0865)Asn+(0.0084)Gln+ (−0.0950)Cit+(−0.0029)Lys+(0.0955)Phe+(−0.1631) Trp; 0.830, 0.857, 0.843, 0.842, 0.838, 0.866, 0.839, 0.846, (5.9220)+(−0.0347)Asn+(0.0121)Gln+ (−0.1045)His+(0.0317)Tyr+(−0.0819)Met+(−0.1044) Trp; 0.842, 0.868, 0.836, 0.824, 0.827, 0.864, 0.868, 0.846, (4.3742)+(0.0074)Gln+(−0.0067)Ala+ (−0.0814)Cit+(−0.1076)Met+(0.0844)Ile+(−0.1569) Trp; 0.802, 0.839, 0.845, 0.851, 0.830, 0.847, 0.856, 0.846, (5.2638)+(−0.0625)Asn+(0.0077)Gln+ (−0.0271)Val+(−0.1255)Met+(0.0579)Leu+(−0.1291) Trp; 0.866, 0.895, 0.843, 0.838, 0.841, 0.846, 0.859, 0.846, (2.3031)+(0.0124)Gln+(−0.1264)His+(0.0070) Pro+(−0.2170)Met+(0.1381)Phe+(−0.1083)Trp; 0.814, 0.838, 0.850, 0.862, 0.851, 0.855, 0.816, 0.846, (6.0237)+(−0.0754)Asn+(0.0086)Gln+(−0.0705)Cit+ (−0.1410)Trp; 0.828, 0.863, 0.852, 0.866, 0.843, 0.822, 0.851, 0.845, (3.1762)+(−0.1039)Asn+(0.0010)Gly+ (0.0060)Gln+(−0.0083)Val+(0.0907)Phe+(−0.1474) Trp; 0.812, 0.846, 0.844, 0.845, 0.841, 0.849, 0.847, 0.845, (5.8225)+(−0.0862)Asn+(0.0084)Gln+ (−0.0688)Cit+(−0.0187)Val+(0.0445)Leu+(−0.1483) Trp; 0.799, 0.833, 0.842, 0.850, 0.819, 0.851, 0.861, 0.845, (5.5360)+(−0.0888)Asn+(0.0066)Gln+ (−0.0032)Ala+(−0.0254)Val+(0.0532)Leu+(−0.1346) Trp; 0.809, 0.841, 0.850, 0.865, 0.847, 0.865, 0.804, 0.845, (5.9980)+(−0.0739)Asn+(0.0019)Gly+(0.0084) Gln+(−0.0016)Ala+(−0.0714)Cit+(−0.1371)Trp; 0.808, 0.838, 0.851, 0.863, 0.852, 0.851, 0.813, 0.845, (5.7387)+(−0.0657)Asn+(0.0087)Gln+(−0.0647)Cit+ (−0.0687)Met+(0.0064)Lys+(−0.1396)Trp; 0.828, 0.854, 0.844, 0.849, 0.837, 0.865, 0.828, 0.845, (6.3750)+(−0.0487)Asn+(0.0120)Gln+(−0.0891)His+ (0.0001)Ala+(−0.0370)Cit+(−0.0999)Trp; 0.830, 0.854, 0.844, 0.850, 0.837, 0.865, 0.828, 0.845, (6.3815)+(−0.0485)Asn+(0.0120)Gln+(−0.0889)His+ (−0.0370)Cit+(−0.0997)Trp; 0.808, 0.838, 0.849, 0.861, 0.850, 0.854, 0.814, 0.845, (6.0191)+(−0.0769) Asn+(0.0085)Gln+(−0.0717)Cit+(0.0021)Arg+ (−0.1413)Trp; 0.824, 0.861, 0.851, 0.866, 0.843, 0.816, 0.855, 0.845, (3.2955)+(−0.1079)Asn+(0.0060)Gln+ (−0.0091)Val+(0.0032)Lys+(0.0884)Phe+(−0.1481) Trp; 0.849, 0.882, 0.838, 0.832, 0.827, 0.859, 0.861, 0.845, (3.3973)+(0.0107)Gln+(−0.1187)His+(−0.0036) Ala+(−0.0613)Cit+(0.1236)Phe+(−0.1262)Trp; 0.801, 0.838, 0.848, 0.853, 0.858, 0.856, 0.812, 0.845, (5.2374)+(0.0073)Gln+(−0.0668)Cit+(0.0001)Arg+ (0.0253)Tyr+(−0.1322)Met+(−0.1461)Trp; 0.807, 0.839, 0.848, 0.853, 0.858, 0.856, 0.811, 0.844, (5.2385)+(0.0073)Gln+(−0.0667)Cit+(0.0253)Tyr+ (−0.1321)Met+(−0.1460)Trp; 0.861, 0.885, 0.829, 0.818, 0.801, 0.875, 0.883, 0.844, (4.9134)+(0.0066) Gln+(−0.0570)Cit+(−0.0378)Val+(−0.1870)Met+ (0.1670)Ile+(−0.1228)Trp; 0.833, 0.861, 0.848, 0.854, 0.849, 0.831, 0.842, 0.844, (3.4802)+(−0.0912)Asn+ (0.0082)Gln+(−0.0940)Cit+(0.0930)Phe+(−0.1645) Trp; 0.788, 0.824, 0.848, 0.864, 0.835, 0.847, 0.831, 0.844, (5.4817)+(−0.0765)Asn+(−0.0006)Gly+ (0.0068)Gln+(−0.0028)Ala+(0.0026)Tyr+(−0.1349) Trp; 0.803, 0.835, 0.849, 0.858, 0.853, 0.849, 0.816, 0.844, (5.8759)+(−0.0832)Asn+(0.0083)Gln+ (−0.0719)Cit+(0.0063)Tyr+(0.0034)Lys+(−0.1467) Trp; 0.807, 0.837, 0.849, 0.857, 0.856, 0.851, 0.813, 0.844, (5.6996)+(−0.0573)Asn+(0.0089)Gln+ (−0.0708)Cit+(0.0045)Val+(−0.0602)Met+(−0.1435) Trp; 0.831, 0.865, 0.844, 0.852, 0.829, 0.820, 0.876, 0.844, (3.5014)+(−0.1103)Asn+(0.0060)Gln+ (−0.0296)Val+(0.0453)Leu+(0.0850)Phe+(−0.1518) Trp; 0.827, 0.861, 0.853, 0.866, 0.855, 0.812, 0.843, 0.844, (2.0627)+(−0.0417)Asn+(0.0081)Gln+ (−0.0089)Arg+(−0.2034)Met+(0.1115)Phe+(−0.1455) Trp; 0.809, 0.840, 0.845, 0.849, 0.845, 0.848, 0.834, 0.844, (5.6309)+(−0.0669)Asn+(0.0083)Gln+ (−0.0036)Ala+(−0.0762)Cit+(0.0191)Leu+(−0.1522) Trp; 0.880, 0.900, 0.831, 0.825, 0.800, 0.853, 0.898, 0.844, (1.6131)+(0.0057)Gln+(−0.0525)Val+(−0.3431) Met+(0.1808)Ile+(0.1304)Phe+(−0.1173)Trp; 0.829, 0.861, 0.848, 0.854, 0.849, 0.831, 0.842, 0.844, (3.4795)+(−0.0908)Asn+(0.0082)Gln+(−0.0937)Cit+ (−0.0005)Arg+(0.0930)Phe+(−0.1645)Trp; 0.824, 0.852, 0.843, 0.850, 0.837, 0.865, 0.824, 0.844, (6.3859)+(−0.0451)Asn+(0.0123)Gln+(−0.0902)His+ (−0.0340)Cit+(−0.0043)Arg+(−0.0988)Trp; 0.817, 0.847, 0.847, 0.844, 0.850, 0.839, 0.858, 0.828, 0.844, (6.2658)+(−0.0673)Asn+(0.0081)Gln+(−0.0054)Ala+ (−0.0773)Cit+(0.0130)Pro+(−0.1416)Trp; 0.824, 0.861, 0.852, 0.864, 0.852, 0.812, 0.847, 0.844, (2.0112)+(−0.0454)Asn+(0.0076)Gln+(0.0016)Tyr+ (−0.2134)Met+(0.1094)Phe+(−0.1459)Trp; 0.810, 0.841, 0.849, 0.863, 0.849, 0.860, 0.802, 0.844, (5.8487)+(−0.0641)Asn+(0.0019)Gly+(0.0089)Gln+ (−0.0685)Cit+(−0.0502)Met+(−0.1355)Trp; 0.836, 0.869, 0.845, 0.851, 0.836, 0.820, 0.867, 0.844, (1.7715)+(0.0065)Gln+(−0.0319)Val+(−0.2619)Met+ (0.0539)Leu+(0.1213)Phe+(−0.1461)Trp; 0.854, 0.879, 0.828, 0.821, 0.791, 0.876, 0.886, 0.844, (5.6074)+(−0.0967)Asn+(0.0077)Gln+(−0.0706)Cit+ (−0.0363)Val+(0.1494)Ile+(−0.1313)Trp; 0.866, 0.894, 0.840, 0.838, 0.836, 0.858, 0.841, 0.843, (2.0299)+ (0.0044)Gly+(0.0119)Gln+(−0.1319)His+(−0.2072) Met+(0.1476)Phe+(−0.1045)Trp; 0.786, 0.824, 0.848, 0.866, 0.837, 0.847, 0.822, 0.843, (5.4570)+(−0.0712) Asn+(0.0072)Gln+(−0.0026)Ala+(−0.0084)Arg+ (0.0048)Tyr+(−0.1345)Trp; 0.829, 0.860, 0.847, 0.852, 0.849, 0.831, 0.842, 0.843, (3.4683)+(−0.0911)Asn+ (0.0082)Gln+(−0.0942)Cit+(0.0018)Leu+(0.0913) Phe+(−0.1660)Trp; 0.833, 0.861, 0.851, 0.863, 0.852, 0.811, 0.846, 0.843, (2.0143)+(−0.0455)Asn+(0.0076) Gln+(−0.2109)Met+(0.1098)Phe+(−0.1455)Trp; 0.793, 0.831, 0.848, 0.862, 0.846, 0.844, 0.821, 0.843, (5.1177)+(−0.0542)Asn+(−0.0002)Gly+(0.0076)Gln+ (0.0182)Tyr+(−0.1223)Met+(−0.1367)Trp; 0.837, 0.865, 0.838, 0.826, 0.840, 0.853, 0.853, 0.843, (4.5403)+(−0.0428)Asn+(0.0087)Gln+(−0.0781)Cit+ (−0.1229)Met+(0.0689)Ile+(−0.1589)Trp; 0.830, 0.863, 0.849, 0.863, 0.844, 0.821, 0.845, 0.843, (3.4816)+(−0.1074)Asn+(0.0056)Gln+(−0.0101)Val+ (0.0148)Orn+(0.0846)Phe+(−0.1431)Trp; 0.835, 0.865, 0.850, 0.856, 0.858, 0.826, 0.833, 0.843, (1.8996)+(0.0083)Gln+(−0.0849)Cit+(−0.0021)Val+ (−0.2102)Met+(0.1306)Phe+(−0.1546)Trp; 0.828, 0.865, 0.849, 0.854, 0.859, 0.826, 0.833, 0.843, (1.8779)+(0.0083)Gln+(−0.0865)Cit+(0.0037)Tyr+ (−0.2157)Met+(0.1267)Phe+(−0.1580)Trp; 0.820, 0.849, 0.848, 0.859, 0.853, 0.872, 0.788, 0.843, (6.7018)+(−0.0985)Asn+(0.0072)Gln+(0.0206)Thr+ (−0.0028)Ala+(−0.0740)Cit+(−0.1456)Trp; 0.788, 0.823, 0.847, 0.865, 0.834, 0.845, 0.829, 0.843, (5.4951)+(−0.0756)Asn+(−0.0007)Gly+(0.0069)Gln+ (−0.0027)Ala+(0.0002)Val+(−0.1344)Trp; 0.796, 0.824, 0.847, 0.865, 0.834, 0.845, 0.829, 0.843, (5.5074)+(−0.0757)Asn+(−0.0007)Gly+(0.0069)Gln+ (−0.0027)Ala+(−0.1341)Trp; 0.787, 0.825, 0.847, 0.863, 0.834, 0.847, 0.827, 0.843, (5.4224)+(−0.0774) Asn+(0.0067)Gln+(−0.0028)Ala+(0.0030)Tyr+ (0.0001)Val+(−0.1351)Trp; 0.841, 0.866, 0.832, 0.819, 0.816, 0.863, 0.874, 0.843, (4.7910)+(0.0072)Gln+ (−0.0086)Ala+(−0.0936)Cit+(−0.0102)Lys+(0.0909) Ile+(−0.1638)Trp; 0.794, 0.825, 0.846, 0.863, 0.834, 0.847, 0.827, 0.843, (5.4282)+(−0.0775)Asn+(0.0067) Gln+(−0.0028)Ala+(0.0031)Tyr+(−0.1350)Trp; 0.790, 0.829, 0.849, 0.863, 0.849, 0.844, 0.815, 0.843, (5.1494)+(−0.0511)Asn+(0.0079)Gln+(−0.0070)Arg+ (0.0196)Tyr+(−0.1191)Met+(−0.1358)Trp; 0.827, 0.861, 0.851, 0.863, 0.851, 0.811, 0.846, 0.843, (2.0069)+(−0.0454)Asn+(0.0076)Gln+(−0.2115)Met+ (0.0008)Leu+(0.1092)Phe+(−0.1460)Trp; 0.798, 0.831, 0.848, 0.861, 0.846, 0.844, 0.820, 0.843, (5.0998)+(−0.0544)Asn+(0.0075)Gln+(0.0184)Tyr+ (−0.1226)Met+(−0.1367)Trp; 0.804, 0.836, 0.847, 0.854, 0.855, 0.848, 0.814, 0.843, (5.8144)+(−0.0763) Asn+(0.0084)Gln+(−0.0758)Cit+(0.0057)Tyr+ (0.0032)Val+(−0.1501)Trp; 0.851, 0.875, 0.833, 0.828, 0.814, 0.868, 0.860, 0.843, (4.8479)+(−0.0763)Asn+ (0.0085)Gln+(−0.0834)Cit+(0.1455)Ile+(−0.0584) Leu+(−0.1487)Trp; 0.856, 0.885, 0.840, 0.838, 0.833, 0.848, 0.851, 0.843, (3.6081)+(−0.0403)Asn+(0.0126) Gln+(−0.1304)His+(−0.0168)Arg+(0.1065)Phe+ (−0.1131) Trp

List (2) of Linear Discriminants Searched in Example 2

The linear discriminants searched in Example 2 above are listed below. Before each equation, "the value of ROC_AUC for the pancreatic cancer group and the healthy group with validation", "the value of ROC_AUC for the pancreatic cancer group and the healthy group without validation", "the value of ROC_AUC for the pancreatic cancer group and the other cancers group", "the value of ROC_AUC for the pancreatic cancer group and the lung cancer group", "the value of ROC_AUC for the pancreatic cancer group and the colorectal cancer group", "the value of ROC_AUC for the pancreatic cancer group and the prostatic cancer group", "the value of ROC_AUC for the pancreatic cancer group and the breast cancer group", and "the average value of the value of ROC_AUC for the pancreatic cancer group and the lung cancer group, the value of ROC_AUC for the pancreatic cancer group and the colorectal cancer group, the value of ROC_AUC for the pancreatic cancer group and the prostatic cancer group, and the value of ROC_AUC for the pancreatic cancer group and the breast cancer group" obtained for the equation are additionally listed.

0.876, 0.897, 0.863, 0.862, 0.862, 0.864, 0.866, 0.864, (2.6773)+(0.0131)Gln+(−0.0833)His+(−0.0369)Cit+ (−0.1942)Met+(0.1325)Phe+(−0.1189)Trp; 0.815, 0.839, 0.865, 0.874, 0.862, 0.879, 0.839, 0.864, (6.3554)+(−0.0849)Asn+(0.0097)Gln+(−0.0031)Ala+ (−0.0554)Cit+(0.0122)Tyr+(−0.1240)Trp; 0.875, 0.897, 0.861, 0.858, 0.856, 0.868, 0.871, 0.863, (4.1845)+(−0.0886)Asn+(0.0124)Gln+(−0.0795)His+ (−0.0439)Cit+(0.1039)Phe+(−0.1254)Trp; 0.844, 0.868, 0.866, 0.876, 0.856, 0.852, 0.867, 0.863, (4.2725)+(−0.1063)Asn+(0.0099)Gln+(−0.0038)Ala+ (−0.0633)Cit+(0.0905)Phe+(−0.1475) Trp; 0.818, 0.842, 0.865, 0.869, 0.870, 0.872, 0.837, 0.862, (5.8158)+(−0.0671)Asn+(0.0103)Gln+(−0.0536)Cit+ (0.0213)Tyr+(−0.0888)Met+(−0.1263)Trp; 0.852, 0.873, 0.867, 0.875, 0.870, 0.842, 0.860, 0.862, (2.9709)+(−0.0695)Asn+(0.0114)Gln+(−0.0601)Cit+ (−0.1650)Met+(0.1155)Phe+(−0.1481)Trp; 0.877, 0.895, 0.861, 0.862, 0.858, 0.856, 0.870, 0.861, (3.0012)+(−0.0367)Asn+(0.0128)Gln+(−0.0871)His+ (−0.1691)Met+(0.1301)Phe+(−0.1171)Trp; 0.849, 0.871, 0.866, 0.877, 0.860, 0.843, 0.863, 0.861, (4.4184)+(−0.1197)Asn+(0.0097)Gln+(−0.0558)Cit+ (−0.0076)Val+(0.1001)Phe+(−0.1461)Trp; 0.846, 0.865, 0.851, 0.844, 0.833, 0.878, 0.888, 0.861, (5.4014)+(−0.0795)Asn+(0.0089)Gln+(−0.0071)Ala+ (−0.0725)Cit+(0.0602)Ile+(−0.1221)Trp; 0.850, 0.871, 0.863, 0.870, 0.862, 0.847, 0.859, 0.860, (4.1784)+ (−0.1095)Asn+(0.0102)Gln+(−0.0648)Cit+(−0.0050) Lys+(0.0905)Phe+(−0.1510)Trp; 0.874, 0.895, 0.858, 0.856, 0.856, 0.855, 0.870, 0.859, (2.5573)+(0.0121) Gln+(−0.0909)His+(0.0123)Tyr+(−0.2108)Met+ (0.1287)Phe+(−0.1198)Trp; 0.817, 0.839, 0.863, 0.878, 0.856, 0.874, 0.827, 0.859, (6.2806)+(−0.0688)Asn+ (0.0103)Gln+(−0.0018)Ala+(−0.0528)Cit+(−0.0466)

Met+(−0.1161)Trp; 0.816, 0.839, 0.861, 0.875, 0.852, 0.873, 0.833, 0.858, (6.5510)+(−0.0865)Asn+(0.0094) Gln+(−0.0028)Ala+(−0.0594)Cit+(0.0068)Arg+ (−0.1198)Trp; 0.816, 0.841, 0.859, 0.868, 0.853, 0.869, 0.843, 0.858, (6.0813)+(−0.0835)Asn+(0.0098)Gln+(−0.0036)Ala+(−0.0596)Cit+(0.0105)Leu+(−0.1236)Trp; 0.820, 0.838, 0.861, 0.875, 0.855, 0.872, 0.830, 0.858, (6.4488)+(−0.0822)Asn+(0.0098)Gln+(−0.0026)Ala+ (−0.0545)Cit+(−0.1189)Trp; 0.815, 0.838, 0.861, 0.875, 0.854, 0.872, 0.830, 0.858, (6.4299)+(−0.0829) Asn+(0.0098)Gln+(−0.0026)Ala+(−0.0545)Cit+ (0.0006)Lys+(−0.1193)Trp; 0.863, 0.881, 0.846, 0.844, 0.814, 0.886, 0.888, 0.858, (6.0987)+(−0.1059)Asn+ (0.0079)Gln+(−0.0561)Cit+(−0.0246)Val+(0.1006) Ile+(−0.1051)Trp; 0.838, 0.861, 0.862, 0.879, 0.845, 0.838, 0.871, 0.858, (4.5654)+(−0.1123)Asn+(0.0076) Gln+(−0.0024)Ala+(−0.0100)Val+(0.1002)Phe+ (−0.1400)Trp; 0.816, 0.838, 0.861, 0.873, 0.856, 0.871, 0.831, 0.858, (6.2809)+(−0.0810)Asn+(0.0098)Gln+ (−0.0030)Ala+(−0.0574)Cit+(0.0023)Val+(−0.1217) Trp; 0.848, 0.868, 0.865, 0.880, 0.860, 0.826, 0.863, 0.857, (3.3302)+(−0.0714)Asn+(0.0094) Gln+(−0.0103)Val+(−0.1688)Met+(0.1280)Phe+ (−0.1379)Trp; 0.821, 0.844, 0.858, 0.865, 0.851, 0.863, 0.849, 0.857, (6.2656)+(−0.1002)Asn+(0.0095)Gln+ (−0.0522)Cit+(−0.0132)Val+(0.0269)Leu+(−0.1204) Trp; 0.813, 0.838, 0.859, 0.867, 0.859, 0.872, 0.831, 0.857, (5.3275)+(0.0086)Gln+(−0.0027)Ala+ (−0.0507)Cit+(0.0266)Tyr+(−0.1304)Met+(−0.1249) Trp; 0.870, 0.890, 0.853, 0.855, 0.840, 0.857, 0.876, 0.857, (4.2458)+(−0.0784)Asn+(0.0110)Gln+ (−0.0865)His+(−0.0023)Ala+(0.1026)Phe+(−0.1193) Trp; 0.846, 0.869, 0.862, 0.872, 0.861, 0.839, 0.853, 0.856, (4.1950)+(−0.1153)Asn+(0.0098)Gln+ (−0.0611)Cit+(−0.0087)Leu+(0.0973)Phe+(−0.1515) Trp; 0.871, 0.894, 0.855, 0.856, 0.851, 0.852, 0.865, 0.856, (2.6471)+(0.0123)Gln+(−0.0905)His+(−0.0020) Arg+(−0.1937)Met+(0.1307)Phe+(−0.1158)Trp; 0.834, 0.855, 0.855, 0.863, 0.845, 0.878, 0.837, 0.856, (6.7550)+(−0.0609)Asn+(0.0118)Gln+(−0.0620)His+ (−0.0012)Ala+(−0.0377)Cit+(−0.0952)Trp; 0.877, 0.896, 0.853, 0.850, 0.850, 0.854, 0.868, 0.856, (2.5522)+(0.0122)Gln+(−0.0940)His+(−0.2001)Met+ (0.0059)Leu+(0.1259)Phe+(−0.1162)Trp; 0.874, 0.893, 0.854, 0.854, 0.850, 0.852, 0.865, 0.855, (2.6456)+ (0.0121)Gln+(−0.0905)His+(−0.0000)Ala+(−0.1962) Met+(0.1311)Phe+(−0.1162)Trp; 0.820, 0.843, 0.857, 0.868, 0.849, 0.868, 0.836, 0.855, (6.4530)+(−0.0810) Asn+(0.0091)Gln+(−0.0041)Ala+(−0.0552)Cit+ (0.0059)Pro+(−0.1177)Trp; 0.876, 0.893, 0.854, 0.854, 0.850, 0.852, 0.865, 0.855, (2.6445)+(0.0121)Gln+ (−0.0905)His+(−0.1963)Met+(0.1311)Phe+(−0.1162) Trp; 0.874, 0.893, 0.854, 0.855, 0.849, 0.852, 0.864, 0.855, (2.6523)+(0.0121)Gln+(−0.0902)His+(−0.0002) Val+(−0.1963)Met+(0.1314)Phe+(−0.1161)Trp; 0.836, 0.858, 0.854, 0.857, 0.851, 0.872, 0.840, 0.855, (6.5444)+(−0.0675)Asn+(0.0117)Gln+(−0.0648)His+ (−0.0387)Cit+(0.0131)Tyr+(−0.1028)Trp; 0.808, 0.832, 0.853, 0.866, 0.829, 0.864, 0.860, 0.855, (6.4282)+(−0.0939)Asn+(0.0075)Gln+(−0.0029)Ala+ (−0.0179)Val+(0.0326)Leu+(−0.1132)Trp; 0.843, 0.866, 0.858, 0.872, 0.844, 0.831, 0.873, 0.855, (4.6216)+(−0.1240)Asn+(0.0075)Gln+(−0.0187)Val+ (0.0156)Leu+(0.0954)Phe+(−0.1391)Trp; 0.872, 0.893, 0.854, 0.853, 0.849, 0.852, 0.863, 0.855, (2.6500)+(0.0119)Gln+(−0.0907)His+(−0.1957)Met+ (0.0024)Orn+(0.1302)Phe+(−0.1160)Trp; 0.836, 0.857, 0.855, 0.863, 0.848, 0.875, 0.832, 0.855, (6.5627)+ (−0.0499)Asn+(0.0122)Gln+(−0.0619)His+(−0.0363) Cit+(−0.0430)Met+(−0.0935)Trp; 0.874, 0.894, 0.854, 0.853, 0.850, 0.850, 0.864, 0.855, (2.5315)+(0.0119) Gln+(−0.0916)His+(−0.2033)Met+(0.0029)Lys+ (0.1306)Phe+(−0.1171)Trp; 0.821, 0.840, 0.859, 0.873, 0.856, 0.867, 0.822, 0.854, (6.1205)+(−0.0704)Asn+ (0.0103)Gln+(−0.0531)Cit+(−0.0570)Met+(−0.1186) Trp; 0.803, 0.830, 0.857, 0.871, 0.848, 0.859, 0.840, 0.854, (5.7371)+(−0.0592)Asn+(0.0082)Gln+ (−0.0024)Ala+(0.0223)Tyr+(−0.0910)Met+(−0.1242) Trp; 0.833, 0.857, 0.853, 0.852, 0.853, 0.876, 0.836, 0.854, (5.7659)+(0.0113)Gln+(−0.0684)His+(−0.0335) Cit+(0.0279)Tyr+(−0.1168)Met+(−0.1013)Trp; 0.844, 0.868, 0.859, 0.867, 0.858, 0.837, 0.855, 0.854, (4.0726)+(−0.1158)Asn+(0.0098)Gln+(−0.0646)Cit+ (−0.0003)Pro+(0.0876)Phe+(−0.1537)Trp; 0.850, 0.868, 0.859, 0.866, 0.858, 0.837, 0.856, 0.854, (4.0736)+(−0.1158)Asn+(0.0098)Gln+(−0.0646)Cit+ (0.0874)Phe+(−0.1537)Trp; 0.832, 0.855, 0.859, 0.875, 0.845, 0.832, 0.865, 0.854, (4.2884)+(−0.1042)Asn+ (0.0075)Gln+(−0.0033)Ala+(−0.0103)Leu+(0.0951) Phe+(−0.1460)Trp; 0.832, 0.856, 0.857, 0.870, 0.842, 0.834, 0.870, 0.854, (4.2512)+(−0.0983)Asn+(0.0076) Gln+(−0.0040)Ala+(−0.0036)Lys+(0.0857)Phe+ (−0.1455)Trp; 0.850, 0.870, 0.845, 0.837, 0.831, 0.873, 0.876, 0.854, (4.3443)+(0.0086)Gln+(−0.0065)Ala+ (−0.0699)Cit+(−0.1457)Met+(0.0719)Ile+(−0.1159) Trp; 0.839, 0.861, 0.849, 0.842, 0.845, 0.865, 0.863, 0.854, (5.3657)+(−0.0871)Asn+(0.0095)Gln+ (−0.0723)Cit+(−0.0074)Lys+(0.0506)Ile+(−0.1284) Trp; 0.841, 0.864, 0.860, 0.876, 0.849, 0.828, 0.861, 0.853, (4.4599)+(−0.1165)Asn+(0.0079) Gln+(−0.0038)Arg+(−0.0112)Val+(0.1003)Phe+ (−0.1418)Trp; 0.816, 0.839, 0.854, 0.867, 0.835, 0.857, 0.855, 0.853, (5.9653)+(−0.0715)Asn+(0.0085) Gln+(−0.0217)Val+(−0.1018)Met+(0.0410)Leu+ (−0.1085)Trp; 0.817, 0.840, 0.857, 0.870, 0.852, 0.867, 0.825, 0.853, (6.2031)+(−0.0741)Asn+(0.0099)Gln+ (−0.0582)Cit+(0.0072)Arg+(−0.0613)Met+(−0.1196) Trp; 0.852, 0.871, 0.838, 0.841, 0.787, 0.885, 0.901, 0.853, (6.3239)+(−0.0898)Asn+(0.0056)Gln+ (−0.0062)Ala+(−0.0277)Val+(0.1121)Ile+(−0.0928) Trp; 0.812, 0.838, 0.858, 0.867, 0.860, 0.860, 0.827, 0.853, (6.1992)+(−0.0911)Asn+(0.0097)Gln+ (−0.0564)Cit+(0.0078)Tyr+(−0.0007)Lys+(−0.1273) Trp; 0.873, 0.893, 0.852, 0.852, 0.844, 0.849, 0.868, 0.853, (4.0710)+(−0.0792)Asn+(0.0116)Gln+ (−0.0890)His+(−0.0058)Arg+(0.1011)Phe+(−0.1209) Trp; 0.868, 0.886, 0.840, 0.833, 0.815, 0.884, 0.881, 0.853, (4.7899)+(0.0075)Gln+(−0.0516)Cit+(−0.0267) Val+(−0.2009)Met+(0.1234)Ile+(−0.0924)Trp; 0.816, 0.838, 0.857, 0.867, 0.859, 0.859, 0.828, 0.853, (6.1771)+(−0.0919)Asn+(0.0096)Gln+(−0.0564)Cit+ (0.0076)Tyr+(−0.1277)Trp; 0.814, 0.839, 0.858, 0.870, 0.857, 0.864, 0.822, 0.853, (5.9708)+(−0.0693)Asn+ (0.0104)Gln+(−0.0552)Cit+(0.0016)Val+(−0.0603) Met+(−0.1209)Trp; 0.886, 0.905, 0.844, 0.843, 0.816, 0.856, 0.897, 0.853, (2.0355)+(0.0066)Gln+(−0.0397) Val+(−0.3168)Met+(0.1284)Ile+(0.1311)Phe+ (−0.1090)Trp; 0.818, 0.840, 0.856, 0.873, 0.848, 0.877, 0.814, 0.853, (6.3593)+(−0.0845)Asn+(0.0024)Gly+ (0.0095)Gln+(−0.0027)Ala+(−0.0576)Cit+(−0.1181) Trp; 0.814, 0.838, 0.857, 0.867, 0.859, 0.859, 0.827, 0.853, (6.1678)+(−0.0919)Asn+(0.0096)Gln+ (−0.0565)Cit+(0.0075)Tyr+(0.0001)Val+(−0.1278) Trp; 0.873, 0.892, 0.851, 0.852, 0.842, 0.848, 0.870, 0.853, (4.2347)+(−0.0860)Asn+(0.0110)Gln+(−0.0853)His+(−0.0024)Val+(0.1046)Phe+(−0.1211)Trp; 0.837, 0.858, 0.851, 0.854, 0.847, 0.868, 0.841, 0.853, (6.0881)+(−0.0392)Asn+(0.0112)Gln+(−0.0715)His+(0.0254)Tyr+(−0.0882)Met+(−0.0993)Trp; 0.873, 0.893, 0.844, 0.848, 0.810, 0.852, 0.899, 0.852, (4.5526)+(−0.1319)Asn+(0.0058)Gln+(−0.0339)Val+(0.0933)Ile+(0.0918)Phe+(−0.1225)Trp; 0.845, 0.867, 0.842, 0.833, 0.823, 0.873, 0.880, 0.852, (5.0406)+(0.0070)Gln+(−0.0086)Ala+(−0.0741)Cit+(−0.0113)Lys+(0.0691)Ile+(−0.1191)Trp; 0.817, 0.839, 0.857, 0.872, 0.854, 0.862, 0.821, 0.852, (6.0399)+(−0.0717)Asn+(0.0102)Gln+(−0.0530)Cit+(−0.0614)Met+(0.0019)Lys+(−0.1196)Trp; 0.851, 0.873, 0.851, 0.847, 0.850, 0.840, 0.873, 0.852, (3.7665)+(−0.1162)Asn+(0.0093)Gln+(−0.0729)Cit+(0.0294)Ile+(0.0726)Phe+(−0.1544)Trp; 0.834, 0.855, 0.852, 0.859, 0.845, 0.871, 0.834, 0.852, (6.6903)+(−0.0647)Asn+(0.0118)Gln+(−0.0630)His+(−0.0389)Cit+(0.0013)Arg+(−0.0973)Trp; 0.871, 0.891, 0.850, 0.849, 0.842, 0.848, 0.870, 0.852, (4.1249)+(−0.0832)Asn+(0.0111)Gln+(−0.0888)His+(−0.0006)Pro+(0.1016)Phe+(−0.1222)Trp; 0.838, 0.855, 0.852, 0.860, 0.845, 0.871, 0.833, 0.852, (6.6752)+(−0.0637)Asn+(0.0119)Gln+(−0.0633)His+(−0.0379)Cit+(−0.0969)Trp; 0.876, 0.897, 0.851, 0.850, 0.846, 0.848, 0.864, 0.852, (2.6021)+(0.0118)Gln+(−0.0903)His+(0.0036)Pro+(−0.2057)Met+(0.1298)Phe+(−0.1159)Trp; 0.844, 0.865, 0.847, 0.838, 0.846, 0.862, 0.861, 0.852, (4.6128)+(−0.0559)Asn+(0.0100)Gln+(−0.0691)Cit+(−0.1294)Met+(0.0581)Ile+(−0.1234)Trp; 0.872, 0.892, 0.849, 0.849, 0.841, 0.847, 0.870, 0.852, (4.1478)+(−0.0822)Asn+(0.0111)Gln+(−0.0885)His+(−0.0011)Lys+(0.1016)Phe+(−0.1218)Trp; 0.812, 0.837, 0.855, 0.865, 0.855, 0.857, 0.830, 0.852, (6.2501)+(−0.0955)Asn+(0.0093)Gln+(−0.0602)Cit+(0.0052)Arg+(0.0070)Tyr+(−0.1284)Trp; 0.876, 0.892, 0.849, 0.848, 0.841, 0.848, 0.869, 0.852, (4.1266)+(−0.0834)Asn+(0.0110)Gln+(−0.0889)His+(0.1011)Phe+(−0.1222)Trp; 0.832, 0.855, 0.855, 0.869, 0.841, 0.830, 0.866, 0.852, (4.1494)+(−0.1004)Asn+(0.0076)Gln+(−0.0041)Ala+(−0.0032)Arg+(0.0835)Phe+(−0.1466)Trp; 0.873, 0.892, 0.849, 0.848, 0.842, 0.848, 0.869, 0.851, (4.1304)+(−0.0835)Asn+(0.0110)Gln+(−0.0887)His+(−0.0003)Leu+(0.1014)Phe+(−0.1222)Trp; 0.842, 0.864, 0.857, 0.873, 0.847, 0.825, 0.861, 0.851, (4.5031)+(−0.1189)Asn+(0.0076)Gln+(−0.0113)Val+(−0.0002)Lys+(0.1006)Phe+(−0.1425)Trp; 0.847, 0.864, 0.857, 0.873, 0.847, 0.825, 0.861, 0.851, (4.5012)+(−0.1192)Asn+(0.0076)Gln+(−0.0114)Val+(0.1005)Phe+(−0.1425)Trp; 0.819, 0.843, 0.855, 0.863, 0.856, 0.858, 0.830, 0.851, (5.6067)+(−0.0680)Asn+(0.0105)Gln+(−0.0579)Cit+(−0.0775)Met+(0.0109)Leu+(−0.1237)Trp; 0.814, 0.839, 0.855, 0.863, 0.855, 0.857, 0.831, 0.851, (5.9974)+(−0.0889)Asn+(0.0099)Gln+(−0.0600)Cit+(−0.0026)Lys+(0.0084)Leu+(−0.1273)Trp; 0.856, 0.875, 0.843, 0.840, 0.825, 0.875, 0.865, 0.851, (5.6391)+(−0.0894)Asn+(0.0081)Gln+(−0.0686)Cit+(0.1097)Ile+(−0.0447)Leu+(−0.1169)Trp; 0.813, 0.838, 0.855, 0.866, 0.851, 0.860, 0.828, 0.851, (6.4138)+(−0.0916)Asn+(0.0095)Gln+(−0.0606)Cit+(0.0068)Arg+(−0.0019)Lys+(−0.1238)Trp; 0.884, 0.901, 0.844, 0.832, 0.839, 0.854, 0.880, 0.851, (2.0499)+(0.0118)Gln+(−0.0940)His+(−0.2274)Met+(0.0420)Ile+(0.1165)Phe+(−0.1146)Trp; 0.833, 0.854, 0.852, 0.857, 0.855, 0.876, 0.816, 0.851, (6.3446)+(−0.0858)Asn+(0.0085)Gln+(−0.0036)Ala+(−0.0827)Cit+(0.0399)Orn+(−0.1185)Trp; 0.844, 0.867, 0.855, 0.861, 0.854, 0.831, 0.859, 0.851, (4.1532)+(−0.1213)Asn+(0.0093)Gln+(−0.0701)Cit+(0.0073)Arg+(0.0880)Phe+(−0.1552)Trp; 0.812, 0.838, 0.854, 0.861, 0.857, 0.855, 0.832, 0.851, (5.9157)+(−0.0939)Asn+(0.0096)Gln+(−0.0597)Cit+(0.0054)Tyr+(0.0067)Leu+(−0.1309)Trp; 0.846, 0.868, 0.857, 0.868, 0.857, 0.832, 0.847, 0.851, (2.4549)+(0.0096)Gln+(−0.0020)Ala+(−0.0570)Cit+(−0.2059)Met+(0.1155)Phe+(−0.1458)Trp; 0.842, 0.863, 0.857, 0.871, 0.851, 0.820, 0.862, 0.851, (2.9539)+(−0.0618)Asn+(0.0090)Gln+(−0.0018)Ala+(−0.1665)Met+(0.1105)Phe+(−0.1453)Trp; 0.859, 0.878, 0.839, 0.838, 0.806, 0.876, 0.883, 0.851, (5.5211)+(−0.0556)Asn+(0.0071)Gln+(−0.0306)Val+(−0.1601)Met+(0.1221)Ile+(−0.0872)Trp; 0.872, 0.890, 0.837, 0.835, 0.795, 0.862, 0.911, 0.851, (6.1834)+(−0.0880)Asn+(−0.0059)Ala+(−0.0341)Val+(0.1111)Ile+(0.0892)Phe+(−0.1065)Trp; 0.861, 0.879, 0.831, 0.811, 0.804, 0.880, 0.907, 0.851, (6.6747)+(−0.0060)Ala+(0.0404)Tyr+(−0.0328)Val+(−0.1943)Met+(0.1415)Ile+(−0.0867)Trp; 0.801, 0.827, 0.853, 0.869, 0.840, 0.856, 0.838, 0.851, (6.3135)+(−0.0839)Asn+(0.0075)Gln+(−0.0030)Ala+(0.0105)Tyr+(−0.0021)Val+(−0.1222)Trp; 0.834, 0.853, 0.853, 0.866, 0.838, 0.829, 0.868, 0.850, (4.1858)+(−0.1024)Asn+(0.0073)Gln+(−0.0042)Ala+(0.0836)Phe+(−0.1471)Trp; 0.835, 0.856, 0.850, 0.857, 0.845, 0.867, 0.833, 0.850, (6.5698)+(−0.0676)Asn+(0.0116)Gln+(−0.0647)His+(−0.0376)Cit+(0.0032)Lys+(−0.0986)Trp; 0.821, 0.844, 0.854, 0.863, 0.853, 0.860, 0.824, 0.850, (5.9896)+(−0.0674)Asn+(0.0099)Gln+(−0.0535)Cit+(0.0049)Pro+(−0.0736)Met+(−0.1185)Trp; 0.818, 0.838, 0.855, 0.868, 0.852, 0.860, 0.820, 0.850, (6.2676)+(−0.0890)Asn+(0.0098)Gln+(−0.0557)Cit+(−0.0003)Lys+(−0.1237)Trp; 0.861, 0.878, 0.835, 0.833, 0.794, 0.879, 0.894, 0.850, (5.1510)+(0.0056)Gln+(−0.0053)Ala+(−0.0295)Val+(−0.1808)Met+(0.1311)Ile+(−0.0826)Trp; 0.822, 0.838, 0.854, 0.868, 0.852, 0.859, 0.821, 0.850, (6.2580)+(−0.0894)Asn+(0.0097)Gln+(−0.0557)Cit+(−0.1239)Trp; 0.806, 0.830, 0.854, 0.867, 0.850, 0.853, 0.830, 0.850, (5.7845)+(−0.0635)Asn+(0.0083)Gln+(0.0215)Tyr+(−0.0025)Val+(−0.0978)Met+(−0.1237)Trp; 0.835, 0.861, 0.852, 0.860, 0.843, 0.847, 0.848, 0.850, (3.9364)+(0.0067)Gln+(−0.0053)Ala+(−0.0610)Cit+(−0.0089)Lys+(0.0823)Phe+(−0.1445)Trp; 0.814, 0.837, 0.854, 0.868, 0.853, 0.858, 0.821, 0.850, (6.2188)+(−0.0885)Asn+(0.0098)Gln+(−0.0566)Cit+(0.0007)Val+(−0.0006)Lys+(−0.1245)Trp; 0.814, 0.837, 0.854, 0.868, 0.853, 0.858, 0.821, 0.850, (6.2188)+(−0.0885)Asn+(0.0098)Gln+(−0.0566)Cit+(0.0007)Val+(−0.0006)Lys+(−0.1245)Trp

List (1) of Logistic Regression Equations Searched in Example 4

The logistic regression equations searched in Example 4 above are listed below. Before each equation, "the value of ROC_AUC for the pancreatic cancer group and the other cancers group with validation", "the value of ROC_AUC for the pancreatic cancer group and the other cancers group without validation", "the value of ROC_AUC for the pancreatic cancer group and the healthy group", "the value of ROC_AUC for the pancreatic cancer group and the lung cancer group", "the value of ROC_AUC for the pancreatic cancer group and the colorectal cancer group", "the value of ROC_AUC for the pancreatic cancer group and the prostatic cancer group", "the value of ROC_AUC for the pancreatic cancer group and the breast cancer group", and "the average value of the value of ROC_AUC for the pancreatic cancer group and the lung cancer group, the value of ROC_AUC for the pancreatic cancer group and the colorectal cancer group, the value of ROC_AUC for the pancreatic cancer group and the prostatic cancer group, and the value of ROC_AUC for the pancreatic cancer group and the breast cancer group" obtained for the equation are additionally listed.

0.854, 0.873, 0.835, 0.891, 0.849, 0.888, 0.863, 0.873, (1.7072)+(−0.0985)Asn+(0.0115)Gln+(−0.0063)Ala+ (−0.0582)Cit+(0.0212)Phe+(−0.0792)Trp; 0.852, 0.871, 0.832, 0.884, 0.849, 0.896, 0.867, 0.874, (2.3113)+(−0.1017)Asn+(0.0110)Gln+(−0.0063)Ala+ (−0.0568)Cit+(0.0111)Ile+(−0.0719)Trp; 0.851, 0.869, 0.820, 0.889, 0.845, 0.892, 0.850, 0.869, (2.6006)+ (−0.1002)Asn+(0.0111)Gln+(−0.0058)Ala+(−0.0561) Cit+(−0.0706)Trp; 0.850, 0.872, 0.823, 0.887, 0.851, 0.892, 0.863, 0.873, (2.3468)+(−0.1053)Asn+(0.0111) Gln+(−0.0063)Ala+(−0.0570)Cit+(0.0137)Tyr+ (−0.0747)Trp; 0.849, 0.870, 0.846, 0.884, 0.866, 0.869, 0.842, 0.865, (1.2353)+(−0.0844)Asn+(0.0123)Gln+ (−0.0572)Cit+(−0.1339)Met+(0.0312)Phe+(−0.0816) Trp; 0.849, 0.870, 0.808, 0.894, 0.845, 0.892, 0.842, 0.868, (2.7671)+(−0.0984)Asn+(0.0120)Gln+ (−0.0048)Ala+(−0.0551)Cit+(−0.0068)Pro+(−0.0739) Trp; 0.849, 0.869, 0.784, 0.884, 0.857, 0.847, 0.870, 0.865, (3.8383)+(−0.0962)Asn+(−0.0121)Gly+ (0.0143)Gln+(−0.0492)Cit+(−0.0112)Pro+(−0.0942) Trp; 0.848, 0.870, 0.819, 0.892, 0.845, 0.893, 0.849, 0.870, (2.7323)+(−0.0997)Asn+(0.0111)Gln+ (−0.0055)Ala+(−0.0544)Cit+(−0.0019)Val+(−0.0677) Trp; 0.848, 0.870, 0.820, 0.889, 0.846, 0.892, 0.850, 0.869, (2.5966)+(−0.0990)Asn+(0.0112)Gln+ (−0.0058)Ala+(−0.0560)Cit+(−0.0008)Lys+(−0.0698) Trp; 0.848, 0.869, 0.821, 0.888, 0.846, 0.891, 0.851, 0.869, (2.5842)+(−0.1004)Asn+(0.0110)Gln+ (−0.0058)Ala+(−0.0575)Cit+(0.0021)Orn+(−0.0706) Trp; 0.848, 0.869, 0.821, 0.887, 0.846, 0.891, 0.853, 0.869, (2.5115)+(−0.1010)Asn+(0.0112)Gln+ (−0.0060)Ala+(−0.0567)Cit+(0.0021)Leu+(−0.0722) Trp; 0.847, 0.871, 0.820, 0.890, 0.849, 0.892, 0.850, 0.870, (2.5117)+(−0.0856)Asn+(0.0118)Gln+ (−0.0051)Ala+(−0.0536)Cit+(−0.0683)Met+(−0.0633) Trp; 0.847, 0.872, 0.836, 0.889, 0.848, 0.900, 0.855, 0.873, (2.5945)+(−0.0937)Asn+(0.0118)Gln+ (−0.0223)His+(−0.0050)Ala+(−0.0487)Cit+(−0.0610) Trp; 0.847, 0.867, 0.816, 0.894, 0.829, 0.878, 0.866, 0.867, (2.2693)+(−0.1096)Asn+(0.0092)Gln+ (−0.0060)Ala+(−0.0061)Val+(0.0201)Phe+(−0.0668) Trp; 0.847, 0.868, 0.804, 0.890, 0.844, 0.880, 0.850, 0.866, (2.9468)+(−0.0090)Ser+(−0.0912)Asn+ (0.0121)Gln+(−0.0062)Ala+(−0.0562)Cit+(−0.0724) Trp; 0.846, 0.867, 0.805, 0.889, 0.841, 0.882, 0.855, 0.867, (2.4617)+(−0.0897)Asn+(0.0121)Gln+ (−0.0093)Thr+(−0.0056)Ala+(−0.0575)Cit+(−0.0664) Trp; 0.846, 0.869, 0.838, 0.886, 0.858, 0.874, 0.842, 0.865, (2.3818)+(−0.1068)Asn+(0.0100)Gln+ (−0.0557)Cit+(−0.0062)Val+(0.0189)Phe+(−0.0831) Trp; 0.846, 0.868, 0.793, 0.881, 0.849, 0.859, 0.882, 0.868, (3.3740)+(−0.0924)Asn+(−0.0110)Gly+ (0.0134)Gln+(−0.0052)Ala+(−0.0504)Cit+(−0.0788) Trp; 0.845, 0.867, 0.823, 0.888, 0.858, 0.865, 0.833, 0.861, (2.0486)+(−0.1048)Asn+(0.0120)Gln+ (−0.0596)Cit+(−0.0115)Pro+(0.0223)Phe+(−0.0965) Trp; 0.845, 0.868, 0.845, 0.882, 0.852, 0.886, 0.852, 0.868, (2.8826)+(−0.1094)Asn+(0.0093)Gln+ (−0.0522)Cit+(−0.0094)Val+(0.0189)Ile+(−0.0729) Trp; 0.845, 0.865, 0.828, 0.888, 0.820, 0.892, 0.878, 0.869, (2.7136)+ (−0.1154)Asn+(0.0087)Gln+(−0.0058)Ala+(−0.0098) Val+(0.0238)Ile+(−0.0565)Trp; 0.844, 0.868, 0.813, 0.890, 0.845, 0.885, 0.842, 0.866, (2.5586)+(−0.0968) Asn+(0.0118)Gln+(−0.0057)Ala+(−0.0484)Cit+ (−0.0106)Arg+(−0.0667)Trp; 0.844, 0.867, 0.858, 0.875, 0.859, 0.877, 0.856, 0.867, (1.9144)+(−0.0985) Asn+(0.0116)Gln+(−0.0373)His+(−0.0484)Cit+ (0.0186)Phe+(−0.0747)Trp; 0.844, 0.866, 0.760, 0.888, 0.843, 0.840, 0.874, 0.861, (4.8087)+(−0.1039)Asn+ (−0.0144)Gly+(0.0131)Gln+(−0.0103)Pro+(−0.0097) Val+(−0.0762)Trp; 0.844, 0.864, 0.788, 0.884, 0.842, 0.828, 0.884, 0.860, (4.1888)+(−0.1114)Asn+ (−0.0146)Gly+(0.0118)Gln+(−0.0126)Val+(0.0169) Phe+(−0.0789)Trp; 0.844, 0.865, 0.835, 0.886, 0.847, 0.873, 0.844, 0.863, (0.6243)+(0.0108)Gln+(−0.0056) Ala+(−0.0583)Cit+(−0.1610)Met+(0.0336)Phe+ (−0.0779)Trp; 0.844, 0.866, 0.807, 0.872, 0.861, 0.838, 0.879, 0.862, (3.0000)+(−0.1069)Asn+(−0.0115)Gly+ (0.0129)Gln+(−0.0551)Cit+(0.0147)Phe+(−0.0994) Trp; 0.844, 0.865, 0.837, 0.882, 0.859, 0.865, 0.832, 0.860, (2.2031)+(−0.1074)Asn+(0.0101)Gln+ (−0.0594)Cit+(−0.0084)Leu+(0.0218)Phe+(−0.0870) Trp; 0.843, 0.864, 0.838, 0.875, 0.861, 0.863, 0.840, 0.860, (2.0925)+(−0.1115)Asn+(0.0100)Gln+ (−0.0612)Cit+(0.0157)Phe+(−0.0921)Trp; 0.843, 0.866, 0.788, 0.881, 0.849, 0.844, 0.877, 0.863, (4.3296)+(−0.0996)Asn+(−0.0132)Gly+(0.0130)Gln+ (−0.0442)Cit+(−0.0091)Val+(−0.0775)Trp; 0.843, 0.865, 0.846, 0.882, 0.836, 0.879, 0.873, 0.867, (1.9077)+(−0.1020)Asn+(0.0111)Gln+(−0.0396)His+ (−0.0051)Ala+(0.0197)Phe+(−0.0605)Trp; 0.843, 0.862, 0.797, 0.869, 0.857, 0.840, 0.871, 0.860, (3.5957)+(−0.1052)Asn+(−0.0118)Gly+(0.0126)Gln+ (−0.0529)Cit+(−0.0929)Trp; 0.843, 0.866, 0.837, 0.878, 0.860, 0.866, 0.843, 0.862, (1.9994)+(−0.1037) Asn+(0.0107)Gln+(−0.0608)Cit+(−0.0051)Lys+ (0.0174)Phe+(−0.0879)Trp; 0.843, 0.861, 0.815, 0.885, 0.827, 0.866, 0.864, 0.860, (1.9633)+(−0.1140)Asn+ (0.0092)Gln+(−0.0066)Ala+(0.0175)Phe+(−0.0750) Trp; 0.843, 0.865, 0.828, 0.894, 0.845, 0.856, 0.838, 0.858, (1.9014)+(−0.0885)Asn+(0.0107)Gln+ (−0.0091)Val+(−0.1551)Met+(0.0330) Phe+(−0.0629) Trp; 0.843, 0.865, 0.800, 0.891, 0.833, 0.868, 0.860, 0.863, (2.0354)+(−0.1115)Asn+(0.0104)Gln+ (−0.0053)Ala+(−0.0086)Pro+(0.0203)Phe+(−0.0792) Trp; 0.843, 0.865, 0.776, 0.886, 0.834, 0.853, 0.883, 0.864, (4.3559)+(−0.1025)Asn+(−0.0135)Gly+ (0.0121)Gln+(−0.0040)Ala+(−0.0090)Val+(−0.0661) Trp; 0.843, 0.864, 0.822, 0.888, 0.837, 0.865, 0.858, 0.862, (1.2887)+(−0.0886)Asn+(0.0111)Gln+ (−0.0052)Ala+(−0.1275)Met+(0.0289)Phe+(−0.0671) Trp; 0.842, 0.862, 0.809, 0.884, 0.852, 0.869, 0.821, 0.856, (2.9444)+(−0.1069)Asn+(0.0115)Gln+ (−0.0567)Cit+(−0.0100)Pro+(−0.0861)Trp; 0.842, 0.864, 0.773, 0.882, 0.850, 0.820, 0.878, 0.858, (3.4727)+(−0.1125)Asn+(−0.0128)Gly+(0.0130)Gln+ (−0.0131)Pro+(0.0163)Phe+(−0.1001)Trp; 0.842, 0.865, 0.810, 0.882, 0.859, 0.871, 0.827, 0.860, (2.7620)+(−0.1110)Asn+(0.0115)Gln+(−0.0572)Cit+ (−0.0106)Pro+(0.0112)Tyr+(−0.0905)Trp; 0.842, 0.860, 0.776, 0.880, 0.839, 0.831, 0.876, 0.856, (4.7447)+(−0.1110)Asn+(−0.0145)Gly+(0.0116)Gln+ (−0.0116)Val+(−0.0727)Trp; 0.842, 0.866, 0.803, 0.894, 0.844, 0.863, 0.840, 0.860, (2.6868)+(−0.1155) Asn+(0.0097)Gln+(−0.0111)Pro+(−0.0071)Val+

(0.0204)Phe+(−0.0795)Trp; 0.842, 0.859, 0.825, 0.885, 0.840, 0.850, 0.836, 0.853, (2.7694)+(−0.1211)Asn+(0.0079)Gln+(−0.0087)Val+(0.0162)Phe+(−0.0747)Trp; 0.842, 0.865, 0.857, 0.877, 0.854, 0.863, 0.853, 0.862, (1.4326)+(−0.0806)Asn+(0.0122)Gln+(−0.0417)His+(−0.1327)Met+(0.0285)Phe+(−0.0597)Trp; 0.842, 0.865, 0.790, 0.876, 0.856, 0.841, 0.867, 0.860, (4.0160)+(−0.0989)Asn+(−0.0126)Gly+(0.0126)Gln+(−0.0502)Cit+(−0.0085)Leu+(−0.0855)Trp; 0.842, 0.862, 0.828, 0.879, 0.856, 0.871, 0.824, 0.858, (2.6469)+(−0.0905)Asn+(0.0110)Gln+(−0.0547)Cit+(−0.0953)Met+(−0.0724)Trp; 0.842, 0.859, 0.830, 0.873, 0.853, 0.865, 0.831, 0.855, (2.7424)+(−0.1124)Asn+(0.0099)Gln+(−0.0593)Cit+(−0.0850)Trp; 0.842, 0.862, 0.791, 0.879, 0.840, 0.841, 0.881, 0.860, (4.4765)+(0.0106)Ser+(−0.1173)Asn+(−0.0166)Gly+(0.0111)Gln+(−0.0116)Val+(−0.0712)Trp; 0.842, 0.862, 0.840, 0.882, 0.837, 0.868, 0.859, 0.861, (2.6309)+(−0.1229)Asn+(0.0075)Gln+(−0.0125)Val+(0.0183)Ile+(0.0140)Phe+(−0.0711)Trp; 0.842, 0.866, 0.764, 0.886, 0.842, 0.843, 0.878, 0.862, (3.8741)+(−0.1013)Asn+(−0.0126)Gly+(0.0130)Gln+(−0.0040)Ala+(−0.0094)Pro+(−0.0831)Trp; 0.842, 0.864, 0.816, 0.889, 0.830, 0.870, 0.862, 0.863, (2.0567)+(−0.1122)Asn+(0.0092)Gln+(−0.0063)Ala+(−0.0049)Leu+(0.0206)Phe+(−0.0720)Trp; 0.842, 0.864, 0.807, 0.869, 0.858, 0.844, 0.876, 0.862, (3.3874)+(0.0083)Ser+(−0.1115)Asn+(−0.0134)Gly+(0.0122)Gln+(−0.0519)Cit+(−0.0914)Trp; 0.842, 0.864, 0.802, 0.886, 0.831, 0.882, 0.861, 0.865, (2.8366)+(−0.1181)Asn+(0.0090)Gln+(−0.0057)Ala+(0.0141)Tyr+(−0.0059)Val+(−0.0636)Trp; 0.841, 0.861, 0.822, 0.865, 0.851, 0.839, 0.889, 0.861, (3.1733)+(−0.1020)Asn+(−0.0120)Gly+(0.0133)Gln+(−0.0464)His+(0.0135)Phe+(−0.0757)Trp; 0.841, 0.860, 0.803, 0.889, 0.823, 0.879, 0.850, 0.860, (3.0004)+(−0.1129)Asn+(0.0090)Gln+(−0.0055)Ala+(−0.0050)Val+(−0.0602)Trp; 0.841, 0.862, 0.793, 0.878, 0.833, 0.844, 0.891, 0.861, (4.4905)+(−0.1142)Asn+(−0.0146)Gly+(0.0114)Gln+(−0.0160)Val+(0.0206)Ile+(−0.0692)Trp; 0.841, 0.867, 0.830, 0.875, 0.868, 0.873, 0.838, 0.864, (2.2861)+(−0.0896)Asn+(0.0110)Gln+(−0.0546)Cit+(0.0182)Tyr+(−0.1193)Met+(−0.0774)Trp; 0.841, 0.865, 0.799, 0.876, 0.857, 0.846, 0.864, 0.861, (3.4698)+(−0.0755)Asn+(−0.0117)Gly+(0.0135)Gln+(−0.0485)Cit+(−0.0992)Met+(−0.0816)Trp; 0.841, 0.864, 0.815, 0.888, 0.830, 0.882, 0.860, 0.865, (2.9758)+(−0.1205)Asn+(0.0094)Gln+(−0.0134)Pro+(−0.0128)Val+(0.0353)Ile+(−0.0680)Trp; 0.841, 0.862, 0.789, 0.878, 0.838, 0.840, 0.887, 0.861, (3.0725)+(−0.1084)Asn+(−0.0117)Gly+(0.0120)Gln+(−0.0057)Ala+(0.0132)Phe+(−0.0835)Trp; 0.841, 0.864, 0.836, 0.881, 0.846, 0.869, 0.853, 0.862, (2.2038)+(−0.1030)Asn+(0.0119)Gln+(−0.0465)His+(−0.0109)Pro+(0.0215)Phe+(−0.0702)Trp; 0.841, 0.862, 0.781, 0.880, 0.836, 0.835, 0.887, 0.859, (4.5981)+(−0.1133)Asn+(−0.0147)Gly+(0.0120)Gln+(−0.0199)Val+(0.0168)Leu+(−0.0749)Trp; 0.841, 0.862, 0.798, 0.874, 0.842, 0.846, 0.881, 0.861, (4.4317)+(−0.0987)Asn+(−0.0137)Gly+(0.0130)Gln+(−0.0332)His+(−0.0082)Val+(−0.0618)Trp; 0.841, 0.865, 0.792, 0.876, 0.848, 0.848, 0.880, 0.863, (4.0089)+(−0.0908)Asn+(−0.0127)Gly+(0.0142)Gln+(−0.0390)His+(−0.0108)Pro+(−0.0739)Trp; 0.841, 0.862, 0.810, 0.875, 0.856, 0.831, 0.864, 0.856, (2.0237)+(−0.0118)Gly+(0.0125)Gln+(−0.0536)Cit+(−0.1846)Met+(0.0262)Phe+(−0.0934)Trp; 0.841, 0.856, 0.800, 0.881, 0.821, 0.871, 0.852, 0.856, (2.6648)+(−0.1149)Asn+(0.0090)Gln+(−0.0062)Ala+(−0.0680)Trp; 0.841, 0.858, 0.812, 0.863, 0.846, 0.842, 0.882, 0.858, (3.7353)+(−0.0993)Asn+(−0.0124)Gly+(0.0130)Gln+(−0.0445)His+(−0.0709)Trp; 0.841, 0.866, 0.819, 0.878, 0.855, 0.884, 0.847, 0.866, (1.5472)+(0.0097)Gln+(−0.0061)Ala+(−0.0560)Cit+(0.0283)Tyr+(−0.1648)Met+(−0.0744)Trp; 0.841, 0.866, 0.827, 0.884, 0.853, 0.882, 0.836, 0.864, (2.9297)+(−0.0966)Asn+(0.0124)Gln+(−0.0298)His+(−0.0464)Cit+(−0.0091)Pro+(−0.0702)Trp; 0.841, 0.865, 0.804, 0.874, 0.843, 0.859, 0.889, 0.866, (3.5734)+(−0.0925)Asn+(−0.0119)Gly+(0.0133)Gln+(−0.0357)His+(−0.0042)Ala+(−0.0643)Trp; 0.841, 0.862, 0.819, 0.882, 0.837, 0.871, 0.854, 0.861, (2.7968)+(−0.0916)Asn+(0.0109)Gln+(−0.0255)Val+(−0.1691)Met+(0.0379)Leu+(−0.0530)Trp; 0.841, 0.861, 0.844, 0.870, 0.852, 0.877, 0.843, 0.860, (2.7090)+(−0.1006)Asn+(0.0112)Gln+(−0.0339)His+(−0.0474)Cit+(−0.0674)Trp; 0.841, 0.863, 0.804, 0.877, 0.854, 0.820, 0.874, 0.856, (2.6558)+(−0.0831)Asn+(−0.0119)Gly+(0.0128)Gln+(−0.1449)Met+(0.0233)Phe+(−0.0864)Trp; 0.841, 0.862, 0.825, 0.882, 0.850, 0.870, 0.826, 0.857, (3.0838)+(−0.1087)Asn+(0.0098)Gln+(−0.0545)Cit+(−0.0051)Val+(−0.0762)Trp; 0.841, 0.860, 0.779, 0.877, 0.834, 0.842, 0.881, 0.859, (3.6115)+(−0.1058)Asn+(−0.0121)Gly+(0.0118)Gln+(−0.0055)Ala+(−0.0788)Trp; 0.841, 0.864, 0.813, 0.868, 0.856, 0.849, 0.882, 0.864, (3.5123)+(−0.0906)Asn+(−0.0116)Gly+(0.0138)Gln+(−0.0336)His+(−0.0414)Cit+(−0.0760)Trp; 0.841, 0.863, 0.828, 0.875, 0.860, 0.856, 0.838, 0.858, (2.3351)+(−0.0052)Ser+(−0.1066)Asn+(0.0105)Gln+(−0.0614)Cit+(0.0147)Phe+(−0.0933)Trp; 0.841, 0.864, 0.797, 0.872, 0.858, 0.842, 0.872, 0.861, (3.5957)+(−0.1014)Asn+(−0.0117)Gly+(0.0128)Gln+(−0.0525)Cit+(−0.0022)Lys+(−0.0909)Trp; 0.840, 0.865, 0.809, 0.889, 0.852, 0.878, 0.818, 0.859, (3.1554)+(−0.1054)Asn+(0.0114)Gln+(−0.0536)Cit+(−0.0093)Pro+(−0.0034)Val+(−0.0801)Trp; 0.840, 0.861, 0.763, 0.880, 0.846, 0.824, 0.871, 0.855, (4.1032)+(−0.1091)Asn+(−0.0132)Gly+(0.0127)Gln+(−0.0122)Pro+(−0.0937)Trp; 0.840, 0.863, 0.820, 0.879, 0.853, 0.870, 0.836, 0.859, (2.5764)+(−0.1086)Asn+(0.0115)Gln+(−0.0578)Cit+(−0.0123)Pro+(0.0157)Ile+(−0.0898)Trp; 0.840, 0.863, 0.835, 0.877, 0.859, 0.862, 0.836, 0.858, (2.1404)+(−0.1108)Asn+(0.0101)Gln+(−0.0611)Cit+(−0.0034)Ile+(0.0166)Phe+(−0.0918)Trp; 0.840, 0.865, 0.837, 0.876, 0.860, 0.872, 0.838, 0.862, (2.3981)+(−0.0898)Asn+(0.0108)Gln+(−0.0551)Cit+(−0.1062)Met+(0.0096)Ile+(−0.0728)Trp; 0.840, 0.864, 0.821, 0.884, 0.854, 0.877, 0.821, 0.859, (2.9704)+(−0.0901)Asn+(0.0110)Gln+(−0.0504)Cit+(−0.0048)Val+(−0.0906)Met+(−0.0644)Trp; 0.840, 0.864, 0.828, 0.882, 0.850, 0.875, 0.839, 0.861, (2.9830)+(−0.1095)Asn+(0.0099)Gln+(−0.0531)Cit+(−0.0103)Val+(0.0105)Leu+(−0.0777)Trp; 0.840, 0.862, 0.813, 0.888, 0.819, 0.883, 0.867, 0.865, (2.8107)+(−0.1126)Asn+(0.0093)Gln+(−0.0058)Ala+(−0.0129)Val+(0.0169)Leu+(−0.0631)Trp; 0.840, 0.862, 0.804, 0.887, 0.826, 0.860, 0.871, 0.861, (1.8017)+(−0.1065)Asn+(0.0101)Gln+(−0.0086)Thr+(−0.0064)Ala+(0.0189)Phe+(−0.0711)Trp; 0.840, 0.864, 0.808, 0.886, 0.853, 0.873, 0.820, 0.858, (2.9330)+(−0.1036)Asn+(0.0117)Gln+(−0.0563)Cit+(−0.0098)Pro+(−0.0023)Lys+(−0.0838)Trp; 0.840, 0.862, 0.815, 0.886, 0.828, 0.867, 0.864, 0.861, (1.9363)+(−0.1104)Asn+(0.0096)Gln+(−0.0065)Ala+(−0.0026)Lys+(0.0179)Phe+(−0.0729)Trp; 0.840, 0.859, 0.830, 0.877, 0.829, 0.881, 0.859, 0.861, (2.7153)+(−0.1033)Asn+(0.0106)Gln+(−0.0369)His+(−0.0048)Ala+(−0.0530)Trp; 0.840, 0.861, 0.828, 0.876, 0.855, 0.870, 0.830, 0.857, (2.7362)+(−0.1068)Asn+(0.0103)Gln+(−0.0587)Cit+(−0.0038)Lys+(−0.0812)Trp; 0.840, 0.862, 0.791, 0.872, 0.857, 0.833, 0.867, 0.857, (3.7777)+(−0.1036)Asn+(−0.0120)Gly+(0.0128)Gln+(−0.0523)Cit+(−0.0061)Ile+(−0.0918)Trp; 0.840, 0.861, 0.791, 0.887, 0.837, 0.825, 0.869, 0.854, (3.0237)+(−0.0139)Gly+(0.0114)Gln+(−0.0117)Val+(−0.1910)Met+(0.0295)Phe+(−0.0774)Trp; 0.840, 0.860, 0.818, 0.882, 0.826, 0.865, 0.867, 0.860, (1.8745)+(−0.1149)Asn+(0.0092)Gln+(−0.0068)Ala+(0.0049)Ile+(0.0165)Phe+(−0.0754)Trp; 0.840, 0.863, 0.852, 0.883, 0.836, 0.878, 0.856, 0.863, (0.8547)+(0.0106)Gln+(−0.0386)His+(−0.0043)Ala+(−0.1722)Met+(0.0308)Phe+(−0.0594)Trp; 0.840, 0.861, 0.786, 0.879, 0.848, 0.811, 0.873, 0.853, (3.8030)+(−0.1144)Asn+(−0.0137)Gly+(0.0112)Gln+(−0.0143)Leu+(0.0193)Phe+(−0.0882)Trp; 0.840, 0.859, 0.831, 0.873, 0.854, 0.865, 0.831, 0.856, (2.7159)+(−0.1126)Asn+(0.0098)Gln+(−0.0594)Cit+(0.0010)Ile+(−0.0852)Trp; 0.840, 0.860, 0.804, 0.889, 0.831, 0.859, 0.840, 0.855, (1.7534)+(−0.1031)Asn+(0.0114)Gln+(−0.0064)Ala+(−0.0225)Arg+(0.0201)Phe+(−0.0691)Trp; 0.839, 0.862, 0.839, 0.879, 0.836, 0.879, 0.857, 0.863, (2.7140)+(−0.0976)Asn+(0.0093)Gln+(−0.0150)Val+(−0.1446)Met+(0.0379)Ile+(−0.0438)Trp

List (1) of Linear Discriminants Searched in Example 4

The linear discriminants searched in Example 4 above are listed below. Before each equation, "the value of ROC_AUC for the pancreatic cancer group and the other cancers group with validation", "the value of ROC_AUC for the pancreatic cancer group and the other cancers group without validation", "the value of ROC_AUC for the pancreatic cancer group and the healthy group", "the value of ROC_AUC for the pancreatic cancer group and the lung cancer group", "the value of ROC_AUC for the pancreatic cancer group and the colorectal cancer group", "the value of ROC_AUC for the pancreatic cancer group and the prostatic cancer group", "the value of ROC_AUC for the pancreatic cancer group and the breast cancer group", and "the average value of the value of ROC_AUC for the pancreatic cancer group and the lung cancer group, the value of ROC_AUC for the pancreatic cancer group and the colorectal cancer group, the value of ROC_AUC for the pancreatic cancer group and the prostatic cancer group, and the value of ROC_AUC for the pancreatic cancer group and the breast cancer group" obtained for the equation are additionally listed.

0.859, 0.874, 0.841, 0.890, 0.853, 0.883, 0.868, 0.873, (5.4468)+(−0.1111)Asn+(0.0122)Gln+(−0.0083)Ala+(−0.0524)Cit+(0.0345)Phe+(−0.1015)Trp; 0.859, 0.874, 0.808, 0.889, 0.852, 0.878, 0.878, 0.874, (6.8056)+(−0.0977)Asn+(−0.0069)Gly+(0.0132)Gln+(−0.0072)Ala+(−0.0462)Cit+(−0.0919)Trp; 0.858, 0.874, 0.848, 0.892, 0.863, 0.868, 0.854, 0.869, (5.6035)+(−0.1337)Asn+(0.0116)Gln+(−0.0452)Cit+(−0.0098)Val+(0.0408)Phe+(−0.1050)Trp; 0.858, 0.872, 0.849, 0.895, 0.857, 0.859, 0.854, 0.866, (4.8108)+(−0.0961)Asn+(0.0115)Gln+(−0.0125)Val+(−0.1461)Met+(0.0663)Phe+(−0.0971)Trp; 0.858, 0.871, 0.811, 0.894, 0.844, 0.895, 0.848, 0.870, (6.5042)+(−0.1023)Asn+(0.0128)Gln+(−0.0067)Ala+(−0.0490)Cit+(−0.0066)Pro+(−0.0903)Trp; 0.857, 0.869, 0.822, 0.890, 0.843, 0.891, 0.854, 0.869, (6.4072)+(−0.1027)Asn+(0.0120)Gln+(−0.0080)Ala+(−0.0507)Cit+(−0.0876)Trp; 0.857, 0.872, 0.800, 0.888, 0.861, 0.855, 0.864, 0.867, (6.7332)+(−0.1105)Asn+(−0.0083)Gly+(0.0144)Gln+(−0.0439)Cit+(−0.0102)Pro+(−0.1075)Trp; 0.857, 0.874, 0.857, 0.886, 0.869, 0.867, 0.853, 0.869, (4.0729)+(−0.0942)Asn+(0.0132)Gln+(−0.0523)Cit+(−0.1417)Met+(0.0541)Phe+(−0.1117)Trp; 0.856, 0.870, 0.833, 0.885, 0.844, 0.894, 0.868, 0.873, (6.1244)+(−0.1050)Asn+(0.0118)Gln+(−0.0087)Ala+(−0.0540)Cit+(0.0138)Ile+(−0.0889)Trp; 0.856, 0.871, 0.823, 0.891, 0.846, 0.894, 0.852, 0.871, (6.2462)+(−0.0877)Asn+(0.0125)Gln+(−0.0073)Ala+(−0.0497)Cit+(−0.0524)Met+(−0.0833)Trp; 0.856, 0.872, 0.835, 0.890, 0.845, 0.901, 0.860, 0.874, (6.4966)+(−0.0951)Asn+(0.0128)Gln+(−0.0248)His+(−0.0074)Ala+(−0.0456)Cit+(−0.0771)Trp; 0.856, 0.870, 0.823, 0.896, 0.850, 0.858, 0.851, 0.864, (5.8194)+(−0.1324)Asn+(0.0113)Gln+(−0.0106)Pro+(−0.0108)Val+(0.0473)Phe+(−0.1078)Trp; 0.855, 0.869, 0.829, 0.895, 0.833, 0.878, 0.871, 0.869, (5.9985)+(−0.1172)Asn+(0.0101)Gln+(−0.0073)Ala+(−0.0092)Val+(0.0417)Phe+(−0.0931)Trp; 0.855, 0.870, 0.795, 0.892, 0.838, 0.868, 0.880, 0.870, (7.5122)+(−0.1003)Asn+(−0.0083)Gly+(0.0116)Gln+(−0.0061)Ala+(−0.0076)Val+(−0.0835)Trp; 0.855, 0.872, 0.824, 0.885, 0.851, 0.890, 0.868, 0.873, (6.2747)+(−0.1094)Asn+(0.0117)Gln+(−0.0086)Ala+(−0.0521)Cit+(0.0214)Tyr+(−0.0981)Trp; 0.855, 0.869, 0.821, 0.890, 0.843, 0.891, 0.853, 0.869, (6.4558)+(−0.1023)Asn+(0.0119)Gln+(−0.0079)Ala+(−0.0503)Cit+(−0.0012)Leu+(−0.0868)Trp; 0.855, 0.871, 0.867, 0.879, 0.863, 0.872, 0.864, 0.870, (5.1147)+(−0.1213)Asn+(0.0130)Gln+(−0.0367)His+(−0.0468)Cit+(0.0353)Phe+(−0.1017)Trp; 0.855, 0.870, 0.815, 0.891, 0.844, 0.889, 0.855, 0.870, (6.5195)+(−0.0041)Ser+(−0.0995)Asn+(0.0124)Gln+(−0.0080)Ala+(−0.0513)Cit+(−0.0879)Trp; 0.855, 0.871, 0.819, 0.892, 0.845, 0.896, 0.850, 0.871, (6.5601)+(−0.0953)Asn+(0.0126)Gln+(−0.0077)Ala+(−0.0510)Cit+(−0.0059)Lys+(−0.0835)Trp; 0.855, 0.872, 0.828, 0.879, 0.869, 0.845, 0.876, 0.867, (5.7732)+(−0.1237)Asn+(−0.0073)Gly+(0.0129)Gln+(−0.0488)Cit+(0.0224)Phe+(−0.1163)Trp; 0.855, 0.870, 0.814, 0.890, 0.842, 0.890, 0.858, 0.870, (6.2561)+(−0.0961)Asn+(0.0126)Gln+(−0.0058)Thr+(−0.0078)Ala+(−0.0496)Cit+(−0.0857)Trp; 0.855, 0.870, 0.845, 0.887, 0.866, 0.860, 0.843, 0.864, (5.3112)+(−0.1294)Asn+(0.0115)Gln+(−0.0500)Cit+(−0.0135)Leu+(0.0430)Phe+(−0.1112)Trp; 0.855, 0.871, 0.815, 0.881, 0.864, 0.858, 0.864, 0.867, (6.2662)+(−0.0895)Asn+(−0.0081)Gly+(0.0138)Gln+(−0.0452)Cit+(−0.0844)Met+(−0.0980)Trp; 0.855, 0.868, 0.814, 0.875, 0.865, 0.848, 0.867, 0.864, (6.4563)+(−0.1169)Asn+(−0.0081)Gly+(0.0129)Gln+(−0.0471)Cit+(−0.1070)Trp; 0.854, 0.870, 0.832, 0.888, 0.862, 0.863, 0.845, 0.865, (5.1434)+(−0.1290)Asn+(0.0132)Gln+(−0.0512)Cit+(−0.0113)Pro+(0.0381)Phe+(−0.1204)Trp; 0.854, 0.870, 0.807, 0.887, 0.855, 0.856, 0.868, 0.866, (7.1793)+(−0.1140)Asn+(−0.0086)Gly+(0.0129)Gln+(−0.0388)Cit+(−0.0081)Val+(−0.0938)Trp; 0.854, 0.870, 0.818, 0.890, 0.850, 0.834, 0.880, 0.864, (6.6708)+(−0.1247)Asn+(−0.0086)Gly+(0.0115)Gln+(−0.0129)Val+(0.0332)Phe+(−0.1013)Trp; 0.854, 0.870, 0.821, 0.893, 0.842, 0.892, 0.851, 0.870, (6.6454)+(−0.1031)Asn+(0.0119)Gln+(−0.0075)Ala+

(−0.0478)Cit+(−0.0031)Val+(−0.0833)Trp; 0.854, 0.869, 0.819, 0.891, 0.844, 0.888, 0.852, 0.869, (6.3509)+(−0.1005)Asn+(0.0122)Gln+(−0.0079)Ala+ (−0.0480)Cit+(−0.0040)Arg+(−0.0868)Trp; 0.854, 0.868, 0.785, 0.890, 0.841, 0.861, 0.873, 0.866, (7.0517)+(−0.0993)Asn+(−0.0082)Gly+(0.0125)Gln+ (−0.0058)Ala+(−0.0081)Pro+(−0.0971)Trp; 0.854, 0.871, 0.844, 0.882, 0.869, 0.872, 0.848, 0.868, (5.2217)+(−0.1212)Asn+(0.0126)Gln+(−0.0549)Cit+ (−0.0099)Lys+(0.0351)Phe+(−0.1109)Trp; 0.854, 0.869, 0.810, 0.885, 0.842, 0.857, 0.889, 0.868, (6.1928)+(−0.1069)Asn+(−0.0070)Gly+(0.0112)Gln+ (−0.0077)Ala+(0.0243)Phe+(−0.1030)Trp; 0.854, 0.869, 0.846, 0.883, 0.850, 0.887, 0.859, 0.870, (6.4355)+(−0.1302)Asn+(0.0110)Gln+(−0.0463)Cit+ (−0.0135)Val+(0.0270)Ile+(−0.0871)Trp; 0.853, 0.867, 0.846, 0.878, 0.865, 0.857, 0.850, 0.862, (5.0782)+ (−0.1336)Asn+(0.0116)Gln+(−0.0542)Cit+(0.0302) Phe+(−0.1166)Trp; 0.853, 0.869, 0.849, 0.886, 0.838, 0.886, 0.877, 0.872, (5.5655)+(−0.1034)Asn+(0.0115) Gln+(−0.0376)His+(−0.0077)Ala+(0.0371)Phe+ (−0.0878)Trp; 0.853, 0.869, 0.817, 0.882, 0.842, 0.875, 0.886, 0.871, (7.0111)+(−0.0902)Asn+(−0.0076)Gly+ (0.0127)Gln+(−0.0318)His+(−0.0066)Ala+(−0.0799) Trp; 0.853, 0.870, 0.826, 0.890, 0.845, 0.891, 0.853, 0.870, (6.3910)+(−0.1037)Asn+(0.0118)Gln+ (−0.0080)Ala+(−0.0544)Cit+(0.0051)Orn+(−0.0878) Trp; 0.853, 0.866, 0.794, 0.884, 0.838, 0.860, 0.879, 0.865, (6.9138)+(−0.1003)Asn+(−0.0078)Gly+ (0.0113)Gln+(−0.0073)Ala+(−0.0936)Trp; 0.853, 0.868, 0.807, 0.883, 0.861, 0.849, 0.859, 0.863, (6.9047)+(−0.1110)Asn+(−0.0086)Gly+(0.0129)Gln+ (−0.0434)Cit+(−0.0093)Leu+(−0.0997)Trp; 0.853, 0.869, 0.874, 0.880, 0.860, 0.865, 0.863, 0.867, (4.2094)+(−0.0824)Asn+(0.0129)Gln+(−0.0437)His+ (−0.1432)Met+(0.0582)Phe+(−0.0944)Trp; 0.853, 0.866, 0.818, 0.884, 0.840, 0.859, 0.881, 0.866, (7.3959)+(−0.1216)Asn+(−0.0093)Gly+(0.0111)Gln+ (−0.0164)Val+(0.0236)Ile+(−0.0865)Trp; 0.853, 0.869, 0.835, 0.873, 0.873, 0.872, 0.845, 0.866, (5.4341)+ (−0.0983)Asn+(0.0123)Gln+(−0.0521)Cit+(0.0295) Tyr+(−0.1187)Met+(−0.1073)Trp; 0.853, 0.869, 0.784, 0.892, 0.847, 0.846, 0.866, 0.863, (7.5590)+(−0.1102) Asn+(−0.0095)Gly+(0.0129)Gln+(−0.0095)Pro+ (−0.0086)Val+(−0.0949)Trp; 0.853, 0.868, 0.849, 0.882, 0.854, 0.863, 0.862, 0.865, (5.2900)+(−0.1174) Asn+(0.0130)Gln+(−0.0434)His+(−0.0116)Pro+ (0.0422)Phe+(−0.1034)Trp; 0.853, 0.867, 0.842, 0.878, 0.862, 0.874, 0.843, 0.864, (5.4579)+(−0.0978)Asn+ (0.0123)Gln+(−0.0533)Cit+(−0.0961)Met+(0.0109) Ile+(−0.0958)Trp; 0.852, 0.869, 0.811, 0.880, 0.862, 0.854, 0.865, 0.866, (6.6439)+(−0.1073)Asn+ (−0.0078)Gly+(0.0136)Gln+(−0.0476)Cit+(−0.0071) Lys+(−0.1013)Trp; 0.852, 0.868, 0.837, 0.888, 0.841, 0.867, 0.872, 0.867, (4.7054)+(−0.0857)Asn+(0.0111) Gln+(−0.0073)Ala+(−0.1151)Met+(0.0507)Phe+ (−0.1001)Trp; 0.852, 0.865, 0.831, 0.880, 0.860, 0.871, 0.829, 0.860, (5.7466)+(−0.0986)Asn+(0.0123)Gln+ (−0.0508)Cit+(−0.0827)Met+(−0.0949)Trp; 0.852, 0.867, 0.835, 0.894, 0.852, 0.859, 0.835, 0.860, (5.5823)+(−0.1259)Asn+(0.0113)Gln+(−0.0161)Arg+ (−0.0125)Val+(0.0434)Phe+(−0.0987)Trp; 0.852, 0.868, 0.800, 0.889, 0.848, 0.849, 0.865, 0.863, (7.2108)+(−0.0903)Asn+(−0.0095)Gly+(0.0123)Gln+ (−0.0096)Val+(−0.0783)Met+(−0.0846)Trp; 0.852, 0.867, 0.848, 0.880, 0.860, 0.881, 0.842, 0.866, (5.9090)+(−0.0895)Asn+(0.0133)Gln+(−0.0300)His+ (−0.0446)Cit+(−0.0765)Met+(−0.0816)Trp; 0.852, 0.866, 0.816, 0.889, 0.835, 0.871, 0.864, 0.865, (5.5582)+(−0.1148)Asn+(0.0110)Gln+(−0.0070)Ala+ (−0.0086)Pro+(0.0373)Phe+(−0.1075)Trp; 0.852, 0.865, 0.834, 0.888, 0.817, 0.899, 0.879, 0.871, (6.8490)+(−0.1135)Asn+(0.0094)Gln+(−0.0080)Ala+ (−0.0143)Val+(0.0341)Ile+(−0.0726)Trp; 0.852, 0.867, 0.798, 0.885, 0.840, 0.862, 0.877, 0.866, (6.7264)+ (−0.0818)Asn+(−0.0079)Gly+(0.0120)Gln+(−0.0065) Ala+(−0.0637)Met+(−0.0885)Trp; 0.852, 0.867, 0.807, 0.882, 0.839, 0.867, 0.885, 0.868, (6.7520)+(0.0088) Ser+(−0.1060)Asn+(−0.0093)Gly+(0.0106)Gln+ (−0.0071)Ala+(−0.0937)Trp; 0.852, 0.866, 0.790, 0.886, 0.836, 0.859, 0.880, 0.865, (6.9225)+(−0.0986) Asn+(−0.0076)Gly+(0.0117)Gln+(−0.0073)Ala+ (−0.0072)Orn+(−0.0931)Trp; 0.852, 0.867, 0.793, 0.888, 0.838, 0.861, 0.875, 0.865, (7.2368)+(−0.0971) Asn+(−0.0083)Gly+(0.0114)Gln+(−0.0067)Ala+ (−0.0075)Leu+(−0.0889)Trp; 0.851, 0.866, 0.816, 0.880, 0.842, 0.883, 0.865, 0.867, (5.9813)+(−0.0886) Asn+(0.0102)Gln+(−0.0078)Ala+(0.0314)Tyr+ (−0.0958)Met+(−0.0966)Trp; 0.851, 0.869, 0.799, 0.887, 0.856, 0.830, 0.873, 0.862, (6.0449)+(−0.1207) Asn+(−0.0084)Gly+(0.0128)Gln+(−0.0119)Pro+ (0.0274)Phe+(−0.1208)Trp; 0.851, 0.867, 0.843, 0.878, 0.865, 0.856, 0.849, 0.862, (5.1230)+(−0.0012)Ser+ (−0.1325)Asn+(0.0117)Gln+(−0.0544)Cit+(0.0298) Phe+(−0.1166)Trp; 0.851, 0.864, 0.799, 0.885, 0.845, 0.842, 0.867, 0.860, (7.4786)+(−0.1154)Asn+ (−0.0095)Gly+(0.0115)Gln+(−0.0106)Val+(−0.0913) Trp; 0.851, 0.868, 0.825, 0.875, 0.862, 0.854, 0.871, 0.866, (6.3238)+(0.0080)Ser+(−0.1217)Asn+ (−0.0094)Gly+(0.0122)Gln+(−0.0451)Cit+(−0.1068) Trp; 0.851, 0.868, 0.845, 0.887, 0.846, 0.877, 0.856, 0.866, (3.8638)+(0.0111)Gln+(−0.0080)Ala+(−0.0523) Cit+(−0.1680)Met+(0.0550)Phe+(−0.1007)Trp; 0.851, 0.864, 0.850, 0.885, 0.839, 0.861, 0.864, 0.863, (5.8647)+(−0.1415)Asn+(0.0093)Gln+(−0.0178)Val+ (0.0218)Ile+(0.0387)Phe+(−0.0969)Trp; 0.851, 0.866, 0.804, 0.885, 0.843, 0.849, 0.875, 0.863, (7.4605)+ (−0.1204)Asn+(−0.0092)Gly+(0.0116)Gln+(−0.0167) Val+(0.0117)Leu+(−0.0904)Trp; 0.851, 0.866, 0.826, 0.890, 0.834, 0.869, 0.864, 0.864, (5.7369)+(−0.1126) Asn+(0.0098)Gln+(−0.0078)Ala+(−0.0113)Leu+ (0.0425)Phe+(−0.0985)Trp; 0.851, 0.868, 0.817, 0.875, 0.866, 0.851, 0.868, 0.865, (6.4428)+(−0.1177)Asn+ (−0.0081)Gly+(0.0127)Gln+(−0.0500)Cit+(0.0040) Orn+(−0.1073)Trp; 0.851, 0.869, 0.828, 0.875, 0.861, 0.861, 0.873, 0.868, (6.5996)+(−0.1055)Asn+ (−0.0079)Gly+(0.0140)Gln+(−0.0311)His+(−0.0407) Cit+(−0.0925)Trp; 0.851, 0.867, 0.830, 0.884, 0.855, 0.882, 0.837, 0.865, (6.3333)+(−0.1084)Asn+(0.0139) Gln+(−0.0305)His+(−0.0434)Cit+(−0.0096)Pro+ (−0.0899)Trp; 0.851, 0.866, 0.817, 0.880, 0.848, 0.855, 0.874, 0.864, (7.3317)+(−0.1066)Asn+(−0.0091)Gly+ (0.0125)Gln+(−0.0265)His+(−0.0076)Val+(−0.0836) Trp; 0.851, 0.867, 0.842, 0.879, 0.865, 0.854, 0.846, 0.861, (5.1442)+(−0.1324)Asn+(0.0116)Gln+ (−0.0530)Cit+(−0.0053)Ile+(0.0323)Phe+(−0.1164) Trp; 0.851, 0.865, 0.824, 0.887, 0.834, 0.874, 0.869, 0.866, (5.6780)+(−0.1058)Asn+(0.0105)Gln+ (−0.0082)Ala+(−0.0075)Lys+(0.0355)Phe+(−0.0981) Trp; 0.851, 0.867, 0.799, 0.884, 0.853, 0.841, 0.869, 0.862, (6.6764)+(0.0097)Ser+(−0.1188) Asn+(−0.0107)Gly+(0.0119)Gln+(−0.0107)Pro+(− 0.1090)Trp; 0.851, 0.868, 0.815, 0.874, 0.867, 0.850, 0.871, 0.865, (6.4098)+(−0.1188)Asn+(−0.0079)Gly+

(0.0128)Gln+(−0.0476)Cit+(0.0044)Tyr+(−0.1093)Trp; 0.851, 0.864, 0.814, 0.885, 0.854, 0.868, 0.827, 0.858, (6.1918)+(−0.1194)Asn+(0.0128)Gln+(−0.0497)Cit+(−0.0099)Pro+(−0.1041)Trp; 0.851, 0.866, 0.794, 0.887, 0.841, 0.859, 0.869, 0.864, (6.7304)+(−0.0935)Asn+(−0.0075)Gly+(0.0123)Gln+(−0.0071)Ala+(−0.0112)Arg+(−0.0910)Trp; 0.851, 0.867, 0.832, 0.889, 0.855, 0.846, 0.849, 0.860, (4.3755)+(−0.0986)Asn+(0.0122)Gln+(−0.0101)Pro+(−0.1241)Met+(0.0556)Phe+(−0.1163)Trp; 0.850, 0.864, 0.827, 0.885, 0.851, 0.871, 0.830, 0.859, (6.5123)+(−0.1234)Asn+(0.0114)Gln+(−0.0460)Cit+(−0.0068)Val+(−0.0925)Trp; 0.850, 0.866, 0.793, 0.884, 0.838, 0.863, 0.876, 0.865, (7.0363)+(−0.0941)Asn+(−0.0077)Gly+(0.0117)Gln+(−0.0071)Ala+(−0.0050)Lys+(−0.0900)Trp; 0.850, 0.866, 0.844, 0.872, 0.857, 0.844, 0.885, 0.865, (5.9570)+(−0.1120)Asn+(−0.0078)Gly+(0.0127)Gln+(−0.0419)His+(0.0257)Phe+(−0.0997)Trp; 0.850, 0.865, 0.846, 0.886, 0.857, 0.843, 0.842, 0.857, (4.4720)+(−0.0960)Asn+(0.0109)Gln+(−0.1334)Met+(−0.0129)Leu+(0.0625)Phe+(−0.1073)Trp; 0.850, 0.865, 0.827, 0.887, 0.839, 0.874, 0.852, 0.863, (6.3928)+(−0.1011)Asn+(0.0112)Gln+(−0.0255)Val+(−0.1199)Met+(0.0330)Leu+(−0.0768)Trp; 0.850, 0.866, 0.812, 0.890, 0.852, 0.877, 0.825, 0.861, (6.5916)+(−0.1185)Asn+(0.0127)Gln+(−0.0451)Cit+(−0.0091)Pro+(−0.0050)Val+(−0.0959)Trp; 0.850, 0.866, 0.814, 0.884, 0.856, 0.820, 0.871, 0.858, (6.3242)+(−0.1193)Asn+(−0.0088)Gly+(0.0111)Gln+(−0.0179)Leu+(0.0357)Phe+(−0.1095)Trp; 0.850, 0.866, 0.796, 0.884, 0.838, 0.859, 0.881, 0.866, (6.8599)+(−0.1008)Asn+(−0.0077)Gly+(0.0112)Gln+(−0.0075)Ala+(0.0024)Ile+(−0.0938)Trp; 0.850, 0.864, 0.851, 0.882, 0.836, 0.883, 0.859, 0.865, (6.2583)+(−0.0987)Asn+(0.0101)Gln+(−0.0189)Val+(−0.1205)Met+(0.0438)Ile+(−0.0702)Trp; 0.850, 0.868, 0.810, 0.878, 0.864, 0.847, 0.864, 0.863, (6.3784)+(−0.1133)Asn+(−0.0080)Gly+(0.0133)Gln+(−0.0433)Cit+(−0.0057)Arg+(−0.1056)Trp; 0.850, 0.866, 0.808, 0.881, 0.851, 0.852, 0.871, 0.864, (6.9842)+(−0.0997)Asn+(−0.0088)Gly+(0.0142)Gln+(−0.0358)His+(−0.0104)Pro+(−0.0923)Trp; 0.850, 0.867, 0.789, 0.887, 0.852, 0.843, 0.863, 0.861, (6.6608)+(−0.0924)Asn+(−0.0092)Gly+(0.0132)Gln+(−0.0095)Pro+(−0.0657)Met+(−0.1023)Trp; 0.850, 0.865, 0.801, 0.883, 0.847, 0.844, 0.870, 0.861, (7.4326)+(−0.1188)Asn+(−0.0092)Gly+(0.0113)Gln+(0.0083)Tyr+(−0.0111)Val+(−0.0950)Trp; 0.850, 0.866, 0.821, 0.879, 0.849, 0.888, 0.854, 0.868, (5.2240)+(0.0101)Gln+(−0.0086)Ala+(−0.0521)Cit+(0.0339)Tyr+(−0.1490)Met+(−0.0969)Trp; 0.850, 0.866, 0.809, 0.886, 0.834, 0.884, 0.865, 0.867, (6.8770)+(−0.1141)Asn+(0.0095)Gln+(−0.0078)Ala+(0.0231)Tyr+(−0.0073)Val+(−0.0901)Trp; 0.850, 0.867, 0.830, 0.881, 0.860, 0.828, 0.876, 0.861, (4.9495)+(−0.0883)Asn+(−0.0078)Gly+(0.0124)Gln+(−0.1375)Met+(0.0427)Phe+(−0.1120)Trp; 0.850, 0.866, 0.797, 0.881, 0.841, 0.860, 0.881, 0.866, (6.8237)+(−0.1039)Asn+(−0.0073)Gly+(0.0110)Gln+(−0.0077)Ala+(0.0102)Tyr+(−0.0983)Trp; 0.850, 0.864, 0.855, 0.882, 0.847, 0.858, 0.855, 0.861, (5.6934)+(−0.1257)Asn+(0.0110)Gln+j(−0.0323)His+(−0.0091)Val+(0.0426)Phe+(−0.0931)Trp; 0.850, 0.867, 0.824, 0.880, 0.862, 0.875, 0.841, 0.864, (6.4621)+(−0.1301)Asn+(0.0111)Gln+(−0.0462)Cit+(0.0181)Tyr+(−0.0079)Val+(−0.1007)Trp; 0.850, 0.867, 0.861, 0.884, 0.840, 0.881, 0.871, 0.869, (4.0370)+(0.0111)Gln+(−0.0441)His+(−0.0071)Ala+(−0.1656)Met+(0.0590)Phe+(−0.0844)Trp; 0.850, 0.864, 0.825, 0.888, 0.830, 0.882, 0.855, 0.864, (6.7756)+(−0.1299)Asn+(0.0106)Gln+(−0.0118)Pro+(−0.0170)Val+(0.0396)Ile+(−0.0859)Trp; 0.850, 0.862, 0.824, 0.883, 0.829, 0.868, 0.871, 0.863, (5.5825)+(−0.1143)Asn+(0.0098)Gln+(−0.0086)Ala+(0.0320)Phe+(−0.1018)Trp; 0.850, 0.864, 0.822, 0.889, 0.851, 0.846, 0.840, 0.856, (5.4733)+(−0.1287)Asn+(0.0109)Gln+(−0.0108)Pro+(−0.0127)Leu+(0.0474)Phe+(−0.1157)Trp

List (2) of Logistic Regression Equations Searched in Example 4

The logistic regression equations searched in Example 4 above are listed below. Before each equation, "the value of ROC_AUC for the pancreatic cancer group and the other cancers group with validation", "the value of ROC_AUC for the pancreatic cancer group and the other cancers group without validation", "the value of ROC_AUC for the pancreatic cancer group and the healthy group", "the value of ROC_AUC for the pancreatic cancer group and the lung cancer group", "the value of ROC_AUC for the pancreatic cancer group and the colorectal cancer group", "the value of ROC_AUC for the pancreatic cancer group and the prostatic cancer group", "the value of ROC_AUC for the pancreatic cancer group and the breast cancer group", and "the average value of the value of ROC_AUC for the pancreatic cancer group and the lung cancer group, the value of ROC_AUC for the pancreatic cancer group and the colorectal cancer group, the value of ROC_AUC for the pancreatic cancer group and the prostatic cancer group, and the value of ROC_AUC for the pancreatic cancer group and the breast cancer group" obtained for the equation are additionally listed.

0.832, 0.854, 0.860, 0.867, 0.842, 0.862, 0.842, 0.853, (0.8883)+(0.0101)Gln+(−0.0453)His+(−0.1983)Met+(0.0032)Ile+(0.0304)Phe+(−0.0647)Trp; 0.811, 0.827, 0.859, 0.830, 0.819, 0.841, 0.822, 0.828, (1.4317)+(0.0059)Gln+(−0.0615)His+(0.0176)Phe+(−0.0796)Trp; 0.838, 0.862, 0.859, 0.873, 0.856, 0.875, 0.834, 0.859, (0.7688)+(0.0114)Gln+(−0.0347)His+(−0.0488)Cit+(−0.1734)Met+(0.0327)Phe+(−0.0727)Trp; 0.832, 0.855, 0.859, 0.868, 0.842, 0.863, 0.839, 0.853, (0.9479)+(0.0102)Gln+(−0.0459)His+(−0.1951)Met+(0.0005)Leu+(0.0306)Phe+(−0.0647)Trp; 0.835, 0.855, 0.858, 0.869, 0.842, 0.863, 0.838, 0.853, (0.9606)+(0.0101)Gln+(−0.0456)His+(−0.1946)Met+(0.0308)Phe+(−0.0646)Trp; 0.830, 0.854, 0.858, 0.868, 0.842, 0.862, 0.837, 0.852, (0.9492)+(0.0100)Gln+(−0.0463)His+(−0.1974)Met+(0.0010)Lys+(0.0310)Phe+(−0.0651)Trp; 0.832, 0.856, 0.858, 0.867, 0.846, 0.864, 0.843, 0.855, (0.8859)+(0.0101)Gln+(−0.0449)His+(0.0079)Tyr+(−0.2036)Met+(0.0287)Phe+(−0.0666)Trp; 0.844, 0.867, 0.858, 0.875, 0.859, 0.877, 0.856, 0.867, (1.9144)+(−0.0985)Asn+(0.0116)Gln+(−0.0373)His+(−0.0484)Cit+(0.0186)Phe+(−0.0747)Trp; 0.810, 0.833, 0.858, 0.844, 0.822, 0.847, 0.820, 0.833, (1.4444)+(0.0069)Gln+(−0.0551)His+(−0.0066)Lys+(−0.0012)Leu+(0.0192)Phe+(−0.0744)Trp; 0.813, 0.834, 0.858, 0.842, 0.823, 0.848, 0.822, 0.834, (1.4226)+(0.0070)Gln+(−0.0556)His+(−0.0070)Lys+(0.0185)Phe+(−0.0747)Trp; 0.801, 0.824, 0.857, 0.836, 0.809, 0.834, 0.814, 0.823, (1.5132)+(0.0064)Gln+(−0.0614)His+(−0.0170)Tyr+(0.0240)Phe+(−0.0738)Trp; 0.838, 0.858, 0.857, 0.878, 0.831, 0.868, 0.853, 0.857, (0.8895)+(0.0079)Gln+(−0.0176)Val+(−0.2523)Met+(0.0391)Ile+(0.0373)Phe+(−0.0600)Trp; 0.842, 0.865, 0.857, 0.877, 0.854, 0.863, 0.853, 0.862, (1.4326)+(−0.0806)Asn+(0.0122)Gln+(−0.0417)His+(−0.1327)Met+(0.0285)Phe+(−0.0597)Trp; 0.810, 0.828, 0.857, 0.837, 0.820, 0.838, 0.814, 0.827, (1.5141)+(0.0058)Gln+(−0.0585)His+(−0.0046)Leu+(0.0205)Phe+(−0.0777)Trp; 0.813, 0.835, 0.856, 0.838, 0.835, 0.855, 0.815, 0.836, (1.2693)+(0.0080)Gln+(−0.0481)His+(−0.0557)Cit+(0.0201)Phe+(−0.0874)Trp; 0.820, 0.844, 0.856, 0.852, 0.841, 0.864, 0.818, 0.844, (1.2255)+(0.0092)Gln+(−0.0419)His+(−0.0565)Cit+(−0.0074)Lys+(0.0216)Phe+(−0.0828)Trp; 0.803, 0.830, 0.856, 0.844, 0.813, 0.844, 0.815, 0.829, (1.4926)+(0.0073)Gln+(−0.0562)His+(−0.0143)Tyr+(−0.0061)Lys+(0.0236)Phe+(−0.0704)Trp; 0.800, 0.824, 0.855, 0.838, 0.810, 0.834, 0.808, 0.823, (1.5624)+(0.0064)Gln+(−0.0594)His+(−0.0159)Tyr+(−0.0031)Leu+(0.0255)Phe+(−0.0730)Trp; 0.832, 0.854, 0.855, 0.865, 0.840, 0.859, 0.851, 0.854, (2.1707)+(−0.1074)Asn+(0.0104)Gln+(−0.0506)His+(−0.0033)Tyr+(0.0180)Phe+(−0.0652)Trp; 0.838, 0.855, 0.855, 0.865, 0.843, 0.858, 0.852, 0.854, (2.1490)+(−0.1092)Asn+(0.0104)Gln+(−0.0504)His+(0.0170)Phe+(−0.0662)Trp; 0.821, 0.844, 0.854, 0.850, 0.833, 0.860, 0.835, 0.845, (3.9190)+(−0.0317)Cit+(−0.0149)Val+(−0.1434)Met+(0.0414)Ile+(0.0240)Phe+(−0.0598)Trp; 0.835, 0.855, 0.853, 0.866, 0.842, 0.859, 0.853, 0.855, (2.1356)+(−0.1071)Asn+(0.0106)Gln+(−0.0493)His+(−0.0017)Lys+(0.0173)Phe+(−0.0654)Trp; 0.813, 0.837, 0.853, 0.844, 0.835, 0.858, 0.806, 0.836, (1.3628)+(0.0079)Gln+(−0.0444)His+(−0.0557)Cit+(−0.0054)Leu+(0.0237)Phe+(−0.0854)Trp; 0.832, 0.856, 0.853, 0.874, 0.847, 0.864, 0.822, 0.852, (1.0094)+(0.0114)Gln+(−0.0439)His+(−0.0175)Arg+(−0.1644)Met+(0.0294)Phe+(−0.0634)Trp; 0.801, 0.824, 0.853, 0.841, 0.806, 0.837, 0.810, 0.823, (1.6890)+(0.0062)Gln+(−0.0559)His+(−0.0132)Tyr+(−0.0043)Val+(0.0252)Phe+(−0.0711)Trp; 0.837, 0.856, 0.853, 0.868, 0.843, 0.859, 0.850, 0.855, (2.2231)+(−0.1084)Asn+(0.0103)Gln+(−0.0483)His+(−0.0033)Leu+(0.0190)Phe+(−0.0649)Trp; 0.836, 0.855, 0.852, 0.867, 0.843, 0.857, 0.848, 0.854, (2.2347)+(−0.1077)Asn+(0.0105)Gln+(−0.0506)His+(−0.0045)Ile+(0.0180)Phe+(−0.0656)Trp; 0.840, 0.863, 0.852, 0.883, 0.838, 0.878, 0.856, 0.863, (0.8547)+(0.0106)Gln+(−0.0386)His+(−0.0043)Ala+(−0.1722)Met+(0.0308)Phe+(−0.0594)Trp; 0.820, 0.841, 0.852, 0.853, 0.823, 0.854, 0.838, 0.842, (3.4029)+(0.0020)Ser+(−0.0158)Val+(−0.1764)Met+(0.0402)Ile+(0.0268)Phe+(−0.0567)Trp; 0.807, 0.833, 0.852, 0.845, 0.826, 0.850, 0.807, 0.832, (1.3754)+(0.0084)Gln+(−0.0483)His+(−0.0548)Cit+(−0.0155)Tyr+(0.0254)Phe+(−0.0821)Trp; 0.804, 0.825, 0.852, 0.835, 0.807, 0.843, 0.821, 0.827, (1.7109)+(0.0059)Gln+(−0.0552)His+(−0.0101)Val+(0.0099)Leu+(0.0178)Phe+(−0.0744)Trp; 0.813, 0.837, 0.851, 0.846, 0.831, 0.858, 0.808, 0.836, (1.4770)+(0.0078)Gln+(−0.0429)His+(−0.0539)Cit+(−0.0043)Val+(0.0228)Phe+(−0.0837)Trp; 0.835, 0.857, 0.851, 0.877, 0.840, 0.866, 0.835, 0.854, (1.2210)+(0.0100)Gln+(−0.0383)His+(−0.0054)Val+(−0.1938)Met+(0.0342)Phe+(−0.0607)Trp; 0.809, 0.836, 0.851, 0.855, 0.826, 0.848, 0.797, 0.832, (1.4109)+(0.0092)Gln+(−0.0555)His+(−0.0276)Arg+(−0.0080)Tyr+(0.0226)Phe+(−0.0720)Trp; 0.819, 0.840, 0.851, 0.854, 0.821, 0.847, 0.839, 0.840, (3.2389)+(−0.0194)Val+(−0.2122)Met+(0.0097)Lys+(0.0427)Ile+(0.0309)Phe+(−0.0610)Trp; 0.810, 0.828, 0.851, 0.840, 0.813, 0.840, 0.817, 0.827, (1.6683)+(0.0058)Gln+(−0.0547)His+(−0.0054)Val+(0.0212)Phe+(−0.0746)Trp; 0.810, 0.833, 0.851, 0.846, 0.820, 0.849, 0.817, 0.833, (1.6012)+(0.0066)Gln+(−0.0516)His+(−0.0041)Val+(−0.0055)Lys+(0.0210)Phe+(−0.0720)Trp; 0.816, 0.837, 0.851, 0.853, 0.830, 0.849, 0.799, 0.833, (1.3773)+(0.0091)Gln+(−0.0556)His+(−0.0286)Arg+(0.0199)Phe+(−0.0745)Trp; 0.839, 0.857, 0.850, 0.872, 0.838, 0.863, 0.852, 0.856, (2.4322)+(−0.1072)Asn+(0.0102)Gln+(−0.0444)His+(−0.0050)Val+(0.0189)Phe+(−0.0612)Trp; 0.816, 0.842, 0.850, 0.852, 0.840, 0.858, 0.806, 0.839, (1.2382)+(0.0096)Gln+(−0.0473)His+(−0.0416)Cit+(−0.0197)Arg+(0.0214)Phe+(−0.0817)Trp; 0.835, 0.859, 0.850, 0.869, 0.847, 0.886, 0.836, 0.860, (2.1595)+(0.0080)Gln+(−0.0500)Cit+(−0.0125)Val+(−0.1881)Met+(0.0368)Ile+(−0.0598)Trp; 0.811, 0.838, 0.850, 0.855, 0.830, 0.851, 0.801, 0.835, (1.3783)+(0.0092)Gln+(−0.0549)His+(−0.0280)Arg+(−0.0010)Lys+(0.0199)Phe+(−0.0739)Trp; 0.818, 0.838, 0.850, 0.843, 0.840, 0.849, 0.813, 0.836, (3.6030)+(−0.0400)Cit+(−0.1257)Met+(0.0411)Ile+(−0.0228)Leu+(0.0269)Phe+(−0.0700)Trp; 0.824, 0.846, 0.850, 0.851, 0.832, 0.862, 0.851, 0.849, (3.4958)+(0.0197)Tyr+(−0.0169)Val+(−0.1900)Met+(0.0398)Ile+(0.0212)Phe+(−0.0598)Trp; 0.828, 0.855, 0.849, 0.863, 0.850, 0.877, 0.826, 0.854, (1.9611)+(0.0097)Gln+(−0.0329)His+(−0.0475)Cit+(−0.1561)Met+(0.0101)Ile+(−0.0631)Trp; 0.827, 0.849, 0.849, 0.861, 0.823, 0.868, 0.855, 0.852, (3.6056)+(−0.0029)Ala+(−0.0139)Val+(−0.1476)Met+(0.0386)Ile+(0.0243)Phe+(−0.0529)Trp; 0.832, 0.858, 0.849, 0.873, 0.838, 0.883, 0.844, 0.860, (1.0945)+(0.0090)Gln+(−0.0329)His+(−0.0066)Ala+(−0.0546)Cit+(0.0224)Phe+(−0.0770)Trp; 0.810, 0.832, 0.849, 0.845, 0.822, 0.843, 0.811, 0.830, (1.6167)+(0.0072)Gln+(−0.0573)His+(−0.0057)Lys+(−0.0092)Ile+(0.0202)Phe+(−0.0740)Trp; 0.801, 0.824, 0.848, 0.841, 0.810, 0.832, 0.801, 0.821, (1.7185)+(0.0069)Gln+(−0.0622)His+(−0.0146)Tyr+(−0.0106)Ile+(0.0253)Phe+(−0.0729)Trp; 0.812, 0.836, 0.848, 0.844, 0.836, 0.852, 0.805, 0.834, (1.4235)+(0.0083)Gln+(−0.0485)His+(−0.0547)Cit+(−0.0084)Ile+(0.0221)Phe+(−0.0860)Trp; 0.811, 0.824, 0.848, 0.831, 0.815, 0.846, 0.809, 0.825, (2.1163)+(0.0056)Gln+(−0.0577)His+(−0.0737)Trp; 0.809, 0.824, 0.848, 0.832, 0.815, 0.846, 0.809, 0.825, (2.1319)+(0.0056)Gln+(−0.0574)His+(−0.0004)Leu+(−0.0735)Trp; 0.833, 0.858, 0.848, 0.879, 0.840, 0.853, 0.847, 0.855, (0.9592)+(0.0121)Gln+(−0.0472)His+(−0.1920)Met+(−0.0243)Orn+(0.0373)Phe+(−0.0657)Trp; 0.815, 0.838, 0.848, 0.858, 0.828, 0.851, 0.797, 0.833, (1.4616)+(0.0090)Gln+(−0.0524)His+(−0.0286)Arg+(−0.0046)Leu+(0.0226)Phe+(−0.0727)Trp; 0.806, 0.833, 0.848, 0.840, 0.827, 0.847, 0.819, 0.833, (1.3150)+(0.0086)Gln+(−0.0506)His+(−0.0475)Cit+(−0.0116)Orn+(0.0226)Phe+(−0.0866)Trp; 0.808, 0.827, 0.848, 0.839, 0.819, 0.834, 0.807, 0.825, (1.6962)+(0.0065)Gln+(−0.0624)His+(−0.0126)Ile+(0.0203)Phe+(−0.0774)Trp; 0.821, 0.840, 0.848, 0.852, 0.823, 0.849, 0.836, 0.840, (3.5940)+(−0.0158)Val+(−0.1719)Met+(0.0401)Ile+(0.0260)Phe+(−0.0568)Trp; 0.817, 0.839, 0.847, 0.852, 0.822, 0.848, 0.836, 0.840, (3.5883)+(0.0003)His+(−0.0159)Val+(−0.1724)Met+(0.0403)Ile+(0.0261)Phe+(−0.0568)Trp; 0.830, 0.852, 0.847, 0.868, 0.839, 0.855, 0.838, 0.850, (1.2919)+(−0.0059)Ser+(0.0107)Gln+(−0.0456)His+(−0.1879)Met+(0.0293)Phe+(−0.0657)Trp; 0.807, 0.828, 0.847, 0.842, 0.814, 0.838, 0.810, 0.826, (1.7332)+(0.0061)Gln+(−0.0570)His+(−0.0039)Val+(−0.0062)Ile+(0.0215)Phe+(−0.0749)Trp; 0.835, 0.857, 0.847, 0.872, 0.841, 0.854, 0.856, 0.855, (2.1735)+(−0.1012)Asn+(0.0115)Gln+(−0.0525)His+(−0.0183)Orn+(0.0209)Phe+(−0.0669)Trp; 0.824, 0.844, 0.847, 0.855, 0.825, 0.855, 0.845, 0.845, (4.1964)+(−0.0366)Asn+(−0.0156)Val+(−0.1313)Met+(0.0398)Ile+(0.0227)Phe+(−0.0531)Trp; 0.822, 0.841, 0.847, 0.848, 0.839, 0.849, 0.824, 0.840, (4.4190)+(−0.0614)Asn+(−0.0403)Cit+(0.0345)Ile+(−0.0238)Leu+(0.0191)Phe+(−0.0731)Trp; 0.822, 0.849, 0.847, 0.856, 0.842, 0.865, 0.834, 0.849, (1.7543)+(0.0088)Gln+(−0.0415)His+(0.0185)Tyr+(−0.2011)Met+(0.0057)Ile+(−0.0612)Trp; 0.804, 0.822, 0.847, 0.833, 0.811, 0.844, 0.804, 0.823, (2.2437)+(0.0057)Gln+(−0.0571)His+(−0.0067)Tyr+(−0.0705)Trp; 0.838, 0.861, 0.847, 0.870, 0.853, 0.877, 0.844, 0.861, (2.6610)+(−0.1010)Asn+(0.0111)Gln+(−0.0339)His+(−0.0475)Cit+(0.0018)Ile+(−0.0678)Trp; 0.801, 0.822, 0.847, 0.832, 0.810, 0.844, 0.805, 0.823, (2.2188)+(0.0057)Gln+(−0.0578)His+(−0.0072)Tyr+(0.0008)Leu+(−0.0708)Trp; 0.827, 0.848, 0.846, 0.862, 0.815, 0.876, 0.858, 0.853, (1.2964)+(0.0071)Gln+(−0.0476)His+(−0.0067)Ala+(0.0194)Phe+(−0.0686)Trp; 0.818, 0.839, 0.846, 0.852, 0.822, 0.848, 0.836, 0.840, (3.5995)+(−0.0002)Thr+(−0.0158)Val+(−0.1712)Met+(0.0401)Ile+(0.0259)Phe+(−0.0567)Trp; 0.824, 0.848, 0.846, 0.863, 0.827, 0.874, 0.835, 0.850, (2.2081)+(0.0080)Gln+(−0.0295)His+(−0.0082)Val+(−0.1935)Met+(0.0236)Ile+(−0.0479)Trp; 0.843, 0.865, 0.846, 0.882, 0.836, 0.879, 0.873, 0.867, (1.9077)+(−0.1020)Asn+(0.0111)Gln+(−0.0396)His+(−0.0051)Ala+(0.0197)Phe+(−0.0605)Trp; 0.826, 0.852, 0.846, 0.869, 0.816, 0.878, 0.858, 0.856, (1.2862)+(0.0078)Gln+(−0.0444)His+(−0.0064)Ala+(−0.0050)Lys+(0.0198)Phe+(−0.0650)Trp; 0.822, 0.849, 0.846, 0.855, 0.842, 0.864, 0.834, 0.849, (1.7216)+(0.0091)Gln+(−0.0451)His+(0.0175)Tyr+(−0.1988)Met+(0.0045)Leu+(−0.0625)Trp; 0.818, 0.840, 0.846, 0.852, 0.820, 0.851, 0.840, 0.841, (3.7058)+(−0.0188)Val+(−0.1737)Met+(0.0369)Ile+(0.0073)Leu+(0.0243)Phe+(−0.0565)Trp; 0.849, 0.870, 0.846, 0.884, 0.866, 0.869, 0.842, 0.865, (1.2353)+(−0.0844)Asn+(0.0123)Gln+(−0.0572)Cit+(−0.1339)Met+(0.0312)Phe+(−0.0816)Trp; 0.827, 0.853, 0.846, 0.861, 0.851, 0.872, 0.823, 0.852, (1.9652)+(0.0102)Gln+(−0.0374)His+(−0.0467)Cit+(−0.1531)Met+(0.0058)Leu+(−0.0647)Trp; 0.806, 0.828, 0.846, 0.837, 0.818, 0.850, 0.811, 0.829, (2.0237)+(0.0067)Gln+(−0.0541)His+(−0.0073)Lys+(0.0032)Leu+(−0.0699)Trp; 0.822, 0.845, 0.846, 0.858, 0.831, 0.862, 0.825, 0.844, (2.0596)+(0.0087)Gln+(−0.0426)His+(−0.1785)Met+(0.0077)Ile+(−0.0551)Trp; 0.838, 0.861, 0.845, 0.870, 0.852, 0.877, 0.844, 0.861, (2.6642)+(−0.1008)Asn+(0.0112)Gln+(−0.0346)His+(−0.0474)Cit+(0.0010)Leu+(−0.0680)Trp; 0.804, 0.826, 0.845, 0.837, 0.819, 0.833, 0.807, 0.824, (1.7177)+(0.0067)Gln+(−0.0653)His+(−0.0171)Ile+(0.0040)Leu+(0.0188)Phe+(−0.0782)Trp; 0.817, 0.845, 0.845, 0.858, 0.831, 0.862, 0.825, 0.844, (2.0573)+(0.0087)Gln+(−0.0424)His+(−0.1778)Met+(−0.0003)Lys+(0.0078)Ile+(−0.0550)Trp; 0.825, 0.848, 0.845, 0.864, 0.814, 0.876, 0.853, 0.852, (1.3320)+(0.0071)Gln+(−0.0466)His+(−0.0066)Ala+(−0.0020)Leu+(0.0207)Phe+(−0.0677)Trp; 0.815, 0.838, 0.845, 0.858, 0.831, 0.848, 0.795, 0.833, (1.5171)+(0.0093)Gln+(−0.0560)His+(−0.0277)Arg+(−0.0073)Ile+(0.0213)Phe+(−0.0735)Trp; 0.838, 0.862, 0.845, 0.870, 0.855, 0.877, 0.845, 0.862, (2.6256)+(−0.1026)Asn+(0.0111)Gln+(−0.0338)His+(−0.0476)Cit+(0.0045)Tyr+(−0.0693)Trp; 0.829, 0.853, 0.845, 0.869, 0.836, 0.856, 0.842, 0.850, (0.9474)+(0.0108)Gln+(−0.0459)His+(−0.0074)Thr+(−0.1743)Met+(0.0289)Phe+(−0.0619)Trp; 0.817, 0.841, 0.845, 0.854, 0.821, 0.847, 0.845, 0.842, (3.7672)+(−0.0158)Val+(−0.1671)Met+(−0.0097)Orn+(0.0439)Ile+(0.0270)Phe+(−0.0574)Trp; 0.821, 0.844, 0.845, 0.856, 0.833, 0.858, 0.825, 0.843, (1.9866)+(0.0092)Gln+(−0.0476)His+(−0.1771)Met+(0.0064)Leu+(−0.0576)Trp; 0.819, 0.845, 0.845, 0.864, 0.810, 0.874, 0.848, 0.849, (1.3242)+(0.0074)Gln+(−0.0483)His+(−0.0064)Ala+(−0.0097)Tyr+(0.0233)Phe+(−0.0659)Trp; 0.824, 0.847, 0.845, 0.854, 0.829, 0.879, 0.843, 0.851, (4.5234)+(−0.0035)Ala+(−0.0342)Cit+(−0.0106)Val+(−0.1031)Met+(0.0385)Ile+(−0.0523)Trp; 0.823, 0.845, 0.845, 0.866, 0.831, 0.842, 0.822, 0.840, (0.8426)+(0.0071)Gln+(−0.2328)Met+(0.0264)Ile+(−0.0171)Leu+(0.0352)Phe+(−0.0745)Trp; 0.845, 0.868, 0.845, 0.882, 0.852, 0.886, 0.852, 0.868, (2.8826)+(−0.1094)Asn+(0.0093)Gln+(−0.0522)Cit+(−0.0094)Val+(0.0189)Ile+(−0.0729)Trp; 0.818, 0.844, 0.844, 0.857, 0.833, 0.857, 0.825, 0.843, (1.9930)+(0.0092)Gln+(−0.0479)His+(−0.1765)Met+(−0.0009)Ile+(0.0068)Leu+(−0.0577)Trp; 0.841, 0.861, 0.844, 0.870, 0.852, 0.877, 0.843, 0.860, (2.7090)+(−0.1006)Asn+(0.0112)Gln+(−0.0339)His+(−0.0474)Cit+(−0.0674)Trp; 0.806, 0.830, 0.844, 0.835, 0.831, 0.838, 0.810, 0.829, (3.5322)+(0.0038)Ser+(−0.0221)His+(−0.1374)Met+(0.0091)Ile+(0.0199)Phe+(−0.0684)Trp; 0.816, 0.840, 0.844, 0.863, 0.825, 0.855, 0.798, 0.835, (1.5894)+(0.0090)Gln+(−0.0487)His+(−0.0284)Arg+(−0.0051)Val+(0.0232)Phe+(−0.0702)Trp; 0.824, 0.847, 0.844, 0.867, 0.811, 0.875, 0.850, 0.851, (1.4335)+(0.0070)Gln+(−0.0441)His+(−0.0064)Ala+(−0.0035)Val+(0.0220)Phe+(−0.0655)Trp; 0.835, 0.854, 0.844, 0.866, 0.842, 0.852, 0.852, 0.853, (2.3932)+(−0.0049)Ser+(−0.1052)Asn+(0.0109)Gln+(−0.0504)His+(0.0160)Phe+(−0.0671)Trp; 0.828, 0.847, 0.844, 0.855, 0.831, 0.875, 0.840, 0.850, (3.4379)+(−0.0060)Ala+(−0.0470)Cit+(0.0336)Ile+(−0.0206)Leu+(0.0211)Phe+(−0.0711)Trp; 0.829, 0.853, 0.844, 0.867, 0.854, 0.850, 0.815, 0.847, (0.6734)+(0.0097)Gln+(−0.0603)Cit+(−0.2015)Met+(0.0053)Ile+(0.0327)Phe+(−0.0882)Trp; 0.839, 0.862, 0.844, 0.872, 0.852, 0.878, 0.843, 0.861, (2.7071)+(−0.0988)Asn+(0.0113)Gln+(−0.0330)His+(−0.0475)Cit+(−0.0013)Lys+(−0.0665)Trp

List (2) of Linear Discriminants Searched in Example 4

The linear discriminants searched in Example 4 above are listed below. Before each equation, "the value of ROC_AUC for the pancreatic cancer group and the other cancers group with validation", "the value of ROC_AUC for the pancreatic cancer group and the other cancers group without validation", "the value of ROC_AUC for the pancreatic cancer group and the healthy group", "the value of ROC_AUC for the pancreatic cancer group and the lung cancer group", "the value of ROC_AUC for the pancreatic cancer group and the colorectal cancer group", "the value of ROC_AUC for the pancreatic cancer group and the prostatic cancer group", "the value of ROC_AUC for the pancreatic cancer group and the breast cancer group", and "the average value of the value of ROC_AUC for the pancreatic cancer group and the lung cancer group, the value of ROC_AUC for the pancreatic cancer group and the colorectal cancer group, the value of ROC_AUC for the pancreatic cancer group and the prostatic cancer group, and the value of ROC_AUC for the pancreatic cancer group and the breast cancer group" obtained for the equation are additionally listed.

0.833, 0.849, 0.880, 0.860, 0.830, 0.861, 0.852, 0.851, (5.7313)+(0.0114)Ser+(−0.0226)Val+(−0.2232)Met+ (0.0489)Ile+(0.0676)Phe+(−0.0795)Trp; 0.843, 0.860, 0.879, 0.871, 0.852, 0.863, 0.849, 0.859, (3.2393)+ (0.0037)Ser+(0.0106)Gln+(−0.0517)His+(−0.2085) Met+(0.0643)Phe+(−0.0934)Trp; 0.847, 0.866, 0.875, 0.874, 0.863, 0.873, 0.848, 0.865, (3.3463)+(0.0126) Gln+(−0.0436)His+(−0.0447)Cit+(−0.1986)Met+ (0.0623)Phe+(−0.0962)Trp; 0.831, 0.849, 0.875, 0.860, 0.832, 0.859, 0.847, 0.849, (6.5393)+(0.0075)Thr+ (−0.0236)Val+(−0.2243)Met+(0.0503)Ile+(0.0644) Phe+(−0.0798)Trp; 0.831, 0.848, 0.875, 0.846, 0.855, 0.862, 0.829, 0.848, (5.6907)+(0.0141)Ser+(−0.0317) His+(0.0235)Tyr+(−0.1891)Met+(0.0540)Phe+ (−0.1005)Trp; 0.845, 0.862, 0.874, 0.868, 0.858, 0.859, 0.858, 0.861, (3.3530)+(0.0109)Gln+(−0.0510)His+ (0.0190)Tyr+(−0.2214)Met+(0.0579)Phe+(−0.1003) Trp; 0.853, 0.869, 0.874, 0.880, 0.860, 0.865, 0.863, 0.867, (4.2094)+(−0.0824)Asn+(0.0129)Gln+ (−0.0437)His+(−0.1432)Met+(0.0582)Phe+(−0.0944) Trp; 0.847, 0.860, 0.874, 0.871, 0.851, 0.858, 0.851, 0.858, (3.4357)+(0.0110)Gln+(−0.0515)His+(−0.2021) Met+(0.0618)Phe+(−0.0934)Trp; 0.843, 0.862, 0.873, 0.875, 0.854, 0.860, 0.846, 0.859, (3.3761)+(0.0122) Gln+(−0.0510)His+(−0.0129)Arg+(−0.1828)Met+ (0.0603)Phe+(−0.0912)Trp; 0.827, 0.842, 0.873, 0.852, 0.837, 0.846, 0.824, 0.840, (5.1029)+(0.0103)Ser+ (−0.1930)Met+(0.0483)Ile+(−0.0349)Leu+(0.0703) Phe+(−0.0947)Trp; 0.842, 0.860, 0.873, 0.871, 0.851, 0.858, 0.851, 0.858, (3.4428)+(0.0110)Gln+(−0.0515) His+(−0.2017)Met+(−0.0004)Ile+(0.0619)Phe+ (−0.0934)Trp; 0.831, 0.847, 0.873, 0.854, 0.847, 0.858, 0.822, 0.845, (6.5948)+(0.0166)Ser+(−0.0568)Asn+ (−0.0244)His+(−0.1212)Met+(0.0564)Phe+(−0.0924) Trp; 0.823, 0.841, 0.873, 0.845, 0.845, 0.852, 0.813, 0.839, (5.9004)+(0.0127)Ser+(−0.0325)His+(0.0022) Thr+(−0.1690)Met+(0.0591)Phe+(−0.0924)Trp; 0.821, 0.840, 0.872, 0.842, 0.842, 0.851, 0.818, 0.838, (5.7918)+(0.0136)Ser+(−0.0319)His+(−0.1675)Met+ (0.0041)Ile+(0.0574)Phe+(−0.0919)Trp; 0.843, 0.861, 0.872, 0.873, 0.851, 0.860, 0.851, 0.859, (3.5849)+ (0.0113)Gln+(−0.0496)His+(−0.1909)Met+(−0.0042) Lys+(0.0619)Phe+(−0.0920)Trp; 0.849, 0.863, 0.872, 0.883, 0.834, 0.865, 0.868, 0.862, (3.5810)+(0.0087) Gln+(−0.0238)Val+(−0.2622)Met+(0.0473)Ile+ (0.0706)Phe+(−0.0865)Trp; 0.841, 0.860, 0.871, 0.871, 0.850, 0.857, 0.852, 0.857, (3.4364)+(0.0111)Gln+ (−0.0511)His+(−0.0013)Thr+(−0.1980)Met+(0.0611) Phe+(−0.0931)Trp; 0.825, 0.840, 0.870, 0.844, 0.843, 0.850, 0.813, 0.838, (5.8961)+(0.0135)Ser+(−0.0317) His+(−0.1628)Met+(0.0582)Phe+(−0.0919)Trp; 0.824, 0.843, 0.870, 0.846, 0.850, 0.857, 0.809, 0.841, (6.1358)+(0.0136)Ser+(−0.0254)His+(−0.0246)Cit+ (−0.1553)Met+(0.0573)Phe+(−0.0933)Trp; 0.843, 0.860, 0.870, 0.875, 0.850, 0.858, 0.846, 0.857, (3.5663)+(0.0108)Gln+(−0.0477)His+(−0.1968)Met+ (−0.0060)Leu+(0.0661)Phe+(−0.0927)Trp; 0.822, 0.840, 0.870, 0.845, 0.844, 0.850, 0.812, 0.838, (5.9269)+(0.0139)Ser+(−0.0312)His+(−0.0025)Arg+ (−0.1585)Met+(0.0579)Phe+(−0.0915)Trp; 0.822, 0.840, 0.869, 0.845, 0.843, 0.852, 0.814, 0.838, (5.9641)+(0.0138)Ser+(−0.0308)His+(−0.1585)Met+ (−0.0016)Lys+(0.0583)Phe+(−0.0914)Trp; 0.847, 0.865, 0.868, 0.880, 0.851, 0.854, 0.863, 0.862, (3.3457)+(0.0126)Gln+(−0.0513)His+(−0.2042)Met+ (−0.0199)Orn+(0.0685)Phe+(−0.0938)Trp; 0.847, 0.864, 0.868, 0.881, 0.847, 0.865, 0.850, 0.861, (3.8166)+(0.0108)Gln+(−0.0403)His+(−0.0082)Val+ (−0.2049) Met+(0.0696)Phe+(−0.0882)Trp; 0.836, 0.851, 0.867, 0.857, 0.857, 0.857, 0.818, 0.847, (6.6277)+(0.0157)Ser+(−0.0622)Asn+(−0.0280)Cit+ (−0.1182)Met+(0.0533)Phe+(−0.1019)Trp; 0.823, 0.842, 0.867, 0.847, 0.844, 0.851, 0.817, 0.840, (5.9967)+(0.0140)Ser+(−0.0306)His+(−0.1613)Met+ (−0.0068)Orn+(0.0602)Phe+(−0.0920)Trp; 0.838, 0.855, 0.867, 0.858, 0.842, 0.863, 0.870, 0.858, (6.6808)+(0.0304)Tyr+(−0.0240)Val+(−0.2256)Met+ (0.0495)Ile+(0.0541)Phe+(−0.0870)Trp; 0.855, 0.871, 0.867, 0.879, 0.863, 0.872, 0.864, 0.870, (5.1147)+ (−0.1213)Asn+(0.0130)Gln+(−0.0367)His+(−0.0468) Cit+(0.0353)Phe+(−0.1017)Trp; 0.831, 0.848, 0.866, 0.845, 0.863, 0.854, 0.821, 0.846, (5.5721)+(0.0124) Ser+(−0.0334)Cit+(0.0250)Tyr+(−0.1942)Met+ (0.0498)Phe+(−0.1139)Trp; 0.837, 0.854, 0.866, 0.856, 0.861, 0.854, 0.836, 0.852, (6.1112)+(0.0162)Ser+ (−0.0693)Asn+(0.0246)Tyr+(−0.1529)Met+(0.0489) Phe+(−0.1123)Trp; 0.823, 0.841, 0.865, 0.843, 0.849, 0.847, 0.812, 0.838, (5.5939)+(0.0121)Ser+(−0.0340) Cit+(−0.1749)Met+(0.0079)Ile+(0.0527)Phe+ (−0.1049)Trp; 0.823, 0.841, 0.865, 0.850, 0.843, 0.850, 0.806, 0.837, (6.0598)+(0.0126)Ser+(−0.0268)His+ (−0.1552)Met+(−0.0084)Leu+(0.0638)Phe+(−0.0910) Trp; 0.832, 0.849, 0.864, 0.857, 0.835, 0.860, 0.849, 0.850, (7.0685)+(−0.0221)Cit+(−0.0209)Val+ (−0.1817)Met+(0.0477)Ile+(0.0568)Phe+(−0.0783) Trp; 0.830, 0.849, 0.864, 0.848, 0.849, 0.843, 0.855, 0.849, (6.4939)+(0.0249)Ser+(−0.0090)Gly+(−0.0267) His+(−0.1616)Met+(0.0530)Phe+(−0.0933)Trp; 0.836, 0.852, 0.864, 0.869, 0.840, 0.843, 0.838, 0.847, (3.2359)+(0.0076)Gln+(−0.2239)Met+(0.0412)Ile+ (−0.0322)Leu+(0.0708)Phe+(−0.1031)Trp; 0.842, 0.859, 0.863, 0.869, 0.848, 0.852, 0.856, 0.857, (5.2008)+(0.0008)Ser+(−0.1224)Asn+(0.0111)Gln+ (−0.0451)His+(0.0345)Phe+(−0.0989)Trp; 0.826, 0.844, 0.862, 0.858, 0.840, 0.854, 0.809, 0.840, (6.3284)+(0.0121)Ser+(−0.0201)His+(−0.0086)Val+ (−0.1642)Met+(0.0656)Phe+(−0.0865)Trp; 0.842, 0.859, 0.862, 0.869, 0.850, 0.852, 0.858, 0.857, (5.2386)+(−0.1225)Asn+(0.0111)Gln+(−0.0451)His+ (0.0025)Tyr+(0.0332)Phe+(−0.0998)Trp; 0.845, 0.859, 0.862, 0.870, 0.849, 0.851, 0.856, 0.856, (5.2312)+ (−0.1218)Asn+(0.0112)Gln+(−0.0451)His+(0.0342) Phe+(−0.0988)Trp; 0.829, 0.846, 0.862, 0.859, 0.826, 0.851, 0.849, 0.846, (6.7116)+(−0.0200)Val+(−0.1902) Met+(0.0516)Ile+(−0.0070)Leu+(0.0608)Phe+ (−0.0785)Trp; 0.824, 0.841, 0.862, 0.847, 0.850, 0.844, 0.804, 0.836, (5.7739)+(0.0112)Ser+(0.0015)Thr+ (−0.0327)Cit+(−0.1711)Met+(0.0548)Phe+(−0.1054) Trp; 0.829, 0.845, 0.862, 0.852, 0.846, 0.843, 0.823, 0.841, (6.2199)+(0.0156)Ser+(−0.0681)Asn+ (−0.1302)Met+(0.0034)Ile+(0.0527)Phe+(−0.1034) Trp; 0.831, 0.845, 0.862, 0.853, 0.848, 0.844, 0.819, 0.841, (6.3132)+(0.0149)Ser+(−0.0690)Asn+(0.0018) Thr+(−0.1309)Met+(0.0540)Phe+(−0.1040)Trp; 0.828, 0.846, 0.861, 0.859, 0.826, 0.851, 0.851, 0.847, (6.8200)+(−0.0004)His+(−0.0224)Val+(−0.1919)Met+ (0.0475)Ile+(0.0589)Phe+(−0.0777)Trp; 0.829, 0.846, 0.861, 0.859, 0.826, 0.852, 0.852, 0.847, (6.6545)+ (−0.0232)Val+(−0.2023)Met+(0.0028)Lys+(0.0480) Ile+(0.0598)Phe+(−0.0786)Trp; 0.850, 0.867, 0.861, 0.884, 0.840, 0.881, 0.871, 0.869, (4.0370)+(0.0111) Gln+(−0.0441)His+(−0.0071)Ala+(−0.1656)Met+ (0.0590)Phe+(−0.0844)Trp; 0.847, 0.864, 0.861, 0.880, 0.851, 0.865, 0.850, 0.862, (3.6131)+(0.0121)Gln+ (−0.0505)His+(−0.0094)Pro+(−0.1825)Met+(0.0649)

Phe+(−0.0977)Trp; 0.833, 0.846, 0.861, 0.859, 0.826, 0.852, 0.850, 0.847, (6.8122)+(−0.0225)Val+(−0.1923) Met+(0.0477)Ile+(0.0589)Phe+(−0.0778)Trp; 0.835, 0.851, 0.861, 0.864, 0.832, 0.857, 0.854, 0.852, (7.8537)+(−0.0508)Asn+ (−0.0220)Val+(−0.1418)Met+(0.0466)Ile+(0.0553) Phe+(−0.0753)Trp; 0.835, 0.852, 0.861, 0.862, 0.835, 0.879, 0.842, 0.854, (6.5739)+(0.0127)Ser+(−0.0243) His+(−0.0067)Ala+(−0.1254)Met+(0.0548)Phe+ (−0.0833)Trp; 0.826, 0.845, 0.861, 0.854, 0.846, 0.846, 0.818, 0.841, (6.3177)+(0.0157)Ser+(−0.0674)Asn+ (−0.0012)Arg+(−0.1247)Met+(0.0533)Phe+(−0.1030) Trp; 0.826, 0.843, 0.861, 0.850, 0.842, 0.847, 0.824, 0.841, (6.5117)+(−0.0332)Cit+(−0.1536)Met+(0.0533) Ile+(−0.0359)Leu+(0.0612)Phe+(−0.0907)Trp; 0.823, 0.841, 0.861, 0.847, 0.849, 0.844, 0.804, 0.836, (5.7692)+(0.0117)Ser+(−0.0329)Cit+(−0.1666)Met+ (0.0008)Orn+(0.0540)Phe+(−0.1049)Trp; 0.821, 0.838, 0.860, 0.842, 0.838, 0.852, 0.819, 0.838, (4.4648)+(0.0082)Gln+(−0.0521)His+(−0.0472)Cit+ (0.0240) Phe+(−0.1033)Trp; 0.824, 0.842, 0.860, 0.845, 0.845, 0.851, 0.820, 0.840, (7.6321)+(0.0112) Ser+(−0.0847)Asn+(−0.0205)His+(−0.0262)Cit+ (0.0345)Phe+(−0.0975)Trp; 0.832, 0.845, 0.860, 0.854, 0.847, 0.843, 0.820, 0.841, (6.3080)+(0.0155)Ser+ (−0.0680)Asn+(−0.1264)Met+(0.0534)Phe+(−0.1033) Trp; 0.816, 0.827, 0.860, 0.832, 0.821, 0.836, 0.821, 0.828, (4.5801)+(0.0064)Gln+(−0.0606)His+(0.0228) Phe+(−0.1005)Trp; 0.809, 0.826, 0.860, 0.835, 0.817, 0.836, 0.817, 0.826, (4.5675)+(0.0066)Gln+(−0.0604) His+(−0.0091)Tyr+(0.0265)Phe+(−0.0969)Trp; 0.828, 0.846, 0.860, 0.859, 0.826, 0.852, 0.851, 0.847, (6.8341)+(−0.0007)Arg+(−0.0225)Val+(−0.1907)Met+ (0.0477)Ile+(0.0588)Phe+(−0.0776)Trp; 0.816, 0.838, 0.860, 0.845, 0.834, 0.852, 0.818, 0.837, (4.4559)+ (0.0084)Gln+(−0.0520) His+(−0.0468)Cit+(−0.0071) Tyr+(0.0269)Phe+(−0.1005)Trp; 0.825, 0.841, 0.860, 0.850, 0.843, 0.854, 0.808, 0.839, (6.2539)+(0.0133) Ser+(−0.0296)His+(−0.0058)Pro+(−0.1457)Met+ (0.0590)Phe+(−0.0945)Trp; 0.846, 0.862, 0.860, 0.873, 0.852, 0.858, 0.859, 0.860, (5.3365)+(−0.1137)Asn+ (0.0118)Gln+(−0.0420)His+(−0.0073)Lys+(0.0373) Phe+(−0.0959)Trp; 0.825, 0.842, 0.860, 0.849, 0.850, 0.848, 0.802, 0.837, (5.9599)+(0.0126)Ser+(−0.0319) Cit+(−0.1558)Met+(−0.0037)Lys+(0.0548)Phe+ (−0.1027)Trp; 0.828, 0.841, 0.860, 0.847, 0.849, 0.843, 0.804, 0.836, (5.7741)+(0.0118)Ser+(−0.0322)Cit+ (−0.1667)Met+(0.0543)Phe+(−0.1048)Trp; 0.831, 0.847, 0.860, 0.859, 0.827, 0.852, 0.854, 0.848, (6.8895)+(−0.0222)Val+(−0.1915)Met+(−0.0055) Orn+(0.0496)Ile+(0.0595)Phe+(−0.0778)Trp; 0.845, 0.863, 0.859, 0.877, 0.854, 0.857, 0.850, 0.860, (4.9605)+(−0.1109)Asn+(0.0129)Gln+(−0.0448)His+ (−0.0163)Arg+(0.0359)Phe+(−0.0953)Trp; 0.830, 0.850, 0.859, 0.859, 0.844, 0.867, 0.827, 0.849, (4.7362)+(0.0100)Gln+(−0.0440)His+(−0.0493)Cit+ (−0.0136)Lys+(0.0313)Phe+(−0.0978)Trp; 0.823, 0.845, 0.859, 0.854, 0.842, 0.858, 0.817, 0.843, (4.2587)+(0.0100)Gln+(−0.0524)His+(−0.0345)Cit+ (−0.0181)Arg+(0.0267)Phe+(−0.0985)Trp; 0.831, 0.846, 0.859, 0.856, 0.847, 0.844, 0.820, 0.842, (6.3562)+(0.0158)Ser+(−0.0655)Asn+(−0.1269)Met+ (−0.0048)Orn+(0.0549)Phe+(−0.1031)Trp; 0.818, 0.838, 0.859, 0.846, 0.837, 0.841, 0.814, 0.834, (7.4338)+(0.0120)Ser+(−0.0844)Asn+(−0.0261)His+ (−0.0053)Arg+(0.0350)Phe+(−0.0949)Trp; 0.823, 0.841, 0.859, 0.846, 0.849, 0.842, 0.806, 0.836, (5.7600)+(0.0112)Ser+(−0.0349)Cit+(0.0033)Arg+ (−0.1716)Met+(0.0546)Phe+(−0.1056)Trp; 0.831, 0.846, 0.859, 0.855, 0.847, 0.846, 0.820, 0.842, (6.3922)+(0.0159)Ser+(−0.0665)Asn+(−0.1215)Met+ (−0.0021)Lys+(0.0537)Phe+(−0.1022)Trp; 0.819, 0.840, 0.859, 0.855, 0.831, 0.849, 0.811, 0.837, (4.2627)+(0.0095)Gln+(−0.0580)His+(−0.0238)Arg+ (−0.0038)Tyr+(0.0284)Phe+(−0.0936)Trp; 0.844, 0.861, 0.859, 0.873, 0.849, 0.849, 0.864, 0.859, (5.1561)+(−0.1186)Asn+(0.0122)Gln+(−0.0454)His+ (−0.0148)Orn+(0.0385)Phe+(−0.0992)Trp; 0.822, 0.842, 0.859, 0.843, 0.855, 0.846, 0.809, 0.838, (7.1177)+(−0.0245)His+(0.0071)Thr+(−0.0262)Cit+ (−0.1480)Met+(0.0513)Phe+(−0.0948)Trp; 0.823, 0.840, 0.859, 0.853, 0.833, 0.848, 0.812, 0.837, (4.2643)+(0.0095)Gln+(−0.0580)His+(−0.0241)Arg+ (0.0269)Phe+(−0.0950)Trp; 0.819, 0.839, 0.859, 0.846, 0.836, 0.844, 0.820, 0.836, (7.5330)+(0.0121)Ser+ (−0.0841)Asn+(−0.0248)His+(−0.0042)Lys+(0.0364) Phe+(−0.0944)Trp; 0.838, 0.853, 0.858, 0.855, 0.853, 0.841, 0.859, 0.852, (6.9057)+(0.0270)Ser+(−0.0612) Asn+(−0.0091)Gly+(−0.1277)Met+(0.0488)Phe+ (−0.1027)Trp; 0.834, 0.850, 0.858, 0.852, 0.854, 0.839, 0.847, 0.848, (6.3156)+(0.0231)Ser+(−0.0087)Gly+ (−0.0233)Cit+(−0.1668)Met+(0.0499)Phe+(−0.1044) Trp; 0.823, 0.836, 0.858, 0.843, 0.834, 0.837, 0.821, 0.834, (7.4516)+(0.0109)Ser+(−0.0888)Asn+(−0.0270)His+(0.0342)Phe+(−0.0962)Trp; 0.835, 0.851, 0.858, 0.852, 0.854, 0.834, 0.855, 0.849, (5.8771)+ (0.0234)Ser+(−0.0091)Gly+(0.0152)Tyr+(−0.1942) Met+(0.0470)Phe+(−0.1114)Trp; 0.818, 0.837, 0.858, 0.841, 0.844, 0.837, 0.815, 0.834, (6.8189)+(−0.0308) His+(0.0060)Thr+(−0.1554)Met+(0.0031)Ile+(0.0508) Phe+(−0.0930)Trp; 0.846, 0.862, 0.858, 0.878, 0.849, 0.851, 0.853, 0.858, (5.4093)+(−0.1206)Asn+(0.0110) Gln+(−0.0380)His+(−0.0110)Leu+(0.0437)Phe+ (−0.0973)Trp; 0.837, 0.851, 0.858, 0.868, 0.844, 0.854, 0.818, 0.846, (7.0621)+(0.0148)Ser+(−0.0652)Asn+ (−0.0106)Val+(−0.1219)Met+(0.0642)Phe+(−0.0901) Trp; 0.821, 0.839, 0.858, 0.842, 0.847, 0.836, 0.819, 0.836, (5.0497)+(0.0117)Ser+(0.0233)Tyr+(−0.2099) Met+(0.0021)Ile+(0.0498)Phe+(−0.1154)Trp; 0.823, 0.842, 0.858, 0.845, 0.851, 0.840, 0.814, 0.837, (5.1803)+(0.0126)Ser+(−0.0051)Arg+(0.0239)Tyr+ (−0.1988)Met+(0.0497)Phe+(−0.1142)Trp; 0.844, 0.860, 0.858, 0.874, 0.850, 0.849, 0.850, 0.856, (5.3633)+(−0.1193)Asn+(0.0115)Gln+(−0.0448)His+ (−0.0111)Ile+(0.0387)Phe+(−0.0985)Trp; 0.822, 0.843, 0.857, 0.857, 0.833, 0.856, 0.814, 0.840, (4.4823)+(0.0098)Gln+(−0.0544)His+(−0.0190)Arg+ (−0.0074)Lys+(0.0300)Phe+(−0.0931)Trp; 0.806, 0.828, 0.857, 0.839, 0.798, 0.870, 0.835, 0.835, (4.9288)+(0.0110)Ser+(−0.0175)His+(−0.0279)Val+ (−0.2471)Met+(0.0594)Ile+(0.0520)Phe; 0.825, 0.843, 0.857, 0.840, 0.854, 0.844, 0.825, 0.841, (6.7583)+ (−0.0303)His+(0.0055)Thr+(0.0214)Tyr+(−0.1732) Met+(0.0469)Phe+(−0.1008)Trp; 0.820, 0.839, 0.857, 0.850, 0.832, 0.855, 0.816, 0.838, (4.7194)+(0.0078) Gln+(−0.0458)His+(−0.0439)Cit+(−0.0051)Val+ (0.0284)Phe+(−0.1000)Trp; 0.841, 0.857, 0.857, 0.869, 0.823, 0.882, 0.875, 0.862, (7.3604)+(−0.0067)Ala+ (−0.0199)Val+(−0.1555)Met+(0.0506)Ile+(0.0532) Phe+(−0.0690)Trp; 0.820, 0.836, 0.857, 0.847, 0.825, 0.847, 0.822, 0.835, (4.8410)+(0.0080)Gln+(−0.0534) His+(−0.0128)Lys+(0.0296)Phe+(−0.0951)Trp; 0.827, 0.844, 0.857, 0.848, 0.850, 0.838, 0.821, 0.839, (7.6779)+(−0.0494)Asn+(−0.0244)His+(0.0079)Thr+ (−0.1163)Met+(0.0491)Phe+(−0.0939)Trp; 0.835, 0.851, 0.857, 0.866, 0.826, 0.879, 0.843, 0.853, (5.3914)+(0.0086)Gln+(−0.0274)His+(−0.0137)Val+(−0.1738)Met+(0.0347)Ile+(−0.0669)Trp; 0.857, 0.874, 0.857, 0.886, 0.869, 0.867, 0.853, 0.869, (4.0729)+(−0.0942)Asn+(0.0132)Gln+(−0.0523)Cit+(−0.1417)Met+(0.0541)Phe+(−0.1117)Trp; 0.818, 0.837, 0.857, 0.844, 0.834, 0.837, 0.821, 0.834, (7.4828)+(0.0111)Ser+(−0.0874)Asn+(−0.0267)His+(−0.0032)Orn+(0.0351)Phe+(−0.0962)Trp; 0.817, 0.838, 0.857, 0.843, 0.846, 0.835, 0.809, 0.833, (6.9264)+(−0.0304)His+(0.0064)Thr+(−0.0019)Arg+(−0.1497)Met+(0.0513)Phe+(−0.0928)Trp; 0.831, 0.846, 0.857, 0.861, 0.825, 0.856, 0.843, 0.846, (7.8869)+(0.0080)Ser+(−0.1053)Asn+(−0.0174)Val+(0.0268)Ile+(0.0379)Phe+(−0.0882)Trp; 0.827, 0.842, 0.856, 0.848, 0.847, 0.846, 0.814, 0.839, (7.4518)+(0.0099)Ser+(−0.0955)Asn+(−0.0369)Cit+(0.0065)Orn+(0.0297)Phe+(−0.1064)Trp

List (1) of Logistic Regression Equations Searched in Example 5

The logistic regression equations searched in Example 5 above are listed below. Before each equation, "the value of ROC_AUC for the pancreatic cancer group and the lung cancer group with validation", "the value of ROC_AUC for the pancreatic cancer group and the lung cancer group without validation", "the value of ROC_AUC for the pancreatic cancer group and the healthy group", "the value of ROC_AUC for the pancreatic cancer group and the other cancers group", "the value of ROC_AUC for the pancreatic cancer group and the colorectal cancer group", "the value of ROC_AUC for the pancreatic cancer group and the prostatic cancer group", "the value of ROC_AUC for the pancreatic cancer group and the breast cancer group", and "the average value of the value of ROC_AUC for the pancreatic cancer group and the lung cancer group, the value of ROC_AUC for the pancreatic cancer group and the colorectal cancer group, the value of ROC_AUC for the pancreatic cancer group and the prostatic cancer group, and the value of ROC_AUC for the pancreatic cancer group and the breast cancer group" obtained for the equation are additionally listed.

0.879, 0.901, 0.799, 0.867, 0.834, 0.859, 0.850, 0.861, (2.5017)+(−0.1544)Asn+(0.0144)Gln+(−0.0136)Pro+(−0.0179)Val+(0.0647)Phe+(−0.0751)Trp; 0.879, 0.900, 0.825, 0.868, 0.840, 0.855, 0.849, 0.861, (1.5408)+(−0.1050)Asn+(0.0143)Gln+(−0.0196)Val+(−0.1804)Met+(0.0788)Phe+(−0.0595)Trp; 0.879, 0.899, 0.808, 0.865, 0.818, 0.870, 0.869, 0.864, (2.4184)+(−0.1460)Asn+(0.0137)Gln+(−0.0063)Ala+(−0.0174)Val+(0.0542)Phe+(−0.0581)Trp; 0.878, 0.899, 0.806, 0.859, 0.832, 0.846, 0.822, 0.850, (2.3121)+(−0.1378)Asn+(0.0149)Gln+(−0.0291)Arg+(−0.0209)Val+(0.0646)Phe+(−0.0644)Trp; 0.877, 0.896, 0.794, 0.863, 0.820, 0.895, 0.843, 0.864, (3.0546)+(−0.1157)Asn+(0.0150)Gln+(−0.0065)Ala+(−0.0363)Cit+(−0.0103)Val+(−0.0537)Trp; 0.877, 0.899, 0.770, 0.854, 0.809, 0.880, 0.810, 0.849, (3.2431)+(−0.0996)Asn+(0.0151)Gln+(−0.0064)Ala+(−0.0237)Arg+(−0.0122)Val+(−0.0440)Trp; 0.876, 0.898, 0.829, 0.870, 0.844, 0.865, 0.854, 0.865, (2.0985)+(−0.1578)Asn+(0.0147)Gln+(−0.0434)Cit+(−0.0184)Val+(0.0625)Phe+(−0.0746)Trp; 0.876, 0.893, 0.817, 0.860, 0.829, 0.849, 0.847, 0.854, (2.9307)+(−0.1647)Asn+(0.0124)Gln+(−0.0209)Val+(0.0566)Phe+(−0.0686)Trp; 0.875, 0.892, 0.780, 0.854, 0.803, 0.884, 0.840, 0.855, (3.6223)+(−0.1220)Asn+(0.0132)Gln+(−0.0067)Ala+(−0.0129)Val+(−0.0490)Trp; 0.874, 0.894, 0.805, 0.860, 0.830, 0.841, 0.846, 0.853, (3.2658)+(−0.0073)Ser+(−0.1562)Asn+(0.0131)Gln+(−0.0209)Val+(0.0537)Phe+(−0.0697)Trp; 0.874, 0.894, 0.806, 0.860, 0.825, 0.846, 0.851, 0.854, (2.7168)+(−0.1504)Asn+(0.0132)Gln+(−0.0088)Thr+(−0.0197)Val+(0.0537)Phe+(−0.0663)Trp; 0.874, 0.898, 0.766, 0.857, 0.808, 0.880, 0.836, 0.855, (3.5580)+(−0.1181)Asn+(0.0142)Gln+(−0.0057)Ala+(−0.0086)Pro+(−0.0110)Val+(−0.0528)Trp; 0.873, 0.891, 0.807, 0.864, 0.828, 0.888, 0.853, 0.865, (2.2278)+(−0.1175)Asn+(0.0154)Gln+(−0.0077)Ala+(−0.0464)Cit+(−0.0694)Trp; 0.873, 0.894, 0.766, 0.854, 0.820, 0.865, 0.816, 0.849, (3.9874)+(−0.1306)Asn+(0.0133)Gln+(−0.0113)Pro+(−0.0132)Val+(−0.0617)Trp; 0.873, 0.894, 0.798, 0.863, 0.827, 0.893, 0.838, 0.863, (2.7457)+(−0.1095)Asn+(0.0149)Gln+(−0.0072)Ala+(−0.0424)Cit+(−0.0107)Leu+(−0.0615)Trp; 0.873, 0.893, 0.789, 0.856, 0.803, 0.886, 0.850, 0.858, (3.5353)+(−0.1236)Asn+(0.0131)Gln+(−0.0068)Ala+(−0.0146)Val+(0.0076)Ile+(−0.0475)Trp; 0.873, 0.896, 0.810, 0.855, 0.811, 0.855, 0.840, 0.850, (0.6642)+(0.0125)Gln+(−0.0052)Ala+(−0.0163)Val+(−0.2337)Met+(0.0706)Phe+(−0.0564)Trp; 0.873, 0.895, 0.767, 0.856, 0.801, 0.880, 0.851, 0.857, (3.3049)+(−0.1056)Asn+(0.0142)Gln+(−0.0107)Thr+(−0.0066)Ala+(−0.0119)Val+(−0.0475)Trp; 0.873, 0.893, 0.769, 0.851, 0.813, 0.873, 0.806, 0.846, (2.9725)+(−0.0932)Asn+(0.0146)Gln+(−0.0074)Ala+(−0.0245)Arg+(−0.0128)Leu+(−0.0524)Trp; 0.873, 0.894, 0.805, 0.860, 0.819, 0.859, 0.860, 0.858, (2.1851)+(−0.1339)Asn+(0.0128)Gln+(−0.0075)Ala+(−0.0221)Leu+(0.0535)Phe+(−0.0678)Trp; 0.872, 0.896, 0.789, 0.865, 0.829, 0.890, 0.844, 0.865, (2.3256)+(−0.1109)Asn+(0.0163)Gln+(−0.0063)Ala+(−0.0432)Cit+(−0.0095)Pro+(−0.0722)Trp; 0.872, 0.893, 0.756, 0.852, 0.799, 0.866, 0.840, 0.850, (4.0269)+(−0.0137)Ser+(−0.1075)Asn+(0.0146)Gln+(−0.0071)Ala+(−0.0129)Val+(−0.0515)Trp; 0.872, 0.891, 0.793, 0.860, 0.828, 0.879, 0.833, 0.858, (2.1632)+(−0.1039)Asn+(0.0161)Gln+(−0.0077)Ala+(−0.0331)Cit+(−0.0180)Arg+(−0.0639)Trp; 0.872, 0.896, 0.760, 0.854, 0.825, 0.869, 0.793, 0.846, (3.6419)+(−0.1091)Asn+(0.0151)Gln+(−0.0226)Arg+(−0.0101)Pro+(−0.0129)Val+(−0.0571)Trp; 0.872, 0.891, 0.819, 0.860, 0.825, 0.852, 0.856, 0.856, (2.9395)+(−0.1699)Asn+(0.0128)Gln+(−0.0274)Val+(0.0126)Leu+(0.0531)Phe+(−0.0668)Trp; 0.872, 0.896, 0.785, 0.861, 0.821, 0.877, 0.837, 0.858, (3.7526)+(−0.1329)Asn+(0.0133)Gln+(−0.0127)Pro+(−0.0174)Val+(0.0198)Ile+(−0.0589)Trp; 0.872, 0.891, 0.822, 0.860, 0.829, 0.851, 0.849, 0.855, (2.8423)+(−0.1619)Asn+(0.0127)Gln+(−0.0065)His+(−0.0202)Val+(0.0568)Phe+(−0.0667)Trp; 0.871, 0.892, 0.780, 0.854, 0.802, 0.883, 0.841, 0.855, (3.6590)+(−0.1254)Asn+(0.0130)Gln+(−0.0067)Ala+(−0.0134)Val+(0.0017)Lys+(−0.0493)Trp; 0.871, 0.892, 0.818, 0.859, 0.828, 0.847, 0.846, 0.853, (2.9627)+(−0.1677)Asn+(0.0123)Gln+(−0.0214)Val+(0.0014)Lys+(0.0567)Phe+(−0.0687)Trp; 0.871, 0.893, 0.832, 0.870, 0.859, 0.859, 0.836, 0.862, (1.8582)+(−0.1462)Asn+(0.0139)Gln+(−0.0518)Cit+(−0.0240)Leu+(0.0618)Phe+(−0.0862)Trp; 0.871, 0.892, 0.778, 0.853, 0.801, 0.883, 0.838, 0.854, (3.6602)+(−0.1232)Asn+(0.0130)Gln+(0.0034)His+(−0.0068)Ala+(−0.0132)Val+(−0.0498)Trp; 0.871, 0.893, 0.818, 0.860, 0.829, 0.849, 0.848, 0.855, (2.9200)+(−0.1649)Asn+(0.0124)Gln+(−0.0211)Val+(0.0010)Ile+(0.0566)Phe+(−0.0684)Trp; 0.871, 0.897, 0.783, 0.863, 0.836, 0.878, 0.821, 0.858, (3.4654)+(−0.1234)Asn+(0.0150)Gln+(−0.0357)Cit+
(−0.0107)Pro+(−0.0106)Val+(−0.0669)Trp; 0.871,
0.894, 0.757, 0.855, 0.818, 0.862, 0.823, 0.849,
(3.6841)+(−0.1155)Asn+(0.0142)Gln+(−0.0099)Thr+
(−0.0107)Pro+(−0.0124)Val+(−0.0608)Trp; 0.871,
0.885, 0.788, 0.848, 0.815, 0.858, 0.814, 0.843,
(4.2016)+(−0.1395)Asn+(0.0118)Gln+(−0.0164)Val+
(−0.0598)Trp; 0.871, 0.892, 0.786, 0.856, 0.800, 0.884,
0.855, 0.858, (3.5356)+(−0.1318)Asn+(0.0137)Gln+
(−0.0064)Ala+(−0.0223)Val+(0.0172)Leu+(−0.0476)
Trp; 0.871, 0.895, 0.783, 0.856, 0.809, 0.883, 0.834,
0.855, (3.3196)+(−0.0940)Asn+(0.0137)Gln+
(−0.0059)Ala+(−0.0119)Val+(−0.0813)Met+(−0.0441)
Trp; 0.871, 0.894, 0.827, 0.871, 0.836, 0.883, 0.878,
0.873, (0.9598)+(−0.1351)Asn+(0.0160)Gln+
(−0.0078)Ala+(−0.0520)Cit+(0.0412)Phe+(−0.0816)
Trp; 0.871, 0.893, 0.764, 0.853, 0.815, 0.869, 0.816,
0.848, (2.4550)+(−0.0982)Asn+(0.0161)Gln+
(−0.0067)Ala+(−0.0235)Arg+(−0.0096)Pro+(−0.0644)
Trp; 0.871, 0.892, 0.776, 0.849, 0.793, 0.878, 0.831,
0.848, (3.8206)+(−0.1186)Asn+(0.0132)Gln+
(−0.0064)Ala+(−0.0133)Tyr+(−0.0124)Val+(−0.0433)
Trp; 0.870, 0.895, 0.747, 0.856, 0.822, 0.855, 0.821,
0.849, (4.3566)+(−0.0117)Ser+(−0.1182)Asn+(0.0145)
Gln+(−0.0114)Pro+(−0.0134)Val+(−0.0652)Trp;
0.870, 0.894, 0.798, 0.863, 0.843, 0.845, 0.839, 0.855,
(2.2275)+(−0.1449)Asn+(0.0134)Gln+(−0.0143)Pro+
(−0.0207)Leu+(0.0611)Phe+(−0.0880)Trp; 0.870,
0.888, 0.802, 0.858, 0.833, 0.870, 0.821, 0.853,
(3.6506)+(−0.1325)Asn+(0.0136)Gln+(−0.0376)Cit+
(−0.0136)Val+(−0.0640)Trp; 0.870, 0.891, 0.757,
0.847, 0.810, 0.861, 0.796, 0.840, (2.9262)+(−0.0988)
Asn+(0.0150)Gln+(−0.0074)Ala+(−0.0240)Arg+
(−0.0184)Ile+(−0.0589)Trp; 0.870, 0.893, 0.804,
0.866, 0.829, 0.892, 0.853, 0.867, (2.2383)+(−0.1100)
Asn+(0.0157)Gln+(−0.0076)Ala+(−0.0462)Cit+
(−0.0036)Lys+(−0.0673)Trp; 0.870, 0.891, 0.785,
0.856, 0.820, 0.878, 0.825, 0.854, (2.7544)+(−0.1122)
Asn+(0.0154)Gln+(−0.0070)Ala+(−0.0444)Cit+
(−0.0185)Ile+(−0.0670)Trp; 0.870, 0.889, 0.779,
0.853, 0.807, 0.876, 0.838, 0.852, (3.3036)+(−0.1156)
Asn+(0.0126)Gln+(−0.0077)Ala+(−0.0137)Leu+
(−0.0579)Trp; 0.870, 0.891, 0.793, 0.864, 0.832, 0.829,
0.885, 0.859, (3.9221)+(−0.1340)Asn+(−0.0131)Gly+
(0.0158)Gln+(−0.0219)Val+(0.0448)Phe+(−0.0796)
Trp; 0.870, 0.887, 0.777, 0.851, 0.812, 0.868, 0.825,
0.848, (2.4154)+(−0.1035)Asn+(0.0149)Gln+
(−0.0082)Ala+(−0.0250)Arg+(−0.0605)Trp; 0.870,
0.887, 0.776, 0.846, 0.817, 0.862, 0.787, 0.838,
(3.8220)+(−0.1157)Asn+(0.0139)Gln+(−0.0248)Arg+
(−0.0159)Val+(−0.0531)Trp; 0.869, 0.894, 0.769,
0.855, 0.820, 0.865, 0.818, 0.849, (3.9537)+(−0.1292)
Asn+(0.0135)Gln+(−0.0032)His+(−0.0113)Pro+
(−0.0129)Val+(−0.0608)Trp; 0.869, 0.886, 0.770,
0.848, 0.817, 0.844, 0.818, 0.841, (4.5838)+(−0.0110)
Ser+(−0.1288)Asn+(0.0129)Gln+(−0.0166)Val+
(−0.0625)Trp; 0.869, 0.892, 0.809, 0.859, 0.826, 0.841,
0.852, 0.853, (2.7855)+(−0.1607)Asn+(0.0136)Gln+
(−0.0189)Val+(−0.0174)Orn+(0.0584)Phe+(−0.0730)
Trp; 0.869, 0.890, 0.784, 0.858, 0.833, 0.859, 0.825,
0.852, (4.0173)+(−0.0107)Ser+(−0.1216)Asn+
(0.0147)Gln+(−0.0370)Cit+(−0.0139)Val+(−0.0667)
Trp; 0.869, 0.892, 0.812, 0.847, 0.806, 0.831, 0.825,
0.839, (3.3304)+(−0.1605)Asn+(0.0130)Gln+
(−0.0378)Tyr+(−0.0203)Val+(0.0723)Phe+(−0.0542)
Trp; 0.869, 0.889, 0.769, 0.854, 0.808, 0.874, 0.846,
0.854, (2.7396)+(−0.1199)Asn+(0.0143)Gln+
(−0.0068)Ala+(−0.0106)Pro+(−0.0701)Trp; 0.869,
0.893, 0.809, 0.867, 0.835, 0.891, 0.848, 0.867,
(2.0980)+(−0.0922)Asn+(0.0156)Gln+(−0.0068)Ala+
(−0.0424)Cit+(−0.0745)Met+(−0.0643)Trp; 0.869,
0.893, 0.766, 0.854, 0.819, 0.864, 0.816, 0.848,
(4.0000)+(−0.1318)Asn+(0.0133)Gln+(−0.0113)Pro+
(−0.0134)Val+(0.0005)Lys+(−0.0618)Trp; 0.869,
0.891, 0.751, 0.863, 0.833, 0.841, 0.868, 0.858,
(4.7039)+(−0.0974)Asn+(−0.0145)Gly+(0.0172)Gln+
(−0.0123)Pro+(−0.0150)Val+(−0.0765)Trp; 0.869,
0.891, 0.808, 0.850, 0.827, 0.843, 0.797, 0.839,
(0.5776)+(0.0144)Gln+(−0.0263)Arg+(−0.0188)Val+
(−0.2381)Met+(0.0788)Phe+(−0.0605)Trp; 0.869,
0.891, 0.802, 0.858, 0.817, 0.884, 0.836, 0.857,
(2.5560)+(−0.1120)Asn+(0.0154)Gln+(−0.0071)Ala+
(−0.0471)Cit+(−0.0183)Tyr+(−0.0614)Trp; 0.869,
0.895, 0.775, 0.858, 0.816, 0.872, 0.837, 0.855,
(3.8763)+(−0.1432)Asn+(0.0143)Gln+(−0.0124)Pro+
(−0.0277)Val+(0.0274)Leu+(−0.0606)Trp; 0.869,
0.890, 0.804, 0.854, 0.844, 0.836, 0.794, 0.841,
(2.2097)+(−0.1272)Asn+(0.0134)Gln+(−0.0300)Arg+
(−0.0274)Leu+(0.0631)Phe+(−0.0756)Trp; 0.868,
0.883, 0.790, 0.852, 0.806, 0.872, 0.853, 0.853,
(2.6780)+(−0.1261)Asn+(0.0130)Gln+(−0.0085)Ala+
(−0.0678)Trp; 0.868, 0.892, 0.790, 0.863, 0.823, 0.878,
0.860, 0.863, (1.8784)+(−0.0968)Asn+(0.0169)Gln+
(−0.0135)Thr+(−0.0073)Ala+(−0.0476)Cit+(−0.0673)
Trp; 0.868, 0.890, 0.793, 0.861, 0.821, 0.858, 0.867,
0.859, (1.5610)+(−0.1371)Asn+(0.0149)Gln+
(−0.0067)Ala+(−0.0125)Pro+(0.0418)Phe+(−0.0840)
Trp; 0.868, 0.891, 0.803, 0.862, 0.838, 0.881, 0.818,
0.857, (3.2905)+(−0.0971)Asn+(0.0142)Gln+
(−0.0331)Cit+(−0.0121)Val+(−0.0973)Met+(−0.0571)
Trp; 0.868, 0.891, 0.765, 0.854, 0.804, 0.873, 0.848,
0.854, (2.9967)+(−0.0973)Asn+(0.0138)Gln+
(−0.0124)Thr+(−0.0074)Ala+(−0.0126)Leu+(−0.0556)
Trp; 0.868, 0.886, 0.725, 0.831, 0.773, 0.867, 0.778,
0.826, (2.8819)+(−0.1086)Asn+(0.0152)Gln+
(−0.0074)Ala+(−0.0259)Arg+(−0.0170)Val; 0.868,
0.890, 0.767, 0.863, 0.821, 0.859, 0.879, 0.862,
(4.3460)+(−0.1007)Asn+(−0.0129)Gly+(0.0163)Gln+
(−0.0053)Ala+(−0.0153)Val+(−0.0615)Trp; 0.868,
0.892, 0.770, 0.852, 0.798, 0.876, 0.841, 0.852,
(3.4683)+(−0.1172)Asn+(0.0145)Gln+(−0.0070)Ala+
(−0.0105)Val+(−0.0181)Orn+(−0.0524)Trp; 0.868,
0.884, 0.818, 0.856, 0.842, 0.832, 0.826, 0.846,
(2.7211)+(−0.1542)Asn+(0.0111)Gln+(−0.0265)Leu+
(0.0551)Phe+(−0.0827)Trp; 0.868, 0.890, 0.760, 0.858,
0.827, 0.838, 0.853, 0.852, (4.5717)+(−0.0861)Asn+
(−0.0138)Gly+(0.0171)Gln+(−0.0230)Arg+(−0.0176)
Val+(−0.0683)Trp; 0.868, 0.889, 0.784, 0.862, 0.826,
0.874, 0.854, 0.861, (2.5701)+(−0.0129)Ser+(−0.1025)
Asn+(0.0167)Gln+(−0.0081)Ala+(−0.0454)Cit+
(−0.0725)Trp; 0.868, 0.891, 0.764, 0.844, 0.790, 0.853,
0.824, 0.839, (1.1007)+(−0.1035)Asn+(0.0148)Gln+
(−0.0057)Ala+(−0.0213)Val+(−0.1699)Met+(0.0641)
Phe; 0.868, 0.886, 0.775, 0.849, 0.811, 0.854, 0.824,
0.844, (3.8432)+(−0.1227)Asn+(0.0129)Gln+
(−0.0113)Thr+(−0.0152)Val+(−0.0579)Trp; 0.868,
0.885, 0.794, 0.850, 0.816, 0.861, 0.819, 0.845,
(4.1486)+(−0.1405)Asn+(0.0117)Gln+(−0.0175)Val+
(0.0051)Ile+(−0.0589)Trp; 0.867, 0.889, 0.763, 0.846,
0.816, 0.852, 0.789, 0.837, (4.1138)+(−0.0085)Ser+
(−0.1076)Asn+(0.0146)Gln+(−0.0237)Arg+(−0.0160)
Val+(−0.0558)Trp; 0.867, 0.889, 0.802, 0.858, 0.820,
0.878, 0.843, 0.857, (3.3758)+(−0.0996)Asn+(0.0143)
Gln+(−0.0330)Val+(−0.1527)Met+(0.0356)Leu+
(−0.0467)Trp; 0.867, 0.889, 0.778, 0.846, 0.817, 0.858, 0.787, 0.838, (3.9146)+(−0.1262)Asn+(0.0135)Gln+(−0.0276)Arg+(−0.0178)Val+(0.0066)Lys+(−0.0538)Trp; 0.867, 0.890, 0.786, 0.857, 0.825, 0.865, 0.829, 0.852, (3.1465)+(−0.1133)Asn+(0.0153)Gln+(−0.0128)Thr+(−0.0413)Cit+(−0.0123)Val+(−0.0627)Trp; 0.867, 0.887, 0.791, 0.853, 0.823, 0.868, 0.811, 0.847, (3.6993)+(−0.0978)Asn+(0.0128)Gln+(−0.0144)Val+(−0.1127)Met+(−0.0514)Trp; 0.867, 0.892, 0.787, 0.859, 0.826, 0.815, 0.872, 0.851, (2.2295)+(−0.0139)Gly+(0.0160)Gln+(−0.0198)Val+(−0.2375)Met+(0.0599)Phe+(−0.0726)Trp; 0.867, 0.891, 0.787, 0.852, 0.826, 0.867, 0.794, 0.845, (3.5652)+(−0.1161)Asn+(0.0146)Gln+(−0.0224)Cit+(−0.0204)Arg+(−0.0143)Val+(−0.0567)Trp; 0.867, 0.888, 0.801, 0.855, 0.819, 0.850, 0.846, 0.851, (1.3118)+(−0.1192)Asn+(0.0154)Gln+(−0.0083)Ala+(−0.0274)Arg+(0.0394)Phe+(−0.0721)Trp; 0.867, 0.893, 0.764, 0.848, 0.809, 0.858, 0.805, 0.841, (4.1690)+(−0.1271)Asn+(0.0134)Gln+(−0.0105)Pro+(−0.0136)Tyr+(−0.0129)Val+(−0.0553)Trp; 0.867, 0.889, 0.767, 0.852, 0.808, 0.863, 0.836, 0.849, (2.2550)+(−0.0915)Asn+(0.0156)Gln+(−0.0097)Thr+(−0.0079)Ala+(−0.0222)Arg+(−0.0592)Trp; 0.867, 0.890, 0.813, 0.869, 0.853, 0.861, 0.850, 0.864, (1.0150)+(−0.1443)Asn+(0.0168)Gln+(−0.0547)Cit+(−0.0161)Pro+(0.0524)Phe+(−0.1028)Trp; 0.867, 0.889, 0.742, 0.835, 0.778, 0.850, 0.804, 0.830, (1.7622)+(−0.1296)Asn+(0.0158)Gln+(−0.0071)Ala+(−0.0283)Arg+(−0.0220)Val+(0.0471)Phe; 0.867, 0.886, 0.768, 0.859, 0.827, 0.836, 0.869, 0.855, (4.9691)+(−0.1110)Asn+(−0.0143)Gly+(0.0155)Gln+(−0.0184)Val+(−0.0725)Trp; 0.867, 0.889, 0.751, 0.840, 0.778, 0.881, 0.809, 0.839, (2.6674)+(−0.1110)Asn+(0.0152)Gln+(−0.0075)Ala+(−0.0266)Arg+(−0.0212)Val+(0.0204)Ile; 0.867, 0.891, 0.758, 0.855, 0.805, 0.871, 0.855, 0.855, (2.5140)+(−0.1026)Asn+(0.0153)Gln+(−0.0113)Thr+(−0.0066)Ala+(−0.0097)Pro+(−0.0680)Trp; 0.867, 0.891, 0.804, 0.864, 0.827, 0.888, 0.853, 0.865, (2.2343)+(−0.1182)Asn+(0.0153)Gln+(0.0022)His+(−0.0078)Ala+(−0.0472)Cit+(−0.0702)Trp; 0.867, 0.890, 0.824, 0.861, 0.848, 0.837, 0.832, 0.852, (1.4661)+(−0.1011)Asn+(0.0128)Gln+(−0.1673)Met+(−0.0215)Leu+(0.0716)Phe+(−0.0740)Trp; 0.867, 0.893, 0.761, 0.852, 0.816, 0.855, 0.816, 0.845, (3.8915)+(−0.1273)Asn+(0.0141)Gln+(−0.0109)Pro+(−0.0117)Val+(−0.0127)Orn+(−0.0647)Trp; 0.866, 0.891, 0.792, 0.858, 0.815, 0.877, 0.849, 0.858, (2.3274)+(−0.1132)Asn+(0.0163)Gln+(−0.0077)Ala+(−0.0368)Cit+(−0.0186)Orn+(−0.0697)Trp; 0.866, 0.891, 0.769, 0.848, 0.813, 0.860, 0.797, 0.840, (3.6054)+(−0.1070)Asn+(0.0144)Gln+(−0.0076)Thr+(−0.0224)Arg+(−0.0151)Val+(−0.0524)Trp; 0.866, 0.884, 0.794, 0.849, 0.817, 0.859, 0.816, 0.844, (4.1462)+(−0.1374)Asn+(0.0120)Gln+(−0.0048)His+(−0.0158)Val+(−0.0585)Trp; 0.866, 0.888, 0.782, 0.848, 0.816, 0.865, 0.797, 0.842, (3.7457)+(−0.1167)Asn+(0.0138)Gln+(−0.0250)Arg+(−0.0176)Val+(0.0070)Ile+(−0.0518)Trp; 0.866, 0.889, 0.801, 0.857, 0.835, 0.830, 0.836, 0.847, (2.4800)+(−0.1360)Asn+(0.0123)Gln+(−0.0118)Thr+(−0.0248)Leu+(0.0514)Phe+(−0.0784)Trp

List (1) of Linear Discriminants Searched in Example 5

The linear discriminants searched in Example 5 above are listed below. Before each equation, "the value of ROC_AUC for the pancreatic cancer group and the lung cancer group with validation", "the value of ROC_AUC for the pancreatic cancer group and the lung cancer group without validation", "the value of ROC_AUC for the pancreatic cancer group and the healthy group", "the value of ROC_AUC for the pancreatic cancer group and the other cancers group", "the value of ROC_AUC for the pancreatic cancer group and the colorectal cancer group", "the value of ROC_AUC for the pancreatic cancer group and the prostatic cancer group", "the value of ROC_AUC for the pancreatic cancer group and the breast cancer group", and "the average value of the value of ROC_AUC for the pancreatic cancer group and the lung cancer group, the value of ROC_AUC for the pancreatic cancer group and the colorectal cancer group, the value of ROC_AUC for the pancreatic cancer group and the prostatic cancer group, and the value of ROC_AUC for the pancreatic cancer group and the breast cancer group" obtained for the equation are additionally listed.

0.889, 0.900, 0.816, 0.870, 0.844, 0.860, 0.856, 0.865, (5.6262)+(−0.1579)Asn+(0.0147)Gln+(−0.0133)Pro+(−0.0175)Val+(0.0680)Phe+(−0.1047)Trp; 0.888, 0.899, 0.843, 0.872, 0.850, 0.857, 0.855, 0.865, (4.4024)+(−0.1075)Asn+(0.0147)Gln+(−0.0196)Val+(−0.1775)Met+(0.0888)Phe+(−0.0925)Trp; 0.887, 0.899, 0.821, 0.868, 0.824, 0.876, 0.872, 0.868, (5.7041)+(−0.1372)Asn+(0.0135)Gln+(−0.0082)Ala+(−0.0168)Val+(0.0597)Phe+(−0.0875)Trp; 0.887, 0.899, 0.823, 0.866, 0.842, 0.856, 0.832, 0.857, (5.4488)+(−0.1451)Asn+(0.0149)Gln+(−0.0236)Arg+(−0.0202)Val+(0.0627)Phe+(−0.0933)Trp; 0.885, 0.897, 0.781, 0.860, 0.816, 0.883, 0.839, 0.859, (6.9326)+(−0.1143)Asn+(0.0143)Gln+(−0.0069)Ala+(−0.0094)Pro+(−0.0106)Val+(−0.0772)Trp; 0.884, 0.894, 0.781, 0.858, 0.829, 0.869, 0.819, 0.853, (6.9669)+(−0.1335)Asn+(0.0140)Gln+(−0.0121)Pro+(−0.0128)Val+(−0.0870)Trp; 0.884, 0.895, 0.765, 0.858, 0.828, 0.857, 0.819, 0.850, (7.2847)+(−0.0106)Ser+(−0.1228)Asn+(0.0152)Gln+(−0.0123)Pro+(−0.0133)Val+(−0.0882)Trp; 0.884, 0.897, 0.786, 0.861, 0.827, 0.872, 0.832, 0.857, (6.9854)+(−0.1425)Asn+(0.0145)Gln+(−0.0126)Pro+(−0.0230)Val+(0.0187)Leu+(−0.0849)Trp; 0.884, 0.895, 0.787, 0.866, 0.823, 0.876, 0.873, 0.867, (7.2130)+(−0.1026)Asn+(−0.0072)Gly+(0.0146)Gln+(−0.0076)Ala+(−0.0133)Val+(−0.0770)Trp; 0.883, 0.895, 0.795, 0.860, 0.815, 0.888, 0.841, 0.860, (6.5615)+(−0.0887)Asn+(0.0138)Gln+(−0.0076)Ala+(−0.0114)Val+(−0.0771)Met+(−0.0674)Trp; 0.883, 0.897, 0.840, 0.872, 0.851, 0.867, 0.857, 0.868, (5.3307)+(−0.1611)Asn+(0.0143)Gln+(−0.0346)Cit+(−0.0181)Val+(0.0628)Phe+(−0.0999)Trp; 0.883, 0.896, 0.786, 0.858, 0.816, 0.887, 0.823, 0.856, (6.6882)+(−0.1000)Asn+(0.0150)Gln+(−0.0080)Ala+(−0.0211)Arg+(−0.0123)Val+(−0.0677)Trp; 0.883, 0.897, 0.820, 0.860, 0.819, 0.864, 0.848, 0.857, (3.8867)+(0.0128)Gln+(−0.0077)Ala+(−0.0159)Val+(−0.2229)Met+(0.0786)Phe+(−0.0839)Trp; 0.883, 0.897, 0.804, 0.867, 0.826, 0.897, 0.850, 0.867, (6.5607)+(−0.1130)Asn+(0.0146)Gln+(−0.0084)Ala+(−0.0332)Cit+(−0.0101)Val+(−0.0731)Trp; 0.883, 0.896, 0.774, 0.867, 0.839, 0.852, 0.859, 0.861, (7.3561)+(−0.1163)Asn+(−0.0086)Gly+(0.0160)Gln+(−0.0122)Pro+(−0.0136)Val+(−0.0918)Trp; 0.882, 0.897, 0.774, 0.858, 0.832, 0.868, 0.802, 0.850, (6.7631)+(−0.1177)Asn+(0.0160)Gln+(−0.0215)Arg+(−0.0116)Pro+(−0.0128)Val+(−0.0819)Trp; 0.882, 0.892, 0.895, 0.858, 0.812, 0.884, 0.846, 0.858, (6.8850)+(−0.1147)Asn+(0.0131)Gln+(−0.0083)Ala+(−0.0123)Val+(−0.0721)Trp; 0.882, 0.895, 0.793, 0.864, 0.840, 0.878, 0.825, 0.859, (6.6455)+(−0.1319)Asn+(0.0155)Gln+(−0.0329)Cit+

(−0.0121)Pro+(−0.0107)Val+(−0.0880)Trp; 0.882, 0.895, 0.781, 0.859, 0.809, 0.882, 0.852, 0.859, (6.5441)+(−0.1000)Asn+(0.0143)Gln+(−0.0107)Thr+ (−0.0081)Ala+(−0.0118)Val+(−0.0706)Trp; 0.882, 0.894, 0.804, 0.864, 0.828, 0.894, 0.841, 0.864, (6.2603)+(−0.1068)Asn+(0.0144)Gln+(−0.0090)Ala+ (−0.0386)Cit+(−0.0116)Leu+(−0.0788)Trp; 0.882, 0.893, 0.820, 0.863, 0.825, 0.864, 0.862, 0.861, (5.3683)+(−0.1256)Asn+(0.0128)Gln+(−0.0090)Ala+ (−0.0224)Leu+(0.0598)Phe+(−0.0956)Trp; 0.882, 0.895, 0.773, 0.859, 0.828, 0.862, 0.825, 0.852, (6.6445)+(−0.1193)Asn+(0.0151)Gln+(−0.0100)Thr+ (−0.0115)Pro+(−0.0124)Val+(−0.0851)Trp; 0.882, 0.895, 0.820, 0.870, 0.844, 0.842, 0.877, 0.864, (6.2093)+(−0.1451)Asn+(−0.0066)Gly+(0.0141)Gln+ (−0.0201)Val+(0.0505)Phe+(−0.0993)Trp; 0.882, 0.894, 0.780, 0.859, 0.824, 0.873, 0.829, 0.855, (5.9832)+(−0.1014)Asn+(0.0159)Gln+(−0.0077)Ala+ (−0.0201)Arg+(−0.0106)Pro+(−0.0877)Trp; 0.882, 0.894, 0.800, 0.862, 0.827, 0.878, 0.839, 0.860, (6.9095)+(−0.1392)Asn+(0.0139)Gln+(−0.0134)Pro+ (−0.0188)Val+(0.0238)Ile+(−0.0821)Trp; 0.882, 0.893, 0.817, 0.862, 0.832, 0.848, 0.853, 0.857, (5.4208)+ (−0.1462)Asn+(0.0139)Gln+(−0.0104)Thr+(−0.0195) Val+(0.0586)Phe+(−0.0960)Trp; 0.882, 0.893, 0.813, 0.865, 0.849, 0.842, 0.842, 0.857, (5.2374)+(−0.1489) Asn+(0.0139)Gln+(−0.0137)Pro+(−0.0218)Leu+ (0.0661)Phe+(−0.1155)Trp; 0.882, 0.895, 0.784, 0.860, 0.832, 0.871, 0.817, 0.854, (6.6358)+(−0.1060)Asn+ (0.0146)Gln+(−0.0108)Pro+(−0.0120)Val+(−0.0770) Met+(−0.0810)Trp; 0.881, 0.895, 0.794, 0.868, 0.833, 0.895, 0.847, 0.868, (5.9674)+(−0.1130)Asn+(0.0160) Gln+(−0.0077)Ala+(−0.0415)Cit+(−0.0105)Pro+ (−0.0895)Trp; 0.881, 0.894, 0.779, 0.858, 0.828, 0.865, 0.819, 0.852, (6.8969)+(−0.1322)Asn+(0.0143)Gln+ (−0.0119)Pro+(−0.0121)Val+(−0.0051)Orn+(−0.0876) Trp; 0.881, 0.892, 0.830, 0.863, 0.837, 0.852, 0.849, 0.858, (5.6927)+(−0.1623)Asn+(0.0127)Gln+ (−0.0203)Val+(0.0616)Phe+(−0.0985)Trp; 0.881, 0.894, 0.781, 0.858, 0.829, 0.869, 0.819, 0.853, (6.9665)+(−0.1335)Asn+(0.0140)Gln+(−0.0121)Pro+ (0.0001)Tyr+(−0.0128)Val+(−0.0870)Trp; 0.881, 0.893, 0.806, 0.861, 0.809, 0.893, 0.859, 0.863, (6.8469)+(−0.1179)Asn+(0.0129)Gln+(−0.0085)Ala+ (−0.0159)Val+(0.0141)Ile+(−0.0686)Trp; 0.881, 0.892, 0.793, 0.856, 0.806, 0.884, 0.842, 0.856, (6.9147)+ (−0.1130)Asn+(0.0131)Gln+(−0.0083)Ala+(−0.0060) Tyr+(−0.0120)Val+(−0.0693)Trp; 0.881, 0.893, 0.778, 0.857, 0.809, 0.877, 0.847, 0.856, (7.1932)+(−0.0103) Ser+(−0.1041)Asn+(0.0142)Gln+(−0.0084)Ala+ (−0.0127)Val+(−0.0730)Trp; 0.881, 0.893, 0.823, 0.863, 0.835, 0.846, 0.850, 0.856, (5.8716)+(−0.0044) Ser+(−0.1570)Asn+(0.0131)Gln+(−0.0203)Val+ (0.0591)Phe+(−0.0983)Trp; 0.880, 0.894, 0.820, 0.856, 0.835, 0.842, 0.810, 0.845, (3.5425)+(0.0140)Gln+ (−0.0214)Arg+(−0.0191)Val+(−0.2368)Met+(0.0827) Phe+(−0.0894)Trp; 0.880, 0.893, 0.811, 0.869, 0.834, 0.897, 0.854, 0.870, (5.9734)+(−0.1014)Asn+(0.0154) Gln+(−0.0094)Ala+(−0.0431)Cit+(−0.0076)Lys+ (−0.0818)Trp; 0.880, 0.892, 0.797, 0.859, 0.808, 0.888, 0.854, 0.860, (6.8944)+(−0.1203)Asn+(0.0133)Gln+ (−0.0082)Ala+(−0.0181)Val+(0.0104)Leu+(−0.0710) Trp; 0.880, 0.892, 0.830, 0.864, 0.838, 0.856, 0.848, 0.859, (5.7140)+(−0.1570)Asn+(0.0130)Gln+ (−0.0195)Val+(−0.0034)Lys+(0.0620)Phe+(−0.0978) Trp; 0.880, 0.892, 0.799, 0.862, 0.828, 0.885, 0.839, 0.861, (6.0615)+(−0.1104)Asn+(0.0148)Gln+ (−0.0090)Ala+(−0.0399)Cit+(−0.0128)Ile+(−0.0850) Trp; 0.880, 0.894, 0.780, 0.858, 0.829, 0.869, 0.817, 0.852, (6.9990)+(−0.1276)Asn+(0.0143)Gln+ (−0.0122)Pro+(−0.0119)Val+(−0.0037)Lys+(−0.0862) Trp; 0.880, 0.892, 0.831, 0.863, 0.835, 0.853, 0.853, 0.858, (5.7311)+(−0.1642)Asn+(0.0128)Gln+ (−0.0231)Val+(0.0052)Leu+(0.0599)Phe+(−0.0974) Trp; 0.880, 0.892, 0.811, 0.863, 0.842, 0.879, 0.820, 0.858, (6.2140)+(−0.1028)Asn+(0.0145)Gln+ (−0.0295)Cit+(−0.0124)Val+(−0.0968)Met+(−0.0767) Trp; 0.880, 0.892, 0.790, 0.857, 0.808, 0.880, 0.846, 0.857, (6.7511)+(−0.1117)Asn+(0.0137)Gln+ (−0.0085)Ala+(−0.0108)Val+(−0.0099)Orn+(−0.0730) Trp; 0.880, 0.892, 0.792, 0.858, 0.812, 0.887, 0.843, 0.859, (6.9106)+(−0.1099)Asn+(0.0133)Gln+ (−0.0084)Ala+(−0.0115)Val+(−0.0030)Lys+(−0.0713) Trp; 0.880, 0.894, 0.814, 0.863, 0.835, 0.824, 0.870, 0.856, (4.4168)+(−0.0089)Gly+(0.0146)Gln+ (−0.0189)Val+(−0.2484)Met+(0.0709)Phe+(−0.0943) Trp; 0.880, 0.893, 0.799, 0.867, 0.841, 0.858, 0.860, 0.863, (7.0140)+(−0.1230)Asn+(−0.0077)Gly+ (0.0151)Gln+(−0.0252)Cit+(−0.0149)Val+(−0.0879) Trp; 0.880, 0.892, 0.783, 0.863, 0.824, 0.865, 0.866, 0.862, (6.9325)+(−0.0931)Asn+(−0.0076)Gly+ (0.0142)Gln+(−0.0083)Ala+(−0.0170)Leu+(−0.0843) Trp; 0.880, 0.894, 0.777, 0.859, 0.814, 0.865, 0.857, 0.857, (6.3357)+(−0.0095)Gly+(0.0145)Gln+ (−0.0072)Ala+(−0.0121)Val+(−0.1494)Met+(−0.0731) Trp; 0.880, 0.892, 0.827, 0.864, 0.837, 0.850, 0.853, 0.858, (5.5559)+(−0.1603)Asn+(0.0132)Gln+ (−0.0191)Val+(−0.0089)Orn+(0.0624)Phe+(−0.0998) Trp; 0.879, 0.893, 0.804, 0.865, 0.833, 0.886, 0.843, 0.864, (5.6813)+(−0.1039)Asn+(0.0155)Gln+ (−0.0094)Ala+(−0.0330)Cit+(−0.0146)Arg+(−0.0837) Trp; 0.879, 0.893, 0.791, 0.865, 0.837, 0.854, 0.858, 0.861, (6.8301)+(−0.0783)Asn+(−0.0092)Gly+ (0.0155)Gln+(−0.0149)Val+(−0.1177)Met+(−0.0794) Trp; 0.879, 0.893, 0.839, 0.871, 0.862, 0.859, 0.839, 0.863, (4.8814)+(−0.1511)Asn+(0.0138)Gln+ (−0.0433)Cit+(−0.0242)Leu+(0.0637)Phe+(−0.1101) Trp; 0.879, 0.890, 0.814, 0.865, 0.830, 0.889, 0.855, 0.866, (5.7663)+(−0.1134)Asn+(0.0147)Gln+ (−0.0096)Ala+(−0.0435)Cit+(−0.0861)Trp; 0.879, 0.893, 0.833, 0.864, 0.836, 0.853, 0.852, 0.859, (5.6873)+(−0.1634)Asn+(0.0126)Gln+(−0.0215)Val+ (0.0047)Ile+(0.0612)Phe+(−0.0973)Trp; 0.879, 0.890, 0.793, 0.862, 0.832, 0.850, 0.861, 0.858, (7.2952)+ (−0.1227)Asn+(−0.0085)Gly+(0.0142)Gln+(−0.0166) Val+(−0.0876)Trp; 0.879, 0.892, 0.815, 0.867, 0.834, 0.892, 0.853, 0.868, (5.5186)+(−0.0871)Asn+(0.0153) Gln+(−0.0088)Ala+(−0.0400)Cit+(−0.0784)Met+ (−0.0804)Trp; 0.879, 0.894, 0.784, 0.863, 0.836, 0.856, 0.846, 0.858, (7.0712)+(−0.1079)Asn+(−0.0079)Gly+ (0.0161)Gln+(−0.0213)Arg+(−0.0164)Val+(−0.0823) Trp; 0.879, 0.893, 0.831, 0.857, 0.825, 0.840, 0.840, 0.849, (5.5862)+(−0.1584)Asn+(0.0131)Gln+ (−0.0256)Tyr+(−0.0196)Val+(0.0733)Phe+(−0.0894) Trp; 0.879, 0.892, 0.792, 0.857, 0.810, 0.884, 0.846, 0.858, (6.9019)+(−0.1155)Asn+(0.0130)Gln+(0.0022) His+(−0.0084)Ala+(−0.0125)Val+(−0.0726)Trp; 0.879, 0.891, 0.779, 0.859, 0.819, 0.882, 0.842, 0.858, (6.3848)+(−0.1030)Asn+(0.0148)Gln+(−0.0078)Ala+ (−0.0109)Pro+(−0.0077)Lys+(−0.0876)Trp; 0.879, 0.892, 0.833, 0.872, 0.840, 0.885, 0.879, 0.874, (4.7127)+(−0.1290)Asn+(0.0150)Gln+(−0.0098)Ala+ (−0.0476)Cit+(0.0408)Phe+(−0.1005)Trp; 0.879, 0.892, 0.782, 0.855, 0.819, 0.876, 0.818, 0.851, (6.3732)+(−0.0919)Asn+(0.0146)Gln+(−0.0087)Ala+(−0.0218)Arg+(−0.0148)Leu+(−0.0745)Trp; 0.879, 0.893, 0.771, 0.864, 0.844, 0.838, 0.850, 0.856, (7.0000)+(−0.1097)Asn+(−0.0090)Gly+(0.0155)Gln+(−0.0127)Pro+(−0.0160)Leu+(−0.1017)Trp; 0.878, 0.890, 0.793, 0.852, 0.826, 0.861, 0.798, 0.844, (6.6960)+(−0.1224)Asn+(0.0144)Gln+(−0.0230)Arg+(−0.0156)Val+(−0.0775)Trp; 0.878, 0.893, 0.801, 0.867, 0.828, 0.884, 0.864, 0.867, (5.4919)+(−0.0996)Asn+(0.0158)Gln+(−0.0102)Thr+(−0.0093)Ala+(−0.0405)Cit+(−0.0843)Trp; 0.878, 0.894, 0.785, 0.859, 0.830, 0.867, 0.820, 0.853, (6.9384)+(−0.1319)Asn+(0.0142)Gln+(−0.0038)His+(−0.0121)Pro+(−0.0124)Val+(−0.0860)Trp; 0.878, 0.892, 0.831, 0.864, 0.838, 0.853, 0.850, 0.858, (5.6808)+(−0.1616)Asn+(0.0127)Gln+(−0.0016)His+(−0.0201)Val+(0.0616)Phe+(−0.0980)Trp; 0.878, 0.892, 0.782, 0.855, 0.813, 0.867, 0.835, 0.852, (5.7538)+(−0.0967)Asn+(0.0156)Gln+(−0.0096)Ala+(−0.0200)Arg+(−0.0165)Orn+(−0.0827)Trp; 0.878, 0.890, 0.811, 0.861, 0.829, 0.877, 0.838, 0.858, (6.3792)+(−0.1045)Asn+(0.0142)Gln+(−0.0279)Val+(−0.1311)Met+(0.0255)Leu+(−0.0702)Trp; 0.878, 0.890, 0.793, 0.856, 0.818, 0.875, 0.835, 0.854, (5.7816)+(−0.1013)Asn+(0.0146)Gln+(−0.0096)Ala+(−0.0211)Arg+(−0.0842)Trp; 0.878, 0.890, 0.795, 0.860, 0.837, 0.860, 0.826, 0.853, (6.8735)+(−0.0096)Ser+(−0.1285)Asn+(0.0147)Gln+(−0.0331)Cit+(−0.0141)Val+(−0.0849)Trp; 0.878, 0.885, 0.801, 0.852, 0.823, 0.859, 0.819, 0.847, (6.9114)+(−0.1396)Asn+(0.0122)Gln+(−0.0158)Val+(−0.0828)Trp; 0.878, 0.891, 0.817, 0.856, 0.820, 0.855, 0.838, 0.851, (3.7293)+(0.0120)Gln+(−0.0088)Ala+(−0.1992)Met+(−0.0195)Leu+(0.0739)Phe+(−0.0925)Trp; 0.878, 0.891, 0.775, 0.853, 0.817, 0.871, 0.812, 0.848, (6.1747)+(−0.0969)Asn+(0.0149)Gln+(−0.0088)Ala+(−0.0208)Arg+(−0.0180)Ile+(−0.0824)Trp; 0.878, 0.889, 0.790, 0.855, 0.812, 0.879, 0.838, 0.854, (6.5522)+(−0.1074)Asn+(0.0126)Gln+(−0.0091)Ala+(−0.0142)Leu+(−0.0794)Trp; 0.878, 0.892, 0.778, 0.866, 0.831, 0.868, 0.869, 0.865, (6.4265)+(−0.1040)Asn+(−0.0068)Gly+(0.0156)Gln+(−0.0073)Ala+(−0.0115)Pro+(−0.0982)Trp; 0.878, 0.890, 0.783, 0.854, 0.809, 0.875, 0.840, 0.853, (6.4197)+(−0.1045)Asn+(0.0135)Gln+(−0.0092)Ala+(−0.0136)Orn+(−0.0117)Leu+(−0.0795)Trp; 0.878, 0.889, 0.776, 0.855, 0.816, 0.873, 0.835, 0.853, (6.3761)+(−0.1128)Asn+(0.0142)Gln+(−0.0077)Ala+(−0.0100)Pro+(−0.0099)Ile+(−0.0907)Trp; 0.878, 0.892, 0.778, 0.858, 0.819, 0.881, 0.834, 0.856, (6.5926)+(−0.1089)Asn+(0.0139)Gln+(−0.0076)Ala+(−0.0096)Pro+(−0.0109)Leu+(−0.0845)Trp; 0.878, 0.891, 0.787, 0.863, 0.827, 0.867, 0.861, 0.862, (5.9954)+(−0.0924)Asn+(−0.0058)Gly+(0.0157)Gln+(−0.0091)Ala+(−0.0200)Arg+(−0.0896)Trp; 0.878, 0.891, 0.820, 0.860, 0.850, 0.842, 0.808, 0.848, (5.0158)+(−0.1329)Asn+(0.0141)Gln+(−0.0251)Arg+(−0.0276)Leu+(0.0632)Phe+(−0.1045)Trp; 0.878, 0.891, 0.816, 0.867, 0.852, 0.823, 0.865, 0.858, (5.8682)+(−0.1317)Asn+(−0.0074)Gly+(0.0133)Gln+(−0.0277)Leu+(0.0496)Phe+(−0.1107)Trp; 0.878, 0.892, 0.763, 0.845, 0.786, 0.866, 0.829, 0.843, (4.0631)+(−0.0946)Asn+(0.0139)Gln+(−0.0085)Ala+(−0.0210)Val+(−0.1618)Met+(0.0588)Phe; 0.878, 0.890, 0.776, 0.855, 0.808, 0.874, 0.845, 0.854, (6.2087)+(−0.0904)Asn+(0.0140)Gln+(−0.0123)Thr+(−0.0087)Ala+(−0.0144)Leu+(−0.0769)Trp; 0.877, 0.891, 0.818, 0.857, 0.834, 0.843, 0.822, 0.848, (3.6186)+(0.0132)Gln+(−0.0103)Pro+(−0.0170)Val+(−0.2461)Met+(0.0860)Phe+(−0.0991)Trp; 0.877, 0.891, 0.794, 0.852, 0.826, 0.859, 0.799, 0.844, (6.6475)+(−0.1264)Asn+(0.0143)Gln+(−0.0250)Arg+(−0.0165)Val+(0.0035)Lys+(−0.0779)Trp; 0.877, 0.888, 0.804, 0.856, 0.830, 0.866, 0.818, 0.851, (6.4700)+(−0.1014)Asn+(0.0133)Gln+(−0.0142)Val+(−0.1045)Met+(−0.0752)Trp; 0.877, 0.890, 0.774, 0.857, 0.813, 0.880, 0.848, 0.858, (6.1290)+(−0.1107)Asn+(0.0150)Gln+(−0.0081)Ala+(−0.0101)Pro+(−0.0146)Orn+(−0.0902)Trp; 0.877, 0.891, 0.795, 0.856, 0.813, 0.881, 0.838, 0.856, (6.2061)+(−0.0850)Asn+(0.0132)Gln+(−0.0085)Ala+(−0.0709)Met+(−0.0116)Leu+(−0.0757)Trp; 0.877, 0.892, 0.773, 0.848, 0.805, 0.880, 0.800, 0.844, (5.7439)+(0.0138)Gln+(−0.0083)Ala+(−0.0216)Arg+(−0.0111)Val+(−0.1216)Met+(−0.0645)Trp; 0.877, 0.889, 0.786, 0.857, 0.822, 0.841, 0.853, 0.851, (7.4364)+(−0.1144)Asn+(−0.0094)Gly+(0.0147)Gln+(−0.0197)Tyr+(−0.0155)Val+(−0.0789)Trp; 0.877, 0.888, 0.727, 0.835, 0.774, 0.878, 0.791, 0.833, (5.8092)+(−0.1082)Asn+(0.0145)Gln+(−0.0095)Ala+(−0.0245)Arg+(−0.0175)Val; 0.877, 0.887, 0.784, 0.851, 0.821, 0.849, 0.821, 0.844, (7.1934)+(−0.0094)Ser+(−0.1302)Asn+(0.0132)Gln+(−0.0162)Val+(−0.0838)Trp; 0.877, 0.889, 0.814, 0.860, 0.833, 0.872, 0.832, 0.857, (6.6160)+(−0.1436)Asn+(0.0139)Gln+(−0.0312)Cit+(−0.0198)Val+(0.0110)Leu+(−0.0825)Trp; 0.877, 0.890, 0.840, 0.865, 0.853, 0.840, 0.841, 0.856, (4.0702)+(−0.1032)Asn+(0.0135)Gln+(−0.1606)Met+(−0.0231)Leu+(0.0822)Phe+(−0.1055)Trp; 0.877, 0.891, 0.806, 0.871, 0.840, 0.883, 0.875, 0.872, (5.9695)+(−0.1050)Asn+(−0.0052)Gly+(0.0156)Gln+(−0.0092)Ala+(−0.0393)Cit+(−0.0909)Trp; 0.877, 0.889, 0.790, 0.849, 0.795, 0.884, 0.830, 0.849, (5.7019)+(0.0122)Gln+(−0.0082)Ala+(−0.0197)Val+(−0.1701)Met+(0.0163)Leu+(−0.06 49)Trp; 0.877, 0.890, 0.784, 0.862, 0.819, 0.859, 0.877, 0.861, (6.1519)+(−0.1002)Asn+(−0.0061)Gly+(0.0151)Gln+(−0.0094)Ala+(−0.0174)Orn+(−0.0921)Trp

List (2) of Logistic Regression Equations Searched in Example 5

The logistic regression equations searched in Example 5 above are listed below. Before each equation, "the value of ROC_AUC for the pancreatic cancer group and the lung cancer group with validation", "the value of ROC_AUC for the pancreatic cancer group and the lung cancer group without validation", "the value of ROC_AUC for the pancreatic cancer group and the healthy group", "the value of ROC_AUC for the pancreatic cancer group and the other cancers group", "the value of ROC_AUC for the pancreatic cancer group and the colorectal cancer group", "the value of ROC_AUC for the pancreatic cancer group and the prostatic cancer group", "the value of ROC_AUC for the pancreatic cancer group and the breast cancer group", and "the average value of the value of ROC_AUC for the pancreatic cancer group and the lung cancer group, the value of ROC_AUC for the pancreatic cancer group and the colorectal cancer group, the value of ROC_AUC for the pancreatic cancer group and the prostatic cancer group, and the value of ROC_AUC for the pancreatic cancer group and the breast cancer group" obtained for the equation are additionally listed.

0.858, 0.882, 0.854, 0.866, 0.854, 0.854, 0.858, 0.862, (0.7428)+(−0.0948)Asn+(0.0147)Gln+(−0.0250)His+(−0.1901)Met+(0.0579)Phe+(−0.0741)Trp; 0.850, 0.872, 0.854, 0.852, 0.838, 0.842, 0.835, 0.847, (0.1340)+(0.0125)Gln+(−0.0287)His+(−0.2660)Met+

(0.0561)Phe+(−0.0760)Trp; 0.849, 0.877, 0.853, 0.859, 0.851, 0.853, 0.835, 0.854, (−0.3557)+(0.0142)Gln+ (−0.0176)His+(−0.0454)Cit+(−0.2515)Met+(0.0595) Phe+(−0.0844)Trp; 0.829, 0.855, 0.852, 0.847, 0.854, 0.845, 0.814, 0.842, (4.2366)+(0.0090)Ser+(−0.0506) Asn+(−0.0181)Cit+(−0.1342)Met+(0.0480)Phe+ (−0.0762)Trp; 0.847, 0.874, 0.852, 0.854, 0.839, 0.849, 0.837, 0.849, (0.1888)+(0.0131)Gln+(−0.0262)His+ (−0.2534)Met+(−0.0053)Lys+(0.0573)Phe+(−0.0743) Trp; 0.814, 0.834, 0.851, 0.825, 0.816, 0.835, 0.816, 0.825, (1.8629)+(0.0072)Gln+(−0.0495)His+(0.0085) Phe+(−0.0904)Trp; 0.815, 0.842, 0.850, 0.835, 0.834, 0.846, 0.812, 0.833, (1.0816)+(0.0096)Gln+(−0.0322) His+(−0.0580)Cit+(0.0197)Phe+(−0.1039)Trp; 0.862, 0.887, 0.849, 0.872, 0.863, 0.864, 0.853, 0.867, (0.4080)+(−0.1010)Asn+(0.0158)Gln+(−0.0511)Cit+ (−0.1773)Met+(0.0598)Phe+(−0.0872)Trp; 0.854, 0.882, 0.849, 0.872, 0.865, 0.869, 0.860, 0.869, (1.3668)+(−0.1519)Asn+(0.0150)Gln+(−0.0162)His+ (−0.0523)Cit+(0.0410)Phe+(−0.0924)Trp; 0.842, 0.869, 0.848, 0.843, 0.822, 0.833, 0.821, 0.836, (0.3205)+(0.0127)Gln+(−0.0317)His+(−0.0234)Tyr+ (−0.2412)Met+(0.0628)Phe+(−0.0681)Trp; 0.842, 0.866, 0.847, 0.844, 0.824, 0.854, 0.821, 0.841, (4.0284)+(0.0066)Ser+(−0.0215)Val+(−0.1905)Met+ (0.0235)Ile+(0.0641)Phe+(−0.0531)Trp; 0.851, 0.877, 0.846, 0.854, 0.846, 0.843, 0.819, 0.846,(−0.0588)+ (0.0148)Gln+(−0.0282)His+(−0.0253)Arg+(−0.2362) Met+(0.0598)Phe+(−0.0718)Trp; 0.828, 0.853, 0.845, 0.841, 0.846, 0.834, 0.800, 0.833, (4.2868)+(0.0091) Ser+(−0.0489)Asn+(−0.0098)Arg+(−0.1330)Met+ (0.0480)Phe+(−0.0729)Trp; 0.819, 0.849, 0.844, 0.841, 0.846, 0.833, 0.817, 0.836, (5.0808)+(0.0052)Ser+ (−0.0891)Asn+(−0.0263)Cit+(−0.0008)Lys+(0.0305) Phe+(−0.0861)Trp; 0.849, 0.870, 0.844, 0.858, 0.845, 0.844, 0.859, 0.855, (1.9743)+(−0.1549)Asn+(0.0132) Gln+(−0.0321)His+(0.0345)Phe+(−0.0834)Trp; 0.827, 0.854, 0.844, 0.850, 0.850, 0.836, 0.847, 0.847, (4.6405)+(0.0158)Ser+(−0.0352)Asn+(−0.0068)Gly+ (−0.1493)Met+(0.0411)Phe+(−0.0800)Trp; 0.847, 0.873, 0.844, 0.845, 0.816, 0.831, 0.842, 0.841, (2.1375)+(−0.1449)Asn+(0.0136)Gln+(−0.0342)His+ (−0.0424)Tyr+(0.0534)Phe+(−0.0658)Trp; 0.825, 0.848, 0.844, 0.844, 0.841, 0.846, 0.832, 0.817, 0.836, (5.0770)+(0.0049)Ser+(−0.0907)Asn+(−0.0265)Cit+ (0.0301)Phe+(−0.0866)Trp; 0.825, 0.857, 0.844, 0.845, 0.839, 0.858, 0.817, 0.843, (0.8822)+(0.0124)Gln+ (−0.0225)His+(−0.0628)Cit+(−0.0158)Lys+(0.0326) Phe+(−0.0992)Trp; 0.818, 0.833, 0.843, 0.823, 0.812, 0.839, 0.808, 0.823, (2.1373)+(0.0072)Gln+(−0.0478) His+(−0.0877)Trp; 0.848, 0.875, 0.843, 0.860, 0.845, 0.850, 0.859, 0.857, (1.9446)+(−0.1433)Asn+(0.0137) Gln+(−0.0299)His+(−0.0060)Lys+(0.0365)Phe+ (−0.0810)Trp; 0.824, 0.852, 0.843, 0.841, 0.843, 0.831, 0.815, 0.835, (4.1715)+(0.0078)Ser+(−0.0549)Asn+ (−0.1513)Met+(0.0019)Lys+(0.0463)Phe+(−0.0764) Trp; 0.828, 0.852, 0.842, 0.841, 0.844, 0.833, 0.812, 0.835, (4.2086)+(0.0081)Ser+(−0.0527)Asn+ (−0.1471)Met+(0.0468)Phe+(−0.0754)Trp; 0.841, 0.865, 0.842, 0.854, 0.842, 0.863, 0.841, 0.853, (4.3533)+(0.0072)Ser+(−0.0423)Asn+(−0.0047)Ala+ (−0.1106)Met+(0.0440)Phe+(−0.0678)Trp; 0.821, 0.846, 0.842, 0.836, 0.845, 0.829, 0.798, 0.829, (3.8441)+(0.0056)Ser+(−0.0198)Cit+(−0.1786)Met+ (0.0461)Phe+(−0.0797)Trp; 0.824, 0.851, 0.841, 0.846, 0.849, 0.829, 0.841, 0.843, (4.4498)+(0.0145)Ser+ (−0.0073)Gly+(−0.0108)Cit+(−0.1718)Met+(0.0398) Phe+(−0.0827)Trp; 0.816, 0.846, 0.841, 0.836, 0.845, 0.828, 0.798, 0.829, (3.8269)+(0.0055)Ser+(−0.0199) Cit+(−0.1805)Met+(0.0006)Lys+(0.0459)Phe+ (−0.0801)Trp; 0.821, 0.849, 0.841, 0.819, 0.794, 0.828, 0.784, 0.814, (1.0434)+(0.0113)Gln+(−0.0327)His+ (−0.0618)Cit+(−0.0563)Tyr+(0.0498)Phe+(−0.0851) Trp; 0.839, 0.864, 0.841, 0.854, 0.839, 0.873, 0.845, 0.855, (5.0156)+(0.0046)Ser+(−0.0661)Asn+ (−0.0057)Ala+(−0.0191)Cit+(0.0314)Phe+(−0.0739) Trp; 0.850, 0.873, 0.840, 0.853, 0.847, 0.839, 0.821, 0.845, (−0.2044)+(0.0133)Gln+(−0.0518)Cit+ (−0.2611)Met+(0.0571)Phe+(−0.0912)Trp; 0.824, 0.858, 0.840, 0.840, 0.836, 0.849, 0.796, 0.835, (0.8827)+(0.0125)Gln+(−0.0379)His+(−0.0341)Cit+ (−0.0328)Arg+(0.0302)Phe+(−0.0928)Trp; 0.828, 0.854, 0.840, 0.842, 0.845, 0.829, 0.813, 0.835, (4.2894)+(0.0094)Ser+(−0.0460)Asn+(−0.1485)Met+ (−0.0127)Orn+(0.0512)Phe+(−0.0757)Trp; 0.823, 0.849, 0.840, 0.832, 0.817, 0.842, 0.815, 0.831, (1.7645)+(0.0094)Gln+(−0.0404)His+(−0.0142)Lys+ (0.0181)Phe+(−0.0838)Trp; 0.835, 0.861, 0.840, 0.851, 0.843, 0.862, 0.831, 0.849, (4.0445)+(0.0049)Ser+ (−0.0049)Ala+(−0.0146)Cit+(−0.1341)Met+(0.0436) Phe+(−0.0704)Trp; 0.825, 0.852, 0.839, 0.840, 0.842, 0.831, 0.813, 0.834, (4.2041)+(0.0089)Ser+(−0.0500) Asn+(−0.0026)Thr+(−0.1429)Met+(0.0462)Phe+ (−0.0746)Trp; 0.817, 0.847, 0.839, 0.833, 0.840, 0.828, 0.789, 0.826, (3.9284)+(0.0063)Ser+(−0.0128)Cit+ (−0.0083)Arg+(−0.1698)Met+(0.0466)Phe+(−0.0770) Trp; 0.819, 0.847, 0.838, 0.838, 0.842, 0.825, 0.817, 0.832, (5.1270)+(0.0052)Ser+(−0.0889)Asn+ (−0.0228)Cit+(−0.0054)Orn+(0.0310)Phe+(−0.0868) Trp; 0.845, 0.870, 0.838, 0.848, 0.833, 0.829, 0.835, 0.842, (0.6178)+(−0.0085)Ser+(0.0134)Gln+(−0.0277) His+(−0.2538)Met+(0.0513)Phe+(−0.0776)Trp; 0.815, 0.845, 0.838, 0.834, 0.843, 0.823, 0.795, 0.826, (3.8019)+(0.0052)Ser+(0.0065)His+(−0.0227)Cit+ (−0.1841)Met+(0.0460)Phe+(−0.0827)Trp; 0.818, 0.846, 0.838, 0.846, 0.850, 0.828, 0.849, 0.843, (5.4768)+(0.0107)Ser+(−0.0790)Asn+(−0.0056)Gly+ (−0.0201)Cit+(0.0236)Phe+(−0.0904)Trp; 0.819, 0.842, 0.838, 0.833, 0.831, 0.853, 0.800, 0.831, (1.7423)+(0.0093)Gln+(−0.0296)His+(−0.0545)Cit+ (−0.0967)Trp; 0.849, 0.875, 0.838, 0.856, 0.849, 0.849, 0.824, 0.849, (−0.1630)+(0.0142)Gln+(−0.0518)Cit+ (−0.2409)Met+(−0.0071)Lys+(0.0593)Phe+(−0.0880) Trp; 0.823, 0.852, 0.838, 0.839, 0.843, 0.825, 0.808, 0.832, (4.1903)+(0.0078)Ser+(−0.0549)Asn+(0.0046) His+(−0.1504)Met+(0.0467)Phe+(−0.0772)Trp; 0.820, 0.845, 0.837, 0.824, 0.816, 0.814, 0.790, 0.816, (5.2767)+(0.0061)Ser+(−0.0846)Asn+(−0.0270)Cit+ (−0.0375)Tyr+(0.0493)Phe+(−0.0740)Trp; 0.817, 0.839, 0.837, 0.807, 0.776, 0.811, 0.782, 0.802, (1.9795)+(0.0084)Gln+(−0.0502)His+(−0.0534)Tyr+ (0.0358)Phe+(−0.0708)Trp; 0.817, 0.846, 0.837, 0.838, 0.845, 0.822, 0.814, 0.832, (5.0582)+(0.0046)Ser+ (−0.0958)Asn+(0.0082)His+(−0.0304)Cit+(0.0301) Phe+(−0.0905)Trp; 0.857, 0.881, 0.837, 0.852, 0.827, 0.840, 0.834, 0.845, (1.5102)+(−0.1492)Asn+(0.0153) Gln+(−0.0648)Cit+(−0.0467)Tyr+(0.0627)Phe+ (−0.0839)Trp; 0.825, 0.852, 0.837, 0.844, 0.846, 0.828, 0.832, 0.840, (4.5273)+(0.0152)Ser+(−0.0074)Gly+ (−0.0089)Arg+(−0.1647)Met+(0.0400)Phe+(−0.0798) Trp; 0.859, 0.883, 0.837, 0.871, 0.866, 0.872, 0.853, 0.868, (1.4133)+(−0.1411)Asn+(0.0151)Gln+ (−0.0593)Cit+(−0.0077)Lys+(0.0430)Phe+(−0.0961) Trp; 0.819, 0.848, 0.837, 0.839, 0.841, 0.830, 0.818, 0.834, (4.9911)+(0.0070)Ser+(−0.0822)Asn+

(-0.0055)Thr+(-0.0251)Cit+(0.0299)Phe+(-0.0844)
Trp; 0.854, 0.879, 0.837, 0.850, 0.835, 0.836, 0.816,
0.841, (0.5649)+(0.0116)Gln+(-0.0186)His+(-0.2464)
Met+(-0.0179)Leu+(0.0691)Phe+(-0.0718)Trp;
0.852, 0.877, 0.837, 0.857, 0.847, 0.845, 0.835, 0.851,
(1.5634)+(-0.1301)Asn+(0.0151)Gln+(-0.0298)His+
(-0.0280)Arg+(0.0417)Phe+(-0.0789)Trp; 0.830,
0.860, 0.836, 0.825, 0.801, 0.835, 0.777, 0.818,
(1.3370)+(0.0122)Gln+(-0.0471)His+(-0.0339)Arg+
(-0.0423)Tyr+(0.0450)Phe+(-0.0690)Trp; 0.829,
0.854, 0.836, 0.834, 0.825, 0.840, 0.792, 0.828,
(1.2668)+(0.0117)Gln+(-0.0469)His+(-0.0386)Arg+
(0.0258)Phe+(-0.0838)Trp; 0.816, 0.846, 0.836, 0.835,
0.841, 0.826, 0.799, 0.828, (3.8669)+(0.0070)Ser+
(-0.0040)Thr+(-0.0185)Cit+(-0.1691)Met+(0.0450)
Phe+(-0.0781)Trp; 0.820, 0.847, 0.835, 0.837, 0.845,
0.827, 0.801, 0.830, (5.0812)+(0.0060)Ser+(-0.0840)
Asn+(-0.0173)Cit+(-0.0112)Arg+(0.0323)Phe+
(-0.0829)Trp; 0.841, 0.870, 0.835, 0.848, 0.830, 0.846,
0.828, 0.843, (5.3439)+(-0.0433)Asn+(-0.0210)Val+
(-0.1218)Met+(0.0202)Ile+(0.0593)Phe+(-0.0510)
Trp; 0.845, 0.871, 0.835, 0.846, 0.833, 0.848, 0.805,
0.839, (4.9169)+(0.0093)Ser+(-0.0553)Asn+
(-0.0165)Val+(-0.1210)Met+(0.0656)Phe+(-0.0552)
Trp; 0.831, 0.861, 0.835, 0.852, 0.840, 0.849, 0.855,
0.851, (4.5027)+(0.0121)Ser+(-0.0062)Gly+(-0.0041)
Ala+(-0.1428)Met+(0.0381)Phe+(-0.0742)Trp; 0.837,
0.866, 0.835, 0.842, 0.822, 0.843, 0.818, 0.837,
(4.6202)+(0.0010)Thr+(-0.0212)Val+(-0.1756)Met+
(0.0220)Ile+(0.0604)Phe+(-0.0539)Trp; 0.858, 0.879,
0.835, 0.867, 0.861, 0.859, 0.851, 0.863, (1.5215)+
(-0.1583)Asn+(0.0143)Gln+(-0.0586)Cit+(0.0393)
Phe+(-0.0991)Trp; 0.856, 0.877, 0.835, 0.857, 0.847,
0.835, 0.843, 0.850, (1.0599)+(-0.1017)Asn+(0.0131)
Gln+(-0.2016)Met+(0.0547)Phe+(-0.0825)Trp; 0.858,
0.884, 0.835, 0.856, 0.848, 0.842, 0.807, 0.845,
(0.1226)+(0.0129)Gln+(-0.0471)Cit+(-0.2338)Met+
(-0.0187)Leu+(0.0725)Phe+(-0.0833)Trp; 0.826,
0.849, 0.834, 0.843, 0.842, 0.824, 0.842, 0.839,
(4.4781)+(0.0146)Ser+(-0.0079)Gly+(-0.1791)Met+
(0.0385)Phe+(-0.0826)Trp; 0.853, 0.878, 0.834, 0.859,
0.848, 0.840, 0.844, 0.852, (1.0584)+(-0.0965)Asn+
(0.0134)Gln+(-0.1950)Met+(-0.0040)Lys+(0.0558)
Phe+(-0.0810)Trp; 0.842, 0.873, 0.834, 0.842, 0.828,
0.826, 0.801, 0.832, (-0.0812)+(0.0137)Gln+
(-0.0559)Cit+(-0.0258)Tyr+(-0.2345)Met+(0.0654)
Phe+(-0.0853)Trp; 0.838, 0.865, 0.834, 0.841, 0.823,
0.842, 0.816, 0.836, (4.5768)+(-0.0192)Val+(-0.1714)
Met+(0.0246)Ile+(-0.0048)Leu+(0.0609)Phe+
(-0.0537)Trp; 0.823, 0.849, 0.834, 0.843, 0.842, 0.821,
0.842, 0.839, (4.4515)+(0.0144)Ser+(-0.0080)Gly+
(-0.1833)Met+(0.0013)Lys+(0.0380)Phe+(-0.0835)
Trp; 0.860, 0.885, 0.834, 0.858, 0.823, 0.862, 0.859,
0.857, (0.0513)+(0.0130)Gln+(-0.0179)His+(-0.0065)
Ala+(-0.2216)Met+(0.0524)Phe+(-0.0679)Trp; 0.836,
0.865, 0.834, 0.840, 0.820, 0.833, 0.825, 0.835,
(4.2506)+(-0.0254)Val+(-0.2105)Met+(0.0096)Lys+
(0.0272)Ile+(0.0623)Phe+(-0.0545)Trp; 0.863, 0.886,
0.834, 0.853, 0.823, 0.845, 0.837, 0.848, (0.6071)+
(0.0117)Gln+(-0.0226)Val+(-0.2849)Met+(0.0182)
Ile+(0.0760)Phe+(-0.0599)Trp; 0.817, 0.849, 0.834,
0.834, 0.839, 0.819, 0.795, 0.825, (3.9336)+(0.0070)
Ser+(-0.0110)Cit+(-0.1814)Met+(-0.0123)Orn+
(0.0500)Phe+(-0.0793)Trp; 0.829, 0.857, 0.834, 0.834,
0.830, 0.826, 0.787, 0.825, (3.8834)+(0.0037)Ser+
(-0.1711)Met+(0.0188)Ile+(-0.0302)Leu+(0.0639)
Phe+(-0.0667)Trp; 0.864, 0.889, 0.833, 0.864, 0.838,
0.867, 0.852, 0.861, (-0.3713)+(0.0143)Gln+
(-0.0066)Ala+(-0.0470)Cit+(-0.2090)Met+(0.0545)
Phe+(-0.0788)Trp; 0.865, 0.885, 0.833, 0.860, 0.843,
0.841, 0.840, 0.852, (2.4858)+(-0.1478)Asn+(0.0122)
Gln+(-0.0184)His+(-0.0240)Leu+(0.0557)Phe+
(-0.0765)Trp; 0.823, 0.853, 0.833, 0.844, 0.844, 0.820,
0.839, 0.839, (4.5097)+(0.0151)Ser+(-0.0071)Gly+
(-0.1764)Met+(-0.0107)Orn+(0.0427)Phe+(-0.0818)
Trp; 0.834, 0.867, 0.833, 0.843, 0.823, 0.844, 0.818,
0.838, (4.6666)+(-0.0029)Cit+(-0.0208)Val+
(-0.1692)Met+(0.0218)Ile+(0.0596)Phe+(-0.0540)
Trp; 0.848, 0.876, 0.833, 0.852, 0.846, 0.839, 0.809,
0.843, (-0.2120)+(0.0143)Gln+(-0.0394)Cit+
(-0.0184)Arg+(-0.2462)Met+(0.0592)Phe+(-0.0864)
Trp; 0.836, 0.863, 0.833, 0.847, 0.836, 0.856, 0.819,
0.843, (4.1396)+(0.0054)Ser+(-0.0050)Ala+(-0.0095)
Arg+(-0.1284)Met+(0.0433)Phe+(-0.0674)Trp;
0.840, 0.866, 0.833, 0.842, 0.822, 0.841, 0.818, 0.837,
(4.6547)+(-0.0210)Val+(-0.1721)Met+(0.0221)Ile+
(0.0597)Phe+(-0.0535)Trp; 0.857, 0.882, 0.833, 0.854,
0.830, 0.823, 0.853, 0.847, (-0.3303)+(0.0173)Gln+
(-0.0335)His+(-0.2786)Met+(-0.0450)Orn+(0.0737)
Phe+(-0.0766)Trp; 0.821, 0.853, 0.832, 0.817, 0.784,
0.825, 0.788, 0.812, (1.9308)+(0.0100)Gln+(-0.0423)
His+(-0.0473)Tyr+(-0.0118)Lys+(0.0402)Phe+
(-0.0675)Trp; 0.871, 0.893, 0.832, 0.870, 0.859, 0.859,
0.836, 0.862, (1.8582)+(-0.1462)Asn+(0.0139)Gln+
(-0.0518)Cit+(-0.0240)Leu+(0.0618)Phe+(-0.0862)
Trp; 0.817, 0.847, 0.832, 0.826, 0.822, 0.813, 0.788,
0.817, (4.5513)+(0.0078)Ser+(-0.0595)Asn+
(-0.0244)Tyr+(-0.1146)Met+(0.0542)Phe+(-0.0692)
Trp; 0.814, 0.841, 0.832, 0.828, 0.831, 0.818, 0.795,
0.821, (3.8053)+(0.0045)Ser+(-0.0007)His+(-0.1948)
Met+(0.0002)Lys+(0.0445)Phe+(-0.0786)Trp; 0.836,
0.867, 0.832, 0.843, 0.824, 0.844, 0.818, 0.838,
(4.7117)+(-0.0207)Val+(-0.1706)Met+(-0.0044)Orn+
(0.0233)Ile+(0.0602)Phe+(-0.0539)Trp; 0.846, 0.873,
0.832, 0.850, 0.823, 0.863, 0.838, 0.849, (4.7306)+
(-0.0034)Ala+(-0.0191)Val+(-0.1422)Met+(0.0208)
Ile+(0.0562)Phe+(-0.0487)Trp; 0.803, 0.819, 0.832,
0.814, 0.819, 0.816, 0.791, 0.811, (4.3020)+(-0.0257)
His+(0.0072)Phe+(-0.0900)Trp; 0.817, 0.841, 0.831,
0.828, 0.831, 0.819, 0.794, 0.821, (3.8098)+(0.0046)
Ser+(-0.0006)His+(-0.1943)Met+(0.0445)Phe+
(-0.0785)Trp; 0.830, 0.858, 0.831, 0.838, 0.839, 0.833,
0.788, 0.830, (4.2940)+(-0.0156)Cit+(-0.1464)Met+
(0.0203)Ile+(-0.0305)Leu+(0.0622)Phe+(-0.0677)
Trp; 0.823, 0.841, 0.831, 0.828, 0.831, 0.818, 0.793,
0.821, (3.8056)+(0.0045)Ser+(-0.1950)Met+(0.0445)
Phe+(-0.0788)Trp; 0.820, 0.850, 0.831, 0.842, 0.850,
0.831, 0.810, 0.835, (4.9150)+(-0.0416)Asn+(0.0005)
Thr+(-0.0162)Cit+(-0.1231)Met+(0.0424)Phe+
(-0.0776)Trp; 0.828, 0.857, 0.831, 0.844, 0.846, 0.838,
0.806, 0.837, (4.3837)+(0.0085)Ser+(-0.0498)Asn+
(-0.0070)Pro+(-0.1239)Met+(0.0493)Phe+(-0.0762)
Trp; 0.820, 0.841, 0.831, 0.828, 0.831, 0.817, 0.793,
0.821, (3.8018)+(0.0045)Ser+(-0.1954)Met+(0.0001)
Lys+(0.0444)Phe+(-0.0789)Trp; 0.822, 0.846, 0.831,
0.830, 0.835, 0.823, 0.782, 0.821, (3.9368)+(0.0059)
Ser+(-0.0112)Arg+(-0.1754)Met+(0.0460)Phe+
(-0.0756)Trp; 0.821, 0.849, 0.831, 0.842, 0.841, 0.821,
0.841, 0.838, (4.4750)+(0.0155)Ser+(-0.0076)Gly+
(-0.0031)Thr+(-0.1713)Met+(0.0379)Phe+(-0.0813)
Trp; 0.835, 0.863, 0.831, 0.852, 0.845, 0.856, 0.836,
0.850, (4.9570)+(-0.0325)Asn+(-0.0046)Ala+
(-0.0121)Cit+(-0.0899)Met+(0.0399)Phe+(-0.0692)
Trp; 0.847, 0.872, 0.831, 0.848, 0.826, 0.836, 0.842, 0.844, (0.1066)+(0.0142)Gln+(−0.0273)His+(−0.0135)Thr+(−0.2376)Met+(0.0514)Phe+(−0.0720)Trp; 0.825, 0.845, 0.831, 0.838, 0.846, 0.821, 0.816, 0.832, (5.4144)+(−0.0821)Asn+(−0.0252)Cit+(0.0280)Phe+(−0.0873)Trp; 0.821, 0.846, 0.831, 0.838, 0.846, 0.821, 0.815, 0.832, (5.4178)+(−0.0818)Asn+(−0.0252)Cit+(−0.0002)Lys+(0.0280)Phe+(−0.0872)Trp

List (2) of Linear Discriminants Searched in Example 5

The linear discriminants searched in Example 5 above are listed below. Before each equation, "the value of ROC_AUC for the pancreatic cancer group and the lung cancer group with validation", "the value of ROC_AUC for the pancreatic cancer group and the lung cancer group without validation", "the value of ROC_AUC for the pancreatic cancer group and the healthy group", "the value of ROC_AUC for the pancreatic cancer group and the other cancers group", "the value of ROC_AUC for the pancreatic cancer group and the colorectal cancer group", "the value of ROC_AUC for the pancreatic cancer group and the prostatic cancer group", "the value of ROC_AUC for the pancreatic cancer group and the breast cancer group", and "the average value of the value of ROC_AUC for the pancreatic cancer group and the lung cancer group, the value of ROC_AUC for the pancreatic cancer group and the colorectal cancer group, the value of ROC_AUC for the pancreatic cancer group and the prostatic cancer group, and the value of ROC_AUC for the pancreatic cancer group and the breast cancer group" obtained for the equation are additionally listed.

0.841, 0.858, 0.864, 0.850, 0.855, 0.851, 0.818, 0.846, (6.6327)+(0.0159)Ser+(−0.0688)Asn+(−0.0166)Cit+(−0.1442)Met+(0.0618)Phe+(−0.0996)Trp; 0.857, 0.877, 0.864, 0.864, 0.858, 0.859, 0.844, 0.859, (2.5401)+(0.0145)Gln+(−0.0299)His+(−0.0372)Cit+(−0.2512)Met+(0.0650)Phe+(−0.1008)Trp; 0.867, 0.883, 0.863, 0.868, 0.858, 0.855, 0.860, 0.864, (3.5162)+(−0.0924)Asn+(0.0149)Gln+(−0.0277)His+(−0.1837)Met+(0.0640)Phe+(−0.1019)Trp; 0.858, 0.873, 0.863, 0.856, 0.843, 0.848, 0.843, 0.852, (2.7828)+(0.0132)Gln+(−0.0366)His+(−0.2574)Met+(0.0629)Phe+(−0.0988)Trp; 0.855, 0.873, 0.861, 0.854, 0.839, 0.844, 0.840, 0.849, (2.8178)+(0.0132)Gln+(−0.0372)His+(−0.0084)Tyr+(−0.2479)Met+(0.0654)Phe+(−0.0958)Trp; 0.856, 0.873, 0.861, 0.856, 0.842, 0.847, 0.844, 0.851, (2.8477)+(−0.0011)Ser+(0.0133)Gln+(−0.0364)His+(−0.2551)Met+(0.0620)Phe+(−0.0989)Trp; 0.838, 0.856, 0.860, 0.847, 0.848, 0.846, 0.821, 0.843, (6.5646)+(0.0156)Ser+(−0.0681)Asn+(−0.0039)His+(−0.1509)Met+(0.0613)Phe+(−0.0989)Trp; 0.858, 0.874, 0.859, 0.857, 0.844, 0.853, 0.845, 0.854, (3.0539)+(0.0137)Gln+(−0.0339)His+(−0.2375)Met+(−0.0072)Lys+(0.0636)Phe+(−0.0971)Trp; 0.851, 0.867, 0.859, 0.847, 0.829, 0.856, 0.827, 0.845, (6.5527)+(0.0108)Ser+(−0.0243)Val+(−0.2233)Met+(0.0285)Ile+(0.0820)Phe+(−0.0762)Trp; 0.842, 0.858, 0.859, 0.853, 0.853, 0.842, 0.849, 0.851, (6.8506)+(0.0218)Ser+(−0.0580)Asn+(−0.0055)Gly+(−0.1580)Met+(0.0561)Phe+(−0.1003)Trp; 0.838, 0.854, 0.859, 0.846, 0.849, 0.842, 0.819, 0.841, (6.5378)+(0.0149)Ser+(−0.0710)Asn+(0.0015)Thr+(−0.1556)Met+(0.0612)Phe+(−0.1009)Trp; 0.860, 0.878, 0.858, 0.858, 0.849, 0.851, 0.832, 0.853, (2.8002)+(0.0151)Gln+(−0.0362)His+(−0.0210)Arg+(−0.2272)Met+(0.0605)Phe+(−0.0951)Trp; 0.840, 0.856, 0.858, 0.847, 0.848, 0.846, 0.819, 0.842, (6.6275)+(0.0159)Ser+(−0.0679)Asn+(−0.1463)Met+(−0.0025)Lys+(0.0613)Phe+(−0.0995)Trp; 0.839, 0.856, 0.857, 0.846, 0.848, 0.843, 0.814, 0.841, (6.5993)+(0.0164)Ser+(−0.0669)Asn+(−0.0061)Arg+(−0.1444)Met+(0.0603)Phe+(−0.0990)Trp; 0.828, 0.847, 0.857, 0.839, 0.846, 0.837, 0.803, 0.833, (6.6634)+(0.0114)Ser+(−0.0078)His+(−0.0158)Cit+(−0.1960)Met+(0.0583)Phe+(−0.0978)Trp; 0.840, 0.854, 0.857, 0.845, 0.847, 0.842, 0.820, 0.841, (6.5342)+(0.0154)Ser+(−0.0700)Asn+(−0.1518)Met+(0.0607)Phe+(−0.1005)Trp; 0.840, 0.857, 0.856, 0.846, 0.847, 0.841, 0.820, 0.842, (6.5852)+(0.0160)Ser+(−0.0647)Asn+(−0.1539)Met+(−0.0093)Orn+(0.0641)Phe+(−0.0997)Trp; 0.866, 0.882, 0.855, 0.871, 0.865, 0.867, 0.861, 0.869, (4.4728)+(−0.1505)Asn+(0.0148)Gln+(−0.0207)His+(−0.0467)Cit+(0.0398)Phe+(−0.1103)Trp; 0.834, 0.854, 0.855, 0.841, 0.842, 0.837, 0.813, 0.836, (6.6129)+(0.0151)Ser+(−0.0715)Asn+(−0.0076)Tyr+(−0.1412)Met+(0.0626)Phe+(−0.0979)Trp; 0.828, 0.845, 0.854, 0.836, 0.840, 0.834, 0.806, 0.831, (6.0074)+(0.0112)Ser+(−0.0117)His+(−0.2017)Met+(0.0579)Phe+(−0.0970)Trp; 0.864, 0.882, 0.854, 0.860, 0.843, 0.838, 0.855, 0.855, (2.4700)+(0.0158)Gln+(−0.0382)His+(−0.2621)Met+(−0.0290)Orn+(0.0747)Phe+(−0.0977)Trp; 0.825, 0.845, 0.854, 0.836, 0.839, 0.834, 0.806, 0.831, (6.0072)+(0.0113)Ser+(−0.0116)His+(−0.0002)Thr+(−0.2011)Met+(0.0578)Phe+(−0.0969)Trp; 0.832, 0.851, 0.854, 0.843, 0.847, 0.844, 0.815, 0.839, (7.7895)+(0.0114)Ser+(−0.1007)Asn+(−0.0221)Cit+(−0.0059)Lys+(0.0400)Phe+(−0.1025)Trp; 0.832, 0.851, 0.854, 0.846, 0.846, 0.833, 0.840, 0.842, (6.4730)+(0.0196)Ser+(−0.0067)Gly+(−0.0067)His+(−0.2004)Met+(0.0524)Phe+(−0.0985)Trp; 0.829, 0.848, 0.853, 0.837, 0.840, 0.837, 0.803, 0.832, (6.1598)+(0.0121)Ser+(−0.0100)His+(−0.1917)Met+(−0.0038)Lys+(0.0588)Phe+(−0.0960)Trp; 0.828, 0.847, 0.853, 0.836, 0.840, 0.835, 0.801, 0.831, (6.1210)+(0.0127)Ser+(−0.0104)His+(−0.0083)Arg+(−0.1890)Met+(0.0575)Phe+(−0.0954)Trp; 0.834, 0.852, 0.853, 0.846, 0.847, 0.834, 0.837, 0.842, (6.4343)+(0.0190)Ser+(−0.0064)Gly+(−0.0098)Cit+(−0.1997)Met+(0.0521)Phe+(−0.1008)Trp; 0.872, 0.887, 0.853, 0.874, 0.868, 0.864, 0.855, 0.869, (3.3147)+(−0.1054)Asn+(0.0157)Gln+(−0.0455)Cit+(−0.1736)Met+(0.0639)Phe+(−0.1118)Trp; 0.842, 0.858, 0.853, 0.839, 0.835, 0.836, 0.799, 0.832, (6.0315)+(0.0091)Ser+(−0.1951)Met+(0.0271)Ile+(−0.0355)Leu+(0.0809)Phe+(−0.0915)Trp; 0.830, 0.848, 0.852, 0.839, 0.846, 0.840, 0.798, 0.833, (6.1744)+(0.0119)Ser+(−0.0177)Cit+(−0.1875)Met+(−0.0043)Lys+(0.0584)Phe+(−0.0991)Trp; 0.857, 0.871, 0.852, 0.850, 0.841, 0.850, 0.815, 0.844, (7.5269)+(0.0155)Ser+(−0.0710)Asn+(−0.0171)Val+(−0.1394)Met+(0.0851)Phe+(−0.0823)Trp; 0.833, 0.847, 0.852, 0.838, 0.845, 0.833, 0.800, 0.831, (5.9829)+(0.0107)Ser+(−0.0181)Cit+(−0.1997)Met+(0.0571)Phe+(−0.1010)Trp; 0.829, 0.847, 0.852, 0.838, 0.846, 0.833, 0.799, 0.831, (5.9827)+(0.0107)Ser+(0.0001)Thr+(−0.0181)Cit+(−0.2000)Met+(0.0571)Phe+(−0.1010)Trp; 0.846, 0.864, 0.852, 0.846, 0.831, 0.851, 0.825, 0.843, (7.3153)+(0.0069)Thr+(−0.0250)Val+(−0.2210)Met+(0.0290)Ile+(0.0782)Phe+(−0.0768)Trp; 0.830, 0.849, 0.852, 0.838, 0.841, 0.831, 0.808, 0.832, (6.1249)+(0.0124)Ser+(−0.0104)His+(−0.1996)Met+(−0.0122)Orn+(0.0627)Phe+(−0.0963)Trp; 0.829, 0.848, 0.852, 0.840, 0.843, 0.837, 0.818, 0.836, (7.6702)+(0.0097)Ser+(−0.1087)Asn+(−0.0011)His+(−0.0228)Cit+(0.0364)Phe+(−0.1051)Trp; 0.822, 0.844, 0.852, 0.834, 0.837, 0.830, 0.803, 0.828, (6.0498)+(0.0110)Ser+(−0.0120)His+(−0.0046)Tyr+(−0.1959)Met+(0.0591)Phe+(−0.0953)Trp; 0.854, 0.874, 0.851, 0.855, 0.838, 0.847, 0.846, 0.851, (2.7951)+(0.0138)Gln+(−0.0346)His+(−0.0069)
Thr+(−0.2353)Met+(0.0586)Phe+(−0.0981)Trp; 0.826,
0.843, 0.851, 0.837, 0.836, 0.851, 0.813, 0.836,
(4.0419)+(0.0093)Gln+(−0.0422)His+(−0.0437)Cit+
(0.0123)Phe+(−0.1087)Trp; 0.833, 0.848, 0.851, 0.840,
0.843, 0.837, 0.817, 0.836, (7.6646)+(0.0096)Ser+
(−0.1092)Asn+(−0.0231)Cit+(0.0363)Phe+(−0.1055)
Trp; 0.829, 0.848, 0.851, 0.837, 0.845, 0.833, 0.795,
0.830, (6.0430)+(0.0117)Ser+(−0.0135)Cit+(−0.0058)
Arg+(−0.1926)Met+(0.0566)Phe+(−0.0997)Trp;
0.828, 0.848, 0.851, 0.836, 0.843, 0.831, 0.796, 0.829,
(6.0141)+(0.0105)Ser+(−0.0180)Cit+(−0.0037)Tyr+
(−0.1951)Met+(0.0580)Phe+(−0.0997)Trp; 0.854,
0.868, 0.850, 0.856, 0.838, 0.877, 0.849, 0.858,
(7.2167)+(0.0136)Ser+(−0.0539)Asn+(−0.0075)Ala+
(−0.1121)Met+(0.0565)Phe+(−0.0877)Trp; 0.864,
0.880, 0.850, 0.854, 0.839, 0.840, 0.826, 0.846,
(3.1852)+(0.0124)Gln+(−0.0243)His+(−0.2406)Met+
(−0.0196)Leu+(0.0799)Phe+(−0.0976)Trp; 0.856,
0.871, 0.850, 0.858, 0.847, 0.845, 0.857, 0.855,
(4.8183)+(−0.1481)Asn+(0.0129)Gln+(−0.0298)His+
(0.0351)Phe+(−0.1080)Trp; 0.862, 0.878, 0.850, 0.860,
0.850, 0.836, 0.850, 0.853, (3.4141)+(0.0034)Ser+
(−0.1051)Asn+(0.0133)Gln+(−0.1917)Met+(0.0626)
Phe+(−0.1123)Trp; 0.835, 0.853, 0.849, 0.845, 0.844,
0.834, 0.833, 0.841, (6.5724)+(0.0202)Ser+(−0.0068)
Gly+(−0.1935)Met+(−0.0038)Lys+(0.0522)Phe+
(−0.0997)Trp; 0.833, 0.852, 0.849, 0.845, 0.844, 0.830,
0.837, 0.841, (6.4109)+(0.0190)Ser+(−0.0070)Gly+
(0.0011)Thr+(−0.2079)Met+(0.0513)Phe+(−0.1017)
Trp; 0.822, 0.834, 0.849, 0.825, 0.816, 0.833, 0.816,
0.824, (4.3714)+(0.0076)Gln+(−0.0504)His+(0.0082)
Phe+(−0.1065)Trp; 0.858, 0.875, 0.849, 0.851, 0.827,
0.839, 0.846, 0.847, (4.7114)+(−0.1427)Asn+(0.0136)
Gln+(−0.0313)His+(−0.0327)Tyr+(0.0516)Phe+
(−0.0951)Trp; 0.834, 0.852, 0.848, 0.845, 0.845, 0.831,
0.832, 0.840, (6.4904)+(0.0202)Ser+(−0.0066)Gly+
(−0.0067)Arg+(−0.1937)Met+(0.0510)Phe+(−0.0996)
Trp; 0.837, 0.851, 0.848, 0.844, 0.844, 0.829, 0.837,
0.840, (6.4094)+(0.0193)Ser+(−0.0069)Gly+(−0.2044)
Met+(0.0510)Phe+(−0.1014)Trp; 0.831, 0.848, 0.848,
0.840, 0.843, 0.835, 0.816, 0.836, (7.6782)+(0.0097)
Ser+(−0.1082)Asn+(−0.0210)Cit+(−0.0027)Orn+
(0.0369)Phe+(−0.1054)Trp; 0.830, 0.849, 0.848, 0.833,
0.828, 0.830, 0.800, 0.827, (7.6726)+(0.0102)Ser+
(−0.1049)Asn+(−0.0215)Cit+(−0.0224)Tyr+(0.0475)
Phe+(−0.0967)Trp; 0.832, 0.850, 0.848, 0.840, 0.843,
0.834, 0.809, 0.834, (7.6642)+(0.0108)Ser+(−0.1044)
Asn+(−0.0174)Cit+(−0.0070)Arg+(0.0365)Phe+
(−0.1038)Trp; 0.849, 0.864, 0.848, 0.845, 0.844, 0.839,
0.802, 0.837, (7.0742)+(0.0143)Ser+(−0.0698)Asn+
(−0.1241)Met+(−0.0229)Leu+(0.0819)Phe+(−0.0937)
Trp; 0.858, 0.876, 0.848, 0.862, 0.850, 0.853, 0.855,
0.859, (4.9806)+(−0.1348)Asn+(0.0137)Gln+
(−0.0266)His+(−0.0098)Lys+(0.0393)Phe+(−0.1048)
Trp; 0.831, 0.851, 0.848, 0.829, 0.810, 0.842, 0.800,
0.825, (3.9499)+(0.0103)Gln+(−0.0433)His+(−0.0418)
Cit+(−0.0382)Tyr+(0.0326)Phe+(−0.0935)Trp; 0.873,
0.887, 0.847, 0.858, 0.828, 0.854, 0.849, 0.854,
(3.3435)+(0.0120)Gln+(−0.0255)Val+(−0.2885)Met+
(0.0255)Ile+(0.0864)Phe+(−0.0863)Trp; 0.831, 0.849,
0.847, 0.840, 0.840, 0.837, 0.819, 0.836, (7.5743)+
(0.0115)Ser+(−0.1038)Asn+(−0.0042)Thr+(−0.0212)
Cit+(0.0363)Phe+(−0.1040)Trp; 0.831, 0.848, 0.847,
0.845, 0.848, 0.832, 0.842, 0.842, (7.8998)+(0.0136)
Ser+(−0.1031)Asn+(−0.0038)Gly+(−0.0187)Cit+
(0.0317)Phe+(−0.1058)Trp; 0.828, 0.847, 0.846, 0.827,
0.817, 0.817, 0.802, 0.821, (7.6595)+(0.0096)Ser+
(−0.1051)Asn+(−0.0073)His+(−0.0238)Tyr+(0.0464)
Phe+(−0.0946)Trp; 0.856, 0.872, 0.846, 0.853, 0.849,
0.837, 0.822, 0.845, (2.4879)+(0.0131)Gln+(−0.0435)
Cit+(−0.2623)Met+(0.0609)Phe+(−0.1121)Trp; 0.838,
0.860, 0.846, 0.848, 0.840, 0.862, 0.819, 0.845,
(4.3920)+(0.0116)Gln+(−0.0329)His+(−0.0451)Cit+
(−0.0175)Lys+(0.0243)Phe+(−0.1033)Trp; 0.835,
0.852, 0.846, 0.845, 0.855, 0.831, 0.813, 0.838,
(7.6871)+(−0.0588)Asn+(0.0069)Thr+(−0.0175)Cit+
(−0.1369)Met+(0.0528)Phe+(−0.1008)Trp; 0.832,
0.847, 0.846, 0.834, 0.836, 0.829, 0.797, 0.827,
(6.0647)+(0.0113)Ser+(−0.1961)Met+(−0.0045)Lys+
(0.0571)Phe+(−0.1000)Trp; 0.828, 0.847, 0.846, 0.834,
0.836, 0.829, 0.797, 0.827, (6.0645)+(0.0113)Ser+
(−0.0001)Thr+(−0.1960)Met+(−0.0045)Lys+(0.0571)
Phe+(−0.1000)Trp; 0.830, 0.849, 0.846, 0.837, 0.842,
0.828, 0.800, 0.830, (6.0387)+(0.0115)Ser+(−0.0099)
Cit+(−0.2015)Met+(−0.0101)Orn+(0.0606)Phe+
(−0.1004)Trp; 0.863, 0.880, 0.846, 0.862, 0.852, 0.851,
0.841, 0.856, (4.5737)+(−0.1307)Asn+(0.0152)Gln+
(−0.0300)His+(−0.0239)Arg+(0.0364)Phe+(−0.1027)
Trp; 0.848, 0.864, 0.846, 0.844, 0.827, 0.844, 0.827,
0.840, (7.4275)+(−0.0203)Val+(−0.1885)Met+
(0.0335)Ile+(−0.0100)Leu+(0.0753)Phe+(−0.0765)
Trp; 0.852, 0.870, 0.845, 0.851, 0.833, 0.849, 0.838,
0.848, (8.4985)+(−0.0543)Asn+(−0.0239)Val+
(−0.1338)Met+(0.0268)Ile+(0.0730)Phe+(−0.0742)
Trp; 0.828, 0.847, 0.845, 0.833, 0.837, 0.831, 0.792,
0.827, (6.1009)+(0.0123)Ser+(−0.0073)Arg+(−0.1892)
Met+(−0.0028)Lys+(0.0564)Phe+(−0.0989)Trp; 0.834,
0.854, 0.845, 0.845, 0.843, 0.828, 0.836, 0.840,
(6.4699)+(0.0196)Ser+(−0.0064)Gly+(−0.2025)Met+
(−0.0097)Orn+(0.0553)Phe+(−0.1005)Trp; 0.848,
0.865, 0.845, 0.852, 0.836, 0.875, 0.836, 0.853,
(6.8606)+(0.0100)Ser+(−0.0080)Ala+(−0.0146)Cit+
(−0.1446)Met+(0.0536)Phe+(−0.0870)Trp; 0.827,
0.847, 0.845, 0.833, 0.838, 0.828, 0.791, 0.826,
(6.0008)+(0.0117)Ser+(0.0005)Thr+(−0.0090)Arg+
(−0.1960)Met+(0.0557)Phe+(−0.0998)Trp; 0.827,
0.848, 0.845, 0.836, 0.838, 0.832, 0.805, 0.831,
(7.6599)+(0.0112)Ser+(−0.1015)Asn+(−0.0057)His+
(−0.0108)Arg+(0.0356)Phe+(−0.1015)Trp; 0.832,
0.844, 0.845, 0.832, 0.835, 0.824, 0.798, 0.825,
(5.8628)+(0.0101)Ser+(−0.2090)Met+(0.0557)Phe+
(−0.1020)Trp; 0.832, 0.847, 0.845, 0.833, 0.837, 0.828,
0.792, 0.826, (6.0006)+(0.0118)Ser+(−0.0088)Arg+
(−0.1946)Met+(0.0555)Phe+(−0.0997)Trp; 0.862,
0.878, 0.844, 0.862, 0.845, 0.842, 0.867, 0.858,
(4.5811)+(−0.1427)Asn+(0.0147)Gln+(−0.0321)His+
(−0.0226)Orn+(0.0425)Phe+(−0.1072)Trp; 0.865,
0.879, 0.844, 0.859, 0.849, 0.834, 0.849, 0.853,
(3.5861)+(−0.1025)Asn+(0.0136)Gln+(−0.1869)Met+
(0.0599)Phe+(−0.1124)Trp; 0.854, 0.872, 0.844, 0.858,
0.847, 0.843, 0.857, 0.855, (4.9507)+(−0.0032)Ser+
(−0.1444)Asn+(0.0132)Gln+(−0.0296)His+(0.0332)
Phe+(−0.1080)Trp; 0.826, 0.847, 0.844, 0.837, 0.837,
0.834, 0.814, 0.833, (7.7612)+(0.0107)Ser+(−0.1025)
Asn+(−0.0046)His+(−0.0061)Lys+(0.0376)Phe+
(−0.1021)Trp; 0.830, 0.845, 0.844, 0.835, 0.836, 0.825,
0.818, 0.831, (7.6449)+(0.0090)Ser+(−0.1101)Asn+
(−0.0071)His+(0.0341)Phe+(−0.1042)Trp; 0.852,
0.873, 0.844, 0.852, 0.846, 0.835, 0.822, 0.844,
(2.5096)+(0.0130)Gln+(−0.0435)Cit+(−0.0052)Tyr+
(−0.2566)Met+(0.0624)Phe+(−0.1103)Trp; 0.828,
0.848, 0.844, 0.834, 0.839, 0.823, 0.796, 0.826,
(6.0007)+(0.0108)Ser+(0.0017)Thr+(−0.2113)
Met+(−0.0133)Orn+(0.0618)Phe+(−0.1012)Trp;

0.832, 0.844, 0.844, 0.835, 0.832, 0.854, 0.807, 0.834, (4.3936)+(0.0093)Gln+(−0.0402)His+(−0.0427)Cit+ (−0.1045)Trp; 0.829, 0.850, 0.844, 0.840, 0.837, 0.822, 0.831, 0.835, (6.5152)+(0.0193)Ser+(−0.0073)Gly+ (−0.0096)Tyr+(−0.1925)Met+(0.0531)Phe+(−0.0981) Trp; 0.853, 0.869, 0.844, 0.848, 0.842, 0.838, 0.810, 0.840, (8.5266)+(−0.0643)Asn+(0.0095)Thr+ (−0.0179)Val+(−0.1409)Met+(0.0792)Phe+(−0.0835) Trp; 0.828, 0.846, 0.844, 0.832, 0.834, 0.829, 0.793, 0.826, (6.1049)+(0.0111)Ser+(−0.0044)Tyr+(−0.1906) Met+(−0.0046)Lys+(0.0582)Phe+(−0.0985)Trp; 0.824, 0.846, 0.844, 0.831, 0.835, 0.825, 0.789, 0.824, (6.0241)+(0.0117)Ser+(−0.0087)Arg+(−0.0030)Tyr+ (−0.1911)Met+(0.0562)Phe+(−0.0987)Trp; 0.831, 0.850, 0.843, 0.835, 0.839, 0.827, 0.794, 0.828, (6.0950)+(0.0127)Ser+(−0.0069)Arg+(−0.1950)Met+ (−0.0114)Orn+(0.0602)Phe+(−0.0991)Trp; 0.825, 0.841, 0.843, 0.816, 0.794, 0.823, 0.793, 0.813, (4.2614)+(0.0087)Gln+(−0.0512)His+(−0.0397)Tyr+ (0.0295)Phe+(−0.0908)Trp; 0.824, 0.834, 0.843, 0.824, 0.813, 0.837, 0.808, 0.823, (4.6044)+(0.0076)Gln+ (−0.0489)His+(−0.1037)Trp; 0.831, 0.850, 0.843, 0.835, 0.837, 0.828, 0.800, 0.829, (6.1095)+(0.0120) Ser+(−0.1986)Met+(−0.0116)Orn+(−0.0027)Lys+ (0.0613)Phe+(−0.0997)Trp; 0.848, 0.865, 0.843, 0.843, 0.824, 0.843, 0.828, 0.840, (8.5066)+(0.0090)Ser+ (−0.1145)Asn+(−0.0209)Val+(0.0118)Ile+(0.0597) Phe+(−0.0848)Trp; 0.825, 0.843, 0.843, 0.830, 0.833, 0.820, 0.794, 0.823, (5.8951)+(0.0099)Ser+(−0.0038) Tyr+(−0.2043)Met+(0.0567)Phe+(−0.1007)Trp; 0.858, 0.876, 0.843, 0.858, 0.853, 0.849, 0.829, 0.852, (2.8311)+(0.0139)Gln+(−0.0442)Cit+(−0.2353)Met+ (−0.0092)Lys+(0.0623)Phe+(−0.1087)Trp; 0.828, 0.844, 0.843, 0.831, 0.833, 0.823, 0.797, 0.824, (5.8677)+(0.0106)Ser+(−0.0013)Thr+(−0.2051)Met+ (0.0553)Phe+(−0.1016)Trp; 0.888, 0.899, 0.843, 0.872, 0.850, 0.857, 0.855, 0.865, (4.4024)+(−0.1075)Asn+ (0.0147)Gln+(−0.0196)Val+(−0.1775)Met+(0.0888) Phe+(−0.0925)Trp; 0.848, 0.865, 0.843, 0.854, 0.837, 0.866, 0.851, 0.855, (7.0521)+(0.0156)Ser+(−0.0046) Gly+(−0.0074)Ala+(−0.1536)Met+(0.0496)Phe+ (−0.0886)Trp

List (1) of Logistic Regression Equations Searched in Example 6

The logistic regression equations searched in Example 6 above are listed below. Before each equation, "the value of ROC_AUC for the pancreatic cancer group and the colorectal cancer group with validation", "the value of ROC_AUC for the pancreatic cancer group and the colorectal cancer group without validation", "the value of ROC_AUC for the pancreatic cancer group and the healthy group", "the value of ROC_AUC for the pancreatic cancer group and the other cancers group", "the value of ROC_AUC for the pancreatic cancer group and the lung cancer group", "the value of ROC_AUC for the pancreatic cancer group and the prostatic cancer group", "the value of ROC_AUC for the pancreatic cancer group and the breast cancer group", and "the average value of the value of ROC_AUC for the pancreatic cancer group and the lung cancer group, the value of ROC_AUC for the pancreatic cancer group and the colorectal cancer group, the value of ROC_AUC for the pancreatic cancer group and the prostatic cancer group, and the value of ROC_AUC for the pancreatic cancer group and the breast cancer group" obtained for the equation are additionally listed.

0.851, 0.874, 0.831, 0.855, 0.845, 0.857, 0.841, 0.854, (5.6692)+(−0.0719)Asn+(0.0072)Gln+(−0.0715)Cit+ (0.0674)Tyr+(−0.1878)Met+(−0.1103)Trp; 0.850, 0.871, 0.830, 0.836, 0.811, 0.833, 0.834, 0.837, (7.7617)+(−0.0729)Asn+(−0.0057)Gly+(−0.0829)Cit+ (0.0409)Tyr+(0.0296)Orn+(−0.1265)Trp; 0.850, 0.873, 0.814, 0.859, 0.857, 0.861, 0.832, 0.856, (6.1359)+ (−0.1088)Asn+(0.0071)Gln+(−0.0672)Cit+(−0.0111) Pro+(0.0505)Tyr+(−0.1271)Trp; 0.849, 0.870, 0.846, 0.846, 0.832, 0.854, 0.826, 0.846, (5.7474)+(−0.1127) Asn+(0.0047)Gln+(−0.0872)Cit+(0.0428)Tyr+ (0.0250)Orn+(−0.1255)Trp; 0.849, 0.867, 0.838, 0.831, 0.809, 0.840, 0.808, 0.831, (7.0356)+(−0.0849)Asn+ (−0.0858)Cit+(0.0454)Tyr+(0.0272)Orn+(−0.1272) Trp; 0.849, 0.870, 0.835, 0.836, 0.815, 0.852, 0.811, 0.837, (7.1656)+(−0.0396)Asn+(−0.0827)Cit+(0.0644) Tyr+(−0.1539)Met+(0.0221)Orn+(−0.1154)Trp; 0.849, 0.871, 0.816, 0.851, 0.844, 0.858, 0.824, 0.849, (5.8529)+(0.0054)Gln+(−0.0752)Cit+(−0.0083)Pro+ (0.0729)Tyr+(−0.2227)Met+(−0.1204)Trp; 0.848, 0.868, 0.825, 0.837, 0.821, 0.852, 0.807, 0.837, (7.1319)+(−0.0848)Cit+(−0.0074)Pro+(0.0688)Tyr+ (−0.1769)Met+(0.0215)Orn+(−0.1210)Trp; 0.848, 0.868, 0.841, 0.839, 0.818, 0.853, 0.822, 0.840, (7.0943)+(−0.0793)Asn+(−0.0024)Ala+(−0.0860)Cit+ (0.0480)Tyr+(0.0271)Orn+(−0.1208)Trp; 0.848, 0.869, 0.826, 0.836, 0.819, 0.844, 0.805, 0.835, (7.5534)+ (−0.0758)Asn+(−0.0856)Cit+(−0.0091)Pro+(0.0501) Tyr+(0.0291)Orn+(−0.1282)Trp; 0.848, 0.868, 0.817, 0.839, 0.827, 0.848, 0.801, 0.836, (7.4652)+(0.0076) Thr+(−0.0677)Cit+(−0.0072)Pro+(0.0744)Tyr+ (−0.2094)Met+(−0.1239)Trp; 0.847, 0.869, 0.839, 0.832, 0.811, 0.841, 0.809, 0.832, (7.1085)+(−0.0806) Asn+(−0.0868)Cit+(0.0455)Tyr+(0.0281)Orn+ (−0.0020)Lys+(−0.1251)Trp; 0.847, 0.868, 0.803, 0.842, 0.829, 0.839, 0.827, 0.841, (8.0010)+(−0.0032) Gly+(−0.0628)Cit+(−0.0063)Pro+(0.0706)Tyr+ (−0.1728)Met+(−0.1209)Trp; 0.847, 0.871, 0.814, 0.857, 0.846, 0.838, 0.869, 0.856, (6.3888)+(−0.1064) Asn+(−0.0072)Gly+(0.0069)Gln+(−0.0612)Cit+ (0.0393)Tyr+(−0.1215)Trp; 0.847, 0.868, 0.825, 0.840, 0.824, 0.843, 0.820, 0.839, (7.1977)+(−0.0275)Asn+ (−0.0640)Cit+(0.0662)Tyr+(−0.1707)Met+(0.0104) Phe+(−0.1193)Trp; 0.847, 0.868, 0.826, 0.837, 0.820, 0.847, 0.812, 0.837, (7.4013)+(−0.0324)Asn+(0.0064) Thr+(−0.0658)Cit+(0.0704)Tyr+(−0.1895)Met+ (−0.1172)Trp; 0.847, 0.866, 0.817, 0.837, 0.821, 0.842, 0.816, 0.836, (7.5014)+(−0.0300)Asn+(−0.0653)Cit+ (0.0703)Tyr+(−0.1702)Met+(−0.1157)Trp; 0.847, 0.867, 0.837, 0.831, 0.810, 0.839, 0.807, 0.831, (7.0571)+(−0.0846)Asn+(−0.0859)Cit+(0.0455)Tyr+ (0.0275)Orn+(−0.0010)Ile+(−0.1269)Trp; 0.846, 0.866, 0.809, 0.838, 0.826, 0.844, 0.809, 0.836, (7.5613)+(−0.0672)Cit+(−0.0065)Pro+(0.0737)Tyr+ (−0.1847)Met+(−0.1211)Trp; 0.846, 0.867, 0.827, 0.849, 0.839, 0.849, 0.836, 0.848, (5.8545)+(−0.1092) Asn+(0.0053)Gln+(−0.0674)Cit+(0.0456)Tyr+ (−0.1244)Trp; 0.846, 0.866, 0.824, 0.837, 0.822, 0.841, 0.813, 0.835, (6.7689)+(−0.0672)Cit+(0.0662)Tyr+ (−0.1984)Met+(0.0116)Phe+(−0.1210)Trp; 0.846, 0.870, 0.818, 0.850, 0.838, 0.842, 0.846, 0.849, (5.9813)+(−0.0053)Gly+(0.0055)Gln+(−0.0705)Cit+ (0.0640)Tyr+(−0.2246)Met+(−0.1145)Trp; 0.846, 0.867, 0.811, 0.836, 0.821, 0.839, 0.808, 0.834, (7.3261)+(−0.0705)Cit+(−0.0066)Pro+(0.0734)Tyr+ (0.0041)Val+(−0.1901)Met+(−0.1275)Trp; 0.846, 0.868, 0.832, 0.837, 0.821, 0.845, 0.811, 0.836, (6.6000)+(0.0065)Thr+(−0.0678)Cit+(0.0657)Tyr+ (−0.2208)Met+(0.0132)Phe+(−0.1230)Trp; 0.846, 0.868, 0.810, 0.841, 0.829, 0.845, 0.814, 0.839, (7.9033)+(−0.0256)Asn+(−0.0642)Cit+(−0.0061)Pro+ (0.0731)Tyr+(−0.1593)Met+(−0.1197)Trp; 0.846, 0.869, 0.835, 0.830, 0.810, 0.836, 0.799, 0.828, (7.1058)+(−0.0739)Asn+(−0.0798)Cit+(−0.0100)Arg+ (0.0471)Tyr+(0.0272)Orn+(−0.1256)Trp; 0.846, 0.867, 0.838, 0.831, 0.809, 0.840, 0.808, 0.831, (7.0362)+ (−0.0849)Asn+(−0.0858)Cit+(0.0454)Tyr+(0.0273) Orn+(−0.0000)Leu+(−0.1272)Trp; 0.846, 0.867, 0.839, 0.831, 0.810, 0.840, 0.808, 0.831, (7.0210)+(−0.0847) Asn+(−0.0857)Cit+(0.0452)Tyr+(0.0272)Orn+ (0.0006)Phe+(−0.1275)Trp; 0.846, 0.869, 0.816, 0.842, 0.830, 0.845, 0.814, 0.839, (7.2685)+(−0.0656)Cit+ (−0.0062)Pro+(0.0694)Tyr+(−0.1834)Met+(0.0102) Phe+(−0.1240)Trp; 0.846, 0.868, 0.838, 0.848, 0.838, 0.853, 0.829, 0.847, (4.8590)+(0.0051)Gln+(−0.0738) Cit+(0.0627)Tyr+(−0.2409)Met+(0.0172)Phe+ (−0.1200)Trp; 0.846, 0.869, 0.826, 0.837, 0.817, 0.842, 0.823, 0.838, (7.2825)+(−0.0044)Gly+(−0.0825)Cit+ (0.0609)Tyr+(−0.1763)Met+(0.0222)Orn+(−0.1180) Trp; 0.846, 0.868, 0.818, 0.839, 0.821, 0.838, 0.825, 0.838, (7.5424)+(−0.0041)Gly+(0.0071)Thr+ (−0.0647)Cit+(0.0670)Tyr+(−0.2093)Met+(−0.1194) Trp; 0.846, 0.865, 0.830, 0.832, 0.813, 0.847, 0.804, 0.832, (6.6662)+(−0.0848)Cit+(0.0660)Tyr+(−0.1954) Met+(0.0189)Orn+(−0.1170)Trp; 0.846, 0.866, 0.818, 0.839, 0.823, 0.845, 0.819, 0.838, (7.5068)+(−0.0280) Asn+(−0.0009)Ala+(−0.0654)Cit+(0.0711)Tyr+ (−0.1674)Met+(−0.1139)Trp; 0.846, 0.868, 0.817, 0.849, 0.841, 0.842, 0.835, 0.846, (6.1483)+(−0.0060) Ser+(−0.1031)Asn+(0.0058)Gln+(−0.0687)Cit+ (0.0451)Tyr+(−0.1261)Trp; 0.846, 0.867, 0.836, 0.828, 0.805, 0.835, 0.805, 0.828, (6.9378)+(−0.0858) Asn+(−0.0874)Cit+(0.0446)Tyr+(0.0024)Val+(0.0267) Orn+(−0.1316)Trp; 0.846, 0.866, 0.834, 0.830, 0.809, 0.839, 0.807, 0.830, (7.1787)+(−0.0020)Ser+(−0.0817) Asn+(−0.0862)Cit+(0.0453)Tyr+(0.0274) Orn+(−0.1279)Trp; 0.845, 0.862, 0.817, 0.833, 0.817, 0.841, 0.806, 0.832, (7.0767)+(−0.0690)Cit+(0.0710) Tyr+(−0.2009)Met+(−0.1171)Trp; 0.845, 0.868, 0.829, 0.849, 0.840, 0.847, 0.838, 0.848, (5.7352)+(−0.1079) Asn+(0.0053)Gln+(−0.0671)Cit+(0.0445)Tyr+ (0.0039)Phe+(−0.1263)Trp; 0.845, 0.867, 0.833, 0.837, 0.818, 0.854, 0.813, 0.838, (6.7229)+(−0.0016)Ala+ (−0.0851)Cit+(0.0669)Tyr+(−0.1865)Met+(0.0196) Orn+(−0.1135)Trp; 0.845, 0.863, 0.819, 0.836, 0.821, 0.846, 0.813, 0.836, (7.1306)+(−0.0013)Ala+(−0.0689) Cit+(0.0719)Tyr+(−0.1938)Met+(−0.1143)Trp; 0.845, 0.864, 0.822, 0.833, 0.816, 0.845, 0.803, 0.832, (6.9630)+(0.0056)Thr+(−0.0697)Cit+(0.0711)Tyr+ (−0.2203)Met+(−0.1186)Trp; 0.845, 0.867, 0.817, 0.840, 0.824, 0.833, 0.831, 0.839, (7.2884)+(−0.0032) Gly+(−0.0631)Cit+(0.0635)Tyr+(−0.1857)Met+ (0.0105)Phe+(−0.1213)Trp; 0.845, 0.865, 0.825, 0.843, 0.831, 0.851, 0.821, 0.842, (5.5455)+(0.0045)Gln+ (−0.0759)Cit+(0.0697)Tyr+(−0.2378)Met+(−0.1148) Trp; 0.845, 0.867, 0.823, 0.838, 0.820, 0.848, 0.817, 0.838, (7.2506)+(0.0034)Ser+(−0.0336)Asn+ (−0.0652)Cit+(0.0711)Tyr+(−0.1743)Met+(−0.1147) Trp; 0.845, 0.864, 0.810, 0.837, 0.820, 0.833, 0.828, 0.836, (7.5972)+(−0.0035)Gly+(−0.0645)Cit+(0.0676) Tyr+(−0.1872)Met+(−0.1176)Trp; 0.845, 0.866, 0.833, 0.831, 0.809, 0.839, 0.810, 0.831, (7.1163)+(−0.0798) Asn+(−0.0043)Thr+(−0.0870)Cit+(0.0468)Tyr+ (0.0282)Orn+(−0.1251)Trp; 0.845, 0.867, 0.825, 0.840, 0.825, 0.847, 0.820, 0.840, (6.8272)+(−0.0012)Ala+ (−0.0671)Cit+(0.0672)Tyr+(−0.1919)Met+(0.0114) Phe+(−0.1183)Trp; 0.845, 0.866, 0.821, 0.842, 0.825, 0.841, 0.836, 0.842, (7.1813)+(0.0076)Ser+(−0.0052) Gly+(−0.0629)Cit+(0.0674)Tyr+(−0.1982)Met+ (−0.1156)Trp; 0.845, 0.866, 0.819, 0.837, 0.819, 0.838, 0.820, 0.836, (7.2585)+(−0.0418)Asn+(−0.0659)Cit+ (0.0720)Tyr+(−0.1918)Met+(0.0078)Lys+(−0.1212) Trp; 0.844, 0.866, 0.809, 0.837, 0.824, 0.839, 0.808, 0.834, (7.2430)+(−0.0686)Cit+(−0.0070)Pro+(0.0757) Tyr+(−0.2111)Met+(0.0065)Lys+(−0.1265)Trp; 0.844, 0.866, 0.810, 0.840, 0.823, 0.837, 0.833, 0.840, (7.8866)+(−0.0257)Asn+(−0.0030)Gly+(−0.0617)Cit+ (0.0674)Tyr+(−0.1627)Met+(−0.1162)Trp; 0.844, 0.866, 0.809, 0.839, 0.826, 0.846, 0.811, 0.838, (7.5711)+(−0.0005)Ala+(−0.0672)Cit+(−0.0063)Pro+ (0.0741)Tyr+(−0.1825)Met+(−0.1199)Trp; 0.844, 0.867, 0.827, 0.846, 0.834, 0.842, 0.833, 0.846, (5.7895)+(−0.1098)Asn+(0.0052)Gln+(−0.0695)Cit+ (0.0448)Tyr+(0.0024)Val+(−0.1287)Trp; 0.844, 0.865, 0.817, 0.833, 0.814, 0.837, 0.814, 0.832, (7.2967)+ (−0.0308)Asn+(−0.0689)Cit+(0.0699)Tyr+(0.0041) Val+(−0.1751)Met+(−0.1225)Trp; 0.844, 0.865, 0.832, 0.832, 0.814, 0.848, 0.801, 0.832, (6.7648)+(−0.0807) Cit+(−0.0054)Arg+(0.0662)Tyr+(−0.1854)Met+ (0.0192)Orn+(−0.1170)Trp; 0.844, 0.865, 0.813, 0.835, 0.819, 0.839, 0.814, 0.834, (7.2574)+(−0.0687)Cit+ (−0.0065)Pro+(0.0745)Tyr+(−0.2011)Met+(0.0089) Leu+(−0.1272)Trp; 0.844, 0.866, 0.835, 0.832, 0.812, 0.850, 0.802, 0.833, (6.6142)+(0.0042)Thr+(−0.0840) Cit+(0.0664)Tyr+(−0.2108)Met+(0.0176)Orn+ (−0.1180)Trp; 0.844, 0.866, 0.828, 0.838, 0.824, 0.845, 0.814, 0.837, (6.5164)+(0.0026)Ser+(−0.0673)Cit+ (0.0664)Tyr+(−0.2045)Met+(0.0125)Phe+(−0.1204) Trp; 0.844, 0.865, 0.823, 0.836, 0.820, 0.848, 0.812, 0.836, (7.0140)+(0.0055)Thr+(−0.0013)Ala+(−0.0695) Cit+(0.0720)Tyr+(−0.2132)Met+(−0.1160)Trp; 0.844, 0.865, 0.813, 0.838, 0.827, 0.846, 0.807, 0.836, (7.3279)+(0.0029)Ser+(−0.0675)Cit+(−0.0067)Pro+ (0.0746)Tyr+(−0.1908)Met+(−0.1206)Trp; 0.844, 0.867, 0.827, 0.848, 0.837, 0.856, 0.832, 0.848, (5.5554)+(0.0047)Gln+(−0.0018)Ala+(−0.0757)Cit+ (0.0709)Tyr+(−0.2296)Met+(−0.1111)Trp; 0.844, 0.866, 0.835, 0.835, 0.817, 0.850, 0.809, 0.836, (6.4516)+(−0.0822)Cit+(0.0626)Tyr+(−0.1933)Met+ (0.0176)Orn+(0.0090)Phe+(−0.1202)Trp; 0.844, 0.868, 0.827, 0.851, 0.842, 0.853, 0.837, 0.850, (5.8878)+(−0.1052)Asn+(0.0056)Gln+(−0.0679)Cit+ (0.0458)Tyr+(−0.0030)Lys+(−0.1214)Trp; 0.844, 0.868, 0.830, 0.857, 0.850, 0.863, 0.851, 0.858, (5.8704)+(−0.1056)Asn+(0.0055)Gln+(−0.0027)Ala+ (−0.0676)Cit+(0.0486)Tyr+(−0.1173)Trp; 0.844, 0.864, 0.824, 0.833, 0.816, 0.834, 0.812, 0.831, (6.5818)+(−0.0706)Cit+(0.0661)Tyr+(0.0037)Val+ (−0.2037)Met+(0.0110)Phe+(−0.1270)Trp; 0.843, 0.866, 0.811, 0.838, 0.827, 0.844, 0.807, 0.836, (7.6240)+(−0.0643)Cit+(−0.0036)Arg+(−0.0064)Pro+ (0.0739)Tyr+(−0.1790)Met+(−0.1208)Trp; 0.843, 0.866, 0.832, 0.840, 0.826, 0.854, 0.813, 0.840, (5.4494)+(0.0038)Gln+(−0.0864)Cit+(0.0660)Tyr+ (−0.2286)Met+(0.0142)Orn+(−0.1149)Trp; 0.843, 0.867, 0.830, 0.849, 0.838, 0.848, 0.838, 0.848, (5.7917)+(−0.1101)Asn+(0.0052)Gln+(−0.0676)Cit+ (0.0452)Tyr+(0.0033)Ile+(−0.1253)Trp; 0.843, 0.867, 0.826, 0.849, 0.840, 0.849, 0.836, 0.848, (5.8645)+ (−0.1092)Asn+(0.0053)Gln+(−0.0673)Cit+(0.0456) Tyr+(−0.0004)Leu+(−0.1240)Trp; 0.843, 0.864, 0.831, 0.829, 0.809, 0.843, 0.801, 0.829, (6.5154)+(−0.0867) Cit+(0.0658)Tyr+(0.0031)Val+(−0.1992)Met+(0.0178) Orn+(−0.1221)Trp; 0.843, 0.865, 0.811, 0.840, 0.824, 0.838, 0.831, 0.839, (7.6202)+(−0.0033)Gly+ (−0.0011)Ala+(−0.0645)Cit+(0.0685)Tyr+(−0.1815) Met+(−0.1151)Trp; 0.843, 0.865, 0.831, 0.855, 0.852, 0.845, 0.849, 0.853, (6.4883)+(−0.0903)Asn+(−0.0089)Gly+(0.0069)Gln+(−0.0800)Cit+(0.0290)Orn+(−0.1034)Trp; 0.843, 0.863, 0.818, 0.833, 0.817, 0.843, 0.806, 0.832, (6.9632)+(0.0013)Ser+(−0.0691)Cit+(0.0713)Tyr+(−0.2039)Met+(−0.1167)Trp; 0.843, 0.863, 0.816, 0.829, 0.811, 0.833, 0.806, 0.828, (6.8562)+(−0.0726)Cit+(0.0706)Tyr+(0.0040)Val+(−0.2062)Met+(−0.1236)Trp; 0.843, 0.865, 0.826, 0.840, 0.826, 0.846, 0.817, 0.839, (5.4601)+(0.0042)Gln+(−0.0781)Cit+(0.0694)Tyr+(0.0027)Val+(−0.2395)Met+(−0.1190)Trp; 0.843, 0.859, 0.813, 0.831, 0.815, 0.830, 0.814, 0.830, (7.3478)+(−0.0782)Asn+(−0.0635)Cit+(0.0492)Tyr+(−0.1269)Trp; 0.843, 0.864, 0.820, 0.835, 0.816, 0.841, 0.818, 0.835, (6.8704)+(−0.0023)Ala+(−0.0735)Cit+(0.0723)Tyr+(0.0053)Val+(−0.1964)Met+(−0.1211)Trp; 0.843, 0.866, 0.816, 0.837, 0.821, 0.842, 0.816, 0.836, (7.5175)+(−0.0283)Asn+(−0.0638)Cit+(−0.0021)Arg+(0.0705)Tyr+(−0.1682)Met+(−0.1157)Trp; 0.843, 0.868, 0.819, 0.847, 0.841, 0.838, 0.825, 0.843, (5.7314)+(−0.1002)Asn+(0.0063)Gln+(−0.0577)Cit+(−0.0159)Arg+(0.0480)Tyr+(−0.1216)Trp; 0.843, 0.865, 0.831, 0.832, 0.813, 0.847, 0.804, 0.832, (6.6496)+(0.0002)Ser+(−0.0848)Cit+(0.0660)Tyr+(−0.1959)Met+(0.0189)Orn+(−0.1169)Trp; 0.843, 0.864, 0.822, 0.833, 0.816, 0.845, 0.803, 0.832, (6.9687)+(−0.0001)Ser+(0.0057)Thr+(−0.0697)Cit+(0.0711)Tyr+(−0.2202)Met+(−0.1186)Trp; 0.842, 0.864, 0.820, 0.837, 0.821, 0.847, 0.814, 0.837, (7.0379)+(0.0010)Ser+(−0.0013)Ala+(−0.0690)Cit+(0.0722)Tyr+(−0.1963)Met+(−0.1141)Trp; 0.842, 0.864, 0.829, 0.831, 0.812, 0.845, 0.803, 0.831, (6.5223)+(−0.0839)Cit+(0.0673)Tyr+(−0.2097)Met+(0.0170)Orn+(0.0032)Lys+(−0.1193)Trp; 0.842, 0.866, 0.824, 0.844, 0.836, 0.847, 0.818, 0.842, (5.5207)+(0.0051)Gln+(−0.0681)Cit+(−0.0105)Arg+(0.0701)Tyr+(−0.2261)Met+(−0.1140)Trp; 0.842, 0.863, 0.816, 0.833, 0.819, 0.840, 0.804, 0.831, (7.1673)+(−0.0653)Cit+(−0.0046)Arg+(0.0712)Tyr+(−0.1930)Met+(−0.1170)Trp; 0.842, 0.865, 0.819, 0.834, 0.813, 0.838, 0.820, 0.834, (7.2332)+(−0.0306)Asn+(−0.0672)Cit+(0.0712)Tyr+(−0.1868)Met+(0.0092)Leu+(−0.1226)Trp; 0.842, 0.864, 0.823, 0.832, 0.816, 0.839, 0.806, 0.831, (6.7337)+(0.0046)Thr+(−0.0706)Cit+(0.0721)Tyr+(−0.2354)Met+(0.0045)Lys+(−0.1217)Trp; 0.842, 0.866, 0.823, 0.837, 0.822, 0.841, 0.811, 0.835, (6.8536)+(−0.0645)Cit+(−0.0034)Arg+(0.0666)Tyr+(−0.1925)Met+(0.0110)Phe+(−0.1208)Trp; 0.842, 0.864, 0.822, 0.830, 0.811, 0.837, 0.802, 0.829, (6.7648)+(0.0052)Thr+(−0.0730)Cit+(0.0706)Tyr+(0.0036)Val+(−0.2233)Met+(−0.1243)Trp; 0.842, 0.860, 0.819, 0.831, 0.813, 0.828, 0.819, 0.830, (7.2067)+(−0.0803)Asn+(−0.0639)Cit+(0.0484)Tyr+(0.0059)Ile+(−0.1284)Trp; 0.842, 0.864, 0.827, 0.838, 0.818, 0.846, 0.830, 0.840, (6.8917)+(−0.0701)Cit+(−0.0075)Pro+(0.0749)Tyr+(−0.2193)Met+(0.0275)Ile+(−0.1224)Trp; 0.842, 0.866, 0.829, 0.842, 0.829, 0.852, 0.818, 0.841, (5.5687)+(0.0042)Gln+(0.0031)Thr+(−0.0759)Cit+(0.0698)Tyr+(−0.2462)Met+(−0.1160)Trp; 0.842, 0.867, 0.818, 0.851, 0.843, 0.845, 0.843, 0.849, (5.8268)+(−0.1085)Asn+(0.0063)Gln+(−0.0072)Thr+(−0.0685)Cit+(0.0478)Tyr+(−0.1208)Trp; 0.842, 0.860, 0.816, 0.838, 0.824, 0.841, 0.827, 0.838, (7.4134)+(−0.0734)Asn+(−0.0023)Ala+(−0.0637)Cit+(0.0521)Tyr+(−0.1207)Trp; 0.842, 0.862, 0.817, 0.832, 0.816, 0.834, 0.809, 0.830, (6.7789)+(−0.0703)Cit+(0.0723)Tyr+(−0.2235)Met+(0.0053)Lys+(−0.1210)Trp; 0.842, 0.865, 0.811, 0.834, 0.816, 0.826, 0.825, 0.833, (7.3813)+(−0.0034)Gly+(−0.0679)Cit+(0.0672)Tyr+(0.0038)Val+(−0.1928)Met+(−0.1240)Trp; 0.842, 0.862, 0.806, 0.835, 0.817, 0.818, 0.840, 0.834, (8.0200)+(−0.0687)Asn+(−0.0050)Gly+(−0.0581)Cit+(0.0458)Tyr+(−0.1260)Trp; 0.841, 0.863, 0.832, 0.828, 0.806, 0.842, 0.807, 0.829, (6.4594)+(−0.0855)Cit+(0.0670)Tyr+(−0.2087)Met+(0.0174)Orn+(0.0076)Leu+(−0.1227)Trp; 0.841, 0.864, 0.817, 0.837, 0.822, 0.844, 0.813, 0.836, (7.2172)+(−0.0013)Ala+(−0.0653)Cit+(−0.0044)Arg+(0.0722)Tyr+(−0.1864)Met+(−0.1143)Trp

List (1) of Linear Discriminants Searched in Example 6

The linear discriminants searched in Example 6 above are listed below. Before each equation, "the value of ROC_AUC for the pancreatic cancer group and the colorectal cancer group with validation", "the value of ROC_AUC for the pancreatic cancer group and the colorectal cancer group without validation", "the value of ROC_AUC for the pancreatic cancer group and the healthy group", "the value of ROC_AUC for the pancreatic cancer group and the other cancers group", "the value of ROC_AUC for the pancreatic cancer group and the lung cancer group", "the value of ROC_AUC for the pancreatic cancer group and the prostatic cancer group", "the value of ROC_AUC for the pancreatic cancer group and the breast cancer group", and "the average value of the value of ROC_AUC for the pancreatic cancer group and the lung cancer group, the value of ROC_AUC for the pancreatic cancer group and the colorectal cancer group, the value of ROC_AUC for the pancreatic cancer group and the prostatic cancer group, and the value of ROC_AUC for the pancreatic cancer group and the breast cancer group" obtained for the equation are additionally listed.

0.862, 0.876, 0.836, 0.862, 0.854, 0.866, 0.850, 0.862, (6.7413)+(−0.0941)Asn+(0.0093)Gln+(−0.0666)Cit+(0.0561)Tyr+(−0.1268)Met+(−0.1224)Trp; 0.861, 0.876, 0.840, 0.849, 0.834, 0.843, 0.836, 0.847, (8.2510)+(−0.0469)Asn+(−0.0498)Cit+(0.0525)Tyr+(−0.1388)Met+(0.0356)Phe+(−0.1294)Trp; 0.860, 0.874, 0.859, 0.845, 0.831, 0.848, 0.818, 0.843, (6.9429)+(0.0121)Thr+(−0.0594)Cit+(0.0463)Tyr+(−0.2151)Met+(0.0479)Phe+(−0.1367)Trp; 0.860, 0.871, 0.841, 0.839, 0.820, 0.854, 0.814, 0.840, (8.8283)+(−0.0615)Asn+(−0.0708)Cit+(0.0534)Tyr+(−0.1019)Met+(0.0231)Orn+(−0.1179)Trp; 0.858, 0.871, 0.842, 0.845, 0.832, 0.840, 0.828, 0.843, (7.2291)+(−0.0552)Cit+(0.0477)Tyr+(−0.1719)Met+(0.0417)Phe+(−0.1318)Trp; 0.857, 0.871, 0.832, 0.840, 0.825, 0.849, 0.808, 0.838, (9.1087)+(−0.0640)Asn+(0.0112)Thr+(−0.0561)Cit+(0.0564)Tyr+(−0.1303)Met+(−0.1204)Trp; 0.857, 0.873, 0.836, 0.849, 0.841, 0.843, 0.829, 0.846, (7.6157)+(−0.0525)Cit+(−0.0057)Pro+(0.0502)Tyr+(−0.1580)Met+(0.0417)Phe+(−0.1349)Trp; 0.857, 0.875, 0.820, 0.865, 0.865, 0.868, 0.838, 0.862, (7.2197)+(−0.1137)Asn+(0.0090)Gln+(−0.0613)Cit+(−0.0095)Pro+(0.0452)Tyr+(−0.1360)Trp; 0.856, 0.874, 0.857, 0.857, 0.853, 0.851, 0.841, 0.855, (4.7009)+(0.0070)Gln+(−0.0685)Cit+(0.0441)Tyr+(−0.2171)Met+(0.0506)Phe+(−0.1384)Trp; 0.856, 0.872, 0.845, 0.853, 0.841, 0.857, 0.843, 0.853, (7.5089)+(−0.0029)Ala+(−0.0544)Cit+(0.0496)Tyr+(−0.1581)Met+(0.0411)Phe+(−0.1274)Trp; 0.856, 0.870, 0.861, 0.849, 0.837, 0.854, 0.831, 0.848, (6.2989)+(0.0102)Ser+(−0.0563)Cit+(0.0477)Tyr+(−0.1949)Met+(0.0483)Phe+(−0.1330)Trp; 0.855, 0.871, 0.852, 0.843, 0.828, 0.848, 0.821, 0.842, (7.0492)+(−0.0679)Cit+(0.0457)Tyr+(−0.1714)Met+(0.0151)Orn+(0.0379)Phe+(−0.1306)Trp; 0.855, 0.872, 0.842, 0.846, 0.835, 0.843, 0.825, 0.844, (7.3230)+(−0.0543)Cit+(0.0474)Tyr+(−0.1681)Met+

(−0.0034)Leu+(0.0436)Phe+(−0.1303)Trp; 0.855, 0.871, 0.843, 0.844, 0.831, 0.840, 0.828, 0.842, (7.1567)+(−0.0553)Cit+(0.0479)Tyr+(−0.1754)Met+ (0.0010)Lys+(0.0418)Phe+(−0.1326)Trp; 0.855, 0.867, 0.818, 0.840, 0.826, 0.842, 0.821, 0.839, (9.1261)+ (−0.0569)Asn+(−0.0525)Cit+(0.0565)Tyr+(−0.0999) Met+(−0.1178)Trp; 0.855, 0.872, 0.828, 0.855, 0.847, 0.847, 0.848, 0.853, (6.5246)+(−0.0045)Gly+(0.0065) Gln+(−0.0666)Cit+(0.0437)Tyr+(−0.1509)Met+ (−0.1216)Trp; 0.854, 0.869, 0.836, 0.843, 0.828, 0.857, 0.821, 0.844, (8.5671)+(0.0088)Ser+(−0.0642)Asn+ (−0.0532)Cit+(0.0577)Tyr+(−0.1104)Met+(−0.1169) Trp; 0.854, 0.868, 0.819, 0.841, 0.825, 0.842, 0.822, 0.840, (8.9561)+(−0.0599)Asn+(−0.0525)Cit+(0.0575) Tyr+(−0.1093)Met+(0.0031)Lys+(−0.1203)Trp; 0.854, 0.870, 0.831, 0.839, 0.820, 0.832, 0.833, 0.839, (9.2964)+(−0.0799)Asn+(−0.0043)Gly+(−0.0645)Cit+ (0.0360)Tyr+(0.0235)Orn+(−0.1248)Trp; 0.854, 0.867, 0.822, 0.847, 0.835, 0.854, 0.833, 0.847, (9.2762)+ (−0.0536)Asn+(−0.0023)Ala+(−0.0523)Cit+(0.0577) Tyr+(−0.0913)Met+(−0.1145)Trp; 0.853, 0.868, 0.819, 0.840, 0.825, 0.843, 0.822, 0.839, (9.0817)+(−0.0567) Asn+(−0.0527)Cit+(0.0566)Tyr+(−0.1018)Met+ (0.0010)Leu+(−0.1185)Trp; 0.853, 0.871, 0.841, 0.846, 0.834, 0.838, 0.835, 0.844, (7.4809)+(−0.0015)Gly+ (−0.0531)Cit+(0.0461)Tyr+(−0.1652)Met+(0.0405) Phe+(−0.1314)Trp; 0.853, 0.868, 0.830, 0.840, 0.820, 0.846, 0.833, 0.842, (8.7118)+(−0.0562)Asn+ (−0.0553)Cit+(0.0576)Tyr+(−0.1194)Met+(0.0147) Ile+(−0.1189)Trp; 0.853, 0.873, 0.821, 0.863, 0.857, 0.847, 0.870, 0.862, (7.5590)+(−0.1142)Asn+ (−0.0066)Gly+(0.0091)Gln+(−0.0565)Cit+(0.0337) Tyr+(−0.1305)Trp; 0.853, 0.864, 0.832, 0.834, 0.821, 0.846, 0.796, 0.832, (7.9167)+(0.0081)Thr+(−0.0631) Cit+(0.0509)Tyr+(−0.1581)Met+(−0.1203)Trp; 0.853, 0.867, 0.818, 0.840, 0.826, 0.843, 0.821, 0.839, (9.1439)+(−0.0569)Asn+(−0.0523)Cit+(0.0566)Tyr+ (−0.0002)Val+(−0.0998)Met+(−0.1175)Trp; 0.853, 0.869, 0.857, 0.868, 0.879, 0.860, 0.841, 0.863, (5.6045)+(−0.0728)Asn+(0.0103)Gln+(−0.0613)Cit+ (−0.1429)Met+(0.0505)Phe+(−0.1170)Trp; 0.853, 0.868, 0.834, 0.857, 0.851, 0.866, 0.842, 0.857, (6.3677)+(0.0059)Gln+(−0.0034)Ala+(−0.0708)Cit+ (0.0512)Tyr+(−0.1486)Met+(−0.1166)Trp; 0.853, 0.870, 0.823, 0.854, 0.851, 0.862, 0.823, 0.852, (6.3261)+(0.0066)Gln+(−0.0697)Cit+(−0.0076)Pro+ (0.0521)Tyr+(−0.1493)Met+(−0.1260)Trp; 0.852, 0.870, 0.828, 0.858, 0.855, 0.860, 0.840, 0.856, (7.1920)+(−0.1090)Asn+(0.0084)Gln+(−0.0643)Cit+ (0.0397)Tyr+(−0.0067)Lys+(−0.1252)Trp; 0.852, 0.872, 0.841, 0.859, 0.855, 0.855, 0.845, 0.857, (6.6480)+(−0.1169)Asn+(0.0077)Gln+(−0.0620)Cit+ (0.0359)Tyr+(0.0126)Phe+(−0.1367)Trp; 0.852, 0.869, 0.827, 0.857, 0.857, 0.858, 0.833, 0.854, (7.2409)+ (−0.1157)Asn+(0.0077)Gln+(−0.0619)Cit+(0.0405) Tyr+(−0.0060)Leu+(−0.1268)Trp; 0.852, 0.868, 0.850, 0.843, 0.826, 0.842, 0.836, 0.843, (6.9305)+(−0.0575) Cit+(0.0488)Tyr+(−0.1861)Met+(0.0121)Ile+(0.0401) Phe+(−0.1322)Trp; 0.852, 0.868, 0.834, 0.865, 0.864, 0.872, 0.857, 0.865, (7.2186)+(−0.1085)Asn+(0.0078) Gln+(−0.0040)Ala+(−0.0631)Cit+(0.0432)Tyr+ (−0.1247)Trp; 0.852, 0.864, 0.838, 0.833, 0.816, 0.848, 0.803, 0.833, (7.6916)+(−0.0762)Cit+(0.0484)Tyr+ (−0.1372)Met+(0.0201)Orn+(−0.1184)Trp; 0.852, 0.866, 0.834, 0.848, 0.840, 0.855, 0.825, 0.846, (6.1119)+(0.0057)Gln+(−0.0714)Cit+(0.0491)Tyr+ (−0.1632)Met+(−0.1214)Trp; 0.852, 0.868, 0.813, 0.843, 0.832, 0.843, 0.819, 0.841, (9.4226)+(−0.0544) Asn+(−0.0504)Cit+(−0.0051)Pro+(0.0585)Tyr+ (−0.0890)Met+(−0.1206)Trp; 0.852, 0.869, 0.832, 0.855, 0.851, 0.853, 0.839, 0.853, (6.9872)+(−0.1169) Asn+(0.0077)Gln+(−0.0630)Cit+(0.0393)Tyr+ (−0.1315)Trp; 0.852, 0.870, 0.828, 0.857, 0.854, 0.853, 0.842, 0.855, (6.9009)+(−0.1142)Asn+(0.0081)Gln+ (−0.0036)Thr+(−0.0626)Cit+(0.0405)Tyr+(−0.1301) Trp; 0.852, 0.868, 0.817, 0.842, 0.827, 0.839, 0.832, 0.842, (9.4049)+(−0.0556)Asn+(−0.0020)Gly+ (−0.0498)Cit+(0.0541)Tyr+(−0.0933)Met+(−0.1177) Trp; 0.852, 0.870, 0.844, 0.846, 0.836, 0.844, 0.828, 0.844, (7.3607)+(−0.0531)Cit+(0.0482)Tyr+(−0.0022) Val+(−0.1726)Met+(0.0432)Phe+(−0.1290)Trp; 0.851, 0.863, 0.830, 0.836, 0.822, 0.846, 0.807, 0.835, (7.6885)+(0.0043)Ser+(−0.0606)Cit+(0.0517)Tyr+ (−0.1403)Met+(−0.1180)Trp; 0.851, 0.866, 0.842, 0.843, 0.828, 0.862, 0.822, 0.845, (7.9827)+(−0.0033) Ala+(−0.0760)Cit+(0.0503)Tyr+(−0.1224)Met+ (0.0209)Orn+(−0.1137)Trp; 0.851, 0.870, 0.830, 0.867, 0.871, 0.842, 0.866, 0.863, (7.2500)+(−0.1025)Asn+ (−0.0076)Gly+(0.0097)Gln+(−0.0528)Cit+(0.0206) Phe+(−0.1235)Trp; 0.851, 0.869, 0.844, 0.845, 0.834, 0.860, 0.815, 0.845, (6.6208)+(0.0052)Gln+(−0.0832) Cit+(0.0469)Tyr+(−0.1637)Met+(0.0157)Orn+ (−0.1212)Trp; 0.851, 0.867, 0.829, 0.838, 0.826, 0.842, 0.806, 0.836, (9.1413)+(−0.0785)Asn+(−0.0693)Cit+ (−0.0081)Pro+(0.0443)Tyr+(0.0264)Orn+(−0.1291) Trp; 0.851, 0.865, 0.839, 0.835, 0.818, 0.838, 0.812, 0.833, (8.6994)+(−0.0857)Asn+(−0.0692)Cit+(0.0394) Tyr+(0.0222)Orn+(−0.1261)Trp; 0.851, 0.867, 0.830, 0.840, 0.826, 0.839, 0.820, 0.838, (8.4478)+(−0.0037) Gly+(0.0101)Thr+(−0.0586)Cit+(0.0465)Tyr+ (−0.1508)Met+(−0.1206)Trp; 0.851, 0.865, 0.844, 0.834, 0.817, 0.855, 0.795, 0.833, (7.6431)+(0.0061) Thr+(−0.0770)Cit+(0.0483)Tyr+(−0.1555)Met+ (0.0180)Orn+(−0.1199)Trp; 0.851, 0.866, 0.824, 0.837, 0.829, 0.849, 0.790, 0.834, (8.3241)+(0.0093)Thr+ (−0.0606)Cit+(−0.0063)Pro+(0.0535)Tyr+(−0.1467) Met+(−0.1240)Trp; 0.851, 0.867, 0.830, 0.837, 0.824, 0.852, 0.798, 0.835, (8.0977)+(−0.0759)Cit+(−0.0069) Pro+(0.0508)Tyr+(−0.1211)Met+(0.0237)Orn+ (−0.1221)Trp; 0.851, 0.870, 0.825, 0.856, 0.853, 0.852, 0.841, 0.854, (7.1163)+(−0.0039)Ser+(−0.1149)Asn+ (0.0081)Gln+(−0.0635)Cit+(0.0392)Tyr+(−0.1319) Trp; 0.851, 0.861, 0.815, 0.834, 0.822, 0.829, 0.814, 0.831, (8.9887)+(−0.0809)Asn+(−0.0516)Cit+(0.0427) Tyr+(−0.1259)Trp; 0.851, 0.866, 0.843, 0.846, 0.827, 0.859, 0.848, 0.850, (7.8294)+(−0.0040)Ala+(−0.0625) Cit+(0.0555)Tyr+(−0.1420)Met+(0.0208)Ile+ (−0.1141)Trp; 0.850, 0.868, 0.845, 0.860, 0.862, 0.842, 0.851, 0.856, (5.1235)+(−0.0933)Asn+(0.0077)Gln+ (0.0473)Tyr+(−0.1702)Met+(0.0469)Phe+(−0.1384) Trp; 0.850, 0.866, 0.837, 0.847, 0.838, 0.853, 0.827, 0.846, (5.9727)+(0.0058)Gln+(−0.0721)Cit+(0.0493) Tyr+(−0.1686)Met+(0.0031)Leu+(−0.1234)Trp; 0.850, 0.866, 0.832, 0.834, 0.820, 0.838, 0.801, 0.831, (8.9450)+(−0.0838)Asn+(−0.0698)Cit+(0.0401)Tyr+ (0.0251)Orn+(−0.0095)Ile+(−0.1244)Trp; 0.850, 0.867, 0.839, 0.836, 0.819, 0.845, 0.808, 0.835, (9.0091)+(−0.0761)Asn+(−0.0727)Cit+(0.0394)Tyr+ (0.0265)Orn+(−0.0063)Lys+(−0.1198)Trp; 0.850, 0.866, 0.834, 0.848, 0.840, 0.856, 0.825, 0.847, (6.1246)+(0.0057)Gln+(−0.0713)Cit+(0.0492)Tyr+ (−0.0002)Val+(−0.1632)Met+(−0.1211)Trp; 0.850, 0.862, 0.824, 0.834, 0.820, 0.840, 0.811, 0.833, (7.9490)+(−0.0602)Cit+(0.0516)Tyr+(−0.1365)Met+ (0.0020)Leu+(−0.1197)Trp; 0.850, 0.865, 0.839, 0.834, 0.817, 0.853, 0.802, 0.834, (7.8845)+(−0.0776)Cit+

(0.0473)Tyr+(−0.1264)Met+(0.0224)Orn+(−0.0032) Lys+(−0.1160)Trp; 0.850, 0.867, 0.834, 0.837, 0.819, 0.843, 0.820, 0.837, (8.1249)+(−0.0030)Gly+ (−0.0727)Cit+(0.0448)Tyr+(−0.1265)Met+(0.0210) Orn+(−0.1183)Trp; 0.850, 0.862, 0.823, 0.835, 0.822, 0.841, 0.811, 0.834, (8.0278)+(−0.0598)Cit+(0.0515) Tyr+(−0.1332)Met+(−0.1184)Trp; 0.850, 0.870, 0.826, 0.856, 0.855, 0.850, 0.833, 0.852, (6.8089)+(−0.1125) Asn+(0.0086)Gln+(−0.0566)Cit+(−0.0112)Arg+ (0.0406)Tyr+(−0.1280)Trp; 0.850, 0.868, 0.832, 0.862, 0.863, 0.852, 0.855, 0.860, (7.7324)+(−0.1031)Asn+ (−0.0079)Gly+(0.0091)Gln+(−0.0700)Cit+(0.0213) Orn+(−0.1133)Trp; 0.850, 0.867, 0.793, 0.863, 0.866, 0.833, 0.870, 0.859, (7.7024)+(−0.1161)Asn+ (−0.0081)Gly+(0.0088)Gln+(−0.0095)Pro+(0.0367) Tyr+(−0.1345)Trp; 0.850, 0.867, 0.839, 0.847, 0.838, 0.857, 0.820, 0.846, (6.1803)+(0.0054)Gln+(0.0040) Thr+(−0.0723)Cit+(0.0490)Tyr+(−0.1736)Met+ (−0.1222)Trp; 0.850, 0.866, 0.845, 0.835, 0.819, 0.854, 0.802, 0.835, (7.3709)+(0.0041)Ser+(−0.0769)Cit+ (0.0486)Tyr+(−0.1440)Met+(0.0200)Orn+(−0.1180) Trp; 0.850, 0.870, 0.843, 0.853, 0.846, 0.859, 0.833, 0.852, (6.8958)+(−0.1183)Asn+(0.0072)Gln+ (−0.0760)Cit+(0.0370)Tyr+(0.0173)Orn+(−0.1312) Trp; 0.850, 0.863, 0.814, 0.838, 0.828, 0.840, 0.809, 0.835, (8.4140)+(−0.0571)Cit+(−0.0057)Pro+(0.0539) Tyr+(−0.1193)Met+(−0.1214)Trp; 0.850, 0.870, 0.848, 0.846, 0.830, 0.849, 0.833, 0.845, (7.6348)+(−0.0196) His+(−0.0494)Cit+(0.0488)Tyr+(−0.1613)Met+ (0.0422)Phe+(−0.1223)Trp; 0.850, 0.864, 0.832, 0.838, 0.819, 0.838, 0.837, 0.839, (7.9697)+(−0.0022)Gly+ (−0.0592)Cit+(0.0500)Tyr+(−0.1438)Met+(0.0145) Ile+(−0.1193)Trp; 0.850, 0.868, 0.875, 0.859, 0.853, 0.858, 0.859, 0.860, (4.5131)+(0.0067)Gln+(−0.0464) His+(0.0415)Tyr+(−0.2036)Met+(0.0584)Phe+(− 0.1196)Trp; 0.850, 0.863, 0.825, 0.844, 0.833, 0.850, 0.829, 0.844, (8.3132)+(−0.0031)Ala+(−0.0590)Cit+ (0.0534)Tyr+(−0.1191)Met+(−0.1139)Trp; 0.850, 0.867, 0.847, 0.848, 0.836, 0.855, 0.836, 0.849, (5.6910)+(0.0057)Gln+(−0.0742)Cit+(0.0503)Tyr+ (−0.1833)Met+(0.0155)Ile+(−0.1225)Trp; 0.849, 0.865, 0.838, 0.833, 0.816, 0.849, 0.802, 0.833, (7.7061)+(−0.0762)Cit+(0.0483)Tyr+(−0.1365)Met+ (0.0203)Orn+(−0.0004)Leu+(−0.1182)Trp; 0.849, 0.865, 0.817, 0.864, 0.869, 0.846, 0.860, 0.860, (7.8536)+(−0.1003)Asn+(−0.0078)Gly+(0.0098)Gln+ (−0.0540)Cit+(−0.1119)Trp; 0.849, 0.867, 0.828, 0.855, 0.854, 0.853, 0.834, 0.852, (7.1131)+(−0.1160) Asn+(0.0078)Gln+(−0.0623)Cit+(0.0398)Tyr+ (−0.0050)Ile+(−0.1306)Trp; 0.849, 0.864, 0.834, 0.834, 0.821, 0.849, 0.795, 0.832, (7.7842)+(0.0018) Ser+(0.0075)Thr+(−0.0632)Cit+(0.0510)Tyr+ (−0.1594)Met+(−0.1200)Trp; 0.849, 0.865, 0.834, 0.843, 0.832, 0.858, 0.815, 0.843, (8.2047)+(0.0082) Thr+(−0.0031)Ala+(−0.0623)Cit+(0.0528)Tyr+ (−0.1442)Met+(−0.1158)Trp; 0.849, 0.864, 0.816, 0.837, 0.825, 0.839, 0.811, 0.835, (8.3035)+(−0.0577) Cit+(−0.0058)Pro+(0.0541)Tyr+(−0.1240)Met+ (0.0031)Leu+(−0.1235)Trp; 0.849, 0.866, 0.842, 0.846, 0.831, 0.859, 0.832, 0.847, (8.9582)+(−0.0769)Asn+ (−0.0038)Ala+(−0.0696)Cit+(0.0432)Tyr+(0.0230) Orn+(−0.1195)Trp; 0.849, 0.863, 0.835, 0.835, 0.816, 0.844, 0.824, 0.836, (7.6049)+(−0.0626)Cit+(0.0526) Tyr+(−0.1533)Met+(0.0155)Ile+(−0.1195)Trp; 0.849, 0.866, 0.820, 0.840, 0.825, 0.842, 0.825, 0.840, (9.1048)+(−0.0593)Asn+(−0.0567)Cit+(0.0059)Arg+ (0.0570)Tyr+(−0.1096)Met+(−0.1193)Trp; 0.849, 0.864, 0.832, 0.834, 0.821, 0.847, 0.795, 0.832, (7.9340)+(0.0081)Thr+(−0.0629)Cit+(0.0510)Tyr+(− 0.0002)Val+(−0.1580)Met+(−0.1199)Trp; 0.849, 0.868, 0.832, 0.856, 0.854, 0.856, 0.839, 0.854, (7.0675)+(−0.1170)Asn+(0.0077)Gln+(−0.0621)Cit+ (0.0397)Tyr+(−0.0011)Val+(−0.1298)Trp; 0.849, 0.865, 0.837, 0.835, 0.819, 0.852, 0.804, 0.835, (7.7848)+(−0.0756)Cit+(0.0487)Tyr+(−0.0014)Val+ (−0.1369)Met+(0.0208)Orn+(−0.1163)Trp; 0.849, 0.865, 0.830, 0.839, 0.823, 0.844, 0.825, 0.839, (7.9489)+(−0.0602)Cit+(−0.0065)Pro+(0.0557)Tyr+ (−0.1420)Met+(0.0190)Ile+(−0.1232)Trp; 0.849, 0.865, 0.830, 0.847, 0.840, 0.852, 0.825, 0.846, (6.2111)+(−0.0027)Ser+(0.0061)Gln+(−0.0716)Cit+ (0.0489)Tyr+(−0.1605)Met+(−0.1218)Trp; 0.849, 0.869, 0.843, 0.852, 0.842, 0.870, 0.833, 0.853, (6.3176)+(0.0071)Gln+(−0.0309)His+(−0.0651)Cit+ (0.0504)Tyr+(−0.1529)Met+(−0.1069)Trp; 0.849, 0.864, 0.832, 0.834, 0.821, 0.845, 0.795, 0.831, (7.9243)+(0.0083)Thr+(−0.0624)Cit+(−0.0009)Arg+ (0.0508)Tyr+(−0.1570)Met+(−0.1201)Trp; 0.849, 0.864, 0.827, 0.844, 0.832, 0.850, 0.828, 0.843, (8.2323)+(−0.0032)Ala+(−0.0600)Cit+(0.0531)Tyr+ (0.0013)Val+(−0.1188)Met+(−0.1157)Trp; 0.849, 0.862, 0.823, 0.835, 0.822, 0.842, 0.811, 0.834, (8.0322)+(−0.0597)Cit+(0.0515)Tyr+(−0.0001)Val+ (−0.1332)Met+(−0.1183)Trp; 0.849, 0.864, 0.833, 0.836, 0.820, 0.846, 0.811, 0.835, (7.5334)+(0.0048) Ser+(−0.0612)Cit+(0.0519)Tyr+(−0.1460)Met+ (0.0030)Leu+(−0.1198)Trp; 0.849, 0.865, 0.845, 0.836, 0.820, 0.843, 0.814, 0.835, (8.4285)+(0.0042)Ser+ (−0.0903)Asn+(−0.0695)Cit+(0.0393)Tyr+(0.0222) Orn+(−0.1261)Trp; 0.849, 0.868, 0.844, 0.844, 0.831, 0.843, 0.830, 0.843, (7.1352)+(−0.0595)Cit+(0.0058) Arg+(0.0478)Tyr+(−0.1841)Met+(0.0431)Phe+ (−0.1337)Trp; 0.849, 0.863, 0.830, 0.836, 0.822, 0.846, 0.807, 0.835, (7.6634)+(0.0044)Ser+(−0.0608)Cit+ (0.0516)Tyr+(0.0003)Val+(−0.1405)Met+(−0.1184) Trp; 0.848, 0.863, 0.846, 0.837, 0.816, 0.850, 0.826, 0.839, (7.1469)+(0.0054)Ser+(−0.0638)Cit+(0.0530) Tyr+(−0.1638)Met+(0.0167)Ile+(−0.1191)Trp; 0.848, 0.863, 0.832, 0.845, 0.834, 0.856, 0.827, 0.845, (8.0011)+(0.0039)Ser+(−0.0030)Ala+(−0.0597)Cit+ (0.0535)Tyr+(−0.1258)Met+(−0.1136)Trp; 0.848, 0.864, 0.818, 0.838, 0.824, 0.833, 0.825, 0.837, (8.4155)+(−0.0026)Gly+(−0.0561)Cit+(0.0485)Tyr+ (−0.1238)Met+(−0.1183)Trp

List (2) of Logistic Regression Equations Searched in Example 6

The logistic regression equations searched in Example 6 above are listed below. Before each equation, "the value of ROC_AUC for the pancreatic cancer group and the colorectal cancer group with validation", "the value of ROC_AUC for the pancreatic cancer group and the colorectal cancer group without validation", "the value of ROC_AUC for the pancreatic cancer group and the healthy group", "the value of ROC_AUC for the pancreatic cancer group and the other cancers group", "the value of ROC_AUC for the pancreatic cancer group and the lung cancer group", "the value of ROC_AUC for the pancreatic cancer group and the prostatic cancer group", "the value of ROC_AUC for the pancreatic cancer group and the breast cancer group", and "the average value of the value of ROC_AUC for the pancreatic cancer group and the lung cancer group, the value of ROC_AUC for the pancreatic cancer group and the colorectal cancer group, the value of ROC_AUC for the pancreatic cancer group and the prostatic cancer group, and the value of ROC_AUC for the pancreatic cancer group and the breast cancer group" obtained for the equation are additionally listed.

0.822, 0.849, 0.870, 0.853, 0.863, 0.864, 0.828, 0.851, (4.0457)+(0.0070)Gln+(−0.0515)His+(0.0059)Thr+ (−0.1935)Met+(0.0373)Phe+(−0.0815)Trp; 0.816, 0.846, 0.867, 0.852, 0.860, 0.857, 0.842, 0.851, (3.8120)+(0.0071)Gln+(−0.0493)His+(−0.1898)Met+ (0.0091)Ile+(0.0363)Phe+(−0.0794)Trp; 0.814, 0.843, 0.865, 0.845, 0.845, 0.853, 0.843, 0.846, (3.9326)+ (0.0076)Gln+(−0.0633)His+(−0.1928)Met+(0.0151) Leu+(0.0318)Phe+(−0.0832)Trp; 0.815, 0.845, 0.864, 0.849, 0.857, 0.852, 0.835, 0.847, (3.9733)+(0.0067) Gln+(−0.0552)His+(−0.1915)Met+(0.0066)Lys+ (0.0373)Phe+(−0.0839)Trp; 0.829, 0.856, 0.862, 0.862, 0.873, 0.865, 0.847, 0.860, (4.3532)+(−0.0698)Asn+ (0.0097)Gln+(−0.0451)His+(−0.1329)Met+(0.0325) Phe+(−0.0772)Trp; 0.792, 0.823, 0.861, 0.830, 0.825, 0.849, 0.841, 0.835, (4.3379)+(0.0035)Gln+(−0.0631) His+(−0.0027)Ala+(0.0100)Leu+(0.0235)Phe+ (−0.0977)Trp; 0.816, 0.844, 0.861, 0.844, 0.847, 0.850, 0.834, 0.844, (4.0571)+(0.0071)Gln+(−0.0612)His+ (0.0065)Val+(−0.1772)Met+(0.0336)Phe+(−0.0857) Trp; 0.819, 0.846, 0.860, 0.852, 0.862, 0.857, 0.831, 0.849, (4.0114)+(0.0072)Gln+(−0.0503)His+(0.0005) Ala+(−0.1800)Met+(0.0363)Phe+(−0.0804)Trp; 0.807, 0.836, 0.860, 0.833, 0.833, 0.844, 0.817, 0.833, (5.8122)+(−0.0364)His+(0.0086)Thr+(−0.1719)Met+ (0.0137)Ile+(0.0317)Phe+(−0.0854)Trp; 0.814, 0.843, 0.860, 0.848, 0.851, 0.852, 0.850, 0.849, (4.9199)+ (−0.0928)Asn+(0.0076)Gln+(−0.0574)His+(0.0073) Leu+(0.0163)Phe+(−0.0871)Trp; 0.822, 0.846, 0.859, 0.853, 0.864, 0.860, 0.834, 0.851, (4.0072)+(0.0073) Gln+(−0.0498)His+(−0.1774)Met+(0.0364)Phe+ (−0.0796)Trp; 0.817, 0.844, 0.859, 0.851, 0.858, 0.853, 0.846, 0.850, (4.9719)+(−0.0954)Asn+(0.0074)Gln+ (−0.0522)His+(0.0021)Lys+(0.0185)Phe+(−0.0856) Trp; 0.791, 0.823, 0.859, 0.823, 0.816, 0.837, 0.830, 0.826, (4.3739)+(0.0037)Gln+(−0.0629)His+(−0.0049) Lys+(0.0114)Leu+(0.0215)Phe+(−0.1003)Trp; 0.796, 0.827, 0.859, 0.828, 0.822, 0.845, 0.837, 0.833, (4.3455)+(0.0034)Gln+(−0.0670)His+(−0.0028)Ala+ (0.0077)Val+(0.0250)Phe+(−0.1011)Trp; 0.822, 0.846, 0.858, 0.853, 0.861, 0.855, 0.846, 0.852, (4.9586)+ (−0.0934)Asn+(0.0076)Gln+(−0.0505)His+(0.0188) Phe+(−0.0842)Trp; 0.818, 0.847, 0.858, 0.855, 0.863, 0.861, 0.848, 0.855, (4.9370)+(−0.0916)Asn+(0.0076) Gln+(−0.0496)His+(−0.0008)Ala+(0.0196)Phe+ (−0.0830)Trp; 0.816, 0.845, 0.858, 0.845, 0.846, 0.846, 0.845, 0.845, (4.8767)+(−0.0938)Asn+(0.0075)Gln+ (−0.0609)His+(0.0063)Val+(0.0188)Phe+(−0.0922) Trp; 0.794, 0.827, 0.858, 0.821, 0.812, 0.831, 0.822, 0.823, (4.3702)+(0.0035)Gln+(−0.0660)His+(0.0077) Val+(−0.0042)Lys+(0.0236)Phe+(−0.1043)Trp; 0.797, 0.821, 0.858, 0.819, 0.813, 0.830, 0.826, 0.822, (4.3809)+(0.0030)Gln+(−0.0646)His+(0.0086)Leu+ (0.0219)Phe+(−0.1028)Trp; 0.796, 0.826, 0.857, 0.837, 0.842, 0.853, 0.832, 0.838, (4.3693)+(0.0036)Gln+ (−0.0529)His+(−0.0022)Ala+(−0.0016)Lys+(0.0258) Phe+(−0.0919)Trp; 0.800, 0.826, 0.857, 0.835, 0.839, 0.850, 0.832, 0.836, (4.3693)+(0.0034)Gln+(−0.0543) His+(−0.0023)Ala+(0.0258)Phe+(−0.0931)Trp; 0.799, 0.828, 0.857, 0.828, 0.829, 0.837, 0.818, 0.828, (4.4040)+(0.0033)Gln+(−0.0549)His+(−0.0020)Lys+ (0.0243)Phe+(−0.0964)Trp; 0.803, 0.826, 0.857, 0.826, 0.826, 0.834, 0.819, 0.826, (4.4043)+(0.0030)Gln+ (−0.0567)His+(0.0242)Phe+(−0.0981)Trp; 0.799, 0.825, 0.856, 0.817, 0.806, 0.823, 0.823, 0.819, (4.3613)+(0.0029)Gln+(−0.0684)His+(0.0069)Val+ (0.0236)Phe+(−0.1068)Trp; 0.811, 0.839, 0.856, 0.835, 0.842, 0.848, 0.800, 0.832, (6.0297)+(0.0019)Ser+ (−0.0368)His+(0.0082)Thr+(−0.1534)Met+(0.0322) Phe+(−0.0850)Trp; 0.830, 0.859, 0.856, 0.856, 0.863, 0.866, 0.825, 0.853, (4.6037)+(0.0080)Gln+(−0.0384) His+(−0.0575)Cit+(−0.1601)Met+(0.0318)Phe+ (−0.0822)Trp; 0.818, 0.847, 0.856, 0.854, 0.862, 0.856, 0.843, 0.852, (4.9921)+(−0.0923)Asn+(0.0077)Gln+ (−0.0506)His+(−0.0023)Ile+(0.0190)Phe+(−0.0838) Trp; 0.816, 0.845, 0.855, 0.854, 0.862, 0.856, 0.848, 0.853, (5.0050)+(−0.0914)Asn+(0.0078)Gln+ (−0.0507)His+(−0.0043)Orn+(0.0193)Phe+(−0.0843) Trp; 0.827, 0.856, 0.855, 0.857, 0.863, 0.865, 0.841, 0.856, (5.4374)+(−0.0773)Asn+(0.0079)Gln+ (−0.0403)His+(−0.0527)Cit+(0.0160)Phe+(−0.0886) Trp; 0.795, 0.826, 0.855, 0.818, 0.808, 0.823, 0.820, 0.819, (4.3684)+(0.0029)Gln+(−0.0676)His+(0.0089) Val+(−0.0044)Leu+(0.0245)Phe+(−0.1068)Trp; 0.818, 0.848, 0.855, 0.857, 0.871, 0.856, 0.839, 0.853, (4.1613)+(0.0081)Gln+(−0.0492)His+(−0.1782)Met+ (−0.0128)Orn+(0.0386)Phe+(−0.0807)Trp; 0.807, 0.835, 0.855, 0.825, 0.819, 0.837, 0.815, 0.826, (6.2118)+(−0.0495)His+(0.0098)Thr+(−0.1688)Met+ (0.0149)Leu+(0.0276)Phe+(−0.0903)Trp; 0.829, 0.857, 0.854, 0.848, 0.848, 0.871, 0.814, 0.848, (5.8334)+(−0.0856)Asn+(0.0070)Gln+(−0.0341)His+ (−0.0759)Cit+(0.0252)Orn+(−0.0832)Trp; 0.835, 0.858, 0.854, 0.846, 0.848, 0.856, 0.808, 0.842, (5.5348)+(−0.0893)Asn+(0.0051)Gln+(−0.0838)Cit+ (0.0263)Orn+(0.0084)Phe+(−0.1077)Trp; 0.800, 0.833, 0.854, 0.840, 0.850, 0.860, 0.818, 0.840, (5.1355)+(0.0055)Gln+(−0.0488)His+(0.0041)Thr+ (−0.1734)Met+(0.0096)Ile+(−0.0642)Trp; 0.817, 0.846, 0.853, 0.852, 0.863, 0.853, 0.834, 0.849, (4.2089)+(−0.0036)Ser+(0.0077)Gln+(−0.0497)His+ (−0.1744)Met+(0.0355)Phe+(−0.0801)Trp; 0.809, 0.836, 0.853, 0.831, 0.835, 0.837, 0.808, 0.829, (5.9667)+(−0.0448)His+(0.0070)Thr+(−0.1730)Met+ (0.0092)Lys+(0.0332)Phe+(−0.0909)Trp; 0.824, 0.848, 0.853, 0.832, 0.830, 0.839, 0.801, 0.829, (5.9620)+ (0.0074)Thr+(−0.0656)Cit+(−0.1745)Met+(0.0231) Ile+(0.0281)Phe+(−0.1031)Trp; 0.800, 0.835, 0.853, 0.833, 0.829, 0.850, 0.826, 0.835, (5.0671)+(0.0062) Gln+(−0.0681)His+(0.0057)Thr+(−0.1904)Met+ (0.0201)Leu+(−0.0719)Trp; 0.814, 0.838, 0.853, 0.834, 0.840, 0.846, 0.801, 0.831, (6.2023)+(−0.0364)His+ (0.0085)Thr+(−0.1512)Met+(0.0316)Phe+(−0.0855) Trp; 0.811, 0.838, 0.853, 0.831, 0.836, 0.838, 0.797, 0.827, (6.1897)+(−0.0376)His+(0.0087)Thr+(0.0010) Ala+(−0.1574)Met+(0.0315)Phe+(−0.0872)Trp; 0.802, 0.832, 0.853, 0.831, 0.832, 0.840, 0.821, 0.831, (5.5437)+(0.0039)Ser+(−0.0337)His+(−0.1517)Met+ (0.0141)Ile+(0.0312)Phe+(−0.0824)Trp; 0.831, 0.858, 0.852, 0.852, 0.845, 0.863, 0.846, 0.853, (4.3912)+ (0.0064)Gln+(−0.0514)His+(0.0516)Tyr+(−0.2316) Met+(0.0226)Phe+(−0.0955)Trp; 0.817, 0.845, 0.852, 0.854, 0.862, 0.854, 0.849, 0.853, (4.8907)+(−0.0922) Asn+(0.0080)Gln+(−0.0490)His+(−0.0038)Thr+ (0.0196)Phe+(−0.0830)Trp; 0.799, 0.831, 0.852, 0.832, 0.827, 0.848, 0.839, 0.836, (4.5889)+(0.0025)Gln+ (−0.0565)His+(−0.0028)Ala+(0.0262)Tyr+(0.0187) Phe+(−0.1029)Trp; 0.820, 0.849, 0.852, 0.857, 0.870, 0.866, 0.836, 0.855, (4.2012)+(0.0079)Gln+(−0.0482) His+(−0.0063)Pro+(−0.1598)Met+(0.0364)Phe+ (−0.0837)Trp; 0.791, 0.823, 0.852, 0.823, 0.817, 0.829, 0.835, 0.826, (4.2681)+(0.0038)Gln+(−0.0624)His+ (−0.0062)Thr+(0.0088)Leu+(0.0231)Phe+(−0.1003) Trp; 0.787, 0.819, 0.852, 0.821, 0.818, 0.828, 0.828, 0.823, (4.5779)+(0.0037)Gln+(−0.0648)His+(−0.0121)

Orn+(0.0092)Leu+(0.0229)Phe+(−0.1034)Trp; 0.816, 0.842, 0.851, 0.837, 0.842, 0.846, 0.807, 0.834, (6.6822)+(−0.0302)Asn+(−0.0328)His+(0.0090)Thr+(−0.1260)Met+(0.0291)Phe+(−0.0845)Trp; 0.795, 0.827, 0.851, 0.838, 0.844, 0.849, 0.840, 0.840, (4.2848)+(0.0041)Gln+(−0.0522)His+(−0.0055)Thr+(−0.0021)Ala+(0.0265)Phe+(−0.0911)Trp; 0.817, 0.845, 0.851, 0.853, 0.861, 0.853, 0.847, 0.852, (5.1736)+(−0.0042)Ser+(−0.0910)Asn+(0.0080)Gln+(−0.0507)His+(0.0180)Phe+(−0.0846)Trp; 0.809, 0.842, 0.851, 0.826, 0.820, 0.849, 0.792, 0.826, (5.1495)+(0.0033)Gln+(−0.0404)His+(−0.0766)Cit+(0.0195)Orn+(0.0172)Phe+(−0.1043)Trp; 0.808, 0.836, 0.851, 0.824, 0.821, 0.831, 0.805, 0.823, (6.2140)+(−0.0491)His+(0.0083)Thr+(0.0071)Val+(−0.1516)Met+(0.0289)Phe+(−0.0928)Trp; 0.834, 0.857, 0.851, 0.850, 0.853, 0.869, 0.814, 0.848, (5.7897)+(−0.0886)Asn+(0.0053)Gln+(−0.0015)Ala+(−0.0858)Cit+(0.0278)Orn+(−0.0973)Trp; 0.823, 0.851, 0.851, 0.851, 0.851, 0.863, 0.842, 0.852, (5.7685)+(−0.0813)Asn+(0.0080)Gln+(−0.0472)His+(−0.0543)Cit+(0.0100)Leu+(−0.0856)Trp; 0.793, 0.826, 0.851, 0.813, 0.794, 0.825, 0.829, 0.818, (4.5317)+(0.0021)Gln+(−0.0669)His+(0.0242)Tyr+(0.0088)Leu+(0.0158)Phe+(−0.1140)Trp; 0.826, 0.854, 0.851, 0.855, 0.857, 0.868, 0.840, 0.855, (5.8304)+(−0.0850)Asn+(0.0077)Gln+(−0.0377)His+(−0.0555)Cit+(0.0078)Ile+(−0.0813)Trp; 0.792, 0.825, 0.850, 0.837, 0.845, 0.847, 0.833, 0.837, (4.5443)+(0.0041)Gln+(−0.0540)His+(−0.0022)Ala+(−0.0112)Orn+(0.0271)Phe+(−0.0938)Trp; 0.797, 0.825, 0.850, 0.834, 0.843, 0.847, 0.821, 0.834, (4.5421)+(0.0038)Gln+(−0.0550)His+(−0.0018)Ala+(−0.0085)Ile+(0.0260)Phe+(−0.0924)Trp; 0.837, 0.858, 0.850, 0.848, 0.850, 0.866, 0.807, 0.845, (5.8033)+(−0.0866)Asn+(0.0058)Gln+(−0.0883)Cit+(0.0298)Orn+(−0.0049)Lys+(−0.0965)Trp; 0.805, 0.837, 0.850, 0.843, 0.846, 0.850, 0.841, 0.843, (5.3970)+(−0.0980)Asn+(0.0075)Gln+(−0.0577)His+(0.0004)Lys+(0.0102)Leu+(−0.0802)Trp; 0.811, 0.837, 0.850, 0.842, 0.845, 0.850, 0.841, 0.843, (5.3938)+(−0.0977)Asn+(0.0076)Gln+(−0.0576)His+(0.0103)Leu+(−0.0800)Trp; 0.792, 0.823, 0.850, 0.819, 0.813, 0.821, 0.824, 0.820, (4.5738)+(0.0037)Gln+(−0.0693)His+(0.0078)Val+(−0.0139)Orn+(0.0252)Phe+(−0.1085)Trp; 0.827, 0.854, 0.850, 0.846, 0.851, 0.845, 0.815, 0.841, (4.1430)+(0.0054)Gln+(−0.0702)Cit+(−0.1900)Met+(0.0191)Ile+(0.0316)Phe+(−0.1007)Trp; 0.817, 0.848, 0.850, 0.852, 0.867, 0.860, 0.818, 0.848, (4.1776)+(0.0086)Gln+(−0.0460)His+(−0.0196)Arg+(−0.1497)Met+(0.0332)Phe+(−0.0773)Trp; 0.798, 0.825, 0.849, 0.829, 0.832, 0.835, 0.827, 0.830, (4.3007)+(0.0038)Gln+(−0.0543)His+(−0.0060)Thr+(0.0253)Phe+(−0.0955)Trp; 0.807, 0.837, 0.849, 0.843, 0.846, 0.850, 0.844, 0.844, (5.3904)+(−0.0965)Asn+(0.0076)Gln+(−0.0573)His+(−0.0006)Ala+(0.0108)Leu+(−0.0791)Trp; 0.799, 0.829, 0.849, 0.823, 0.816, 0.833, 0.824, 0.825, (4.5722)+(0.0024)Gln+(−0.0569)His+(0.0239)Tyr+(−0.0022)Lys+(0.0180)Phe+(−0.1069)Trp; 0.794, 0.825, 0.849, 0.820, 0.811, 0.825, 0.831, 0.823, (4.2729)+(0.0037)Gln+(−0.0658)His+(−0.0059)Thr+(0.0068)Val+(0.0244)Phe+(−0.1039)Trp; 0.796, 0.828, 0.849, 0.812, 0.793, 0.820, 0.823, 0.816, (4.5205)+(0.0021)Gln+(−0.0693)His+(0.0224)Tyr+(0.0063)Val+(0.0176)Phe+(−0.1157)Trp; 0.794, 0.825, 0.849, 0.830, 0.833, 0.836, 0.827, 0.830, (4.3037)+(0.0038)Gln+(−0.0538)His+(−0.0059)Thr+(−0.0005)Lys+(0.0253)Phe+(−0.0951)Trp; 0.836, 0.856, 0.849, 0.844, 0.847, 0.859, 0.804, 0.841, (5.7897)+(−0.0922)Asn+(0.0052)Gln+(−0.0857)Cit+(0.0278)Orn+(−0.1020)Trp; 0.801, 0.828, 0.849, 0.821, 0.812, 0.829, 0.823, 0.823, (4.5646)+(0.0021)Gln+(−0.0589)His+(0.0239)Tyr+(0.0181)Phe+(−0.1088)Trp; 0.810, 0.842, 0.849, 0.847, 0.848, 0.857, 0.844, 0.848, (5.2333)+(−0.0746)Asn+(0.0091)Gln+(−0.0597)His+(−0.1225)Met+(0.0171)Leu+(−0.0685)Trp; 0.811, 0.842, 0.849, 0.830, 0.840, 0.839, 0.776, 0.824, (6.6704)+(−0.0318)His+(0.0119)Thr+(−0.0163)Arg+(−0.1329)Met+(0.0289)Phe+(−0.0854)Trp; 0.803, 0.830, 0.849, 0.827, 0.827, 0.826, 0.823, 0.827, (5.7665)+(−0.0422)His+(−0.1658)Met+(0.0094)Lys+(0.0098)Ile+(0.0318)Phe+(−0.0891)Trp; 0.834, 0.856, 0.849, 0.844, 0.847, 0.859, 0.804, 0.841, (5.7989)+(−0.0921)Asn+(0.0052)Gln+(−0.0858)Cit+(0.0279)Orn+(−0.0006)Ile+(−0.1018)Trp; 0.806, 0.838, 0.849, 0.827, 0.821, 0.842, 0.809, 0.827, (5.1326)+(0.0042)Gln+(−0.0505)His+(−0.0593)Cit+(0.0075)Leu+(0.0181)Phe+(−0.1065)Trp; 0.832, 0.856, 0.849, 0.845, 0.847, 0.859, 0.804, 0.842, (5.8035)+(−0.0922)Asn+(0.0052)Gln+(−0.0857)Cit+(0.0279)Orn+(−0.0007)Leu+(−0.1011)Trp; 0.796, 0.832, 0.848, 0.839, 0.847, 0.854, 0.822, 0.839, (5.1013)+(0.0054)Gln+(−0.0516)His+(−0.1702)Met+(0.0048)Lys+(0.0079)Ile+(−0.0660)Trp; 0.791, 0.823, 0.848, 0.829, 0.835, 0.834, 0.820, 0.828, (4.5886)+(0.0039)Gln+(−0.0552)His+(−0.0113)Orn+(−0.0014)Lys+(0.0255)Phe+(−0.0973)Trp; 0.811, 0.840, 0.848, 0.835, 0.842, 0.843, 0.801, 0.831, (6.4219)+(−0.0355)His+(0.0092)Thr+(−0.1507)Met+(−0.0066)Orn+(0.0324)Phe+(−0.0865)Trp; 0.823, 0.854, 0.848, 0.849, 0.840, 0.854, 0.855, 0.851, (5.1755)+(−0.1116)Asn+(0.0070)Gln+(−0.0522)His+(0.0366)Tyr+(0.0104)Phe+(−0.0981)Trp; 0.790, 0.817, 0.848, 0.822, 0.816, 0.847, 0.829, 0.828, (4.9852)+(0.0031)Gln+(−0.0632)His+(−0.0023)Ala+(0.0132)Leu+(−0.0876)Trp; 0.812, 0.843, 0.848, 0.843, 0.847, 0.862, 0.818, 0.843, (5.1065)+(0.0045)Gln+(−0.0407)His+(−0.0023)Ala+(−0.0595)Cit+(0.0227)Phe+(−0.0981)Trp; 0.794, 0.823, 0.848, 0.827, 0.833, 0.831, 0.819, 0.826, (4.5935)+(0.0037)Gln+(−0.0564)His+(−0.0115)Orn+(0.0254)Phe+(−0.0985)Trp; 0.807, 0.838, 0.848, 0.844, 0.858, 0.833, 0.827, 0.839, (3.3646)+(0.0045)Gln+(−0.0045)Val+(−0.2143)Met+(0.0181)Ile+(0.0375)Phe+(−0.0948)Trp; 0.797, 0.827, 0.848, 0.820, 0.814, 0.817, 0.826, 0.821, (4.7359)+(−0.0071)Ser+(0.0039)Gln+(−0.0666)His+(0.0061)Val+(0.0229)Phe+(−0.1070)Trp; 0.828, 0.851, 0.848, 0.835, 0.833, 0.850, 0.795, 0.832, (6.9364)+(−0.0552)Asn+(−0.0016)Ala+(−0.0835)Cit+(0.0294)Orn+(0.0112)Phe+(−0.1032)Trp; 0.806, 0.837, 0.848, 0.843, 0.846, 0.847, 0.844, 0.843, (5.4499)+(−0.0957)Asn+(0.0078)Gln+(−0.0581)His+(−0.0044)Orn+(0.0108)Leu+(−0.0803)Trp; 0.801, 0.830, 0.847, 0.824, 0.820, 0.835, 0.817, 0.825, (5.8651)+(0.0050)Ser+(−0.0458)His+(−0.1451)Met+(0.0143)Leu+(0.0271)Phe+(−0.0868)Trp; 0.812, 0.837, 0.847, 0.837, 0.844, 0.843, 0.813, 0.834, (6.3477)+(0.0051)Ser+(−0.0331)Asn+(−0.0294)His+(−0.1029)Met+(0.0287)Phe+(−0.0814)Trp; 0.827, 0.853, 0.847, 0.846, 0.843, 0.857, 0.832, 0.846, (5.8232)+(−0.0817)Asn+(0.0079)Gln+(−0.0518)His+(−0.0593)Cit+(0.0090)Val+(−0.0901)Trp; 0.814, 0.844, 0.847, 0.854, 0.861, 0.865, 0.846, 0.854, (5.3017)+(−0.0842)Asn+(0.0086)Gln+(−0.0431)His+(−0.1104)Met+(0.0125)Ile+(−0.0628)Trp; 0.805, 0.834, 0.847, 0.824, 0.821, 0.831, 0.808, 0.823, (5.8236)+(0.0053)Ser+(−0.0478)His+(0.0077)Val+(−0.1340)Met+(0.0287)Phe+(−0.0904)Trp; 0.801, 0.833, 0.847, 0.832, 0.834, 0.847, 0.809, 0.831, (5.2756)+(0.0057)Gln+(−0.0645)His+(0.0040)Thr+(0.0085)Val+(−0.1633)Met+(−0.0737)Trp; 0.833, 0.856, 0.847, 0.842, 0.841, 0.854, 0.803, 0.839, (5.7383)+(−0.0931)Asn+(0.0050)Gln+(−0.0875)Cit+(0.0028)Val+(0.0269)Orn+(−0.1075)Trp; 0.800, 0.825, 0.847, 0.826, 0.835, 0.829, 0.803, 0.823, (4.6321)+(0.0036)Gln+(−0.0570)His+(−0.0115)Ile+(0.0249)Phe+(−0.0957)Trp; 0.800, 0.833, 0.847, 0.840, 0.850, 0.858, 0.812, 0.838, (5.3399)+(0.0053)Gln+(−0.0529)His+(0.0033)Thr+(−0.1680)Met+(0.0049)Lys+(−0.0673)Trp; 0.794, 0.816, 0.847, 0.813, 0.806, 0.831, 0.814, 0.817, (4.9732)+(0.0027)Gln+(−0.0645)His+(0.0119)Leu+(−0.0927)Trp

List (2) of Linear Discriminants Searched in Example 6

The linear discriminants searched in Example 6 above are listed below. Before each equation, "the value of ROC_AUC for the pancreatic cancer group and the colorectal cancer group with validation", "the value of ROC_AUC for the pancreatic cancer group and the colorectal cancer group without validation", "the value of ROC_AUC for the pancreatic cancer group and the healthy group", "the value of ROC_AUC for the pancreatic cancer group and the other cancers group", "the value of ROC_AUC for the pancreatic cancer group and the lung cancer group", "the value of ROC_AUC for the pancreatic cancer group and the prostatic cancer group", "the value of ROC_AUC for the pancreatic cancer group and the breast cancer group", and "the average value of the value of ROC_AUC for the pancreatic cancer group and the lung cancer group, the value of ROC_AUC for the pancreatic cancer group and the colorectal cancer group, the value of ROC_AUC for the pancreatic cancer group and the prostatic cancer group, and the value of ROC_AUC for the pancreatic cancer group and the breast cancer group" obtained for the equation are additionally listed.

0.835, 0.856, 0.885, 0.856, 0.862, 0.858, 0.839, 0.853, (4.7750)+(0.0066)Gln+(−0.0466)His+(0.0084)Thr+(−0.1967)Met+(0.0666)Phe+(−0.1057)Trp; 0.830, 0.847, 0.879, 0.841, 0.844, 0.850, 0.811, 0.838, (6.3287)+(0.0082)Ser+(−0.0354)His+(0.0106)Thr+(−0.1818)Met+(0.0636)Phe+(−0.1048)Trp; 0.832, 0.854, 0.879, 0.857, 0.864, 0.857, 0.845, 0.855, (4.5078)+(0.0044)Ser+(0.0068)Gln+(−0.0446)His+(−0.1778)Met+(0.0652)Phe+(−0.1034)Trp; 0.850, 0.868, 0.875, 0.859, 0.853, 0.858, 0.859, 0.860, (4.5131)+(0.0067)Gln+(−0.0464)His+(0.0415)Tyr+(−0.2036)Met+(0.0584)Phe+(−0.1196)Trp; 0.842, 0.861, 0.874, 0.847, 0.836, 0.858, 0.840, 0.849, (5.8514)+(0.0112)Ser+(−0.0351)His+(0.0451)Tyr+(−0.1899)Met+(0.0558)Phe+(−0.1194)Trp; 0.843, 0.861, 0.874, 0.867, 0.877, 0.860, 0.857, 0.864, (5.4146)+(−0.0732)Asn+(0.0098)Gln+(−0.0393)His+(−0.1330)Met+(0.0569)Phe+(−0.1021)Trp; 0.833, 0.852, 0.873, 0.856, 0.864, 0.853, 0.846, 0.854, (4.7041)+(0.0072)Gln+(−0.0445)His+(−0.1723)Met+(0.0010)Ile+(0.0629)Phe+(−0.1036)Trp; 0.832, 0.853, 0.872, 0.856, 0.864, 0.853, 0.846, 0.854, (4.7480)+(0.0073)Gln+(−0.0442)His+(−0.1698)Met+(−0.0005)Lys+(0.0629)Phe+(−0.1034)Trp; 0.832, 0.853, 0.872, 0.856, 0.864, 0.853, 0.845, 0.854, (4.7112)+(0.0073)Gln+(−0.0449)His+(−0.1718)Met+(0.0006)Leu+(0.0627)Phe+(−0.1037)Trp; 0.835, 0.853, 0.872, 0.857, 0.865, 0.854, 0.846, 0.854, (4.7280)+(0.0073)Gln+(−0.0444)His+(−0.1713)Met+(0.0630)Phe+(−0.1036)Trp; 0.832, 0.853, 0.872, 0.857, 0.866, 0.854, 0.846, 0.855, (4.7677)+(0.0072)Gln+(−0.0432)His+(−0.0008)Val+(−0.1718)Met+(0.0634)Phe+(−0.1030)Trp; 0.834, 0.855, 0.871, 0.861, 0.871, 0.850, 0.852, 0.857, (4.7622)+(0.0081)Gln+(−0.0434)His+(−0.1739)Met+(−0.0123)Orn+(0.0662)Phe+(−0.1044)Trp; 0.823, 0.842, 0.871, 0.839, 0.842, 0.846, 0.821, 0.838, (6.1502)+(0.0114)Ser+(−0.0320)His+(−0.1569)Met+(0.0047)Ile+(0.0595)Phe+(−0.1018)Trp; 0.833, 0.852, 0.871, 0.861, 0.870, 0.863, 0.851, 0.859, (4.8549)+(0.0073)Gln+(−0.0426)His+(−0.0016)Ala+(−0.1636)Met+(0.0627)Phe+(−0.1016)Trp; 0.835, 0.857, 0.870, 0.860, 0.870, 0.858, 0.840, 0.856, (4.6757)+(0.0083)Gln+(−0.0434)His+(−0.0124)Arg+(−0.1513)Met+(0.0604)Phe+(−0.1006)Trp; 0.827, 0.846, 0.870, 0.838, 0.841, 0.840, 0.812, 0.835, (6.8948)+(−0.0343)His+(0.0126)Thr+(−0.1757)Met+(0.0036)Ile+(0.0589)Phe+(−0.1054)Trp; 0.826, 0.847, 0.870, 0.842, 0.848, 0.849, 0.814, 0.839, (7.1174)+(−0.0323)His+(0.0125)Thr+(−0.0016)Ala+(−0.1639)Met+(0.0590)Phe+(−0.1035)Trp; 0.844, 0.864, 0.869, 0.860, 0.866, 0.864, 0.833, 0.857, (5.0647)+(0.0091)Gln+(−0.0334)His+(−0.0581)Cit+(−0.1734)Met+(0.0589)Phe+(−0.1056)Trp; 0.829, 0.848, 0.869, 0.838, 0.842, 0.840, 0.807, 0.834, (7.0009)+(−0.0338)His+(0.0125)Thr+(−0.1709)Met+(−0.0004)Leu+(0.0595)Phe+(−0.1054)Trp; 0.826, 0.848, 0.869, 0.838, 0.842, 0.840, 0.807, 0.834, (7.0012)+(−0.0340)His+(0.0126)Thr+(−0.1710)Met+(−0.0001)Lys+(0.0593)Phe+(−0.1054)Trp; 0.831, 0.847, 0.869, 0.838, 0.842, 0.840, 0.807, 0.834, (6.9942)+(−0.0341)His+(0.0126)Thr+(−0.1713)Met+(0.0593)Phe+(−0.1054)Trp; 0.827, 0.847, 0.869, 0.839, 0.844, 0.842, 0.805, 0.835, (7.0613)+(−0.0318)His+(0.0126)Thr+(−0.0016)Val+(−0.1729)Met+(0.0603)Phe+(−0.1044)Trp; 0.829, 0.851, 0.869, 0.838, 0.843, 0.842, 0.796, 0.833, (7.1912)+(−0.0326)His+(0.0151)Thr+(−0.0095)Arg+(−0.1597)Met+(0.0574)Phe+(−0.1037)Trp; 0.824, 0.843, 0.868, 0.843, 0.851, 0.840, 0.822, 0.839, (6.3042)+(0.0115)Thr+(−0.0104)Val+(−0.2152)Met+(0.0227)Ile+(0.0629)Phe+(−0.1080)Trp; 0.823, 0.843, 0.868, 0.839, 0.844, 0.846, 0.815, 0.837, (6.3043)+(0.0111)Ser+(−0.0316)His+(−0.1509)Met+(−0.0002)Leu+(0.0599)Phe+(−0.1019)Trp; 0.822, 0.842, 0.868, 0.839, 0.844, 0.846, 0.816, 0.837, (6.2737)+(0.0110)Ser+(−0.0321)His+(−0.1527)Met+(0.0006)Lys+(0.0599)Phe+(−0.1022)Trp; 0.824, 0.843, 0.868, 0.844, 0.849, 0.854, 0.823, 0.842, (6.4322)+(0.0108)Ser+(−0.0301)His+(−0.0013)Ala+(−0.1441)Met+(0.0594)Phe+(−0.1003)Trp; 0.826, 0.843, 0.868, 0.839, 0.844, 0.847, 0.815, 0.837, (6.2988)+(0.0111)Ser+(−0.0317)His+(−0.1511)Met+(0.0599)Phe+(−0.1019)Trp; 0.822, 0.842, 0.868, 0.839, 0.844, 0.847, 0.815, 0.837, (6.3189)+(0.0111)Ser+(−0.0312)His+(−0.0003)Val+(−0.1512)Met+(0.0600)Phe+(−0.1017)Trp; 0.828, 0.849, 0.868, 0.840, 0.845, 0.840, 0.808, 0.835, (7.1759)+(−0.0328)His+(0.0140)Thr+(−0.1746)Met+(−0.0077)Orn+(0.0613)Phe+(−0.1062)Trp; 0.844, 0.863, 0.867, 0.842, 0.830, 0.848, 0.828, 0.842, (6.5893)+(−0.0369)His+(0.0115)Thr+(0.0437)Tyr+(−0.2052)Met+(0.0547)Phe+(−0.1221)Trp; 0.841, 0.861, 0.867, 0.842, 0.842, 0.849, 0.797, 0.837, (7.7857)+(−0.0223)His+(0.0149)Thr+(−0.0491)Cit+(−0.1717)Met+(0.0548)Phe+(−0.1074)Trp; 0.830, 0.848, 0.867, 0.846, 0.851, 0.854, 0.823, 0.844, (7.0759)+(0.0136)Ser+(−0.0459)Asn+(−0.0257)His+(−0.1226)Met+(0.0554)Phe+(−0.1006)Trp; 0.834, 0.852, 0.866, 0.843, 0.847, 0.842, 0.814, 0.839, (7.9229)+(−0.0447)Asn+(−0.0283)His+(0.0142)Thr+(−0.1444)Met+(0.0542)Phe+(−0.1046)Trp; 0.824, 0.844, 0.866, 0.841, 0.845, 0.846, 0.819, 0.838, (6.3750)+(0.0113)Ser+(−0.0310)His+(−0.1507)Met+ (−0.0033)Orn+(0.0605)Phe+(−0.1021)Trp; 0.841, 0.857, 0.866, 0.840, 0.844, 0.848, 0.791, 0.835, (6.7740)+(0.0068)Ser+(0.0115)Thr+(−0.0553)Cit+(−0.1877)Met+(0.0567)Phe+(−0.1179)Trp; 0.825, 0.845, 0.866, 0.840, 0.845, 0.849, 0.811, 0.837, (6.3684)+(0.0123)Ser+(−0.0303)His+(−0.0065)Arg+(−0.1397)Met+(0.0585)Phe+(−0.1002)Trp; 0.833, 0.850, 0.865, 0.843, 0.850, 0.839, 0.811, 0.837, (6.7437)+(0.0097)Ser+(−0.0600)Asn+(0.0098)Thr+(−0.1567)Met+ (0.0563)Phe+(−0.1173)Trp; 0.826, 0.845, 0.865, 0.854, 0.868, 0.842, 0.844, 0.850, (4.5855)+(0.0053)Gln+(−0.0102)Val+(−0.2080)Met+(0.0200)Ile+(0.0644)Phe+ (−0.1098)Trp; 0.820, 0.837, 0.865, 0.842, 0.851, 0.841, 0.828, 0.839, (5.7758)+(0.0089)Ser+(−0.0087)Val+(−0.1895)Met+(0.0202)Ile+(0.0618)Phe+(−0.1060)Trp; 0.836, 0.852, 0.864, 0.840, 0.840, 0.845, 0.811, 0.837, (6.4386)+(0.0108)Ser+(−0.0536)Cit+(−0.1663)Met+ (0.0106)Ile+(0.0523)Phe+(−0.1131)Trp; 0.833, 0.853, 0.863, 0.860, 0.872, 0.859, 0.845, 0.857, (4.9038)+ (0.0081)Gln+(−0.0419)His+(−0.0071)Pro+(−0.1583) Met+(0.0642)Phe+(−0.1083)Trp; 0.842, 0.858, 0.863, 0.839, 0.838, 0.841, 0.798, 0.834, (7.1060)+(0.0135) Thr+(−0.0572)Cit+(−0.1907)Met+(0.0101)Ile+ (0.0521)Phe+(−0.1180)Trp; 0.829, 0.849, 0.863, 0.856, 0.865, 0.851, 0.850, 0.854, (6.3399)+(−0.1007)Asn+ (0.0081)Gln+(−0.0420)His+(−0.0000)Val+(0.0309) Phe+(−0.1053)Trp; 0.831, 0.849, 0.863, 0.856, 0.865, 0.851, 0.850, 0.854, (6.3386)+(−0.1007)Asn+(0.0081) Gln+(−0.0420)His+(0.0308)Phe+(−0.1053)Trp; 0.828, 0.849, 0.863, 0.848, 0.847, 0.840, 0.853, 0.847, (6.8868)+(0.0203)Ser+(−0.0083)Gly+(−0.0288)His+ (−0.1425)Met+(0.0575)Phe+(−0.1048)Trp; 0.833, 0.852, 0.863, 0.842, 0.845, 0.854, 0.806, 0.839, (7.0529)+(0.0115)Ser+(−0.0199)His+(−0.0457)Cit+(−0.1445)Met+(0.0547)Phe+(−0.1032)Trp; 0.828, 0.849, 0.862, 0.856, 0.865, 0.850, 0.851, 0.854, (6.3566)+(−0.0005)Ser+(−0.1005)Asn+(0.0081)Gln+(−0.0420) His+(0.0307)Phe+(−0.1053)Trp; 0.821, 0.839, 0.862, 0.839, 0.849, 0.832, 0.816, 0.834, (5.5659)+(0.0083) Ser+(−0.1741)Met+(0.0220)Ile+(−0.0162)Leu+ (0.0645)Phe+(−0.1118)Trp; 0.829, 0.849, 0.862, 0.856, 0.865, 0.850, 0.852, 0.854, (6.3041)+(−0.0997)Asn+ (0.0082)Gln+(−0.0417)His+(−0.0012)Thr+(0.0310) Phe+(−0.1049)Trp; 0.842, 0.861, 0.862, 0.864, 0.870, 0.868, 0.849, 0.862, (6.6307)+(−0.0962)Asn+(0.0095) Gln+(−0.0324)His+(−0.0535)Cit+(0.0266)Phe+(−0.1073)Trp; 0.845, 0.862, 0.862, 0.853, 0.864, 0.847, 0.809, 0.845, (4.9646)+(0.0069)Gln+(0.0085)Thr+(−0.0668)Cit+(−0.2085)Met+(0.0592)Phe+(−0.1238) Trp; 0.856, 0.870, 0.861, 0.849, 0.837, 0.854, 0.831, 0.848, (6.2989)+(0.0102)Ser+(−0.0563)Cit+(0.0477) Tyr+(−0.1949)Met+(0.0483)Phe+(−0.1330)Trp; 0.830, 0.850, 0.861, 0.858, 0.868, 0.856, 0.850, 0.856, (6.4072)+(−0.0961)Asn+(0.0084)Gln+(−0.0397)His+ (−0.0046)Lys+(0.0328)Phe+(−0.1032)Trp; 0.842, 0.859, 0.861, 0.836, 0.836, 0.844, 0.780, 0.830, (7.2191)+(0.0113)Thr+(−0.0664)Cit+(−0.1726)Met+ (0.0139)Orn+(0.0485)Phe+(−0.1168)Trp; 0.833, 0.851, 0.861, 0.846, 0.850, 0.825, 0.843, 0.842, (6.2953)+ (0.0165)Ser+(−0.0095)Gly+(0.0104)Thr+(−0.1883) Met+(0.0594)Phe+(−0.1251)Trp; 0.845, 0.861, 0.861, 0.844, 0.847, 0.848, 0.798, 0.839, (8.2542)+(−0.0415) Asn+(0.0150)Thr+(−0.0507)Cit+(−0.1521)Met+ (0.0491)Phe+(−0.1149)Trp; 0.838, 0.854, 0.861, 0.837, 0.837, 0.851, 0.791, 0.833, (6.5845)+(0.0094)Ser+(−0.0666)Cit+(−0.1530)Met+(0.0177)Orn+(0.0480)Phe+ (−0.1126)Trp; 0.830, 0.850, 0.861, 0.858, 0.867, 0.852, 0.853, 0.856, (6.3558)+(−0.0996)Asn+(0.0084)Gln+(−0.0417)His+(−0.0061)Orn+(0.0322)Phe+(−0.1058) Trp; 0.829, 0.849, 0.861, 0.858, 0.870, 0.852, 0.847, 0.854, (6.4511)+(−0.1005)Asn+(0.0080)Gln+(−0.0378)His+(−0.0054)Leu+(0.0344)Phe+(−0.1046) Trp; 0.840, 0.855, 0.861, 0.846, 0.852, 0.855, 0.808, 0.842, (7.4662)+(0.0127)Ser+(−0.0419)Asn+(−0.0466)Cit+(−0.1258)Met+(0.0499)Phe+(−0.1095) Trp; 0.827, 0.849, 0.860, 0.862, 0.872, 0.867, 0.862, 0.862, (6.4302)+(−0.0953)Asn+(0.0081)Gln+(−0.0393)His+(−0.0025)Ala+(0.0326)Phe+(−0.1021) Trp; 0.807, 0.826, 0.860, 0.825, 0.827, 0.827, 0.819, 0.825, (5.6387)+(0.0034)Gln+(−0.0527)His+(0.0009) Val+(0.0282)Phe+(−0.1097)Trp; 0.824, 0.844, 0.860, 0.841, 0.848, 0.850, 0.809, 0.838, (6.6200)+(0.0112) Ser+(−0.0287)His+(−0.0049)Pro+(−0.1387)Met+ (0.0598)Phe+(−0.1050)Trp; 0.821, 0.840, 0.860, 0.831, 0.840, 0.820, 0.797, 0.824, (5.4732)+(0.0067)Ser+ (0.0076)Thr+(−0.1949)Met+(0.0028)Ile+(0.0608) Phe+(−0.1223)Trp; 0.811, 0.826, 0.860, 0.826, 0.828, 0.828, 0.819, 0.826, (5.6897)+(0.0033)Gln+(−0.0513) His+(0.0286)Phe+(−0.1090)Trp; 0.828, 0.847, 0.860, 0.832, 0.843, 0.826, 0.778, 0.823, (5.7500)+(0.0081) Ser+(0.0108)Thr+(−0.0127)Arg+(−0.1771)Met+ (0.0594)Phe+(−0.1189)Trp; 0.817, 0.838, 0.859, 0.841, 0.846, 0.856, 0.821, 0.840, (6.2129)+(0.0053)Gln+(−0.0482)His+(0.0045)Thr+(−0.1235)Met+(0.0088) Leu+(−0.0845)Trp; 0.837, 0.859, 0.859, 0.864, 0.870, 0.841, 0.876, 0.862, (5.4692)+(−0.0070)Gly+(0.0085) Gln+(−0.0426)His+(−0.1550)Met+(0.0577)Phe+(−0.1064)Trp; 0.809, 0.832, 0.859, 0.832, 0.836, 0.839, 0.818, 0.831, (5.7477)+(0.0046)Gln+(−0.0497)His+ (0.0028)Val+(−0.0097)Lys+(0.0316)Phe+(−0.1061) Trp; 0.842, 0.858, 0.859, 0.839, 0.843, 0.843, 0.785, 0.832, (7.5521)+(0.0141)Thr+(−0.0552)Cit+(−0.1713) Met+(−0.0030)Lys+(0.0530)Phe+(−0.1161)Trp; 0.835, 0.854, 0.859, 0.848, 0.842, 0.842, 0.854, 0.848, (6.1029)+(0.0480)Tyr+(−0.0117)Val+(−0.2202)Met+ (0.0273)Ile+(0.0526)Phe+(−0.1209)Trp; 0.860, 0.874, 0.859, 0.845, 0.831, 0.848, 0.818, 0.843, (6.9429)+ (0.0121)Thr+(−0.0594)Cit+(0.0463)Tyr+(−0.2151) Met+(0.0479)Phe+(−0.1367)Trp; 0.842, 0.857, 0.859, 0.845, 0.850, 0.852, 0.798, 0.839, (7.5772)+(0.0133) Thr+(−0.0022)Ala+(−0.0545)Cit+(−0.1673)Met+ (0.0529)Phe+(−0.1141)Trp; 0.841, 0.858, 0.859, 0.840, 0.844, 0.843, 0.787, 0.833, (7.4685)+(0.0135)Thr+(−0.0534)Cit+(−0.0019)Val+(−0.1797)Met+(0.0547) Phe+(−0.1154)Trp; 0.804, 0.826, 0.859, 0.840, 0.846, 0.856, 0.843, 0.843, (5.7909)+(0.0039)Gln+(−0.0489) His+(−0.0045)Ala+(0.0024)Val+(0.0309)Phe+(−0.1046)Trp; 0.825, 0.843, 0.858, 0.837, 0.852, 0.828, 0.794, 0.829, (6.0754)+(0.0056)Ser+(0.0089)Thr+(−0.0053)Val+(−0.1927)Met+(0.0643)Phe+(−0.1147) Trp; 0.823, 0.841, 0.858, 0.832, 0.843, 0.823, 0.791, 0.824, (5.7463)+(0.0071)Ser+(0.0085)Thr+(−0.1836) Met+(−0.0035)Lys+(0.0611)Phe+(−0.1201)Trp; 0.841, 0.857, 0.858, 0.849, 0.849, 0.842, 0.838, 0.847, (7.1001)+(0.0175)Ser+(−0.0066)Gly+(−0.0442)Cit+(−0.1473)Met+(0.0522)Phe+(−0.1150)Trp; 0.844, 0.857, 0.858, 0.838, 0.841, 0.840, 0.788, 0.831, (7.3543)+ (0.0132)Thr+(−0.0552)Cit+(−0.1786)Met+(0.0532) Phe+(−0.1179)Trp; 0.840, 0.857, 0.858, 0.838, 0.841, 0.839, 0.788, 0.831, (7.3518)+(0.0132)Thr+(−0.0553) Cit+(0.0002)Arg+(−0.1789)Met+(0.0532)Phe+(−0.1180)Trp; 0.808, 0.829, 0.858, 0.843, 0.850, 0.858, 0.841, 0.844, (5.9101)+(0.0038)Gln+(−0.0456)His+(−

0.0043)Ala+(0.0319)Phe+(−0.1032)Trp; 0.829, 0.850, 0.857, 0.840, 0.846, 0.843, 0.801, 0.835, (7.3449)+(−0.0311)His+(0.0137)Thr+(−0.0056)Pro+(−0.1609) Met+(0.0599)Phe+(−0.1093)Trp; 0.843, 0.859, 0.857, 0.839, 0.844, 0.841, 0.784, 0.832, (7.4594)+(0.0130) Thr+(−0.0542)Cit+(−0.1740)Met+(−0.0037)Leu+ (0.0552)Phe+(−0.1163)Trp; 0.835, 0.853, 0.857, 0.839, 0.834, 0.826, 0.832, 0.836, (4.9461)+(0.0090)Ser+ (0.0425)Tyr+(−0.2123)Met+(0.0050)Ile+(0.0541)Phe+ (−0.1370)Trp; 0.823, 0.843, 0.857, 0.839, 0.854, 0.819, 0.809, 0.831, (4.3521)+(0.0027)Ser+(0.0040)Gln+ (0.0054)Thr+(−0.2041)Met+(0.0630)Phe+(−0.1262) Trp; 0.827, 0.841, 0.857, 0.831, 0.840, 0.819, 0.794, 0.823, (5.5659)+(0.0066)Ser+(0.0076)Thr+(−0.1913) Met+(0.0610)Phe+(−0.1223)Trp; 0.821, 0.841, 0.857, 0.837, 0.847, 0.826, 0.807, 0.830, (6.0719)+(0.0090) Thr+(−0.1880)Met+(0.0215)Ile+(−0.0165)Leu+ (0.0640)Phe+(−0.1150)Trp; 0.812, 0.833, 0.857, 0.834, 0.840, 0.840, 0.816, 0.832, (5.8826)+(0.0045)Gln+(−0.0459)His+(−0.0090)Lys+(0.0325)Phe+(−0.1046) Trp; 0.853, 0.869, 0.857, 0.868, 0.879, 0.860, 0.841, 0.863, (5.6045)+(−0.0728)Asn+(0.0103)Gln+(−0.0613)Cit+(−0.1429)Met+(0.0505)Phe+(−0.1170) Trp; 0.836, 0.855, 0.857, 0.856, 0.870, 0.836, 0.834, 0.849, (5.3166)+(−0.0835)Asn+(0.0074)Gln+(0.0075) Thr+(−0.1613)Met+(0.0561)Phe+(−0.1225)Trp; 0.848, 0.863, 0.857, 0.850, 0.842, 0.845, 0.845, 0.849, (6.4101)+(0.0131)Ser+(−0.0699)Asn+(0.0499)Tyr+(−0.1645)Met+(0.0474)Phe+(−0.1332)Trp; 0.835, 0.854, 0.857, 0.859, 0.874, 0.843, 0.840, 0.853, (4.9875)+ (0.0058)Ser+(−0.0829)Asn+(0.0074)Gln+(−0.1472) Met+(0.0560)Phe+(−0.1197)Trp; 0.844, 0.861, 0.857, 0.851, 0.845, 0.823, 0.863, 0.848, (5.7670)+(0.0170) Ser+(−0.0073)Gly+(0.0351)Tyr+(−0.1905)Met+ (0.0532)Phe+(−0.1350)Trp; 0.828, 0.845, 0.857, 0.843, 0.851, 0.838, 0.821, 0.839, (6.5849)+(0.0126)Ser+(−0.0559)Asn+(−0.1341)Met+(0.0038)Ile+(0.0530)Phe+ (−0.1133)Trp; 0.821, 0.846, 0.857, 0.833, 0.829, 0.851, 0.801, 0.832, (6.0414)+(0.0046)Gln+(−0.0396)His+(−0.0673)Cit+(0.0130)Orn+(0.0205)Phe+(−0.1104)Trp; 0.808, 0.832, 0.857, 0.834, 0.842, 0.840, 0.815, 0.832, (5.9095)+(0.0044)Gln+(−0.0448)His+(−0.0087)Lys+ (−0.0016)Leu+(0.0334)Phe+(−0.1045)Trp; 0.814, 0.836, 0.857, 0.842, 0.851, 0.860, 0.816, 0.841, (6.3887)+(0.0050)Gln+(−0.0414)His+(0.0036)Thr+(−0.1159)Met+(0.0058)Ile+(−0.0823)Trp; 0.838, 0.859, 0.857, 0.855, 0.859, 0.876, 0.823, 0.854, (7.2421)+(−0.0971)Asn+(0.0087)Gln+(−0.0275)His+(−0.0714) Cit+(0.0201)Orn+(−0.0961)Trp; 0.840, 0.859, 0.857, 0.853, 0.861, 0.847, 0.823, 0.847, (4.7303)+(0.0076) Gln+(−0.0666)Cit+(−0.1912)Met+(0.0082)Ile+ (0.0548)Phe+(−0.1207)Trp

List (1) of Logistic Regression Equations Searched in Example 7

The logistic regression equations searched in Example 7 above are listed below. Before each equation, "the value of ROC_AUC for the pancreatic cancer group and the prostatic cancer group with validation", "the value of ROC_AUC for the pancreatic cancer group and the prostatic cancer group without validation", "the value of ROC_AUC for the pancreatic cancer group and the healthy group", "the value of ROC_AUC for the pancreatic cancer group and the other cancers group", "the value of ROC_AUC for the pancreatic cancer group and the lung cancer group", "the value of ROC_AUC for the pancreatic cancer group and the colorectal cancer group", and "the average value of the value of ROC_AUC for the pancreatic cancer group and the lung cancer group, the value of ROC_AUC for the pancreatic cancer group and the colorectal cancer group, and the value of ROC_AUC for the pancreatic cancer group and the prostatic cancer group" obtained for the equation are additionally listed.

0.877, 0.907, 0.895, 0.804, 0.799, 0.752, 0.819, (3.0499)+ (0.0406)Ser+(−0.0121)Ala+(−0.0402)Val+(−0.1789) Met+(0.1361)Ile; 0.874, 0.914, 0.889, 0.824, 0.829, 0.766, 0.836, (1.8050)+(0.0287)Ser+(0.0081)Gln+(−0.0133)Ala+(−0.0421)Val+(−0.2379)Met+(0.1384)Ile; 0.873, 0.911, 0.872, 0.841, 0.854, 0.785, 0.850, (3.2506)+(0.0146)Gln+(−0.0127)Ala+(−0.0711)Cit+(−0.0454)Val+(−0.2177)Met+(0.1443)Ile; 0.872, 0.909, 0.906, 0.801, 0.796, 0.747, 0.817, (3.3965)+(0.0311) Ser+(0.0246)Thr+(−0.0128)Ala+(−0.0466)Val+(−0.2635)Met+(0.1591)Ile; 0.872, 0.909, 0.898, 0.804, 0.798, 0.752, 0.820, (1.9444)+(0.0409)Ser+(−0.0141) Ala+(−0.0498)Val+(−0.2446)Met+(0.0197)Lys+ (0.1613)Ile; 0.871, 0.906, 0.896, 0.810, 0.813, 0.753, 0.824, (3.0424)+(0.0387)Ser+(0.0297)His+(−0.0131) Ala+(−0.0487)Val+(−0.2265)Met+(0.1561)Ile; 0.871, 0.910, 0.897, 0.808, 0.801, 0.761, 0.824, (3.3274)+ (0.0409)Ser+(−0.0117)Ala+(−0.0293)Cit+(−0.0398) Val+(−0.1603)Met+(0.1354)Ile; 0.871, 0.910, 0.886, 0.795, 0.791, 0.736, 0.812, (2.9136)+(0.0391)Ser+(−0.0129)Ala+(−0.0439)Val+(−0.1895)Met+(0.1445) Ile+(0.0213)Trp; 0.871, 0.909, 0.904, 0.809, 0.804, 0.758, 0.824, (2.5705)+(0.0423)Ser+(−0.0115)Ala+(−0.0427)Val+(−0.1878)Met+(0.1360)Ile+(0.0134)Phe; 0.871, 0.907, 0.894, 0.803, 0.797, 0.753, 0.819, (3.0263)+(0.0422)Ser+(−0.0117)Ala+(−0.0466)Val+(−0.1894)Met+(0.1237)Ile+(0.0178)Leu; 0.870, 0.913, 0.906, 0.806, 0.790, 0.766, 0.823, (2.4936)+(0.0432) Ser+(−0.0118)Ala+(0.0462)Tyr+(−0.0485)Val+(−0.2565)Met+(0.1511)Ile; 0.870, 0.906, 0.897, 0.803, 0.796, 0.754, 0.819, (3.0382)+(0.0402)Ser+(−0.0120) Ala+(−0.0407)Val+(−0.1802)Met+(0.0043)Orn+ (0.1345)Ile; 0.869, 0.906, 0.893, 0.800, 0.794, 0.747, 0.816, (3.1053)+(0.0413)Ser+(−0.0187)Asn+(−0.0122)Ala+(−0.0403)Val+(−0.1520)Met+(0.1375)Ile; 0.869, 0.911, 0.844, 0.821, 0.852, 0.728, 0.830, (3.6477)+(−0.1046)Asn+(0.0141)Gln+(−0.0129)Ala+ (−0.0256)Pro+(−0.0496)Val+(0.1669)Ile; 0.868, 0.906, 0.842, 0.816, 0.830, 0.745, 0.827, (3.9145)+(−0.1050) Asn+(0.0147)Gln+(−0.0158)Ala+(−0.0820)Cit+(−0.0437)Val+(0.1389)Ile; 0.867, 0.908, 0.854, 0.793, 0.801, 0.717, 0.808, (2.5456)+(0.0259)Ser+(−0.1002) Asn+(0.0075)Gln+(−0.0164)Ala+(−0.0403)Val+ (0.1270)Ile; 0.865, 0.898, 0.867, 0.777, 0.776, 0.711, 0.795, (3.8433)+(0.0389)Ser+(−0.0574)Asn+(−0.0145)Ala+(−0.0373)Cit+(−0.0394)Val+(0.1275)Ile; 0.865, 0.912, 0.902, 0.802, 0.793, 0.753, 0.819, (2.8640)+(0.0372)Ser+(−0.0135)Ala+(0.0205)Arg+(−0.0437)Val+(−0.2293)Met+(0.1532)Ile; 0.865, 0.914, 0.884, 0.822, 0.829, 0.761, 0.835, (3.6660)+(0.0086) Gln+(0.0244)Thr+(−0.0136)Ala+(−0.0488)Val+(−0.2914)Met+(0.1546)Ile; 0.865, 0.907, 0.891, 0.811, 0.816, 0.749, 0.824, (3.7418)+(0.0379)Ser+(−0.0109) Ala+(−0.0113)Pro+(−0.0427)Val+(−0.1565)Met+ (0.1486)Ile; 0.864, 0.917, 0.864, 0.842, 0.867, 0.765, 0.850, (3.2795)+(0.0145)Gln+(−0.0114)Ala+(−0.0234)Pro+(−0.0513)Val+(−0.2086)Met+(0.1692)Ile; 0.864, 0.904, 0.880, 0.807, 0.804, 0.757, 0.822, (6.4815)+(−0.0134)Ala+(−0.0621)Cit+(0.0404)Arg+ (−0.0464)Val+(−0.1757)Met+(0.1534)Ile; 0.864, 0.906, 0.896, 0.807, 0.799, 0.762, 0.822, (6.2885)+ (0.0375)Thr+(−0.0124)Ala+(−0.0376)Cit+(−0.0494)

Val+(−0.2412)Met+(0.1628)Ile; 0.864, 0.898, 0.861, 0.764, 0.762, 0.690, 0.783, (2.7856)+(0.0404)Ser+(−0.0938)Asn+(−0.0176)Ala+(−0.0470)Val+(0.0160) Lys+(0.1421)Ile; 0.863, 0.898, 0.864, 0.772, 0.771, 0.701, 0.790, (3.4932)+(0.0376)Ser+(−0.0658)Asn+(−0.0152)Ala+(−0.0395)Val+(0.1263)Ile; 0.863, 0.892, 0.848, 0.777, 0.779, 0.711, 0.794, (3.8688)+(0.0304) Ser+(−0.0164)Ala+(−0.0455)Cit+(−0.0380)Val+ (0.1120)Ile; 0.862, 0.892, 0.838, 0.768, 0.773, 0.691, 0.785, (3.4307)+(0.0273)Ser+(−0.0177)Ala+(−0.0373) Val+(0.1054)Ile; 0.862, 0.905, 0.831, 0.818, 0.845, 0.732, 0.827, (3.7841)+(0.0113)Gln+(−0.0162)Ala+(−0.0585)Cit+(−0.0201)Pro+(−0.0455)Val+(0.1396)Ile; 0.862, 0.892, 0.885, 0.830, 0.830, 0.794, 0.839, (1.4679)+(0.0224)Ser+(0.0106)Gln+(−0.0645)Cit+(−0.0500)Val+(−0.3305)Met+(0.1556)Ile; 0.861, 0.902, 0.862, 0.765, 0.761, 0.694, 0.786, (3.4150)+(0.0353) Ser+(−0.0913)Asn+(−0.0170)Ala+(0.0192)Arg+(−0.0419)Val+(0.1393)Ile; 0.861, 0.911, 0.870, 0.828, 0.842, 0.761, 0.838, (3.2184)+(0.0111)Gln+(−0.0132) Ala+(−0.0439)Val+(−0.2077)Met+(0.1344)Ile; 0.861, 0.894, 0.830, 0.801, 0.823, 0.720, 0.812, (3.7223)+(−0.0870)Asn+(0.0100)Gln+(−0.0160)Ala+(−0.0424) Val+(0.1267)Ile; 0.861, 0.898, 0.864, 0.772, 0.769, 0.706, 0.791, (3.4579)+(0.0372)Ser+(−0.0704)Asn+(−0.0149)Ala+(−0.0403)Val+(0.0085)Orn+(0.1246)Ile; 0.860, 0.903, 0.822, 0.820, 0.840, 0.745, 0.829, (2.5839)+(0.0123)Gln+(−0.0180)Ala+(−0.0933)Cit+ (−0.0160)Pro+(0.1735)Ile+(−0.0857)Leu; 0.860, 0.907, 0.895, 0.804, 0.796, 0.756, 0.820, (3.2301)+ (0.0443)Ser+(−0.0029)Gly+(−0.0119)Ala+(−0.0403) Val+(−0.1807)Met+(0.1358)Ile; 0.859, 0.890, 0.905, 0.800, 0.783, 0.774, 0.816, (2.8315)+(0.0312)Ser+ (0.0223)Thr+(−0.0416)Cit+(−0.0522)Val+(−0.3341) Met+(0.1697)Ile; 0.859, 0.895, 0.843, 0.785, 0.798, 0.705, 0.799, (4.0937)+(0.0273)Ser+(−0.0151)Ala+(−0.0154)Pro+(−0.0408)Val+(0.1272)Ile; 0.859, 0.895, 0.825, 0.807, 0.838, 0.715, 0.816, (3.6909)+(0.0090) Gln+(−0.0160)Ala+(−0.0233)Pro+(−0.0459)Val+ (0.1389)Ile; 0.859, 0.895, 0.897, 0.795, 0.765, 0.780, 0.814, (2.3171)+(0.0426)Ser+(−0.0369)Cit+(0.0544) Tyr+(−0.0577)Val+(−0.3487)Met+(0.1682)Ile; 0.859, 0.905, 0.866, 0.789, 0.796, 0.713, 0.805, (4.1103)+ (0.0358)Ser+(−0.0610)Asn+(−0.0129)Ala+(−0.0140) Pro+(−0.0425)Val+(0.1452)Ile; 0.859, 0.900, 0.861, 0.766, 0.765, 0.693, 0.786, (3.6380)+(0.0339)Ser+(−0.0808)Asn+(0.0105)Thr+(−0.0161)Ala+(−0.0412) Val+(0.1322)Ile; 0.859, 0.894, 0.860, 0.768, 0.767, 0.700, 0.787, (3.4924)+(0.0388)Ser+(−0.0697)Asn+(−0.0149)Ala+(−0.0454)Val+(0.1160)Ile+(0.0159)Leu; 0.858, 0.901, 0.852, 0.829, 0.840, 0.772, 0.838, (1.8392)+(0.0145)Gln+(−0.0164)Ala+(−0.0957)Cit+ (−0.1504)Met+(0.1590)Ile+(−0.0746)Leu; 0.858, 0.896, 0.846, 0.822, 0.848, 0.743, 0.829, (3.2627)+(−0.1568)Asn+(0.0168)Gln+(−0.0623)Cit+(−0.0290) Pro+(−0.0560)Val+(0.1759)Ile; 0.858, 0.900, 0.889, 0.804, 0.802, 0.752, 0.818, (5.9958)+(0.0352)Thr+(−0.0126)Ala+(−0.0500)Val+(−0.2580)Met+(0.1616)Ile; 0.858, 0.885, 0.893, 0.798, 0.782, 0.771, 0.813, (2.5428)+(0.0397)Ser+(−0.0359)Cit+(−0.0470)Val+(−0.2580)Met+(0.1513)Ile; 0.858, 0.914, 0.874, 0.829, 0.838, 0.769, 0.840, (3.0001)+(0.0109)Gln+(−0.0126) Ala+(0.0335)Tyr+(−0.0501)Val+(−0.2630)Met+ (0.1449)Ile; 0.858, 0.898, 0.854, 0.775, 0.782, 0.696, 0.792, (3.5574)+(0.0359)Ser+(−0.0834)Asn+(0.0225) His+(−0.0163)Ala+(−0.0455)Val+(0.1400)Ile; 0.858, 0.894, 0.886, 0.826, 0.828, 0.787, 0.836, (2.7972)+ (0.0118)Gln+(0.0191)Thr+(−0.0733)Cit+(−0.0554) Val+(−0.3788)Met+(0.1690)Ile; 0.858, 0.894, 0.833, 0.770, 0.762, 0.712, 0.789, (3.0835)+(0.0252)Ser+(−0.0192)Ala+(−0.0851)Cit+(0.0179)Arg+(0.1508)Ile+ (−0.0734)Leu; 0.857, 0.890, 0.836, 0.776, 0.773, 0.718, 0.793, (3.0854)+(0.0294)Ser+(−0.0175)Ala+(−0.0646) Cit+(0.1380)Ile+(−0.0672)Leu; 0.857, 0.900, 0.890, 0.801, 0.797, 0.750, 0.815, (6.0223)+(0.0410)Thr+(−0.0122)Ala+(−0.0638)Val+(−0.2943)Met+(0.1436) Ile+(0.0347)Leu; 0.857, 0.910, 0.870, 0.830, 0.848, 0.760, 0.839, (3.1052)+(0.0120)Gln+(−0.0135)Ala+(−0.0435)Val+(−0.2153)Met+(−0.0102)Orn+(0.1397)Ile; 0.857, 0.897, 0.853, 0.791, 0.800, 0.717, 0.805, (4.2897)+(0.0303)Ser+(−0.0146)Ala+(−0.0342)Cit+(−0.0130)Pro+(−0.0403)Val+(0.1270)Ile; 0.857, 0.892, 0.867, 0.828, 0.832, 0.786, 0.837, (2.5832)+(0.0139) Gln+(−0.0769)Cit+(−0.0528)Val+(−0.3151)Met+ (0.1570)Ile; 0.857, 0.895, 0.877, 0.827, 0.828, 0.789, 0.837, (2.6930)+(0.0125)Gln+(−0.0905)Cit+(0.0196) Arg+(−0.0556)Val+(−0.3549)Met+(0.1713)Ile; 0.857, 0.895, 0.854, 0.765, 0.766, 0.691, 0.784, (3.4388)+ (0.0368)Ser+(−0.0683)Asn+(−0.0158)Ala+(−0.0419) Val+(0.1308)Ile+(0.0135)Trp; 0.857, 0.906, 0.875, 0.827, 0.842, 0.763, 0.837, (2.9477)+(0.0100)Gln+(−0.0140)Ala+(−0.0502)Val+(−0.2536)Met+(0.0138) Lys+(0.1490)Ile; 0.857, 0.900, 0.870, 0.846, 0.864, 0.790, 0.851, (2.5434)+(0.0169)Gln+(−0.0594)Cit+(−0.0230)Pro+(−0.0575)Val+(−0.2953)Met+(0.1812)Ile; 0.857, 0.889, 0.891, 0.799, 0.775, 0.780, 0.815, (2.6896)+(0.0379)Ser+(−0.0547)Cit+(−0.0483)Val+(−0.2479)Met+(0.0250)Orn+(0.1398)Ile; 0.856, 0.893, 0.838, 0.768, 0.772, 0.691, 0.786, (3.4271)+(0.0272) Ser+(−0.0177)Ala+(−0.0373)Val+(0.0008)Orn+ (0.1051)Ile; 0.856, 0.899, 0.836, 0.788, 0.787, 0.726, 0.804, (3.3509)+(0.0284)Ser+(−0.0162)Ala+(−0.0601) Cit+(−0.0084)Pro+(0.1519)Ile+(−0.0706)Leu; 0.856, 0.898, 0.871, 0.828, 0.824, 0.795, 0.839, (2.5863)+ (0.0143)Gln+(−0.0787)Cit+(0.0496)Tyr+(−0.0626) Val+(−0.4003)Met+(0.1719)Ile; 0.856, 0.898, 0.872, 0.810, 0.818, 0.748, 0.821, (5.9124)+(0.0078)Gly+(−0.0121)Ala+(−0.0412)Cit+(−0.0420)Val+(−0.0905) Met+(0.1313)Ile; 0.855, 0.895, 0.843, 0.778, 0.768, 0.725, 0.796, (3.0505)+(0.0335)Ser+(−0.0316)Asn+(−0.0166)Ala+(−0.0603)Cit+(0.1406)Ile+(−0.0641)Leu; 0.855, 0.899, 0.849, 0.775, 0.774, 0.706, 0.793, (3.8752)+(0.0268)Ser+(−0.0182)Ala+(−0.0618)Cit+ (0.0162)Arg+(−0.0393)Val+(0.1173)Ile; 0.855, 0.896, 0.852, 0.781, 0.781, 0.715, 0.797, (3.9231)+(0.0304) Ser+(−0.0164)Ala+(−0.0504)Cit+(−0.0319)Val+ (0.1240)Ile+(−0.0164)Leu; 0.855, 0.903, 0.887, 0.803, 0.793, 0.760, 0.819, (5.7717)+(0.0386)Thr+(−0.0122) Ala+(0.0496)Tyr+(−0.0607)Val+(−0.3491)Met+ (0.1793)Ile; 0.855, 0.900, 0.832, 0.801, 0.826, 0.712, 0.812, (3.1275)+(0.0128)Ser+(0.0072)Gln+(−0.0164) Ala+(−0.0220)Pro+(−0.0443)Val+(0.1356)Ile; 0.855, 0.897, 0.824, 0.809, 0.841, 0.715, 0.817, (3.7322)+ (0.0096)Gln+(−0.0155)Ala+(−0.0241)Pro+(−0.0450) Val+(−0.0031)Lys+(0.1382)Ile; 0.855, 0.904, 0.889, 0.812, 0.818, 0.752, 0.825, (6.5665)+(0.0343)Thr+(−0.0114)Ala+(−0.0117)Pro+(−0.0524)Val+(−0.2395) Met+(0.1748)Ile; 0.854, 0.907, 0.862, 0.827, 0.841, 0.762, 0.837, (3.2724)+(−0.0426)Asn+(0.0120)Gln+(−0.0133)Ala+(−0.0438)Val+(−0.1613)Met+(0.1368)Ile; 0.854, 0.891, 0.895, 0.793, 0.766, 0.775, 0.811, (1.8590)+(0.0421)Ser+(0.0528)Tyr+(−0.0584)Val+(−0.3709)Met+(0.1702)Ile; 0.854, 0.900, 0.888, 0.802, 0.799, 0.750, 0.816, (6.0654)+(−0.0155)Asn+(0.0360)

Thr+(−0.0127)Ala+(−0.0499)Val+(−0.2400)Met+
(0.1630)Ile; 0.854, 0.897, 0.869, 0.773, 0.773, 0.702,
0.791, (3.2158)+(0.0385)Ser+(−0.0678)Asn+(−
0.0149)Ala+(−0.0410)Val+(0.1264)Ile+(0.0079)Phe;
0.854, 0.900, 0.889, 0.803, 0.802, 0.749, 0.817,
(6.0284)+(0.0359)Thr+(−0.0127)Ala+(−0.0499)Val+
(−0.2595)Met+(−0.0029)Orn+(0.1631)Ile; 0.854,
0.898, 0.888, 0.806, 0.808, 0.751, 0.819, (5.6950)+
(0.0289)Thr+(−0.0136)Ala+(−0.0545)Val+(−0.2696)
Met+(0.0117)Lys+(0.1676)Ile; 0.854, 0.894, 0.845,
0.768, 0.770, 0.694, 0.786, (3.4259)+(0.0290)Ser+(−
0.0084)His+(−0.0170)Ala+(−0.0353)Val+(0.1023)Ile;
0.854, 0.893, 0.837, 0.768, 0.773, 0.691, 0.785,
(3.4296)+(0.0274)Ser+(−0.0177)Ala+(−0.0383)Val+
(0.1035)Ile+(0.0028)Leu; 0.854, 0.901, 0.824, 0.814,
0.824, 0.753, 0.826, (2.5302)+(−0.0860)Asn+(0.0153)
Gln+(−0.0185)Ala+(−0.1030)Cit+(0.1517)Ile+(−
0.0712)Leu; 0.854, 0.899, 0.848, 0.804, 0.824, 0.722,
0.815, (5.9360)+(0.0082)Gly+(−0.0134)Ala+(−
0.0388)Cit+(−0.0144)Pro+(−0.0424)Val+(0.1336)Ile;
0.854, 0.893, 0.830, 0.802, 0.824, 0.720, 0.812,
(3.7050)+(−0.0869)Asn+(0.0102)Gln+(−0.0161)Ala+
(−0.0422)Val+(−0.0021)Orn+(0.1273)Ile; 0.854,
0.891, 0.848, 0.777, 0.779, 0.711, 0.794, (3.8714)+
(0.0303)Ser+(0.0005)His+(−0.0164)Ala+(−0.0456)
Cit+(−0.0381)Val+(0.1122)Ile; 0.854, 0.894, 0.891,
0.808, 0.793, 0.780, 0.822, (0.8790)+(0.0322)Ser+
(0.0063)Gln+(0.0517)Tyr+(−0.0600)Val+(−0.4205)
Met+(0.1715)Ile; 0.853, 0.895, 0.838, 0.796, 0.809,
0.722, 0.809, (3.2537)+(0.0140)Ser+(0.0069)Gln+(−
0.0181)Ala+(−0.0663)Cit+(−0.0401)Val+(0.1149)Ile;
0.853, 0.892, 0.899, 0.796, 0.780, 0.764, 0.812,
(2.5496)+(0.0324)Ser+(0.0274)Thr+(−0.0707)Val+(−
0.4062)Met+(0.1451)Ile+(0.0461)Leu; 0.853, 0.910,
0.872, 0.824, 0.835, 0.760, 0.835, (3.3387)+(0.0097)
Gln+(−0.0140)Ala+(0.0136)Arg+(−0.0454)Val+(−
0.2275)Met+(0.1422)Ile; 0.853, 0.900, 0.884, 0.807,
0.813, 0.747, 0.820, (5.8451)+(0.0314)His+(0.0340)
Thr+(−0.0137)Ala+(−0.0592)Val+(−0.3052)Met+
(0.1829)Ile; 0.853, 0.894, 0.855, 0.781, 0.775, 0.727,
0.798, (3.9165)+(0.0302)Ser+(−0.0157)Ala+(−0.0654)
Cit+(−0.0399)Val+(0.0235)Orn+(0.1034)Ile; 0.853,
0.892, 0.846, 0.777, 0.778, 0.710, 0.793, (3.8648)+
(0.0302)Ser+(−0.0165)Ala+(−0.0456)Cit+(−0.0383)
Val+(0.1125)Ile+(0.0023)Trp; 0.853, 0.894, 0.899,
0.799, 0.779, 0.773, 0.815, (2.5079)+(0.0358)Ser+(−
0.0597)Cit+(0.0250)Arg+(−0.0515)Val+(−0.3189)
Met+(0.1728)Ile; 0.853, 0.894, 0.829, 0.801, 0.809,
0.735, 0.813, (2.1340)+(0.0131)Ser+(0.0081)Gln+(−
0.0194)Ala+(−0.0888)Cit+(0.1439)Ile+(−0.0743)Leu;
0.853, 0.902, 0.861, 0.769, 0.764, 0.702, 0.789,
(3.3789)+(0.0378)Ser+(−0.0746)Asn+(−0.0156)Ala+
(0.0166)Tyr+(−0.0425)Val+(0.1301)Ile; 0.853, 0.885,
0.891, 0.794, 0.779, 0.762, 0.809, (2.1611)+(0.0392)
Ser+(−0.0480)Val+(−0.2807)Met+(0.1521)Ile; 0.852,
0.888, 0.897, 0.791, 0.766, 0.770, 0.808, (2.2714)+
(0.0316)Ser+(0.0231)Thr+(0.0575)Tyr+(−0.0649)Val+
(−0.4616)Met+(0.1911)Ile; 0.852, 0.886, 0.889, 0.804,
0.793, 0.773, 0.817, (2.5336)+(0.0383)Ser+(0.0215)
His+(−0.0411)Cit+(−0.0534)Val+(−0.2934)Met+
(0.1659)Ile; 0.852, 0.878, 0.885, 0.795, 0.787, 0.759,
0.808, (5.2691)+(0.0342)Thr+(−0.0406)Cit+(−0.0551)
Val+(−0.3347)Met+(0.1739)Ile; 0.852, 0.895, 0.844,
0.785, 0.799, 0.705, 0.800, (4.0912)+(0.0270)Ser+(−
0.0151)Ala+(−0.0157)Pro+(−0.0411)Val+(0.0034)
Orn+(0.1262)Ile; 0.852, 0.892, 0.847, 0.777, 0.778,
0.711, 0.794, (3.9086)+(0.0303)Ser+(−0.0164)Ala+(−
0.0455)Cit+(−0.0377)Val+(0.1120)Ile+(−0.0011)Phe;
0.852, 0.889, 0.816, 0.801, 0.813, 0.734, 0.812,
(2.7806)+(0.0089)Gln+(−0.0202)Ala+(−0.1039)Cit+
(0.0130)Arg+(0.1532)Ile+(−0.0795)Leu

List (1) of Linear Discriminants Searched in Example 7

The linear discriminants searched in Example 7 above are listed below. Before each equation, "the value of ROC_AUC for the pancreatic cancer group and the prostatic cancer group with validation", "the value of ROC_AUC for the pancreatic cancer group and the prostatic cancer group without validation", "the value of ROC_AUC for the pancreatic cancer group and the healthy group", "the value of ROC_AUC for the pancreatic cancer group and the other cancers group", "the value of ROC_AUC for the pancreatic cancer group and the lung cancer group", "the value of ROC_AUC for the pancreatic cancer group and the colorectal cancer group", and "the average value of the value of ROC_AUC for the pancreatic cancer group and the lung cancer group, the value of ROC_AUC for the pancreatic cancer group and the colorectal cancer group, and the value of ROC_AUC for the pancreatic cancer group and the prostatic cancer group" obtained for the equation are additionally listed.

0.889, 0.914, 0.864, 0.834, 0.844, 0.774, 0.844, (5.0859)+
(0.0109)Gln+(−0.0171)Ala+(−0.0452)Cit+(−0.0389)
Val+(−0.1548)Met+(0.1284)Ile; 0.888, 0.912, 0.883,
0.817, 0.820, 0.758, 0.830, (4.2244)+(0.0244)Ser+
(0.0058)Gln+(−0.0176)Ala+(−0.0382)Val+(−0.1788)
Met+(0.1319)Ile; 0.888, 0.907, 0.886, 0.803, 0.798,
0.751, 0.818, (5.2330)+(0.0342)Ser+(−0.0170)Ala+(−
0.0368)Val+(−0.1509)Met+(0.1323)Ile; 0.888, 0.911,
0.905, 0.814, 0.811, 0.763, 0.828, (3.9212)+(0.0380)
Ser+(−0.0160)Ala+(−0.0426)Val+(−0.1846)Met+
(0.1388)Ile+(0.0358)Phe; 0.887, 0.909, 0.852, 0.820,
0.833, 0.752, 0.832, (5.2382)+(0.0091)Gln+(−0.0176)
Ala+(−0.0397)Val+(−0.1581)Met+(0.1265)Ile; 0.886,
0.907, 0.887, 0.805, 0.799, 0.756, 0.821, (5.4168)+
(0.0347)Ser+(−0.0165)Ala+(−0.0246)Cit+(−0.0361)
Val+(−0.1422)Met+(0.1331)Ile; 0.886, 0.911, 0.887,
0.801, 0.794, 0.747, 0.817, (5.4113)+(0.0284)Ser+
(0.0124)Thr+(−0.0177)Ala+(−0.0384)Val+(−0.1808)
Met+(0.1375)Ile; 0.886, 0.910, 0.894, 0.805, 0.791,
0.763, 0.822, (4.9603)+(0.0350)Ser+(−0.0175)Ala+
(0.0518)Tyr+(−0.0451)Val+(−0.2283)Met+(0.1452)
Ile; 0.885, 0.909, 0.885, 0.804, 0.800, 0.750, 0.820,
(5.1334)+(0.0336)Ser+(0.0076)His+(−0.0172)Ala+(−
0.0387)Val+(−0.1574)Met+(0.1365)Ile; 0.885, 0.909,
0.886, 0.800, 0.794, 0.747, 0.816, (5.0407)+(0.0361)
Ser+(−0.0168)Ala+(−0.0446)Val+(−0.1632)Met+
(0.1200)Ile+(0.0226)Leu; 0.885, 0.909, 0.881, 0.799,
0.795, 0.741, 0.815, (5.1188)+(0.0337)Ser+(−0.0174)
Ala+(−0.0385)Val+(−0.1546)Met+(0.1360)Ile+
(0.0103)Trp; 0.885, 0.912, 0.859, 0.836, 0.858, 0.761,
0.844, (5.1053)+(0.0114)Gln+(−0.0154)Ala+(−
0.0193)Pro+(−0.0456)Val+(−0.1536)Met+(0.1567)Ile;
0.885, 0.909, 0.839, 0.816, 0.831, 0.742, 0.827,
(5.6785)+(−0.0836)Asn+(0.0106)Gln+(−0.0184)Ala+
(−0.0445)Cit+(−0.0374)Val+(0.1214)Ile; 0.885, 0.904,
0.855, 0.779, 0.776, 0.712, 0.797, (5.8722)+(0.0304)
Ser+(−0.0707)Asn+(−0.0184)Ala+(−0.0355)Val+
(0.1234)Ile; 0.884, 0.907, 0.841, 0.819, 0.846, 0.732,
0.828, (5.7402)+(−0.0940)Asn+(0.0119)Gln+(−
0.0163)Ala+(−0.0211)Pro+(−0.0449)Val+(0.1544)Ile;
0.884, 0.908, 0.887, 0.803, 0.799, 0.749, 0.819,
(4.8169)+(0.0329)Ser+(−0.0175)Ala+(−0.0394)Val+(−
0.1681)Met+(0.0072)Lys+(0.1378)Ile; 0.884, 0.908,
0.849, 0.797, 0.804, 0.725, 0.813, (5.0488)+(0.0206)

Ser+(−0.0938)Asn+(0.0061)Gln+(−0.0191)Ala+(−0.0368)Val+(0.1230)Ile; 0.884, 0.906, 0.883, 0.801, 0.797, 0.747, 0.817, (5.4787)+(0.0353)Ser+(−0.0245) Asn+(−0.0168)Ala+(−0.0367)Val+(−0.1284)Met+ (0.1335)Ile; 0.883, 0.907, 0.887, 0.799, 0.793, 0.747, 0.816, (5.1392)+(0.0305)Ser+(−0.0182)Ala+(0.0142) Arg+(−0.0382)Val+(−0.1711)Met+(0.1393)Ile; 0.883, 0.906, 0.859, 0.793, 0.799, 0.720, 0.808, (6.2281)+ (0.0316)Ser+(−0.0654)Asn+(−0.0163)Ala+(−0.0145) Pro+(−0.0397)Val+(0.1469)Ile; 0.883, 0.906, 0.832, 0.816, 0.839, 0.733, 0.826, (5.0766)+(0.0094)Gln+(−0.0180)Ala+(−0.0436)Cit+(−0.0191)Pro+(−0.0418) Val+(0.1394)Ile; 0.883, 0.905, 0.888, 0.801, 0.796, 0.748, 0.817, (5.2204)+(0.0337)Ser+(−0.0169)Ala+(−0.0373)Val+(−0.1522)Met+(0.0065)Orn+(0.1298)Ile; 0.882, 0.907, 0.886, 0.802, 0.796, 0.751, 0.818, (5.3105)+(0.0362)Ser+(−0.0016)Gly+(−0.0168)Ala+ (−0.0368)Val+(−0.1527)Met+(0.1323)Ile; 0.882, 0.910, 0.862, 0.822, 0.825, 0.767, 0.834, (5.1908)+ (0.0087)Gln+(−0.0179)Ala+(0.0430)Tyr+(−0.0465) Val+(−0.2179)Met+(0.1368)Ile; 0.881, 0.908, 0.852, 0.820, 0.833, 0.752, 0.831, (5.2315)+(0.0091)Gln+(−0.0176)Ala+(−0.0396)Val+(−0.1582)Met+(−0.0007) Orn+(0.1268)Ile; 0.881, 0.907, 0.884, 0.809, 0.814, 0.747, 0.822, (5.5923)+(0.0347)Ser+(−0.0153)Ala+(−0.0130)Pro+(−0.0404)Val+(−0.1363)Met+(0.1521)Ile; 0.880, 0.907, 0.847, 0.822, 0.837, 0.754, 0.833, (5.5183)+(−0.0448)Asn+(0.0101)Gln+(−0.0173)Ala+ (−0.0398)Val+(−0.1217)Met+(0.1286)Ile; 0.880, 0.913, 0.862, 0.830, 0.840, 0.769, 0.841, (3.2318)+ (0.0105)Gln+(−0.0278)Pro+(0.0580)Tyr+(−0.0620) Val+(−0.2907)Met+(0.1812)Ile; 0.880, 0.902, 0.861, 0.784, 0.781, 0.721, 0.801, (5.9949)+(0.0308)Ser+(−0.0636)Asn+(−0.0180)Ala+(−0.0257)Cit+(−0.0348) Val+(0.1242)Ile; 0.879, 0.908, 0.850, 0.819, 0.832, 0.749, 0.830, (5.2157)+(0.0090)Gln+(−0.0177)Ala+(−0.0402)Val+(−0.1589)Met+(0.1276)Ile+(0.0029)Trp; 0.879, 0.902, 0.857, 0.780, 0.776, 0.717, 0.798, (5.8969)+(0.0298)Ser+(−0.0750)Asn+(−0.0183)Ala+ (−0.0364)Val+(0.0106)Orn+(0.1198)Ile; 0.879, 0.908, 0.853, 0.820, 0.833, 0.753, 0.831, (5.1537)+(0.0013) Gly+(0.0087)Gln+(−0.0177)Ala+(−0.0395)Val+(−0.1569)Met+(0.1267)Ile; 0.879, 0.908, 0.853, 0.822, 0.834, 0.756, 0.833, (5.2667)+(0.0096)Gln+(−0.0091) His+(−0.0174)Ala+(−0.0374)Val+(−0.1528)Met+ (0.1214)Ile; 0.879, 0.908, 0.869, 0.817, 0.826, 0.755, 0.830, (5.4077)+(0.0074)Gln+(0.0149)Thr+(−0.0183) Ala+(−0.0410)Val+(−0.1935)Met+(0.1340)Ile; 0.878, 0.907, 0.851, 0.820, 0.832, 0.754, 0.831, (5.1231)+ (0.0094)Gln+(−0.0174)Ala+(−0.0455)Val+(−0.1667) Met+(0.1173)Ile+(0.0164)Leu; 0.878, 0.905, 0.865, 0.828, 0.843, 0.765, 0.838, (4.5753)+(0.0093)Gln+(−0.0170)Ala+(−0.0433)Val+(−0.1757)Met+(0.1299) Ile+(0.0215)Phe; 0.878, 0.904, 0.854, 0.779, 0.776, 0.711, 0.797, (5.8641)+(0.0303)Ser+(−0.0708)Asn+(−0.0185)Ala+(−0.0356)Val+(0.1237)Ile+(0.0008)Trp; 0.878, 0.907, 0.857, 0.821, 0.834, 0.754, 0.832, (4.9840)+(0.0086)Gln+(−0.0179)Ala+(−0.0415)Val+ (−0.1693)Met+(0.0054)Lys+(0.1307)Ile; 0.878, 0.899, 0.830, 0.806, 0.825, 0.726, 0.817, (5.8504)+(−0.0870) Asn+(0.0089)Gln+(−0.0189)Ala+(−0.0382)Val+ (0.1196)Ile; 0.878, 0.902, 0.850, 0.777, 0.774, 0.711, 0.796, (5.7854)+(0.0316)Ser+(−0.0759)Asn+(−0.0183)Ala+(−0.0410)Val+(0.1144)Ile+(0.0160)Leu; 0.878, 0.904, 0.853, 0.778, 0.776, 0.710, 0.797, (5.6760)+(0.0294)Ser+(−0.0768)Asn+(−0.0188)Ala+ (−0.0370)Val+(0.0044)Lys+(0.1263)Ile; 0.878, 0.903, 0.852, 0.778, 0.775, 0.712, 0.797, (6.0289)+(0.0274) Ser+(−0.0785)Asn+(0.0059)Thr+(−0.0189)Ala+(−0.0361)Val+(0.1252)Ile; 0.877, 0.894, 0.832, 0.769, 0.771, 0.696, 0.787, (5.1118)+(0.0222)Ser+(−0.0205) Ala+(−0.0349)Val+(0.1105)Ile; 0.877, 0.904, 0.854, 0.780, 0.778, 0.713, 0.798, (5.8368)+(0.0295)Ser+(−0.0708)Asn+(0.0008)Gly+(−0.0185)Ala+(−0.0355) Val+(0.1235)Ile; 0.877, 0.904, 0.866, 0.799, 0.795, 0.745, 0.814, (7.4944)+(−0.0188)Ala+(−0.0579)Cit+ (0.0387)Arg+(−0.0401)Val+(−0.1376)Met+(0.1463) Ile; 0.877, 0.907, 0.853, 0.778, 0.771, 0.714, 0.797, (5.8649)+(0.0297)Ser+(−0.0799)Asn+(−0.0189)Ala+ (0.0165)Tyr+(−0.0379)Val+(0.1256)Ile; 0.877, 0.903, 0.852, 0.776, 0.773, 0.709, 0.795, (5.9419)+(0.0268) Ser+(−0.0879)Asn+(−0.0197)Ala+(0.0149)Arg+(−0.0369)Val+(0.1308)Ile; 0.877, 0.902, 0.851, 0.781, 0.781, 0.713, 0.798, (5.8149)+(0.0297)Ser+(−0.0780) Asn+(0.0099)His+(−0.0187)Ala+(−0.0380)Val+ (0.1289)Ile; 0.876, 0.900, 0.866, 0.782, 0.781, 0.718, 0.800, (5.2550)+(0.0318)Ser+(−0.0782)Asn+(−0.0181)Ala+(−0.0383)Val+(0.1256)Ile+(0.0187)Phe; 0.876, 0.896, 0.843, 0.779, 0.780, 0.711, 0.796, (5.3713)+(0.0238)Ser+(−0.0197)Ala+(−0.0335)Cit+(−0.0341)Val+(0.1133)Ile; 0.876, 0.907, 0.860, 0.817, 0.829, 0.751, 0.829, (5.3043)+(0.0079)Gln+(−0.0184) Ala+(0.0105)Arg+(−0.0404)Val+(−0.1690)Met+ (0.1319)Ile; 0.876, 0.909, 0.847, 0.812, 0.810, 0.759, 0.826, (8.3155)+(−0.0147)Ala+(−0.0159)Pro+(0.0616) Tyr+(−0.0523)Val+(−0.1569)Met+(0.1622)Ile; 0.875, 0.902, 0.862, 0.836, 0.855, 0.771, 0.843, (3.2313)+ (0.0124)Gln+(−0.0465)Cit+(−0.0237)Pro+(−0.0505) Val+(−0.2054)Met+(0.1627)Ile; 0.875, 0.902, 0.880, 0.843, 0.869, 0.773, 0.848, (2.1201)+(0.0112)Gln+(−0.0255)Pro+(−0.0590)Val+(−0.2410)Met+(0.1706) Ile+(0.0439)Phe; 0.874, 0.902, 0.874, 0.804, 0.800, 0.755, 0.819, (7.6755)+(0.0283)Thr+(−0.0175)Ala+(−0.0339)Cit+(−0.0403)Val+(−0.1661)Met+(0.1394)Ile; 0.874, 0.895, 0.832, 0.769, 0.771, 0.697, 0.787, (5.1032)+(0.0217)Ser+(−0.0205)Ala+(−0.0352)Val+ (0.0041)Orn+(0.1088)Ile; 0.874, 0.900, 0.834, 0.809, 0.829, 0.731, 0.820, (5.9023)+(−0.0868)Asn+(0.0091) Gln+(−0.0186)Ala+(−0.0371)Val+(0.1172)Ile+(−0.0071)Trp; 0.874, 0.895, 0.843, 0.817, 0.842, 0.738, 0.825, (3.9047)+(−0.1206)Asn+(0.0126)Gln+(−0.0453)Cit+(−0.0265)Pro+(−0.0500)Val+(0.1585)Ile; 0.873, 0.900, 0.847, 0.789, 0.796, 0.716, 0.804, (5.7240)+(0.0252)Ser+(−0.0176)Ala+(−0.0265)Cit+(−0.0142)Pro+(−0.0385)Val+(0.1368)Ile; 0.873, 0.897, 0.867, 0.799, 0.799, 0.745, 0.813, (7.4475)+(0.0250) Thr+(−0.0179)Ala+(−0.0408)Val+(−0.1687)Met+ (0.1367)Ile; 0.873, 0.901, 0.865, 0.807, 0.818, 0.739, 0.819, (7.8313)+(0.0255)Thr+(−0.0162)Ala+(−0.0128) Pro+(−0.0444)Val+(−0.1548)Met+(0.1565)Ile; 0.873, 0.894, 0.839, 0.769, 0.767, 0.700, 0.787, (5.3222)+ (0.0245)Ser+(−0.0152)His+(−0.0197)Ala+(−0.0311) Val+(0.1040)Ile; 0.873, 0.900, 0.851, 0.796, 0.814, 0.712, 0.809, (6.6258)+(0.0107)Gly+(−0.0172)Ala+(−0.0355)Cit+(−0.0155)Pro+(−0.0396)Val+(0.1411)Ile; 0.873, 0.901, 0.834, 0.805, 0.825, 0.722, 0.816, (5.6692)+(−0.0870)Asn+(0.0027)Gly+(0.0082)Gln+(−0.0191)Ala+(−0.0380)Val+(0.1205)Ile; 0.873, 0.902, 0.868, 0.804, 0.798, 0.759, 0.819, (6.2881)+(0.0100) Gly+(−0.0183)Ala+(0.0616)Tyr+(−0.0473)Val+(−0.1885)Met+(0.1411)Ile; 0.873, 0.894, 0.842, 0.782, 0.793, 0.703, 0.797, (5.5535)+(0.0241)Ser+(−0.0181) Ala+(−0.0154)Pro+(−0.0394)Val+(0.1367)Ile; 0.872, 0.897, 0.842, 0.784, 0.794, 0.706, 0.799, (5.7455)+

(0.0253)Ser+(−0.0177)Ala+(−0.0157)Pro+(−0.0385)
Val+(−0.0031)Lys+(0.1358)Ile; 0.872, 0.898, 0.842,
0.785, 0.795, 0.707, 0.800, (5.5167)+(0.0259)Ser+(−
0.0027)Thr+(−0.0178)Ala+(−0.0153)Pro+(−0.0391)
Val+(0.1362)Ile; 0.872, 0.894, 0.832, 0.769, 0.771,
0.696, 0.787, (5.1178)+(0.0221)Ser+(−0.0205)Ala+(−
0.0347)Val+(0.1109)Ile+(−0.0007)Leu; 0.872, 0.894,
0.837, 0.772, 0.773, 0.702, 0.790, (5.1793)+(0.0226)
Ser+(−0.0203)Ala+(−0.0339)Val+(0.1087)Ile+(−
0.0059)Trp; 0.872, 0.902, 0.818, 0.819, 0.839, 0.744,
0.828, (4.3698)+(0.0092)Gln+(−0.0190)Ala+(−
0.0647)Cit+(−0.0133)Pro+(0.1499)Ile+(−0.0727)Leu;
0.872, 0.895, 0.835, 0.769, 0.772, 0.695, 0.787,
(4.9662)+(0.0223)Ser+(−0.0205)Ala+(−0.0355)Val+
(0.1107)Ile+(0.0039)Phe; 0.872, 0.898, 0.827, 0.803,
0.824, 0.721, 0.814, (5.7877)+(−0.0918)Asn+(0.0092)
Gln+(−0.0188)Ala+(−0.0430)Val+(0.1119)Ile+
(0.0135)Leu; 0.872, 0.900, 0.847, 0.778, 0.775, 0.714,
0.796, (5.4824)+(0.0251)Ser+(−0.0091)His+(−0.0193)
Ala+(−0.0317)Cit+(−0.0319)Val+(0.1092)Ile; 0.871,
0.899, 0.835, 0.807, 0.826, 0.728, 0.818, (5.5960)+(−
0.0901)Asn+(0.0090)Gln+(−0.0187)Ala+(−0.0396)
Val+(0.1206)Ile+(0.0090)Phe; 0.871, 0.898, 0.831,
0.800, 0.816, 0.722, 0.812, (6.0160)+(−0.0970)Asn+
(0.0079)Gln+(0.0082)Thr+(−0.0195)Ala+(−0.0388)
Val+(0.1228)Ile; 0.871, 0.897, 0.830, 0.805, 0.824,
0.727, 0.816, (5.8935)+(−0.0879)Asn+(0.0087)Gln+(−
0.0188)Ala+(−0.0386)Val+(0.0043)Orn+(0.1182)Ile;
0.871, 0.890, 0.849, 0.816, 0.845, 0.734, 0.823,
(3.2521)+(−0.1343)Asn+(0.0113)Gln+(−0.0284)Pro+
(−0.0560)Val+(0.1630)Ile+(0.0298)Phe; 0.871, 0.895,
0.833, 0.771, 0.772, 0.699, 0.789, (5.2033)+(0.0227)
Ser+(−0.0203)Ala+(−0.0344)Val+(−0.0015)Lys+
(0.1099)Ile; 0.871, 0.893, 0.829, 0.803, 0.829, 0.716,
0.813, (5.2203)+(0.0076)Gln+(−0.0185)Ala+(−
0.0199)Pro+(−0.0428)Val+(0.1384)Ile; 0.871, 0.894,
0.830, 0.769, 0.771, 0.695, 0.786, (5.0943)+(0.0213)
Ser+(−0.0208)Ala+(0.0023)Arg+(−0.0351)Val+
(0.1112)Ile; 0.871, 0.898, 0.847, 0.796, 0.815, 0.713,
0.809, (7.3141)+(−0.0436)Asn+(0.0099)Gly+(−
0.0163)Ala+(−0.0160)Pro+(−0.0412)Val+(0.1469)Ile;
0.871, 0.897, 0.846, 0.782, 0.776, 0.724, 0.799,
(5.4563)+(0.0223)Ser+(−0.0192)Ala+(−0.0504)Cit+(−
0.0356)Val+(0.0221)Orn+(0.1055)Ile; 0.871, 0.899,
0.836, 0.789, 0.800, 0.711, 0.803, (8.3595)+(−0.0678)
Asn+(0.0198)Thr+(−0.0170)Ala+(−0.0144)Pro+(−
0.0429)Val+(0.1487)Ile; 0.871, 0.895, 0.837, 0.771,
0.775, 0.697, 0.789, (5.0555)+(0.0252)Ser+(−0.0045)
Thr+(−0.0200)Ala+(−0.0344)Val+(0.1102)Ile; 0.871,
0.900, 0.835, 0.798, 0.813, 0.721, 0.811, (5.9904)+(−
0.0972)Asn+(0.0078)Gln+(−0.0198)Ala+(0.0117)
Arg+(−0.0390)Val+(0.1257)Ile; 0.871, 0.896, 0.839,
0.795, 0.816, 0.710, 0.807, (4.6855)+(0.0132)Ser+
(0.0055)Gln+(−0.0188)Ala+(−0.0190)Pro+(−0.0415)
Val+(0.1386)Ile; 0.870, 0.893, 0.828, 0.775, 0.783,
0.696, 0.791, (4.6677)+(0.0170)Ser+(0.0025)Gln+(−
0.0211)Ala+(−0.0354)Val+(0.1086)Ile; 0.870, 0.896,
0.845, 0.781, 0.782, 0.714, 0.797, (5.4134)+(0.0241)
Ser+(−0.0195)Ala+(−0.0334)Cit+(−0.0335)Val+
(0.1121)Ile+(−0.0038)Trp; 0.870, 0.899, 0.831, 0.806,
0.825, 0.728, 0.817, (5.8480)+(−0.0845)Asn+(0.0091)
Gln+(−0.0044)His+(−0.0188)Ala+(−0.0371)Val+
(0.1171)Ile; 0.870, 0.896, 0.846, 0.789, 0.798, 0.714,
0.803, (5.6854)+(0.0250)Ser+(−0.0176)Ala+(−0.0157)
Pro+(−0.0377)Val+(0.1335)Ile+(−0.0111)Trp; 0.870,
0.898, 0.827, 0.790, 0.790, 0.728, 0.805, (4.9798)+
(0.0245)Ser+(−0.0186)Ala+(−0.0457)Cit+(−0.0089)
Pro+(0.1426)Ile+(−0.0641)Leu; 0.870, 0.900, 0.840,
0.826, 0.838, 0.770, 0.836, (4.3138)+(0.0102)Gln+(−
0.0184)Ala+(−0.0642)Cit+(−0.1069)Met+(0.1371)Ile+
(−0.0659)Leu; 0.870, 0.898, 0.818, 0.814, 0.824, 0.754,
0.825, (4.7702)+(−0.0547)Asn+(0.0099)Gln+(−
0.0193)Ala+(−0.0636)Cit+(0.1331)Ile+(−0.0653)Leu;
0.870, 0.897, 0.850, 0.791, 0.798, 0.721, 0.805,
(7.0384)+(−0.0404)Asn+(0.0099)Gly+(−0.0180)Ala+
(−0.0363)Cit+(−0.0356)Val+(0.1222)Ile; 0.870, 0.901,
0.866, 0.804, 0.794, 0.762, 0.819, (7.2269)+(0.0258)
Thr+(−0.0184)Ala+(0.0510)Tyr+(−0.0490)Val+(−
0.2458)Met+(0.1496)Ile; 0.870, 0.896, 0.842, 0.782,
0.793, 0.703, 0.797, (5.5448)+(0.0236)Ser+(−0.0181)
Ala+(−0.0155)Pro+(−0.0399)Val+(0.0055)Orn+
(0.1345)Ile; 0.870, 0.894, 0.846, 0.772, 0.772, 0.704,
0.790, (5.3689)+(0.0186)Ser+(−0.0212)Ala+(−0.0488)
Cit+(0.0156)Arg+(−0.0351)Val+(0.1190)Ile; 0.869,
0.895, 0.833, 0.770, 0.772, 0.696, 0.788, (5.0899)+
(0.0216)Ser+(0.0005)Gly+(−0.0206)Ala+(−0.0349)
Val+(0.1106)Ile; 0.869, 0.901, 0.851, 0.797, 0.788,
0.750, 0.813, (7.1204)+(−0.0191)Ala+(0.0259)Arg+
(0.0537)Tyr+(−0.0490)Val+(−0.2142)Met+(0.1507)Ile

List (2) of Logistic Regression Equations Searched in Example 7

The logistic regression equations searched in Example 7 above are listed below. Before each equation, "the value of ROC_AUC for the pancreatic cancer group and the prostatic cancer group with validation", "the value of ROC_AUC for the pancreatic cancer group and the prostatic cancer group without validation", "the value of ROC_AUC for the pancreatic cancer group and the healthy group", "the value of ROC_AUC for the pancreatic cancer group and the other cancers group", "the value of ROC_AUC for the pancreatic cancer group and the lung cancer group", "the value of ROC_AUC for the pancreatic cancer group and the colorectal cancer group", and "the average value of the value of ROC_AUC for the pancreatic cancer group and the lung cancer group, the value of ROC_AUC for the pancreatic cancer group and the colorectal cancer group, and the value of ROC_AUC for the pancreatic cancer group and the prostatic cancer group" obtained for the equation are additionally listed.

0.787, 0.856, 0.911, 0.807, 0.794, 0.798, 0.816,
(−0.4061)+(0.0399)Ser+(−0.2141)Met+(0.1298)Ile+(−
0.0658)Leu+(0.0402)Phe+(−0.0539)Trp; 0.845, 0.887,
0.907, 0.802, 0.793, 0.768, 0.816, (1.4919)+(0.0330)
Ser+(0.0236)Thr+(−0.0587)Val+(−0.3796)Met+
(0.1721)Ile+(0.0320)Phe; 0.766, 0.842, 0.907, 0.810,
0.786, 0.825, 0.818, (2.7409)+(0.0412)Ser+(−0.0481)
His+(0.0105)Thr+(−0.1506)Met+(0.0196)Phe+(−
0.0683)Trp; 0.872, 0.909, 0.906, 0.801, 0.796, 0.747,
0.817, (3.3965)+(0.0311)Ser+(0.0246)Thr+(−0.0128)
Ala+(−0.0466)Val+(−0.2635)Met+(0.1591)Ile; 0.847,
0.888, 0.906, 0.802, 0.791, 0.769, 0.816, (1.4566)+
(0.0427)Ser+(−0.0507)Val+(−0.2852)Met+(0.1486)
Ile+(0.0258)Phe+(−0.0079)Trp; 0.870, 0.913, 0.906,
0.806, 0.790, 0.766, 0.823, (2.4936)+(0.0432)Ser+(−
0.0118)Ala+(0.0462)Tyr+(−0.0485)Val+(−0.2565)
Met+(0.1511)Ile; 0.840, 0.884, 0.906, 0.804, 0.794,
0.774, 0.817, (0.1031)+(0.0419)Ser+(−0.0611)Val+(−
0.3616)Met+(0.0157)Lys+(0.1732)Ile+(0.0341)Phe;
0.837, 0.890, 0.905, 0.800, 0.788, 0.766, 0.814,
(1.1161)+(0.0402)Ser+(0.0132)Arg+(−0.0550)Val+(−
0.3329)Met+(0.1633)Ile+(0.0280)Phe; 0.859, 0.890,
0.905, 0.800, 0.783, 0.774, 0.816, (2.8315)+(0.0312)
Ser+(0.0223)Thr+(−0.0416)Cit+(−0.0522)Val+(−
0.3341)Met+(0.1697)Ile; 0.840, 0.887, 0.904, 0.798, 0.786, 0.765, 0.813, (2.5575)+(0.0314)Ser+(0.0204)
Thr+(−0.0510)Val+(−0.3475)Met+(0.1657)Ile+(−0.0106)Trp; 0.871, 0.909, 0.904, 0.809, 0.804, 0.758,
0.824, (2.5705)+(0.0423)Ser+(−0.0115)Ala+(−0.0427)
Val+(−0.1878)Met+(0.1360)Ile+(0.0134)Phe; 0.769,
0.845, 0.904, 0.837, 0.833, 0.839, 0.839, (3.9929)+
(0.0400)Ser+(0.0086)Thr+(−0.0166)Val+(−0.1972)
Met+(0.0304)Phe+(−0.0775)Trp; 0.757, 0.832, 0.903,
0.846, 0.848, 0.850, 0.843, (0.6788)+(0.0326)Ser+
(0.0074)Gln+(−0.2186)Met+(0.0155)Phe+(−0.1029)
Trp; 0.768, 0.840, 0.903, 0.797, 0.769, 0.813, 0.807,
(0.1065)+(0.0395)Ser+(0.0074)Thr+(−0.2230)Met+
(0.0523)Ile+(0.0032)Phe+(−0.0885)Trp; 0.783, 0.851,
0.903, 0.839, 0.834, 0.840, 0.842, (0.7685)+(0.0313)
Ser+(0.0107)Gln+(−0.0649)His+(−0.1807)Met+
(0.0214)Phe+(−0.0676)Trp; 0.865, 0.912, 0.902, 0.802,
0.793, 0.753, 0.819, (2.8640)+(0.0372)Ser+(−0.0135)
Ala+(0.0205)Arg+(−0.0437)Val+(−0.2293)Met+
(0.1532)Ile; 0.764, 0.844, 0.902, 0.797, 0.769, 0.809,
0.807, (0.2468)+(0.0393)Ser+(0.0081)Thr+(−0.2243)
Met+(−0.0048)Orn+(0.0562)Ile+(−0.0875)Trp; 0.753,
0.826, 0.902, 0.826, 0.816, 0.838, 0.827, (2.3570)+
(0.0391)Ser+(0.0053)Thr+(−0.1808)Met+(0.0138)
Phe+(−0.0941)Trp; 0.849, 0.893, 0.902, 0.798, 0.774,
0.778, 0.815, (1.4618)+(0.0434)Ser+(0.0469)Tyr+(−0.0595)Val+(−0.3666)Met+(0.1679)Ile+(0.0143)Phe;
0.845, 0.888, 0.902, 0.818, 0.821, 0.776, 0.828,
(0.1275)+(0.0321)Ser+(0.0069)Gln+(−0.0548)Val+(−0.3477)Met+(0.1541)Ile+(0.0292)Phe; 0.750, 0.829,
0.902, 0.829, 0.820, 0.841, 0.830, (2.7046)+(0.0394)
Ser+(−0.0334)Asn+(0.0075)Thr+(−0.1510)Met+
(0.0156)Phe+(−0.0941)Trp; 0.849, 0.885, 0.901, 0.799,
0.788, 0.765, 0.813, (1.3699)+(0.0422)Ser+(−0.0521)
Val+(−0.2912)Met+(0.1519)Ile+(0.0255)Phe; 0.845,
0.894, 0.901, 0.791, 0.772, 0.759, 0.808, (3.2528)+
(0.0397)Ser+(−0.0098)Gly+(0.0290)Thr+(−0.0550)
Val+(−0.3919)Met+(0.1778)Ile; 0.845, 0.888, 0.901,
0.797, 0.785, 0.764, 0.812, (1.4189)+(0.0428)Ser+(−0.0176)Asn+(−0.0520)Val+(−0.2679)Met+(0.1528)
Ile+(0.0258)Phe; 0.778, 0.846, 0.901, 0.784, 0.746,
0.800, 0.797, (1.0109)+(0.0400)Ser+(−0.0431)His+
(0.0099)Thr+(−0.1847)Met+(0.0516)Ile+(−0.0627)
Trp; 0.776, 0.840, 0.901, 0.796, 0.767, 0.810, 0.806,
(0.2150)+(0.0392)Ser+(0.0071)Thr+(−0.2212)Met+
(0.0532)Ile+(−0.0873)Trp; 0.766, 0.844, 0.901, 0.813,
0.795, 0.819, 0.819, (0.8719)+(0.0382)Ser+(0.0063)
Thr+(−0.0121)Pro+(−0.1778)Met+(0.0598)Ile+(−0.0914)Trp; 0.755, 0.841, 0.901, 0.796, 0.768, 0.809,
0.806, (0.2359)+(0.0392)Ser+(0.0070)Thr+(−0.0015)
Tyr+(−0.2193)Met+(0.0533)Ile+(−0.0869)Trp; 0.842,
0.885, 0.900, 0.799, 0.788, 0.765, 0.813, (1.3987)+
(0.0418)Ser+(−0.0522)Val+(−0.2913)Met+(0.0033)
Orn+(0.1505)Ile+(0.0246)Phe; 0.840, 0.885, 0.900,
0.803, 0.791, 0.774, 0.817, (1.5211)+(0.0390)Ser+(−0.0520)Val+(−0.3244)Met+(0.0134)Lys+(0.1634)Ile+
(−0.0146)Trp; 0.838, 0.888, 0.900, 0.799, 0.784, 0.768,
0.814, (1.7262)+(0.0473)Ser+(−0.0041)Gly+(−0.0517)
Val+(−0.2911)Met+(0.1510)Ile+(0.0239)Phe; 0.765,
0.836, 0.900, 0.798, 0.773, 0.812, 0.807, (0.0541)+
(0.0418)Ser+(−0.2012)Met+(0.0007)Lys+(0.0512)Ile+
(0.0015)Phe+(−0.0851)Trp; 0.755, 0.836, 0.900, 0.798,
0.770, 0.814, 0.807, (−0.0500)+(0.0412)Ser+(0.0061)
Arg+(−0.2132)Met+(0.0536)Ile+(0.0022)Phe+(−0.0885)Trp; 0.852, 0.887, 0.900, 0.803, 0.791, 0.774,
0.817, (1.7457)+(0.0427)Ser+(−0.0341)Cit+(−0.0509)
Val+(−0.2679)Met+(0.1506)Ile+(0.0246)Phe; 0.768,
0.839, 0.900, 0.837, 0.836, 0.838, 0.837, (3.7251)+
(0.0418)Ser+(−0.0166)Val+(−0.1762)Met+(0.0031)
Lys+(0.0287)Phe+(−0.0760)Trp; 0.765, 0.841, 0.900,
0.796, 0.768, 0.809, 0.806, (0.3181)+(0.0390)Ser+
(0.0078)Thr+(−0.2195)Met+(−0.0013)Ile+(0.0529)
Ile+(−0.0861)Trp; 0.753, 0.837, 0.900, 0.798, 0.773,
0.811, 0.807, (0.1262)+(0.0418)Ser+(−0.0031)Tyr+(−0.1953)Met+(0.0511)Ile+(0.0022)Phe+(−0.0836)Trp;
0.767, 0.849, 0.900, 0.815, 0.800, 0.817, 0.822,
(0.7019)+(0.0407)Ser+(−0.0123)Pro+(−0.1573)Met+
(0.0573)Ile+(0.0038)Phe+(−0.0896)Trp; 0.783, 0.846,
0.899, 0.785, 0.748, 0.803, 0.799, (0.7119)+(0.0440)
Ser+(−0.0418)His+(−0.1561)Met+(0.0480)Ile+
(0.0049)Phe+(−0.0595)Trp; 0.832, 0.891, 0.899, 0.796,
0.784, 0.759, 0.811, (1.8597)+(0.0323)Ser+(0.0144)
Thr+(−0.0557)Val+(−0.3670)Met+(0.0086)Lys+
(0.1750)Ile; 0.853, 0.894, 0.899, 0.799, 0.779, 0.773,
0.815, (2.5079)+(0.0358)Ser+(−0.0597)Cit+(0.0250)
Arg+(−0.0515)Val+(−0.3189)Met+(0.1728)Ile; 0.763,
0.836, 0.899, 0.808, 0.783, 0.828, 0.816, (2.3381)+
(0.0437)Ser+(−0.0492)His+(−0.1301)Met+(0.0054)
Lys+(0.0179)Phe+(−0.0679)Trp; 0.753, 0.838, 0.899,
0.797, 0.770, 0.812, 0.807, (0.0362)+(0.0413)Ser+
(0.0071)Arg+(−0.2149)Met+(−0.0048)Orn+(0.0575)
Ile+(−0.0880)Trp; 0.831, 0.888, 0.899, 0.793, 0.780,
0.757, 0.808, (2.3644)+(0.0309)Ser+(0.0180)Thr+
(0.0035)Arg+(−0.0531)Val+(−0.3565)Met+(0.1710)
Ile; 0.853, 0.892, 0.899, 0.796, 0.780, 0.764, 0.812,
(2.5496)+(0.0324)Ser+(0.0274)Thr+(−0.0707)Val+(−0.4062)Met+(0.1451)Ile+(0.0461)Leu; 0.851, 0.893,
0.899, 0.797, 0.770, 0.782, 0.815, (1.9332)+(0.0425)
Ser+(0.0529)Tyr+(−0.0570)Val+(−0.3650)Met+
(0.1672)Ile+(−0.0077)Trp; 0.841, 0.887, 0.899, 0.798,
0.786, 0.764, 0.812, (1.5611)+(0.0426)Ser+(−0.0554)
Val+(−0.2950)Met+(0.1435)Ile+(0.0122)Leu+(0.0198)
Phe; 0.772, 0.836, 0.899, 0.797, 0.771, 0.811, 0.806,
(0.1129)+(0.0416)Ser+(−0.2006)Met+(0.0006)Lys+
(0.0516)Ile+(−0.0846)Trp; 0.763, 0.837, 0.899, 0.797,
0.769, 0.812, 0.806, (0.0333)+(0.0410)Ser+(0.0059)
Arg+(−0.2123)Met+(0.0542)Ile+(−0.0877)Trp; 0.754,
0.839, 0.899, 0.798, 0.770, 0.813, 0.807, (0.0984)+
(0.0410)Ser+(0.0065)Arg+(−0.2105)Met+(−0.0010)
Lys+(0.0542)Ile+(−0.0868)Trp; 0.792, 0.851, 0.899,
0.803, 0.767, 0.826, 0.814, (0.8107)+(0.0383)Ser+
(0.0108)Thr+(−0.0446)Cit+(−0.2057)Met+(0.0551)
Ile+(−0.0874)Trp; 0.833, 0.882, 0.899, 0.820, 0.798,
0.815, 0.832, (4.9562)+(0.0414)Ser+(0.0278)Thr+(−0.0638)Val+(−0.3446)Met+(0.0994)Leu+(−0.0711)
Trp; 0.825, 0.886, 0.899, 0.799, 0.785, 0.770, 0.814,
(2.1351)+(0.0379)Ser+(0.0123)Arg+(−0.0482)Val+(−0.3089)Met+(0.1579)Ile+(−0.0124)Trp; 0.782, 0.857,
0.899, 0.795, 0.771, 0.795, 0.807, (0.5033)+(0.0376)
Ser+(0.0252)Tyr+(−0.2367)Met+(0.1213)Ile+(−0.0531)Leu+(−0.0562)Trp; 0.766, 0.838, 0.899, 0.800,
0.775, 0.812, 0.808, (0.1040)+(0.0421)Ser+(−0.1990)
Met+(−0.0026)Orn+(0.0523)Ile+(0.0020)Phe+(−0.0842)Trp; 0.842, 0.896, 0.899, 0.811, 0.813, 0.759,
0.823, (2.2023)+(0.0398)Ser+(−0.0153)Pro+(−0.0542)
Val+(−0.2462)Met+(0.1642)Ile+(0.0285)Phe; 0.838,
0.886, 0.898, 0.793, 0.780, 0.758, 0.808, (2.4345)+
(0.0307)Ser+(0.0196)Thr+(−0.0529)Val+(−0.3523)
Met+(0.0013)Orn+(0.1689)Ile; 0.779, 0.836, 0.898,
0.799, 0.773, 0.812, 0.807, (0.1169)+(0.0418)Ser+(−0.1989)Met+(0.0510)Ile+(0.0013)Phe+(−0.0842)Trp;
0.760, 0.838, 0.898, 0.809, 0.786, 0.825, 0.817,
(2.6855)+(0.0431)Ser+(−0.0468)His+(0.0046)Arg+(−0.1275)Met+(0.0172)Phe+(−0.0652)Trp; 0.755, 0.836,
0.898, 0.797, 0.772, 0.810, 0.806, (0.1422)+(0.0416)

Ser+(−0.0019)Tyr+(−0.1981)Met+(0.0006)Lys+
(0.0518)Ile+(−0.0840)Trp; 0.847, 0.887, 0.898, 0.793,
0.781, 0.757, 0.808, (2.4351)+(0.0308)Ser+(0.0198)
Thr+(−0.0529)Val+(−0.3530)Met+(0.1697)Ile; 0.839,
0.883, 0.898, 0.802, 0.795, 0.767, 0.815, (1.3018)+
(0.0415)Ser+(0.0135)His+(−0.0562)Val+(−0.3154)
Met+(0.1609)Ile+(0.0259)Phe; 0.830, 0.886, 0.898,
0.795, 0.783, 0.761, 0.810, (1.4446)+(0.0374)Ser+
(0.0048)Arg+(−0.0545)Val+(−0.3403)Met+(0.0111)
Lys+(0.1701)Ile; 0.769, 0.837, 0.898, 0.798, 0.773,
0.810, 0.807, (0.1887)+(0.0416)Ser+(−0.0020)Tyr+(−
0.1962)Met+(0.0517)Ile+(−0.0832)Trp; 0.761, 0.826,
0.898, 0.826, 0.819, 0.835, 0.827, (2.3360)+(0.0405)
Ser+(−0.1633)Met+(0.0123)Phe+(−0.0909)Trp; 0.753,
0.838, 0.898, 0.796, 0.768, 0.811, 0.805, (0.1271)+
(0.0394)Ser+(0.0055)Thr+(0.0036)Arg+(−0.2243)
Met+(0.0544)Ile+(−0.0889)Trp; 0.770, 0.845, 0.898,
0.783, 0.743, 0.804, 0.797, (0.7499)+(0.0421)Ser+(−
0.0450)His+(0.0103)Arg+(−0.1751)Met+(0.0545)Ile+
(−0.0634)Trp; 0.872, 0.909, 0.898, 0.804, 0.798, 0.752,
0.820, (1.9444)+(0.0409)Ser+(−0.0141)Ala+(−0.0498)
Val+(−0.2446)Met+(0.0197)Lys+(0.1613)Ile; 0.787,
0.851, 0.898, 0.803, 0.765, 0.830, 0.815, (0.6431)+
(0.0391)Ser+(−0.0590)Cit+(0.0211)Arg+(−0.2103)
Met+(0.0617)Ile+(−0.0960)Trp; 0.783, 0.851, 0.898,
0.796, 0.779, 0.788, 0.806, (0.7806)+(0.0359)Ser+
(0.0029)Thr+(−0.2110)Met+(0.1124)Ile+(−0.0447)
Leu+(−0.0553)Trp; 0.751, 0.826, 0.898, 0.826, 0.820,
0.836, 0.827, (2.3934)+(0.0405)Ser+(−0.1612)Met+(−
0.0008)Lys+(0.0120)Phe+(−0.0899)Trp; 0.767, 0.837,
0.898, 0.793, 0.761, 0.813, 0.804, (0.7266)+(0.0451)
Ser+(−0.0064)Gly+(0.0122)Thr+(−0.2369)Met+
(0.0535)Ile+(−0.0895)Trp; 0.755, 0.850, 0.898, 0.814,
0.797, 0.816, 0.821, (0.7671)+(0.0404)Ser+(−0.0125)
Pro+(0.0052)Tyr+(−0.1625)Met+(0.0579)Ile+(−
0.0898)Trp; 0.771, 0.843, 0.898, 0.838, 0.837, 0.835,
0.838, (4.0479)+(0.0425)Ser+(−0.0215)Asn+(−
0.0157)Val+(−0.1429)Met+(0.0277)Phe+(−0.0715)
Trp; 0.787, 0.838, 0.898, 0.798, 0.773, 0.811, 0.807,
(0.1611)+(0.0417)Ser+(−0.1986)Met+(0.0514)Ile+(−
0.0838)Trp; 0.765, 0.840, 0.898, 0.819, 0.808, 0.822,
0.823, (−1.3681)+(0.0342)Ser+(0.0072)Gln+(−0.2506)
Met+(0.0486)Ile+(0.0053)Phe+(−0.0963)Trp; 0.762,
0.838, 0.898, 0.798, 0.773, 0.811, 0.807, (0.1189)+
(0.0419)Ser+(−0.2007)Met+(−0.0023)Orn+(0.0007)
Lys+(0.0530)Ile+(−0.0844)Trp; 0.762, 0.845, 0.898,
0.811, 0.794, 0.815, 0.818, (0.7179)+(0.0391)Ser+
(0.0082)Arg+(−0.0125)Pro+(−0.1741)Met+(0.0620)
Ile+(−0.0939)Trp; 0.846, 0.894, 0.898, 0.794, 0.764,
0.778, 0.812, (0.8674)+(0.0411)Ser+(0.0658)Tyr+(−
0.0692)Val+(−0.4644)Met+(0.0167)Lys+(0.1956)Ile;
0.772, 0.846, 0.898, 0.783, 0.741, 0.807, 0.798,
(0.7633)+(0.0441)Ser+(−0.0443)His+(0.0124)Tyr+(−
0.1685)Met+(0.0480)Ile+(−0.0602)Trp; 0.774, 0.846,
0.898, 0.819, 0.810, 0.816, 0.824, (3.7367)+(0.0442)
Ser+(−0.0356)His+(−0.0123)Val+(−0.1301)Met+
(0.0268)Phe+(−0.0542)Trp; 0.751, 0.826, 0.897, 0.825,
0.818, 0.835, 0.826, (2.2889)+(0.0405)Ser+(−0.1639)
Met+(0.0011)Leu+(0.0113)Phe+(−0.0913)Trp; 0.766,
0.836, 0.897, 0.807, 0.786, 0.821, 0.814, (2.6417)+
(0.0433)Ser+(0.0083)Asn+(−0.0464)His+(−0.1277)
Met+(0.0158)Phe+(−0.0625)Trp; 0.761, 0.826, 0.897,
0.829, 0.823, 0.838, 0.829, (2.6077)+(0.0411)Ser+(−
0.0261)Asn+(−0.1345)Met+(0.0131)Phe+(−0.0898)
Trp; 0.832, 0.892, 0.897, 0.801, 0.797, 0.756, 0.815,
(3.3038)+(0.0284)Ser+(0.0196)Thr+(−0.0147)Pro+(−
0.0547)Val+(−0.3097)Met+(0.1831)Ile; 0.782, 0.850,
0.897, 0.796, 0.779, 0.789, 0.806, (0.5053)+(0.0367)
Ser+(−0.2127)Met+(0.0039)Lys+(0.1158)Ile+(−
0.0473)Leu+(−0.0569)Trp; 0.776, 0.844, 0.897, 0.782,
0.744, 0.799, 0.796, (0.8779)+(0.0432)Ser+(−0.0419)
His+(−0.1553)Met+(0.0024)Orn+(0.0482)Ile+(−
0.0582)Trp; 0.770, 0.837, 0.897, 0.809, 0.788, 0.823,
0.816, (2.7102)+(0.0435)Ser+(−0.0451)His+(−0.1198)
Met+(0.0160)Phe+(−0.0629)Trp; 0.852, 0.889, 0.897,
0.801, 0.786, 0.774, 0.816, (1.7797)+(0.0393)Ser+(−
0.0363)Cit+(−0.0537)Val+(−0.3102)Met+(0.0125)
Lys+(0.1682)Ile; 0.766, 0.842, 0.897, 0.829, 0.809,
0.849, 0.833, (2.8945)+(0.0394)Ser+(0.0095)Thr+(−
0.0428)Cit+(−0.1675)Met+(0.0161)Phe+(−0.0970)
Trp; 0.757, 0.838, 0.897, 0.798, 0.773, 0.810, 0.807,
(0.1935)+(0.0418)Ser+(−0.0016)Tyr+(−0.1966)Met+
(−0.0021)Orn+(0.0528)Ile+(−0.0832)Trp; 0.769,
0.842, 0.897, 0.796, 0.770, 0.806, 0.806, (0.5416)+
(0.0393)Ser+(−0.0291)Asn+(0.0084)Thr+(−0.1912)
Met+(0.0538)Ile+(−0.0869)Trp; 0.871, 0.910, 0.897,
0.808, 0.801, 0.761, 0.824, (3.3274)+(0.0409)Ser+(−
0.0117)Ala+(−0.0293)Cit+(−0.0398)Val+(−0.1603)
Met+(0.1354)Ile; 0.859, 0.895, 0.897, 0.795, 0.765,
0.780, 0.814, (2.3171)+(0.0426)Ser+(−0.0369)Cit+
(0.0544)Tyr+(−0.0577)Val+(−0.3487)Met+(0.1682)
Ile; 0.767, 0.848, 0.897, 0.812, 0.798, 0.813, 0.819,
(0.8303)+(0.0401)Ser+(−0.0123)Pro+(−0.1569)Met+
(0.0005)Orn+(0.0582)Ile+(−0.0883)Trp; 0.852, 0.888,
0.897, 0.791, 0.766, 0.770, 0.808, (2.2714)+(0.0316)
Ser+(0.0231)Thr+(0.0575)Tyr+(−0.0649)Val+(−
0.4616)Met+(0.1911)Ile; 0.848, 0.884, 0.897, 0.795,
0.783, 0.762, 0.810, (1.4167)+(0.0382)Ser+(−0.0543)
Val+(−0.3324)Met+(0.0125)Lys+(0.1682)Ile; 0.870,
0.906, 0.897, 0.803, 0.796, 0.754, 0.819, (3.0382)+
(0.0402)Ser+(−0.0120)Ala+(−0.0407)Val+(−0.1802)
Met+(0.0043)Orn+(0.1345)Ile; 0.775, 0.848, 0.897,
0.812, 0.797, 0.812, 0.819, (0.8305)+(0.0402)Ser+(−
0.0122)Pro+(−0.1568)Met+(0.0584)Ile+(−0.0883)Trp;
0.767, 0.849, 0.897, 0.813, 0.800, 0.810, 0.820,
(0.9285)+(0.0402)Ser+(−0.0123)Pro+(−0.1530)Met+
(−0.0012)Lys+(0.0582)Ile+(−0.0868)Trp

List (2) of Linear Discriminants Searched in Example 7

The linear discriminants searched in Example 7 above are listed below. Before each equation, "the value of ROC_AUC for the pancreatic cancer group and the prostatic cancer group with validation", "the value of ROC_AUC for the pancreatic cancer group and the prostatic cancer group without validation", "the value of ROC_AUC for the pancreatic cancer group and the healthy group", "the value of ROC_AUC for the pancreatic cancer group and the other cancers group", "the value of ROC_AUC for the pancreatic cancer group and the lung cancer group", "the value of ROC_AUC for the pancreatic cancer group and the colorectal cancer group", and "the average value of the value of ROC_AUC for the pancreatic cancer group and the lung cancer group, the value of ROC_AUC for the pancreatic cancer group and the colorectal cancer group, and the value of ROC_AUC for the pancreatic cancer group and the prostatic cancer group" obtained for the equation are additionally listed.

0.859, 0.885, 0.925, 0.819, 0.809, 0.795, 0.830, (1.6394)+
(0.0387)Ser+(−0.0455)Val+(−0.2545)Met+(0.1283)
Ile+(0.0546)Phe+(−0.0299)Trp; 0.819, 0.855, 0.925,
0.822, 0.810, 0.820, 0.829, (0.8073)+(0.0364)Ser+(−
0.2030)Met+(0.1178)Ile+(−0.0647)Leu+(0.0578)Phe+
(−0.0648)Trp; 0.861, 0.892, 0.917, 0.807, 0.788, 0.786,
0.822, (1.2830)+(0.0364)Ser+(0.0328)Tyr+(−0.0547)
Val+(−0.3122)Met+(0.1451)Ile+(0.0444)Phe; 0.855, 0.884, 0.917, 0.805, 0.796, 0.772, 0.817, (1.1869)+
(0.0330)Ser+(0.0086)Thr+(−0.0523)Val+(−0.2940)
Met+(0.1427)Ile+(0.0555)Phe; 0.847, 0.881, 0.916,
0.804, 0.796, 0.772, 0.816, (1.1400)+(0.0359)Ser+
(0.0037)Arg+(−0.0511)Val+(−0.2757)Met+(0.1404)
Ile+(0.0531)Phe; 0.852, 0.882, 0.915, 0.816, 0.818,
0.776, 0.825, (0.5185)+(0.0298)Ser+(0.0040)Gln+(−
0.0515)Val+(−0.2886)Met+(0.1379)Ile+(0.0511)Phe;
0.855, 0.885, 0.914, 0.801, 0.787, 0.774, 0.815,
(1.4582)+(0.0381)Ser+(−0.0133)His+(−0.0470)Val+(−
0.2554)Met+(0.1313)Ile+(0.0525)Phe; 0.781, 0.829,
0.914, 0.854, 0.857, 0.865, 0.850, (1.6910)+(0.0271)
Ser+(0.0058)Gln+(−0.1824)Met+(−0.0027)Leu+
(0.0278)Phe+(−0.0977)Trp; 0.863, 0.888, 0.913, 0.802,
0.792, 0.768, 0.816, (1.6900)+(0.0388)Ser+(−0.0430)
Asn+(−0.0504)Val+(−0.2279)Met+(0.1409)Ile+
(0.0530)Phe; 0.851, 0.882, 0.913, 0.805, 0.798, 0.772,
0.817, (0.8294)+(0.0361)Ser+(−0.0528)Val+(−0.2835)
Met+(0.0048)Lys+(0.1426)Ile+(0.0546)Phe; 0.779,
0.823, 0.913, 0.835, 0.826, 0.854, 0.835, (2.6420)+
(0.0366)Ser+(0.0049)Tyr+(−0.1614)Met+(0.0250)
Phe+(−0.0903)Trp; 0.856, 0.879, 0.913, 0.802, 0.794,
0.771, 0.815, (1.2512)+(0.0368)Ser+(−0.0505)Val+(−
0.2680)Met+(0.1384)Ile+(0.0518)Phe; 0.776, 0.824,
0.913, 0.834, 0.827, 0.849, 0.833, (2.6819)+(0.0357)
Ser+(−0.1556)Met+(0.0061)Orn+(−0.0028)Leu+
(0.0262)Phe+(−0.0876)Trp; 0.862, 0.887, 0.913, 0.806,
0.794, 0.777, 0.819, (1.5875)+(0.0375)Ser+(−0.0335)
Cit+(−0.0493)Val+(−0.2533)Met+(0.1395)Ile+
(0.0515)Phe; 0.793, 0.821, 0.912, 0.834, 0.828, 0.850,
0.833, (2.6509)+(0.0366)Ser+(−0.1555)Met+(0.0265)
Phe+(−0.0891)Trp; 0.782, 0.823, 0.912, 0.831, 0.825,
0.845, 0.831, (2.5358)+(0.0361)Ser+(−0.1575)Met+
(0.0056)Orn+(0.0244)Phe+(−0.0884)Trp; 0.773,
0.822, 0.912, 0.837, 0.829, 0.855, 0.836, (2.7656)+
(0.0363)Ser+(0.0057)Tyr+(−0.1606)Met+(−0.0022)
Leu+(0.0264)Phe+(−0.0899)Trp; 0.815, 0.853, 0.912,
0.846, 0.838, 0.854, 0.848, (1.8742)+(0.0274)Ser+
(0.0093)Gln+(−0.0669)His+(−0.1684)Met+(0.0374)
Phe+(−0.0669)Trp; 0.805, 0.845, 0.912, 0.820, 0.796,
0.837, 0.826, (3.4001)+(0.0382)Ser+(−0.0523)His+
(0.0061)Thr+(−0.1457)Met+(0.0379)Phe+(−0.0630)
Trp; 0.791, 0.829, 0.912, 0.852, 0.854, 0.861, 0.848,
(1.5432)+(0.0275)Ser+(0.0058)Gln+(−0.1842)Met+
(0.0258)Phe+(−0.0984)Trp; 0.818, 0.852, 0.912, 0.798,
0.759, 0.820, 0.810, (1.4300)+(0.0432)Ser+(−0.0477)
His+(−0.1657)Met+(0.0415)Ile+(0.0293)Phe+(−
0.0605)Trp; 0.779, 0.829, 0.912, 0.853, 0.856, 0.863,
0.849, (1.5550)+(0.0274)Ser+(0.0059)Gln+(−0.1843)
Met+(−0.0018)Orn+(0.0265)Phe+(−0.0988)Trp;
0.784, 0.823, 0.912, 0.836, 0.830, 0.851, 0.835,
(2.7434)+(0.0364)Ser+(−0.1543)Met+(−0.0016)Leu+
(0.0277)Phe+(−0.0886)Trp; 0.849, 0.879, 0.912, 0.802,
0.793, 0.771, 0.814, (1.2798)+(0.0363)Ser+(−0.0506)
Val+(−0.2678)Met+(0.0040)Orn+(0.1367)Ile+(0.0509)
Phe; 0.776, 0.829, 0.912, 0.851, 0.853, 0.861, 0.848,
(1.5439)+(0.0275)Ser+(0.0058)Gln+(0.0011)Tyr+(−
0.1854)Met+(0.0255)Phe+(−0.0987)Trp; 0.796, 0.841,
0.911, 0.864, 0.867, 0.873, 0.860, (1.9967)+(0.0277)
Ser+(−0.0557)Asn+(0.0072)Gln+(−0.1368)Met+
(0.0276)Phe+(−0.1002)Trp; 0.792, 0.834, 0.911, 0.811,
0.789, 0.830, 0.818, (0.6202)+(0.0402)Ser+(−0.1911)
Met+(−0.0054)Orn+(0.0461)Ile+(0.0222)Phe+(−
0.0873)Trp; 0.853, 0.882, 0.911, 0.802, 0.792, 0.771,
0.815, (1.2814)+(0.0371)Ser+(−0.0525)Val+(−0.2695)
Met+(0.1342)Ile+(0.0070)Leu+(0.0494)Phe; 0.770,
0.822, 0.911, 0.832, 0.824, 0.850, 0.832, (2.5316)+
(0.0361)Ser+(0.0043)Tyr+(−0.1624)Met+(0.0054)
Orn+(0.0231)Phe+(−0.0895)Trp; 0.866, 0.893, 0.911,
0.815, 0.822, 0.760, 0.825, (2.0101)+(0.0383)Ser+(−
0.0194)Pro+(−0.0555)Val+(−0.2381)Met+(0.1692)
Ile+(0.0552)Phe; 0.771, 0.821, 0.911, 0.835, 0.827,
0.853, 0.834, (2.6482)+(0.0373)Ser+(−0.0017)Thr+
(0.0052)Tyr+(−0.1572)Met+(0.0243)Phe+(−0.0895)
Trp; 0.803, 0.842, 0.911, 0.852, 0.853, 0.857, 0.851,
(4.4894)+(0.0357)Ser+(−0.0265)Asn+(−0.0138)Val+
(−0.1282)Met+(0.0413)Phe+(−0.0729)Trp; 0.776,
0.822, 0.910, 0.835, 0.830, 0.850, 0.834, (2.7554)+
(0.0371)Ser+(−0.0016)Thr+(−0.1500)Met+(−0.0017)
Leu+(0.0272)Phe+(−0.0878)Trp; 0.797, 0.840, 0.910,
0.827, 0.814, 0.836, 0.830, (−0.1760)+(0.0313)Ser+
(0.0051)Gln+(−0.2131)Met+(0.0400)Ile+(0.0204)
Phe+(−0.0952)Trp; 0.791, 0.838, 0.910, 0.848, 0.849,
0.852, 0.846, (4.1952)+(0.0342)Ser+(0.0009)Thr+(−
0.0142)Val+(−0.1563)Met+(0.0411)Phe+(−0.0730)
Trp; 0.786, 0.831, 0.910, 0.809, 0.786, 0.829, 0.815,
(0.6370)+(0.0395)Ser+(0.0024)Tyr+(−0.1934)Met+
(0.0432)Ile+(0.0198)Phe+(−0.0875)Trp; 0.855, 0.887,
0.910, 0.804, 0.789, 0.779, 0.818, (1.6257)+(0.0420)
Ser+(−0.0043)Gly+(−0.0499)Val+(−0.2682)Met+
(0.1382)Ile+(0.0491)Phe; 0.802, 0.838, 0.909, 0.847,
0.849, 0.851, 0.846, (4.1917)+(0.0346)Ser+(−0.0142)
Val+(−0.1540)Met+(0.0408)Phe+(−0.0727)Trp; 0.797,
0.845, 0.909, 0.851, 0.846, 0.862, 0.851, (4.2901)+
(0.0344)Ser+(0.0172)Tyr+(−0.0153)Val+(−0.1740)
Met+(0.0367)Phe+(−0.0756)Trp; 0.791, 0.832, 0.909,
0.810, 0.788, 0.827, 0.816, (0.6399)+(0.0397)Ser+(−
0.0004)Thr+(−0.1897)Met+(0.0433)Ile+(0.0204)Phe+
(−0.0867)Trp; 0.783, 0.821, 0.909, 0.833, 0.828, 0.848,
0.832, (2.6569)+(0.0373)Ser+(−0.0016)Thr+(−0.1515)
Met+(0.0260)Phe+(−0.0883)Trp; 0.798, 0.832, 0.909,
0.810, 0.788, 0.827, 0.816, (0.6369)+(0.0395)Ser+(−
0.1907)Met+(0.0433)Ile+(0.0205)Phe+(−0.0869)Trp;
0.788, 0.830, 0.908, 0.810, 0.789, 0.827, 0.815,
(0.6970)+(0.0400)Ser+(−0.0021)Arg+(−0.1869)Met+
(0.0430)Ile+(0.0199)Phe+(−0.0857)Trp; 0.799, 0.841,
0.908, 0.814, 0.787, 0.834, 0.821, (3.1997)+(0.0398)
Ser+(−0.0514)His+(−0.1338)Met+(0.0102)Orn+
(0.0317)Phe+(−0.0594)Trp; 0.793, 0.835, 0.908, 0.808,
0.787, 0.823, 0.815, (1.1478)+(0.0401)Ser+(−0.1769)
Met+(−0.0056)Lys+(0.0437)Ile+(0.0187)Phe+(−
0.0814)Trp; 0.788, 0.828, 0.908, 0.838, 0.831, 0.853,
0.837, (3.0682)+(0.0378)Ser+(−0.0326)Asn+(0.0005)
Thr+(−0.1252)Met+(0.0278)Phe+(−0.0890)Trp; 0.802,
0.845, 0.908, 0.830, 0.819, 0.835, 0.833, (4.3232)+
(0.0385)Ser+(−0.0413)His+(−0.0098)Val+(−0.1342)
Met+(0.0437)Phe+(−0.0549)Trp; 0.800, 0.844, 0.908,
0.819, 0.798, 0.835, 0.826, (3.3748)+(0.0404)Ser+(−
0.0495)His+(0.0004)Arg+(−0.1319)Met+(0.0355)
Phe+(−0.0618)Trp; 0.781, 0.827, 0.908, 0.832, 0.827,
0.843, 0.832, (3.1718)+(0.0365)Ser+(0.0015)Thr+(−
0.1454)Met+(−0.0056)Lys+(0.0252)Phe+(−0.0843)
Trp; 0.785, 0.828, 0.908, 0.836, 0.828, 0.852, 0.836,
(3.0792)+(0.0383)Ser+(−0.0302)Asn+(−0.0020)Arg+
(−0.1229)Met+(0.0269)Phe+(−0.0877)Trp; 0.782,
0.829, 0.908, 0.837, 0.829, 0.853, 0.837, (3.0578)+
(0.0380)Ser+(−0.0324)Asn+(0.0054)Tyr+(−0.1303)
Met+(0.0260)Phe+(−0.0901)Trp; 0.769, 0.819, 0.908,
0.830, 0.824, 0.843, 0.829, (2.5234)+(0.0374)Ser+(−
0.0033)Thr+(−0.1495)Met+(0.0068)Orn+(0.0228)
Phe+(−0.0867)Trp; 0.810, 0.844, 0.908, 0.819, 0.797,
0.836, 0.826, (3.3810)+(0.0405)Ser+(−0.0494)His+(−
0.1313)Met+(0.0353)Phe+(−0.0617)Trp; 0.806, 0.844,
0.908, 0.819, 0.797, 0.836, 0.826, (3.3834)+(0.0405)

Ser+(−0.0002)Asn+(−0.0494)His+(−0.1311)Met+ (0.0353)Phe+(−0.0617)Trp; 0.842, 0.873, 0.908, 0.816, 0.816, 0.784, 0.824, (4.1550)+(0.0238)Thr+(−0.0499) Val+(−0.2634)Met+(0.1320)Ile+(0.0496)Phe+(− 0.0243)Trp; 0.795, 0.828, 0.908, 0.838, 0.831, 0.853, 0.837, (3.0653)+(0.0380)Ser+(−0.0322)Asn+(− 0.1242)Met+(0.0276)Phe+(−0.0888)Trp; 0.788, 0.827, 0.908, 0.838, 0.831, 0.853, 0.837, (3.0623)+(0.0380) Ser+(−0.0322)Asn+(−0.1242)Met+(0.0001)Leu+ (0.0276)Phe+(−0.0888)Trp; 0.803, 0.849, 0.908, 0.818, 0.787, 0.843, 0.826, (3.3971)+(0.0408)Ser+(−0.0528) His+(0.0189)Tyr+(−0.1518)Met+(0.0302)Phe+(− 0.0645)Trp; 0.777, 0.823, 0.907, 0.834, 0.829, 0.849, 0.833, (2.8679)+(0.0374)Ser+(−0.0049)Arg+(−0.1461) Met+(−0.0022)Leu+(0.0265)Phe+(−0.0858)Trp; 0.775, 0.821, 0.907, 0.832, 0.826, 0.848, 0.832, (2.7471)+(0.0375)Ser+(0.0006)Thr+(−0.0050)Arg+(− 0.1491)Met+(0.0251)Phe+(−0.0867)Trp; 0.780, 0.821, 0.907, 0.832, 0.826, 0.846, 0.831, (2.7438)+(0.0377) Ser+(−0.0047)Arg+(−0.1479)Met+(0.0250)Phe+(− 0.0865)Trp; 0.800, 0.845, 0.907, 0.867, 0.878, 0.864, 0.862, (3.0948)+(0.0245)Ser+(0.0063)Gln+(−0.0151) Val+(−0.1849)Met+(0.0410)Phe+(−0.0817)Trp; 0.861, 0.888, 0.906, 0.808, 0.795, 0.779, 0.821, (3.3913)+ (0.0305)Ser+(0.0041)Thr+(−0.0388)Val+(−0.2230) Met+(0.1218)Ile+(−0.0241)Trp; 0.790, 0.827, 0.906, 0.833, 0.827, 0.845, 0.833, (3.1423)+(0.0371)Ser+(− 0.1424)Met+(−0.0053)Lys+(0.0248)Phe+(−0.0839) Trp; 0.781, 0.827, 0.906, 0.833, 0.827, 0.845, 0.833, (3.1421)+(0.0371)Ser+(−0.1424)Met+(−0.0053)Lys+ (0.0000)Leu+(0.0248)Phe+(−0.0839)Trp; 0.785, 0.831, 0.906, 0.850, 0.856, 0.853, 0.847, (2.1609)+ (0.0273)Ser+(0.0064)Gln+(−0.1677)Met+(−0.0079) Lys+(0.0233)Phe+(−0.0918)Trp; 0.781, 0.824, 0.906, 0.833, 0.826, 0.849, 0.833, (2.9560)+(0.0374)Ser+(− 0.0372)Asn+(−0.1222)Met+(0.0084)Orn+(0.0246) Phe+(−0.0878)Trp; 0.777, 0.828, 0.906, 0.833, 0.825, 0.847, 0.833, (3.1277)+(0.0371)Ser+(0.0038)Tyr+(− 0.1471)Met+(−0.0052)Lys+(0.0237)Phe+(−0.0850) Trp; 0.772, 0.823, 0.906, 0.832, 0.825, 0.848, 0.832, (2.7349)+(0.0377)Ser+(−0.0047)Arg+(0.0049)Tyr+(− 0.1538)Met+(0.0235)Phe+(−0.0878)Trp; 0.805, 0.845, 0.906, 0.819, 0.798, 0.835, 0.826, (3.4430)+(0.0405) Ser+(−0.0489)His+(−0.1297)Met+(−0.0007)Lys+ (0.0350)Phe+(−0.0612)Trp; 0.804, 0.845, 0.906, 0.820, 0.808, 0.822, 0.825, (1.1919)+(0.0410)Ser+(−0.0151) Pro+(−0.1612)Met+(0.0598)Ile+(0.0208)Phe+(− 0.0943)Trp; 0.803, 0.843, 0.906, 0.814, 0.789, 0.832, 0.822, (3.1179)+(0.0413)Ser+(−0.0509)His+(−0.1343) Met+(0.0051)Leu+(0.0318)Phe+(−0.0623)Trp; 0.770, 0.819, 0.906, 0.827, 0.821, 0.839, 0.827, (2.6188)+ (0.0374)Ser+(−0.0067)Arg+(−0.1474)Met+(0.0080) Orn+(0.0213)Phe+(−0.0845)Trp; 0.794, 0.839, 0.906, 0.847, 0.848, 0.851, 0.846, (4.3044)+(0.0348)Ser+(− 0.0138)Val+(−0.1499)Met+(−0.0017)Lys+(0.0398) Phe+(−0.0715)Trp; 0.800, 0.835, 0.906, 0.811, 0.788, 0.828, 0.817, (1.0631)+(0.0415)Ser+(−0.0424)Asn+(− 0.1515)Met+(0.0459)Ile+(0.0216)Phe+(−0.0864)Trp; 0.796, 0.841, 0.906, 0.842, 0.840, 0.845, 0.842, (4.1524)+(0.0328)Ser+(−0.0168)Val+(−0.1591)Met+ (0.0156)Orn+(0.0374)Phe+(−0.0679)Trp; 0.779, 0.828, 0.905, 0.833, 0.826, 0.844, 0.833, (3.1338)+ (0.0375)Ser+(−0.0019)Arg+(−0.1406)Met+(−0.0048) Lys+(0.0244)Phe+(−0.0834)Trp; 0.778, 0.825, 0.905, 0.829, 0.823, 0.839, 0.829, (3.0497)+(0.0366)Ser+(− 0.1434)Met+(0.0071)Orn+(−0.0058)Lys+(0.0219) Phe+(−0.0826)Trp; 0.888, 0.911, 0.905, 0.814, 0.811, 0.763, 0.828, (3.9212)+(0.0380)Ser+(−0.0160)Ala+(− 0.0426)Val+(−0.1846)Met+(0.1388)Ile+(0.0358)Phe; 0.866, 0.897, 0.905, 0.811, 0.787, 0.796, 0.827, (3.1432)+(0.0334)Ser+(0.0477)Tyr+(−0.0449)Val+(− 0.2823)Met+(0.1298)Ile+(−0.0300)Trp; 0.784, 0.832, 0.904, 0.853, 0.859, 0.858, 0.850, (1.4842)+(0.0295) Ser+(0.0063)Gln+(−0.0064)Thr+(−0.1698)Met+ (0.0236)Phe+(−0.0961)Trp; 0.795, 0.838, 0.904, 0.845, 0.844, 0.851, 0.844, (4.4818)+(0.0350)Ser+(−0.0281) Cit+(−0.0131)Val+(−0.1413)Met+(0.0402)Phe+(− 0.0715)Trp; 0.786, 0.826, 0.904, 0.836, 0.831, 0.848, 0.835, (3.4140)+(0.0382)Ser+(−0.0284)Asn+(− 0.1173)Met+(−0.0043)Lys+(0.0261)Phe+(−0.0847) Trp; 0.788, 0.836, 0.904, 0.845, 0.846, 0.849, 0.844, (4.2580)+(0.0354)Ser+(−0.0039)Arg+(−0.0141)Val+ (−0.1477)Met+(0.0394)Phe+(−0.0707)Trp; 0.863, 0.888, 0.903, 0.810, 0.794, 0.787, 0.823, (3.6413)+ (0.0330)Ser+(−0.0331)Cit+(−0.0376)Val+(−0.1994) Met+(0.1223)Ile+(−0.0213)Trp; 0.769, 0.822, 0.903, 0.831, 0.822, 0.849, 0.831, (3.0434)+(0.0416)Ser+(− 0.0042)Gly+(0.0011)Tyr+(−0.1575)Met+(0.0237) Phe+(−0.0875)Trp; 0.858, 0.887, 0.903, 0.806, 0.793, 0.778, 0.819, (3.3252)+(0.0317)Ser+(−0.0392)Val+(− 0.2144)Met+(0.0077)Orn+(0.1179)Ile+(−0.0221)Trp; 0.794, 0.835, 0.903, 0.806, 0.781, 0.824, 0.813, (1.0512)+(0.0454)Ser+(−0.0049)Gly+(−0.1923)Met+ (0.0443)Ile+(0.0175)Phe+(−0.0847)Trp; 0.791, 0.837, 0.903, 0.844, 0.841, 0.852, 0.843, (4.4934)+(0.0388) Ser+(−0.0036)Gly+(−0.0138)Val+(−0.1546)Met+ (0.0383)Phe+(−0.0715)Trp; 0.786, 0.833, 0.903, 0.852, 0.857, 0.857, 0.849, (1.5600)+(0.0284)Ser+(0.0071) Gln+(−0.0128)Arg+(−0.1697)Met+(0.0216)Phe+(− 0.0935)Trp; 0.772, 0.823, 0.903, 0.830, 0.821, 0.848, 0.830, (3.0737)+(0.0412)Ser+(−0.0046)Gly+(0.0019) Thr+(−0.1612)Met+(0.0244)Phe+(−0.0880)Trp; 0.783, 0.822, 0.903, 0.831, 0.822, 0.849, 0.831, (3.0498)+ (0.0416)Ser+(−0.0043)Gly+(−0.1562)Met+(0.0240) Phe+(−0.0873)Trp; 0.792, 0.836, 0.903, 0.836, 0.824, 0.854, 0.838, (3.0762)+(0.0358)Ser+(−0.0372)Cit+ (0.0053)Arg+(−0.1472)Met+(0.0288)Phe+(−0.0888) Trp; 0.777, 0.822, 0.903, 0.833, 0.825, 0.849, 0.832, (3.1720)+(0.0414)Ser+(−0.0043)Gly+(−0.1547)Met+ (−0.0021)Leu+(0.0255)Phe+(−0.0866)Trp; 0.771, 0.821, 0.903, 0.830, 0.821, 0.847, 0.830, (3.0605)+ (0.0417)Ser+(−0.0040)Gly+(−0.0020)Arg+(−0.1530) Met+(0.0235)Phe+(−0.0863)Trp; 0.785, 0.836, 0.903, 0.853, 0.852, 0.863, 0.851, (1.9995)+(0.0342)Ser+(− 0.0072)Gly+(0.0070)Gln+(−0.1910)Met+(0.0214) Phe+(−0.0972)Trp; 0.780, 0.831, 0.903, 0.839, 0.837, 0.846, 0.838, (3.3346)+(0.0361)Ser+(−0.0097)Pro+(− 0.1308)Met+(0.0080)Orn+(0.0251)Phe+(−0.0934)Trp; 0.819, 0.858, 0.902, 0.813, 0.790, 0.819, 0.822, (2.2718)+(0.0320)Ser+(0.0294)Tyr+(−0.2078)Met+ (0.1025)Ile+(−0.0485)Leu+(−0.0652)Trp; 0.855, 0.888, 0.902, 0.807, 0.795, 0.777, 0.820, (3.3430)+ (0.0323)Ser+(0.0006)Arg+(−0.0384)Val+(−0.2135) Met+(0.1206)Ile+(−0.0235)Trp; 0.821, 0.851, 0.902, 0.810, 0.796, 0.805, 0.817, (2.3989)+(0.0319)Ser+(− 0.1700)Met+(0.0944)Ile+(−0.0402)Leu+(−0.0594)Trp

List (1) of Logistic Regression Equations Searched in Example 8

The logistic regression equations searched in Example 8 above are listed below. Before each equation, "the value of ROC_AUC for the pancreatic cancer group and the breast cancer group with validation", "the value of ROC_AUC for the pancreatic cancer group and the breast cancer group without validation", "the value of ROC_AUC for the pancreatic cancer group and the healthy group", "the value of ROC_AUC for the pancreatic cancer group and the other cancers group", "the value of ROC_AUC for the pancreatic cancer group and the lung cancer group", "the value of ROC_AUC for the pancreatic cancer group and the colorectal cancer group", and "the average value of the value of ROC_AUC for the pancreatic cancer group and the lung cancer group, the value of ROC_AUC for the pancreatic cancer group and the colorectal cancer group, and the value of ROC_AUC for the pancreatic cancer group and the breast cancer group" obtained for the equation are additionally listed.

0.945, 0.965, 0.856, 0.937, 0.919, 0.922, 0.936, (19.7721)+(−0.1860)Asn+(−0.0214)Gly+(−0.0294)Arg+(0.1519)Tyr+(−0.0325)Val+(−0.1932)Trp; 0.943, 0.962, 0.845, 0.931, 0.915, 0.910, 0.929, (18.2716)+(−0.1808)Asn+(−0.0209)Gly+(0.1319)Tyr+(−0.0291)Val+(−0.0849)Met+(−0.1671)Trp; 0.942, 0.961, 0.843, 0.928, 0.914, 0.904, 0.926, (18.6950)+(−0.2049)Asn+(−0.0227)Gly+(0.1247)Tyr+(−0.0313)Val+(−0.1689)Trp; 0.940, 0.964, 0.852, 0.931, 0.908, 0.914, 0.929, (18.5628)+(−0.1809)Asn+(−0.0213)Gly+(0.1403)Tyr+(−0.0261)Val+(−0.0149)Lys+(−0.1804)Trp; 0.939, 0.967, 0.829, 0.925, 0.898, 0.903, 0.922, (19.2936)+(−0.1920)Asn+(−0.0216)Gly+(0.1768)Tyr+(−0.0310)Val+(−0.0428)Orn+(−0.2144)Trp; 0.939, 0.962, 0.843, 0.931, 0.916, 0.908, 0.929, (19.1391)+(−0.2047)Asn+(−0.0227)Gly+(0.1279)Tyr+(−0.0303)Val+(−0.0160)Phe+(−0.1678)Trp; 0.938, 0.963, 0.834, 0.929, 0.915, 0.904, 0.927, (18.4477)+(−0.1783)Asn+(−0.0211)Gly+(−0.0102)Ala+(0.1495)Tyr+(−0.0246)Val+(−0.1848)Trp; 0.938, 0.962, 0.838, 0.929, 0.914, 0.904, 0.926, (18.5187)+(−0.1989)Asn+(−0.0223)Gly+(−0.0039)Thr+(0.1257)Tyr+(−0.0307)Val+(−0.1660)Trp; 0.938, 0.961, 0.844, 0.929, 0.913, 0.905, 0.926, (18.6585)+(−0.2034)Asn+(−0.0223)Gly+(−0.0051)Cit+(0.1250)Tyr+(−0.0309)Val+(−0.1696)Trp; 0.937, 0.960, 0.853, 0.921, 0.903, 0.893, 0.919, (14.2988)+(−0.0198)Gly+(−0.0185)Ala+(0.1778)Tyr+(−0.0453)Lys+(0.0589)Ile+(−0.2460)Trp; 0.936, 0.961, 0.839, 0.926, 0.908, 0.902, 0.924, (15.5250)+(−0.0179)Gly+(−0.0145)Ala+(0.1906)Tyr+(−0.1690)Met+(−0.0266)Lys+(−0.2415)Trp; 0.936, 0.952, 0.832, 0.919, 0.910, 0.886, 0.916, (13.9656)+(−0.0178)Gly+(−0.0153)Ala+(0.1596)Tyr+(−0.2595)Met+(−0.2181)Trp; 0.936, 0.965, 0.867, 0.929, 0.914, 0.899, 0.926, (16.5833)+(0.0280)Ser+(−0.2436)Asn+(−0.0259)Gly+(0.1294)Tyr+(−0.0295)Val+(−0.1576)Trp; 0.935, 0.962, 0.870, 0.941, 0.920, 0.938, 0.940, (18.8523)+(−0.1698)Asn+(−0.0207)Gly+(−0.0278)Arg+(0.1337)Tyr+(−0.0451)Leu+(−0.2089)Trp; 0.935, 0.954, 0.827, 0.921, 0.904, 0.898, 0.919, (15.5136)+(−0.0218)Gly+(−0.0152)Ala+(0.1870)Tyr+(−0.0365)Lys+(−0.2577)Trp; 0.935, 0.958, 0.826, 0.917, 0.902, 0.884, 0.914, (15.0724)+(−0.0164)Gly+(−0.0156)Ala+(0.2082)Tyr+(−0.2478)Met+(−0.0445)Orn+(−0.2598)Trp; 0.934, 0.964, 0.850, 0.929, 0.910, 0.907, 0.927, (17.3759)+(−0.1143)Asn+(−0.0180)Gly+(−0.0144)Ala+(0.1820)Tyr+(−0.0310)Lys+(−0.2361)Trp; 0.934, 0.960, 0.858, 0.926, 0.915, 0.897, 0.924, (17.5160)+(−0.1971)Asn+(−0.0223)Gly+(0.1061)Tyr+(−0.0379)Val+(0.0390)Ile+(−0.1469)Trp; 0.933, 0.956, 0.826, 0.920, 0.911, 0.885, 0.917, (14.7011)+(−0.0195)Gly+(−0.0128)Ala+(0.1600)Tyr+(−0.0115)Val+(−0.2308)Met+(−0.2077)Trp; 0.933, 0.956, 0.846, 0.923, 0.905, 0.899, 0.920, (15.5936)+(−0.0203)Gly+(−0.0275)His+(−0.0142)Ala+(0.1768)Tyr+(−0.0313)Lys+(−0.2379)Trp; 0.933, 0.955, 0.836, 0.919, 0.901, 0.891, 0.916, (16.2475)+(−0.1293)Asn+(−0.0178)Gly+(−0.0149)Ala+(0.1739)Tyr+(−0.0420)Orn+(−0.2480)Trp; 0.933, 0.962, 0.834, 0.925, 0.912, 0.892, 0.922, (18.4104)+(−0.2075)Asn+(−0.0230)Gly+(0.1248)Tyr+(−0.0486)Val+(0.0337)Leu+(−0.1596)Trp; 0.933, 0.957, 0.841, 0.919, 0.910, 0.882, 0.916, (12.7704)+(0.0158)Ser+(−0.0200)Gly+(−0.0151)Ala+(0.1649)Tyr+(−0.2878)Met+(−0.2158)Trp; 0.933, 0.959, 0.861, 0.928, 0.909, 0.909, 0.926, (16.6886)+(−0.1353)Asn+(−0.0146)Gly+(−0.0174)Ala+(−0.0709)Cit+(0.1542)Tyr+(−0.2304)Trp; 0.932, 0.956, 0.865, 0.933, 0.920, 0.919, 0.932, (17.8934)+(−0.1885)Asn+(−0.0219)Gly+(0.1074)Tyr+(−0.0427)Leu+(−0.1860)Trp; 0.932, 0.961, 0.846, 0.930, 0.906, 0.919, 0.928, (18.6123)+(−0.1766)Asn+(−0.0211)Gly+(0.1599)Tyr+(−0.0436)Orn+(−0.0448)Leu+(−0.2264)Trp; 0.932, 0.961, 0.892, 0.917, 0.891, 0.892, 0.914, (12.7382)+(−0.0270)Ala+(−0.1091)Cit+(0.1739)Tyr+(−0.0494)Lys+(0.1149)Ile+(−0.2253)Trp; 0.932, 0.958, 0.857, 0.929, 0.914, 0.909, 0.927, (16.6371)+(−0.1199)Asn+(−0.0175)Gly+(−0.0160)Ala+(−0.0322)Arg+(0.1667)Tyr+(−0.2438)Trp; 0.932, 0.953, 0.829, 0.920, 0.911, 0.889, 0.918, (14.5685)+(−0.0183)Gly+(−0.0153)Ala+(0.1628)Tyr+(−0.2435)Met+(−0.0186)Phe+(−0.2174)Trp; 0.932, 0.957, 0.827, 0.924, 0.908, 0.901, 0.922, (16.1441)+(−0.0220)Gly+(−0.0153)Ala+(0.1898)Tyr+(−0.0347)Lys+(−0.0218)Phe+(−0.2544)Trp; 0.932, 0.955, 0.846, 0.922, 0.909, 0.896, 0.920, (14.8528)+(−0.0153)Gly+(−0.0170)Ala+(−0.0561)Cit+(0.1709)Tyr+(−0.2161)Met+(−0.2359)Trp; 0.932, 0.953, 0.830, 0.920, 0.912, 0.886, 0.917, (14.3526)+(−0.0184)Gly+(−0.0144)Ala+(0.1591)Tyr+(−0.2409)Met+(−0.0090)Leu+(−0.2174)Trp; 0.931, 0.960, 0.859, 0.929, 0.903, 0.919, 0.927, (17.4730)+(−0.1593)Asn+(−0.0189)Ala+(−0.0859)Cit+(0.1918)Tyr+(−0.0280)Lys+(−0.2234)Trp; 0.931, 0.960, 0.864, 0.936, 0.914, 0.930, 0.935, (17.7847)+(−0.1585)Asn+(−0.0208)Gly+(0.1310)Tyr+(−0.0193)Lys+(−0.0298)Leu+(−0.2023)Trp; 0.931, 0.955, 0.828, 0.931, 0.917, 0.916, 0.929, (15.1833)+(−0.0229)Gly+(−0.0305)Arg+(0.1523)Tyr+(−0.0235)Val+(−0.1789)Met+(−0.2015)Trp; 0.931, 0.951, 0.821, 0.920, 0.903, 0.898, 0.918, (15.2754)+(−0.0207)Gly+(−0.0103)Thr+(−0.0148)Ala+(0.1882)Tyr+(−0.0341)Lys+(−0.2458)Trp; 0.931, 0.959, 0.841, 0.924, 0.899, 0.907, 0.922, (16.0715)+(−0.0188)Gly+(−0.0166)Ala+(−0.0509)Cit+(0.1942)Tyr+(−0.0317)Lys+(−0.2679)Trp; 0.931, 0.957, 0.863, 0.935, 0.921, 0.923, 0.934, (18.3571)+(−0.1881)Asn+(−0.0221)Gly+(0.1111)Tyr+(−0.0408)Leu+(−0.0171)Phe+(−0.1843)Trp; 0.931, 0.955, 0.822, 0.920, 0.905, 0.892, 0.917, (15.8004)+(−0.0227)Gly+(−0.0141)Ala+(0.1839)Tyr+(−0.0068)Val+(−0.0331)Lys+(−0.2473)Trp; 0.931, 0.963, 0.819, 0.927, 0.914, 0.895, 0.924, (19.3362)+(−0.2361)Asn+(−0.0246)Gly+(0.0353)His+(0.1325)Tyr+(−0.0382)Val+(−0.1807)Trp; 0.931, 0.957, 0.814, 0.916, 0.884, 0.897, 0.913, (16.1310)+(−0.0213)Gly+(−0.0146)Ala+(0.2199)Tyr+(−0.0367)Orn+(−0.0311)Lys+(−0.2948)Trp; 0.931, 0.953, 0.839, 0.926, 0.913, 0.906, 0.924, (14.9224)+(−0.0172)Gly+(−0.0158)Ala+(−0.0269)Arg+(0.1821)Tyr+(−0.2001)Met+(−0.2469)Trp; 0.930, 0.953, 0.835, 0.918, 0.909, 0.884, 0.915, (13.3776)+(−0.0169)Gly+(−0.0168)Ala+(0.1532)Tyr+(−0.2681)Met+(0.0193)Ile+(−0.2103)Trp; 0.930, 0.956, 0.843, 0.922, 0.911, 0.893, 0.920, (15.5012)+(−0.0214)Gly+(−0.0162)Ala+(0.0056)Pro+(0.1831)Tyr+(−0.0401)Lys+(−0.2513)Trp; 0.930, 0.963, 0.833, 0.929, 0.910, 0.908, 0.927, (18.6294)+(−

0.1987)Asn+(−0.0223)Gly+(−0.0058)Pro+(0.1346)
Tyr+(−0.0299)Val+(−0.1767)Trp; 0.930, 0.960, 0.848,
0.930, 0.918, 0.907, 0.928, (17.8737)+(−0.1634)Asn+
(−0.0201)Gly+(−0.0124)Ala+(0.1429)Tyr+(−0.0304)
Leu+(−0.2040)Trp; 0.930, 0.956, 0.824, 0.922, 0.908,
0.895, 0.919, (14.1671)+(−0.0227)Gly+(0.0040)Gln+
(−0.0153)Ala+(0.1800)Tyr+(−0.0397)Lys+(−0.2508)
Trp; 0.929, 0.956, 0.833, 0.901, 0.874, 0.863, 0.898,
(11.0189)+(−0.0238)Ala+(0.1862)Tyr+(−0.0464)Orn+
(−0.0480)Lys+(0.0979)Ile+(−0.2219)Trp; 0.929,
0.954, 0.828, 0.921, 0.904, 0.898, 0.919, (15.4882)+(−
0.0218)Gly+(−0.0153)Ala+(0.1873)Tyr+(−0.0368)
Lys+(0.0009)Leu+(−0.2582)Trp; 0.929, 0.958, 0.834,
0.927, 0.904, 0.913, 0.925, (16.5859)+(−0.0204)Gly+
(−0.0162)Ala+(−0.0269)Arg+(0.2107)Tyr+(−0.0310)
Lys+(−0.2841)Trp; 0.929, 0.955, 0.830, 0.921, 0.905,
0.896, 0.919, (14.8299)+(0.0085)Ser+(−0.0235)Gly+
(−0.0150)Ala+(0.1904)Tyr+(−0.0376)Lys+(−0.2587)
Trp; 0.929, 0.954, 0.828, 0.918, 0.909, 0.882, 0.915,
(13.7957)+(−0.0177)Gly+(−0.0065)Thr+(−0.0149)
Ala+(0.1605)Tyr+(−0.2347)Met+(−0.2138)Trp; 0.928,
0.956, 0.848, 0.922, 0.911, 0.892, 0.920, (15.5990)+(−
0.1429)Asn+(−0.0194)Gly+(−0.0149)Ala+(0.1291)
Tyr+(−0.2079)Trp; 0.928, 0.955, 0.859, 0.925, 0.906,
0.909, 0.923, (15.7802)+(−0.1780)Asn+(−0.0196)Ala+
(−0.1054)Cit+(0.1536)Tyr+(−0.2061)Trp; 0.928,
0.957, 0.883, 0.932, 0.915, 0.919, 0.930, (15.7143)+
(0.0305)Ser+(−0.2338)Asn+(−0.0255)Gly+(0.1141)
Tyr+(−0.0410)Leu+(−0.1715)Trp; 0.928, 0.956, 0.848,
0.922, 0.911, 0.891, 0.919, (14.4104)+(−0.0167)Gly+
(−0.0336)His+(−0.0143)Ala+(0.1516)Tyr+(−0.2112)
Met+(−0.2011)Trp; 0.928, 0.955, 0.818, 0.919, 0.888,
0.905, 0.916, (16.1039)+(−0.0202)Gly+(−0.0171)Ala+
(−0.0410)Arg+(0.2243)Tyr+(−0.0454)Orn+(−0.3189)
Trp; 0.928, 0.955, 0.882, 0.934, 0.913, 0.929, 0.932,
(16.4372)+(−0.1106)Asn+(−0.0192)Gly+(−0.0364)
His+(0.1264)Tyr+(−0.0285)Lys+(−0.1935)Trp; 0.928,
0.952, 0.832, 0.919, 0.910, 0.886, 0.916, (13.9641)+(−
0.0178)Gly+(−0.0153)Ala+(0.0000)Pro+(0.1595)Tyr+
(−0.2595)Met+(−0.2180)Trp; 0.927, 0.950, 0.812,
0.919, 0.907, 0.893, 0.917, (13.8882)+(−0.0231)Gly+
(0.1310)Tyr+(−0.0217)Val+(−0.2380)Met+(−0.1781)
Trp; 0.927, 0.948, 0.796, 0.908, 0.893, 0.877, 0.906,
(13.0373)+(−0.0176)Ala+(0.2102)Tyr+(−0.3645)Met+
(−0.0525)Orn+(−0.2193)Trp; 0.927, 0.962, 0.836,
0.931, 0.919, 0.906, 0.929, (17.0704)+(−0.2285)Asn+
(−0.0240)Gly+(0.0056)Gln+(0.1137)Tyr+(−0.0320)
Val+(−0.1577)Trp; 0.927, 0.955, 0.866, 0.935, 0.920,
0.926, 0.934, (17.4567)+(−0.1669)Asn+(−0.0206)
Gly+(0.1134)Tyr+(−0.0722)Met+(−0.0394)Leu+(−
0.1828)Trp; 0.927, 0.953, 0.834, 0.903, 0.882, 0.862,
0.899, (10.5201)+(−0.0204)Thr+(−0.0225)Ala+
(0.1669)Tyr+(−0.0496)Lys+(0.0851)Ile+(−0.1799)Trp;
0.927, 0.952, 0.833, 0.921, 0.904, 0.900, 0.919,
(14.6656)+(−0.0213)Gly+(−0.0170)Ala+(−0.0414)
Arg+(0.1714)Tyr+(−0.2699)Trp; 0.927, 0.953, 0.868,
0.936, 0.914, 0.938, 0.935, (16.2015)+(−0.1073)Asn+
(−0.0194)Gly+(0.1392)Tyr+(−0.0897)Met+(−0.0309)
Lys+(−0.2105)Trp; 0.926, 0.955, 0.832, 0.920, 0.912,
0.885, 0.917, (13.2893)+(−0.0180)Gly+(0.0017)Gln+
(−0.0153)Ala+(0.1555)Tyr+(−0.2670)Met+(−0.2134)
Trp; 0.926, 0.951, 0.813, 0.913, 0.896, 0.885, 0.911,
(14.0525)+(−0.0170)Ala+(0.2217)Tyr+(−0.3129)Met+
(−0.0447)Orn+(−0.0176)Lys+(−0.2287)Trp; 0.926,
0.943, 0.811, 0.902, 0.897, 0.858, 0.899, (12.9309)+(−
0.0255)Gly+(−0.0158)Ala+(0.1244)Tyr+(−0.2339)
Trp; 0.926, 0.952, 0.864, 0.934, 0.912, 0.934, 0.933,
(16.3460)+(−0.1262)Asn+(−0.0207)Gly+(0.1315)Tyr+
(−0.0334)Lys+(−0.2145)Trp; 0.926, 0.956, 0.864,
0.933, 0.920, 0.919, 0.932, (17.9000)+(−0.1886)Asn+
(−0.0220)Gly+(0.1076)Tyr+(−0.0002)Ile+(−0.0427)
Leu+(−0.1861)Trp; 0.926, 0.953, 0.825, 0.925, 0.907,
0.909, 0.923, (14.7538)+(−0.0224)Gly+(0.1545)Tyr+
(−0.0166)Val+(−0.1813)Met+(−0.0217)Lys+(−0.1983)
Trp; 0.926, 0.950, 0.827, 0.925, 0.908, 0.912, 0.923,
(15.6837)+(−0.0262)Gly+(−0.0290)Arg+(0.1608)Tyr+
(−0.0204)Val+(−0.0210)Lys+(−0.2305)Trp; 0.926,
0.954, 0.854, 0.918, 0.907, 0.886, 0.916, (14.2981)+(−
0.0208)Gly+(−0.0676)His+(−0.0139)Ala+(0.1262)
Tyr+(−0.1988)Trp; 0.926, 0.946, 0.819, 0.921, 0.909,
0.904, 0.920, (15.3785)+(−0.0281)Gly+(−0.0419)Arg+
(0.1444)Tyr+(−0.0269)Val+(−0.2218)Trp; 0.926,
0.959, 0.834, 0.914, 0.889, 0.886, 0.911, (15.4621)+(−
0.0195)Gly+(−0.0639)His+(−0.0141)Ala+(0.1778)
Tyr+(−0.0458)Orn+(−0.2444)Trp; 0.926, 0.956, 0.851,
0.926, 0.917, 0.897, 0.923, (15.5754)+(−0.0969)Asn+
(−0.0165)Gly+(−0.0147)Ala+(0.1540)Tyr+(−0.1825)
Met+(−0.2075)Trp; 0.926, 0.955, 0.866, 0.921, 0.911,
0.891, 0.919, (14.1295)+(0.0273)Ser+(−0.1871)Asn+
(−0.0231)Gly+(−0.0145)Ala+(0.1350)Tyr+(−0.1992)
Trp; 0.926, 0.955, 0.846, 0.926, 0.894, 0.924, 0.924,
(16.4740)+(−0.1179)Asn+(−0.0198)Gly+(0.1615)Tyr+
(−0.0308)Orn+(−0.0315)Lys+(−0.2373)Trp; 0.926,
0.954, 0.815, 0.923, 0.908, 0.899, 0.920, (16.9420)+(−
0.0245)Gly+(−0.0139)Ala+(−0.0434)Arg+(0.1893)
Tyr+(−0.0195)Val+(−0.2614)Trp; 0.926, 0.953, 0.848,
0.914, 0.895, 0.885, 0.911, (11.9904)+(−0.0221)Ala+
(0.1867)Tyr+(−0.2787)Met+(−0.0388)Lys+(0.0756)
Ile+(−0.1870)Trp; 0.925, 0.959, 0.869, 0.937, 0.921,
0.927, 0.935, (17.8321)+(−0.1846)Asn+(−0.0209)
Gly+(−0.0167)Cit+(0.1097)Tyr+(−0.0418)Leu+(−
0.1871)Trp; 0.925, 0.958, 0.859, 0.926, 0.907, 0.907,
0.924, (15.6209)+(−0.0183)Gly+(−0.0567)His+(−
0.0149)Ala+(−0.0360)Arg+(0.1653)Tyr+(−0.2352)
Trp; 0.925, 0.956, 0.864, 0.935, 0.924, 0.922, 0.934,
(16.7684)+(−0.2019)Asn+(−0.0229)Gly+(0.0037)
Gln+(0.0987)Tyr+(−0.0427)Leu+(−0.1790)Trp; 0.925,
0.956, 0.832, 0.920, 0.887, 0.910, 0.918, (15.8037)+(−
0.2082)Asn+(0.1740)Tyr+(−0.0257)Val+(−0.1788)
Met+(−0.0481)Orn+(−0.1578)Trp; 0.925, 0.955, 0.798,
0.915, 0.891, 0.891, 0.912, (14.7090)+(−0.0226)Gly+
(0.1806)Tyr+(−0.0223)Val+(−0.2174)Met+(−0.0426)
Orn+(−0.2171)Trp; 0.925, 0.955, 0.873, 0.935, 0.910,
0.936, 0.934, (16.2745)+(−0.1252)Asn+(−0.0195)
Gly+(−0.0151)Cit+(0.1319)Tyr+(−0.0326)Lys+(−
0.2131)Trp; 0.925, 0.953, 0.843, 0.921, 0.901, 0.904,
0.919, (14.6029)+(−0.0186)Ala+(−0.0729)Cit+
(0.1982)Tyr+(−0.2438)Met+(−0.0226)Lys+(−0.2219)
Trp; 0.925, 0.951, 0.813, 0.912, 0.891, 0.885, 0.909,
(14.2251)+(−0.1875)Asn+(−0.0166)Ala+(0.1617)Tyr+
(−0.0542)Orn+(−0.1972)Trp; 0.925, 0.949, 0.898,
0.928, 0.912, 0.918, 0.927, (13.7121)+(−0.0209)Gly+
(−0.0815)His+(−0.0281)Arg+(0.0983)Tyr+(−0.1762)
Trp; 0.925, 0.958, 0.807, 0.917, 0.897, 0.886, 0.914,
(16.4874)+(−0.2226)Asn+(−0.0129)Ala+(0.1765)Tyr+
(−0.0193)Val+(−0.0525)Orn+(−0.1802)Trp; 0.925,
0.958, 0.859, 0.928, 0.906, 0.913, 0.926, (15.6232)+(−
0.1300)Asn+(−0.0187)Ala+(−0.0890)Cit+(0.1729)
Tyr+(−0.1691)Met+(−0.2059)Trp; 0.925, 0.957, 0.859,
0.934, 0.922, 0.918, 0.932, (17.6413)+(−0.1786)Asn+
(−0.0212)Gly+(−0.0075)Thr+(0.1100)Tyr+(−0.0417)
Leu+(−0.1801)Trp; 0.925, 0.955, 0.823, 0.919, 0.896,
0.897, 0.916, (15.6904)+(−0.1567)Asn+(−0.0176)Ala+
(−0.0346)Arg+(0.1966)Tyr+(−0.0486)Orn+(−0.2395)

Trp; 0.925, 0.954, 0.842, 0.917, 0.905, 0.885, 0.915, (14.0720)+(−0.0193)Gly+(−0.0614)His+(−0.0139) Thr+(−0.0134)Ala+(0.1326)Tyr+(−0.1877)Trp; 0.925, 0.948, 0.797, 0.907, 0.893, 0.872, 0.904, (12.5917)+(−0.0175)Ala+(0.2088)Tyr+(−0.3771)Met+(−0.0531) Orn+(0.0170)Phe+(−0.2220)Trp; 0.925, 0.947, 0.844, 0.934, 0.920, 0.934, 0.934, (14.4805)+(−0.0223)Gly+(−0.0287)Arg+(0.1367)Tyr+(−0.1646)Met+(−0.0311) Leu+(−0.2103)Trp; 0.924, 0.954, 0.855, 0.923, 0.904, 0.905, 0.921, (14.8267)+(−0.0185)Gly+(−0.0460)His+(−0.0161)Ala+(−0.0548)Cit+(0.1444)Tyr+(−0.2256) Trp; 0.924, 0.952, 0.830, 0.917, 0.903, 0.890, 0.915, (15.4019)+(−0.1670)Asn+(−0.0176)Ala+(0.1748)Tyr+(−0.0359)Lys+(−0.1844)Trp; 0.924, 0.961, 0.873, 0.928, 0.915, 0.903, 0.926, (16.1644)+(−0.1179)Asn+(−0.0173)Gly+(−0.0477)His+(−0.0138)Ala+(0.1276) Tyr+(−0.1856)Trp

List (1) of Linear Discriminants Searched in Example 8

The linear discriminants searched in Example 8 above are listed below. Before each equation, "the value of ROC_AUC for the pancreatic cancer group and the breast cancer group with validation", "the value of ROC_AUC for the pancreatic cancer group and the breast cancer group without validation", "the value of ROC_AUC for the pancreatic cancer group and the healthy group", "the value of ROC_AUC for the pancreatic cancer group and the other cancers group", "the value of ROC_AUC for the pancreatic cancer group and the lung cancer group", "the value of ROC_AUC for the pancreatic cancer group and the colorectal cancer group", and "the average value of the value of ROC_AUC for the pancreatic cancer group and the lung cancer group, the value of ROC_AUC for the pancreatic cancer group and the colorectal cancer group, and the value of ROC_AUC for the pancreatic cancer group and the breast cancer group" obtained for the equation are additionally listed.

0.947, 0.963, 0.857, 0.932, 0.910, 0.917, 0.930, (16.5080)+(−0.1847)Asn+(−0.0136)Gly+(0.1059)Tyr+(−0.0166)Val+(−0.0144)Lys+(−0.1261)Trp; 0.947, 0.963, 0.887, 0.926, 0.917, 0.890, 0.923, (15.4522)+(0.0407)Ser+(−0.2621)Asn+(−0.0204)Gly+(0.0901) Tyr+(−0.0238)Val+(−0.1073)Trp; 0.946, 0.961, 0.856, 0.931, 0.916, 0.911, 0.929, (16.3693)+(−0.2032)Asn+(−0.0143)Gly+(0.0911)Tyr+(−0.0205)Val+(−0.1222) Trp; 0.946, 0.964, 0.867, 0.938, 0.921, 0.925, 0.937, (16.6747)+(−0.1853)Asn+(−0.0142)Gly+(−0.0165) Arg+(0.1002)Tyr+(−0.0198)Val+(−0.1310)Trp; 0.945, 0.964, 0.851, 0.931, 0.907, 0.914, 0.928, (16.3302)+(−0.1982)Asn+(−0.0137)Gly+(0.1050)Tyr+(−0.0184) Val+(−0.0221)Orn+(−0.1288)Trp; 0.945, 0.962, 0.844, 0.930, 0.917, 0.902, 0.927, (16.0086)+(−0.1827)Asn+(−0.0115)Gly+(−0.0089)Ala+(0.1042)Tyr+(−0.0142) Val+(−0.1271)Trp; 0.945, 0.959, 0.858, 0.907, 0.881, 0.869, 0.903, (11.1280)+(−0.0097)Gly+(−0.0205)Ala+(0.1331)Tyr+(−0.0405)Lys+(0.0966)Ile+(−0.1673)Trp; 0.944, 0.960, 0.895, 0.910, 0.882, 0.877, 0.906, (11.7959)+(−0.0251)Ala+(−0.0900)Cit+(0.1411)Tyr+(−0.0407)Lys+(0.1263)Ile+(−0.1856)Trp; 0.944, 0.962, 0.853, 0.934, 0.917, 0.918, 0.932, (17.5529)+(−0.2011)Asn+(−0.0145)Gly+(0.1006)Tyr+(−0.0198) Val+(−0.0362)Phe+(−0.1205)Trp; 0.944, 0.961, 0.848, 0.931, 0.914, 0.912, 0.929, (16.2146)+(−0.1878)Asn+(−0.0134)Gly+(−0.0126)Thr+(0.0973)Tyr+(−0.0189) Val+(−0.1200)Trp; 0.944, 0.960, 0.854, 0.930, 0.911, 0.912, 0.928, (15.2276)+(−0.1416)Asn+(−0.0098) Gly+(−0.0117)Ala+(0.1260)Tyr+(−0.0207)Lys+(−0.1443)Trp; 0.944, 0.960, 0.858, 0.933, 0.914, 0.920, 0.931, (16.1002)+(−0.1600)Asn+(−0.0131)Gly+(0.1159)Tyr+(−0.0179)Val+(−0.1568)Met+(−0.1278) Trp; 0.943, 0.962, 0.843, 0.931, 0.913, 0.912, 0.929, (16.4600)+(−0.2005)Asn+(−0.0145)Gly+(−0.0054) Pro+(0.0991)Tyr+(−0.0195)Val+(−0.1249)Trp; 0.942, 0.960, 0.867, 0.933, 0.916, 0.918, 0.931, (16.5160)+(−0.1988)Asn+(−0.0140)Gly+(−0.0190)Cit+(0.0919) Tyr+(−0.0186)Val+(−0.1282)Trp; 0.941, 0.962, 0.854, 0.932, 0.916, 0.912, 0.930, (14.9371)+(−0.2207)Asn+(−0.0147)Gly+(0.0048)Gln+(0.0831)Tyr+(−0.0217) Val+(−0.1161)Trp; 0.941, 0.960, 0.871, 0.932, 0.918, 0.914, 0.931, (16.5717)+(−0.1866)Asn+(−0.0139) Gly+(−0.0240)His+(0.0870)Tyr+(−0.0167)Val+(−0.1176)Trp; 0.941, 0.954, 0.826, 0.918, 0.901, 0.889, 0.915, (12.1179)+(−0.0106)Gly+(−0.0117)Ala+(0.1440)Tyr+(−0.2897)Met+(−0.1605)Trp; 0.940, 0.956, 0.830, 0.924, 0.906, 0.902, 0.921, (12.7376)+(−0.0103)Gly+(−0.0115)Ala+(0.1511)Tyr+(−0.2252) Met+(−0.0157)Lys+(−0.1579)Trp; 0.940, 0.955, 0.817, 0.919, 0.906, 0.889, 0.917, (12.0399)+(−0.0119)Gly+(−0.0131)Ala+(0.1263)Tyr+(−0.0268)Lys+(−0.1583) Trp; 0.940, 0.957, 0.868, 0.930, 0.912, 0.916, 0.928, (15.4763)+(−0.1546)Asn+(−0.0097)Gly+(−0.0124) Ala+(−0.0541)Cit+(0.1083)Tyr+(−0.1552)Trp; 0.940, 0.959, 0.855, 0.931, 0.906, 0.922, 0.929, (15.6243)+(−0.1898)Asn+(−0.0134)Gly+(0.1050)Tyr+(−0.0275) Orn+(−0.0239)Leu+(−0.1400)Trp; 0.940, 0.955, 0.816, 0.918, 0.902, 0.888, 0.915, (12.3851)+(−0.0099)Gly+(−0.0114)Ala+(0.1608)Tyr+(−0.2771)Met+(−0.0286) Orn+(−0.1649)Trp; 0.940, 0.958, 0.854, 0.928, 0.914, 0.905, 0.926, (14.7420)+(−0.1429)Asn+(−0.0107) Gly+(−0.0122)Ala+(−0.0172)Arg+(0.1125)Tyr+(−0.1549)Trp; 0.939, 0.959, 0.843, 0.925, 0.903, 0.907, 0.923, (12.8941)+(−0.0112)Gly+(−0.0131)Ala+(−0.0453)Cit+(0.1270)Tyr+(−0.0236)Lys+(−0.1657)Trp; 0.939, 0.959, 0.811, 0.924, 0.910, 0.896, 0.922, (13.1099)+(−0.0121)Gly+(−0.0133)Ala+(0.1333)Tyr+(−0.0249)Lys+(−0.0329)Phe+(−0.1560)Trp; 0.939, 0.955, 0.837, 0.921, 0.902, 0.898, 0.919, (14.6581)+(−0.1573)Asn+(−0.0099)Gly+(−0.0122)Ala+(0.1240) Tyr+(−0.0316)Orn+(−0.1517)Trp; 0.939, 0.955, 0.845, 0.914, 0.907, 0.872, 0.911, (10.6239)+(0.0293)Ser+(−0.0148)Gly+(−0.0125)Ala+(0.1523)Tyr+(−0.3524) Met+(−0.1562)Trp; 0.939, 0.955, 0.825, 0.919, 0.905, 0.889, 0.916, (12.5337)+(−0.0111)Gly+(−0.0104)Ala+(0.1436)Tyr+(−0.0056)Val+(−0.2875)Met+(−0.1538) Trp; 0.939, 0.959, 0.854, 0.925, 0.906, 0.904, 0.923, (14.3597)+(−0.1172)Asn+(−0.0097)Gly+(−0.0114) Ala+(0.1303)Tyr+(−0.1746)Met+(−0.1492)Trp; 0.939, 0.959, 0.881, 0.937, 0.916, 0.934, 0.936, (15.9776)+(−0.1880)Asn+(−0.0136)Gly+(−0.0357)Cit+(0.0894) Tyr+(−0.0223)Leu+(−0.1425)Trp; 0.938, 0.957, 0.871, 0.939, 0.922, 0.935, 0.938, (15.9323)+(−0.1756)Asn+(−0.0140)Gly+(−0.0180)Arg+(0.0973)Tyr+(−0.0263) Leu+(−0.1424)Trp; 0.938, 0.955, 0.866, 0.919, 0.914, 0.879, 0.916, (13.1790)+(0.0371)Ser+(−0.2085)Asn+(−0.0159)Gly+(−0.0138)Ala+(0.1030)Tyr+(−0.1369) Trp; 0.938, 0.960, 0.848, 0.926, 0.911, 0.898, 0.923, (16.3220)+(−0.2038)Asn+(−0.0147)Gly+(0.0915)Tyr+(−0.0362)Val+(0.0305)Leu+(−0.1208)Trp; 0.938, 0.957, 0.869, 0.935, 0.914, 0.931, 0.934, (15.2147)+(−0.1496)Asn+(−0.0130)Gly+(0.1127)Tyr+(−0.1625) Met+(−0.0211)Leu+(−0.1395)Trp; 0.938, 0.957, 0.857, 0.930, 0.908, 0.917, 0.928, (15.5841)+(−0.1546)Asn+(−0.0144)Ala+(−0.0496)Cit+(0.1320)Tyr+(−0.0194) Lys+(−0.1521)Trp; 0.938, 0.952, 0.844, 0.920, 0.907, 0.894, 0.918, (14.3471)+(−0.1601)Asn+(−0.0107) Gly+(−0.0126)Ala+(0.1033)Tyr+(−0.1466)Trp; 0.938, 0.958, 0.876, 0.927, 0.913, 0.905, 0.925, (15.6470)+(−0.1385)Asn+(−0.0102)Gly+(−0.0477)His+(−0.0111)Ala+(0.0965)Tyr+(−0.1270)Trp; 0.938, 0.957, 0.870, 0.898, 0.899, 0.826, 0.894, (14.4031)+(−0.1984)Asn+(−0.0182)Ala+(0.0946)Tyr+(−0.0405)Val+(0.1414)Ile+(−0.1133)Trp; 0.938, 0.955, 0.829, 0.893, 0.863, 0.846, 0.888, (10.1586)+(−0.0245)Ala+(0.1579)Tyr+(−0.0387)Orn+(−0.0396)Lys+(0.1157)Ile+(−0.1772)Trp; 0.938, 0.955, 0.826, 0.922, 0.896, 0.910, 0.920, (12.5518)+(−0.0137)Gly+(0.1473)Tyr+(−0.0099)Val+(−0.3155)Met+(−0.0247)Orn+(−0.1580)Trp; 0.938, 0.957, 0.860, 0.924, 0.911, 0.896, 0.921, (13.3437)+(−0.0116)Gly+(−0.0466)His+(−0.0118)Ala+(0.1118)Tyr+(−0.0191)Lys+(−0.1384)Trp; 0.938, 0.954, 0.800, 0.914, 0.895, 0.883, 0.911, (12.3842)+(−0.0102)Gly+(−0.0213)Thr+(−0.0129)Ala+(0.1337)Tyr+(−0.0221)Lys+(−0.1492)Trp; 0.937, 0.955, 0.897, 0.926, 0.913, 0.905, 0.924, (14.7173)+(0.0403)Ser+(−0.2536)Asn+(−0.0201)Gly+(0.0863)Tyr+(−0.0344)Leu+(−0.1182)Trp; 0.937, 0.957, 0.875, 0.930, 0.917, 0.910, 0.928, (13.9507)+(−0.0120)Gly+(−0.0592)His+(−0.0114)Ala+(−0.0282)Arg+(0.1050)Tyr+(−0.1471)Trp; 0.937, 0.953, 0.829, 0.895, 0.870, 0.849, 0.891, (10.7321)+(−0.0256)Thr+(−0.0233)Ala+(0.1469)Tyr+(−0.0383)Lys+(0.1041)Ile+(−0.1579)Trp; 0.937, 0.954, 0.831, 0.918, 0.902, 0.890, 0.915, (12.0889)+(−0.0104)Gly+(−0.0121)Ala+(0.0017)Pro+(0.1426)Tyr+(−0.2931)Met+(−0.1599)Trp; 0.937, 0.954, 0.846, 0.922, 0.907, 0.899, 0.920, (12.9961)+(−0.0100)Gly+(−0.0118)Ala+(−0.0441)Cit+(0.1441)Tyr+(−0.2649)Met+(−0.1673)Trp; 0.937, 0.953, 0.882, 0.909, 0.904, 0.858, 0.905, (16.0905)+(−0.2100)Asn+(−0.0159)Gly+(0.0744)Tyr+(−0.0462)Val+(0.1138)Ile+(−0.1069)Trp; 0.937, 0.958, 0.824, 0.926, 0.909, 0.904, 0.924, (12.5889)+(−0.0119)Gly+(−0.0128)Ala+(−0.0188)Arg+(0.1309)Tyr+(−0.0213)Lys+(−0.1665)Trp; 0.937, 0.949, 0.834, 0.920, 0.900, 0.905, 0.918, (12.4904)+(−0.0144)Gly+(0.1329)Tyr+(−0.0120)Val+(−0.3245)Met+(−0.1515)Trp; 0.937, 0.954, 0.869, 0.933, 0.916, 0.924, 0.932, (15.5873)+(−0.1951)Asn+(−0.0141)Gly+(0.0873)Tyr+(−0.0276)Leu+(−0.1330)Trp; 0.937, 0.953, 0.854, 0.909, 0.893, 0.870, 0.905, (11.0454)+(−0.0094)Gly+(−0.0170)Ala+(0.1417)Tyr+(−0.3112)Met+(0.0646)Ile+(−0.1681)Trp; 0.937, 0.954, 0.854, 0.922, 0.907, 0.899, 0.920, (13.3413)+(−0.0105)Gly+(−0.0412)His+(−0.0108)Ala+(0.1291)Tyr+(−0.2305)Met+(−0.1422)Trp; 0.936, 0.957, 0.852, 0.916, 0.900, 0.884, 0.913, (12.9722)+(−0.0118)Gly+(−0.0613)His+(−0.0119)Ala+(0.1048)Tyr+(−0.0249)Orn+(−0.1395)Trp; 0.936, 0.956, 0.816, 0.920, 0.906, 0.889, 0.917, (12.0468)+(−0.0119)Gly+(−0.0131)Ala+(0.1262)Tyr+(−0.0001)Val+(−0.0267)Lys+(−0.1582)Trp; 0.936, 0.953, 0.864, 0.917, 0.908, 0.881, 0.914, (12.9335)+(−0.0123)Gly+(−0.0681)His+(−0.0121)Ala+(0.0875)Tyr+(−0.1326)Trp; 0.936, 0.955, 0.901, 0.925, 0.901, 0.912, 0.923, (13.6542)+(0.0419)Ser+(−0.2060)Asn+(−0.0196)Gly+(0.1123)Tyr+(−0.0301)Lys+(−0.1388)Trp; 0.936, 0.953, 0.842, 0.927, 0.913, 0.909, 0.925, (12.8082)+(−0.0106)Gly+(−0.0115)Ala+(−0.0194)Arg+(0.1488)Tyr+(−0.2507)Met+(−0.1681)Trp; 0.936, 0.956, 0.870, 0.934, 0.913, 0.928, 0.932, (15.6590)+(−0.1730)Asn+(−0.0135)Gly+(0.1043)Tyr+(−0.0168)Lys+(−0.0177)Leu+(−0.1380)Trp; 0.936, 0.953, 0.824, 0.919, 0.904, 0.892, 0.916, (12.4561)+(−0.0107)Gly+(−0.0119)Ala+(0.1455)Tyr+(−0.2805)Met+(−0.0109)Phe+(−0.1597)Trp; 0.936, 0.953, 0.919, 0.927, 0.911, 0.911, 0.925, (14.4885)+(0.0371)Ser+(−0.1934)Asn+(−0.0192)Gly+(−0.0699)His+(0.0714)Tyr+(−0.1141)Trp; 0.936, 0.954, 0.856, 0.925, 0.909, 0.905, 0.923, (14.9924)+(−0.1717)Asn+(−0.0154)Ala+(−0.0627)Cit+(0.1122)Tyr+(−0.1563)Trp; 0.936, 0.957, 0.812, 0.921, 0.907, 0.890, 0.918, (11.1096)+(−0.0121)Gly+(0.0026)Gln+(−0.0134)Ala+(0.1238)Tyr+(−0.0287)Lys+(−0.1563)Trp; 0.936, 0.958, 0.839, 0.923, 0.905, 0.896, 0.920, (14.8034)+(−0.1502)Asn+(−0.0120)Ala+(0.1354)Tyr+(−0.0098)Val+(−0.1821)Met+(−0.1355)Trp; 0.936, 0.954, 0.808, 0.916, 0.895, 0.889, 0.913, (12.0702)+(−0.0116)Gly+(−0.0130)Ala+(0.1357)Tyr+(−0.0198)Orn+(−0.0236)Lys+(−0.1620)Trp; 0.936, 0.956, 0.838, 0.925, 0.914, 0.898, 0.923, (16.1477)+(−0.1582)Asn+(−0.0109)Gly+(−0.0127)Ala+(0.1174)Tyr+(−0.0509)Phe+(−0.1427)Trp; 0.936, 0.957, 0.863, 0.928, 0.906, 0.914, 0.926, (14.8516)+(−0.1293)Asn+(−0.0140)Ala+(−0.0527)Cit+(0.1374)Tyr+(−0.1708)Met+(−0.1572)Trp; 0.936, 0.957, 0.867, 0.922, 0.905, 0.898, 0.920, (14.7218)+(−0.1226)Asn+(−0.0374)His+(−0.0134)Ala+(0.1252)Tyr+(−0.1562)Met+(−0.1332)Trp; 0.936, 0.956, 0.834, 0.920, 0.908, 0.887, 0.917, (12.0287)+(−0.0114)Gly+(−0.0139)Ala+(0.0044)Pro+(0.1231)Tyr+(−0.0287)Lys+(−0.1566)Trp; 0.936, 0.952, 0.843, 0.932, 0.913, 0.929, 0.931, (13.3270)+(−0.0143)Gly+(−0.0226)Arg+(0.1389)Tyr+(−0.0121)Val+(−0.2773)Met+(−0.1600)Trp; 0.936, 0.956, 0.857, 0.928, 0.897, 0.926, 0.926, (14.8306)+(−0.1568)Asn+(−0.0131)Gly+(0.1191)Tyr+(−0.0233)Orn+(−0.0198)Lys+(−0.1540)Trp; 0.935, 0.956, 0.844, 0.928, 0.917, 0.904, 0.926, (15.3753)+(−0.1731)Asn+(−0.0109)Gly+(−0.0106)Ala+(0.1040)Tyr+(−0.0165)Leu+(−0.1356)Trp; 0.935, 0.955, 0.888, 0.932, 0.917, 0.920, 0.931, (16.0507)+(−0.1678)Asn+(−0.0136)Gly+(−0.0415)His+(0.0809)Tyr+(−0.0169)Leu+(−0.1231)Trp; 0.935, 0.955, 0.854, 0.932, 0.912, 0.924, 0.931, (15.5051)+(−0.1765)Asn+(−0.0130)Gly+(−0.0162)Thr+(0.0958)Tyr+(−0.0254)Leu+(−0.1287)Trp; 0.935, 0.949, 0.872, 0.924, 0.902, 0.917, 0.923, (13.0474)+(−0.0137)Gly+(−0.0518)His+(0.1132)Tyr+(−0.2621)Met+(−0.1438)Trp; 0.935, 0.951, 0.840, 0.919, 0.907, 0.892, 0.917, (11.1397)+(0.0267)Ser+(−0.0184)Gly+(0.1398)Tyr+(−0.0125)Val+(−0.3839)Met+(−0.1473)Trp; 0.935, 0.955, 0.817, 0.920, 0.902, 0.897, 0.918, (12.0468)+(−0.0123)Gly+(−0.0132)Ala+(−0.0301)Arg+(0.1297)Tyr+(−0.0248)Orn+(−0.1789)Trp; 0.935, 0.956, 0.849, 0.927, 0.896, 0.922, 0.925, (14.9546)+(−0.1717)Asn+(0.1391)Tyr+(−0.0155)Val+(−0.2103)Met+(−0.0281)Orn+(−0.1382)Trp; 0.935, 0.955, 0.864, 0.922, 0.911, 0.893, 0.920, (14.3376)+(0.0176)Ser+(−0.1990)Asn+(−0.0167)Ala+(−0.0661)Cit+(0.1131)Tyr+(−0.1522)Trp; 0.935, 0.955, 0.801, 0.916, 0.900, 0.883, 0.913, (14.0874)+(−0.1543)Asn+(−0.0185)Thr+(−0.0148)Ala+(0.1343)Tyr+(−0.0276)Orn+(−0.1442)Trp; 0.935, 0.952, 0.840, 0.914, 0.900, 0.880, 0.911, (10.8203)+(0.0236)Ser+(−0.0155)Gly+(−0.0140)Ala+(0.1298)Tyr+(−0.0314)Lys+(−0.1545)Trp; 0.935, 0.950, 0.811, 0.914, 0.900, 0.886, 0.912, (12.2540)+(−0.0097)Gly+(−0.0151)Thr+(−0.0119)Ala+(0.1445)Tyr+(−0.2381)Met+(−0.1539)Trp; 0.935, 0.955, 0.823, 0.919, 0.900, 0.896, 0.917, (14.7476)+(−0.1586)Asn+(−0.0144)Ala+(0.1432)Tyr+(−0.0249)Orn+(−0.0188)Lys+(−0.1482)Trp; 0.935, 0.957, 0.822, 0.920, 0.900, 0.897, 0.918, (14.0739)+(−0.1276)Asn+(−0.0136)Ala+(0.1568)Tyr+(−0.1877)Met+(−0.0328)Orn+(−0.1544)Trp; 0.935, 0.956, 0.866, 0.923, 0.907, 0.897, 0.920, (13.1599)+(−0.0120)Gly+(−0.0565)His+(−0.0124)Ala+(−0.0288)Cit+(0.0917)Tyr+(−0.1422)Trp; 0.935, 0.954, 0.848, 0.919, 0.912, 0.883, 0.916, (14.7472)+(−0.0125)Gly+(−0.0667)His+(−0.0122)Ala+(0.1020)Tyr+(−0.0514)Phe+(−0.1290)Trp; 0.934, 0.956, 0.817, 0.920, 0.903, 0.892, 0.917, (15.0014)+(−0.1917)Asn+(−0.0131)Ala+(0.1274)Tyr+(−0.0092)Val+(−0.0307)Orn+(−0.1386)Trp; 0.934, 0.954, 0.826, 0.918, 0.901, 0.889, 0.915, (12.1119)+(−0.0106)Gly+(−0.0118)Ala+(0.1440)Tyr+(−0.2899)Met+(0.0002)Leu+(−0.1606)Trp; 0.934, 0.953, 0.821, 0.916, 0.904, 0.882, 0.913, (10.9010)+(−0.0107)Gly+(0.0033)Gln+(−0.0120)Ala+(0.1417)Tyr+(−0.3117)Met+(−0.1582)Trp; 0.934, 0.954, 0.862, 0.895, 0.872, 0.845, 0.891, (10.1814)+(−0.0252)Ala+(0.0068)Pro+(0.1339)Tyr+(−0.0472)Lys+(0.1043)Ile+(−0.1663)Trp; 0.934, 0.955, 0.840, 0.923, 0.904, 0.905, 0.921, (14.8658)+(−0.1515)Asn+(−0.0183)Thr+(−0.0150)Ala+(−0.0497)Cit+(0.1206)Tyr+(−0.1477)Trp; 0.934, 0.953, 0.851, 0.928, 0.897, 0.929, 0.926, (14.1169)+(−0.1226)Asn+(−0.0124)Gly+(0.1356)Tyr+(−0.2046)Met+(−0.0316)Orn+(−0.1602)Trp; 0.934, 0.955, 0.818, 0.921, 0.905, 0.897, 0.919, (14.6476)+(−0.1394)Asn+(−0.0183)Thr+(−0.0143)Ala+(0.1373)Tyr+(−0.0194)Lys+(−0.1376)Trp; 0.934, 0.952, 0.899, 0.925, 0.909, 0.910, 0.924, (12.5242)+(0.0388)Ser+(−0.1621)Asn+(−0.0187)Gly+(0.1221)Tyr+(−0.2685)Met+(−0.1466)Trp; 0.934, 0.949, 0.845, 0.891, 0.865, 0.846, 0.887, (10.1038)+(−0.0243)Ala+(0.1393)Tyr+(−0.0448)Lys+(0.1060)Ile+(−0.1693)Trp; 0.934, 0.948, 0.834, 0.921, 0.893, 0.918, 0.920, (11.7488)+(−0.0134)Gly+(0.1493)Tyr+(−0.3266)Met+(−0.0313)Orn+(−0.1722)Trp; 0.934, 0.953, 0.828, 0.920, 0.908, 0.891, 0.917, (14.4137)+(−0.1406)Asn+(−0.0093)Gly+(−0.0184)Thr+(−0.0125)Ala+(0.1134)Tyr+(−0.1400)Trp; 0.934, 0.951, 0.861, 0.925, 0.901, 0.918, 0.923, (13.0882)+(−0.0131)Gly+(−0.0449)His+(0.1309)Tyr+(−0.2602)Met+(−0.0256)Orn+(−0.1508)Trp; 0.934, 0.952, 0.831, 0.920, 0.908, 0.893, 0.918, (14.6503)+(−0.1578)Asn+(−0.0147)Ala+(0.1316)Tyr+(−0.0230)Lys+(−0.1437)Trp; 0.934, 0.953, 0.830, 0.923, 0.904, 0.907, 0.921, (11.4657)+(−0.0146)Gly+(0.0028)Gln+(0.1308)Tyr+(−0.0122)Val+(−0.3437)Met+(−0.1493)Trp

List (2) of Logistic Regression Equations Searched in Example 8

The logistic regression equations searched in Example 8 above are listed below. Before each equation, "the value of ROC_AUC for the pancreatic cancer group and the breast cancer group with validation", "the value of ROC_AUC for the pancreatic cancer group and the breast cancer group without validation", "the value of ROC_AUC for the pancreatic cancer group and the healthy group", "the value of ROC_AUC for the pancreatic cancer group and the other cancers group", "the value of ROC_AUC for the pancreatic cancer group and the lung cancer group", "the value of ROC_AUC for the pancreatic cancer group and the colorectal cancer group", and "the average value of the value of ROC_AUC for the pancreatic cancer group and the lung cancer group, the value of ROC_AUC for the pancreatic cancer group and the colorectal cancer group, and the value of ROC_AUC for the pancreatic cancer group and the breast cancer group" obtained for the equation are additionally listed.

0.878, 0.923, 0.927, 0.909, 0.900, 0.901, 0.908, (9.6001)+(0.0010)Gln+(−0.1052)His+(−0.0386)Arg+(0.0762)Tyr+(0.0049)Ile+(−0.1257)Trp; 0.856, 0.914, 0.927, 0.906, 0.919, 0.882, 0.905, (8.8698)+(0.0050)Gln+(−0.1070)His+(−0.0297)Cit+(−0.0255)Arg+(0.0249)Ile+(−0.0876)Trp; 0.878, 0.925, 0.926, 0.915, 0.905, 0.913, 0.914, (9.4249)+(0.0020)Gln+(−0.0976)His+(−0.0257)Cit+(−0.0351)Arg+(0.0781)Tyr+(−0.1311)Trp; 0.856, 0.909, 0.926, 0.899, 0.915, 0.871, 0.898, (8.5944)+(0.0042)Gln+(−0.1176)His+(−0.0314)Arg+(0.0224)Ile+(0.0210)Phe+(−0.0870)Trp; 0.883, 0.923, 0.925, 0.912, 0.899, 0.912, 0.911, (9.9732)+(−0.0965)His+(−0.0219)Cit+(−0.0338)Arg+(0.0784)Tyr+(0.0045)Ile+(−0.1313)Trp; 0.852, 0.905, 0.925, 0.890, 0.905, 0.857, 0.889, (9.7626)+(−0.0840)His+(−0.0351)Arg+(0.0775)Ile+(−0.0405)Leu+(0.0236)Phe+(−0.0852)Trp; 0.859, 0.911, 0.924, 0.898, 0.906, 0.872, 0.896, (8.8638)+(0.0075)Gln+(−0.1049)His+(−0.0193)Arg+(−0.0250)Lys+(0.0456)Ile+(−0.0809)Trp; 0.877, 0.922, 0.924, 0.908, 0.907, 0.891, 0.907, (9.8083)+(−0.0784)His+(−0.0460)Arg+(0.0750)Tyr+(0.0530)Ile+(−0.0358)Leu+(−0.1225)Trp; 0.879, 0.923, 0.923, 0.908, 0.898, 0.901, 0.907, (9.8751)+(−0.1039)His+(−0.0376)Arg+(0.0774)Tyr+(0.0043)Ile+(0.0030)Phe+(−0.1276)Trp; 0.852, 0.909, 0.923, 0.898, 0.912, 0.869, 0.897, (9.6098)+(0.0024)Gln+(−0.0889)His+(−0.0357)Arg+(0.0729)Ile+(−0.0357)Leu+(−0.0792)Trp; 0.888, 0.924, 0.923, 0.909, 0.900, 0.901, 0.908, (9.9446)+(−0.1035)His+(−0.0375)Arg+(0.0780)Tyr+(0.0046)Ile+(−0.1272)Trp; 0.839, 0.905, 0.922, 0.894, 0.910, 0.864, 0.893, (10.3931)+(−0.0806)His+(−0.0101)Cit+(−0.0305)Arg+(0.0755)Ile+(−0.0371)Leu+(−0.0825)Trp; 0.883, 0.924, 0.922, 0.911, 0.901, 0.905, 0.910, (9.7155)+(0.0010)Gln+(−0.1041)His+(−0.0384)Arg+(0.0793)Tyr+(−0.1277)Trp; 0.879, 0.923, 0.922, 0.913, 0.900, 0.914, 0.912, (10.0421)+(−0.0958)His+(−0.0218)Cit+(−0.0337)Arg+(0.0809)Tyr+(0.0010)Phe+(−0.1332)Trp; 0.875, 0.923, 0.922, 0.910, 0.901, 0.904, 0.909, (9.5308)+(0.0011)Gln+(−0.1051)His+(−0.0387)Arg+(0.0778)Tyr+(0.0054)Phe+(−0.1280)Trp; 0.886, 0.923, 0.921, 0.913, 0.900, 0.914, 0.912, (10.0671)+(−0.0956)His+(−0.0220)Cit+(−0.0337)Arg+(0.0812)Tyr+(−0.1331)Trp; 0.867, 0.907, 0.921, 0.900, 0.917, 0.873, 0.899, (9.2775)+(0.0038)Gln+(−0.1150)His+(−0.0292)Arg+(0.0247)Ile+(−0.0826)Trp; 0.893, 0.924, 0.921, 0.910, 0.898, 0.905, 0.909, (10.0339)+(−0.1026)His+(−0.0374)Arg+(0.0809)Tyr+(−0.1290)Trp; 0.883, 0.924, 0.920, 0.909, 0.898, 0.903, 0.908, (9.9431)+(−0.1031)His+(−0.0375)Arg+(0.0799)Tyr+(0.0037)Phe+(−0.1294)Trp; 0.856, 0.907, 0.920, 0.895, 0.908, 0.865, 0.893, (10.4038)+(−0.0830)His+(−0.0327)Arg+(0.0770)Ile+(−0.0383)Leu+(−0.0808)Trp; 0.857, 0.912, 0.920, 0.898, 0.905, 0.872, 0.897, (8.3365)+(0.0077)Gln+(−0.0942)His+(−0.0392)Cit+(−0.0285)Lys+(0.0450)Ile+(−0.0831)Trp; 0.854, 0.902, 0.918, 0.895, 0.913, 0.867, 0.894, (10.1863)+(−0.1042)His+(−0.0185)Cit+(−0.0211)Arg+(0.0244)Ile+(0.0154)Phe+(−0.0922)Trp; 0.845, 0.897, 0.918, 0.883, 0.897, 0.851, 0.882, (9.0563)+(−0.0936)His+(−0.0351)Cit+(0.0462)Ile+(−0.0209)Leu+(0.0101)Phe+(−0.0839)Trp; 0.873, 0.903, 0.918, 0.896, 0.913, 0.870, 0.895, (10.6087)+(−0.1088)His+(−0.0235)Arg+(0.0256)Ile+(−0.0853)Trp; 0.859, 0.910, 0.918, 0.890, 0.896, 0.858, 0.888, (8.0345)+(0.0061)Gln+(−0.1078)His+(−0.0304)Lys+(0.0433)Ile+(0.0228)Phe+(−0.0800)Trp; 0.864, 0.903, 0.917, 0.894, 0.910, 0.866, 0.893, (10.1783)+(−0.1106)His+(−0.0248)Arg+(0.0239)Ile+(0.0167)Phe+(−0.0888)Trp; 0.845, 0.912, 0.916, 0.893, 0.901, 0.863, 0.892, (10.8910)+(−0.0765)His+(−0.0203)Arg+(−0.0162)Lys+(0.0819)Ile+(−0.0320)Leu+(−0.0813)Trp; 0.862, 0.906, 0.916, 0.892, 0.904, 0.861, 0.890, (10.5355)+(−0.0976)His+(−0.0126)Arg+(−0.0200)Lys+(0.0412)Ile+(0.0220)Phe+(−0.0891)Trp; 0.885, 0.921, 0.916, 0.909, 0.900, 0.905, 0.909, (10.2678)+(−0.0925)His+(−0.0396)Arg+(0.0892)Tyr+(−0.0102)Leu+(−0.1337)Trp; 0.851, 0.895, 0.915, 0.885, 0.899, 0.857, 0.884, (9.3770)+(−0.0927)His+(−0.0351)Cit+(0.0470)Ile+(−0.0205)Leu+(−0.0821)Trp; 0.886, 0.936, 0.915, 0.926, 0.917, 0.923, 0.925, (11.1011)+(−0.1844)Asn+(0.0062)Gln+(−0.0780)His+(−0.0271)Arg+(0.0716)Tyr+(−0.1071)Trp; 0.876, 0.920, 0.915, 0.909, 0.901, 0.903, 0.908, (10.0831)+(−0.0930)His+(−0.0400)Arg+(0.0877)Tyr+(−0.0108)Leu+(0.0084)Phe+(−0.1348)Trp; 0.874, 0.921, 0.915, 0.910, 0.901, 0.905, 0.909, (10.1698)+(0.0003)Gln+(−0.0931)His+(−0.0398)Arg+(0.0886)Tyr+(−0.0100)Leu+(−0.1333)Trp; 0.851, 0.905, 0.915, 0.890, 0.899, 0.862, 0.889, (10.2816)+(−0.0898)His+(−0.0242)Cit+(−0.0225)Lys+(0.0415)Ile+(0.0199)Phe+(−0.0906)Trp; 0.860, 0.902, 0.915, 0.897, 0.915, 0.872, 0.896, (10.5947)+(−0.1021)His+(−0.0201)Cit+(−0.0197)Arg+(0.0261)Ile+(−0.0894)Trp; 0.848, 0.898, 0.914, 0.879, 0.894, 0.841, 0.877, (8.7586)+(−0.1076)His+(0.0447)Ile+(−0.0216)Leu+(0.0086)Phe+(−0.0739)Trp; 0.880, 0.923, 0.914, 0.912, 0.900, 0.911, 0.911, (10.3061)+(−0.0863)His+(−0.0210)Cit+(−0.0361)Arg+(0.0895)Tyr+(−0.0100)Leu+(−0.1375)Trp; 0.860, 0.904, 0.914, 0.914, 0.902, 0.919, 0.868, 0.900, (8.7347)+(0.0074)Gln+(−0.1182)His+(−0.0271)Arg+(−0.0340)Orn+(0.0347)Ile+(−0.0829)Trp; 0.840, 0.896, 0.913, 0.886, 0.899, 0.859, 0.885, (8.9963)+(0.0011)Gln+(−0.0949)His+(−0.0380)Cit+(0.0440)Ile+(−0.0187)Leu+(−0.0821)Trp; 0.889, 0.938, 0.913, 0.927, 0.909, 0.931, 0.926, (12.9372)+(−0.1672)Asn+(−0.0593)His+(−0.0312)Cit+(−0.0174)Arg+(0.0835)Tyr+(−0.1279)Trp; 0.873, 0.924, 0.913, 0.911, 0.918, 0.887, 0.910, (14.1381)+(−0.1398)Asn+(−0.0613)His+(−0.0223)Cit+(−0.0137)Lys+(0.0219)Ile+(−0.0808)Trp; 0.850, 0.908, 0.913, 0.888, 0.894, 0.858, 0.886, (8.9650)+(0.0048)Gln+(−0.0968)His+(−0.0279)Lys+(0.0630)Ile+(−0.0151)Leu+(−0.0723)Trp; 0.829, 0.893, 0.913, 0.880, 0.893, 0.848, 0.878, (6.9815)+(0.0070)Gln+(−0.1203)His+(−0.0170)Arg+(−0.0236)Lys+(0.0803)Ile+(−0.0295)Leu; 0.865, 0.906, 0.913, 0.890, 0.897, 0.861, 0.888, (8.8005)+(0.0058)Gln+(−0.1058)His+(−0.0290)Lys+(0.0444)Ile+(−0.0755)Trp; 0.844, 0.903, 0.913, 0.900, 0.917, 0.880, 0.900, (8.4103)+(0.0059)Gln+(−0.1058)His+(−0.0297)Cit+(−0.0249)Arg+(0.0261)Phe+(−0.0931)Trp; 0.853, 0.897, 0.912, 0.885, 0.895, 0.860, 0.884, (9.5213)+(−0.1040)His+(−0.0362)Cit+(0.0198)Ile+(0.0084)Phe+(−0.0902)Trp; 0.864, 0.906, 0.912, 0.884, 0.882, 0.860, 0.883, (8.2547)+(−0.1087)His+(0.0439)Tyr+(0.0252)Ile+(−0.0164)Leu+(−0.0941)Trp; 0.857, 0.902, 0.912, 0.898, 0.916, 0.875, 0.898, (8.8568)+(0.0046)Gln+(−0.1133)His+(−0.0288)Arg+(0.0260)Phe+(−0.0884)Trp; 0.850, 0.902, 0.912, 0.898, 0.916, 0.875, 0.898, (8.8496)+(0.0046)Gln+(−0.1137)His+(−0.0288)Arg+(0.0004)Leu+(0.0258)Phe+(−0.0884)Trp; 0.854, 0.905, 0.911, 0.893, 0.904, 0.865, 0.892, (11.0651)+(−0.0894)His+(−0.0185)Cit+(−0.0076)Arg+(−0.0192)Lys+(0.0423)Ile+(−0.0880)Trp; 0.858, 0.895, 0.911, 0.886, 0.898, 0.862, 0.885, (9.7757)+(−0.1031)His+(−0.0363)Cit+(0.0209)Ile+(−0.0885)Trp; 0.843, 0.903, 0.911, 0.888, 0.896, 0.860, 0.886, (10.5209)+(−0.0775)His+(−0.0227)Cit+(−0.0215)Lys+(0.0694)Ile+(−0.0216)Leu+(−0.0811)Trp; 0.874, 0.924, 0.911, 0.906, 0.912, 0.880, 0.905, (13.6158)+(−0.1402)Asn+(−0.0713)His+(−0.0156)Lys+(0.0215)Ile+(0.0135)Phe+(−0.0766)Trp; 0.845, 0.906, 0.911, 0.905, 0.922, 0.886, 0.905, (9.1990)+(0.0055)Gln+(−0.1051)His+(−0.0314)Cit+(−0.0217)Arg+(0.0038)Leu+(−0.0884)Trp; 0.860, 0.907, 0.910, 0.885, 0.882, 0.862, 0.884, (8.3024)+(−0.1085)His+(0.0443)Tyr+(0.0252)Ile+(−0.0163)Leu+(−0.0019)Phe+(−0.0939)Trp; 0.855, 0.898, 0.910, 0.880, 0.893, 0.843, 0.878, (9.0287)+(−0.1068)His+(0.0455)Ile+(−0.0213)Leu+(−0.0722)Trp; 0.838, 0.897, 0.910, 0.877, 0.890, 0.840, 0.875, (9.1904)+(−0.0011)Gln+(−0.1042)His+(0.0479)Ile+(−0.0234)Leu+(0.0083)Phe+(−0.0747)Trp; 0.854, 0.907, 0.910, 0.885, 0.890, 0.851, 0.883, (10.4124)+(−0.0856)His+(−0.0229)Lys+(0.0703)Ile+(−0.0224)Leu+(−0.0752)Trp; 0.848, 0.906, 0.910, 0.883, 0.889, 0.849, 0.881, (9.7873)+(−0.0866)His+(−0.0241)Lys+(0.0707)Ile+(−0.0233)Leu+(0.0210)Phe+(−0.0788)Trp; 0.917, 0.952, 0.910, 0.908, 0.888, 0.874, 0.905, (12.0134)+(−0.0750)His+(−0.0226)Ala+(0.1357)Tyr+(−0.0433)Lys+(0.0960)Ile+(−0.1473)Trp; 0.864, 0.922, 0.910, 0.906, 0.914, 0.878, 0.905, (13.9693)+(−0.1394)Asn+(−0.0710)His+(−0.0005)Pro+(−0.0147)Lys+(0.0231)Ile+(−0.0734)Trp; 0.861, 0.910, 0.910, 0.891, 0.881, 0.877, 0.889, (8.6416)+(−0.0913)His+(−0.0449)Cit+(0.0518)Tyr+(0.0246)Ile+(−0.0160)Leu+(−0.1099)Trp; 0.846, 0.907, 0.910, 0.891, 0.904, 0.857, 0.890, (10.8127)+(−0.0790)His+(−0.0271)Arg+(−0.0252)Orn+(0.0869)Ile+(−0.0403)Leu+(−0.0825)Trp; 0.868, 0.906, 0.909, 0.893, 0.906, 0.862, 0.891, (11.0959)+(−0.0955)His+(−0.0113)Arg+(−0.0192)Lys+(0.0422)Ile+(−0.0847)Trp; 0.857, 0.902, 0.909, 0.891, 0.901, 0.867, 0.890, (10.8521)+(−0.0882)His+(−0.0242)Cit+(−0.0213)Lys+(0.0424)Ile+(−0.0870)Trp; 0.847, 0.897, 0.909, 0.880, 0.893, 0.844, 0.878, (9.4678)+(−0.0011)Gln+(−0.1032)His+(0.0488)Ile+(−0.0232)Leu+(−0.0731)Trp; 0.898, 0.934, 0.909, 0.921, 0.905, 0.922, 0.921, (9.9364)+(−0.0678)His+(−0.0228)Arg+(0.1032)Tyr+(−0.2902)Met+(0.0304)Phe+(−0.1309)Trp; 0.882, 0.922, 0.909, 0.907, 0.915, 0.879, 0.905, (13.9887)+(−0.1405)Asn+(−0.0704)His+(−0.0149)Lys+(0.0224)Ile+(−0.0735)Trp; 0.867, 0.921, 0.909, 0.906, 0.915, 0.879, 0.905, (13.9854)+(−0.1386)Asn+(−0.0701)His+(−0.0064)Met+(−0.0147)Lys+(0.0224)Ile+(−0.0733)Trp; 0.869, 0.922, 0.909, 0.906, 0.915, 0.879, 0.905, (13.9674)+(−0.1414)Asn+(−0.0703)His+(0.0010)Arg+(−0.0152)Lys+(0.0223)Ile+(−0.0730)Trp; 0.848, 0.898, 0.908, 0.888, 0.901, 0.862, 0.887, (8.7919)+(0.0025)Gln+(−0.1058)His+(−0.0429)Cit+(0.0193)Ile+(−0.0876)Trp; 0.902, 0.940, 0.908, 0.926, 0.901, 0.934, 0.925, (12.4034)+(−0.1371)Asn+(−0.0424)His+(−0.0386)Cit+(0.0954)Tyr+(−0.1758)Met+(−0.1255)Trp; 0.882, 0.936, 0.908, 0.923, 0.911, 0.919, 0.922, (12.7284)+(0.0009)Ser+(−0.1668)Asn+(−0.0699)His+(−0.0230)Arg+(0.0823)Tyr+(−0.1190)Trp; 0.870, 0.926, 0.908, 0.913, 0.917, 0.894, 0.912, (13.5663)+(−0.1599)Asn+(−0.0658)His+(−0.0299)Cit+(0.0032)Ile+(0.0120)Phe+(−0.0827)Trp; 0.843, 0.897, 0.908, 0.887, 0.898, 0.863, 0.886, (8.4470)+(0.0027)Gln+(−0.1069)His+(−0.0432)Cit+(0.0178)Ile+(0.0099)Phe+(−0.0896)Trp; 0.838, 0.890, 0.908, 0.877, 0.890, 0.846, 0.876, (6.1643)+(0.0088)Gln+(−0.1408)His+(−0.0124)Arg+(−0.0275)Lys+(0.0435)Ile+(0.0104)Phe; 0.895, 0.936, 0.908, 0.924, 0.909, 0.926, 0.924, (9.5592)+(0.0028)Gln+(−0.0715)His+(−0.0243)Arg+(0.1018)Tyr+(−0.2678)Met+(−0.1206)Trp; 0.893, 0.936, 0.908, 0.923, 0.911, 0.919, 0.922, (12.7996)+(−0.1646)Asn+(−0.0701)His+(−0.0229)Arg+(0.0820)Tyr+(−0.1195)Trp; 0.887, 0.936, 0.908, 0.924, 0.912, 0.923, 0.924, (12.9743)+(−0.1657)Asn+(−0.0693)His+(−0.0222)Arg+(0.0833)Tyr+(−0.0068)

Phe+(−0.1184)Trp; 0.872, 0.926, 0.908, 0.917, 0.926, 0.897, 0.916, (10.7486)+(−0.1900)Asn+(0.0100)Gln+ (−0.0896)His+(−0.0197)Arg+(0.0165)Phe+(−0.0661) Trp; 0.868, 0.921, 0.908, 0.906, 0.912, 0.882, 0.905, (14.1516)+(−0.0023)Ser+(−0.1355)Asn+(−0.0708) His+(−0.0148)Lys+(0.0225)Ile+(−0.0756)Trp; 0.858, 0.902, 0.908, 0.900, 0.918, 0.877, 0.899, (9.6592)+ (0.0042)Gln+(−0.1120)His+(−0.0255)Arg+(0.0026) Leu+(−0.0828)Trp; 0.844, 0.896, 0.907, 0.873, 0.878, 0.839, 0.871, (7.1016)+(0.0059)Gln+(−0.1236)His+(− 0.0282)Lys+(0.0739)Ile+(−0.0244)Leu; 0.833, 0.904, 0.907, 0.894, 0.909, 0.865, 0.893, (9.3694)+(0.0046) Gln+(−0.1205)His+(−0.0238)Arg+(−0.0096)Pro+ (0.0380)Ile+(−0.0832)Trp; 0.915, 0.952, 0.907, 0.929, 0.911, 0.919, 0.927, (13.1055)+(0.0246)Ser+(−0.1652) Asn+(−0.0220)Gly+(−0.0550)His+(0.0798)Tyr+(− 0.1402)Trp; 0.871, 0.924, 0.907, 0.914, 0.918, 0.898, 0.913, (13.8954)+(−0.1569)Asn+(−0.0662)His+(− 0.0271)Cit+(−0.0013)Arg+(0.0056)Ile+(−0.0798)Trp; 0.869, 0.926, 0.907, 0.913, 0.917, 0.894, 0.912, (13.7453)+(−0.1599)Asn+(−0.0648)His+(−0.0283) Cit+(−0.0018)Arg+(0.0136)Phe+(−0.0841)Trp; 0.865, 0.917, 0.907, 0.889, 0.895, 0.850, 0.887, (9.5610)+(− 0.0680)His+(−0.0515)Arg+(0.0712)Tyr+(−0.0348) Val+(0.0951)Ile+(−0.1019)Trp; 0.854, 0.900, 0.907, 0.897, 0.917, 0.873, 0.897, (8.9866)+(0.0046)Gln+(− 0.1077)His+(−0.0288)Arg+(−0.0035)Val+(0.0284) Phe+(−0.0874)Trp; 0.850, 0.906, 0.907, 0.905, 0.922, 0.886, 0.905, (9.3514)+(0.0054)Gln+(−0.1016)His+(− 0.0302)Cit+(−0.0217)Arg+(−0.0878)Trp; 0.869, 0.907, 0.907, 0.885, 0.879, 0.864, 0.884, (8.4769)+(−0.1175) His+(0.0479)Tyr+(0.0032)Ile+(−0.1006)Trp; 0.854, 0.910, 0.907, 0.898, 0.906, 0.876, 0.897, (12.5091)+(− 0.0195)Ser+(−0.0783)His+(−0.0273)Arg+(0.0748)Ile+ (−0.0375)Leu+(−0.0924)Trp; 0.840, 0.897, 0.907, 0.871, 0.875, 0.836, 0.869, (6.6755)+(0.0060)Gln+(− 0.1246)His+(−0.0289)Lys+(0.0743)Ile+(−0.0251) Leu+(0.0113)Phe; 0.829, 0.894, 0.907, 0.876, 0.884, 0.846, 0.875, (6.7089)+(0.0072)Gln+(−0.1209)His+(− 0.0213)Cit+(−0.0284)Lys+(0.0722)Ile+(−0.0224)Leu; 0.879, 0.923, 0.907, 0.909, 0.900, 0.902, 0.908, (10.4669)+(−0.0816)His+(−0.0193)Cit+(−0.0374) Arg+(0.0952)Tyr+(−0.0094)Val+(−0.1365)Trp; 0.876, 0.925, 0.907, 0.913, 0.917, 0.894, 0.912, (13.7038)+(− 0.1617)Asn+(−0.0645)His+(−0.0298)Cit+(0.0129) Phe+(−0.0835)Trp; 0.870, 0.923, 0.907, 0.909, 0.915, 0.887, 0.908, (13.5547)+(−0.1521)Asn+(−0.0781)His+ (−0.0086)Arg+(0.0055)Ile+(0.0110)Phe+(−0.0764) Trp; 0.860, 0.901, 0.906, 0.883, 0.892, 0.851, 0.881, (10.1853)+(−0.0988)His+(−0.0238)Lys+(0.0415)Ile+ (0.0191)Phe+(−0.0843)Trp; 0.845, 0.907, 0.906, 0.876, 0.886, 0.828, 0.874, (10.8001)+(−0.0636)His+(− 0.0267)Arg+(−0.0353)Val+(−0.0186)Lys+(0.1318)Ile+ (−0.0615)Trp; 0.840, 0.901, 0.906, 0.874, 0.870, 0.844, 0.872, (6.7544)+(0.0049)Gln+(−0.1223)His+(0.0298) Tyr+(−0.0317)Lys+(0.0706)Ile+(−0.0256)Leu

List (2) of Linear Discriminants Searched in Example 8

The linear discriminants searched in Example 8 above are listed below. Before each equation, "the value of ROC_AUC for the pancreatic cancer group and the breast cancer group with validation", "the value of ROC_AUC for the pancreatic cancer group and the breast cancer group without validation", "the value of ROC_AUC for the pancreatic cancer group and the healthy group", "the value of ROC_AUC for the pancreatic cancer group and the other cancers group", "the value of ROC_AUC for the pancreatic cancer group and the lung cancer group", "the value of ROC_AUC for the pancreatic cancer group and the colorectal cancer group", and "the average value of the value of ROC_AUC for the pancreatic cancer group and the lung cancer group, the value of ROC_AUC for the pancreatic cancer group and the colorectal cancer group, and the value of ROC_AUC for the pancreatic cancer group and the breast cancer group" obtained for the equation are additionally listed.

0.896, 0.924, 0.943, 0.907, 0.901, 0.893, 0.906, (10.5615)+(0.0037)Gln+(−0.1087)His+(−0.0445)Arg+ (0.0653)Tyr+(0.0380)Ile+(−0.1489)Trp; 0.895, 0.921, 0.943, 0.902, 0.897, 0.885, 0.901, (11.7120)+(−0.0796) His+(−0.0490)Arg+(0.0724)Tyr+(0.0897)Ile+(− 0.0380)Leu+(−0.1510)Trp; 0.882, 0.917, 0.943, 0.902, 0.912, 0.873, 0.901, (10.4832)+(0.0072)Gln+(−0.1152) His+(−0.0273)Cit+(−0.0334)Arg+(0.0505)Ile+(− 0.1141)Trp; 0.883, 0.913, 0.942, 0.900, 0.911, 0.872, 0.899, (10.5912)+(0.0066)Gln+(−0.1228)His+(− 0.0359)Arg+(0.0473)Ile+(−0.1069)Trp; 0.878, 0.910, 0.942, 0.899, 0.911, 0.874, 0.898, (10.3696)+(0.0067) Gln+(−0.1228)His+(−0.0366)Arg+(0.0469)Ile+ (0.0053)Phe+(−0.1082)Trp; 0.876, 0.911, 0.941, 0.893, 0.901, 0.863, 0.892, (11.1623)+(0.0049)Gln+(−0.1018) His+(−0.0405)Arg+(0.0916)Ile+(−0.0320)Leu+(− 0.1048)Trp; 0.895, 0.921, 0.940, 0.908, 0.898, 0.902, 0.907, (11.7459)+(−0.0948)His+(−0.0213)Cit+(− 0.0381)Arg+(0.0714)Tyr+(0.0400)Ile+(−0.1586)Trp; 0.882, 0.916, 0.939, 0.900, 0.909, 0.870, 0.899, (10.2523)+(0.0079)Gln+(−0.1137)His+(−0.0243)Arg+ (−0.0173)Lys+(0.0587)Ile+(−0.0985)Trp; 0.876, 0.913, 0.938, 0.900, 0.911, 0.871, 0.898, (10.5605)+ (0.0067)Gln+(−0.1234)His+(−0.0349)Arg+(−0.0018) Pro+(0.0491)Ile+(−0.1059)Trp; 0.900, 0.927, 0.937, 0.909, 0.898, 0.898, 0.908, (12.6498)+(−0.1023)His+ (−0.0383)Arg+(0.0775)Tyr+(0.0388)Ile+(−0.0307) Phe+(−0.1495)Trp; 0.884, 0.914, 0.936, 0.900, 0.914, 0.868, 0.899, (9.9586)+(0.0086)Gln+(−0.1245)His+(− 0.0316)Arg+(−0.0252)Orn+(0.0559)Ile+(−0.1032)Trp; 0.914, 0.939, 0.935, 0.920, 0.927, 0.890, 0.919, (11.6880)+(−0.0161)Gly+(0.0087)Gln+(−0.1109)His+ (−0.0326)Arg+(0.0504)Ile+(−0.1027)Trp; 0.902, 0.923, 0.934, 0.908, 0.898, 0.901, 0.907, (11.6884)+(− 0.1016)His+(−0.0405)Arg+(0.0710)Tyr+(0.0375)Ile+ (−0.1527)Trp; 0.926, 0.945, 0.933, 0.925, 0.913, 0.912, 0.923, (13.3589)+(−0.0158)Gly+(−0.0857)His+(− 0.0354)Arg+(0.0757)Tyr+(0.0401)Ile+(−0.1518)Trp; 0.885, 0.917, 0.933, 0.902, 0.908, 0.878, 0.901, (10.9845)+(−0.0122)Ser+(0.0075)Gln+(−0.1190)His+ (−0.0335)Arg+(0.0494)Ile+(−0.1086)Trp; 0.913, 0.936, 0.931, 0.915, 0.923, 0.881, 0.913, (13.5929)+ (0.0203)Ser+(−0.0187)Gly+(−0.1029)His+(−0.0261) Arg+(0.0483)Ile+(−0.0997)Trp; 0.893, 0.923, 0.931, 0.905, 0.891, 0.898, 0.904, (11.6722)+(−0.1017)His+ (−0.0382)Arg+(−0.0052)Pro+(0.0766)Tyr+(0.0418) Ile+(−0.1536)Trp; 0.886, 0.920, 0.931, 0.897, 0.900, 0.867, 0.896, (9.8279)+(0.0079)Gln+(−0.0960)His+(− 0.0483)Cit+(−0.0254)Lys+(0.0659)Ile+(−0.1057)Trp; 0.878, 0.907, 0.931, 0.891, 0.900, 0.860, 0.889, (12.7518)+(−0.0908)His+(−0.0349)Arg+(0.0984)Ile+ (−0.0366)Leu+(−0.1047)Trp; 0.874, 0.908, 0.931, 0.890, 0.900, 0.857, 0.888, (12.3164)+(−0.0891)His+ (−0.0367)Arg+(0.0998)Ile+(−0.0383)Leu+(0.0127) Phe+(−0.1077)Trp; 0.874, 0.910, 0.931, 0.892, 0.901, 0.860, 0.891, (12.7898)+(−0.0872)His+(−0.0130)Cit+ (−0.0332)Arg+(0.0989)Ile+(−0.0358)Leu+(−0.1082) Trp; 0.907, 0.932, 0.930, 0.913, 0.923, 0.878, 0.911, (14.5433)+(−0.0162)Gly+(−0.0706)His+(−0.0305) Arg+(0.1130)Ile+(−0.0447)Leu+(−0.1001)Trp; 0.892, 0.924, 0.929, 0.895, 0.894, 0.861, 0.893, (11.7007)+(−0.0696)His+(−0.0523)Arg+(0.0755)Tyr+(−0.0280)Val+(0.1034)Ile+(−0.1467)Trp; 0.865, 0.907, 0.929, 0.891, 0.900, 0.862, 0.889, (12.7663)+(−0.0909)His+(−0.0341)Arg+(−0.0012)Pro+(0.0997)Ile+(−0.0367)Leu+(−0.1041)Trp; 0.876, 0.911, 0.928, 0.892, 0.901, 0.860, 0.891, (12.8033)+(−0.0866)His+(−0.0266)Arg+(−0.0096)Lys+(0.0996)Ile+(−0.0328)Leu+(−0.1003)Trp; 0.872, 0.910, 0.928, 0.893, 0.901, 0.865, 0.892, (12.7713)+(−0.1058)His+(−0.0190)Cit+(−0.0245)Arg+(−0.0005)Pro+(0.0507)Ile+(−0.1120)Trp; 0.885, 0.910, 0.928, 0.894, 0.903, 0.865, 0.893, (12.7657)+(−0.1057)His+(−0.0191)Cit+(−0.0248)Arg+(0.0503)Ile+(−0.1123)Trp; 0.877, 0.910, 0.928, 0.895, 0.904, 0.866, 0.893, (12.9164)+(−0.1059)His+(−0.0192)Cit+(−0.0242)Arg+(0.0506)Ile+(−0.0044)Phe+(−0.1113)Trp; 0.900, 0.927, 0.927, 0.902, 0.886, 0.887, 0.900, (11.5713)+(−0.0828)His+(−0.0250)Arg+(0.0890)Tyr+(−0.0244)Lys+(0.0511)Ile+(−0.1525)Trp; 0.902, 0.930, 0.927, 0.912, 0.911, 0.889, 0.910, (15.7882)+(−0.1398)Asn+(−0.0689)His+(−0.0330)Cit+(−0.0112)Lys+(0.0428)Ile+(−0.0927)Trp; 0.879, 0.912, 0.927, 0.888, 0.890, 0.855, 0.886, (9.5328)+(0.0064)Gln+(−0.1093)His+(−0.0254)Lys+(0.0581)Ile+(0.0109)Phe+(−0.0950)Trp; 0.878, 0.911, 0.927, 0.895, 0.901, 0.868, 0.893, (12.8747)+(−0.0935)His+(−0.0262)Cit+(−0.0122)Arg+(−0.0150)Lys+(0.0611)Ile+(−0.1069)Trp; 0.914, 0.939, 0.926, 0.914, 0.916, 0.882, 0.912, (11.1729)+(−0.0158)Gly+(0.0080)Gln+(−0.1004)His+(−0.0203)Lys+(0.0589)Ile+(−0.0909)Trp; 0.905, 0.936, 0.926, 0.918, 0.914, 0.900, 0.917, (12.6371)+(−0.1861)Asn+(0.0103)Gln+(−0.0831)His+(−0.0526)Cit+(0.0262)Ile+(−0.0947)Trp; 0.899, 0.928, 0.926, 0.911, 0.914, 0.889, 0.910, (15.4137)+(0.0066)Ser+(−0.1637)Asn+(−0.0771)His+(−0.0330)Cit+(0.0287)Ile+(−0.0930)Trp; 0.897, 0.924, 0.926, 0.909, 0.894, 0.906, 0.908, (12.1993)+(−0.0089)Ser+(−0.0975)His+(−0.0379)Arg+(0.0712)Tyr+(0.0391)Ile+(−0.1542)Trp; 0.876, 0.914, 0.926, 0.890, 0.899, 0.851, 0.888, (11.0445)+(0.0054)Gln+(−0.0933)His+(−0.0438)Arg+(−0.0246)Val+(0.1058)Ile+(−0.0992)Trp; 0.872, 0.908, 0.926, 0.889, 0.892, 0.862, 0.887, (12.4787)+(−0.0894)His+(−0.0345)Cit+(0.0014)Pro+(−0.0200)Lys+(0.0613)Ile+(−0.1063)Trp; 0.870, 0.907, 0.926, 0.892, 0.904, 0.859, 0.890, (12.8262)+(−0.1120)His+(−0.0263)Arg+(−0.0006)Pro+(0.0488)Ile+(−0.0032)Phe+(−0.1062)Trp; 0.876, 0.907, 0.925, 0.889, 0.892, 0.861, 0.887, (12.3896)+(−0.0900)His+(−0.0337)Cit+(−0.0195)Lys+(0.0621)Ile+(0.0031)Phe+(−0.1064)Trp; 0.890, 0.922, 0.925, 0.913, 0.905, 0.909, 0.912, (10.9127)+(0.0037)Gln+(−0.0988)His+(−0.0410)Arg+(0.0730)Tyr+(0.0021)Leu+(−0.1470)Trp; 0.888, 0.907, 0.925, 0.893, 0.905, 0.862, 0.892, (12.7085)+(−0.1117)His+(−0.0270)Arg+(0.0480)Ile+(−0.1073)Trp; 0.885, 0.915, 0.925, 0.901, 0.908, 0.876, 0.900, (10.3213)+(0.0091)Gln+(−0.1112)His+(−0.0241)Arg+(−0.1761)Met+(0.0520)Ile+(−0.0913)Trp; 0.881, 0.910, 0.925, 0.892, 0.899, 0.862, 0.890, (12.7530)+(−0.1081)His+(−0.0083)Cit+(−0.0224)Arg+(−0.0131)Orn+(0.0535)Ile+(−0.1076)Trp; 0.875, 0.907, 0.925, 0.892, 0.905, 0.861, 0.891, (12.7166)+(−0.1118)His+(−0.0266)Arg+(−0.0007)Pro+(0.0487)Ile+(−0.1069)Trp; 0.874, 0.909, 0.925, 0.891, 0.900, 0.861, 0.890, (12.7260)+(−0.1105)His+(−0.0231)Arg+(0.0004)Pro+(−0.0152)Orn+(0.0529)Ile+(−0.1053)Trp; 0.882, 0.913, 0.925, 0.894, 0.900, 0.863, 0.892, (13.3747)+(−0.0108)Ser+(−0.0849)His+(−0.0320)Arg+(0.1028)Ile+(−0.0384)Leu+(−0.1061)Trp; 0.881, 0.908, 0.925, 0.889, 0.892, 0.862, 0.887, (12.5014)+(−0.0904)His+(−0.0336)Cit+(−0.0192)Lys+(0.0622)Ile+(−0.1058)Trp; 0.881, 0.907, 0.925, 0.892, 0.905, 0.861, 0.891, (12.8361)+(−0.1119)His+(−0.0266)Arg+(0.0483)Ile+(−0.0037)Phe+(−0.1064)Trp; 0.901, 0.928, 0.924, 0.907, 0.909, 0.878, 0.905, (16.0042)+(−0.1870)Asn+(−0.0435)His+(−0.0319)Cit+(0.0932)Ile+(−0.0495)Leu+(−0.0864)Trp; 0.895, 0.926, 0.924, 0.912, 0.920, 0.888, 0.911, (12.6275)+(−0.1644)Asn+(0.0099)Gln+(−0.1006)His+(−0.0174)Arg+(0.0256)Ile+(−0.0849)Trp; 0.893, 0.923, 0.924, 0.915, 0.906, 0.914, 0.914, (10.9400)+(0.0039)Gln+(−0.0916)His+(−0.0155)Cit+(−0.0395)Arg+(0.0741)Tyr+(−0.1507)Trp; 0.884, 0.909, 0.924, 0.891, 0.899, 0.861, 0.890, (12.7311)+(−0.1106)His+(−0.0229)Arg+(−0.0149)Orn+(0.0532)Ile+(−0.1051)Trp; 0.880, 0.910, 0.924, 0.888, 0.893, 0.855, 0.886, (10.0166)+(0.0061)Gln+(−0.1101)His+(−0.0242)Lys+(0.0583)Ile+(−0.0930)Trp; 0.877, 0.909, 0.924, 0.891, 0.899, 0.861, 0.890, (12.7606)+(−0.1107)His+(−0.0228)Arg+(−0.0149)Orn+(0.0533)Ile+(−0.0009)Phe+(−0.1049)Trp; 0.914, 0.940, 0.924, 0.917, 0.921, 0.884, 0.915, (14.4226)+(−0.0151)Gly+(−0.0910)His+(−0.0140)Arg+(−0.0094)Lys+(0.0574)Ile+(−0.0989)Trp; 0.878, 0.912, 0.924, 0.892, 0.901, 0.857, 0.890, (12.7774)+(−0.0892)His+(−0.0305)Arg+(−0.0163)Orn+(0.1051)Ile+(−0.0373)Leu+(−0.1023)Trp; 0.873, 0.910, 0.924, 0.892, 0.902, 0.861, 0.891, (12.7745)+(−0.1020)His+(−0.0168)Arg+(0.0014)Pro+(−0.0143)Lys+(0.0562)Ile+(−0.1011)Trp; 0.875, 0.904, 0.923, 0.881, 0.887, 0.847, 0.880, (11.3813)+(−0.0947)His+(−0.0339)Cit+(0.0750)Ile+(−0.0231)Leu+(−0.1108)Trp; 0.897, 0.923, 0.923, 0.913, 0.906, 0.908, 0.912, (10.9813)+(0.0035)Gln+(−0.0964)His+(−0.0411)Arg+(0.0739)Tyr+(−0.1469)Trp; 0.883, 0.910, 0.923, 0.892, 0.901, 0.861, 0.891, (12.7883)+(−0.1027)His+(−0.0164)Arg+(−0.0137)Lys+(0.0571)Ile+(−0.1007)Trp; 0.909, 0.934, 0.923, 0.916, 0.920, 0.889, 0.914, (14.4257)+(−0.0153)Gly+(−0.0935)His+(−0.0109)Cit+(−0.0199)Arg+(0.0524)Ile+(−0.1063)Trp; 0.873, 0.908, 0.923, 0.886, 0.890, 0.855, 0.884, (12.2612)+(−0.0795)His+(−0.0331)Cit+(−0.0188)Lys+(0.0904)Ile+(−0.0219)Leu+(−0.1036)Trp; 0.912, 0.934, 0.923, 0.918, 0.898, 0.921, 0.918, (11.9502)+(−0.0675)His+(−0.0236)Arg+(0.1184)Tyr+(−0.3005)Met+(0.0390)Ile+(−0.1568)Trp; 0.910, 0.936, 0.923, 0.905, 0.887, 0.887, 0.903, (11.4866)+(−0.0966)His+(−0.0344)Arg+(0.0886)Tyr+(−0.0339)Orn+(0.0467)Ile+(−0.1591)Trp; 0.897, 0.924, 0.923, 0.896, 0.876, 0.884, 0.895, (11.1211)+(−0.0665)His+(−0.0458)Cit+(0.0869)Tyr+(−0.0325)Lys+(0.0581)Ile+(−0.1576)Trp; 0.893, 0.926, 0.923, 0.913, 0.908, 0.903, 0.912, (15.1663)+(−0.1644)Asn+(−0.0654)Cit+(0.0044)Pro+(−0.0184)Lys+(0.0337)Ile+(−0.1159)Trp; 0.878, 0.910, 0.923, 0.892, 0.902, 0.860, 0.891, (12.5796)+(−0.1020)His+(−0.0167)Arg+(−0.0141)Lys+(0.0570)Ile+(0.0061)Phe+(−0.1020)Trp; 0.872, 0.910, 0.923, 0.884, 0.884, 0.850, 0.881, (10.2978)+(0.0049)Gln+(−0.1007)His+(−0.0230)Lys+(0.0778)Ile+(−0.0152)Leu+(−0.0923)Trp; 0.911, 0.935, 0.922, 0.911, 0.911, 0.881, 0.909, (14.1119)+(−0.0150)Gly+(−0.0826)His+(−0.0229)Cit+(−0.0142)Lys+(0.0608)Ile+(−0.1017)Trp; 0.881, 0.913, 0.922, 0.895, 0.900, 0.868, 0.894, (13.1702)+(−0.0067)Ser+(−0.1002)His+(−0.0150)Arg+(−0.0128)Lys+(0.0577)Ile+(−0.1020)Trp; 0.879, 0.912, 0.922, 0.895, 0.907, 0.861, 0.893, (13.1744)+(−0.0786)His+(−0.0232)Arg+(−0.1345)Met+(0.1020)Ile+(−0.0365)

Leu+(−0.0929)Trp; 0.869, 0.909, 0.922, 0.888, 0.893, 0.856, 0.886, (10.0135)+(0.0062)Gln+(−0.1104)His+(−0.0005)Pro+(−0.0240)Lys+(0.0587)Ile+(−0.0929)Trp; 0.930, 0.950, 0.922, 0.918, 0.902, 0.893, 0.915, (12.5111)+(−0.0154)Gly+(−0.0709)His+(0.0841)Tyr+(−0.0271)Lys+(0.0516)Ile+(−0.1420)Trp; 0.912, 0.936, 0.922, 0.907, 0.912, 0.867, 0.905, (13.0273)+(0.0198)Ser+(−0.0184)Gly+(−0.0948)His+(−0.0171)Lys+(0.0557)Ile+(−0.0899)Trp; 0.897, 0.925, 0.922, 0.906, 0.913, 0.877, 0.905, (15.2500)+(0.0073)Ser+(−0.1563)Asn+(−0.0885)His+(−0.0074)Arg+(0.0264)Ile+(−0.0855)Trp; 0.886, 0.918, 0.922, 0.895, 0.905, 0.858, 0.894, (12.4065)+(−0.0962)His+(−0.0161)Arg+(−0.1564)Met+(0.0507)Ile+(0.0231)Phe+(−0.0992)Trp; 0.878, 0.910, 0.922, 0.891, 0.900, 0.859, 0.890, (12.7961)+(−0.1028)His+(−0.0145)Arg+(−0.0107)Orn+(−0.0122)Lys+(0.0599)Ile+(−0.0998)Trp; 0.928, 0.948, 0.922, 0.914, 0.914, 0.874, 0.912, (15.5554)+(0.0353)Ser+(−0.2340)Asn+(−0.0199)Gly+(0.0981)Ile+(−0.0695)Leu+(−0.0719)Trp; 0.875, 0.909, 0.922, 0.886, 0.872, 0.873, 0.885, (10.2052)+(0.0008)Gln+(−0.1006)His+(−0.0431)Cit+(0.0477)Tyr+(0.0357)Ile+(−0.1449)Trp; 0.917, 0.936, 0.921, 0.915, 0.919, 0.886, 0.914, (14.4010)+(−0.0154)Gly+(−0.0969)His+(−0.0212)Arg+(0.0512)Ile+(−0.1034)Trp; 0.883, 0.910, 0.921, 0.895, 0.902, 0.869, 0.894, (13.2008)+(−0.0085)Ser+(−0.1078)His+(−0.0244)Arg+(0.0495)Ile+(−0.1085)Trp; 0.869, 0.907, 0.921, 0.883, 0.888, 0.849, 0.881, (10.6236)+(0.0021)Gln+(−0.0990)His+(−0.0380)Cit+(0.0707)Ile+(−0.0202)Leu+(−0.1118)Trp; 0.897, 0.929, 0.921, 0.912, 0.914, 0.890, 0.911, (15.6380)+(−0.1496)Asn+(−0.0762)His+(−0.0320)Cit+(−0.0023)Arg+(0.0323)Ile+(−0.0959)Trp; 0.895, 0.925, 0.921, 0.903, 0.907, 0.872, 0.901, (15.2549)+(0.0091)Ser+(−0.1546)Asn+(−0.0811)His+(−0.0123)Lys+(0.0350)Ile+(−0.0797)Trp; 0.912, 0.936, 0.921, 0.909, 0.912, 0.873, 0.907, (13.6749)+(−0.0160)Gly+(−0.0733)His+(−0.0134)Lys+(0.0991)Ile+(−0.0322)Leu+(−0.0922)Trp; 0.911, 0.935, 0.921, 0.915, 0.918, 0.886, 0.913, (14.3947)+(−0.0152)Gly+(−0.0965)His+(−0.0191)Arg+(−0.0077)Orn+(0.0538)Ile+(−0.1023)Trp; 0.880, 0.912, 0.921, 0.885, 0.872, 0.865, 0.883, (10.3226)+(−0.0890)His+(−0.0409)Cit+(0.0473)Tyr+(0.0628)Ile+(−0.0206)Leu+(−0.1422)Trp; 0.896, 0.926, 0.921, 0.904, 0.906, 0.874, 0.902, (15.5396)+(−0.1387)Asn+(−0.0806)His+(−0.0107)Orn+(−0.0093)Lys+(0.0407)Ile+(−0.0832)Trp; 0.896, 0.924, 0.921, 0.914, 0.906, 0.909, 0.913, (11.8572)+(0.0028)Gln+(−0.0953)His+(−0.0387)Arg+(0.0796)Tyr+(−0.0208)Phe+(−0.1453)Trp; 0.875, 0.910, 0.920, 0.894, 0.903, 0.866, 0.893, (13.2183)+(−0.0086)Ser+(−0.1080)His+(−0.0238)Arg+(−0.0009)Pro+(0.0505)Ile+(−0.1080)Trp; 0.874, 0.906, 0.920, 0.886, 0.892, 0.857, 0.885, (10.2651)+(0.0036)Gln+(−0.1114)His+(−0.0413)Cit+(0.0439)Ile+(−0.1143)Trp; 0.873, 0.907, 0.920, 0.879, 0.880, 0.844, 0.877, (11.6730)+(−0.0896)His+(−0.0196)Lys+(0.0863)Ile+(−0.0227)Leu+(0.0078)Phe+(−0.0957)Trp; 0.928, 0.947, 0.920, 0.930, 0.918, 0.919, 0.928, (12.7898)+(0.0225)Ser+(−0.0193)Gly+(−0.0809)His+(−0.0379)Arg+(0.0840)Tyr+(−0.1457)Trp; 0.909, 0.935, 0.920, 0.920, 0.907, 0.916, 0.919, (14.4930)+(−0.1522)Asn+(−0.0750)His+(−0.0203)Arg+(0.0765)Tyr+(0.0169)Ile+(−0.1361)Trp; 0.908, 0.936, 0.920, 0.926, 0.917, 0.922, 0.925, (12.8808)+(−0.1740)Asn+(0.0072)Gln+(−0.0802)His+(−0.0237)Arg+(0.0696)Tyr+(−0.1255)Trp; 0.905, 0.929, 0.920, 0.912, 0.913, 0.890, 0.911, (15.6038)+(−0.1524)Asn+(−0.0758)His+(−0.0334)Cit+(0.0315)Ile+(−0.0956)Trp; 0.910, 0.935, 0.920, 0.916, 0.921, 0.888, 0.915, (14.7806)+(−0.0155)Gly+(−0.0974)His+(−0.0200)Arg+(0.0520)Ile+(−0.0109)Phe+(−0.1007)Trp; 0.879, 0.912, 0.920, 0.896, 0.903, 0.868, 0.894, (13.3032)+(−0.0092)Ser+(−0.1008)His+(−0.0215)Cit+(−0.0217)Arg+(0.0522)Ile+(−0.1142)Trp; 0.877, 0.909, 0.920, 0.888, 0.890, 0.860, 0.886, (12.4932)+(−0.0923)His+(−0.0283)Cit+(−0.0057)Orn+(−0.0181)Lys+(0.0628)Ile+(−0.1041)Trp

List of Logistic Regression Equations Searched in Example 2 (ROC_AUC Value: 0.500 or Greater)

The logistic regression equations searched in Example 2 above are listed below. Before each equation, "the value of ROC_AUC for the pancreatic cancer group and the healthy group with validation", "the value of ROC_AUC for the pancreatic cancer group and the healthy group without validation", "the value of ROC_AUC for the pancreatic cancer group and the other cancers group", "the value of ROC_AUC for the pancreatic cancer group and the lung cancer group", "the value of ROC_AUC for the pancreatic cancer group and the colorectal cancer group", "the value of ROC_AUC for the pancreatic cancer group and the prostatic cancer group", "the value of ROC_AUC for the pancreatic cancer group and the breast cancer group", and "the average value of the value of ROC_AUC for the pancreatic cancer group and the lung cancer group, the value of ROC_AUC for the pancreatic cancer group and the colorectal cancer group, the value of ROC_AUC for the pancreatic cancer group and the prostatic cancer group, and the value of ROC_AUC for the pancreatic cancer group and the breast cancer group" obtained for the equation are additionally listed.

0.826, 0.840, 0.800, 0.804, 0.811, 0.753, 0.801, 0.792, (3.2646)+(0.0697)Phe+(−0.1735)Trp; 0.817, 0.828, 0.774, 0.782, 0.778, 0.801, 0.727, 0.772, (3.1922)+(0.0271)Ser+(−0.1525)Trp; 0.812, 0.822, 0.774, 0.762, 0.777, 0.766, 0.804, 0.777, (4.2601)+(0.0495)Ile+(−0.1715)Trp; 0.812, 0.825, 0.809, 0.812, 0.810, 0.827, 0.789, 0.809, (8.8631)+(−0.0763)His+(−0.0949)Trp; 0.804, 0.815, 0.736, 0.717, 0.737, 0.829, 0.719, 0.750, (4.1731)+(0.0357)Ser+(−0.1324)Hi s; 0.802, 0.817, 0.816, 0.822, 0.831, 0.822, 0.765, 0.810, (7.5229)+(−0.0626)Cit+(−0.1412)Trp; 0.802, 0.815, 0.793, 0.803, 0.802, 0.783, 0.754, 0.786, (5.1431)+(0.0173)Orn+(−0.1504)Trp; 0.801, 0.814, 0.795, 0.806, 0.800, 0.781, 0.766, 0.788, (5.4341)+(0.0049)Pro+(−0.1498)Trp; 0.801, 0.813, 0.781, 0.775, 0.769, 0.829, 0.787, 0.790, (4.1211)+(0.0092)Gln+(−0.1498)His; 0.799, 0.812, 0.792, 0.804, 0.802, 0.788, 0.745, 0.785, (5.3459)+(0.0083)Thr+(−0.1543)Trp; 0.798, 0.812, 0.808, 0.824, 0.807, 0.794, 0.775, 0.800, (4.4293)+(0.0032)Gln+(−0.1532)Trp; 0.797, 0.811, 0.747, 0.721, 0.745, 0.783, 0.795, 0.761, (4.6715)+(−0.1432)His+(0.0732)Phe; 0.796, 0.806, 0.741, 0.704, 0.738, 0.798, 0.804, 0.761, (5.5422)+(−0.1341)His+(0.0453)Ile; 0.795, 0.807, 0.819, 0.832, 0.822, 0.807, 0.783, 0.811, (7.2003)+(−0.0494)Asn+(−0.1313)Trp; 0.794, 0.808, 0.803, 0.819, 0.806, 0.792, 0.765, 0.796, (5.8643)+(−0.0006)Val+(−0.1435)Trp; 0.794, 0.808, 0.794, 0.802, 0.802, 0.777, 0.770, 0.788, (5.3577)+(0.0086)Leu+(−0.1545)Trp; 0.793, 0.805, 0.816, 0.832, 0.812, 0.816, 0.784, 0.811, (6.3477)+(−0.0032)Ala+(−0.1356)Trp; 0.793, 0.807, 0.802, 0.819, 0.804, 0.789, 0.762, 0.793, (5.9803)+(−0.0056)Tyr+(−0.1416)Trp; 0.792, 0.807, 0.802, 0.816, 0.806, 0.788, 0.767, 0.794, (5.7122)+(0.0009)Lys+(−0.1463)Trp; 0.791, 0.806, 0.817, 0.834, 0.820, 0.811, 0.769, 0.809, (6.9335)+(−0.0867)Met+(−0.1276)Trp; 0.791, 0.807, 0.805, 0.818, 0.809, 0.790, 0.773, 0.798, (5.9630)+(−0.0009)Gly+(−0.1445)Trp; 0.787, 0.801, 0.748, 0.720, 0.759, 0.808, 0.756, 0.761, (6.1253)+(−0.1299)His+(0.0330)Orn; 0.784, 0.796, 0.745, 0.727, 0.750, 0.804, 0.741, 0.756, (6.4709)+(−0.1329)His+(0.0149)Thr; 0.784, 0.802, 0.805, 0.822, 0.812, 0.795, 0.752, 0.795, (6.3448)+(−0.0090)Arg+(−0.1399)Trp; 0.778, 0.788, 0.751, 0.725, 0.755, 0.801, 0.779, 0.765, (6.5324)+(−0.1304)His+(0.0128)Leu; 0.775, 0.786, 0.763, 0.748, 0.762, 0.810, 0.770, 0.772, (6.9613)+(−0.1208)His+(0.0015)Val; 0.775, 0.788, 0.756, 0.747, 0.754, 0.813, 0.742, 0.764, (6.6776)+(0.0028)Gly+(−0.1206)His; 0.775, 0.786, 0.775, 0.766, 0.765, 0.822, 0.784, 0.784, (7.3273)+(−0.1124)His+(−0.0021)Ala; 0.773, 0.785, 0.752, 0.734, 0.753, 0.797, 0.764, 0.762, (6.6331)+(−0.1215)His+(0.0052)Pro; 0.772, 0.785, 0.769, 0.758, 0.766, 0.811, 0.776, 0.778, (7.3401)+(−0.0143)Asn+(−0.1136)His; 0.772, 0.783, 0.758, 0.744, 0.757, 0.803, 0.766, 0.768, (6.7145)+(−0.1239)His+(0.0042)Lys; 0.770, 0.785, 0.766, 0.757, 0.761, 0.809, 0.768, 0.774, (7.2279)+(−0.1150)His+(−0.0062)Tyr; 0.767, 0.785, 0.775, 0.768, 0.771, 0.817, 0.773, 0.782, (7.4695)+(−0.1078)His+(−0.0493)Met; 0.766, 0.784, 0.766, 0.753, 0.764, 0.812, 0.768, 0.774, (7.2408)+(−0.1161)His+(−0.0036)Arg; 0.761, 0.778, 0.764, 0.750, 0.768, 0.810, 0.758, 0.771, (7.3735)+(−0.1115)His+(−0.0257)Cit; 0.760, 0.771, 0.696, 0.684, 0.626, 0.781, 0.814, 0.726, (0.9619)+(−0.0559)Val+(0.1493)Ile; 0.755, 0.773, 0.737, 0.764, 0.736, 0.813, 0.613, 0.731, (0.2571)+(0.0364)Ser+(−0.2519)Met; 0.738, 0.754, 0.739, 0.730, 0.737, 0.757, 0.755, 0.745, (1.8923)+(−0.2844)Met+(0.0530)Ile; 0.737, 0.752, 0.758, 0.772, 0.765, 0.712, 0.734, 0.746, (0.4707)+(−0.3046)Met+(0.0871)Phe; 0.729, 0.744, 0.681, 0.679, 0.631, 0.746, 0.746, 0.701, (−0.1029)+(0.1443)Ile+(−0.0904)Leu; 0.724, 0.743, 0.707, 0.720, 0.698, 0.771, 0.648, 0.709, (0.7877)+(0.0397)Ser+(−0.1603)Asn; 0.712, 0.731, 0.738, 0.769, 0.748, 0.764, 0.620, 0.725, (2.6702)+(0.0178)Thr+(−0.2686)Met; 0.707, 0.725, 0.742, 0.761, 0.740, 0.745, 0.693, 0.735, (2.9233)+(0.0080)Pro+(−0.2391)Me t; 0.704, 0.721, 0.742, 0.762, 0.744, 0.767, 0.671, 0.736, (2.4989)+(−0.2277)Met+(0.0223)Orn; 0.704, 0.723, 0.732, 0.729, 0.642, 0.819, 0.864, 0.764, (0.0800)+(−0.0136)Ala+(0.0441)Ile; 0.703, 0.722, 0.778, 0.814, 0.761, 0.782, 0.713, 0.768, (1.4382)+(0.0045)Gln+(−0.2387)Met; 0.703, 0.719, 0.775, 0.798, 0.775, 0.768, 0.721, 0.765, (3.9824)+(−0.0433)Asn+(−0.1605)Met; 0.703, 0.723, 0.789, 0.817, 0.767, 0.811, 0.743, 0.785, (3.5534)+(−0.0040)Ala+(−0.1658)Met; 0.699, 0.720, 0.765, 0.781, 0.785, 0.773, 0.676, 0.754, (4.3007)+(−0.0614)Cit+(−0.1733)Met; 0.695, 0.716, 0.776, 0.813, 0.764, 0.787, 0.697, 0.765, (3.8103)+(−0.0065)Val+(−0.1747)Met; 0.695, 0.713, 0.760, 0.788, 0.758, 0.764, 0.685, 0.749, (3.0856)+(0.0006)Gly+(−0.2055)Met; 0.694, 0.712, 0.766, 0.794, 0.763, 0.770, 0.694, 0.755, (3.3474)+(−0.1943)Met+(−0.0022)Lys; 0.693, 0.712, 0.759, 0.784, 0.758, 0.758, 0.697, 0.749, (3.0295)+(−0.2128)Met+(0.0031)Leu; 0.692, 0.714, 0.766, 0.796, 0.767, 0.768, 0.684, 0.754, (3.5146)+(−0.0079)Arg+(−0.1897)Met; 0.688, 0.708, 0.774, 0.787, 0.761, 0.821, 0.736, 0.776, (3.4870)+(−0.0086)Ala+(−0.0780)Cit; 0.688, 0.710, 0.759, 0.791, 0.753, 0.756, 0.687, 0.747, (3.3052)+(−0.0074)Tyr+(−0.1906)Met; 0.687, 0.707, 0.800, 0.821, 0.762, 0.827, 0.801, 0.803, (4.0397)+(−0.0851)Asn+(−0.0064)Ala; 0.685, 0.709, 0.757, 0.766, 0.770, 0.754, 0.707, 0.749, (4.3414)+(−0.0921)Asn+(−0.0679)Cit; 0.679, 0.702, 0.751, 0.796, 0.724, 0.739, 0.696, 0.739, (4.2548)+(−0.0854)Asn+(−0.0363)Tyr; 0.679, 0.698, 0.787, 0.822, 0.763, 0.795, 0.737, 0.779, (4.9678)+(−0.0972)Asn+(−0.0120)Val; 0.675, 0.701, 0.715, 0.755, 0.715, 0.732, 0.596, 0.699, (3.3013)+(−0.0711)Cit+(−0.0448)Tyr; 0.672, 0.699, 0.623, 0.683, 0.584, 0.706, 0.486, 0.615, (−0.4769)+(0.0218)Ser+(−0.0572)Tyr; 0.669, 0.694, 0.704, 0.733, 0.618, 0.847, 0.702, 0.725, (−0.8615)+(0.0218)Ser+(−0.0099)Ala; 0.668, 0.689, 0.736, 0.756, 0.660, 0.815, 0.789, 0.755, (1.0885)+(−0.0125)Ala+(0.0096)Pro; 0.667, 0.689, 0.677, 0.647, 0.668, 0.732, 0.736, 0.696, (1.0698)+(−0.0265)Lys+(0.0364)Ile; 0.667, 0.687, 0.627, 0.668, 0.570, 0.645, 0.625, 0.627, (0.7224)+(−0.0702)Tyr+(0.0336)Ile; 0.666, 0.689, 0.720, 0.713, 0.712, 0.706, 0.762, 0.723, (2.1733)+(−0.1195)Asn+(0.0213)Ile; 0.665, 0.690, 0.754, 0.775, 0.681, 0.814, 0.806, 0.769, (0.0534)+(−0.0112)Ala+(0.0327)Phe; 0.662, 0.686, 0.728, 0.735, 0.729, 0.725, 0.713, 0.725, (2.5997)+(−0.1214)Asn+(0.0169)Orn; 0.662, 0.685, 0.734, 0.740, 0.734, 0.693, 0.745, 0.728, (1.9869)+(−0.1259)Asn+(0.0297)Phe; 0.661, 0.691, 0.639, 0.647, 0.638, 0.762, 0.535, 0.645, (−0.6030)+(0.0285)Ser+(−0.0227)Lys; 0.660, 0.680, 0.644, 0.717, 0.589, 0.609, 0.589, 0.626, (0.1635)+(−0.0781)Tyr+(0.0525)Phe; 0.660, 0.685, 0.758, 0.816, 0.687, 0.821, 0.708, 0.758, (2.6325)+(−0.0068)Ala+(−0.0337)Tyr; 0.659, 0.684, 0.788, 0.823, 0.742, 0.845, 0.749, 0.790, (2.4815)+(−0.0080)Ala+(−0.0175)Arg; 0.659, 0.684, 0.768, 0.792, 0.751, 0.740, 0.760, 0.761, (1.6188)+(−0.1401)Asn+(0.0047)Gln; 0.656, 0.686, 0.789, 0.821, 0.735, 0.858, 0.766, 0.795, (2.7346)+(−0.0074)Ala+(−0.0108)Lys; 0.655, 0.686, 0.729, 0.802, 0.681, 0.760, 0.611, 0.714, (2.8329)+(−0.0389)Tyr+(−0.0100)Val; 0.655, 0.678, 0.765, 0.796, 0.754, 0.753, 0.718, 0.755, (3.8161)+(−0.1017)Asn+(−0.0101)Leu; 0.654, 0.681, 0.744, 0.765, 0.673, 0.835, 0.770, 0.761, (0.8298)+(−0.0104)Ala+(0.0158)Orn; 0.653, 0.676, 0.735, 0.758, 0.729, 0.722, 0.695, 0.726, (2.8947)+(−0.1145)Asn+(0.0017)Gly; 0.653, 0.684, 0.629, 0.648, 0.653, 0.741, 0.450, 0.623, (−1.5623)+(0.0264)Ser+(−0.0341)Arg; 0.653, 0.681, 0.759, 0.776, 0.753, 0.757, 0.730, 0.754, (3.7433)+(−0.0898)Asn+(−0.0085)Lys; 0.652, 0.678, 0.787, 0.837, 0.715, 0.867, 0.743, 0.791, (2.4040)+(−0.0069)Ala+(−0.0089)Val; 0.651, 0.674, 0.610, 0.597, 0.649, 0.696, 0.505, 0.612, (−1.3060)+(0.0227)Ser+(−0.0930)Cit; 0.648, 0.673, 0.736, 0.752, 0.730, 0.709, 0.724, 0.729, (2.9528)+(−0.1135)Asn+(0.0018)Pro; 0.646, 0.676, 0.754, 0.777, 0.756, 0.739, 0.702, 0.743, (3.4803)+(−0.0950)Asn+(−0.0123)Arg; 0.646, 0.674, 0.733, 0.748, 0.731, 0.712, 0.709, 0.725, (2.9573)+(−0.1231)Asn+(0.0056)Thr; 0.645, 0.670, 0.771, 0.805, 0.692, 0.855, 0.783, 0.784, (1.1266)+(0.0006)Gln+(−0.0096)Ala; 0.645, 0.674, 0.717, 0.771, 0.689, 0.750, 0.606, 0.704, (2.9686)+(−0.0405)Tyr+(−0.0113)Lys; 0.644, 0.670, 0.636, 0.601, 0.699, 0.702, 0.553, 0.639, (0.0045)+(−0.1113)Cit+(0.0318)Orn; 0.643, 0.676, 0.709, 0.774, 0.691, 0.729, 0.564, 0.689, (2.8079)+(−0.0184)Arg+(−0.0455)Ty r; 0.642, 0.671, 0.727, 0.731, 0.754, 0.773, 0.625, 0.721, (3.2166)+(−0.0736)Cit+(−0.0142)Lys; 0.642, 0.668, 0.777, 0.806, 0.706, 0.851, 0.797, 0.790, (1.6342)+(−0.0013)Gly+(−0.0093)Ala; 0.642, 0.671, 0.776, 0.815, 0.703, 0.855, 0.765, 0.785, (1.6244)+(−0.0088)Ala+(−0.0039)Leu; 0.641, 0.665, 0.641, 0.708, 0.600, 0.670, 0.525, 0.626, (1.2368)+(−0.0616)Tyr+(0.0176)Orn; 0.641, 0.669, 0.777, 0.810, 0.701, 0.854, 0.794, 0.790, (1.5960)+(−

0.0029)Thr+(−0.0090)Ala; 0.640, 0.661, 0.627, 0.594, 0.664, 0.663, 0.611, 0.633, (−0.0873)+(−0.0926)Cit+(0.0212)Ile; 0.639, 0.663, 0.700, 0.735, 0.637, 0.754, 0.697, 0.706, (1.2645)+(−0.0316)Val+(0.0321)Leu; 0.637, 0.660, 0.720, 0.746, 0.727, 0.755, 0.612, 0.710, (2.7084)+(−0.0684)Cit+(−0.0110)Val; 0.637, 0.663, 0.642, 0.714, 0.592, 0.658, 0.546, 0.628, (1.5667)+(0.0048)Pro+(−0.0616)Tyr; 0.635, 0.659, 0.704, 0.721, 0.729, 0.737, 0.581, 0.692, (1.9881)+(−0.0784)Cit+(−0.0111)Leu; 0.634, 0.668, 0.696, 0.775, 0.656, 0.712, 0.562, 0.676, (2.1802)+(−0.0486)Tyr+(−0.0070)Leu; 0.632, 0.661, 0.690, 0.696, 0.729, 0.716, 0.574, 0.679, (1.7181)+(−0.0714)Cit+(−0.0136)Arg; 0.631, 0.658, 0.670, 0.753, 0.618, 0.680, 0.554, 0.651, (1.4409)+(0.0007)Gln+(−0.0560)Tyr; 0.631, 0.656, 0.726, 0.753, 0.730, 0.751, 0.626, 0.715, (2.3484)+(−0.0162)Arg+(−0.0139)Lys; 0.630, 0.659, 0.690, 0.692, 0.715, 0.705, 0.627, 0.684, (1.4777)+(−0.0058)Thr+(−0.0810)Cit; 0.626, 0.657, 0.696, 0.767, 0.645, 0.679, 0.627, 0.679, (2.3462)+(−0.0027)Gly+(−0.0552)Tyr; 0.626, 0.648, 0.652, 0.651, 0.689, 0.689, 0.551, 0.645, (0.7903)+(0.0012)Gly+(−0.0878)Cit; 0.626, 0.657, 0.671, 0.750, 0.622, 0.681, 0.554, 0.652, (1.8014)+(−0.0007)Thr+(−0.0540)Tyr; 0.625, 0.646, 0.664, 0.662, 0.697, 0.690, 0.582, 0.657, (1.0033)+(−0.0855)Cit+(−0.0003)Pro; 0.625, 0.651, 0.636, 0.684, 0.596, 0.738, 0.520, 0.635, (−0.5966)+(0.0186)Ser+(−0.0150)Val; 0.624, 0.657, 0.689, 0.737, 0.653, 0.756, 0.591, 0.684, (0.8263)+(−0.0178)Val+(0.0220)Orn; 0.623, 0.654, 0.685, 0.689, 0.693, 0.738, 0.620, 0.685, (1.3552)+(0.0218)Orn+(−0.0227)Lys; 0.622, 0.647, 0.662, 0.660, 0.692, 0.689, 0.583, 0.656, (0.5838)+(0.0008)Gln+(−0.0880)Cit; 0.621, 0.653, 0.748, 0.807, 0.728, 0.790, 0.603, 0.732, (2.8091)+(−0.0205)Arg+(−0.0129)Val; 0.620, 0.651, 0.689, 0.740, 0.641, 0.693, 0.652, 0.682, (0.0155)+(−0.0192)Val+(0.0395)Phe; 0.620, 0.651, 0.744, 0.790, 0.716, 0.802, 0.640, 0.737, (2.5515)+(−0.0106)Val+(−0.0108)Lys; 0.617, 0.647, 0.696, 0.701, 0.695, 0.706, 0.676, 0.695, (0.8491)+(−0.0220)Lys+(0.0271)Phe; 0.615, 0.639, 0.644, 0.636, 0.681, 0.658, 0.577, 0.638, (0.3037)+(−0.0884)Cit+(0.0129)Phe; 0.611, 0.638, 0.724, 0.742, 0.719, 0.746, 0.673, 0.720, (1.9680)+(−0.0011)Gly+(−0.0183)Lys; 0.611, 0.647, 0.722, 0.747, 0.709, 0.757, 0.656, 0.718, (1.2350)+(0.0014)Gln+(−0.0199)Ly s; 0.611, 0.641, 0.708, 0.726, 0.702, 0.744, 0.649, 0.705, (1.6959)+(0.0014)Pro+(−0.0191)Lys; 0.610, 0.635, 0.646, 0.645, 0.666, 0.665, 0.591, 0.642, (−0.0841)+(−0.0308)Arg+(0.0193)Ile; 0.609, 0.638, 0.720, 0.742, 0.712, 0.752, 0.657, 0.716, (1.8217)+(−0.0012)Thr+(−0.0180)Lys; 0.607, 0.636, 0.688, 0.743, 0.641, 0.730, 0.608, 0.681, (1.2424)+(0.0047)Pro+(−0.0170)Val; 0.605, 0.638, 0.723, 0.757, 0.713, 0.762, 0.626, 0.715, (1.9476)+(−0.0162)Lys+(−0.0053)Leu; 0.605, 0.635, 0.742, 0.794, 0.692, 0.768, 0.691, 0.736, (1.9032)+(−0.0023)Gly+(−0.0149)Val; 0.603, 0.644, 0.599, 0.600, 0.567, 0.693, 0.597, 0.614, (−2.5189)+(0.0324)Ser+(−0.0236)Thr; 0.599, 0.633, 0.716, 0.777, 0.669, 0.764, 0.619, 0.707, (1.5073)+(−0.0001)Gln+(−0.0149)Val; 0.596, 0.634, 0.736, 0.792, 0.688, 0.771, 0.661, 0.728, (1.7582)+(−0.0046)Thr+(−0.0140)Val; 0.596, 0.627, 0.665, 0.685, 0.698, 0.695, 0.525, 0.651, (0.3433)+(−0.0306)Arg+(0.0128)Orn; 0.595, 0.629, 0.728, 0.786, 0.733, 0.753, 0.548, 0.705, (1.9642)+(−0.0239)Arg+(−0.0135)Leu; 0.592, 0.622, 0.687, 0.720, 0.705, 0.691, 0.562, 0.670, (0.2892)+(0.0012)Gln+(−0.0295)Arg; 0.591, 0.623, 0.701, 0.732, 0.713, 0.701, 0.594, 0.685, (0.9755)+(−0.0037)Thr+(−0.0249)Arg;

0.590, 0.620, 0.683, 0.713, 0.705, 0.690, 0.555, 0.666, (0.7635)+(−0.0276)Arg+(0.0001)Pro; 0.590, 0.621, 0.688, 0.716, 0.709, 0.689, 0.567, 0.671, (0.8327)+(−0.0004)Gly+(−0.0273)Arg; 0.589, 0.623, 0.531, 0.479, 0.520, 0.596, 0.644, 0.560, (−3.2575)+(0.0302)Ser+(−0.0083)Gly; 0.583, 0.619, 0.672, 0.697, 0.695, 0.670, 0.556, 0.655, (0.2642)+(−0.0289)Arg+(0.0109)Phe; 0.579, 0.624, 0.454, 0.413, 0.483, 0.602, 0.395, 0.473, (−1.8253)+(0.0271)Ser+(−0.0049)Gln; 0.574, 0.613, 0.577, 0.622, 0.564, 0.677, 0.415, 0.570, (−1.8132)+(0.0190)Ser+(−0.0170)Leu; 0.572, 0.618, 0.639, 0.620, 0.603, 0.638, 0.767, 0.657, (−0.8939)+(−0.0159)Thr+(0.0180)Ile; 0.569, 0.605, 0.394, 0.342, 0.393, 0.534, 0.430, 0.425, (−4.4991)+(0.0200)Ser+(0.0115)Ile; 0.552, 0.621, 0.683, 0.686, 0.656, 0.698, 0.718, 0.690, (−0.4947)+(−0.0157)Thr+(0.0121)Orn; 0.550, 0.599, 0.467, 0.456, 0.465, 0.593, 0.407, 0.480, (−3.4533)+(0.0200)Ser+(−0.0027)Pro; 0.544, 0.591, 0.705, 0.725, 0.674, 0.674, 0.738, 0.703, (−0.0754)+(−0.0006)Gly+(−0.0126)Thr; 0.542, 0.586, 0.732, 0.788, 0.700, 0.739, 0.646, 0.718, (0.9960)+(−0.0087)Thr+(−0.0146)Leu; 0.538, 0.593, 0.661, 0.721, 0.652, 0.707, 0.486, 0.642, (−0.0989)+(0.0130)Orn+(−0.0199)Leu; 0.538, 0.592, 0.700, 0.722, 0.669, 0.677, 0.723, 0.698, (−0.1305)+(−0.0001)Gln+(−0.0128)Thr; 0.536, 0.584, 0.656, 0.721, 0.640, 0.626, 0.540, 0.632, (−0.7104)+(−0.0235)Leu+(0.0296)Phe; 0.534, 0.581, 0.428, 0.406, 0.430, 0.559, 0.387, 0.445, (−3.6022)+(0.0197)Ser+(−0.0032)Phe; 0.533, 0.576, 0.725, 0.785, 0.698, 0.718, 0.625, 0.707, (0.7956)+(−0.0023)Gly+(−0.0173)Leu; 0.532, 0.593, 0.690, 0.708, 0.658, 0.665, 0.725, 0.689, (−0.4103)+(−0.0135)Thr+(0.0056)Phe; 0.530, 0.592, 0.700, 0.723, 0.668, 0.678, 0.723, 0.698, (−0.1545)+(−0.0129)Thr+(0.0000)Pro; 0.524, 0.572, 0.669, 0.742, 0.645, 0.692, 0.510, 0.647, (0.2198)+(0.0018)Pro+(−0.0186)Leu; 0.521, 0.571, 0.437, 0.424, 0.432, 0.546, 0.405, 0.452, (−3.5449)+(0.0206)Ser+(−0.0062)Orn; 0.521, 0.573, 0.687, 0.758, 0.671, 0.713, 0.515, 0.664, (0.5502)+(−0.0005)Gln+(−0.0169) Leu 0.847, 0.863, 0.807, 0.794, 0.809, 0.813, 0.833, 0.813, (6.1203)+(−0.1057)His+(0.1038)Phe+(−0.1160)Trp; 0.843, 0.861, 0.766, 0.764, 0.770, 0.765, 0.763, 0.766, (0.3860)+(0.0285)Ser+(0.0708)Phe+(−0.1800)Trp; 0.841, 0.852, 0.788, 0.762, 0.789, 0.818, 0.835, 0.801, (7.5109)+(−0.0925)His+(0.0651)Ile+(−0.1199)Trp; 0.837, 0.851, 0.786, 0.780, 0.786, 0.849, 0.754, 0.793, (5.9269)+(0.0370)Ser+(−0.0914)His+(−0.0960)Trp; 0.835, 0.847, 0.775, 0.766, 0.739, 0.813, 0.848, 0.791, (5.0718)+(−0.0408)Val+(0.1480)Ile+(−0.1381)Trp; 0.833, 0.848, 0.787, 0.782, 0.771, 0.804, 0.820, 0.795, (4.8174)+(0.1394)Ile+(−0.0646)Leu+(−0.1464)Trp; 0.832, 0.846, 0.821, 0.826, 0.811, 0.845, 0.810, 0.823, (5.8821)+(0.0098)Gln+(−0.1088)His+(−0.1000)Trp; 0.830, 0.845, 0.796, 0.793, 0.801, 0.835, 0.765, 0.798, (8.3046)+(−0.0932)His+(0.0211)Thr+(−0.1065)Trp; 0.828, 0.847, 0.811, 0.820, 0.813, 0.770, 0.809, 0.803, (3.4267)+(−0.0070)Val+(0.0829)Phe+(−0.1635)Trp; 0.828, 0.843, 0.803, 0.815, 0.800, 0.838, 0.753, 0.801, (4.9322)+(0.0381)Ser+(−0.0943)Asn+(−0.1322)Trp; 0.828, 0.842, 0.803, 0.816, 0.803, 0.844, 0.739, 0.800, (4.3243)+(0.0350)Ser+(−0.1297)Met+(−0.1329)Trp; 0.827, 0.841, 0.744, 0.727, 0.745, 0.776, 0.766, 0.753, (1.4558)+(0.0279)Ser+(0.0512)Ile+(−0.1787)Trp; 0.826, 0.839, 0.793, 0.776, 0.804, 0.807, 0.807, 0.798, (6.0150)+(−0.0807)Cit+(0.0621)Ile+(−0.1723)Trp; 0.826, 0.843, 0.797, 0.787, 0.806, 0.827, 0.783, 0.801, (8.0435)+(−0.0898)His+(0.0369)Orn+(−0.0989)Trp; 0.825, 0.845, 0.824, 0.830, 0.832, 0.776, 0.826, 0.816, (4.7154)+(−0.0675)Asn+
(0.0782)Phe+(−0.1556)Trp; 0.825, 0.837, 0.709, 0.671,
0.711, 0.796, 0.744, 0.731, (0.7000)+(0.0434)Ser+(−
0.1690)His+(0.0910)Phe; 0.824, 0.845, 0.803, 0.810,
0.809, 0.756, 0.806, 0.795, (2.4095)+(0.0022)Gln+
(0.0670)Phe+(−0.1787)Trp; 0.824, 0.841, 0.795, 0.796,
0.810, 0.837, 0.727, 0.793, (4.8137)+(0.0312)Ser+(−
0.0712)Cit+(−0.1507)Trp; 0.824, 0.837, 0.705, 0.655,
0.706, 0.816, 0.756, 0.733, (2.1410)+(0.0395)Ser+(−
0.1546)His+(0.0546)Ile; 0.823, 0.844, 0.826, 0.834,
0.836, 0.786, 0.816, 0.818, (3.9066)+(−0.1992)Met+
(0.1112)Phe+(−0.1427)Trp; 0.822, 0.839, 0.811, 0.810,
0.829, 0.788, 0.797, 0.806, (4.6574)+(−0.0877)Cit+
(0.0903)Phe+(−0.1721)Trp; 0.822, 0.842, 0.792, 0.794,
0.807, 0.751, 0.787, 0.785, (3.0429)+(0.0058)Thr+
(0.0671)Phe+(−0.1790)Trp; 0.822, 0.839, 0.774, 0.762,
0.781, 0.744, 0.813, 0.775, (2.9066)+(0.0405)Ile+
(0.0456)Phe+(−0.1860)Trp; 0.822, 0.841, 0.797, 0.801,
0.807, 0.750, 0.800, 0.789, (3.1910)+(0.0022)Pro+
(0.0675)Phe+(−0.1750)Trp; 0.821, 0.843, 0.821, 0.828,
0.814, 0.798, 0.834, 0.819, (3.6992)+(−0.0060)Ala+
(0.0835)Phe+(−0.1607)Trp; 0.821, 0.837, 0.798, 0.794,
0.801, 0.814, 0.790, 0.800, (8.4039)+(−0.0805)His+
(0.0085)Pro+(−0.1012)Trp; 0.821, 0.835, 0.801, 0.794,
0.831, 0.824, 0.740, 0.797, (6.8352)+(−0.1114)Cit+
(0.0546)Orn+(−0.1576)Trp; 0.821, 0.842, 0.802, 0.808,
0.812, 0.755, 0.801, 0.794, (3.2872)+(−0.0019)Leu+
(0.0716)Phe+(−0.1719)Trp; 0.821, 0.841, 0.798, 0.801,
0.809, 0.754, 0.796, 0.790, (3.1971)+(0.0053)Orn+
(0.0661)Phe+(−0.1736)Trp; 0.821, 0.839, 0.784, 0.772,
0.740, 0.850, 0.859, 0.805, (4.6883)+(−0.0544)Val+(−
0.2751)Met+(0.1901)Ile; 0.821, 0.840, 0.801, 0.805,
0.812, 0.753, 0.803, 0.793, (3.3119)+(−0.0002)Gly+
(0.0696)Phe+(−0.1733)Trp; 0.820, 0.845, 0.808, 0.813,
0.818, 0.767, 0.806, 0.801, (3.5616)+(−0.0050)Lys+
(0.0755)Phe+(−0.1678)Trp; 0.818, 0.838, 0.794, 0.811,
0.793, 0.747, 0.786, 0.784, (3.5386)+(−0.0340)Tyr+
(0.0898)Phe+(−0.1607)Trp; 0.817, 0.831, 0.794, 0.776,
0.803, 0.814, 0.811, 0.801, (8.3524)+(−0.0941)His+
(0.0241)Leu+(−0.1113)Trp; 0.816, 0.833, 0.802, 0.819,
0.816, 0.815, 0.718, 0.792, (6.6981)+(0.0249)Thr+(−
0.1682)Met+(−0.1414)Trp; 0.816, 0.830, 0.767, 0.748,
0.754, 0.807, 0.813, 0.780, (2.0184)+(0.0088)Gln+(−
0.1733)His+(0.0702)Phe; 0.815, 0.832, 0.797, 0.787,
0.777, 0.817, 0.852, 0.808, (5.0478)+(−0.0082)Ala+
(0.0672)Ile+(−0.1566)Trp; 0.815, 0.830, 0.793, 0.802,
0.785, 0.835, 0.756, 0.795, (3.7617)+(0.0278)Ser+(−
0.0037)Ala+(−0.1426)Trp; 0.814, 0.832, 0.765, 0.768,
0.772, 0.788, 0.725, 0.763, (2.8485)+(0.0270)Ser+
(0.0046)Pro+(−0.1571)Trp; 0.814, 0.837, 0.809, 0.815,
0.824, 0.761, 0.793, 0.798, (3.9358)+(−0.0169)Arg+
(0.0791)Phe+(−0.1682)Trp; 0.814, 0.828, 0.801, 0.799,
0.804, 0.813, 0.791, 0.802, (8.1974)+(−0.0879)His+
(0.0110)Lys+(−0.1046)Trp; 0.813, 0.830, 0.790, 0.789,
0.790, 0.803, 0.786, 0.792, (3.6198)+(0.0383)Ser+(−
0.0082)Gly+(−0.1524)Trp; 0.813, 0.830, 0.803, 0.808,
0.804, 0.832, 0.769, 0.803, (8.5172)+(0.0028)Gly+(−
0.0799)His+(−0.0940)Trp; 0.813, 0.826, 0.744, 0.719,
0.708, 0.814, 0.834, 0.768, (5.3459)+(−0.0998)His+(−
0.0349)Val+(0.1274)Ile; 0.813, 0.826, 0.752, 0.741,
0.741, 0.835, 0.742, 0.765, (2.9114)+(0.0285)Ser+
(0.0059)Gln+(−0.1503)His; 0.813, 0.826, 0.757, 0.727,
0.747, 0.817, 0.816, 0.776, (3.0138)+(0.0083)Gln+(−
0.1623)His+(0.0428)Ile; 0.812, 0.830, 0.771, 0.777,
0.777, 0.799, 0.723, 0.769, (2.9095)+(0.0258)Ser+
(0.0108)Orn+(−0.1557)Trp; 0.812, 0.828, 0.802, 0.795,
0.811, 0.819, 0.793, 0.804, (8.6020)+(−0.0875)His+
(0.0079)Val+(−0.1054)Trp; 0.811, 0.828, 0.779, 0.787,
0.782, 0.812, 0.726, 0.777, (3.5040)+(0.0291)Ser+(−
0.0048)Lys+(−0.1458)Trp; 0.810, 0.827, 0.777, 0.788,
0.777, 0.808, 0.724, 0.774, (3.4604)+(0.0273)Ser+(−
0.0085)Tyr+(−0.1480)Trp; 0.810, 0.828, 0.763, 0.762,
0.771, 0.788, 0.732, 0.763, (2.5854)+(0.0277)Ser+
(0.0099)Leu+(−0.1631)Trp; 0.810, 0.827, 0.778, 0.770,
0.777, 0.769, 0.807, 0.780, (3.5132)+(0.0019)Gln+
(0.0481)Ile+(−0.1761)Trp; 0.810, 0.827, 0.795, 0.786,
0.796, 0.799, 0.816, 0.799, (5.6954)+(−0.1645)Met+
(0.0656)Ile+(−0.1435)Trp; 0.810, 0.826, 0.777, 0.785,
0.780, 0.805, 0.732, 0.776, (3.1987)+(0.0284)Ser+(−
0.0023)Thr+(−0.1503)Trp; 0.810, 0.822, 0.713, 0.674,
0.723, 0.814, 0.725, 0.734, (3.1069)+(0.0389)Ser+(−
0.1528)His+(0.0197)Leu; 0.809, 0.828, 0.774, 0.782,
0.778, 0.801, 0.727, 0.772, (3.1956)+(0.0271)Ser+(−
0.0000)Val+(−0.1525)Trp; 0.809, 0.826, 0.804, 0.807,
0.827, 0.824, 0.734, 0.798, (6.9782)+(0.0146)Thr+(−
0.0722)Cit+(−0.1572)Trp; 0.809, 0.825, 0.810, 0.812,
0.810, 0.827, 0.789, 0.810, (8.8689)+(−0.0762)His+(−
0.0001)Ala+(−0.0948)Trp; 0.809, 0.828, 0.774, 0.782,
0.778, 0.801, 0.726, 0.772, (3.2050)+(0.0272)Ser+(−
0.0000)Gln+(−0.1524)Trp; 0.808, 0.827, 0.726, 0.697,
0.735, 0.826, 0.714, 0.743, (3.7633)+(0.0330)Ser+(−
0.1411)His+(0.0244)Orn; 0.808, 0.826, 0.793, 0.784,
0.792, 0.791, 0.821, 0.797, (5.7175)+(−0.0548)Asn+
(0.0503)Ile+(−0.1556)Trp; 0.808, 0.827, 0.827, 0.836,
0.837, 0.829, 0.778, 0.820, (5.3892)+(0.0055)Gln+(−
0.0743)Cit+(−0.1543)Trp; 0.808, 0.822, 0.773, 0.761,
0.776, 0.766, 0.803, 0.776, (4.2285)+(0.0012)Orn+
(0.0490)Ile+(−0.1716)Trp; 0.808, 0.822, 0.750, 0.723,
0.734, 0.813, 0.813, 0.771, (5.3562)+(−0.1130)His+
(0.1080)Ile+(−0.0454)Leu; 0.808, 0.825, 0.811, 0.814,
0.810, 0.827, 0.789, 0.810, (8.9680)+(−0.0058)Asn+(−
0.0747)His+(−0.0944)Trp; 0.807, 0.827, 0.809, 0.803,
0.814, 0.829, 0.799, 0.811, (8.5780)+(−0.0825)His+
(0.0182)Tyr+(−0.1025)Trp; 0.807, 0.820, 0.769, 0.738,
0.748, 0.836, 0.847, 0.792, (5.9932)+(−0.1222)His+(−
0.0065)Ala+(0.0581)Ile; 0.807, 0.826, 0.782, 0.794,
0.790, 0.816, 0.706, 0.777, (3.8894)+(0.0312)Ser+(−
0.0178)Arg+(−0.1448)Trp; 0.806, 0.819, 0.722, 0.695,
0.726, 0.819, 0.713, 0.738, (3.6702)+(0.0365)Ser+(−
0.1381)His+(0.0064)Pro; 0.806, 0.819, 0.747, 0.724,
0.744, 0.831, 0.754, 0.763, (4.3049)+(0.0422)Ser+(−
0.0047)Gly+(−0.1309)His; 0.806, 0.825, 0.769, 0.758,
0.773, 0.764, 0.796, 0.773, (4.0910)+(0.0035)Thr+
(0.0484)Ile+(−0.1746)Trp; 0.805, 0.822, 0.775, 0.763,
0.779, 0.767, 0.808, 0.779, (4.3381)+(−0.0004)Gly+
(0.0493)Ile+(−0.1712)Trp; 0.805, 0.823, 0.771, 0.769,
0.765, 0.766, 0.795, 0.774, (4.8101)+(−0.0217)Tyr+
(0.0537)Ile+(−0.1610)Trp; 0.805, 0.823, 0.804, 0.802,
0.823, 0.808, 0.766, 0.800, (7.1369)+(−0.0711)Cit+
(0.0084)Pro+(−0.1501)Trp; 0.804, 0.826, 0.809, 0.811,
0.810, 0.827, 0.789, 0.809, (8.8109)+(−0.0768)His+
(0.0012)Arg+(−0.0952)Trp; 0.804, 0.821, 0.753, 0.740,
0.751, 0.839, 0.727, 0.764, (4.8557)+(0.0410)Ser+(−
0.0580)Asn+(−0.1163)His; 0.804, 0.825, 0.811, 0.814,
0.811, 0.827, 0.788, 0.810, (8.9122)+(−0.0749)His+(−
0.0084)Met+(−0.0941)Trp; 0.804, 0.820, 0.807, 0.818,
0.794, 0.815, 0.798, 0.806, (6.0813)+(−0.0065)Ala+
(0.0108)Pro+(−0.1376)Trp; 0.804, 0.823, 0.806, 0.819,
0.815, 0.807, 0.753, 0.798, (7.0940)+(−0.0817)Asn+
(0.0180)Thr+(−0.1425)Trp; 0.803, 0.824, 0.837, 0.854,
0.832, 0.827, 0.813, 0.831, (5.2819)+(−0.0842)Asn+
(0.0066)Gln+(−0.1385)Trp; 0.803, 0.818, 0.746, 0.731,
0.738, 0.841, 0.730, 0.760, (4.3899)+(0.0357)Ser+(−
0.1271)His+(−0.0019)Ala; 0.803, 0.819, 0.805, 0.802, 0.791, 0.846, 0.811, 0.813, (4.5718)+(−0.0590)Asn+ (0.0113)Gln+(−0.1379)His; 0.803, 0.820, 0.806, 0.808, 0.790, 0.849, 0.798, 0.811, (4.3417)+(0.0108)Gln+(− 0.1346)His+(−0.0961)Met; 0.803, 0.818, 0.826, 0.699, 0.733, 0.821, 0.717, 0.742, (3.7074)+(0.0371)Ser+(− 0.1426)His+(0.0051)Val; 0.803, 0.821, 0.775, 0.764, 0.777, 0.769, 0.807, 0.779, (4.3262)+(−0.0019)Pro+ (0.0518)Ile+(−0.1706)Trp; 0.803, 0.825, 0.760, 0.752, 0.759, 0.850, 0.716, 0.769, (4.6315)+(0.0395)Ser+(− 0.1137)His+(−0.0967)Met; 0.803, 0.821, 0.803, 0.798, 0.824, 0.798, 0.777, 0.799, (6.9309)+(−0.0715)Cit+ (0.0162)Leu+(−0.1593)Trp; 0.803, 0.822, 0.779, 0.765, 0.781, 0.779, 0.808, 0.783, (4.8509)+(−0.0077)Lys+ (0.0554)Ile+(−0.1621)Trp; 0.802, 0.817, 0.735, 0.695, 0.733, 0.785, 0.810, 0.756, (4.2572)+(−0.1461)His+ (0.0325)Ile+(0.0507)Phe; 0.802, 0.818, 0.826, 0.833, 0.838, 0.832, 0.777, 0.820, (8.3805)+(−0.0347)Asn+(− 0.0578)Cit+(−0.1321)Trp; 0.802, 0.813, 0.768, 0.748, 0.762, 0.819, 0.798, 0.782, (3.5916)+(0.0092)Gln+(− 0.1620)His+(0.0129)Leu; 0.802, 0.817, 0.768, 0.752, 0.765, 0.823, 0.777, 0.779, (3.9165)+(0.0081)Gln+(− 0.1538)His+(0.0212)Orn; 0.801, 0.823, 0.813, 0.815, 0.819, 0.833, 0.779, 0.812, (9.2144)+(−0.0654)His+(− 0.0311)Cit+(−0.0986)Trp; 0.801, 0.819, 0.801, 0.815, 0.799, 0.788, 0.773, 0.794, (4.3239)+(0.0027)Gln+ (0.0039)Pro+(−0.1561)Trp; 0.801, 0.816, 0.732, 0.712, 0.733, 0.827, 0.711, 0.746, (4.1517)+(0.0343)Ser+(− 0.1354)His+(0.0035)Thr; 0.801, 0.814, 0.729, 0.687, 0.729, 0.796, 0.788, 0.750, (5.1464)+(−0.1456)His+ (0.0119)Thr+(0.0436)Ile; 0.801, 0.818, 0.824, 0.832, 0.834, 0.834, 0.778, 0.819, (7.7964)+(−0.0021)Ala+(− 0.0603)Cit+(−0.1349)Trp; 0.801, 0.815, 0.793, 0.793, 0.774, 0.843, 0.798, 0.802, (4.3649)+(0.0093)Gln+(− 0.1435)His+(−0.0024)Ala; 0.801, 0.817, 0.811, 0.814, 0.831, 0.812, 0.765, 0.805, (7.2700)+(−0.0686)Cit+ (0.0045)Val+(−0.1507)Trp; 0.801, 0.821, 0.783, 0.765, 0.789, 0.798, 0.809, 0.790, (4.7615)+(−0.1213)His+(− 0.1757)Met+(0.1150)Phe; 0.801, 0.820, 0.796, 0.798, 0.790, 0.792, 0.805, 0.796, (5.6507)+(−0.0234)Val+ (0.0470)Leu+(−0.1506)Trp; 0.800, 0.816, 0.738, 0.719, 0.737, 0.831, 0.720, 0.752, (4.2496)+(0.0359)Ser+(− 0.1311)His+(−0.0011)Lys; 0.800, 0.822, 0.831, 0.852, 0.824, 0.828, 0.791, 0.824, (4.8052)+(0.0061)Gln+(− 0.1296)Met+(−0.1348)Trp; 0.800, 0.813, 0.770, 0.762, 0.760, 0.820, 0.775, 0.779, (4.1381)+(−0.0083)Gln+(− 0.1538)His+(0.0072)Thr; 0.800, 0.820, 0.810, 0.819, 0.815, 0.799, 0.784, 0.804, (6.8969)+(−0.0563)Asn+ (0.0063)Pro+(−0.1355)Trp; 0.800, 0.815, 0.729, 0.706, 0.728, 0.783, 0.756, 0.743, (3.8156)+(0.0049)Gly+(− 0.1500)His+(0.0793)Phe; 0.799, 0.817, 0.728, 0.697, 0.732, 0.773, 0.770, 0.743, (4.1977)+(−0.1568)His+ (0.0141)Thr+(0.0711)Phe; 0.799, 0.818, 0.810, 0.819, 0.819, 0.805, 0.774, 0.804, (6.6221)+(−0.0626)Asn+ (0.0241)Orn+(−0.1347)Trp; 0.799, 0.819, 0.788, 0.797, 0.797, 0.778, 0.755, 0.782, (4.9954)+(0.0033)Pro+ (0.0146)Orn+(−0.1529)Trp; 0.799, 0.818, 0.810, 0.818, 0.826, 0.824, 0.745, 0.804, (7.2294)+(0.0021)Gly+(− 0.0662)Cit+(−0.1419)Trp; 0.799, 0.818, 0.788, 0.798, 0.795, 0.781, 0.749, 0.781, (5.1587)+(0.0066)Thr+ (0.0037)Pro+(−0.1561)Trp; 0.799, 0.812, 0.777, 0.766, 0.768, 0.824, 0.790, 0.787, (3.9080)+(0.0093)Gln+(− 0.1550)His+(0.0027)Val; 0.798, 0.817, 0.743, 0.729, 0.748, 0.833, 0.705, 0.754, (4.6112)+(0.0384)Ser+(− 0.1262)His+(−0.0138)Arg; 0.798, 0.813, 0.781, 0.775, 0.769, 0.829, 0.788, 0.790, (4.1316)+(−0.0002)Gly+ (0.0093)Gln+(−0.1498)His; 0.798, 0.813, 0.782, 0.777, 0.770, 0.830, 0.788, 0.791, (4.1650)+(0.0093)Gln+(− 0.1490)His+(−0.0008)Lys; 0.798, 0.812, 0.755, 0.749, 0.670, 0.843, 0.881, 0.786, (2.4334)+(−0.0107)Ala+(− 0.0528)Val+(0.1714)Ile; 0.798, 0.819, 0.805, 0.816, 0.810, 0.799, 0.771, 0.799, (6.6861)+(0.0096)Pro+(− 0.1264)Met+(−0.1290)Trp; 0.798, 0.815, 0.737, 0.720, 0.736, 0.828, 0.717, 0.750, (4.2895)+(0.0356)Ser+(− 0.1300)His+(−0.0046)Tyr; 0.798, 0.816, 0.813, 0.819, 0.829, 0.814, 0.762, 0.806, (7.2107)+(−0.0638)Cit+ (0.0033)Lys+(−0.1461)Trp; 0.797, 0.811, 0.771, 0.761, 0.761, 0.820, 0.786, 0.782, (3.9323)+(0.0090)Gln+(− 0.1519)His+(0.0037)Pro; 0.797, 0.817, 0.796, 0.808, 0.802, 0.794, 0.752, 0.789, (5.3565)+(−0.0037)Val+ (0.0209)Orn+(−0.1438)Trp; 0.797, 0.816, 0.823, 0.831, 0.835, 0.828, 0.770, 0.816, (7.9208)+(−0.0559)Cit+(− 0.0474)Met+(−0.1314)Trp; 0.797, 0.815, 0.771, 0.752, 0.756, 0.816, 0.818, 0.786, (4.9478)+(−0.1345)His+(− 0.0044)Ala+(0.0817)Phe; 0.797, 0.813, 0.738, 0.720, 0.743, 0.830, 0.706, 0.750, (4.4233)+(0.0368)Ser+(− 0.1250)His+(−0.0296)Cit; 0.797, 0.816, 0.797, 0.809, 0.800, 0.787, 0.765, 0.791, (5.6255)+(0.0058)Pro+(− 0.0028)Val+(−0.1449)Trp; 0.797, 0.817, 0.817, 0.819, 0.834, 0.822, 0.771, 0.811, (7.3477)+(−0.0649)Cit+ (0.0076)Tyr+(−0.1456)Trp; 0.797, 0.815, 0.755, 0.749, 0.740, 0.778, 0.787, 0.764, (4.9925)+(−0.1332)His+(− 0.0409)Tyr+(0.0989)Phe; 0.797, 0.817, 0.739, 0.704, 0.742, 0.790, 0.785, 0.755, (4.2734)+(−0.1473)His+ (0.0224)Orn+(0.0642)Phe; 0.796, 0.817, 0.799, 0.811, 0.805, 0.789, 0.763, 0.792, (4.2821)+(0.0023)Gln+ (0.0135)Orn+(−0.1554)Trp; 0.796, 0.810, 0.765, 0.758, 0.705, 0.832, 0.859, 0.788, (5.2744)+(−0.1234)Asn+(− 0.0559)Val+(0.1648)Ile; 0.796, 0.816, 0.799, 0.814, 0.802, 0.790, 0.759, 0.791, (4.4453)+(0.0024)Gln+ (0.0055)Thr+(−0.1576)Trp; 0.796, 0.817, 0.816, 0.820, 0.830, 0.823, 0.767, 0.810, (7.3786)+(−0.0655)Cit+ (0.0035)Arg+(−0.1428)Trp; 0.796, 0.815, 0.788, 0.797, 0.798, 0.785, 0.742, 0.781, (4.9842)+(0.0053)Thr+ (0.0138)Orn+(−0.1553)Trp; 0.796, 0.818, 0.779, 0.770, 0.785, 0.773, 0.793, 0.780, (5.0473)+(−0.0151)Arg+ (0.0524)Ile+(−0.1642)Trp; 0.796, 0.813, 0.733, 0.688, 0.738, 0.802, 0.793, 0.755, (5.1743)+(−0.1399)His+ (0.0207)Orn+(0.0397)Ile; 0.796, 0.814, 0.794, 0.807, 0.801, 0.794, 0.743, 0.786, (5.5010)+(0.0089)Thr+(− 0.0019)Val+(−0.1510)Trp; 0.796, 0.815, 0.791, 0.799, 0.797, 0.774, 0.773, 0.786, (5.1953)+(0.0039)Pro+ (0.0061)Leu+(−0.1559)Trp; 0.795, 0.809, 0.726, 0.689, 0.725, 0.798, 0.774, 0.747, (4.8966)+(0.0041)Gly+(− 0.1388)His+(0.0479)Ile; 0.795, 0.813, 0.755, 0.735, 0.748, 0.789, 0.797, 0.767, (4.7788)+(−0.1369)His+(− 0.0061)Val+(0.0850)Phe; 0.795, 0.816, 0.798, 0.808, 0.803, 0.780, 0.773, 0.791, (5.6160)+(−0.0010)Gly+ (0.0049)Pro+(−0.1495)Trp; 0.795, 0.814, 0.794, 0.794, 0.783, 0.842, 0.780, 0.800, (4.2855)+(0.0113)Gln+(− 0.1468)His+(−0.0180)Arg; 0.795, 0.813, 0.805, 0.820, 0.800, 0.821, 0.763, 0.801, (5.9142)+(0.0119)Thr+(− 0.0044)Ala+(−0.1462)Trp; 0.795, 0.813, 0.807, 0.818, 0.804, 0.814, 0.778, 0.804, (5.7061)+(−0.0046)Ala+ (0.0233)Orn+(−0.1394)Trp; 0.794, 0.813, 0.797, 0.806, 0.804, 0.782, 0.768, 0.790, (5.3946)+(−0.0015)Gly+ (0.0182)Orn+(−0.1500)Trp; 0.794, 0.807, 0.744, 0.709, 0.741, 0.801, 0.804, 0.764, (5.6225)+(−0.1339)His+(− 0.0017)Pro+(0.0476)Ile; 0.794, 0.811, 0.748, 0.722, 0.746, 0.785, 0.793, 0.761, (4.6778)+(−0.1427)His+(− 0.0011)Leu+(0.0746)Phe; 0.794, 0.815, 0.789, 0.795, 0.798, 0.776, 0.761, 0.783, (4.9700)+(0.0150)Orn+ (0.0051)Leu+(−0.1554)Trp; 0.794, 0.814, 0.792, 0.808, 0.793, 0.783, 0.756, 0.785, (5.7771)+(0.0063)Pro+(− 0.0142)Tyr+(−0.1432)Trp; 0.794, 0.814, 0.805, 0.816, 0.812, 0.811, 0.756, 0.799, (6.2480)+(−0.1144)Met+ (0.0265)Orn+(−0.1300)Trp; 0.794, 0.811, 0.816, 0.831, 0.817, 0.796, 0.788, 0.808, (6.8947)+(−0.0617)Asn+ (0.0064)Lys+(−0.1383)Trp; 0.794, 0.814, 0.792, 0.806, 0.801, 0.793, 0.740, 0.785, (5.5662)+(0.0100)Thr+(− 0.0030)Lys+(−0.1515)Trp; 0.794, 0.811, 0.783, 0.782, 0.767, 0.827, 0.785, 0.790, (4.2965)+(0.0093)Gln+(− 0.1450)His+(−0.0093)Tyr; 0.794, 0.813, 0.797, 0.807, 0.808, 0.783, 0.761, 0.790, (5.6920)+(−0.0024)Gly+ (0.0101)Thr+(−0.1556)Trp; 0.793, 0.811, 0.744, 0.716, 0.743, 0.780, 0.794, 0.758, (4.6082)+(−0.1435)His+ (0.0014)Pro+(0.0715)Phe; 0.793, 0.816, 0.794, 0.805, 0.804, 0.786, 0.752, 0.787, (5.3204)+(0.0192)Orn+(− 0.0025)Lys+(−0.1469)Trp; 0.793, 0.815, 0.795, 0.807, 0.800, 0.783, 0.765, 0.789, (5.4706)+(0.0049)Pro+(− 0.0004)Lys+(−0.1493)Trp; 0.793, 0.814, 0.765, 0.735, 0.765, 0.808, 0.814, 0.781, (6.2924)+(−0.1115)His+(− 0.1437)Met+(0.0614)Ile; 0.793, 0.811, 0.809, 0.828, 0.807, 0.797, 0.776, 0.802, (4.5282)+(0.0032)Gln+(− 0.0014)Val+(−0.1505)Trp; 0.793, 0.807, 0.747, 0.712, 0.746, 0.801, 0.806, 0.766, (5.8441)+(−0.0156)Asn+(− 0.1291)His+(0.0452)Ile; 0.793, 0.813, 0.825, 0.844, 0.811, 0.828, 0.802, 0.821, (4.7615)+(0.0040)Gln+(− 0.0042)Ala+(−0.1437)Trp; 0.793, 0.815, 0.800, 0.812, 0.801, 0.785, 0.779, 0.794, (4.1968)+(0.0029)Gln+ (0.0070)Leu+(−0.1604)Trp; 0.792, 0.810, 0.758, 0.736, 0.756, 0.789, 0.801, 0.770, (5.1249)+(−0.0297)Asn+(− 0.1346)His+(0.0762)Phe; 0.792, 0.813, 0.788, 0.807, 0.793, 0.786, 0.731, 0.779, (5.6817)+(0.0106)Thr+(− 0.0143)Tyr+(−0.1488)Trp; 0.792, 0.813, 0.807, 0.829, 0.801, 0.797, 0.769, 0.799, (4.6193)+(0.0036)Gln+(− 0.0114)Tyr+(−0.1477)Trp; 0.792, 0.814, 0.785, 0.792, 0.796, 0.774, 0.750, 0.778, (5.0110)+(0.0075)Thr+ (0.0072)Leu+(−0.1615)Trp; 0.792, 0.811, 0.791, 0.805, 0.795, 0.790, 0.745, 0.784, (5.4696)+(−0.0144)Tyr+ (0.0208)Orn+(−0.1432)Trp; 0.792, 0.806, 0.825, 0.841, 0.821, 0.824, 0.793, 0.820, (7.3985)+(−0.0434)Asn+(− 0.0021)Ala+(−0.1270)Trp; 0.792, 0.813, 0.810, 0.828, 0.809, 0.798, 0.775, 0.802, (4.5134)+(0.0034)Gln+(− 0.0019)Lys+(−0.1508)Trp; 0.792, 0.810, 0.745, 0.721, 0.734, 0.792, 0.795, 0.761, (6.1180)+(−0.1249)His+(− 0.0267)Tyr+(0.0521)Ile; 0.791, 0.812, 0.815, 0.830, 0.814, 0.792, 0.793, 0.807, (4.6372)+(−0.0022)Gly+ (0.0036)Gln+(−0.1532)Trp; 0.791, 0.814, 0.767, 0.764, 0.774, 0.827, 0.717, 0.770, (7.1487)+(−0.1158)His+ (0.0279)Thr+(−0.1455)Met; 0.791, 0.810, 0.749, 0.723, 0.747, 0.787, 0.795, 0.763, (4.8024)+(−0.1410) His+(−0.0023)Lys+(0.0755)Phe; 0.791, 0.810, 0.786, 0.779, 0.777, 0.835, 0.785, 0.794, (4.2753)+(0.0099) Gln+(−0.1424)His+(−0.0345)Cit; 0.790, 0.808, 0.819, 0.834, 0.822, 0.808, 0.784, 0.812, (7.2274)+(−0.0493) Asn+(−0.0003)Val+(−0.1307)Trp; 0.790, 0.811, 0.797, 0.810, 0.806, 0.789, 0.750, 0.789, (6.0790)+(−0.0122) Arg+(0.0062)Pro+(−0.1447)Trp; 0.790, 0.807, 0.744, 0.707, 0.742, 0.801, 0.804, 0.763, (5.7493)+(−0.1302) His+(−0.0034)Lys+(0.0477)Ile; 0.790, 0.808, 0.822, 0.837, 0.825, 0.816, 0.780, 0.815, (7.4464)+(−0.0291) Asn+(−0.0612)Met+(−0.1251)Trp; 0.790, 0.811, 0.725, 0.737, 0.728, 0.755, 0.665, 0.721, (−3.8956)+(0.0461) Ser+(−0.3860)Met+(0.1074)Phe; 0.790, 0.808, 0.813, 0.828, 0.816, 0.801, 0.771, 0.804, (6.4637)+(−0.1161) Met+(0.0086)Lys+(−0.1362)Trp; 0.790, 0.810, 0.817, 0.832, 0.820, 0.809, 0.779, 0.810, (7.1177)+(−0.0507) Asn+(0.0006)Gly+(−0.1311)Trp; 0.790, 0.808, 0.764, 0.741, 0.764, 0.828, 0.780, 0.778, (6.4775)+(−0.1222) His+(−0.0034)Ala+(0.0360)Or n; 0.789, 0.808, 0.810, 0.818, 0.815, 0.792, 0.790, 0.804, (6.7362)+(−0.0523) Asn+(0.0099)Leu+(−0.1411)Trp; 0.788, 0.812, 0.817, 0.838, 0.817, 0.809, 0.764, 0.807, (4.7182)+(0.0047) Gln+(−0.0162)Arg+(−0.1483)Trp; 0.788, 0.808, 0.820, 0.833, 0.823, 0.807, 0.786, 0.812, (7.1489)+(−0.0506) Asn+(0.0027)Tyr+(−0.1325)Trp; 0.788, 0.808, 0.711, 0.692, 0.713, 0.786, 0.704, 0.724, (−2.2756)+(0.0463) Ser+(−0.3598)Met+(0.0667)Ile; 0.787, 0.807, 0.751, 0.726, 0.752, 0.785, 0.788, 0.763, (4.9596)+(−0.1397) His+(−0.0076)Arg+(0.0755)Phe; 0.787, 0.805, 0.742, 0.708, 0.742, 0.797, 0.796, 0.761, (5.7860)+(−0.1311) His+(−0.0055)Arg+(0.0456)Ile; 0.787, 0.810, 0.790, 0.807, 0.807, 0.793, 0.708, 0.779, (6.1198)+(0.0151) Thr+(−0.0190)Arg+(−0.1520)Trp; 0.787, 0.808, 0.802, 0.817, 0.806, 0.791, 0.765, 0.794, (5.7631)+(−0.0011) Val+(0.0014)Lys+(−0.1448)Trp; 0.787, 0.807, 0.821, 0.838, 0.823, 0.819, 0.777, 0.814, (7.0144)+(−0.0012) Ala+(−0.0771)Met+(−0.1262)Trp; 0.786, 0.807, 0.807, 0.813, 0.800, 0.806, 0.804, 0.806, (5.8190)+(−0.0048) Ala+(0.0147)Leu+(−0.1472)Trp; 0.786, 0.808, 0.735, 0.708, 0.746, 0.805, 0.735, 0.749, (5.8708)+(−0.1387) His+(0.0106)Thr+(0.0275)Orn; 0.786, 0.809, 0.823, 0.833, 0.831, 0.815, 0.786, 0.816, (6.7016)+(0.0220) Tyr+(−0.1228)Met+(−0.1333)Trp; 0.786, 0.807, 0.797, 0.804, 0.804, 0.777, 0.780, 0.791, (5.5030)+(−0.0008) Gly+(0.0085)Leu+(−0.1541)Trp; 0.786, 0.804, 0.817, 0.832, 0.813, 0.816, 0.787, 0.812, (6.4245)+(−0.0005) Gly+(−0.0032)Ala+(−0.1355)Trp; 0.786, 0.805, 0.819, 0.834, 0.822, 0.808, 0.780, 0.811, (7.2801)+(−0.0464) Asn+(−0.0027)Arg+(−0.1306)Trp; 0.786, 0.807, 0.802, 0.819, 0.803, 0.790, 0.762, 0.794, (5.9934)+(−0.0053) Tyr+(−0.0002)Val+(−0.1413)Trp; 0.786, 0.808, 0.794, 0.806, 0.808, 0.796, 0.735, 0.786, (5.8391)+(−0.0158) Arg+(0.0243)Orn+(−0.1443)Trp; 0.786, 0.804, 0.814, 0.829, 0.810, 0.815, 0.786, 0.810, (6.2303)+(−0.0036) Ala+(0.0019)Val+(−0.1384)Trp; 0.786, 0.805, 0.814, 0.829, 0.808, 0.813, 0.786, 0.809, (6.0922)+(−0.0036) Ala+(0.0030)Lys+(−0.1395)Trp; 0.785, 0.806, 0.800, 0.817, 0.801, 0.785, 0.762, 0.791, (5.8544)+(−0.0071) Tyr+(0.0017)Lys+(−0.1435)Trp; 0.785, 0.806, 0.816, 0.834, 0.820, 0.811, 0.766, 0.808, (6.8851)+(0.0003) Gly+(−0.0874)Met+(−0.1276)Trp; 0.785, 0.809, 0.795, 0.802, 0.803, 0.777, 0.772, 0.788, (5.4835)+(−0.0018) Lys+(0.0097)Leu+(−0.1528)Trp; 0.785, 0.807, 0.805, 0.819, 0.808, 0.790, 0.774, 0.798, (6.0235)+(−0.0009) Gly+(−0.0006)Val+(−0.1432)Trp; 0.785, 0.801, 0.761, 0.751, 0.755, 0.824, 0.756, 0.772, (6.7803)+(−0.1262) His+(0.0162)Thr+(−0.0030)Ala; 0.785, 0.808, 0.792, 0.804, 0.795, 0.776, 0.767, 0.786, (5.6121)+(−0.0103) Tyr+(0.0100)Leu+(−0.1501)Trp; 0.785, 0.806, 0.817, 0.831, 0.812, 0.820, 0.788, 0.813, (6.2724)+(−0.0034) Ala+(0.0036)Tyr+(−0.1371)Trp; 0.785, 0.806, 0.804, 0.821, 0.806, 0.786, 0.770, 0.796, (6.1519)+(−0.0009) Gly+(−0.0057)Tyr+(−0.1412)Trp; 0.785, 0.797, 0.756, 0.731, 0.749, 0.809, 0.798, 0.772, (6.6774)+(−0.1230) His+(−0.0200)Val+(0.0435)Leu; 0.784, 0.800, 0.741, 0.703, 0.746, 0.798, 0.792, 0.760, (5.8176)+(−0.1253) His+(−0.0340)Cit+(0.0475)Ile; 0.784, 0.804, 0.818, 0.835, 0.815, 0.818, 0.776, 0.811, (6.6717)+(−0.0028) Ala+(−0.0065)Arg+(−0.1332)Trp; 0.784, 0.804, 0.740, 0.714, 0.751, 0.809, 0.735, 0.752, (5.8436)+(0.0022) Gly+(−0.1317)His+(0.0321)Orn; 0.784, 0.802, 0.740, 0.706, 0.751, 0.804, 0.760, 0.755, (5.8858)+(−0.1364) His+(0.0294)Orn+(0.0081)Leu; 0.784, 0.806, 0.804, 0.817, 0.809, 0.787, 0.773, 0.797, (5.8656)+(−0.0009) Gly+(0.0011)Lys+(−0.1462)Trp; 0.783, 0.802, 0.757, 0.744, 0.761, 0.810, 0.745, 0.765, (7.1127)+(−0.0416) Asn+(−0.1237)His+(0.0189)Thr; 0.783, 0.800, 0.731, 0.703, 0.737, 0.793, 0.749, 0.745, (5.9361)+(−0.1454)
His+(0.0149)Thr+(0.0130)Leu; 0.783, 0.806, 0.814, 0.830, 0.820, 0.805, 0.769, 0.806, (6.7969)+(0.0022)
Val+(−0.0927)Met+(−0.1308)Trp; 0.783, 0.806, 0.817, 0.835, 0.820, 0.810, 0.767, 0.808, (6.9855)+(−0.0014)
Arg+(−0.0843)Met+(−0.1273)Trp; 0.783, 0.801, 0.748, 0.721, 0.752, 0.783, 0.787, 0.761, (4.9427)+(−0.1364)
His+(−0.0316)Cit+(0.0770)Phe; 0.783, 0.802, 0.751, 0.725, 0.760, 0.810, 0.759, 0.764, (6.2198)+(−0.1266)
His+(−0.0021)Val+(0.0348)Orn; 0.783, 0.805, 0.805, 0.811, 0.813, 0.792, 0.780, 0.799, (6.3971)+(−0.1169)
Met+(0.0160)Leu+(−0.1379)Trp; 0.782, 0.802, 0.741, 0.711, 0.751, 0.805, 0.754, 0.755, (5.9329)+(−0.1309)
His+(0.0030)Pro+(0.0306)Orn; 0.782, 0.803, 0.756, 0.730, 0.767, 0.814, 0.761, 0.768, (6.5383)+(−0.0242)
Asn+(−0.1227)His+(0.0345)Orn; 0.782, 0.799, 0.746, 0.738, 0.746, 0.803, 0.725, 0.753, (6.8094)+(−0.1265)
His+(0.0175)Thr+(−0.0178)Tyr; 0.781, 0.805, 0.751, 0.731, 0.757, 0.809, 0.749, 0.762, (6.5160)+(−0.1228)
His+(−0.0191)Tyr+(0.0379)Orn; 0.781, 0.796, 0.744, 0.726, 0.749, 0.803, 0.740, 0.754, (6.4251)+(−0.1340)
His+(0.0148)Thr+(0.0007)Val; 0.781, 0.807, 0.766, 0.744, 0.777, 0.824, 0.758, 0.776, (6.6441)+(−0.1159)
His+(−0.0764)Met+(0.0375)Orn; 0.781, 0.797, 0.738, 0.718, 0.744, 0.795, 0.738, 0.749, (6.2349)+(−0.1338)
His+(0.0135)Thr+(0.0035)Pro; 0.781, 0.796, 0.740, 0.725, 0.744, 0.803, 0.728, 0.750, (6.3053)+(0.0014)
Gly+(−0.1332)His+(0.0140)Thr; 0.781, 0.797, 0.746, 0.729, 0.751, 0.805, 0.741, 0.756, (6.5100)+(−0.1324)
His+(0.0151)Thr+(−0.0006)Lys; 0.780, 0.801, 0.748, 0.720, 0.759, 0.807, 0.756, 0.760, (6.1382)+(−0.1297)
His+(0.0331)Orn+(−0.0002)Lys; 0.779, 0.795, 0.767, 0.746, 0.760, 0.817, 0.800, 0.781, (6.8557)+(−0.1243)
His+(−0.0038)Ala+(0.0168)Leu; 0.779, 0.802, 0.764, 0.760, 0.734, 0.817, 0.800, 0.778, (3.1078)+(−0.2396)
Met+(0.1675)Ile+(−0.0812)Leu; 0.778, 0.802, 0.805, 0.822, 0.812, 0.795, 0.753, 0.795, (6.3459)+(−0.0090)
Arg+(−0.0000)Val+(−0.1399)Trp; 0.778, 0.797, 0.768, 0.770, 0.693, 0.843, 0.864, 0.793, (1.7786)+(−0.0118)
Ala+(0.1676)Ile+(−0.0861)Leu; 0.778, 0.798, 0.748, 0.736, 0.758, 0.808, 0.716, 0.754, (6.9726)+(−0.1297)
His+(0.0192)Thr+(−0.0139)Arg; 0.778, 0.804, 0.796, 0.806, 0.806, 0.779, 0.760, 0.788, (5.9216)+(−0.0104)
Arg+(0.0097)Leu+(−0.1501)Trp; 0.778, 0.793, 0.738, 0.714, 0.743, 0.801, 0.747, 0.751, (5.9686)+(0.0036)
Gly+(−0.1351)His+(0.0144)Leu; 0.777, 0.800, 0.800, 0.817, 0.809, 0.787, 0.746, 0.790, (6.0966)+(−0.0127)
Arg+(0.0047)Lys+(−0.1455)Trp; 0.777, 0.802, 0.806, 0.822, 0.814, 0.795, 0.757, 0.797, (6.4087)+(−0.0004)
Gly+(−0.0088)Arg+(−0.1399)Trp; 0.777, 0.790, 0.731, 0.724, 0.676, 0.807, 0.809, 0.754, (2.9430)+(−0.0292)
Arg+(−0.0568)Val+(0.1623)Ile; 0.777, 0.793, 0.768, 0.756, 0.752, 0.824, 0.792, 0.781, (6.9352)+(−0.1113)
His+(−0.0052)Ala+(0.0098)Pro; 0.776, 0.799, 0.750, 0.724, 0.764, 0.811, 0.744, 0.761, (6.4860)+(−0.1257)
His+(−0.0094)Arg+(0.0359)Orn; 0.776, 0.803, 0.805, 0.822, 0.811, 0.795, 0.753, 0.795, (6.3683)+(−0.0088)
Arg+(−0.0011)Tyr+(−0.1393)Trp; 0.775, 0.796, 0.745, 0.709, 0.771, 0.818, 0.730, 0.757, (6.3753)+(−0.1195)
His+(−0.0645)Cit+(0.0505)Orn; 0.773, 0.789, 0.746, 0.719, 0.750, 0.794, 0.775, 0.759, (6.3352)+(−0.1304)
His+(0.0033)Pro+(0.0107)Leu; 0.773, 0.791, 0.746, 0.729, 0.756, 0.810, 0.725, 0.755, (6.7791)+(−0.1261)
His+(0.0164)Thr+(−0.0315)Cit; 0.773, 0.789, 0.751, 0.739, 0.751, 0.808, 0.741, 0.760, (6.4815)+(0.0030)
Gly+(−0.1251)His+(0.0023)Val; 0.773, 0.789, 0.773, 0.760, 0.766, 0.821, 0.789, 0.784, (7.1829)+(−0.1170)
His+(−0.0028)Ala+(0.0033)Val; 0.773, 0.788, 0.757, 0.733, 0.759, 0.801, 0.784, 0.769, (6.8054)+(−0.0139)
Asn+(−0.1260)His+(0.0128)Leu; 0.773, 0.790, 0.767, 0.762, 0.757, 0.823, 0.759, 0.775, (6.9417)+(0.0027)
Gly+(−0.1151)His+(−0.0021)Ala; 0.772, 0.787, 0.751, 0.725, 0.754, 0.801, 0.778, 0.764, (6.4821)+(−0.1311)
His+(0.0008)Lys+(0.0124)Leu; 0.771, 0.788, 0.741, 0.726, 0.743, 0.798, 0.736, 0.751, (6.1975)+(0.0030)
Gly+(−0.1244)His+(0.0054)Pro; 0.771, 0.787, 0.770, 0.760, 0.759, 0.818, 0.786, 0.781, (6.9282)+(−0.1189)
His+(−0.0026)Ala+(0.0057)Lys; 0.771, 0.788, 0.751, 0.733, 0.748, 0.794, 0.772, 0.762, (6.8495)+(−0.1257)
His+(−0.0142)Tyr+(0.0148)Leu; 0.771, 0.785, 0.753, 0.736, 0.753, 0.798, 0.765, 0.763, (6.6606)+(−0.1205)
His+(0.0054)Pro+(−0.0006)Val; 0.770, 0.791, 0.720, 0.705, 0.658, 0.804, 0.831, 0.749, (2.6163)+(−0.0523)
Val+(−0.0156)Lys+(0.1573)Ile; 0.770, 0.785, 0.719, 0.702, 0.667, 0.799, 0.814, 0.746, (2.1097)+(−0.0648)
Cit+(−0.0522)Val+(0.1505)Ile; 0.770, 0.787, 0.778, 0.770, 0.768, 0.820, 0.790, 0.787, (7.5427)+(−0.0118)
Asn+(−0.1091)His+(−0.0020)Ala; 0.770, 0.786, 0.767, 0.754, 0.765, 0.811, 0.775, 0.776, (7.2389)+(−0.0133)
Asn+(−0.1160)His+(0.0012)Val; 0.770, 0.788, 0.713, 0.718, 0.641, 0.784, 0.799, 0.736, (2.5533)+(−0.0453)
Tyr+(−0.0510)Val+(0.1527)Ile; 0.770, 0.788, 0.761, 0.754, 0.758, 0.814, 0.745, 0.768, (7.0163)+(−0.0207)
Asn+(0.0033)Gly+(−0.1146)His; 0.769, 0.785, 0.748, 0.730, 0.748, 0.795, 0.764, 0.759, (6.4125)+(−0.1253)
His+(0.0048)Pro+(0.0030)Lys; 0.769, 0.788, 0.759, 0.742, 0.759, 0.800, 0.772, 0.768, (6.9636)+(−0.0185)
Asn+(−0.1158)His+(0.0055)Pro; 0.769, 0.786, 0.775, 0.767, 0.766, 0.822, 0.784, 0.785, (7.3567)+(−0.1119)
His+(−0.0020)Ala+(−0.0016)Tyr; 0.769, 0.785, 0.749, 0.738, 0.748, 0.804, 0.743, 0.758, (6.3294)+(0.0028)
Gly+(−0.1262)His+(0.0042)Lys; 0.769, 0.787, 0.752, 0.743, 0.747, 0.794, 0.755, 0.760, (6.9241)+(−0.1148)
His+(0.0068)Pro+(−0.0162)Tyr; 0.769, 0.784, 0.758, 0.743, 0.757, 0.803, 0.767, 0.768, (6.6973)+(−0.1245)
His+(0.0005)Val+(0.0040)Lys; 0.769, 0.788, 0.753, 0.729, 0.756, 0.800, 0.774, 0.765, (6.6793)+(−0.1286)
His+(−0.0030)Arg+(0.0127)Leu; 0.768, 0.793, 0.765, 0.755, 0.763, 0.805, 0.764, 0.772, (7.1084)+(−0.1057)
His+(0.0082)Pro+(−0.0867)Met; 0.768, 0.790, 0.765, 0.745, 0.769, 0.800, 0.783, 0.774, (7.0516)+(−0.1178)
His+(−0.0865)Met+(0.0181)Leu; 0.768, 0.787, 0.757, 0.751, 0.754, 0.811, 0.740, 0.764, (6.7995)+(0.0027)
Gly+(−0.1186)His+(−0.0040)Tyr; 0.768, 0.790, 0.764, 0.787, 0.762, 0.818, 0.668, 0.759, (1.4313)+(0.0426)
Ser+(−0.0855)Asn+(−0.1762)Met; 0.768, 0.783, 0.764, 0.750, 0.762, 0.801, 0.776, 0.772, (7.0329)+(−0.0227)
Asn+(−0.1189)His+(0.0057)Lys; 0.767, 0.786, 0.763, 0.752, 0.760, 0.806, 0.768, 0.772, (7.1377)+(−0.1181)
His+(−0.0089)Tyr+(0.0023)Val; 0.767, 0.791, 0.768, 0.765, 0.763, 0.822, 0.744, 0.774, (7.0860)+(0.0032)
Gly+(−0.1098)His+(−0.0546)Met; 0.767, 0.786, 0.756, 0.750, 0.755, 0.812, 0.736, 0.763, (6.8908)+(0.0031)
Gly+(−0.1181)His+(−0.0051)Arg; 0.767, 0.787, 0.779, 0.773, 0.771, 0.822, 0.782, 0.787, (7.5575)+(−0.1062)
His+(−0.0013)Ala+(−0.0403)Met; 0.766, 0.787, 0.775, 0.766, 0.766, 0.822, 0.784, 0.784, (7.4498)+(−0.1112)
His+(−0.0020)Ala+(−0.0027)Arg; 0.765, 0.784, 0.770, 0.762, 0.764, 0.810, 0.773, 0.777, (7.4515)+(−0.0130)
Asn+(−0.1115)His+(−0.0052)Tyr; 0.765, 0.782, 0.759, 0.751, 0.752, 0.801, 0.765, 0.767, (6.8983)+(−0.1206)
His+(−0.0119)Tyr+(0.0059)Lys; 0.765, 0.781, 0.754, 0.746, 0.759, 0.815, 0.722, 0.761, (6.9164)+(0.0038)
Gly+(−0.1134)His+(−0.0312)Cit; 0.764, 0.787, 0.772, 0.761, 0.770, 0.812, 0.773, 0.779, (7.3339)+(−0.1117)His+(0.0029)Val+(−0.0571)Met; 0.764, 0.785, 0.754, 0.737, 0.756, 0.800, 0.758, 0.763, (6.8590)+(−0.1188)His+(−0.0052)Arg+(0.0055)Pro; 0.764, 0.785, 0.764, 0.749, 0.764, 0.810, 0.768, 0.773, (7.1366)+(−0.1188)His+(−0.0036)Arg+(0.0015)Val; 0.763, 0.780, 0.751, 0.725, 0.761, 0.797, 0.768, 0.763, (6.8232)+(−0.1237)His+(−0.0274)Cit+(0.0134)Leu; 0.763, 0.785, 0.775, 0.768, 0.771, 0.817, 0.774, 0.782, (7.4745)+(−0.0004)Asn+(−0.1078)His+(−0.0490)Met; 0.763, 0.780, 0.714, 0.734, 0.660, 0.765, 0.738, 0.724, (2.1382)+(−0.0567)Tyr+(0.1557)Ile+(−0.0852)Leu; 0.763, 0.776, 0.670, 0.653, 0.601, 0.781, 0.779, 0.704, (−0.7855)+(0.0165)Ser+(−0.0556)Val+(0.1474)Ile; 0.763, 0.784, 0.769, 0.758, 0.766, 0.811, 0.775, 0.777, (7.4187)+(−0.0123)Asn+(−0.1129)His+(−0.0024)Arg; 0.762, 0.786, 0.771, 0.762, 0.769, 0.808, 0.771, 0.777, (6.9998)+(−0.1142)His+(−0.0846)Met+(0.0096)Lys; 0.762, 0.780, 0.752, 0.732, 0.759, 0.801, 0.755, 0.762, (6.9361)+(−0.1148)His+(−0.0268)Cit+(0.0054)Pro; 0.761, 0.775, 0.709, 0.696, 0.638, 0.785, 0.839, 0.740, (1.5523)+(−0.0030)Gly+(−0.0562)Val+(0.1505)Ile; 0.761, 0.779, 0.776, 0.767, 0.773, 0.825, 0.772, 0.784, (7.6847)+(−0.1047)His+(−0.0024)Ala+(−0.0275)Cit; 0.761, 0.774, 0.697, 0.679, 0.636, 0.779, 0.815, 0.727, (2.5091)+(−0.0032)Gln+(−0.0562)Val+(0.1550)Ile; 0.760, 0.783, 0.767, 0.758, 0.762, 0.810, 0.768, 0.774, (7.3600)+(−0.1138)His+(−0.0031)Arg+(−0.0055)Tyr; 0.760, 0.773, 0.698, 0.692, 0.627, 0.783, 0.800, 0.726, (1.1194)+(−0.0448)Val+(0.1770)Ile+(−0.0364)Leu; 0.760, 0.775, 0.708, 0.699, 0.636, 0.790, 0.820, 0.736, (1.2005)+(−0.0053)Pro+(−0.0558)Val+(0.1564)Ile; 0.760, 0.785, 0.775, 0.767, 0.770, 0.816, 0.773, 0.782, (7.4896)+(−0.1077)His+(−0.0005)Arg+(−0.0486)Met; 0.759, 0.785, 0.775, 0.765, 0.772, 0.817, 0.776, 0.783, (7.4082)+(−0.1085)His+(0.0049)Tyr+(−0.0574)Met; 0.759, 0.778, 0.761, 0.744, 0.767, 0.805, 0.758, 0.769, (7.2302)+(−0.1151)His+(−0.0269)Cit+(0.0022)Val; 0.759, 0.780, 0.758, 0.744, 0.760, 0.800, 0.761, 0.766, (6.9309)+(−0.1226)His+(−0.0077)Arg+(0.0062)Lys; 0.758, 0.778, 0.769, 0.757, 0.773, 0.812, 0.764, 0.777, (7.6368)+(−0.0137)Asn+(−0.1072)His+(−0.0256)Cit; 0.758, 0.775, 0.758, 0.743, 0.763, 0.801, 0.757, 0.766, (7.0221)+(−0.1172)His+(−0.0256)Cit+(0.0042)Lys; 0.758, 0.774, 0.693, 0.680, 0.620, 0.777, 0.819, 0.724, (0.3392)+(−0.0570)Val+(0.1469)Ile+(0.0168)Phe; 0.757, 0.778, 0.766, 0.757, 0.768, 0.808, 0.758, 0.773, (7.5009)+(−0.1091)His+(−0.0253)Cit+(−0.0051)Tyr; 0.757, 0.781, 0.775, 0.767, 0.779, 0.817, 0.761, 0.781, (7.7415)+(−0.1023)His+(−0.0246)Cit+(−0.0459)Met; 0.757, 0.772, 0.707, 0.696, 0.636, 0.788, 0.823, 0.736, (1.4159)+(−0.0063)Thr+(−0.0547)Val+(0.1495)Ile; 0.755, 0.775, 0.752, 0.752, 0.709, 0.799, 0.805, 0.767, (3.2170)+(−0.0959)Asn+(0.1425)Ile+(−0.0828)Leu; 0.755, 0.778, 0.760, 0.774, 0.745, 0.814, 0.718, 0.763, (0.5617)+(0.0467)Ser+(−0.0073)Gly+(−0.2492)Met; 0.755, 0.778, 0.764, 0.750, 0.768, 0.810, 0.758, 0.771, (7.3593)+(−0.1116)His+(−0.0260)Cit+(0.0004)Arg; 0.754, 0.779, 0.749, 0.762, 0.770, 0.821, 0.619, 0.743, (1.6186)+(0.0369)Ser+(−0.0672)Cit+(−0.2258)Met; 0.754, 0.778, 0.773, 0.765, 0.744, 0.811, 0.827, 0.787, (2.3927)+(−0.0080)Ala+(−0.2302)Met+(0.0660)Ile; 0.754, 0.777, 0.759, 0.786, 0.742, 0.844, 0.661, 0.758, (0.6519)+(0.0352)Ser+(−0.0029)Ala+(−0.2233)Met; 0.754, 0.780, 0.733, 0.760, 0.740, 0.816, 0.586, 0.726, (0.2631)+(0.0340)Ser+(0.0084)Thr+(−0.2814)Met; 0.752, 0.772, 0.690, 0.675, 0.624, 0.781, 0.805, 0.721, (0.7114)+(−0.0565)Val+(0.0086)Orn+(0.1475)Ile; 0.752, 0.775, 0.747, 0.737, 0.755, 0.734, 0.768, 0.749, (0.0520)+(−0.3443)Met+(0.0421)Ile+(0.0671)Phe; 0.751, 0.775, 0.708, 0.724, 0.707, 0.784, 0.612, 0.707, (−0.2763)+(0.0394)Ser+(0.0104)Pro+(−0.3014)Met; 0.750, 0.776, 0.723, 0.740, 0.727, 0.791, 0.620, 0.720, (−0.4704)+(0.0391)Ser+(−0.2831)Met+(0.0104)Leu; 0.750, 0.769, 0.783, 0.805, 0.779, 0.749, 0.758, 0.773, (1.1531)+(−0.0138)Val+(−0.2755)Met+(0.1120)Phe; 0.747, 0.769, 0.762, 0.783, 0.724, 0.845, 0.724, 0.769, (1.7482)+(0.0379)Ser+(−0.1364)Asn+(−0.0056)Ala; 0.746, 0.776, 0.727, 0.748, 0.729, 0.810, 0.610, 0.724, (−0.1296)+(0.0353)Ser+(−0.2683)Met+(0.0164)Orn; 0.746, 0.774, 0.740, 0.769, 0.736, 0.814, 0.619, 0.735, (−0.0743)+(0.0352)Ser+(0.0011)Gln+(−0.2585)Met; 0.746, 0.773, 0.738, 0.763, 0.738, 0.815, 0.615, 0.733, (0.1400)+(0.0368)Ser+(0.0045)Tyr+(−0.2607)Met; 0.746, 0.770, 0.731, 0.741, 0.741, 0.797, 0.638, 0.729, (2.1540)+(0.0396)Ser+(−0.1421)Asn+(−0.0700)Cit; 0.746, 0.771, 0.738, 0.765, 0.738, 0.820, 0.608, 0.732, (0.4582)+(0.0365)Ser+(−0.2389)Met+(−0.0028)Lys; 0.745, 0.773, 0.741, 0.771, 0.748, 0.816, 0.597, 0.733, (0.7127)+(0.0374)Ser+(−0.0122)Arg+(−0.2308)Met; 0.745, 0.774, 0.746, 0.776, 0.741, 0.830, 0.621, 0.742, (0.7664)+(0.0349)Ser+(−0.0036)Val+(−0.2345)Met; 0.744, 0.763, 0.725, 0.741, 0.743, 0.697, 0.663, 0.711, (−0.4451)+(0.0224)Thr+(−0.3883)Met+(0.0934)Phe; 0.744, 0.762, 0.781, 0.796, 0.772, 0.761, 0.777, 0.777, (0.8574)+(−0.0052)Ala+(−0.2608)Met+(0.0912)Phe; 0.744, 0.765, 0.752, 0.739, 0.748, 0.779, 0.772, 0.760, (2.6270)+(−0.2513)Met+(−0.0101)Lys+(0.0585)Ile; 0.742, 0.766, 0.753, 0.735, 0.770, 0.774, 0.748, 0.757, (3.0275)+(−0.0670)Cit+(−0.2520)Met+(0.0553)Ile; 0.742, 0.764, 0.716, 0.706, 0.691, 0.800, 0.738, 0.733, (1.6755)+(−0.0852)Cit+(0.1568)Ile+(−0.0897)Leu; 0.741, 0.761, 0.771, 0.794, 0.767, 0.729, 0.747, 0.759, (−1.3017)+(0.0045)Gln+(−0.3394)Met+(0.0874)Phe; 0.740, 0.764, 0.748, 0.759, 0.757, 0.709, 0.730, 0.739, (0.3020)+(0.0070)Pro+(−0.3324)Met+(0.0853)Phe; 0.740, 0.760, 0.761, 0.742, 0.729, 0.830, 0.832, 0.783, (2.1633)+(−0.0140)Ala+(−0.0933)Cit+(0.0592)Ile; 0.740, 0.760, 0.769, 0.780, 0.778, 0.736, 0.746, 0.760, (0.9836)+(−0.2817)Met+(−0.0070)Lys+(0.0910)Phe; 0.740, 0.763, 0.691, 0.690, 0.687, 0.732, 0.672, 0.695, (−1.2217)+(0.0446)Ser+(−0.1933)Asn+(0.0490)Met; 0.738, 0.760, 0.750, 0.749, 0.739, 0.768, 0.763, 0.755, (0.3569)+(0.0040)Gln+(−0.3138)Met+(0.0524)Ile; 0.738, 0.756, 0.717, 0.709, 0.723, 0.744, 0.706, 0.721, (1.3103)+(0.0177)Thr+(−0.3453)Met+(0.0533)Ile; 0.737, 0.756, 0.747, 0.737, 0.746, 0.760, 0.766, 0.752, (2.3078)+(−0.0199)Asn+(−0.2612)Met+(0.0511)Ile; 0.737, 0.757, 0.750, 0.767, 0.761, 0.718, 0.703, 0.737, (0.0077)+(0.0025)Gly+(−0.3154)Met+(0.0905)Phe; 0.737, 0.763, 0.713, 0.703, 0.673, 0.777, 0.773, 0.732, (1.5790)+(−0.0149)Lys+(0.1433)Ile+(−0.0805)Leu; 0.737, 0.754, 0.768, 0.782, 0.777, 0.721, 0.747, 0.757, (1.2362)+(−0.0369)Asn+(−0.2652)Met+(0.0849)Phe; 0.736, 0.757, 0.738, 0.728, 0.737, 0.752, 0.757, 0.743, (1.8799)+(0.0023)Pro+(−0.2903)Met+(0.0503)Ile; 0.736, 0.757, 0.752, 0.764, 0.761, 0.720, 0.724, 0.742, (0.2273)+(−0.3116)Met+(0.0129)Orn+(0.0820)Phe; 0.735, 0.762, 0.753, 0.782, 0.729, 0.825, 0.677, 0.753, (2.6428)+(0.0370)Ser+(−0.1453)Asn+(−0.0107)Val; 0.734, 0.754, 0.735, 0.725, 0.734, 0.757, 0.750, 0.741, (1.7322)+(−0.2876)Met+(0.0071)Orn+(0.0504)Ile; 0.734, 0.757, 0.729, 0.721, 0.728, 0.755, 0.732, 0.734, (1.5227)+(0.0022)Gly+(−0.2920)Met+(0.0545)Ile;

0.734, 0.759, 0.725, 0.759, 0.705, 0.784, 0.637, 0.721,
(1.8544)+(0.0382)Ser+(−0.1364)Asn+(−0.0309)Tyr;
0.732, 0.756, 0.674, 0.657, 0.664, 0.754, 0.685, 0.690,
(−0.6580)+(0.0427)Ser+(−0.1756)Asn+(0.0295)Ile;
0.732, 0.754, 0.746, 0.738, 0.747, 0.760, 0.754, 0.750,
(2.2765)+(−0.0085)Arg+(−0.2689)Met+(0.0528)Ile;
0.731, 0.753, 0.725, 0.730, 0.697, 0.783, 0.725, 0.734,
(2.2252)+(−0.0321)Arg+(0.1596)Ile+(−0.0944)Leu;
0.730, 0.751, 0.754, 0.742, 0.760, 0.826, 0.725, 0.763,
(2.8460)+(−0.0116)Ala+(−0.1225)Cit+(0.0535)Orn;
0.729, 0.754, 0.764, 0.782, 0.774, 0.723, 0.727, 0.751,
(0.8766)+(−0.0094)Arg+(−0.2888)Met+(0.0877)Phe;
0.729, 0.751, 0.764, 0.784, 0.771, 0.720, 0.728, 0.751,
(0.6223)+(−0.2897)Met+(−0.0090)Leu+(0.0957)Phe;
0.729, 0.752, 0.701, 0.700, 0.649, 0.763, 0.768, 0.720,
(0.2540)+(−0.0070)Pro+(0.1559)Ile+(−0.0916)Leu;
0.728, 0.749, 0.778, 0.774, 0.725, 0.835, 0.861, 0.799,
(2.7575)+(−0.0883)Asn+(−0.0105)Ala+(0.0457)Ile;
0.727, 0.749, 0.717, 0.716, 0.666, 0.767, 0.792, 0.735,
(1.1557)+(−0.0150)Thr+(0.1545)Ile+(−0.0920)Leu;
0.727, 0.751, 0.760, 0.751, 0.699, 0.833, 0.858, 0.785,
(2.0924)+(−0.0111)Ala+(−0.0196)Lys+(0.0576)Ile;
0.727, 0.751, 0.749, 0.776, 0.746, 0.704, 0.719, 0.736,
(0.7541)+(−0.0268)Tyr+(−0.2652)Met+(0.0949)Phe;
0.726, 0.752, 0.758, 0.763, 0.784, 0.735, 0.710, 0.748,
(1.4416)+(−0.0644)Cit+(−0.2735)Met+(0.0916)Phe;
0.726, 0.751, 0.733, 0.731, 0.723, 0.746, 0.749, 0.737,
(2.1541)+(−0.0156)Tyr+(−0.2573)Met+(0.0542)Ile;
0.725, 0.754, 0.782, 0.791, 0.756, 0.816, 0.787, 0.787,
(4.0489)+(−0.0363)Val+(−0.2236)Met+(0.0626)Leu;
0.725, 0.752, 0.722, 0.745, 0.721, 0.783, 0.623, 0.718,
(1.2211)+(0.0406)Ser+(−0.1411)Asn+(−0.0154)Arg;
0.725, 0.751, 0.747, 0.764, 0.779, 0.783, 0.606, 0.733,
(3.9391)+(0.0228)Thr+(−0.0713)Cit+(−0.2554)Met;
0.724, 0.753, 0.751, 0.744, 0.789, 0.795, 0.656, 0.746,
(3.5164)+(−0.0968)Cit+(−0.2017)Met+(0.0460)Orn;
0.724, 0.749, 0.745, 0.729, 0.780, 0.787, 0.688, 0.746,
(3.7326)+(−0.1110)Asn+(−0.1028)Cit+(0.0450)Orn;
0.723, 0.747, 0.681, 0.674, 0.635, 0.748, 0.747, 0.701,
(0.5731)+(−0.0014)Gln+(0.1452)Ile+(−0.0899)Leu;
0.723, 0.748, 0.772, 0.785, 0.744, 0.806, 0.767, 0.776,
(3.5498)+(−0.0079)Ala+(0.0140)Pro+(−0.1927)Met;
0.723, 0.746, 0.671, 0.666, 0.620, 0.730, 0.751, 0.692,
(−1.1447)+(0.1442)Ile+(−0.0959)Leu+(0.0285)Phe;
0.723, 0.747, 0.641, 0.632, 0.592, 0.741, 0.691, 0.664,
(−1.9553)+(0.0163)Ser+(0.1425)Ile+(−0.0887)Leu;
0.723, 0.750, 0.720, 0.735, 0.711, 0.798, 0.644, 0.722,
(1.3728)+(0.0403)Ser+(−0.1361)Asn+(−0.0091)Lys;
0.720, 0.746, 0.715, 0.728, 0.703, 0.777, 0.661, 0.717,
(0.7730)+(0.0412)Ser+(−0.1516)Asn+(−0.0046)Thr;
0.720, 0.747, 0.700, 0.706, 0.695, 0.769, 0.642, 0.703,
(0.4568)+(0.0394)Ser+(−0.1693)Asn+(0.0136)Orn;
0.720, 0.744, 0.724, 0.721, 0.710, 0.772, 0.725, 0.732,
(1.0301)+(0.0475)Ser+(−0.1581)Asn+(−0.0059)Gly;
0.719, 0.743, 0.756, 0.781, 0.768, 0.765, 0.654, 0.742,
(3.6825)+(−0.0587)Asn+(0.0207)Thr+(−0.2199)Met;
0.719, 0.744, 0.696, 0.690, 0.644, 0.748, 0.780, 0.715,
(0.4305)+(−0.0026)Gly+(0.1447)Ile+(−0.0907)Leu;
0.718, 0.744, 0.682, 0.680, 0.630, 0.746, 0.748, 0.701,
(−0.0598)+(−0.0014)Orn+(0.1448)Ile+(−0.0903)Leu;
0.718, 0.747, 0.724, 0.744, 0.710, 0.792, 0.651, 0.724,
(1.2781)+(0.0386)Ser+(−0.1542)Asn+(−0.0057)Leu;
0.716, 0.739, 0.692, 0.699, 0.684, 0.757, 0.641, 0.695,
(0.5591)+(0.0400)Ser+(−0.1649)Asn+(0.0029)Pro;
0.715, 0.737, 0.759, 0.787, 0.749, 0.803, 0.676, 0.754,
(3.2559)+(−0.0103)Val+(−0.1926)Met+(0.0321)Orn;
0.714, 0.736, 0.802, 0.831, 0.789, 0.794, 0.756, 0.792,
(2.0338)+(−0.0691)Asn+(0.0063)Gln+(−0.1839)Met;
0.714, 0.740, 0.716, 0.733, 0.702, 0.775, 0.661, 0.718,
(0.2302)+(0.0382)Ser+(−0.1720)Asn+(0.0021)Gln;
0.714, 0.736, 0.724, 0.747, 0.733, 0.750, 0.626, 0.714,
(2.4827)+(0.0158)Thr+(0.0071)Pro+(−0.2907)Met;
0.713, 0.742, 0.766, 0.799, 0.756, 0.811, 0.669, 0.759,
(3.0994)+(0.0185)Thr+(−0.0043)Ala+(−0.2318)Met;
0.713, 0.739, 0.785, 0.809, 0.764, 0.755, 0.784, 0.778,
(3.3010)+(−0.1273)Asn+(−0.0191)Val+(0.0755)Phe;
0.712, 0.742, 0.759, 0.799, 0.760, 0.807, 0.614, 0.745,
(3.4295)+(0.0193)Thr+(−0.0077)Val+(−0.2413)Met;
0.711, 0.737, 0.679, 0.668, 0.585, 0.815, 0.811, 0.720,
(−2.4641)+(0.0235)Ser+(−0.0143)Ala+(0.0473)Ile;
0.710, 0.734, 0.734, 0.745, 0.719, 0.830, 0.668, 0.740,
(1.1144)+(0.0249)Ser+(−0.0091)Ala+(−0.0852)Cit;
0.710, 0.732, 0.730, 0.744, 0.729, 0.758, 0.676, 0.727,
(2.4003)+(0.0067)Pro+(−0.2523)Met+(0.0184)Orn;
0.709, 0.734, 0.768, 0.789, 0.746, 0.810, 0.727, 0.768,
(2.8987)+(−0.0050)Ala+(−0.1855)Met+(0.0261)Orn;
0.709, 0.734, 0.697, 0.714, 0.715, 0.757, 0.571, 0.689,
(2.6812)+(−0.1070)Cit+(−0.0592)Tyr+(0.0475)Orn;
0.709, 0.732, 0.756, 0.771, 0.757, 0.751, 0.719, 0.749,
(3.6758)+(−0.0395)Asn+(0.0076)Pro+(−0.1974)Met;
0.709, 0.733, 0.758, 0.771, 0.762, 0.773, 0.706, 0.753,
(3.3754)+(−0.0499)Asn+(−0.1796)Met+(0.0244)Orn;
0.709, 0.732, 0.753, 0.754, 0.696, 0.815, 0.827, 0.773,
(1.2719)+(−0.0122)Ala+(−0.0207)Arg+(0.0470)Ile;
0.709, 0.734, 0.770, 0.794, 0.754, 0.802, 0.716, 0.767,
(4.6800)+(−0.1161)Asn+(−0.0166)Val+(0.0369)Orn;
0.709, 0.735, 0.790, 0.801, 0.755, 0.804, 0.825, 0.796,
(2.4449)+(−0.1032)Asn+(−0.0085)Ala+(0.0518)Phe;
0.709, 0.734, 0.752, 0.790, 0.749, 0.772, 0.640, 0.738,
(1.3967)+(0.0035)Gln+(0.0152)Thr+(−0.2857)Met;
0.709, 0.735, 0.752, 0.761, 0.771, 0.766, 0.680, 0.745,
(4.0694)+(−0.0632)Cit+(0.0086)Pro+(−0.2096)Met;
0.707, 0.731, 0.729, 0.754, 0.740, 0.765, 0.615, 0.719,
(2.2980)+(0.0140)Thr+(−0.2706)Met+(0.0156)Orn;
0.706, 0.736, 0.677, 0.708, 0.681, 0.756, 0.530, 0.669,
(0.9989)+(0.0246)Ser+(−0.0785)Cit+(−0.0478)Tyr;
0.705, 0.732, 0.801, 0.813, 0.789, 0.829, 0.772, 0.801,
(5.3131)+(−0.0674)Asn+(−0.0063)Ala+(−0.0676)Cit;
0.705, 0.732, 0.782, 0.807, 0.787, 0.792, 0.696, 0.770,
(2.1230)+(0.0061)Gln+(−0.0732)Cit+(−0.2136)Met;
0.705, 0.730, 0.741, 0.771, 0.750, 0.762, 0.630, 0.728,
(2.7756)+(−0.0008)Gly+(0.0183)Thr+(−0.2684)Met;
0.705, 0.730, 0.801, 0.837, 0.764, 0.827, 0.761, 0.797,
(1.8230)+(0.0045)Gln+(−0.0041)Ala+(−0.2001)Met;
0.705, 0.727, 0.748, 0.765, 0.751, 0.782, 0.673, 0.743,
(2.9347)+(−0.2023)Met+(0.0268)Orn+(−0.0070)Lys;
0.705, 0.732, 0.596, 0.620, 0.546, 0.685, 0.573, 0.606,
(−1.7471)+(0.0230)Ser+(−0.0738)Tyr+(0.0362)Ile;
0.704, 0.729, 0.753, 0.779, 0.739, 0.758, 0.707, 0.746,
(1.3604)+(0.0041)Gln+(0.0074)Pro+(−0.2675)Met;
0.704, 0.732, 0.736, 0.772, 0.755, 0.765, 0.579, 0.718,
(3.2808)+(0.0223)Thr+(−0.0164)Arg+(−0.2560)Met;
0.704, 0.729, 0.736, 0.781, 0.708, 0.684, 0.716, 0.722,
(2.5464)+(−0.1004)Asn+(−0.0629)Tyr+(0.0685)Phe;
0.704, 0.733, 0.741, 0.776, 0.699, 0.849, 0.660, 0.746,
(0.1779)+(0.0266)Ser+(−0.0082)Ala+(−0.0243)Arg;
0.704, 0.729, 0.755, 0.784, 0.740, 0.773, 0.695, 0.748,
(3.8632)+(0.0111)Pro+(−0.0102)Val+(−0.2081)Met;
0.704, 0.727, 0.746, 0.765, 0.745, 0.751, 0.696, 0.739,
(3.1772)+(0.0082)Pro+(−0.2263)Met+(−0.0031)Lys;
0.703, 0.730, 0.738, 0.770, 0.748, 0.772, 0.611, 0.725,
(3.0415)+(0.0190)Thr+(−0.2511)Met+(−0.0051)Lys;
0.703, 0.733, 0.612, 0.568, 0.614, 0.739, 0.631, 0.638,
(−1.9031)+(0.0330)Ser+(−0.0328)Lys+(0.0445)Ile;

0.703, 0.730, 0.733, 0.760, 0.744, 0.753, 0.623, 0.720, (2.4849)+(0.0180)Thr+(−0.2794)Met+(0.0037)Leu;
0.703, 0.728, 0.773, 0.787, 0.730, 0.793, 0.810, 0.780, (5.3423)+(−0.1196)Asn+(−0.0393)Val+(0.0550)Leu;
0.703, 0.732, 0.737, 0.719, 0.750, 0.748, 0.747, 0.741, (3.2433)+(−0.1014)Asn+(−0.0751)Cit+(0.0287)Ile;
0.702, 0.732, 0.718, 0.689, 0.777, 0.813, 0.601, 0.720, (2.9594)+(−0.1128)Cit+(0.0544)Orn+(−0.0225)Lys;
0.702, 0.726, 0.738, 0.759, 0.739, 0.745, 0.678, 0.730, (2.7991)+(0.0008)Gly+(0.0081)Pro+(−0.2412)Met;
0.702, 0.731, 0.734, 0.773, 0.739, 0.759, 0.602, 0.718, (2.8884)+(0.0185)Thr+(−0.0121)Tyr+(−0.2498)Met;
0.702, 0.735, 0.796, 0.812, 0.797, 0.819, 0.733, 0.790, (4.8035)+(−0.0046)Ala+(−0.0642)Cit+(−0.1280)Met;
0.702, 0.728, 0.720, 0.716, 0.630, 0.805, 0.856, 0.752, (0.0336)+(−0.0148)Ala+(0.0055)Pro+(0.0392)Ile;
0.702, 0.726, 0.720, 0.742, 0.633, 0.786, 0.796, 0.739, (1.5289)+(−0.0105)Ala+(−0.0464)Tyr+(0.0519)Ile;
0.702, 0.729, 0.747, 0.765, 0.759, 0.776, 0.657, 0.739, (2.9766)+(−0.0132)Arg+(−0.2080)Met+(0.0262)Orn;
0.701, 0.726, 0.758, 0.787, 0.746, 0.782, 0.690, 0.751, (1.3109)+(0.0034)Gln+(−0.2490)Met+(0.0176)Orn;
0.701, 0.724, 0.760, 0.760, 0.741, 0.818, 0.756, 0.769, (3.2929)+(−0.0124)Ala+(−0.0844)Cit+(0.0123)Pro;
0.701, 0.724, 0.777, 0.787, 0.736, 0.820, 0.807, 0.787, (3.8514)+(−0.0890)Asn+(−0.0097)Ala+(0.0106)Pro;
0.701, 0.727, 0.719, 0.787, 0.665, 0.699, 0.666, 0.704, (0.9960)+(−0.0670)Tyr+(−0.0154)Val+(0.0803)Phe;
0.700, 0.727, 0.775, 0.790, 0.793, 0.775, 0.698, 0.764, (4.9949)+(−0.0392)Asn+(−0.0594)Cit+(−0.1347)Met;
0.700, 0.727, 0.763, 0.769, 0.740, 0.804, 0.766, 0.770, (1.6184)+(−0.0109)Ala+(−0.0852)Cit+(0.0489)Phe;
0.700, 0.722, 0.771, 0.797, 0.770, 0.771, 0.703, 0.760, (3.8178)+(−0.0463)Asn+(0.0014)Gly+(−0.1606)Met;
0.700, 0.725, 0.798, 0.822, 0.780, 0.809, 0.762, 0.793, (4.3442)+(−0.0428)Asn+(−0.0039)Ala+(−0.1241)Met;
0.699, 0.728, 0.737, 0.764, 0.728, 0.740, 0.680, 0.728, (3.1978)+(0.0089)Pro+(−0.0158)Tyr+(−0.2140)Met;
0.699, 0.728, 0.748, 0.769, 0.751, 0.753, 0.685, 0.739, (3.3247)+(−0.0092)Arg+(0.0083)Pro+(−0.2236)Met;
0.699, 0.729, 0.793, 0.837, 0.769, 0.810, 0.714, 0.783, (2.0695)+(0.0046)Gln+(−0.0069)Val+(−0.2098)Met;
0.699, 0.726, 0.756, 0.777, 0.779, 0.780, 0.637, 0.743, (3.9881)+(0.0026)Gly+(−0.0659)Cit+(−0.1770)Met;
0.698, 0.720, 0.743, 0.762, 0.744, 0.767, 0.674, 0.737, (2.5228)+(−0.0002)Gly+(−0.2274)Met+(0.0224)Orn;
0.698, 0.724, 0.743, 0.762, 0.741, 0.746, 0.692, 0.735, (2.9703)+(0.0082)Pro+(−0.2366)Met+(−0.0011)Leu;
0.697, 0.724, 0.745, 0.741, 0.663, 0.817, 0.873, 0.773, (0.5464)+(−0.0075)Thr+(−0.0128)Ala+(0.0466)Ile;
0.697, 0.722, 0.783, 0.817, 0.767, 0.795, 0.715, 0.773, (1.6816)+(0.0048)Gln+(−0.2216)Met+(−0.0045)Lys;
0.697, 0.730, 0.678, 0.693, 0.665, 0.709, 0.644, 0.678, (2.1992)+(−0.0781)Cit+(−0.0618)Tyr+(0.0398)Ile;
0.697, 0.722, 0.743, 0.763, 0.744, 0.768, 0.671, 0.736, (2.5402)+(−0.2249)Met+(0.0228)Orn+(−0.0012)Leu;
0.697, 0.722, 0.732, 0.727, 0.644, 0.817, 0.864, 0.763, (0.3244)+(−0.0005)Gln+(−0.0134)Ala+(0.0445)Ile;
0.696, 0.725, 0.732, 0.729, 0.643, 0.818, 0.864, 0.763, (−0.2114)+(−0.0139)Ala+(0.0420)Ile+(0.0088)Phe;
0.696, 0.718, 0.775, 0.799, 0.775, 0.769, 0.719, 0.766, (4.0295)+(−0.0427)Asn+(−0.1579)Met+(−0.0007)Lys;
0.696, 0.721, 0.782, 0.794, 0.749, 0.827, 0.786, 0.789, (3.5468)+(−0.0971)Asn+(−0.0075)Ala+(0.0246)Orn;
0.696, 0.722, 0.783, 0.823, 0.771, 0.791, 0.694, 0.770, (1.6766)+(0.0054)Gln+(−0.0142)Arg+(−0.2204)Met;
0.696, 0.723, 0.787, 0.816, 0.765, 0.812, 0.737, 0.783, (3.4744)+(0.0005)Gly+(−0.0040)Ala+(−0.1671)Met;
0.696, 0.722, 0.791, 0.818, 0.769, 0.816, 0.744, 0.787, (3.6265)+(−0.0040)Ala+(−0.1620)Met+(−0.0010)Lys;
0.695, 0.723, 0.795, 0.830, 0.770, 0.824, 0.735, 0.790, (3.9431)+(−0.0031)Ala+(−0.0048)Val+(−0.1526)Met;
0.695, 0.721, 0.782, 0.817, 0.764, 0.783, 0.724, 0.772, (1.4961)+(−0.0009)Gly+(0.0046)Gln+(−0.2380)Met;
0.695, 0.721, 0.816, 0.843, 0.770, 0.843, 0.820, 0.819, (2.5124)+(−0.1142)Asn+(0.0050)Gln+(−0.0067)Ala;
0.695, 0.721, 0.685, 0.682, 0.714, 0.795, 0.556, 0.687, (1.0121)+(0.0298)Ser+(−0.0794)Cit+(−0.0192)Lys;
0.695, 0.720, 0.760, 0.772, 0.780, 0.767, 0.678, 0.750, (4.0944)+(−0.0627)Cit+(−0.1866)Met+(0.0050)Leu;
0.695, 0.721, 0.730, 0.727, 0.640, 0.817, 0.862, 0.762, (0.0306)+(−0.0136)Ala+(0.0020)Orn+(0.0433)Ile;
0.695, 0.727, 0.750, 0.749, 0.769, 0.724, 0.730, 0.743, (2.8641)+(−0.1101)Asn+(−0.0727)Cit+(0.0411)Phe;
0.695, 0.719, 0.774, 0.795, 0.774, 0.766, 0.722, 0.764, (3.9071)+(−0.0426)Asn+(−0.1649)Met+(0.0013)Leu;
0.694, 0.724, 0.814, 0.854, 0.777, 0.826, 0.777, 0.809, (3.3276)+(−0.1300)Asn+(0.0057)Gln+(−0.0132)Val;
0.694, 0.722, 0.735, 0.731, 0.648, 0.817, 0.867, 0.766, (0.1922)+(−0.0006)Gly+(−0.0135)Ala+(0.0439)Ile;
0.694, 0.720, 0.712, 0.740, 0.668, 0.708, 0.729, 0.711, (3.2246)+(−0.0883)Asn+(−0.0521)Tyr+(0.0357)Ile;
0.693, 0.723, 0.784, 0.803, 0.780, 0.780, 0.746, 0.777, (2.3580)+(−0.1318)Asn+(0.0071)Gln+(−0.0812)Cit;
0.693, 0.725, 0.604, 0.659, 0.557, 0.641, 0.526, 0.596, (−2.3653)+(0.0237)Ser+(−0.0836)Tyr+(0.0567)Phe;
0.693, 0.721, 0.735, 0.763, 0.729, 0.759, 0.656, 0.726, (2.7186)+(−0.0146)Tyr+(−0.2029)Met+(0.0242)Orn;
0.693, 0.718, 0.776, 0.800, 0.779, 0.770, 0.713, 0.766, (4.1345)+(−0.0399)Asn+(−0.0050)Arg+(−0.1545)Met;
0.693, 0.721, 0.774, 0.809, 0.757, 0.776, 0.712, 0.764, (1.3401)+(0.0044)Gln+(−0.2452)Met+(0.0024)Leu;
0.693, 0.719, 0.793, 0.825, 0.779, 0.802, 0.729, 0.784, (4.9530)+(−0.0537)Asn+(−0.0078)Val+(−0.1146)Met;
0.693, 0.724, 0.784, 0.806, 0.764, 0.806, 0.755, 0.783, (3.2879)+(−0.0046)Ala+(−0.1795)Met+(0.0070)Leu;
0.693, 0.720, 0.766, 0.782, 0.785, 0.776, 0.676, 0.755, (4.3747)+(−0.0612)Cit+(−0.1690)Met+(−0.0010)Lys;
0.692, 0.724, 0.767, 0.796, 0.767, 0.766, 0.694, 0.756, (5.2257)+(−0.0737)Asn+(−0.0616)Cit+(−0.0299)Tyr;
0.692, 0.718, 0.772, 0.801, 0.767, 0.762, 0.712, 0.760, (4.2145)+(−0.0452)Asn+(−0.0107)Tyr+(−0.1389)Met;
0.691, 0.728, 0.732, 0.758, 0.679, 0.859, 0.680, 0.744, (0.4512)+(0.0274)Ser+(−0.0071)Ala+(−0.0153)Lys;
0.691, 0.717, 0.734, 0.787, 0.658, 0.753, 0.738, 0.734, (0.8325)+(−0.0083)Ala+(−0.0578)Tyr+(0.0647)Phe;
0.691, 0.723, 0.776, 0.797, 0.789, 0.792, 0.682, 0.765, (4.6715)+(−0.0572)Cit+(−0.0044)Val+(−0.1559)Met;
0.691, 0.720, 0.774, 0.817, 0.752, 0.778, 0.705, 0.763, (1.5803)+(0.0045)Gln+(−0.0077)Tyr+(−0.2246)Met;
0.691, 0.720, 0.741, 0.761, 0.755, 0.759, 0.643, 0.730, (4.0158)+(−0.0997)Asn+(0.0041)Gly+(−0.0739)Cit;
0.691, 0.720, 0.794, 0.824, 0.777, 0.815, 0.733, 0.787, (3.8364)+(−0.0039)Ala+(−0.0068)Arg+(−0.1543)Met;
0.690, 0.721, 0.686, 0.720, 0.637, 0.733, 0.668, 0.689, (0.3358)+(0.0362)Ser+(−0.0104)Gly+(−0.0620)Tyr;
0.690, 0.715, 0.709, 0.711, 0.732, 0.790, 0.601, 0.708, (1.9860)+(−0.1027)Cit+(−0.0155)Val+(0.0491)Orn;
0.690, 0.721, 0.764, 0.779, 0.783, 0.770, 0.678, 0.753, (4.2287)+(−0.0635)Cit+(0.0025)Arg+(−0.1767)Met;
0.690, 0.719, 0.777, 0.804, 0.759, 0.818, 0.713, 0.774, (4.1831)+(−0.0068)Ala+(−0.0720)Cit+(−0.0230)Tyr;
0.690, 0.725, 0.672, 0.728, 0.664, 0.767, 0.476, 0.659, (0.4665)+(0.0269)Ser+(−0.0255)Arg+(−0.0457)Tyr;

0.689, 0.722, 0.788, 0.817, 0.765, 0.810, 0.741, 0.783,
(3.5905)+(−0.0040)Ala+(−0.0023)Tyr+(−0.1621)Met;
0.688, 0.718, 0.705, 0.751, 0.673, 0.698, 0.657, 0.695,
(1.4875)+(−0.0652)Tyr+(−0.0158)Lys+(0.0658)Phe;
0.688, 0.714, 0.763, 0.792, 0.762, 0.770, 0.687, 0.753,
(3.2655)+(0.0005)Gly+(−0.1956)Met+(−0.0022)Lys;
0.688, 0.720, 0.765, 0.783, 0.783, 0.773, 0.672, 0.753,
(4.3828)+(−0.0611)Cit+(−0.0047)Tyr+(−0.1648)Me t;
0.688, 0.715, 0.810, 0.842, 0.774, 0.844, 0.778, 0.809,
(5.0618)+(−0.0850)Asn+(−0.0039)Ala+(−0.0089)Val;
0.688, 0.717, 0.776, 0.813, 0.764, 0.789, 0.694, 0.765,
(3.7789)+(0.0002)Gly+(−0.0065)Val+(−0.1753)Met;
0.687, 0.714, 0.756, 0.781, 0.755, 0.759, 0.687, 0.746,
(2.9155)+(0.0007)Gly+(−0.2150)Met+(0.0033)Leu;
0.687, 0.711, 0.779, 0.797, 0.756, 0.825, 0.748, 0.781,
(2.1936)+(0.0031)Gln+(−0.0093)Ala+(−0.0855)Cit;
0.686, 0.715, 0.762, 0.784, 0.761, 0.767, 0.699, 0.753,
(3.2479)+(−0.2017)Met+(−0.0038)Lys+(0.0050)Leu;
0.686, 0.715, 0.726, 0.763, 0.705, 0.729, 0.667, 0.716,
(3.8237)+(−0.0965)Asn+(−0.0456)Tyr+(0.0270)Orn;
0.686, 0.717, 0.787, 0.809, 0.753, 0.827, 0.772, 0.790,
(3.9179)+(−0.1048)Asn+(0.0102)Thr+(−0.0071)Ala;
0.686, 0.715, 0.790, 0.828, 0.746, 0.812, 0.764, 0.787,
(4.6033)+(−0.0747)Asn+(−0.0050)Ala+(−0.0236)Tyr;
0.686, 0.712, 0.763, 0.793, 0.764, 0.769, 0.673, 0.750,
(3.4071)+(0.0008)Gly+(−0.0081)Arg+(−0.1909)Met;
0.685, 0.710, 0.766, 0.784, 0.754, 0.822, 0.707, 0.767,
(3.2394)+(0.0017)Gly+(−0.0086)Ala+(−0.0810)Cit;
0.685, 0.713, 0.767, 0.796, 0.768, 0.771, 0.684, 0.755,
(3.5609)+(−0.0075)Arg+(−0.1869)Met+(−0.0008)Lys;
0.685, 0.716, 0.775, 0.813, 0.762, 0.786, 0.696, 0.764,
(3.7237)+(−0.0069)Val+(−0.1803)Met+(0.0017)Lys;
0.685, 0.713, 0.780, 0.806, 0.776, 0.794, 0.713, 0.772,
(5.6126)+(−0.0859)Asn+(−0.0552)Cit+(−0.0093)Val;
0.684, 0.715, 0.763, 0.789, 0.766, 0.762, 0.687, 0.751,
(3.3782)+(−0.0078)Arg+(−0.1982)Met+(0.0030)Leu;
0.683, 0.717, 0.776, 0.815, 0.763, 0.788, 0.695, 0.765,
(3.8382)+(−0.0020)Tyr+(−0.0064)Val+(−0.1715)Met;
0.683, 0.713, 0.774, 0.826, 0.737, 0.759, 0.727, 0.762,
(2.6567)+(−0.1160)Asn+(0.0055)Gln+(−0.0404)Tyr;
0.683, 0.713, 0.770, 0.806, 0.754, 0.790, 0.697, 0.762,
(4.9807)+(−0.1229)Asn+(0.0129)Thr+(−0.0140)Val;
0.683, 0.711, 0.784, 0.829, 0.753, 0.799, 0.721, 0.775,
(5.2932)+(−0.0855)Asn+(−0.0208)Tyr+(−0.0097)V al;
0.683, 0.714, 0.788, 0.802, 0.779, 0.839, 0.734, 0.789,
(4.2447)+(−0.0074)Ala+(−0.0738)Cit+(−0.0069)Lys;
0.683, 0.708, 0.766, 0.780, 0.754, 0.817, 0.719, 0.768,
(3.2644)+(0.0044)Thr+(−0.0091)Ala+(−0.0812)Cit;
0.683, 0.711, 0.748, 0.752, 0.762, 0.748, 0.706, 0.742,
(4.1503)+(−0.0959)Asn+(−0.0691)Cit+(0.0029)Pro;
0.683, 0.717, 0.711, 0.762, 0.636, 0.836, 0.647, 0.720,
(0.3637)+(0.0223)Ser+(−0.0070)Ala+(−0.0355)Tyr;
0.682, 0.712, 0.758, 0.791, 0.752, 0.758, 0.681, 0.746,
(3.2465)+(0.0003)Gly+(−0.0070)Tyr+(−0.1921)Met;
0.682, 0.715, 0.741, 0.749, 0.762, 0.748, 0.670, 0.732,
(4.2078)+(−0.1131)Asn+(0.0102)Thr+(−0.0722)Cit;
0.682, 0.708, 0.771, 0.780, 0.756, 0.816, 0.741, 0.773,
(3.3435)+(−0.0090)Ala+(−0.0795)Cit+(0.0030)Leu;
0.682, 0.713, 0.683, 0.700, 0.646, 0.721, 0.691, 0.689,
(2.3941)+(−0.0530)Tyr+(−0.0191)Lys+(0.0466)Ile;
0.682, 0.711, 0.762, 0.794, 0.757, 0.766, 0.688, 0.751,
(3.4544)+(−0.0068)Tyr+(−0.1828)Met+(−0.0020)Lys;
0.682, 0.710, 0.797, 0.822, 0.759, 0.828, 0.785, 0.799,
(3.8919)+(−0.0879)Asn+(0.0012)Gly+(−0.0064)Ala;
0.682, 0.711, 0.735, 0.720, 0.726, 0.756, 0.778, 0.745,
(2.9314)+(−0.0856)Asn+(−0.0161)Lys+(0.0340)Ile;
0.682, 0.714, 0.694, 0.712, 0.608, 0.811, 0.741, 0.718,
(−2.3006)+(0.0224)Ser+(−0.0118)Ala+(0.0340)Phe;
0.681, 0.708, 0.778, 0.791, 0.766, 0.823, 0.733, 0.778,
(3.5964)+(−0.0084)Ala+(−0.0752)Cit+(−0.0030)Arg;
0.681, 0.707, 0.694, 0.659, 0.717, 0.761, 0.692, 0.707,
(2.4775)+(−0.0814)Cit+(−0.0233)Lys+(0.0444)Ile;
0.680, 0.711, 0.697, 0.773, 0.653, 0.660, 0.617, 0.676,
(0.5611)+(−0.0730)Tyr+(−0.0189)Leu+(0.0764)Phe;
0.680, 0.711, 0.698, 0.734, 0.695, 0.718, 0.592, 0.685,
(3.1112)+(−0.0727)Cit+(0.0059)Pro+(−0.0535)Tyr;
0.680, 0.713, 0.764, 0.797, 0.762, 0.764, 0.677, 0.750,
(3.6363)+(−0.0078)Arg+(−0.0069)Tyr+(−0.1771)Met;
0.680, 0.706, 0.780, 0.799, 0.763, 0.827, 0.729, 0.780,
(3.7935)+(−0.0075)Ala+(−0.0727)Cit+(−0.0040)Val;
0.680, 0.712, 0.709, 0.770, 0.670, 0.766, 0.585, 0.698,
(2.3261)+(−0.0462)Tyr+(−0.0132)Val+(0.0294)Orn;
0.680, 0.712, 0.687, 0.730, 0.675, 0.675, 0.607, 0.671,
(1.4091)+(−0.0758)Cit+(−0.0711)Tyr+(0.0632)Phe;
0.680, 0.707, 0.765, 0.796, 0.739, 0.776, 0.730, 0.760,
(4.9611)+(−0.1058)Asn+(0.0081)Pro+(−0.0155)Val;
0.680, 0.710, 0.755, 0.785, 0.751, 0.751, 0.687, 0.743,
(3.1642)+(−0.0082)Tyr+(−0.1987)Met+(0.0034)Leu;
0.679, 0.708, 0.707, 0.752, 0.696, 0.815, 0.531, 0.699,
(0.6244)+(0.0249)Ser+(−0.0278)Arg+(−0.0126)Val;
0.679, 0.714, 0.779, 0.819, 0.771, 0.790, 0.685, 0.766,
(4.1123)+(−0.0072)Arg+(−0.0064)Val+(−0.1618)Met;
0.679, 0.710, 0.729, 0.769, 0.701, 0.716, 0.690, 0.719,
(4.1127)+(−0.0887)Asn+(0.0061)Pro+(−0.0449)Tyr;
0.678, 0.712, 0.686, 0.678, 0.668, 0.762, 0.690, 0.699,
(−0.0670)+(0.0404)Ser+(−0.0088)Gly+(−0.0230)Lys;
0.678, 0.709, 0.804, 0.826, 0.770, 0.837, 0.795, 0.807,
(4.2986)+(−0.0769)Asn+(−0.0060)Ala+(−0.0041)Lys;
0.677, 0.707, 0.766, 0.782, 0.777, 0.769, 0.700, 0.757,
(4.7394)+(−0.0877)Asn+(−0.0650)Cit+(−0.0060)Leu;
0.677, 0.710, 0.766, 0.776, 0.780, 0.775, 0.704, 0.759,
(4.8155)+(−0.0775)Asn+(−0.0656)Cit+(−0.0063)Lys;
0.677, 0.704, 0.727, 0.772, 0.650, 0.788, 0.722, 0.733,
(2.5799)+(−0.0100)Ala+(0.0124)Pro+(−0.0425)Tyr;
0.677, 0.708, 0.727, 0.734, 0.653, 0.833, 0.786, 0.752,
(−0.4582)+(0.0313)Ser+(−0.0074)Gly+(−0.0098)Ala;
0.676, 0.711, 0.729, 0.777, 0.711, 0.725, 0.641, 0.714,
(4.2199)+(−0.1080)Asn+(0.0132)Thr+(−0.0445)Tyr;
0.676, 0.703, 0.722, 0.770, 0.711, 0.739, 0.606, 0.707,
(2.1176)+(0.0030)Gln+(−0.0782)Cit+(−0.0497)Tyr;
0.676, 0.711, 0.805, 0.830, 0.773, 0.826, 0.788, 0.804,
(4.2511)+(−0.0760)Asn+(−0.0061)Ala+(−0.0079)Arg;
0.676, 0.707, 0.802, 0.825, 0.765, 0.830, 0.797, 0.804,
(4.1313)+(−0.0846)Asn+(−0.0062)Ala+(−0.0017)Leu;
0.676, 0.710, 0.776, 0.790, 0.734, 0.820, 0.795, 0.785,
(1.3332)+(−0.0091)Ala+(−0.0150)Lys+(0.0464)Phe;
0.675, 0.712, 0.729, 0.755, 0.647, 0.850, 0.745, 0.749,
(−0.6360)+(0.0289)Ser+(−0.0137)Thr+(−0.0082)Ala;
0.675, 0.699, 0.667, 0.664, 0.680, 0.740, 0.595, 0.670,
(−0.6502)+(0.0316)Ser+(−0.0176)Thr+(−0.0815)Cit;
0.675, 0.709, 0.757, 0.766, 0.770, 0.754, 0.707, 0.749,
(4.3427)+(−0.0921)Asn+(−0.0678)Cit+(−0.0001)Arg;
0.674, 0.715, 0.667, 0.713, 0.646, 0.770, 0.516, 0.661,
(0.6099)+(0.0268)Ser+(−0.0375)Tyr+(−0.0156)Lys;
0.674, 0.707, 0.758, 0.773, 0.721, 0.829, 0.745, 0.767,
(2.3528)+(−0.0082)Ala+(0.0271)Orn+(−0.0155)Lys;
0.674, 0.711, 0.675, 0.696, 0.685, 0.785, 0.521, 0.672,
(−0.0125)+(0.0307)Ser+(−0.0212)Arg+(−0.0172)Lys;
0.673, 0.703, 0.749, 0.796, 0.722, 0.741, 0.686, 0.736,
(4.1822)+(−0.0869)Asn+(0.0005)Gly+(−0.0359)Tyr;
0.673, 0.702, 0.783, 0.821, 0.758, 0.796, 0.722, 0.774,
(4.8438)+(−0.0993)Asn+(0.0010)Gly+(−0.0120)Val;
0.673, 0.706, 0.762, 0.809, 0.734, 0.757, 0.698, 0.749,
(4.4799)+(−0.0838)Asn+(−0.0330)Tyr+(−0.0045)Leu;

0.672, 0.703, 0.759, 0.781, 0.727, 0.823, 0.725, 0.764, (1.9774)+(−0.0092)Ala+(−0.0226)Arg+(0.0240)Orn;
0.672, 0.706, 0.679, 0.692, 0.595, 0.814, 0.726, 0.707, (−1.1331)+(0.0214)Ser+(−0.0129)Ala+(0.0096)Pro;
0.672, 0.705, 0.756, 0.759, 0.756, 0.739, 0.760, 0.753, (2.5668)+(−0.1010)Asn+(−0.0124)Lys+(0.0408)Phe;
0.671, 0.701, 0.755, 0.773, 0.702, 0.821, 0.771, 0.767, (2.6204)+(−0.0106)Ala+(0.0106)Pro+(−0.0123)Lys;
0.671, 0.703, 0.762, 0.786, 0.759, 0.707, 0.742, 0.748, (2.4528)+(−0.1206)Asn+(−0.0205)Leu+(0.0570)Phe;
0.671, 0.704, 0.673, 0.738, 0.628, 0.765, 0.526, 0.664, (0.6891)+(0.0202)Ser+(−0.0421)Tyr+(−0.0094)Val;
0.671, 0.698, 0.701, 0.745, 0.703, 0.725, 0.560, 0.683, (3.1206)+(0.0047)Thr+(−0.0736)Cit+(−0.0492)Tyr;
0.670, 0.700, 0.722, 0.764, 0.722, 0.744, 0.594, 0.706, (3.4706)+(−0.0698)Cit+(−0.0422)Tyr+(−0.0033)Leu;
0.670, 0.703, 0.672, 0.668, 0.677, 0.734, 0.626, 0.676, (−1.1998)+(0.0359)Ser+(−0.0073)Gly+(−0.0333)Arg;
0.670, 0.702, 0.757, 0.798, 0.734, 0.753, 0.697, 0.746, (4.4701)+(−0.0780)Asn+(−0.0329)Tyr+(−0.0040)Lys;
0.670, 0.700, 0.765, 0.804, 0.695, 0.801, 0.782, 0.771, (0.6504)+(−0.0085)Ala+(−0.0136)Val+(0.0552)Phe;
0.670, 0.701, 0.773, 0.796, 0.733, 0.806, 0.772, 0.776, (0.9830)+(−0.0100)Ala+(−0.0207)Arg+(0.0413)Phe;
0.670, 0.704, 0.758, 0.803, 0.738, 0.748, 0.690, 0.745, (4.4809)+(−0.0762)Asn+(−0.0086)Arg+(−0.0342)Tyr;
0.669, 0.700, 0.749, 0.770, 0.748, 0.763, 0.688, 0.742, (3.4810)+(−0.1136)Asn+(0.0253)Orn+(−0.0150)Leu;
0.669, 0.697, 0.757, 0.780, 0.706, 0.818, 0.754, 0.765, (2.2570)+(−0.0113)Ala+(−0.0190)Arg+(0.0105)Pro;
0.668, 0.698, 0.732, 0.773, 0.653, 0.869, 0.687, 0.746, (0.2214)+(0.0209)Ser+(−0.0075)Ala+(−0.0085)Val;
0.668, 0.701, 0.714, 0.755, 0.714, 0.732, 0.593, 0.698, (3.2818)+(0.0001)Gly+(−0.0713)Cit+(−0.0447)Tyr;
0.668, 0.703, 0.694, 0.710, 0.628, 0.846, 0.678, 0.716, (−0.0649)+(0.0255)Ser+(−0.0025)Gln+(−0.0093)Ala;
0.668, 0.701, 0.739, 0.784, 0.731, 0.767, 0.616, 0.724, (3.9012)+(−0.0636)Cit+(−0.0350)Tyr+(−0.0070)Val;
0.667, 0.704, 0.657, 0.707, 0.615, 0.733, 0.558, 0.653, (−0.4991)+(0.0281)Ser+(−0.0121)Thr+(−0.0460)Tyr;
0.667, 0.702, 0.615, 0.661, 0.594, 0.703, 0.475, 0.608, (0.2513)+(0.0257)Ser+(−0.0025)Gln+(−0.0533)Tyr;
0.667, 0.698, 0.788, 0.826, 0.767, 0.800, 0.722, 0.779, (5.1565)+(−0.0882)Asn+(−0.0076)Arg+(−0.0116)Val;
0.667, 0.699, 0.787, 0.823, 0.761, 0.795, 0.738, 0.779, (4.9413)+(−0.0995)Asn+(−0.0124)Val+(0.0011)Lys;
0.667, 0.703, 0.622, 0.613, 0.623, 0.728, 0.566, 0.633, (−2.0771)+(0.0314)Ser+(−0.0282)Lys+(0.0370)Phe;
0.667, 0.699, 0.728, 0.742, 0.651, 0.797, 0.803, 0.748, (0.0729)+(−0.0134)Ala+(0.0085)Pro+(0.0255)Phe;
0.666, 0.700, 0.760, 0.784, 0.675, 0.847, 0.811, 0.779, (2.2684)+(−0.0078)Ala+(−0.0291)Val+(0.0409)Leu;
0.666, 0.698, 0.742, 0.743, 0.750, 0.764, 0.706, 0.741, (3.3712)+(−0.0951)Asn+(0.0256)Orn+(−0.0128)Lys;
0.665, 0.700, 0.593, 0.649, 0.554, 0.672, 0.468, 0.586, (−0.6777)+(0.0217)Ser+(0.0049)Pro+(−0.0642)Tyr;
0.665, 0.699, 0.717, 0.770, 0.653, 0.759, 0.677, 0.715, (2.6975)+(−0.0414)Tyr+(−0.0275)Val+(0.0346)Leu;
0.665, 0.696, 0.692, 0.677, 0.694, 0.733, 0.700, 0.701, (1.6389)+(−0.0168)Arg+(−0.0217)Lys+(0.0367)Ile;
0.664, 0.690, 0.662, 0.697, 0.631, 0.683, 0.618, 0.657, (1.8322)+(−0.0214)Arg+(−0.0607)Tyr+(0.0365)Ile;
0.664, 0.696, 0.728, 0.777, 0.664, 0.800, 0.680, 0.730, (2.0851)+(−0.0076)Ala+(−0.0411)Tyr+(0.0233)Orn;
0.664, 0.701, 0.739, 0.772, 0.745, 0.771, 0.617, 0.726, (4.1175)+(−0.0671)Cit+(−0.0342)Tyr+(−0.0086)Lys;
0.664, 0.694, 0.690, 0.682, 0.739, 0.762, 0.556, 0.685, (1.3113)+(−0.1091)Cit+(0.0421)Orn+(−0.0173)Leu;
0.664, 0.699, 0.724, 0.765, 0.728, 0.741, 0.596, 0.707, (3.5317)+(−0.0650)Cit+(−0.0065)Arg+(−0.0423)Tyr;
0.664, 0.697, 0.648, 0.648, 0.689, 0.738, 0.497, 0.643, (−0.5081)+(0.0262)Ser+(−0.0723)Cit+(−0.0209)Arg;
0.663, 0.699, 0.745, 0.747, 0.731, 0.729, 0.783, 0.748, (0.9948)+(−0.1452)Asn+(0.0042)Gln+(0.0190)Ile;
0.663, 0.692, 0.750, 0.785, 0.677, 0.827, 0.752, 0.760, (2.3233)+(−0.0100)Ala+(0.0120)Pro+(−0.0114)Val;
0.663, 0.701, 0.611, 0.669, 0.573, 0.694, 0.474, 0.603, (−0.6651)+(0.0203)Ser+(−0.0614)Tyr+(0.0110)Orn;
0.663, 0.702, 0.684, 0.713, 0.665, 0.810, 0.552, 0.685, (0.3394)+(0.0258)Ser+(−0.0086)Val+(−0.0166)Lys;
0.662, 0.698, 0.756, 0.792, 0.694, 0.843, 0.726, 0.764, (1.8353)+(−0.0076)Ala+(−0.0121)Val+(0.0269)Orn;
0.662, 0.700, 0.755, 0.772, 0.741, 0.710, 0.772, 0.749, (0.7250)+(−0.1522)Asn+(0.0045)Gln+(0.0268)Phe;
0.661, 0.694, 0.791, 0.827, 0.768, 0.781, 0.750, 0.782, (2.3138)+(−0.1314)Asn+(0.0051)Gln+(−0.0117)Leu;
0.661, 0.693, 0.722, 0.735, 0.723, 0.695, 0.705, 0.714, (1.6206)+(−0.1332)Asn+(0.0025)Gly+(0.0324)Phe;
0.661, 0.696, 0.774, 0.835, 0.711, 0.842, 0.699, 0.771, (3.1741)+(−0.0054)Ala+(−0.0274)Tyr+(−0.0067)Val;
0.661, 0.697, 0.685, 0.751, 0.654, 0.661, 0.595, 0.665, (1.1401)+(−0.0212)Arg+(−0.0698)Tyr+(0.0586)Phe;
0.661, 0.697, 0.723, 0.714, 0.723, 0.699, 0.767, 0.726, (1.7288)+(−0.1267)Asn+(0.0164)Ile+(0.0178)Phe;
0.661, 0.697, 0.726, 0.727, 0.731, 0.700, 0.733, 0.723, (1.8171)+(−0.1311)Asn+(0.0129)Orn+(0.0242)Phe;
0.661, 0.696, 0.784, 0.810, 0.763, 0.780, 0.760, 0.778, (2.2172)+(−0.1171)Asn+(0.0053)Gln+(−0.0105)Lys;
0.661, 0.700, 0.695, 0.718, 0.616, 0.836, 0.700, 0.718, (−1.0863)+(0.0206)Ser+(−0.0105)Ala+(0.0099)Orn;
0.660, 0.696, 0.733, 0.733, 0.731, 0.727, 0.741, 0.733, (2.5602)+(−0.1007)Asn+(−0.0152)Arg+(0.0236)Ile;
0.660, 0.694, 0.717, 0.709, 0.714, 0.713, 0.746, 0.721, (2.0377)+(−0.1242)Asn+(0.0102)Orn+(0.0175)Ile;
0.660, 0.687, 0.617, 0.665, 0.558, 0.611, 0.616, 0.612, (−0.1331)+(−0.0822)Tyr+(0.0257)Ile+(0.0356)Phe;
0.660, 0.699, 0.774, 0.827, 0.726, 0.826, 0.698, 0.769, (3.3584)+(−0.0060)Ala+(−0.0144)Arg+(−0.0289)Tyr;
0.660, 0.685, 0.647, 0.685, 0.587, 0.648, 0.670, 0.648, (1.2520)+(−0.0023)Gly+(−0.0705)Tyr+(0.0331)Ile;
0.659, 0.687, 0.626, 0.666, 0.569, 0.643, 0.624, 0.625, (0.7200)+(0.0002)Pro+(−0.0704)Tyr+(0.0334)Ile;
0.659, 0.699, 0.638, 0.705, 0.599, 0.720, 0.480, 0.626, (−0.1000)+(0.0213)Ser+(−0.0523)Tyr+(−0.0056)Leu;
0.659, 0.695, 0.722, 0.735, 0.648, 0.812, 0.778, 0.743, (0.7227)+(−0.0128)Ala+(0.0088)Pro+(0.0109)Orn;
0.659, 0.688, 0.690, 0.667, 0.675, 0.745, 0.742, 0.707, (1.2211)+(−0.0044)Pro+(−0.0262)Lys+(0.0427)Ile;
0.658, 0.692, 0.704, 0.703, 0.698, 0.707, 0.717, 0.707, (1.8408)+(−0.1259)Asn+(0.0025)Gly+(0.0229)Ile;
0.658, 0.693, 0.691, 0.731, 0.678, 0.741, 0.579, 0.682, (2.6442)+(−0.0469)Tyr+(0.0291)Orn+(−0.0161)Lys;
0.658, 0.690, 0.696, 0.764, 0.645, 0.722, 0.603, 0.683, (2.7831)+(0.0084)Pro+(−0.0475)Tyr+(−0.0126)Val;
0.658, 0.698, 0.741, 0.756, 0.672, 0.809, 0.797, 0.759, (−0.1640)+(−0.0116)Ala+(0.0115)Orn+(0.0280)Phe;
0.658, 0.686, 0.625, 0.664, 0.570, 0.643, 0.626, 0.626, (0.8474)+(−0.0003)Gln+(−0.0698)Tyr+(0.0339)Ile;
0.658, 0.689, 0.678, 0.647, 0.669, 0.733, 0.739, 0.697, (1.0995)+(−0.0002)Gly+(−0.0265)Lys+(0.0363)Ile;
0.658, 0.692, 0.680, 0.653, 0.668, 0.731, 0.741, 0.698, (0.7503)+(0.0008)Gln+(−0.0273)Lys+(0.0361)Ile;
0.657, 0.689, 0.743, 0.759, 0.669, 0.816, 0.801, 0.761, (1.3334)+(−0.0013)Gly+(−0.0124)Ala+(0.0097)Pro;

0.657, 0.696, 0.710, 0.742, 0.627, 0.856, 0.694, 0.730,
(−0.6636)+(0.0216)Ser+(−0.0094)Ala+(−0.0029)Leu;
0.657, 0.692, 0.754, 0.769, 0.746, 0.742, 0.743, 0.750,
(1.4785)+(−0.1437)Asn+(0.0041)Gln+(0.0121)Orn;
0.657, 0.689, 0.686, 0.657, 0.674, 0.735, 0.751, 0.704,
(1.1759)+(−0.0033)Thr+(−0.0252)Lys+(0.0370)Ile;
0.657, 0.685, 0.618, 0.657, 0.564, 0.645, 0.606, 0.618,
(0.5682)+(−0.0718)Tyr+(0.0074)Orn+(0.0311)Ile;
0.657, 0.689, 0.746, 0.764, 0.672, 0.815, 0.802, 0.763,
(1.5255)+(−0.0063)Thr+(−0.0119)Ala+(0.0104)Pro;
0.657, 0.693, 0.600, 0.562, 0.659, 0.712, 0.494, 0.607,
(−1.8027)+(0.0200)Ser+(−0.1129)Cit+(0.0254)Orn;
0.657, 0.690, 0.736, 0.754, 0.660, 0.815, 0.788, 0.754,
(1.1851)+(−0.0002)Gln+(−0.0124)Ala+(0.0097)Pro;
0.657, 0.694, 0.674, 0.650, 0.743, 0.737, 0.552, 0.670,
(0.8893)+(−0.0969)Cit+(−0.0171)Arg+(0.0349)Orn;
0.656, 0.694, 0.774, 0.824, 0.719, 0.840, 0.710, 0.773,
(3.3375)+(−0.0059)Ala+(−0.0269)Tyr+(−0.0077)Lys;
0.656, 0.684, 0.637, 0.675, 0.581, 0.649, 0.645, 0.637,
(0.8708)+(−0.0031)Thr+(−0.0675)Tyr+(0.0342)Ile;
0.656, 0.686, 0.720, 0.732, 0.721, 0.725, 0.682, 0.715,
(2.4533)+(−0.1245)Asn+(0.0014)Gly+(0.0166)Orn;
0.656, 0.685, 0.681, 0.735, 0.672, 0.721, 0.528, 0.664,
(2.3664)+(−0.0236)Arg+(−0.0538)Tyr+(0.0257)Orn;
0.656, 0.695, 0.681, 0.723, 0.693, 0.786, 0.469, 0.668,
(−0.3477)+(0.0254)Ser+(−0.0309)Arg+(−0.0124)Leu;
0.656, 0.694, 0.746, 0.760, 0.753, 0.709, 0.722, 0.736,
(2.3290)+(−0.1089)Asn+(−0.0146)Arg+(0.0332)Phe;
0.655, 0.700, 0.628, 0.626, 0.638, 0.754, 0.521, 0.635,
(−0.8227)+(0.0273)Ser+(0.0163)Orn+(−0.0256)Lys;
0.655, 0.691, 0.665, 0.630, 0.664, 0.726, 0.712, 0.683,
(0.8771)+(0.0133)Orn+(−0.0283)Lys+(0.0330)Ile;
0.655, 0.690, 0.675, 0.644, 0.666, 0.729, 0.736, 0.694,
(0.8061)+(−0.0273)Lys+(0.0344)Ile+(0.0090)Phe;
0.655, 0.689, 0.716, 0.709, 0.711, 0.703, 0.751, 0.719,
(2.1464)+(−0.1254)Asn+(0.0029)Thr+(0.0204)Ile;
0.654, 0.688, 0.764, 0.798, 0.695, 0.807, 0.785, 0.771,
(0.2354)+(−0.0099)Ala+(−0.0119)Leu+(0.0455)Phe;
0.654, 0.688, 0.744, 0.771, 0.673, 0.820, 0.766, 0.758,
(1.5477)+(−0.0115)Ala+(0.0106)Pro+(−0.0079)Leu;
0.654, 0.694, 0.739, 0.750, 0.755, 0.744, 0.675, 0.731,
(3.0146)+(−0.1030)Asn+(−0.0164)Arg+(0.0212)Orn;
0.654, 0.690, 0.792, 0.833, 0.741, 0.838, 0.756, 0.792,
(1.5232)+(0.0025)Gln+(−0.0085)Ala+(−0.0213)Arg;
0.654, 0.689, 0.759, 0.778, 0.687, 0.815, 0.816, 0.774,
(0.2429)+(−0.0009)Gly+(−0.0111)Ala+(0.0322)Phe;
0.653, 0.688, 0.726, 0.763, 0.722, 0.800, 0.584, 0.717,
(2.3817)+(−0.0266)Arg+(−0.0168)Val+(0.0320)Orn;
0.653, 0.684, 0.629, 0.697, 0.581, 0.609, 0.561, 0.612,
(−0.0701)+(−0.0807)Tyr+(0.0119)Orn+(0.0481)Phe;
0.653, 0.685, 0.628, 0.697, 0.574, 0.602, 0.578, 0.613,
(0.1053)+(0.0032)Pro+(−0.0814)Tyr+(0.0497)Phe;
0.653, 0.690, 0.754, 0.774, 0.682, 0.814, 0.807, 0.769,
(0.1270)+(−0.0002)Gln+(−0.0112)Ala+(0.0330)Phe;
0.653, 0.689, 0.761, 0.783, 0.689, 0.811, 0.819, 0.776,
(0.3087)+(−0.0049)Thr+(−0.0107)Ala+(0.0348)Phe;
0.653, 0.697, 0.659, 0.681, 0.656, 0.759, 0.536, 0.658,
(−1.3617)+(0.0325)Ser+(−0.0144)Thr+(−0.0254)Arg;
0.653, 0.682, 0.667, 0.682, 0.676, 0.756, 0.541, 0.664,
(0.4470)+(0.0218)Ser+(−0.0760)Cit+(−0.0106)Val;
0.652, 0.686, 0.727, 0.733, 0.727, 0.722, 0.712, 0.723,
(2.5793)+(−0.1218)Asn+(0.0004)Pro+(0.0166)Orn;
0.652, 0.690, 0.588, 0.573, 0.609, 0.703, 0.498, 0.596,
(−2.7706)+(0.0280)Ser+(−0.0386)Arg+(0.0237)Ile;
0.652, 0.687, 0.760, 0.824, 0.679, 0.823, 0.713, 0.760,
(1.9241)+(0.0017)Gln+(−0.0071)Ala+(−0.0363)Tyr;
0.652, 0.687, 0.777, 0.812, 0.764, 0.760, 0.726, 0.766,
(1.8410)+(−0.1232)Asn+(0.0058)Gln+(−0.0181)Arg;
0.652, 0.688, 0.723, 0.718, 0.713, 0.714, 0.765, 0.728,
(2.1977)+(−0.1179)Asn+(−0.0018)Pro+(0.0237)Ile;
0.652, 0.685, 0.764, 0.791, 0.746, 0.741, 0.745, 0.756,
(1.5790)+(−0.1410)Asn+(0.0007)Gly+(0.0046)Gln;
0.651, 0.693, 0.684, 0.653, 0.732, 0.739, 0.624, 0.687,
(0.8315)+(−0.0118)Thr+(−0.1077)Cit+(0.0391)Orn;
0.651, 0.693, 0.629, 0.630, 0.631, 0.752, 0.530, 0.636,
(−0.7616)+(0.0289)Ser+(0.0024)Pro+(−0.0238)Lys;
0.651, 0.679, 0.633, 0.610, 0.661, 0.696, 0.591, 0.639,
(−1.1438)+(0.0291)Ser+(−0.0052)Gly+(−0.0870)Cit;
0.651, 0.690, 0.793, 0.828, 0.752, 0.851, 0.744, 0.794,
(3.1003)+(−0.0070)Ala+(−0.0125)Arg+(−0.0076)Lys;
0.650, 0.681, 0.695, 0.710, 0.650, 0.759, 0.702, 0.705,
(−0.0269)+(0.0302)Ser+(−0.0090)Gly+(−0.0151)Val;
0.650, 0.694, 0.632, 0.635, 0.638, 0.757, 0.523, 0.638,
(−0.1023)+(0.0307)Ser+(−0.0017)Gln+(−0.0214)Lys;
0.650, 0.686, 0.725, 0.732, 0.727, 0.686, 0.733, 0.719,
(1.9238)+(−0.1357)Asn+(0.0047)Thr+(0.0287)Phe;
0.650, 0.686, 0.732, 0.739, 0.733, 0.691, 0.744, 0.727,
(1.9784)+(−0.1262)Asn+(0.0003)Pro+(0.0293)Phe;
0.649, 0.688, 0.793, 0.832, 0.730, 0.860, 0.773, 0.799,
(1.9157)+(0.0022)Gln+(−0.0077)Ala+(−0.0128)Lys;
0.649, 0.684, 0.764, 0.787, 0.746, 0.736, 0.758, 0.757,
(1.5901)+(−0.1407)Asn+(0.0047)Gln+(0.0007)Pro;
0.649, 0.696, 0.657, 0.667, 0.643, 0.771, 0.581, 0.665,
(−0.6144)+(0.0325)Ser+(−0.0110)Thr+(−0.0182)Lys;
0.649, 0.681, 0.760, 0.794, 0.749, 0.754, 0.700, 0.749,
(3.6586)+(−0.1046)Asn+(0.0012)Gly+(−0.0098)Leu;
0.649, 0.681, 0.643, 0.716, 0.589, 0.609, 0.588, 0.626,
(0.1787)+(−0.0000)Gln+(−0.0781)Tyr+(0.0525)Phe;
0.649, 0.686, 0.725, 0.732, 0.727, 0.722, 0.706, 0.722,
(2.5807)+(−0.1257)Asn+(0.0023)Thr+(0.0157)Orn;
0.649, 0.677, 0.646, 0.651, 0.676, 0.730, 0.511, 0.642,
(−0.3162)+(0.0223)Ser+(−0.0859)Cit+(−0.0104)Leu;
0.649, 0.685, 0.761, 0.783, 0.748, 0.736, 0.746, 0.754,
(1.6120)+(−0.1463)Asn+(0.0045)Gln+(0.0033)Thr;
0.649, 0.684, 0.789, 0.823, 0.744, 0.841, 0.757, 0.791,
(2.5406)+(−0.0004)Gly+(−0.0080)Ala+(−0.0173)Arg;
0.649, 0.684, 0.750, 0.762, 0.745, 0.751, 0.728, 0.747,
(3.6181)+(−0.0921)Asn+(0.0030)Pro+(−0.0094)Lys;
0.649, 0.682, 0.768, 0.822, 0.701, 0.812, 0.733, 0.767,
(3.0178)+(−0.0019)Gly+(−0.0066)Ala+(−0.0346)Tyr;
0.649, 0.681, 0.666, 0.733, 0.611, 0.612, 0.641, 0.649,
(0.7056)+(−0.0025)Gly+(−0.0786)Tyr+(0.0525)Phe;
0.648, 0.688, 0.786, 0.814, 0.734, 0.854, 0.772, 0.794,
(2.6655)+(−0.0077)Ala+(−0.0118)Lys+(0.0030)Leu;
0.648, 0.685, 0.755, 0.785, 0.751, 0.751, 0.690, 0.744,
(3.7436)+(−0.1170)Asn+(0.0075)Thr+(−0.0113)Leu;
0.648, 0.686, 0.780, 0.818, 0.737, 0.842, 0.728, 0.781,
(2.3527)+(0.0036)Thr+(−0.0084)Ala+(−0.0196)Arg;
0.648, 0.684, 0.798, 0.848, 0.751, 0.857, 0.717, 0.793,
(3.3069)+(−0.0059)Ala+(−0.0157)Arg+(−0.0081)Val;
0.648, 0.680, 0.750, 0.778, 0.739, 0.738, 0.706, 0.740,
(3.7264)+(−0.1055)Asn+(0.0044)Pro+(−0.0131)Leu;
0.647, 0.691, 0.641, 0.649, 0.638, 0.763, 0.535, 0.646,
(−0.5867)+(0.0285)Ser+(−0.0225)Lys+(−0.0003)Leu;
0.647, 0.681, 0.571, 0.527, 0.613, 0.675, 0.525, 0.585,
(−2.4726)+(0.0230)Ser+(−0.1000)Cit+(0.0226)Ile;
0.647, 0.686, 0.731, 0.746, 0.687, 0.798, 0.734, 0.741,
(2.6236)+(−0.0298)Val+(−0.0142)Lys+(0.0398)Leu;
0.647, 0.686, 0.748, 0.809, 0.677, 0.817, 0.685, 0.747,
(2.5029)+(0.0031)Thr+(−0.0070)Ala+(−0.0362)Tyr;
0.647, 0.689, 0.613, 0.624, 0.638, 0.711, 0.464, 0.609,
(−2.4918)+(0.0275)Ser+(−0.0369)Arg+(0.0181)Phe;
0.647, 0.681, 0.647, 0.719, 0.592, 0.610, 0.596, 0.629,
(0.2123)+(−0.0010)Thr+(−0.0772)Tyr+(0.0525)Phe;

0.647, 0.683, 0.676, 0.745, 0.644, 0.719, 0.530, 0.660,
(1.7456)+(−0.0545)Tyr+(0.0227)Orn+(−0.0110)Leu;
0.647, 0.684, 0.731, 0.806, 0.680, 0.761, 0.614, 0.715,
(2.2816)+(0.0013)Gln+(−0.0412)Tyr+(−0.0103)Val;
0.646, 0.682, 0.681, 0.742, 0.659, 0.697, 0.556, 0.663,
(2.6606)+(−0.0199)Arg+(0.0059)Pro+(−0.0535)Tyr;
0.646, 0.685, 0.793, 0.822, 0.740, 0.853, 0.780, 0.799,
(2.8889)+(−0.0009)Gly+(−0.0074)Ala+(−0.0107)Lys;
0.646, 0.683, 0.750, 0.817, 0.700, 0.758, 0.670, 0.736,
(3.4045)+(−0.0027)Gly+(−0.0396)Tyr+(−0.0099)Val;
0.646, 0.685, 0.764, 0.785, 0.761, 0.765, 0.713, 0.756,
(3.9062)+(−0.0829)Asn+(−0.0087)Arg+(−0.0068)Lys;
0.645, 0.684, 0.792, 0.831, 0.747, 0.848, 0.739, 0.791,
(2.6329)+(−0.0076)Ala+(−0.0173)Arg+(−0.0027)Leu;
0.645, 0.685, 0.750, 0.817, 0.722, 0.793, 0.598, 0.732,
(3.6600)+(−0.0161)Arg+(−0.0321)Tyr+(−0.0092)Val;
0.645, 0.687, 0.795, 0.839, 0.739, 0.871, 0.740, 0.797,
(3.0632)+(−0.0062)Ala+(−0.0066)Val+(−0.0074)Lys;
0.645, 0.685, 0.758, 0.816, 0.686, 0.821, 0.708, 0.758,
(2.6269)+(−0.0068)Ala+(−0.0338)Tyr+(0.0001)Leu;
0.645, 0.683, 0.752, 0.773, 0.746, 0.760, 0.704, 0.746,
(3.5770)+(−0.0931)Asn+(0.0013)Gly+(−0.0083)Lys;
0.645, 0.684, 0.623, 0.640, 0.649, 0.735, 0.447, 0.618,
(−1.6470)+(0.0265)Ser+(−0.0346)Arg+(0.0009)Pro;
0.645, 0.685, 0.782, 0.816, 0.728, 0.855, 0.749, 0.787,
(2.6443)+(0.0036)Thr+(−0.0076)Ala+(−0.0121)Lys;
0.645, 0.682, 0.755, 0.772, 0.691, 0.827, 0.793, 0.771,
(1.2016)+(−0.0075)Thr+(−0.0097)Ala+(0.0206)Orn;
0.644, 0.677, 0.753, 0.768, 0.687, 0.832, 0.793, 0.770,
(1.1321)+(−0.0018)Gly+(−0.0103)Ala+(0.0166)Orn;
0.644, 0.686, 0.618, 0.628, 0.649, 0.731, 0.447, 0.614,
(−0.9345)+(0.0290)Ser+(−0.0020)Gln+(−0.0315)Arg;
0.644, 0.677, 0.724, 0.745, 0.717, 0.710, 0.691, 0.716,
(2.7479)+(−0.1177)Asn+(0.0018)Gly+(0.0020)Pro;
0.644, 0.677, 0.603, 0.583, 0.647, 0.699, 0.493, 0.605,
(−0.5312)+(0.0259)Ser+(−0.0023)Gln+(−0.0876)Cit;
0.644, 0.687, 0.722, 0.797, 0.676, 0.756, 0.596, 0.706,
(2.7471)+(0.0021)Thr+(−0.0407)Tyr+(−0.0102)Val;
0.644, 0.682, 0.746, 0.775, 0.748, 0.745, 0.664, 0.733,
(3.2769)+(−0.0985)Asn+(0.0019)Gly+(−0.0127)Arg;
0.643, 0.687, 0.719, 0.746, 0.706, 0.796, 0.620, 0.717,
(2.1246)+(−0.0131)Val+(0.0301)Orn+(−0.0147)Lys;
0.643, 0.679, 0.790, 0.844, 0.712, 0.870, 0.750, 0.794,
(1.9236)+(0.0011)Gln+(−0.0071)Ala+(−0.0091)Val;
0.643, 0.676, 0.633, 0.651, 0.580, 0.748, 0.610, 0.647,
(−0.7525)+(0.0187)Ser+(−0.0322)Val+(0.0328)Leu;
0.643, 0.678, 0.726, 0.748, 0.722, 0.715, 0.681, 0.716,
(2.8137)+(−0.1251)Asn+(0.0014)Gly+(0.0051)Thr;
0.643, 0.680, 0.693, 0.743, 0.664, 0.720, 0.601, 0.682,
(2.8587)+(0.0057)Pro+(−0.0480)Tyr+(−0.0123)Lys;
0.642, 0.679, 0.766, 0.792, 0.757, 0.759, 0.719, 0.757,
(4.0030)+(−0.0908)Asn+(−0.0056)Lys+(−0.0066)Leu;
0.642, 0.675, 0.795, 0.842, 0.726, 0.858, 0.769, 0.799,
(2.6892)+(−0.0015)Gly+(−0.0068)Ala+(−0.0089)Val;
0.642, 0.681, 0.743, 0.762, 0.675, 0.834, 0.767, 0.759,
(0.9937)+(−0.0004)Gln+(−0.0103)Ala+(0.0164)Orn;
0.642, 0.676, 0.677, 0.701, 0.623, 0.758, 0.669, 0.688,
(0.6592)+(−0.0344)Val+(0.0218)Orn+(0.0318)Leu;
0.642, 0.682, 0.727, 0.783, 0.710, 0.748, 0.598, 0.710,
(3.3389)+(−0.0133)Arg+(−0.0381)Tyr+(−0.0078)Lys;
0.641, 0.686, 0.625, 0.638, 0.655, 0.741, 0.445, 0.620,
(−1.7250)+(0.0257)Ser+(−0.0355)Arg+(0.0065)Orn;
0.641, 0.674, 0.617, 0.568, 0.676, 0.688, 0.572, 0.626,
(−0.5498)+(−0.1116)Cit+(0.0266)Orn+(0.0142)Ile;
0.641, 0.672, 0.593, 0.573, 0.632, 0.667, 0.513, 0.596,
(−2.2208)+(0.0233)Ser+(−0.0974)Cit+(0.0168)Phe;
0.641, 0.680, 0.746, 0.766, 0.748, 0.731, 0.698, 0.736,
(3.3356)+(−0.0975)Asn+(−0.0131)Arg+(0.0025)Pro;
0.641, 0.673, 0.612, 0.599, 0.649, 0.696, 0.505, 0.612,
(−1.2775)+(0.0227)Ser+(−0.0928)Cit+(−0.0003)Pro;
0.641, 0.676, 0.653, 0.625, 0.713, 0.719, 0.557, 0.653,
(0.2902)+(−0.1121)Cit+(−0.0033)Pro+(0.0350)Orn;
0.640, 0.672, 0.701, 0.712, 0.722, 0.751, 0.594, 0.695,
(1.9962)+(−0.0195)Arg+(0.0255)Orn+(−0.0181)Lys;
0.640, 0.667, 0.704, 0.715, 0.694, 0.754, 0.659, 0.705,
(2.4618)+(−0.0642)Cit+(−0.0261)Val+(0.0287)Leu;
0.640, 0.678, 0.741, 0.758, 0.739, 0.753, 0.693, 0.736,
(3.6877)+(−0.1041)Asn+(0.0093)Thr+(−0.0106)Lys;
0.639, 0.678, 0.770, 0.803, 0.768, 0.761, 0.693, 0.756,
(4.1198)+(−0.0885)Asn+(−0.0110)Arg+(−0.0092)Leu;
0.639, 0.679, 0.751, 0.782, 0.686, 0.836, 0.739, 0.761,
(1.1714)+(−0.0094)Ala+(0.0192)Orn+(−0.0076)Leu;
0.639, 0.678, 0.716, 0.789, 0.687, 0.736, 0.569, 0.695,
(1.7627)+(0.0029)Gln+(−0.0230)Arg+(−0.0490)Tyr;
0.638, 0.675, 0.736, 0.747, 0.753, 0.790, 0.636, 0.731,
(1.9404)+(0.0036)Gln+(−0.0815)Cit+(−0.0173)Lys;
0.638, 0.678, 0.725, 0.786, 0.688, 0.760, 0.616, 0.713,
(2.1046)+(0.0025)Gln+(−0.0429)Tyr+(−0.0134)Lys;
0.638, 0.671, 0.654, 0.630, 0.696, 0.689, 0.606, 0.655,
(0.6815)+(−0.0762)Cit+(−0.0162)Arg+(0.0238)Ile;
0.638, 0.670, 0.630, 0.598, 0.694, 0.698, 0.534, 0.631,
(−0.1067)+(0.0008)Gly+(−0.1123)Cit+(0.0316)Orn;
0.638, 0.676, 0.716, 0.724, 0.746, 0.777, 0.586, 0.708,
(2.9874)+(0.0017)Gly+(−0.0766)Cit+(−0.0144)Lys;
0.637, 0.676, 0.743, 0.762, 0.754, 0.790, 0.634, 0.735,
(3.6206)+(−0.0661)Cit+(−0.0073)Val+(−0.0094)Lys;
0.637, 0.670, 0.664, 0.636, 0.685, 0.688, 0.676, 0.671,
(0.5203)+(−0.0087)Thr+(−0.0861)Cit+(0.0243)Ile;
0.637, 0.675, 0.706, 0.698, 0.737, 0.739, 0.640, 0.704,
(1.8805)+(−0.0786)Cit+(−0.0192)Lys+(0.0413)Phe;
0.637, 0.679, 0.786, 0.837, 0.714, 0.868, 0.742, 0.790,
(2.3947)+(0.0002)Thr+(−0.0069)Ala+(−0.0089)Val;
0.637, 0.679, 0.740, 0.802, 0.705, 0.785, 0.618, 0.728,
(3.3349)+(−0.0334)Tyr+(−0.0079)Val+(−0.0069)Lys;
0.637, 0.674, 0.718, 0.717, 0.747, 0.765, 0.624, 0.713,
(3.0730)+(−0.0746)Cit+(0.0026)Pro+(−0.0151)Lys;
0.637, 0.675, 0.729, 0.743, 0.729, 0.708, 0.711, 0.723,
(2.8856)+(−0.1236)Asn+(0.0051)Thr+(0.0012)Pro;
0.637, 0.677, 0.673, 0.748, 0.629, 0.696, 0.552, 0.656,
(2.1275)+(0.0066)Pro+(−0.0554)Tyr+(−0.0106)Leu;
0.636, 0.673, 0.734, 0.783, 0.714, 0.739, 0.643, 0.720,
(1.2547)+(−0.0239)Arg+(−0.0179)Val+(0.0494)Phe;
0.636, 0.668, 0.723, 0.746, 0.751, 0.755, 0.582, 0.709,
(2.5804)+(−0.0664)Cit+(−0.0121)Arg+(−0.0102)Leu;
0.635, 0.679, 0.687, 0.755, 0.677, 0.720, 0.502, 0.663,
(2.6760)+(0.0075)Thr+(−0.0228)Arg+(−0.0510)Tyr;
0.635, 0.675, 0.681, 0.717, 0.635, 0.785, 0.603, 0.685,
(−0.4725)+(0.0269)Ser+(−0.0153)Thr+(−0.0117)Val;
0.635, 0.674, 0.638, 0.600, 0.705, 0.706, 0.550, 0.640,
(0.4236)+(−0.0010)Gln+(−0.1102)Cit+(0.0336)Orn;
0.635, 0.671, 0.727, 0.760, 0.696, 0.748, 0.690, 0.724,
(1.1048)+(−0.0147)Val+(−0.0140)Lys+(0.0489)Phe;
0.635, 0.672, 0.620, 0.654, 0.581, 0.693, 0.562, 0.622,
(−2.1273)+(0.0193)Ser+(−0.0196)Val+(0.0411)Phe;
0.635, 0.676, 0.565, 0.522, 0.534, 0.666, 0.668, 0.598,
(−3.9146)+(0.0361)Ser+(−0.0293)Thr+(0.0273)Ile;
0.634, 0.670, 0.623, 0.691, 0.576, 0.657, 0.518, 0.610,
(1.1391)+(0.0037)Pro+(−0.0659)Tyr+(0.0154)Orn;
0.634, 0.670, 0.673, 0.738, 0.617, 0.662, 0.623, 0.660,
(2.1797)+(−0.0029)Gly+(0.0050)Pro+(−0.0625)Tyr;
0.634, 0.667, 0.699, 0.717, 0.702, 0.719, 0.632, 0.692,
(1.0527)+(−0.0712)Cit+(−0.0157)Val+(0.0466)Phe;
0.634, 0.671, 0.730, 0.736, 0.757, 0.775, 0.624, 0.723,
(3.2572)+(−0.0732)Cit+(−0.0136)Lys+(−0.0014)Leu;

0.634, 0.675, 0.736, 0.761, 0.746, 0.724, 0.655, 0.721, (3.3851)+(−0.1100)Asn+(0.0094)Thr+(−0.0161)Arg;
0.634, 0.669, 0.734, 0.764, 0.743, 0.770, 0.612, 0.722, (3.2372)+(−0.0576)Cit+(−0.0109)Arg+(−0.0106)Val;
0.634, 0.674, 0.699, 0.759, 0.675, 0.743, 0.559, 0.684, (2.8790)+(0.0061)Thr+(−0.0442)Tyr+(−0.0133)Lys;
0.634, 0.672, 0.738, 0.769, 0.734, 0.766, 0.641, 0.728, (1.4062)+(0.0027)Gln+(−0.0196)Arg+(−0.0156)Lys;
0.634, 0.670, 0.726, 0.732, 0.754, 0.771, 0.622, 0.720, (3.2458)+(−0.0720)Cit+(−0.0018)Arg+(−0.0138)Lys;
0.633, 0.669, 0.633, 0.597, 0.696, 0.696, 0.552, 0.635, (−0.1111)+(−0.1114)Cit+(0.0313)Orn+(0.0025)Phe;
0.633, 0.660, 0.609, 0.578, 0.650, 0.664, 0.567, 0.615, (−0.4475)+(0.0020)Gly+(−0.0965)Cit+(0.0224)Ile;
0.633, 0.669, 0.674, 0.730, 0.629, 0.678, 0.613, 0.663, (1.9469)+(−0.0037)Gly+(−0.0636)Tyr+(0.0205)Orn;
0.633, 0.680, 0.725, 0.793, 0.707, 0.754, 0.561, 0.704, (3.1195)+(−0.0178)Arg+(−0.0410)Tyr+(−0.0058)Leu;
0.632, 0.671, 0.729, 0.779, 0.697, 0.745, 0.649, 0.718, (3.3215)+(−0.0019)Gly+(−0.0415)Tyr+(−0.0107)Lys;
0.632, 0.671, 0.780, 0.810, 0.704, 0.851, 0.808, 0.793, (1.2611)+(−0.0017)Gly+(0.0009)Gln+(−0.0096)Ala;
0.632, 0.661, 0.629, 0.596, 0.666, 0.669, 0.613, 0.636, (0.0296)+(−0.0922)Cit+(0.0221)Ile+(−0.0031)Phe;
0.632, 0.666, 0.685, 0.717, 0.628, 0.707, 0.703, 0.689, (0.2354)+(−0.0313)Val+(0.0254)Leu+(0.0294)Phe;
0.632, 0.666, 0.723, 0.753, 0.658, 0.756, 0.758, 0.731, (1.7106)+(−0.0023)Gly+(−0.0315)Val+(0.0320)Leu;
0.631, 0.673, 0.717, 0.721, 0.749, 0.775, 0.600, 0.711, (3.1124)+(0.0045)Thr+(−0.0761)Cit+(−0.0160)Lys;
0.631, 0.661, 0.641, 0.613, 0.672, 0.680, 0.621, 0.646, (0.1161)+(−0.0915)Cit+(−0.0047)Pro+(0.0278)Ile;
0.631, 0.673, 0.718, 0.772, 0.690, 0.751, 0.605, 0.705, (2.9800)+(−0.0403)Tyr+(−0.0111)Lys+(−0.0005)Leu;
0.631, 0.661, 0.718, 0.744, 0.725, 0.757, 0.605, 0.708, (2.6635)+(0.0003)Gly+(−0.0689)Cit+(−0.0110)Val;
0.631, 0.668, 0.780, 0.809, 0.708, 0.854, 0.802, 0.793, (1.7446)+(−0.0010)Gly+(−0.0023)Thr+(−0.0091)Ala;
0.631, 0.660, 0.702, 0.724, 0.705, 0.747, 0.608, 0.696, (2.5068)+(−0.0687)Cit+(0.0049)Pro+(−0.0131)Val;
0.631, 0.661, 0.723, 0.748, 0.728, 0.757, 0.620, 0.713, (2.7662)+(−0.0009)Thr+(−0.0679)Cit+(−0.0108)Val;
0.631, 0.674, 0.721, 0.782, 0.699, 0.722, 0.604, 0.702, (3.0951)+(−0.0016)Gly+(−0.0175)Arg+(−0.0464)Tyr;
0.631, 0.666, 0.660, 0.721, 0.619, 0.688, 0.566, 0.648, (1.4204)+(−0.0049)Thr+(−0.0581)Tyr+(0.0204)Orn;
0.631, 0.671, 0.780, 0.815, 0.700, 0.852, 0.803, 0.793, (1.1791)+(0.0011)Gln+(−0.0042)Thr+(−0.0092)Ala;
0.630, 0.662, 0.717, 0.735, 0.737, 0.743, 0.611, 0.707, (2.2249)+(−0.0035)Thr+(−0.0761)Cit+(−0.0102)Leu;
0.630, 0.660, 0.696, 0.713, 0.719, 0.730, 0.580, 0.685, (1.8697)+(−0.0791)Cit+(0.0027)Pro+(−0.0130)Leu;
0.630, 0.672, 0.645, 0.629, 0.608, 0.695, 0.727, 0.665, (−2.1524)+(0.0417)Ser+(−0.0072)Gly+(−0.0229)Thr;
0.630, 0.672, 0.738, 0.774, 0.703, 0.787, 0.679, 0.736, (2.5885)+(−0.0203)Arg+(−0.0301)Val+(0.0333)Leu;
0.630, 0.661, 0.711, 0.725, 0.719, 0.728, 0.646, 0.704, (1.3493)+(−0.0174)Arg+(−0.0174)Lys+(0.0299)Phe;
0.630, 0.661, 0.627, 0.594, 0.664, 0.664, 0.611, 0.633, (−0.0980)+(0.0000)Gln+(−0.0927)Cit+(0.0212)Ile;
0.630, 0.662, 0.723, 0.752, 0.720, 0.766, 0.621, 0.715, (1.9553)+(0.0007)Gln+(−0.0725)Cit+(−0.0114)Val;
0.630, 0.664, 0.699, 0.729, 0.643, 0.752, 0.701, 0.706, (1.7076)+(−0.0009)Gln+(−0.0318)Val+(0.0332)Leu;
0.630, 0.671, 0.777, 0.820, 0.699, 0.856, 0.767, 0.786, (1.2964)+(0.0007)Gln+(−0.0089)Ala+(−0.0043)Leu;
0.629, 0.664, 0.640, 0.706, 0.603, 0.667, 0.522, 0.625, (1.3865)+(−0.0004)Gln+(−0.0611)Tyr+(0.0182)Orn;
0.629, 0.658, 0.683, 0.714, 0.622, 0.735, 0.688, 0.690, (1.1178)+(0.0035)Pro+(−0.0321)Val+(0.0301)Leu;
0.629, 0.662, 0.688, 0.703, 0.711, 0.695, 0.592, 0.675, (0.6462)+(−0.0820)Cit+(−0.0192)Leu+(0.0407)Phe;
0.629, 0.659, 0.699, 0.718, 0.726, 0.740, 0.565, 0.687, (1.8733)+(0.0007)Gly+(−0.0796)Cit+(−0.0109)Leu;
0.628, 0.667, 0.783, 0.817, 0.714, 0.854, 0.785, 0.793, (1.8980)+(−0.0014)Gly+(−0.0087)Ala+(−0.0041)Leu;
0.628, 0.661, 0.680, 0.685, 0.708, 0.711, 0.587, 0.673, (1.2728)+(0.0019)Gly+(−0.0067)Thr+(−0.0836)Cit;
0.627, 0.665, 0.643, 0.717, 0.590, 0.657, 0.547, 0.628, (1.4184)+(0.0003)Gln+(0.0047)Pro+(−0.0621)Tyr;
0.627, 0.662, 0.703, 0.707, 0.720, 0.714, 0.651, 0.698, (0.7401)+(0.0020)Gln+(−0.0081)Thr+(−0.0848)Cit;
0.627, 0.664, 0.678, 0.687, 0.720, 0.717, 0.538, 0.665, (1.5037)+(0.0015)Gly+(−0.0736)Cit+(−0.0139)Arg;
0.626, 0.671, 0.780, 0.819, 0.706, 0.856, 0.777, 0.790, (1.7696)+(−0.0024)Thr+(−0.0085)Ala+(−0.0034)Leu;
0.625, 0.660, 0.708, 0.731, 0.724, 0.742, 0.588, 0.696, (1.3034)+(0.0016)Gln+(−0.0822)Cit+(−0.0120)Leu;
0.625, 0.669, 0.698, 0.782, 0.649, 0.715, 0.566, 0.678, (1.7190)+(0.0011)Gln+(−0.0502)Tyr+(−0.0077)Leu;
0.625, 0.659, 0.686, 0.690, 0.726, 0.712, 0.573, 0.675, (1.6569)+(−0.0715)Cit+(−0.0139)Arg+(0.0007)Pro;
0.624, 0.664, 0.715, 0.748, 0.651, 0.757, 0.727, 0.721, (1.5590)+(−0.0043)Thr+(−0.0307)Val+(0.0320)Leu;
0.624, 0.668, 0.675, 0.715, 0.637, 0.701, 0.629, 0.671, (−0.3879)+(−0.0213)Val+(0.0192)Orn+(0.0358)Phe;
0.623, 0.658, 0.717, 0.741, 0.724, 0.742, 0.622, 0.708, (2.2409)+(−0.0168)Arg+(0.0021)Pro+(−0.0146)Lys;
0.623, 0.663, 0.705, 0.779, 0.644, 0.684, 0.651, 0.690, (1.7768)+(−0.0035)Gly+(0.0016)Gln+(−0.0585)Tyr;
0.623, 0.659, 0.688, 0.686, 0.713, 0.705, 0.629, 0.683, (1.4265)+(−0.0061)Thr+(−0.0812)Cit+(0.0008)Pro;
0.622, 0.654, 0.728, 0.754, 0.733, 0.749, 0.633, 0.718, (2.4127)+(−0.0004)Gly+(−0.0160)Arg+(−0.0139)Lys;
0.622, 0.666, 0.723, 0.795, 0.680, 0.712, 0.631, 0.705, (2.7777)+(−0.0027)Gly+(−0.0491)Tyr+(−0.0071)Leu;
0.621, 0.664, 0.652, 0.722, 0.601, 0.661, 0.569, 0.638, (1.6786)+(−0.0022)Thr+(0.0050)Pro+(−0.0598)Tyr;
0.621, 0.657, 0.716, 0.743, 0.727, 0.748, 0.602, 0.705, (2.2883)+(0.0033)Thr+(−0.0178)Arg+(−0.0149)Lys;
0.621, 0.660, 0.624, 0.651, 0.606, 0.748, 0.504, 0.627, (0.3633)+(0.0233)Ser+(−0.0030)Gln+(−0.0139)Val;
0.620, 0.664, 0.760, 0.822, 0.733, 0.802, 0.620, 0.744, (1.9317)+(0.0023)Gln+(−0.0241)Arg+(−0.0135)Val;
0.620, 0.661, 0.678, 0.671, 0.688, 0.712, 0.649, 0.680, (0.6381)+(0.0193)Orn+(−0.0251)Lys+(0.0224)Phe;
0.620, 0.662, 0.720, 0.756, 0.680, 0.761, 0.678, 0.719, (1.4259)+(−0.0034)Gly+(−0.0180)Val+(0.0244)Orn;
0.619, 0.658, 0.693, 0.706, 0.724, 0.715, 0.580, 0.681, (0.8227)+(0.0022)Gln+(−0.0743)Cit+(−0.0169)Arg;
0.618, 0.648, 0.653, 0.653, 0.690, 0.691, 0.552, 0.646, (0.8148)+(0.0012)Gly+(−0.0876)Cit+(−0.0002)Pro;
0.618, 0.663, 0.702, 0.705, 0.707, 0.747, 0.647, 0.702, (1.4906)+(−0.0051)Thr+(0.0241)Orn+(−0.0210)Lys;
0.618, 0.662, 0.697, 0.704, 0.731, 0.719, 0.590, 0.686, (1.8192)+(−0.0020)Thr+(−0.0710)Cit+(−0.0123)Arg;
0.618, 0.656, 0.724, 0.775, 0.703, 0.767, 0.600, 0.711, (2.6680)+(−0.0222)Arg+(0.0061)Pro+(−0.0155)Val;
0.617, 0.666, 0.720, 0.757, 0.683, 0.776, 0.661, 0.719, (1.3333)+(−0.0095)Thr+(−0.0166)Val+(0.0278)Orn;
0.617, 0.668, 0.696, 0.774, 0.699, 0.712, 0.561, 0.676, (2.1779)+(0.0000)Thr+(−0.0487)Tyr+(−0.0070)Leu;
0.617, 0.663, 0.634, 0.675, 0.598, 0.752, 0.512, 0.634, (−0.7619)+(0.0162)Ser+(−0.0169)Val+(0.0149)Orn;

0.615, 0.656, 0.752, 0.803, 0.736, 0.797, 0.620, 0.739,
(3.1437)+(−0.0166)Arg+(−0.0109)Val+(−0.0059)Lys;
0.615, 0.648, 0.655, 0.655, 0.688, 0.691, 0.558, 0.648,
(0.5282)+(0.0010)Gly+(0.0006)Gln+(−0.0891)Cit;
0.615, 0.648, 0.733, 0.771, 0.735, 0.760, 0.609, 0.719,
(2.5834)+(−0.0169)Arg+(−0.0110)Lys+(−0.0064)Leu;
0.615, 0.648, 0.666, 0.666, 0.696, 0.692, 0.583, 0.659,
(0.6154)+(0.0009)Gln+(−0.0878)Cit+(−0.0006)Pro;
0.614, 0.659, 0.685, 0.724, 0.660, 0.760, 0.580, 0.681,
(1.5065)+(−0.0016)Gln+(−0.0176)Val+(0.0249)Orn;
0.614, 0.658, 0.690, 0.761, 0.640, 0.678, 0.618, 0.674,
(2.3071)+(−0.0030)Gly+(0.0019)Thr+(−0.0571)Tyr;
0.614, 0.658, 0.678, 0.760, 0.622, 0.686, 0.574, 0.661,
(1.4409)+(0.0009)Gln+(−0.0018)Thr+(−0.0547)Tyr;
0.614, 0.654, 0.709, 0.750, 0.730, 0.759, 0.519, 0.689,
(1.5995)+(−0.0286)Arg+(0.0234)Orn+(−0.0180)Leu;
0.614, 0.653, 0.617, 0.659, 0.577, 0.718, 0.515, 0.617,
(−0.7319)+(0.0181)Ser+(0.0042)Pro+(−0.0168)Val;
0.613, 0.659, 0.751, 0.801, 0.714, 0.810, 0.653, 0.745,
(1.9753)+(0.0015)Gln+(−0.0107)Val+(−0.0123)Lys;
0.613, 0.655, 0.668, 0.668, 0.710, 0.682, 0.572, 0.658,
(0.8739)+(−0.0733)Cit+(−0.0151)Arg+(0.0179)Phe;
0.613, 0.655, 0.674, 0.668, 0.697, 0.679, 0.634, 0.670,
(0.7006)+(−0.0071)Thr+(−0.0833)Cit+(0.0173)Phe;
0.612, 0.640, 0.631, 0.624, 0.671, 0.665, 0.544, 0.626,
(−0.0117)+(0.0016)Gly+(−0.0915)Cit+(0.0143)Phe;
0.612, 0.651, 0.656, 0.662, 0.626, 0.717, 0.655, 0.665,
(−1.2187)+(0.0302)Ser+(−0.0087)Gly+(−0.0174)Leu;
0.611, 0.653, 0.698, 0.698, 0.705, 0.737, 0.660, 0.700,
(1.6400)+(−0.0018)Gly+(0.0228)Orn+(−0.0225)Lys;
0.611, 0.655, 0.720, 0.759, 0.691, 0.779, 0.635, 0.716,
(2.4074)+(0.0053)Pro+(−0.0128)Val+(−0.0115)Lys;
0.611, 0.654, 0.685, 0.689, 0.693, 0.738, 0.620, 0.685,
(1.3546)+(0.0000)Pro+(0.0218)Orn+(−0.0227)Lys;
0.611, 0.650, 0.756, 0.812, 0.735, 0.787, 0.633, 0.742,
(2.9984)+(−0.0011)Gly+(−0.0199)Arg+(−0.0130)V al;
0.610, 0.653, 0.698, 0.716, 0.704, 0.754, 0.597, 0.693,
(1.5613)+(0.0238)Orn+(−0.0196)Lys+(−0.0078)Leu;
0.609, 0.655, 0.672, 0.716, 0.632, 0.742, 0.590, 0.670,
(0.7196)+(0.0034)Pro+(−0.0189)Val+(0.0201)Orn;
0.609, 0.655, 0.742, 0.800, 0.727, 0.793, 0.579, 0.725,
(2.7162)+(0.0035)Thr+(−0.0226)Arg+(−0.0135)Val;
0.608, 0.650, 0.710, 0.754, 0.663, 0.692, 0.705, 0.704,
(0.4073)+(−0.0019)Gly+(−0.0190)Val+(0.0387)Phe;
0.608, 0.648, 0.669, 0.670, 0.675, 0.678, 0.648, 0.668,
(0.1708)+(−0.0062)Thr+(−0.0268)Arg+(0.0210)Ile;
0.608, 0.650, 0.758, 0.799, 0.727, 0.797, 0.683, 0.752,
(2.8271)+(−0.0016)Gly+(−0.0108)Val+(−0.0104)Lys;
0.608, 0.653, 0.688, 0.694, 0.692, 0.740, 0.625, 0.688,
(1.1885)+(0.0005)Gln+(0.0212)Orn+(−0.0230)Lys;
0.607, 0.652, 0.742, 0.788, 0.714, 0.803, 0.634, 0.735,
(2.5172)+(0.0013)Thr+(−0.0107)Val+(−0.0114)Lys;
0.607, 0.645, 0.701, 0.704, 0.701, 0.704, 0.692, 0.700,
(0.9834)+(−0.0007)Gly+(−0.0219)Lys+(0.0268)Phe;
0.606, 0.654, 0.716, 0.764, 0.663, 0.706, 0.708, 0.710,
(0.3654)+(−0.0061)Thr+(−0.0181)Val+(0.0415)Phe;
0.606, 0.644, 0.660, 0.661, 0.675, 0.680, 0.609, 0.656,
(0.0297)+(−0.0300)Arg+(−0.0036)Pro+(0.0240)Ile;
0.606, 0.639, 0.645, 0.638, 0.680, 0.661, 0.578, 0.639,
(0.1051)+(0.0005)Gln+(−0.0896)Cit+(0.0121)Phe;
0.605, 0.647, 0.710, 0.735, 0.702, 0.716, 0.653, 0.701,
(0.8139)+(−0.0182)Lys+(−0.0124)Leu+(0.0393)Phe;
0.605, 0.648, 0.673, 0.723, 0.622, 0.682, 0.643, 0.667,
(−0.0138)+(0.0031)Pro+(−0.0201)Val+(0.0363)Phe;
0.605, 0.649, 0.696, 0.700, 0.695, 0.706, 0.676, 0.694,
(0.8463)+(0.0001)Pro+(−0.0221)Lys+(0.0270)Phe;
0.605, 0.649, 0.702, 0.708, 0.699, 0.710, 0.687, 0.701,
(0.9024)+(−0.0020)Thr+(−0.0212)Lys+(0.0275)Phe;
0.604, 0.654, 0.585, 0.575, 0.573, 0.687, 0.561, 0.599,
(−1.6078)+(0.0349)Ser+(−0.0026)Gln+(−0.0209)Thr;
0.604, 0.646, 0.719, 0.771, 0.728, 0.704, 0.572, 0.694,
(0.7574)+(−0.0269)Arg+(−0.0217)Leu+(0.0410)Phe;
0.604, 0.649, 0.701, 0.708, 0.695, 0.714, 0.685, 0.700,
(0.5105)+(0.0010)Gln+(−0.0228)Lys+(0.0260)Phe;
0.604, 0.649, 0.688, 0.734, 0.648, 0.690, 0.650, 0.680,
(0.4529)+(−0.0011)Gln+(−0.0190)Val+(0.0416)Phe;
0.603, 0.637, 0.647, 0.641, 0.683, 0.661, 0.576, 0.640,
(0.3469)+(−0.0879)Cit+(−0.0013)Pro+(0.0149)Phe;
0.602, 0.646, 0.736, 0.756, 0.722, 0.755, 0.697, 0.732,
(1.3798)+(−0.0018)Gly+(0.0018)Gln+(−0.0199)Lys;
0.601, 0.640, 0.717, 0.732, 0.710, 0.742, 0.672, 0.714,
(1.8809)+(−0.0011)Gly+(0.0014)Pro+(−0.0189)Lys;
0.601, 0.655, 0.647, 0.676, 0.611, 0.749, 0.575, 0.653,
(−1.4968)+(0.0299)Ser+(−0.0198)Thr+(−0.0105)Leu;
0.600, 0.648, 0.734, 0.759, 0.717, 0.762, 0.681, 0.730,
(1.2324)+(0.0016)Gln+(−0.0028)Thr+(−0.0189)Lys;
0.600, 0.646, 0.715, 0.738, 0.703, 0.750, 0.655, 0.711,
(1.2098)+(0.0013)Gln+(0.0011)Pro+(−0.0202)Lys;
0.600, 0.636, 0.641, 0.642, 0.663, 0.665, 0.577, 0.637,
(−0.1569)+(0.0004)Gly+(−0.0311)Arg+(0.0196)Ile;
0.600, 0.654, 0.586, 0.580, 0.553, 0.667, 0.612, 0.603,
(−3.3757)+(0.0338)Ser+(−0.0259)Thr+(0.0165)Phe;
0.599, 0.638, 0.726, 0.744, 0.720, 0.748, 0.678, 0.722,
(1.9796)+(−0.0011)Gly+(−0.0006)Thr+(−0.0180)Lys;
0.599, 0.639, 0.641, 0.637, 0.669, 0.670, 0.571, 0.637,
(−0.2096)+(−0.0320)Arg+(0.0066)Orn+(0.0171)Ile;
0.598, 0.637, 0.714, 0.762, 0.660, 0.737, 0.682, 0.710,
(1.7211)+(−0.0024)Gly+(0.0048)Pro+(−0.0170)Val;
0.598, 0.635, 0.649, 0.651, 0.668, 0.670, 0.590, 0.645,
(−0.3177)+(0.0006)Gln+(−0.0318)Arg+(0.0189)Ile;
0.597, 0.643, 0.713, 0.731, 0.704, 0.745, 0.662, 0.711,
(1.7506)+(−0.0020)Thr+(0.0017)Pro+(−0.0183)Lys;
0.597, 0.645, 0.696, 0.711, 0.718, 0.724, 0.593, 0.686,
(0.6085)+(−0.0073)Thr+(−0.0267)Arg+(0.0168)Orn;
0.595, 0.635, 0.734, 0.763, 0.724, 0.757, 0.660, 0.726,
(2.1797)+(−0.0013)Gly+(−0.0158)Lys+(−0.0056)Leu;
0.594, 0.644, 0.408, 0.325, 0.446, 0.563, 0.440, 0.443,
(−2.6256)+(0.0293)Ser+(−0.0060)Gln+(0.0198)Ile;
0.593, 0.641, 0.527, 0.472, 0.537, 0.609, 0.593, 0.553,
(−1.6391)+(0.0354)Ser+(−0.0072)Gly+(−0.0043)Gln;
0.593, 0.638, 0.711, 0.743, 0.702, 0.751, 0.620, 0.704,
(1.8560)+(0.0026)Pro+(−0.0165)Lys+(−0.0071)Leu;
0.593, 0.637, 0.746, 0.800, 0.692, 0.766, 0.698, 0.739,
(1.7261)+(−0.0025)Gly+(0.0004)Gln+(−0.0151)Val;
0.593, 0.635, 0.685, 0.738, 0.641, 0.728, 0.606, 0.678,
(1.5239)+(−0.0006)Gln+(0.0049)Pro+(−0.0168)Val;
0.592, 0.652, 0.592, 0.581, 0.565, 0.697, 0.601, 0.611,
(−2.8016)+(0.0323)Ser+(−0.0261)Thr+(0.0104)Orn;
0.592, 0.645, 0.730, 0.769, 0.713, 0.767, 0.637, 0.721,
(1.3757)+(0.0015)Gln+(−0.0175)Lys+(−0.0056)Leu;
0.591, 0.636, 0.647, 0.644, 0.667, 0.668, 0.594, 0.643,
(0.0425)+(−0.0305)Arg+(0.0204)Ile+(−0.0037)Phe;
0.591, 0.635, 0.735, 0.796, 0.735, 0.761, 0.556, 0.712,
(1.1864)+(0.0021)Gln+(−0.0272)Arg+(−0.0146)Leu;
0.591, 0.644, 0.583, 0.576, 0.555, 0.675, 0.595, 0.600,
(−2.7073)+(0.0330)Ser+(−0.0251)Thr+(0.0022)Pro;
0.590, 0.638, 0.726, 0.759, 0.716, 0.762, 0.632, 0.717,
(1.9844)+(−0.0011)Thr+(−0.0157)Lys+(−0.0053)Leu;
0.590, 0.631, 0.673, 0.694, 0.705, 0.705, 0.529, 0.658,
(0.4140)+(−0.0303)Arg+(−0.0011)Pro+(0.0137)Orn;
0.589, 0.627, 0.672, 0.688, 0.703, 0.698, 0.548, 0.659,
(0.4351)+(−0.0006)Gly+(−0.0303)Arg+(0.0130)Orn;
0.588, 0.633, 0.502, 0.429, 0.492, 0.580, 0.658, 0.540,
(−3.8716)+(0.0301)Ser+(−0.0081)Gly+(0.0098)Ile;

0.587, 0.635, 0.707, 0.758, 0.657, 0.736, 0.658, 0.702, (1.6617)+(−0.0065)Thr+(0.0055)Pro+(−0.0160)Val; 0.587, 0.629, 0.566, 0.530, 0.549, 0.628, 0.652, 0.590, (−2.9399)+(0.0304)Ser+(−0.0082)Gly+(−0.0026)Pro; 0.585, 0.634, 0.750, 0.802, 0.699, 0.767, 0.705, 0.743, (2.0426)+(−0.0018)Gly+(−0.0034)Thr+(−0.0142)Val; 0.585, 0.627, 0.667, 0.688, 0.697, 0.695, 0.530, 0.652, (0.1680)+(0.0005)Gln+(−0.0312)Arg+(0.0121)Orn; 0.585, 0.627, 0.736, 0.789, 0.740, 0.750, 0.577, 0.714, (2.1260)+(−0.0009)Gly+(−0.0234)Arg+(−0.0136)Leu; 0.584, 0.623, 0.689, 0.722, 0.706, 0.694, 0.562, 0.671, (0.2990)+(0.0012)Gln+(−0.0295)Arg+(−0.0002)Pro; 0.584, 0.627, 0.712, 0.748, 0.715, 0.711, 0.614, 0.697, (0.3627)+(0.0017)Gln+(−0.0053)Thr+(−0.0268)Arg; 0.583, 0.636, 0.740, 0.799, 0.689, 0.773, 0.667, 0.732, (1.5339)+(0.0006)Gln+(−0.0053)Thr+(−0.0140)Val; 0.583, 0.622, 0.694, 0.726, 0.708, 0.689, 0.586, 0.677, (0.3474)+(−0.0008)Gly+(0.0013)Gln+(−0.0294)Arg; 0.583, 0.627, 0.709, 0.763, 0.716, 0.734, 0.535, 0.687, (1.8698)+(−0.0251)Arg+(0.0037)Pro+(−0.0161)Leu; 0.582, 0.622, 0.702, 0.733, 0.713, 0.700, 0.597, 0.686, (0.9886)+(−0.0001)Gly+(−0.0037)Thr+(−0.0249)Arg; 0.582, 0.629, 0.729, 0.786, 0.735, 0.753, 0.551, 0.706, (1.9831)+(−0.0006)Thr+(−0.0235)Arg+(−0.0133)Leu; 0.581, 0.621, 0.687, 0.716, 0.708, 0.689, 0.566, 0.670, (0.8214)+(−0.0004)Gly+(−0.0274)Arg+(0.0001)Pro; 0.579, 0.622, 0.697, 0.727, 0.709, 0.697, 0.593, 0.681, (0.9313)+(−0.0041)Thr+(−0.0250)Arg+(0.0007)Pro; 0.579, 0.626, 0.662, 0.680, 0.695, 0.685, 0.531, 0.648, (0.0884)+(−0.0311)Arg+(0.0117)Orn+(0.0062)Phe; 0.579, 0.635, 0.565, 0.580, 0.576, 0.699, 0.404, 0.565, (−0.7368)+(0.0244)Ser+(−0.0035)Gln+(−0.0142)Leu; 0.576, 0.625, 0.562, 0.600, 0.548, 0.628, 0.441, 0.554, (−2.8622)+(0.0193)Ser+(−0.0236)Leu+(0.0301)Phe; 0.575, 0.619, 0.673, 0.698, 0.695, 0.670, 0.559, 0.656, (0.2853)+(−0.0001)Gly+(−0.0288)Arg+(0.0108)Phe; 0.575, 0.624, 0.693, 0.719, 0.704, 0.682, 0.606, 0.678, (0.4214)+(−0.0046)Thr+(−0.0260)Arg+(0.0128)Phe; 0.574, 0.621, 0.676, 0.704, 0.696, 0.675, 0.560, 0.659, (−0.0683)+(0.0009)Gln+(−0.0304)Arg+(0.0096)Phe; 0.573, 0.623, 0.544, 0.498, 0.532, 0.616, 0.641, 0.572, (−2.8896)+(0.0303)Ser+(−0.0084)Gly+(−0.0061)Phe; 0.573, 0.620, 0.675, 0.703, 0.697, 0.673, 0.556, 0.657, (0.2802)+(−0.0287)Arg+(−0.0006)Pro+(0.0117)Phe; 0.570, 0.625, 0.713, 0.749, 0.693, 0.746, 0.637, 0.706, (0.6602)+(−0.0129)Thr+(0.0215)Orn+(−0.0178)Leu; 0.569, 0.623, 0.456, 0.415, 0.443, 0.597, 0.489, 0.486, (−4.2643)+(0.0205)Ser+(−0.0060)Pro+(0.0197)Ile; 0.566, 0.627, 0.465, 0.428, 0.491, 0.612, 0.399, 0.483, (−1.7722)+(0.0270)Ser+(−0.0048)Gln+(−0.0008)Pro; 0.565, 0.624, 0.435, 0.388, 0.468, 0.572, 0.395, 0.456, (−2.1461)+(0.0276)Ser+(−0.0052)Gln+(0.0074)Phe; 0.561, 0.616, 0.541, 0.497, 0.526, 0.597, 0.646, 0.566, (−3.0559)+(0.0308)Ser+(−0.0082)Gly+(−0.0051)Orn; 0.556, 0.618, 0.637, 0.618, 0.600, 0.638, 0.764, 0.655, (−0.9160)+(0.0001)Gly+(−0.0160)Thr+(0.0181)Ile; 0.555, 0.618, 0.634, 0.609, 0.605, 0.633, 0.761, 0.652, (−0.6774)+(−0.0006)Gln+(−0.0152)Thr+(0.0184)Ile; 0.555, 0.617, 0.650, 0.634, 0.612, 0.659, 0.766, 0.668, (−0.8340)+(−0.0148)Thr+(−0.0033)Pro+(0.0223)Ile; 0.555, 0.628, 0.449, 0.405, 0.481, 0.599, 0.390, 0.469, (−1.8542)+(0.0270)Ser+(−0.0050)Gln+(0.0018)Orn; 0.555, 0.618, 0.574, 0.618, 0.565, 0.680, 0.402, 0.566, (−1.8983)+(0.0182)Ser+(0.0055)Orn+(−0.0181)Leu; 0.554, 0.608, 0.565, 0.607, 0.552, 0.663, 0.407, 0.558, (−1.8728)+(0.0189)Ser+(0.0014)Pro+(−0.0180)Leu; 0.553, 0.606, 0.714, 0.763, 0.684, 0.671, 0.676, 0.698, (−0.0661)+(−0.0103)Thr+(−0.0212)Leu+(0.0341)Phe; 0.550, 0.626, 0.635, 0.607, 0.606, 0.648, 0.756, 0.654, (−1.1019)+(−0.0170)Thr+(0.0065)Orn+(0.0161)Ile; 0.549, 0.615, 0.643, 0.624, 0.608, 0.653, 0.764, 0.662, (−0.5794)+(−0.0153)Thr+(0.0207)Ile+(−0.0092)Phe; 0.547, 0.601, 0.410, 0.361, 0.403, 0.575, 0.439, 0.444, (−3.9086)+(0.0198)Ser+(0.0164)Ile+(−0.0150)Phe; 0.538, 0.621, 0.688, 0.688, 0.664, 0.693, 0.734, 0.695, (−0.4056)+(−0.0007)Gly+(−0.0154)Thr+(0.0122)Orn; 0.533, 0.621, 0.674, 0.672, 0.656, 0.690, 0.706, 0.681, (−0.2638)+(−0.0006)Gln+(−0.0151)Thr+(0.0128)Orn; 0.530, 0.584, 0.742, 0.794, 0.711, 0.728, 0.679, 0.728, (1.1970)+(−0.0013)Gly+(−0.0079)Thr+(−0.0148)Leu; 0.530, 0.594, 0.701, 0.747, 0.685, 0.716, 0.603, 0.688, (0.4425)+(−0.0030)Gly+(0.0151)Orn+(−0.0204)Leu; 0.528, 0.582, 0.708, 0.759, 0.674, 0.715, 0.641, 0.697, (0.9378)+(−0.0101)Thr+(0.0034)Pro+(−0.0167)Leu; 0.528, 0.622, 0.686, 0.692, 0.661, 0.700, 0.715, 0.692, (−0.4550)+(−0.0154)Thr+(−0.0008)Pro+(0.0126)Orn; 0.528, 0.599, 0.466, 0.456, 0.465, 0.591, 0.408, 0.480, (−3.4755)+(0.0200)Ser+(−0.0027)Pro+(0.0004)Phe; 0.527, 0.589, 0.737, 0.797, 0.696, 0.742, 0.659, 0.724, (0.7102)+(0.0007)Gln+(−0.0096)Thr+(−0.0149)Leu; 0.526, 0.621, 0.681, 0.683, 0.655, 0.695, 0.719, 0.688, (−0.5559)+(−0.0158)Thr+(0.0118)Orn+(0.0015)Phe; 0.526, 0.590, 0.414, 0.372, 0.404, 0.520, 0.467, 0.441, (−4.2575)+(0.0216)Ser+(−0.0122)Orn+(0.0157)Ile; 0.525, 0.591, 0.706, 0.726, 0.675, 0.675, 0.739, 0.704, (−0.0943)+(−0.0006)Gly+(0.0001)Gln+(−0.0126)Thr; 0.524, 0.590, 0.691, 0.745, 0.671, 0.638, 0.631, 0.671, (−0.2627)+(−0.0021)Gly+(−0.0233)Leu+(0.0289)Phe; 0.522, 0.596, 0.638, 0.694, 0.630, 0.632, 0.512, 0.617, (−0.9720)+(0.0108)Orn+(−0.0252)Leu+(0.0272)Phe; 0.519, 0.597, 0.655, 0.701, 0.662, 0.705, 0.480, 0.637, (0.4763)+(−0.0013)Gln+(0.0154)Orn+(−0.0194)Leu; 0.518, 0.592, 0.695, 0.711, 0.666, 0.661, 0.739, 0.694, (−0.3335)+(−0.0004)Gly+(−0.0132)Thr+(0.0052)Phe; 0.516, 0.590, 0.705, 0.726, 0.674, 0.674, 0.737, 0.703, (−0.0734)+(−0.0006)Gly+(−0.0126)Thr+(−0.0000)Pro; 0.516, 0.592, 0.469, 0.462, 0.463, 0.587, 0.413, 0.481, (−3.3459)+(0.0204)Ser+(−0.0023)Pro+(−0.0039)Orn; 0.515, 0.594, 0.688, 0.705, 0.659, 0.664, 0.722, 0.688, (−0.3432)+(−0.0002)Gln+(−0.0133)Thr+(0.0059)Phe; 0.514, 0.581, 0.647, 0.712, 0.630, 0.616, 0.532, 0.622, (−0.7417)+(0.0011)Pro+(−0.0241)Leu+(0.0289)Phe; 0.513, 0.592, 0.700, 0.722, 0.669, 0.678, 0.723, 0.698, (−0.1324)+(−0.0001)Gln+(−0.0129)Thr+(0.0000)Pro; 0.511, 0.573, 0.707, 0.767, 0.678, 0.696, 0.614, 0.689, (0.7028)+(−0.0024)Gly+(0.0019)Pro+(−0.0187)Leu; 0.511, 0.590, 0.651, 0.711, 0.641, 0.696, 0.480, 0.632, (−0.1366)+(0.0010)Pro+(0.0124)Orn+(−0.0205)Leu; 0.510, 0.585, 0.652, 0.706, 0.646, 0.627, 0.542, 0.630, (−0.2737)+(−0.0010)Gln+(−0.0231)Leu+(0.0313)Phe; 0.509, 0.576, 0.725, 0.786, 0.698, 0.718, 0.627, 0.707, (0.7731)+(−0.0024)Gly+(0.0001)Gln+(−0.0173)Leu; 0.505, 0.594, 0.692, 0.710, 0.661, 0.668, 0.725, 0.691, (−0.4065)+(−0.0134)Thr+(−0.0003)Pro+(0.0060)Phe; 0.501, 0.572, 0.438, 0.425, 0.434, 0.547, 0.404, 0.452, (−3.5143)+(0.0206)Ser+(−0.0060)Orn+(−0.0006)Phe 0.868, 0.887, 0.812, 0.814, 0.816, 0.826, 0.787, 0.811, (−0.6936)+(0.0495)Ser+(−0.2897)Met+(0.1345)Phe+(−0.1458)Trp; 0.867, 0.887, 0.767, 0.742, 0.767, 0.829, 0.787, 0.781, (1.8981)+(0.0482)Ser+(−0.1330)His+(0.1211)Phe+(−0.1189)Trp; 0.859, 0.880, 0.788, 0.765, 0.799, 0.810, 0.807, 0.795, (5.5872)+(−0.1248)His+(0.0227)Thr+(0.1034)Phe+(−0.1281)Trp; 0.859, 0.879, 0.818, 0.810, 0.812, 0.831, 0.842, 0.824, (3.3687)+(0.0094)Gln+(−0.1373)His+(0.1016)Phe+(−0.1198)Trp; 0.858, 0.873, 0.755, 0.719, 0.757, 0.828, 0.795, 0.775, (3.8688)+(0.0418)Ser+(−0.1122)His+(0.0756)Ile+(−0.1226)Trp; 0.858, 0.878, 0.802, 0.806, 0.796, 0.815, 0.796, 0.803, (1.4379)+(0.0468)Ser+(−0.1406)Asn+(0.0925)Phe+(−0.1494)Trp; 0.857, 0.876, 0.767, 0.742, 0.776, 0.835, 0.770, 0.781, (−0.3631)+(0.0601)Ser+(−0.1472)His+(−0.2802)Met+(0.1624) Phe; 0.852, 0.871, 0.791, 0.760, 0.793, 0.812, 0.852, 0.804, (5.7984)+(−0.1096)His+(0.0488)Ile+(0.0764) Phe+(−0.1294)Trp; 0.852, 0.870, 0.796, 0.784, 0.752, 0.839, 0.888, 0.816, (1.7025)+(−0.0640)Val+(−0.3892) Met+(0.2012)Ile+(0.1197)Phe; 0.852, 0.872, 0.808, 0.798, 0.778, 0.844, 0.873, 0.823, (6.6666)+(−0.0432) Val+(−0.1839)Met+(0.1753)Ile+(−0.1070)Trp; 0.852, 0.870, 0.782, 0.766, 0.781, 0.831, 0.788, 0.792, (1.7250)+(0.0453)Ser+(−0.2355)Met+(0.0785)Ile+(−0.1464)Trp; 0.851, 0.868, 0.777, 0.768, 0.743, 0.797, 0.861, 0.792, (3.1638)+(−0.0441)Val+(0.1421)Ile+(0.0684)Phe+(−0.1578)Trp; 0.850, 0.867, 0.771, 0.744, 0.784, 0.822, 0.777, 0.782, (2.8932)+(0.0351)Ser+(−0.0931)Cit+(0.0687)Ile+(−0.1868)Trp; 0.850, 0.866, 0.799, 0.780, 0.793, 0.829, 0.842, 0.811, (4.9396)+(0.0088)Gln+(−0.1221)His+(0.0645)Ile+(−0.1245) Trp; 0.849, 0.864, 0.776, 0.748, 0.778, 0.820, 0.816, 0.791, (7.0898)+(−0.1081)His+(0.0181)Thr+(0.0644) Ile+(−0.1288)Trp; 0.848, 0.868, 0.770, 0.751, 0.729, 0.872, 0.831, 0.796, (1.0778)+(0.0407)Ser+(−0.0537) Val+(−0.3400)Met+(0.1986)Ile; 0.847, 0.868, 0.801, 0.781, 0.810, 0.815, 0.825, 0.808, (5.9199)+(−0.1114) His+(0.0225)Orn+(0.0932)Phe+(−0.1159)Trp; 0.847, 0.868, 0.809, 0.812, 0.833, 0.786, 0.764, 0.799, (2.8552)+(0.0368)Thr+(−0.3410)Met+(0.1295)Phe+(−0.1602)Trp; 0.847, 0.862, 0.797, 0.791, 0.746, 0.844, 0.886, 0.817, (5.8480)+(−0.0079)Ala+(−0.0409)Val+(0.1684)Ile+(−0.1273)Trp; 0.847, 0.867, 0.796, 0.784, 0.797, 0.820, 0.809, 0.803, (5.3440)+(0.0046)Gly+(−0.1128)His+(0.1088)Phe+(−0.1149)Trp; 0.846, 0.862, 0.782, 0.765, 0.756, 0.825, 0.853, 0.800, (7.1512)+(−0.0690)His+(−0.0299)Val+(0.1370)Ile+(−0.1095)Trp; 0.846, 0.872, 0.778, 0.777, 0.780, 0.783, 0.771, 0.778, (0.6197)+(0.0338)Ser+(−0.0124)Lys+(0.0844)Phe+(−0.1674)Trp; 0.846, 0.864, 0.788, 0.783, 0.771, 0.792, 0.832, 0.794, (2.9278)+(0.1367)Ile+(−0.0728)Leu+(0.0636)Phe+(−0.1605)Trp; 0.845, 0.867, 0.802, 0.786, 0.806, 0.808, 0.832, 0.808, (5.9787)+(−0.1062)His+(0.0042)Pro+(0.0998)Phe+(−0.1185)Trp; 0.845, 0.864, 0.781, 0.768, 0.740, 0.868, 0.837, 0.803, (3.9962)+(0.0311)Thr+(−0.0608)Val+(−0.3891)Met+(0.2090) Ile; 0.845, 0.867, 0.776, 0.782, 0.770, 0.777, 0.773, 0.776, (0.5852)+(0.0287)Ser+(−0.0073)Val+(0.0843) Phe+(−0.1708)Trp; 0.845, 0.863, 0.807, 0.793, 0.809, 0.812, 0.833, 0.812, (6.1244)+(−0.1061)His+(0.0006) Val+(0.1029)Phe+(−0.1166)Trp; 0.845, 0.861, 0.795, 0.776, 0.784, 0.827, 0.844, 0.808, (7.2040)+(−0.0764) His+(0.1160)Ile+(−0.0374)Leu+(−0.1146)Trp; 0.844, 0.861, 0.769, 0.754, 0.773, 0.835, 0.754, 0.779, (5.3551)+(0.0386)Ser+(−0.0976)His+(0.0099)Pro+(−0.1040)Trp; 0.844, 0.862, 0.791, 0.776, 0.764, 0.835, 0.855, 0.807, (6.2375)+(−0.0640)Cit+(−0.0362)Val+(0.1489)Ile+(−0.1415)Trp; 0.843, 0.865, 0.812, 0.801, 0.814, 0.818, 0.835, 0.817, (6.3125)+(−0.0124)Asn+(−0.1023)His+(0.1040)Phe+(−0.1146)Trp; 0.843, 0.864, 0.818, 0.808, 0.814, 0.830, 0.843, 0.824, (6.2917)+(−0.1021)His+(−0.0028)Ala+(0.1090)Phe+(−0.1131) Trp; 0.843, 0.863, 0.803, 0.783, 0.809, 0.810, 0.836, 0.809, (6.1579)+(−0.1100)His+(0.0102)Leu+(0.0940) Phe+(−0.1216)Trp; 0.843, 0.860, 0.777, 0.768, 0.793, 0.797, 0.754, 0.778, (1.1802)+(0.0372)Ser+(−0.1027) Cit+(0.0987)Phe+(−0.1854)Trp; 0.843, 0.859, 0.809, 0.805, 0.775, 0.843, 0.867, 0.822, (5.7424)+(−0.0082) Ala+(0.1610)Ile+(−0.0664)Leu+(−0.1350)Trp; 0.842, 0.859, 0.798, 0.791, 0.758, 0.840, 0.870, 0.815, (6.8143)+(−0.0695)Asn+(−0.0424)Val+(0.1546)Ile+(−0.1154)Trp; 0.842, 0.866, 0.827, 0.817, 0.834, 0.827, 0.838, 0.829, (6.1768)+(−0.0922)His+(−0.1319)Met+(0.1301)Phe+(−0.1062)Trp; 0.842, 0.862, 0.780, 0.766, 0.788, 0.847, 0.750, 0.788, (5.5527)+(0.0338)Ser+(−0.1006)His+(0.0284)Orn+(−0.0991)Trp; 0.841, 0.859, 0.783, 0.752, 0.791, 0.822, 0.823, 0.797, (7.2352)+(−0.1007)His+(0.0228)Orn+(0.0594)Ile+(−0.1205)Trp; 0.841, 0.861, 0.756, 0.742, 0.720, 0.817, 0.821, 0.775, (2.7061)+(0.0256)Ser+(−0.0402)Val+(0.1469)Ile+(−0.1474)Trp; 0.841, 0.857, 0.801, 0.779, 0.791, 0.838, 0.855, 0.816, (7.8145)+(−0.0856)His+(−0.0049)Ala+(0.0743)Ile+(−0.1162)Trp; 0.840, 0.862, 0.803, 0.788, 0.805, 0.810, 0.830, 0.808, (5.9127)+(−0.1100)His+(0.0052)Lys+(0.1000)Phe+(−0.1200)Trp; 0.840, 0.863, 0.781, 0.785, 0.792, 0.786, 0.746, 0.777, (0.8091)+(0.0353)Ser+(−0.0284)Arg+(0.0879)Phe+(−0.1742) Trp; 0.840, 0.856, 0.799, 0.800, 0.792, 0.852, 0.776, 0.805, (4.6131)+(0.0288)Ser+(0.0066)Gln+(−0.1102)His+(−0.0990)Trp; 0.840, 0.857, 0.773, 0.753, 0.784, 0.834, 0.758, 0.782, (5.1823)+(0.0402)Ser+(−0.1098) His+(0.0120)Val+(−0.1100)Trp; 0.839, 0.857, 0.760, 0.729, 0.772, 0.825, 0.768, 0.774, (4.7218)+(0.0420) Ser+(−0.1164)His+(0.0313)Leu+(−0.1150)Trp; 0.839, 0.857, 0.776, 0.763, 0.768, 0.823, 0.792, 0.787, (2.8672)+(0.0433)Ser+(−0.1153)Asn+(0.0572)Ile+(−0.1517)Trp; 0.839, 0.862, 0.744, 0.704, 0.745, 0.841, 0.776, 0.767, (2.1986)+(0.0514)Ser+(−0.1264)His+(−0.2196)Met+(0.0830)Ile; 0.839, 0.861, 0.793, 0.795, 0.778, 0.811, 0.806, 0.798, (0.7514)+(0.0301)Ser+(−0.0068)Ala+(0.0855)Phe+(−0.1659)Trp; 0.839, 0.857, 0.769, 0.745, 0.789, 0.808, 0.760, 0.775, (3.7383)+(−0.1490)His+(0.0429)Thr+(−0.3207)Met+(0.1423)Phe; 0.839, 0.856, 0.798, 0.797, 0.796, 0.859, 0.764, 0.804, (6.4883)+(0.0411)Ser+(−0.0461)Asn+(−0.0805)His+(−0.0932)Trp; 0.838, 0.859, 0.763, 0.753, 0.746, 0.814, 0.791, 0.776, (2.2558)+(0.0259)Ser+(0.1387)Ile+(−0.0624)Leu+(−0.1558)Trp; 0.838, 0.861, 0.763, 0.761, 0.766, 0.761, 0.763, 0.763, (0.3487)+(0.0284)Ser+(0.0015)Pro+(0.0693)Phe+(−0.1812)Trp; 0.838, 0.861, 0.767, 0.768, 0.770, 0.766, 0.762, 0.766, (0.4098)+(0.0285)Ser+(−0.0019)Leu+(0.0727)Phe+(−0.1786) Trp; 0.838, 0.862, 0.810, 0.798, 0.812, 0.817, 0.831, 0.815, (6.2982)+(−0.1037)His+(−0.0050)Arg+(0.1052)Phe+(−0.1153)Trp; 0.838, 0.854, 0.778, 0.753, 0.777, 0.821, 0.814, 0.791, (6.9014)+(0.0041)Gly+(−0.0990)His+(0.0678)Ile+(−0.1183)Trp; 0.838, 0.861, 0.774, 0.774, 0.773, 0.775, 0.776, 0.774, (0.2426)+(0.0325)Ser+(−0.0071)Thr+(0.0745)Phe+(−0.1744) Trp; 0.838, 0.863, 0.808, 0.801, 0.806, 0.814, 0.830, 0.813, (6.1545)+(−0.1031)His+(−0.0154)Tyr+(0.1119) Phe+(−0.1109)Trp; 0.838, 0.855, 0.804, 0.799, 0.786, 0.826, 0.841, 0.813, (6.0808)+(−0.0486)Asn+(0.1377) Ile+(−0.0625)Leu+(−0.1335)Trp; 0.837, 0.858, 0.779, 0.771, 0.783, 0.848, 0.740, 0.785, (6.0131)+(0.0326) Ser+(−0.0989)His+(0.0111)Thr+(−0.1019)Trp; 0.837, 0.857, 0.790, 0.782, 0.820, 0.841, 0.713, 0.789, (4.6027)+(0.0276)Ser+(−0.1146)Cit+(0.0484)Orn+(−0.1654)Trp; 0.837, 0.859, 0.766, 0.776, 0.760, 0.764, 0.753, 0.763, (0.5464)+(0.0307)Ser+(−0.0422)Tyr+(0.0961)Phe+(−0.1664)Trp; 0.837, 0.854, 0.809, 0.798, 0.807, 0.831, 0.824, 0.815, (5.3566)+(0.0099)Gln+(−0.1282)His+(0.0250)Leu+(−0.1168)Trp; 0.837, 0.855, 0.786, 0.791, 0.787, 0.828, 0.738, 0.786, (3.6885)+(0.0399)Ser+(0.0129)Pro+(−0.1933)Met+(−0.1350)Trp; 0.836, 0.853, 0.789, 0.762, 0.789, 0.817, 0.836, 0.801, (7.4907)+(−0.0926)His+(0.0006)Pro+(0.0644)Ile+(−0.1201)Trp; 0.836, 0.852, 0.788, 0.762, 0.788, 0.818, 0.835, 0.801, (7.4632)+(0.0027)Asn+(−0.0934)His+(0.0653)Ile+(−0.1202)Trp; 0.836, 0.862, 0.761, 0.756, 0.767, 0.766, 0.756, 0.761, (0.7507)+(0.0312)Ser+(−0.0017)Gln+(0.0730)Phe+(−0.1768)Trp; 0.836, 0.856, 0.796, 0.795, 0.795, 0.860, 0.757, 0.802, (6.1565)+(0.0388)Ser+(−0.0829)His+(−0.0539)Met+(−0.0922)Trp; 0.836, 0.851, 0.736, 0.697, 0.715, 0.844, 0.803, 0.765, (2.4233)+(0.0412)Ser+(−0.1423)His+(−0.0074)Ala+(0.0706)Ile; 0.836, 0.855, 0.800, 0.787, 0.789, 0.836, 0.828, 0.810, (6.1927)+(−0.0732)Cit+(0.1445)Ile+(−0.0583)Leu+(−0.1486)Trp; 0.836, 0.853, 0.787, 0.760, 0.788, 0.816, 0.836, 0.800, (7.3754)+(−0.0953)His+(0.0030)Lys+(0.0633)Ile+(−0.1220)Trp; 0.836, 0.856, 0.806, 0.799, 0.790, 0.832, 0.838, 0.815, (6.1190)+(−0.1498)Met+(0.1521)Ile+(−0.0618)Leu+(−0.1243)Trp; 0.836, 0.857, 0.743, 0.725, 0.748, 0.752, 0.778, 0.750, (0.0321)+(0.0282)Ser+(0.0410)Ile+(0.0467)Phe+(−0.1924)Trp; 0.835, 0.860, 0.781, 0.770, 0.785, 0.764, 0.812, 0.783, (0.8860)+(0.0394)Ser+(−0.0080)Gly+(0.0665)Phe+(−0.1768)Trp; 0.835, 0.852, 0.835, 0.842, 0.825, 0.856, 0.823, 0.836, (6.2303)+(−0.0477)Asn+(0.0114)Gln+(−0.1009)His+(−0.0967)Trp; 0.835, 0.861, 0.768, 0.767, 0.771, 0.764, 0.766, 0.767, (0.3827)+(0.0289)Ser+(−0.0037)Orn+(0.0733)Phe+(−0.1799)Trp; 0.835, 0.853, 0.774, 0.758, 0.750, 0.828, 0.827, 0.791, (2.0142)+(0.0307)Ser+(−0.0093)Ala+(0.0731)Ile+(−0.1641)Trp; 0.835, 0.854, 0.783, 0.770, 0.788, 0.847, 0.763, 0.792, (5.6027)+(0.0377)Ser+(−0.0990)His+(0.0199)Tyr+(−0.1043)Trp; 0.835, 0.854, 0.793, 0.765, 0.798, 0.825, 0.832, 0.805, (7.7949)+(−0.0751)His+(−0.0448)Cit+(0.0687)Ile+(−0.1275)Trp; 0.834, 0.851, 0.785, 0.780, 0.786, 0.848, 0.753, 0.792, (5.9101)+(0.0370)Ser+(−0.0917)His+(0.0002)Ala+(−0.0962)Trp; 0.834, 0.852, 0.782, 0.774, 0.783, 0.844, 0.754, 0.789, (5.6352)+(0.0358)Ser+(−0.0975)His+(0.0063)Lys+(−0.1016)Trp; 0.834, 0.851, 0.810, 0.813, 0.803, 0.842, 0.791, 0.812, (6.0421)+(0.0082)Gln+(−0.1143)His+(0.0137)Thr+(−0.1073)Trp; 0.834, 0.855, 0.808, 0.812, 0.815, 0.847, 0.755, 0.807, (8.8275)+(−0.0828)His+(0.0309)Thr+(−0.1132)Met+(−0.1022)Trp; 0.834, 0.853, 0.816, 0.812, 0.814, 0.836, 0.818, 0.820, (5.4534)+(0.0102)Gln+(−0.1239)His+(0.0097)Val+(−0.1123)Trp; 0.834, 0.854, 0.814, 0.819, 0.823, 0.859, 0.750, 0.813, (6.0473)+(0.0405)Ser+(−0.0809)Asn+(−0.0633)Cit+(−0.1326)Trp; 0.834, 0.854, 0.788, 0.777, 0.800, 0.831, 0.761, 0.792, (7.8145)+(−0.1004)His+(0.0165)Thr+(0.0288)Orn+(−0.1072)Trp; 0.834, 0.850, 0.738, 0.709, 0.738, 0.810, 0.762, 0.755, (1.2617)+(0.0555)Ser+(−0.1047)Asn+(−0.1496)His+(0.1097)Phe; 0.833, 0.852, 0.810, 0.808, 0.810, 0.838, 0.797, 0.813, (5.7609)+(0.0085)Gln+(−0.1139)His+(0.0253)Orn+(−0.1025)Trp; 0.833, 0.852, 0.788, 0.762, 0.789, 0.818, 0.835, 0.801, (7.5060)+(−0.0927)His+(0.0004)Tyr+(0.0650)Ile+(−0.1200)Trp; 0.833, 0.859, 0.812, 0.797, 0.821, 0.819, 0.825, 0.815, (6.4158)+(−0.0901)His+(−0.0521)Cit+(0.1152)Phe+(−0.1253)Trp; 0.833, 0.852, 0.773, 0.763, 0.739, 0.812, 0.842, 0.789, (4.8036)+(−0.0417)Val+(0.0115)Orn+(0.1461)Ile+(−0.1393)Trp; 0.833, 0.851, 0.811, 0.812, 0.805, 0.835, 0.805, 0.814, (5.7123)+(0.0094)Gln+(−0.1120)His+(0.0071)Pro+(−0.1050)Trp; 0.833, 0.847, 0.789, 0.784, 0.793, 0.822, 0.768, 0.792, (8.0392)+(−0.0941)His+(0.0187)Thr+(0.0059)Pro+(−0.1095)Trp; 0.833, 0.851, 0.789, 0.764, 0.790, 0.820, 0.834, 0.802, (7.5890)+(−0.0916)His+(−0.0019)Arg+(0.0652)Ile+(−0.1195)Trp; 0.832, 0.849, 0.793, 0.785, 0.791, 0.845, 0.783, 0.801, (6.0170)+(0.0442)Ser+(−0.0053)Gly+(−0.0883)His+(−0.0968)Trp; 0.832, 0.853, 0.791, 0.785, 0.798, 0.856, 0.747, 0.797, (6.2172)+(0.0386)Ser+(−0.0802)His+(−0.0357)Cit+(−0.0996)Trp; 0.832, 0.848, 0.801, 0.788, 0.830, 0.803, 0.771, 0.798, (4.5988)+(−0.1254)Cit+(0.0457)Orn+(0.0749)Phe+(−0.1801)Trp; 0.832, 0.848, 0.776, 0.768, 0.739, 0.811, 0.847, 0.791, (4.7921)+(0.0007)Gln+(−0.0405)Val+(0.1467)Ile+(−0.1401)Trp; 0.832, 0.858, 0.813, 0.801, 0.807, 0.833, 0.839, 0.820, (0.8683)+(0.0127)Gln+(−0.1563)His+(−0.2363)Met+(0.1260)Phe; 0.832, 0.849, 0.777, 0.757, 0.790, 0.811, 0.778, 0.784, (7.7615)+(−0.1131)His+(0.0218)Thr+(0.0251)Leu+(−0.1231)Trp; 0.832, 0.850, 0.770, 0.761, 0.736, 0.811, 0.838, 0.786, (4.8075)+(0.0056)Thr+(−0.0413)Val+(0.1476)Ile+(−0.1427)Trp; 0.831, 0.847, 0.777, 0.768, 0.739, 0.812, 0.852, 0.793, (5.1738)+(−0.0006)Gly+(−0.0408)Val+(0.1480)Ile+(−0.1376)Trp; 0.831, 0.849, 0.804, 0.803, 0.809, 0.839, 0.769, 0.805, (8.9090)+(−0.0386)Asn+(−0.0857)His+(0.0248)Thr+(−0.1052)Trp; 0.831, 0.849, 0.804, 0.787, 0.813, 0.816, 0.820, 0.809, (4.2918)+(0.0047)Gln+(−0.0911)Cit+(0.0618)Ile+(−0.1841)Trp; 0.831, 0.850, 0.780, 0.774, 0.800, 0.824, 0.722, 0.780, (4.3970)+(0.0326)Ser+(−0.0821)Cit+(0.0095)Pro+(−0.1628)Trp; 0.831, 0.849, 0.789, 0.788, 0.769, 0.805, 0.820, 0.796, (3.9802)+(0.0021)Gln+(0.1386)Ile+(−0.0651)Leu+(−0.1514)Trp; 0.831, 0.847, 0.823, 0.829, 0.812, 0.847, 0.812, 0.825, (5.9272)+(0.0099)Gln+(−0.1077)His+(−0.0006)Ala+(−0.0993)Trp; 0.831, 0.848, 0.776, 0.769, 0.737, 0.816, 0.845, 0.792, (5.0725)+(−0.0343)Val+(0.1637)Ile+(−0.0217)Leu+(−0.1350)Trp; 0.831, 0.847, 0.813, 0.797, 0.805, 0.839, 0.853, 0.824, (6.6077)+(−0.0078)Ala+(−0.0782)Cit+(0.0801)Ile+(−0.1575)Trp; 0.830, 0.846, 0.699, 0.649, 0.698, 0.801, 0.761, 0.727, (0.2117)+(0.0436)Ser+(−0.1732)His+(0.0360)Ile+(0.0678)Phe; 0.830, 0.848, 0.777, 0.767, 0.740, 0.818, 0.850, 0.794, (5.3363)+(−0.0402)Val+(−0.0038)Lys+(0.1498)Ile+(−0.1338)Trp; 0.830, 0.848, 0.775, 0.769, 0.737, 0.810, 0.844, 0.790, (5.3708)+(−0.0126)Tyr+(−0.0400)Val+(0.1488)Ile+(−0.1327)Trp; 0.830, 0.851, 0.831, 0.838, 0.819, 0.856, 0.816, 0.833, (5.9044)+(0.0108)Gln+(−0.1018)His+(−0.0566)Met+(−0.0952)Trp; 0.830, 0.849, 0.787, 0.781, 0.770, 0.805, 0.820, 0.794, (4.7452)+(0.0028)Orn+(0.1385)Ile+(−0.0647)Leu+(−0.1466)Trp; 0.830, 0.855, 0.840, 0.851, 0.842, 0.798, 0.834, 0.831, (1.6077)+(0.0063)Gln+(−0.2432)Met+(0.1124)Phe+(−0.1488)Trp; 0.830, 0.848, 0.789, 0.796, 0.788, 0.826, 0.750, 0.790, (4.4666)+(0.0401)Ser+(−0.1088)Asn+(0.0079)Pro+(−0.1356)Trp; 0.830, 0.855, 0.841, 0.851, 0.841, 0.802, 0.844, 0.835, (3.1099)+(−0.0982)Asn+(0.0059)Gln+(0.0746)Phe+(−0.1606)Trp; 0.829, 0.845, 0.789, 0.765, 0.814, 0.815, 0.784, 0.794, (5.7602)+(−0.1121)Cit+(0.0395)Orn+(0.0510)Ile+(−0.1782)Trp; 0.829, 0.854, 0.799, 0.776, 0.800, 0.828, 0.837, 0.810, (7.7863)+(−0.0798)His+(−0.0851)Met+(0.0715)Ile+(−0.1120)Trp; 0.829, 0.848, 0.793, 0.773, 0.807, 0.786, 0.822, 0.797, (4.1507)+(−0.0952)Cit+(0.0503)Ile+(0.0657)Phe+(−0.1880)Trp; 0.829, 0.847, 0.821, 0.826, 0.811, 0.845, 0.809, 0.823, (5.8736)+(0.0001)Gly+(0.0098)Gln+(−0.1089)His+(−

0.1000)Trp; 0.829, 0.846, 0.791, 0.780, 0.803, 0.823, 0.773, 0.795, (8.0622)+(−0.1033)His+(0.0205)Thr+ (0.0074)Val+(−0.1153)Trp; 0.829, 0.850, 0.811, 0.816, 0.824, 0.858, 0.738, 0.809, (5.3014)+(0.0362)Ser+(− 0.0595)Cit+(−0.1015)Met+(−0.1322)Trp; 0.829, 0.850, 0.788, 0.784, 0.790, 0.851, 0.749, 0.793, (6.1599)+(0.0387)Ser+(−0.0885)His+(−0.0087)Arg+ (−0.0935)Trp; 0.829, 0.846, 0.731, 0.701, 0.720, 0.823, 0.770, 0.753, (0.9324)+(0.0445)Ser+(−0.1600)His+(− 0.0048)Ala+(0.0994)Phe; 0.829, 0.848, 0.783, 0.776, 0.747, 0.822, 0.845, 0.798, (6.0528)+(−0.0187)Arg+(− 0.0425)Val+(0.1569)Ile+(−0.1281)Trp; 0.829, 0.852, 0.802, 0.811, 0.802, 0.763, 0.807, 0.796, (3.3228)+ (0.0042)Pro+(−0.0082)Val+(0.0808)Phe+(−0.1647) Trp; 0.829, 0.846, 0.787, 0.766, 0.804, 0.809, 0.790, 0.792, (5.6036)+(0.0109)Thr+(−0.0876)Cit+(0.0608) Ile+(−0.1828)Trp; 0.829, 0.846, 0.715, 0.674, 0.703, 0.823, 0.768, 0.742, (2.2744)+(0.0369)Ser+(−0.1381) His+(0.1008)Ile+(−0.0337)Leu; 0.828, 0.848, 0.787, 0.783, 0.770, 0.805, 0.820, 0.794, (4.7835)+(0.0007) Thr+(0.1389)Ile+(−0.0644)Leu+(−0.1470)Trp; 0.828, 0.846, 0.776, 0.768, 0.739, 0.813, 0.849, 0.792, (5.1250)+(−0.0016)Pro+(−0.0407)Val+(0.1500)Ile+(− 0.1376)Trp; 0.828, 0.849, 0.788, 0.783, 0.772, 0.804, 0.824, 0.796, (4.9098)+(−0.0005)Gly+(0.1392)Ile+(− 0.0645)Leu+(−0.1461)Trp; 0.828, 0.847, 0.816, 0.819, 0.808, 0.838, 0.809, 0.818, (5.6906)+(0.0092)Gln+(− 0.1127)His+(0.0057)Lys+(−0.1046)Trp; 0.828, 0.848, 0.820, 0.821, 0.813, 0.845, 0.815, 0.824, (5.7459)+ (0.0097)Gln+(−0.1148)His+(0.0152)Tyr+(−0.1061) Trp; 0.828, 0.848, 0.828, 0.828, 0.841, 0.808, 0.817, 0.823, (5.6837)+(−0.0504)Asn+(−0.0816)Cit+(0.0953) Phe+(−0.1596)Trp; 0.828, 0.846, 0.726, 0.683, 0.724, 0.827, 0.772, 0.752, (2.8591)+(0.0473)Ser+(−0.0729) Asn+(−0.1376)His+(0.0587)Ile; 0.828, 0.843, 0.724, 0.689, 0.726, 0.812, 0.747, 0.744, (1.1550)+(0.0475) Ser+(−0.1605)His+(−0.0124)Lys+(0.1035)Phe; 0.828, 0.847, 0.812, 0.828, 0.808, 0.849, 0.754, 0.810, (5.1227)+(0.0391)Ser+(−0.0638)Asn+(−0.0785)Met+ (−0.1277)Trp; 0.828, 0.849, 0.791, 0.777, 0.804, 0.820, 0.783, 0.796, (7.8247)+(−0.0917)His+(0.0061)Pro+ (0.0327)Orn+(−0.1030)Trp; 0.827, 0.849, 0.799, 0.811, 0.807, 0.845, 0.716, 0.795, (4.6547)+(0.0294)Ser+ (0.0152)Thr+(−0.1745)Met+(−0.1408)Trp; 0.827, 0.845, 0.809, 0.822, 0.802, 0.847, 0.761, 0.808, (5.0939)+(0.0377)Ser+(−0.0893)Asn+(−0.0015)Ala+ (−0.1295)Trp; 0.827, 0.852, 0.801, 0.802, 0.794, 0.769, 0.836, 0.800, (3.4551)+(−0.0264)Val+(0.0414)Leu+ (0.0783)Phe+(−0.1718)Trp; 0.827, 0.847, 0.818, 0.834, 0.811, 0.847, 0.772, 0.816, (4.0201)+(0.0346)Ser+(− 0.1139)Asn+(0.0041)Gln+(−0.1359)Trp; 0.827, 0.850, 0.786, 0.776, 0.793, 0.806, 0.784, 0.790, (5.1661)+ (0.0248)Thr+(−0.2423)Met+(0.0661)Ile+(−0.1533) Trp; 0.827, 0.848, 0.799, 0.808, 0.799, 0.837, 0.747, 0.798, (4.5281)+(0.0374)Ser+(−0.1072)Asn+(0.0208) Orn+(−0.1346)Trp; 0.827, 0.844, 0.714, 0.665, 0.717, 0.824, 0.759, 0.741, (2.5591)+(0.0437)Ser+(−0.1436) His+(−0.0125)Lys+(0.0645)Ile; 0.827, 0.845, 0.793, 0.787, 0.800, 0.826, 0.768, 0.795, (8.0144)+(−0.0971) His+(0.0190)Thr+(0.0053)Lys+(−0.1096)Trp; 0.827, 0.847, 0.787, 0.782, 0.771, 0.805, 0.820, 0.795, (4.9183)+(−0.0014)Lys+(0.1392)Ile+(−0.0637)Leu+(− 0.1450)Trp; 0.827, 0.846, 0.785, 0.785, 0.764, 0.804, 0.813, 0.791, (5.3062)+(−0.0195)Tyr+(0.1428)Ile+(− 0.0641)Leu+(−0.1374)Trp; 0.827, 0.846, 0.799, 0.800, 0.800, 0.841, 0.769, 0.802, (8.4236)+(−0.0912)His+ (0.0218)Thr+(−0.0013)Ala+(−0.1053)Trp; 0.827, 0.851, 0.833, 0.832, 0.850, 0.810, 0.815, 0.827, (4.9049)+(−0.0733)Cit+(−0.1545)Met+(0.1213)Phe+ (−0.1501)Trp; 0.827, 0.847, 0.829, 0.834, 0.822, 0.856, 0.811, 0.831, (6.0384)+(0.0103)Gln+(−0.0971)His+(− 0.0361)Cit+(−0.1033)Trp; 0.827, 0.844, 0.721, 0.703, 0.711, 0.796, 0.737, 0.737, (0.9223)+(0.0443)Ser+(− 0.1561)His+(−0.0445)Tyr+(0.1167)Phe; 0.827, 0.852, 0.834, 0.843, 0.836, 0.792, 0.833, 0.826, (4.9195)+(− 0.0704)Asn+(−0.0076)Val+(0.0926)Phe+(−0.1432) Trp; 0.827, 0.849, 0.799, 0.809, 0.805, 0.762, 0.789, 0.791, (3.1688)+(0.0077)Thr+(−0.0081)Val+(0.0811) Phe+(−0.1696)Trp; 0.827, 0.850, 0.808, 0.799, 0.815, 0.787, 0.835, 0.809, (3.5338)+(−0.2354)Met+(0.0529) Ile+(0.0869)Phe+(−0.1526)Trp; 0.827, 0.845, 0.826, 0.834, 0.817, 0.849, 0.806, 0.827, (6.0110)+(0.0113) Gln+(−0.1081)His+(−0.0133)Arg+(−0.0973)Trp; 0.826, 0.848, 0.800, 0.798, 0.811, 0.841, 0.754, 0.801, (8.6973)+(−0.0816)His+(0.0235)Thr+(−0.0402)Cit+(− 0.1118)Trp; 0.826, 0.846, 0.789, 0.786, 0.771, 0.812, 0.821, 0.797, (4.9708)+(−0.0039)Pro+(0.1460)Ile+(− 0.0657)Leu+(−0.1450)Trp; 0.826, 0.849, 0.806, 0.816, 0.809, 0.770, 0.797, 0.798, (3.3064)+(−0.0084)Val+ (0.0116)Orn+(0.0776)Phe+(−0.1620)Trp; 0.826, 0.842, 0.716, 0.678, 0.690, 0.828, 0.790, 0.747, (2.4994)+ (0.0345)Ser+(−0.1225)His+(−0.0289)Val+(0.1190)Ile; 0.826, 0.845, 0.795, 0.793, 0.800, 0.835, 0.762, 0.797, (8.2697)+(0.0003)Gly+(−0.0934)His+(0.0209)Thr+(− 0.1063)Trp; 0.826, 0.851, 0.813, 0.827, 0.811, 0.771, 0.810, 0.805, (2.5428)+(0.0024)Gln+(−0.0073)Val+ (0.0802)Phe+(−0.1689)Trp; 0.826, 0.844, 0.724, 0.693, 0.719, 0.804, 0.760, 0.744, (−0.0269)+(0.0379)Ser+ (0.0042)Gln+(−0.1801)His+(0.0873)Phe; 0.826, 0.846, 0.796, 0.786, 0.742, 0.867, 0.884, 0.820, (4.8910)+(− 0.0055)Ala+(−0.0528)Val+(−0.2382)Met+(0.1962)Ile; 0.826, 0.847, 0.785, 0.764, 0.754, 0.849, 0.858, 0.806, (6.4465)+(−0.0623)His+(−0.0425)Val+(−0.2014)Met+ (0.1680)Ile; 0.826, 0.847, 0.751, 0.730, 0.749, 0.797, 0.774, 0.762, (1.9569)+(0.0345)Ser+(−0.0151)Lys+ (0.0633)Ile+(−0.1628)Trp; 0.826, 0.845, 0.759, 0.734, 0.761, 0.778, 0.808, 0.770, (1.8343)+(0.0391)Ser+(− 0.0078)Gly+(0.0503)Ile+(−0.1780)Trp; 0.826, 0.852, 0.813, 0.816, 0.826, 0.783, 0.799, 0.806, (4.7103)+(− 0.1025)Asn+(0.0179)Thr+(0.0754)Phe+(−0.1634)Trp; 0.826, 0.841, 0.721, 0.678, 0.716, 0.823, 0.771, 0.747, (1.3899)+(0.0338)Ser+(0.0043)Gln+(−0.1663)His+ (0.0516)Ile; 0.826, 0.846, 0.782, 0.771, 0.805, 0.819, 0.738, 0.783, (3.9934)+(0.0327)Ser+(−0.0816)Cit+ (0.0184)Leu+(−0.1713)Trp; 0.826, 0.847, 0.788, 0.762, 0.804, 0.818, 0.798, 0.796, (7.8351)+(−0.1031)His+ (0.0312)Orn+(0.0199)Leu+(−0.1126)Trp; 0.825, 0.845, 0.796, 0.786, 0.825, 0.790, 0.765, 0.792, (4.2249)+(0.0140)Thr+(−0.0971)Cit+(0.0876)Phe+(− 0.1863)Trp; 0.825, 0.839, 0.716, 0.677, 0.717, 0.799, 0.760, 0.738, (0.8595)+(0.0474)Ser+(−0.0029)Gly+(− 0.1674)His+(0.0891)Phe; 0.825, 0.849, 0.796, 0.807, 0.800, 0.838, 0.731, 0.794, (3.8520)+(0.0340)Ser+(− 0.1511)Met+(0.0222)Orn+(−0.1358)Trp; 0.825, 0.839, 0.768, 0.750, 0.719, 0.839, 0.869, 0.794, (5.6712)+(− 0.0866)His+(−0.0066)Ala+(−0.0356)Val+(0.1435)Ile; 0.825, 0.850, 0.816, 0.819, 0.826, 0.777, 0.811, 0.808, (3.7488)+(0.0077)Pro+(−0.2244)Met+(0.1082)Phe+(− 0.1441)Trp; 0.825, 0.847, 0.786, 0.786, 0.793, 0.820, 0.749, 0.787, (2.9723)+(0.0407)Ser+(−0.1830)Met+ (0.0237)Leu+(−0.1459)Trp; 0.825, 0.844, 0.779, 0.764, 0.740, 0.851, 0.850, 0.801, (4.2474)+(−0.0569)Val+(− 0.2918)Met+(0.0254)Orn+(0.1891)Ile; 0.825, 0.848, 0.801, 0.792, 0.781, 0.809, 0.863, 0.811, (3.4695)+(−

0.0094)Ala+(0.0570)Ile+(0.0568)Phe+(−0.1709)Trp; 0.825, 0.848, 0.832, 0.843, 0.838, 0.792, 0.821, 0.823, (4.0106)+(−0.0055)Val+(−0.1937)Met+(0.1205)Phe+ (−0.1359)Trp; 0.825, 0.846, 0.796, 0.792, 0.803, 0.833, 0.768, 0.799, (8.2465)+(−0.0944)His+(0.0205)Thr+ (0.0050)Tyr+(−0.1083)Trp; 0.825, 0.845, 0.799, 0.809, 0.799, 0.840, 0.742, 0.798, (5.0944)+(0.0351)Ser+(− 0.1065)Asn+(0.0084)Thr+(−0.1374)Trp; 0.825, 0.839, 0.715, 0.663, 0.715, 0.816, 0.778, 0.743, (2.2774)+ (0.0451)Ser+(−0.0039)Gly+(−0.1532)His+(0.0536)Ile; 0.824, 0.842, 0.804, 0.817, 0.803, 0.846, 0.741, 0.802, (4.3447)+(0.0349)Ser+(−0.0002)Ala+(−0.1279)Met+ (−0.1326)Trp; 0.824, 0.845, 0.814, 0.821, 0.810, 0.839, 0.787, 0.814, (4.6255)+(0.0454)Ser+(−0.0076)Gly+(− 0.1269)Met+(−0.1326)Trp; 0.824, 0.842, 0.813, 0.805, 0.840, 0.835, 0.762, 0.811, (7.9934)+(−0.0506)Asn+(− 0.1077)Cit+(0.0583)Orn+(−0.1443)Trp; 0.824, 0.844, 0.829, 0.837, 0.838, 0.791, 0.820, 0.821, (4.2708)+(− 0.0186)Asn+(−0.1817)Met+(0.1099)Phe+(−0.1408) Trp; 0.824, 0.843, 0.802, 0.815, 0.804, 0.837, 0.740, 0.799, (4.1442)+(0.0340)Ser+(−0.1451)Met+(0.0047) Lys+(−0.1372)Trp; 0.824, 0.843, 0.802, 0.814, 0.799, 0.834, 0.755, 0.800, (4.8290)+(0.0376)Ser+(−0.1001) Asn+(0.0030)Lys+(−0.1352)Trp; 0.824, 0.843, 0.793, 0.783, 0.804, 0.828, 0.769, 0.796, (7.7986)+(0.0020) Gly+(−0.0922)His+(0.0361)Orn+(−0.0980)Trp; 0.824, 0.845, 0.795, 0.781, 0.807, 0.823, 0.784, 0.799, (7.9900)+(−0.0956)His+(0.0047)Val+(0.0337)Orn+(− 0.1050)Trp; 0.824, 0.842, 0.744, 0.714, 0.709, 0.805, 0.848, 0.769, (3.8311)+(−0.1147)His+(−0.0364)Val+ (0.1156)Ile+(0.0627)Phe; 0.824, 0.846, 0.794, 0.773, 0.782, 0.847, 0.838, 0.810, (3.0854)+(0.0111)Gln+(− 0.1404)His+(−0.1937)Met+(0.0647)Ile; 0.824, 0.847, 0.812, 0.828, 0.809, 0.847, 0.752, 0.809, (3.5073)+ (0.0315)Ser+(0.0032)Gln+(−0.1476)Met+(−0.1366) Trp; 0.823, 0.840, 0.749, 0.733, 0.692, 0.855, 0.830, 0.778, (2.6416)+(0.0435)Ser+(−0.1848)Asn+(− 0.0564)Val+(0.1742)Ile; 0.823, 0.842, 0.751, 0.733, 0.748, 0.785, 0.783, 0.762, (1.3069)+(0.0339)Ser+(− 0.0098)Thr+(0.0550)Ile+(−0.1714)Trp; 0.823, 0.844, 0.796, 0.798, 0.805, 0.835, 0.748, 0.796, (8.7711)+(− 0.0909)His+(0.0252)Thr+(−0.0126)Arg+(−0.1062) Trp; 0.823, 0.847, 0.811, 0.820, 0.813, 0.770, 0.810, 0.803, (3.4357)+(−0.0000)Gly+(−0.0070)Val+(0.0829) Phe+(−0.1635)Trp; 0.823, 0.848, 0.758, 0.725, 0.766, 0.826, 0.780, 0.774, (5.8041)+(−0.1283)His+(0.0327) Thr+(−0.2487)Met+(0.0694)Ile; 0.823, 0.848, 0.809, 0.817, 0.793, 0.788, 0.838, 0.809, (3.6329)+(−0.0084) Ala+(0.0088)Pro+(0.0794)Phe+(−0.1620)Trp; 0.823, 0.849, 0.799, 0.800, 0.815, 0.768, 0.785, 0.792, (3.4271)+(0.0104)Thr+(−0.0090)Lys+(0.0753)Phe+(− 0.1737)Trp; 0.823, 0.843, 0.793, 0.795, 0.811, 0.835, 0.719, 0.790, (4.8416)+(0.0291)Ser+(0.0048)Thr+(− 0.0742)Cit+(−0.1554)Trp; 0.823, 0.845, 0.836, 0.843, 0.830, 0.813, 0.846, 0.833, (4.8475)+(−0.0576)Asn+(− 0.0048)Ala+(0.0879)Phe+(−0.1481)Trp; 0.823, 0.843, 0.814, 0.817, 0.809, 0.836, 0.799, 0.815, (5.2563)+ (0.0481)Ser+(−0.0913)Asn+(−0.0073)Gly+(−0.1336) Trp; 0.823, 0.842, 0.803, 0.809, 0.811, 0.850, 0.741, 0.803, (5.0720)+(0.0313)Ser+(−0.0023)Ala+(−0.0684) Cit+(−0.1435)Trp; 0.823, 0.847, 0.810, 0.816, 0.805, 0.795, 0.815, 0.808, (3.3924)+(0.0108)Thr+(−0.0071) Ala+(0.0812)Phe+(−0.1693)Trp; 0.823, 0.843, 0.816, 0.824, 0.840, 0.842, 0.725, 0.808, (7.7700)+(0.0280) Thr+(−0.0628)Cit+(−0.1480)Met+(−0.1411)Trp; 0.823, 0.840, 0.781, 0.764, 0.794, 0.808, 0.779, 0.786, (5.3945)+(0.0040)Gly+(−0.0885)Cit+(0.0647)Ile+(−

0.1744)Trp; 0.823, 0.846, 0.811, 0.815, 0.817, 0.854, 0.756, 0.810, (3.7672)+(0.0377)Ser+(0.0329)Tyr+(− 0.1848)Met+(−0.1427)Trp; 0.822, 0.841, 0.781, 0.786, 0.762, 0.834, 0.769, 0.788, (3.4525)+(0.0283)Ser+(− 0.0071)Ala+(0.0112)Pro+(−0.1448)Trp; 0.822, 0.836, 0.713, 0.680, 0.711, 0.799, 0.742, 0.733, (0.7961)+ (0.0431)Ser+(−0.1648)His+(−0.0035)Val+(0.0969) Phe; 0.822, 0.841, 0.746, 0.719, 0.725, 0.795, 0.827, 0.767, (3.5737)+(−0.1257)His+(0.1043)Ile+(−0.0558) Leu+(0.0707)Phe; 0.822, 0.844, 0.802, 0.793, 0.807, 0.832, 0.790, 0.806, (8.1624)+(−0.0874)His+(−0.0014) Ala+(0.0381)Orn+(−0.0971)Trp; 0.822, 0.839, 0.797, 0.787, 0.826, 0.822, 0.742, 0.794, (6.6466)+(−0.1136) Cit+(0.0053)Pro+(0.0516)Orn+(−0.1628)Trp; 0.822, 0.840, 0.793, 0.775, 0.804, 0.806, 0.808, 0.798, (5.9868)+(−0.0815)Cit+(0.0013)Pro+(0.0607)Ile+(− 0.1730)Trp; 0.822, 0.847, 0.819, 0.827, 0.827, 0.778, 0.812, 0.811, (4.4054)+(−0.0721)Asn+(0.0019)Gly+ (0.0801)Phe+(−0.1554)Trp; 0.822, 0.842, 0.804, 0.789, 0.812, 0.817, 0.818, 0.809, (6.8072)+(−0.0327)Asn+(− 0.0753)Cit+(0.0612)Ile+(−0.1629)Trp; 0.822, 0.847, 0.822, 0.831, 0.832, 0.787, 0.801, 0.813, (3.4599)+ (0.0022)Gly+(−0.2067)Met+(0.1140)Phe+(−0.1427) Trp; 0.822, 0.838, 0.811, 0.804, 0.832, 0.841, 0.760, 0.809, (7.3871)+(−0.0047)Ala+(−0.1128)Cit+(0.0607) Orn+(−0.1448)Trp; 0.822, 0.843, 0.794, 0.781, 0.804, 0.824, 0.782, 0.798, (7.7222)+(−0.0961)His+(0.0329) Orn+(0.0072)Lys+(−0.1051)Trp; 0.822, 0.845, 0.802, 0.793, 0.810, 0.830, 0.786, 0.805, (8.2801)+(−0.0150) Asn+(−0.0858)His+(0.0377)Orn+(−0.0977)Trp; 0.822, 0.840, 0.746, 0.728, 0.746, 0.776, 0.771, 0.755, (1.5426)+(0.0288)Ser+(−0.0073)Orn+(0.0543)Ile+(− 0.1783)Trp; 0.822, 0.845, 0.753, 0.740, 0.757, 0.799, 0.746, 0.761, (2.0871)+(0.0350)Ser+(−0.0260)Arg+ (0.0585)Ile+(−0.1705)Trp; 0.822, 0.841, 0.789, 0.785, 0.812, 0.826, 0.726, 0.787, (4.3822)+(0.0320)Ser+(− 0.0794)Cit+(0.0060)Val+(−0.1629)Trp; 0.822, 0.840, 0.795, 0.783, 0.783, 0.822, 0.835, 0.805, (2.3417)+(− 0.0780)Asn+(0.0116)Gln+(−0.1598)His+(0.0775)Phe; 0.821, 0.844, 0.804, 0.813, 0.802, 0.840, 0.759, 0.803, (4.7828)+(0.0384)Ser+(−0.0983)Asn+(0.0068)Tyr+(− 0.1350)Trp; 0.821, 0.848, 0.813, 0.822, 0.816, 0.774, 0.811, 0.806, (3.5653)+(−0.0064)Val+(−0.0026)Lys+ (0.0847)Phe+(−0.1614)Trp; 0.821, 0.838, 0.798, 0.791, 0.830, 0.828, 0.732, 0.795, (6.6189)+(0.0070)Thr+(− 0.1126)Cit+(0.0506)Orn+(−0.1639)Trp; 0.821, 0.845, 0.792, 0.791, 0.777, 0.812, 0.812, 0.798, (5.8598)+(− 0.0193)Arg+(0.1507)Ile+(−0.0691)Leu+(−0.1367)Trp; 0.821, 0.843, 0.801, 0.812, 0.799, 0.836, 0.753, 0.800, (4.7908)+(0.0383)Ser+(−0.0950)Asn+(0.0013)Val+(− 0.1345)Trp; 0.821, 0.843, 0.817, 0.815, 0.834, 0.801, 0.802, 0.813, (4.9214)+(−0.0877)Cit+(−0.0042)Lys+ (0.0951)Phe+(−0.1677)Trp; 0.821, 0.841, 0.707, 0.666, 0.711, 0.799, 0.740, 0.729, (0.6425)+(0.0422)Ser+(− 0.1707)His+(0.0097)Orn+(0.0874)Phe; 0.821, 0.839, 0.782, 0.758, 0.755, 0.850, 0.854, 0.804, (3.4009)+ (0.0083)Gln+(−0.1498)His+(−0.0065)Ala+(0.0558) Ile; 0.821, 0.837, 0.707, 0.668, 0.709, 0.794, 0.742, 0.728, (0.6625)+(0.0434)Ser+(−0.1693)His+(0.0012) Pro+(0.0895)Phe; 0.821, 0.840, 0.792, 0.785, 0.745, 0.860, 0.861, 0.812, (3.2291)+(0.0039)Gln+(−0.0540) Val+(−0.3077)Met+(0.1887)Ile; 0.821, 0.838, 0.707, 0.668, 0.709, 0.796, 0.745, 0.729, (0.6638)+(0.0436) Ser+(−0.1704)His+(0.0029)Leu+(0.0876)Phe; 0.821, 0.847, 0.824, 0.834, 0.813, 0.798, 0.841, 0.822, (2.5743)+(0.0032)Gln+(−0.0066)Ala+(0.0806)Phe+(− 0.1673)Trp; 0.821, 0.850, 0.815, 0.823, 0.820, 0.773, 0.816, 0.808, (2.5403)+(0.0031)Gln+(−0.0073)Lys+
(0.0744)Phe+(−0.1724)Trp; 0.821, 0.844, 0.800, 0.793,
0.801, 0.773, 0.838, 0.801, (4.3282)+(−0.0658)Asn+
(0.0395)Ile+(0.0549)Phe+(−0.1688)Trp; 0.821, 0.843,
0.786, 0.776, 0.742, 0.849, 0.859, 0.807, (4.3158)+(−
0.0570)Val+(−0.3044)Met+(0.0078)Lys+(0.1925)Ile;
0.821, 0.840, 0.803, 0.801, 0.798, 0.826, 0.803, 0.807,
(8.6130)+(−0.0758)His+(−0.0035)Ala+(0.0116)Pro+
(−0.0986)Trp; 0.821, 0.845, 0.817, 0.818, 0.830, 0.796,
0.804, 0.812, (3.0066)+(0.0045)Gln+(−0.0964)Cit+
(0.0862)Phe+(−0.1806)Trp; 0.821, 0.839, 0.798, 0.780,
0.808, 0.814, 0.816, 0.804, (6.4963)+(−0.0800)Cit+(−
0.0063)Lys+(0.0668)Ile+(−0.1650)Trp; 0.821, 0.844,
0.799, 0.784, 0.824, 0.837, 0.760, 0.801, (8.4227)+(−
0.0693)His+(−0.0798)Cit+(0.0587)Orn+(−0.1115)Trp;
0.821, 0.841, 0.804, 0.817, 0.804, 0.843, 0.744, 0.802,
(5.0975)+(0.0394)Ser+(−0.0859)Asn+(−0.0090)Arg+
(−0.1298)Trp; 0.821, 0.846, 0.826, 0.832, 0.833, 0.781,
0.825, 0.818, (4.7404)+(−0.0676)Asn+(−0.0021)Leu+
(0.0802)Phe+(−0.1539)Trp; 0.821, 0.837, 0.708, 0.659,
0.708, 0.815, 0.759, 0.735, (2.1978)+(0.0395)Ser+(−
0.1543)His+(−0.0018)Pro+(0.0571)Ile; 0.821, 0.849,
0.818, 0.821, 0.827, 0.773, 0.824, 0.811, (4.6563)+(−
0.0699)Asn+(0.0034)Pro+(0.0750)Phe+(−0.1574)Trp;
0.821, 0.843, 0.826, 0.828, 0.829, 0.817, 0.824, 0.825,
(4.9871)+(−0.0055)Ala+(−0.0855)Cit+(0.1039)Phe+
(−0.1612)Trp; 0.821, 0.839, 0.808, 0.803, 0.833, 0.830,
0.751, 0.804, (5.5816)+(0.0035)Gln+(−0.1140)Cit+
(0.0498)Orn+(−0.1651)Trp; 0.821, 0.842, 0.803, 0.816,
0.806, 0.844, 0.732, 0.800, (4.5256)+(0.0364)Ser+(−
0.0086)Arg+(−0.1186)Met+(−0.1304)Trp; 0.821,
0.837, 0.711, 0.673, 0.712, 0.798, 0.745, 0.732,
(0.6824)+(0.0442)Ser+(−0.1678)His+(−0.0016)Thr+
(0.0916)Phe; 0.821, 0.840, 0.791, 0.789, 0.793, 0.818,
0.770, 0.793, (8.0410)+(0.0028)Gly+(−0.0842)His+
(0.0085)Pro+(−0.0999)Trp; 0.821, 0.838, 0.803, 0.795,
0.835, 0.830, 0.740, 0.800, (7.2015)+(−0.1128)Cit+
(0.0582)Orn+(−0.0045)Lys+(−0.1516)Trp; 0.821,
0.843, 0.797, 0.786, 0.806, 0.827, 0.785, 0.801,
(7.9860)+(−0.0911)His+(0.0054)Tyr+(0.0356)Orn+(−
0.1010)Trp; 0.820, 0.841, 0.739, 0.717, 0.743, 0.777,
0.762, 0.750, (1.8760)+(0.0309)Ser+(−0.0018)Gln+
(0.0529)Ile+(−0.1751)Trp; 0.820, 0.844, 0.822, 0.828,
0.832, 0.788, 0.807, 0.814, (3.7571)+(−0.2062)Met+
(0.0121)Orn+(0.1044)Phe+(−0.1418)Trp; 0.820,
0.843, 0.787, 0.789, 0.788, 0.818, 0.759, 0.789,
(4.0203)+(0.0409)Ser+(−0.1056)Asn+(0.0150)Leu+(−
0.1436)Trp; 0.820, 0.846, 0.819, 0.824, 0.827, 0.780,
0.815, 0.812, (4.6656)+(−0.0728)Asn+(0.0119)Orn+
(0.0709)Phe+(−0.1547)Trp; 0.820, 0.845, 0.833, 0.841,
0.836, 0.801, 0.829, 0.827, (4.0312)+(−0.0024)Ala+(−
0.1819)Met+(0.1131)Phe+(−0.1403)Trp; 0.820, 0.841,
0.803, 0.795, 0.822, 0.782, 0.797, 0.799, (4.5507)+(−
0.0914)Cit+(0.0052)Pro+(0.0855)Phe+(−0.1756)Trp;
0.820, 0.840, 0.792, 0.784, 0.798, 0.809, 0.793, 0.796,
(7.8709)+(−0.0898)His+(0.0076)Pro+(0.0095)Lys+(−
0.1092)Trp; 0.820, 0.841, 0.796, 0.799, 0.811, 0.839,
0.726, 0.794, (4.9275)+(0.0317)Ser+(−0.0703)Cit+(−
0.0017)Lys+(−0.1483)Trp; 0.820, 0.838, 0.720, 0.688,
0.730, 0.802, 0.727, 0.737, (0.9230)+(0.0488)Ser+(−
0.1613)His+(−0.0224)Arg+(0.1010)Phe; 0.820, 0.837,
0.708, 0.659, 0.708, 0.814, 0.760, 0.735, (2.1004)+
(0.0413)Ser+(−0.1519)His+(−0.0037)Thr+(0.0557)Ile;
0.820, 0.842, 0.802, 0.806, 0.815, 0.840, 0.735, 0.799,
(4.1992)+(0.0279)Ser+(0.0024)Gln+(−0.0755)Cit+(−
0.1555)Trp; 0.820, 0.838, 0.790, 0.771, 0.799, 0.810,
0.810, 0.797, (8.1128)+(−0.0944)His+(0.0055)Pro+

(0.0210)Leu+(−0.1135)Trp; 0.820, 0.844, 0.826, 0.835,
0.818, 0.800, 0.835, 0.822, (3.7508)+(−0.0053)Ala+(−
0.0041)Val+(0.0896)Phe+(−0.1563)Trp; 0.820, 0.835,
0.796, 0.791, 0.826, 0.826, 0.727, 0.792, (6.5880)+
(0.0017)Gly+(−0.1135)Cit+(0.0543)Orn+(−0.1581)
Trp; 0.820, 0.842, 0.746, 0.738, 0.740, 0.778, 0.758,
0.754, (2.0254)+(0.0284)Ser+(−0.0242)Tyr+(0.0558)
Ile+(−0.1671)Trp; 0.820, 0.839, 0.793, 0.775, 0.804,
0.806, 0.808, 0.798, (5.9893)+(−0.0812)Cit+(0.0007)
Arg+(0.0620)Ile+(−0.1726)Trp; 0.819, 0.840, 0.814,
0.814, 0.829, 0.791, 0.800, 0.809, (4.6843)+(−0.0860)
Cit+(−0.0021)Val+(0.0935)Phe+(−0.1689)Trp; 0.819,
0.840, 0.747, 0.731, 0.747, 0.782, 0.766, 0.757,
(1.5135)+(0.0281)Ser+(−0.0027)Pro+(0.0546)Ile+(−
0.1775)Trp; 0.819, 0.842, 0.795, 0.805, 0.800, 0.833,
0.734, 0.793, (3.8344)+(0.0366)Ser+(0.0051)Val+(−
0.1446)Met+(−0.1402)Trp; 0.819, 0.842, 0.808, 0.792,
0.818, 0.821, 0.821, 0.813, (6.6752)+(−0.0659)Cit+(−
0.1095)Met+(0.0690)Ile+(−0.1520)Trp; 0.819, 0.836,
0.784, 0.760, 0.770, 0.836, 0.837, 0.801, (3.4714)+(−
0.0644)Asn+(0.0107)Gln+(−0.1505)His+(0.0434)Ile;
0.819, 0.841, 0.780, 0.768, 0.737, 0.849, 0.850, 0.801,
(4.3739)+(0.0021)Gly+(−0.0544)Val+(−0.2823)Met+
(0.1909)Ile; 0.819, 0.837, 0.781, 0.763, 0.744, 0.845,
0.856, 0.802, (5.8218)+(−0.0986)His+(−0.0072)Ala+
(0.1275)Ile+(−0.0490)Leu; 0.819, 0.845, 0.797, 0.801,
0.807, 0.753, 0.795, 0.789, (2.4413)+(0.0018)Gln+
(0.0038)Thr+(0.0659)Phe+(−0.1813)Trp; 0.819, 0.840,
0.795, 0.807, 0.806, 0.810, 0.726, 0.787, (6.4477)+
(0.0236)Thr+(0.0085)Pro+(−0.1986)Met+(−0.1414)
Trp; 0.819, 0.835, 0.801, 0.794, 0.831, 0.824, 0.740,
0.797, (6.8299)+(−0.1115)Cit+(0.0001)Val+(0.0545)
Orn+(−0.1579)Trp; 0.819, 0.837, 0.712, 0.669, 0.719,
0.819, 0.738, 0.736, (2.4734)+(0.0444)Ser+(−0.1468)
His+(−0.0188)Arg+(0.0578)Ile; 0.819, 0.845, 0.790,
0.777, 0.751, 0.855, 0.861, 0.811, (5.1987)+(−0.0400)
Cit+(−0.0526)Val+(−0.2529)Met+(0.1872)Ile; 0.819,
0.835, 0.783, 0.768, 0.792, 0.817, 0.781, 0.789,
(7.7903)+(0.0040)Gly+(−0.1008)His+(0.0259)Leu+(−
0.1106)Trp; 0.819, 0.837, 0.797, 0.787, 0.804, 0.812,
0.795, 0.800, (8.2935)+(−0.0874)His+(0.0069)Pro+
(0.0056)Val+(−0.1076)Trp; 0.819, 0.846, 0.806, 0.814,
0.811, 0.759, 0.806, 0.798, (2.4211)+(0.0023)Gln+(−
0.0027)Leu+(0.0696)Phe+(−0.1766)Trp; 0.819, 0.844,
0.807, 0.814, 0.813, 0.757, 0.814, 0.799, (2.5496)+(−
0.0011)Gly+(0.0024)Gln+(0.0660)Phe+(−0.1783)Trp;
0.819, 0.838, 0.710, 0.674, 0.703, 0.807, 0.752, 0.734,
(2.6390)+(0.0390)Ser+(−0.1448)His+(−0.0245)Tyr+
(0.0606)Ile; 0.819, 0.837, 0.808, 0.801, 0.837, 0.834,
0.749, 0.805, (7.3107)+(−0.1036)Cit+(−0.0665)Met+
(0.0563)Orn+(−0.1431)Trp; 0.819, 0.842, 0.778, 0.768,
0.783, 0.745, 0.815, 0.778, (2.3450)+(0.0015)Gln+
(0.0396)Ile+(0.0442)Phe+(−0.1894)Trp; 0.819, 0.840,
0.802, 0.800, 0.813, 0.831, 0.765, 0.802, (4.9203)+
(0.0384)Ser+(−0.0055)Gly+(−0.0648)Cit+(−0.1503)
Trp; 0.819, 0.841, 0.789, 0.778, 0.743, 0.854, 0.866,
0.810, (5.4149)+(−0.0352)Asn+(−0.0549)Val+(−
0.2354)Met+(0.1889)Ile; 0.818, 0.841, 0.787, 0.771,
0.747, 0.851, 0.864, 0.808, (4.4779)+(0.0172)Tyr+(−
0.0562)Val+(−0.3039)Met+(0.1932)Ile; 0.818, 0.837,
0.784, 0.773, 0.740, 0.852, 0.853, 0.805, (4.7133)+(−
0.0495)Val+(−0.2688)Met+(0.2025)Ile+(−0.0173)Leu;
0.818, 0.846, 0.800, 0.808, 0.804, 0.752, 0.805, 0.792,
(2.4110)+(0.0021)Gln+(0.0014)Pro+(0.0657)Phe+(−
0.1794)Trp; 0.818, 0.843, 0.816, 0.821, 0.811, 0.795,
0.828, 0.814, (3.6151)+(−0.0064)Ala+(0.0105)Orn+
(0.0767)Phe+(−0.1602)Trp; 0.818, 0.844, 0.821, 0.828, 0.814, 0.797, 0.832, 0.818, (3.6279)+(0.0004)Gly+(−0.0060)Ala+(0.0838)Phe+(−0.1610)Trp; 0.818, 0.844, 0.786, 0.771, 0.790, 0.766, 0.831, 0.789, (3.4864)+(−0.0111)Lys+(0.0475)Ile+(0.0550) Phe+(−0.1761)Trp; 0.818, 0.842, 0.777, 0.794, 0.779, 0.742, 0.755, 0.767, (3.1694)+(0.0120)Thr+(−0.0445)Tyr+(0.0907)Phe+(−0.1687)Trp; 0.818, 0.842, 0.795, 0.796, 0.812, 0.836, 0.727, 0.793, (4.7061)+(0.0312)Ser+(−0.0726)Cit+(0.0049)Tyr+(−0.1536)Trp; 0.818, 0.840, 0.796, 0.799, 0.812, 0.839, 0.725, 0.794, (4.9229)+(0.0319)Ser+(−0.0672)Cit+(−0.0046)Arg+(−0.1489)Trp; 0.818, 0.835, 0.755, 0.726, 0.742, 0.808, 0.824, 0.775, (1.8011)+(0.0083)Gln+(−0.1742)His+(0.0298)Ile+(0.0498)Phe; 0.818, 0.836, 0.796, 0.784, 0.827, 0.815, 0.749, 0.794, (6.5469)+(−0.1141)Cit+(0.0515)Orn+(0.0098)Leu+(−0.1682)Trp; 0.818, 0.843, 0.792, 0.797, 0.819, 0.760, 0.749, 0.781, (3.7422)+(0.0153)Thr+(−0.0270)Arg+(0.0783)Phe+(−0.1803)Trp; 0.818, 0.845, 0.802, 0.794, 0.811, 0.833, 0.782, 0.805, (8.1896)+(−0.0845)His+(−0.0339)Met+(0.0384)Orn+(−0.0957)Trp; 0.818, 0.838, 0.704, 0.653, 0.707, 0.816, 0.754, 0.732, (2.1105)+(0.0385)Ser+(−0.1565)His+(0.0077)Orn+(0.0522)Ile; 0.818, 0.838, 0.801, 0.797, 0.803, 0.816, 0.795, 0.803, (8.5784)+(−0.0102)Asn+(−0.0777)His+(0.0086)Pro+(−0.1004)Trp; 0.817, 0.839, 0.798, 0.799, 0.819, 0.787, 0.762, 0.792, (4.0024)+(0.0037)Gly+(−0.0942)Cit+(0.0934)Phe+(−0.1738)Trp; 0.817, 0.843, 0.798, 0.818, 0.791, 0.752, 0.792, 0.788, (2.4214)+(0.0031)Gln+(−0.0376)Tyr+(0.0880)Phe+(−0.1667)Trp; 0.817, 0.837, 0.792, 0.776, 0.800, 0.809, 0.805, 0.798, (6.1603)+(−0.0786)Cit+(−0.0073)Tyr+(0.0630)Ile+(−0.1686)Trp; 0.817, 0.842, 0.798, 0.802, 0.808, 0.750, 0.803, 0.791, (3.2524)+(−0.0003)Gly+(0.0022)Pro+(0.0673)Phe+(−0.1748)Trp; 0.817, 0.844, 0.826, 0.833, 0.837, 0.780, 0.815, 0.816, (4.8783)+(−0.0571)Asn+(−0.0093)Arg+(0.0818)Phe+(−0.1554)Trp; 0.817, 0.842, 0.790, 0.792, 0.805, 0.747, 0.786, 0.783, (3.0209)+(0.0052)Thr+(0.0012)Pro+(0.0661)Phe+(−0.1793)Trp; 0.817, 0.839, 0.812, 0.810, 0.829, 0.787, 0.797, 0.806, (4.6997)+(−0.0867)Cit+(−0.0013)Arg+(0.0906)Phe+(−0.1716) Trp; 0.817, 0.837, 0.818, 0.824, 0.839, 0.837, 0.745, 0.811, (8.3908)+(−0.0711)Asn+(0.0226)Thr+(−0.0679)Cit+(−0.1462)Trp; 0.817, 0.842, 0.795, 0.795, 0.810, 0.750, 0.794, 0.787, (3.2765)+(−0.0014)Gly+(0.0069)Thr+(0.0658)Phe+(−0.1792)Trp; 0.817, 0.841, 0.782, 0.771, 0.739, 0.847, 0.856, 0.803, (4.6877)+(0.0034)Pro+(−0.0546)Val+(−0.2834)Met+(0.1866) Ile; 0.817, 0.844, 0.799, 0.804, 0.807, 0.752, 0.800, 0.791, (3.2164)+(0.0025)Pro+(−0.0031)Leu+(0.0702) Phe+(−0.1726)Trp; 0.817, 0.839, 0.816, 0.834, 0.821, 0.833, 0.743, 0.808, (5.1219)+(0.0047)Gln+(0.0218) Thr+(−0.1900)Met+(−0.1459)Trp; 0.817, 0.844, 0.794, 0.798, 0.807, 0.753, 0.785, 0.786, (3.0698)+(0.0060) Thr+(−0.0028)Leu+(0.0697)Phe+(−0.1769)Trp; 0.817, 0.838, 0.809, 0.805, 0.803, 0.815, 0.828, 0.813, (3.7503)+(0.0055)Gln+(−0.2027)Met+(0.0651)Ile+(−0.1494)Trp; 0.817, 0.843, 0.825, 0.831, 0.834, 0.784, 0.817, 0.816, (3.8804)+(−0.2014)Met+(0.0028)Leu+(0.1088)Phe+(−0.1444)Trp; 0.817, 0.839, 0.774, 0.762, 0.781, 0.743, 0.814, 0.775, (2.9276)+(−0.0001)Gly+(0.0405)Ile+(0.0455)Phe+(−0.1859)Trp; 0.817, 0.839, 0.809, 0.804, 0.827, 0.786, 0.799, 0.804, (4.6225)+(−0.0886)Cit+(0.0037)Leu+(0.0868)Phe+(−0.1750)Trp; 0.817, 0.837, 0.787, 0.776, 0.763, 0.831, 0.837, 0.802, (2.2663)+(0.0089)Gln+(−0.1642)His+(−0.0045)Ala+(0.0782)Phe; 0.817, 0.846, 0.803, 0.806, 0.814, 0.763, 0.804, 0.797, (3.5025)+(0.0027)Pro+(−0.0056)Lys+(0.0734)Phe+(−0.1691)Trp; 0.817, 0.842, 0.796, 0.799, 0.806, 0.750, 0.798, 0.788, (3.1515)+(0.0018)Pro+(0.0040)Orn+(0.0651)Phe+(−0.1748)Trp; 0.817, 0.844, 0.822, 0.828, 0.830, 0.773, 0.825, 0.814, (4.6894)+(−0.0697)Asn+(0.0012)Lys+(0.0772)Phe+(−0.1565)Trp; 0.817, 0.843, 0.821, 0.830, 0.831, 0.776, 0.811, 0.812, (3.6313)+(−0.2158)Met+(0.0056)Lys+(0.1086)Phe+(−0.1471)Trp; 0.817, 0.843, 0.827, 0.835, 0.836, 0.787, 0.813, 0.818, (4.0199)+(−0.0030)Arg+(−0.1938)Met+(0.1115)Phe+(−0.1425)Trp; 0.817, 0.833, 0.709, 0.660, 0.715, 0.816, 0.746, 0.734, (2.3089)+(0.0414)Ser+(−0.1445)His+(−0.0406)Cit+(0.0570)Ile; 0.817, 0.835, 0.811, 0.825, 0.825, 0.825, 0.735, 0.802, (7.4658)+(−0.0458)Asn+(0.0267)Thr+(−0.1335)Met+(−0.1382)Trp; 0.816, 0.842, 0.804, 0.824, 0.798, 0.761, 0.794, 0.794, (3.6487)+(−0.0319)Tyr+(−0.0061)Val+(0.1000)Phe+(−0.1528)Trp; 0.816, 0.842, 0.784, 0.800, 0.779, 0.738, 0.781, 0.775, (3.4300)+(0.0048)Pro+(−0.0388)Tyr+(0.0875)Phe+(−0.1622)Trp; 0.816, 0.833, 0.767, 0.750, 0.756, 0.839, 0.787, 0.783, (2.9524)+(0.0361)Ser+(−0.0059)Gly+(0.0065)Gln+(−0.1506) His; 0.816, 0.845, 0.802, 0.809, 0.809, 0.757, 0.805, 0.795, (2.4243)+(0.0021)Gln+(0.0019)Orn+(0.0658) Phe+(−0.1785)Trp; 0.816, 0.842, 0.792, 0.794, 0.805, 0.751, 0.788, 0.784, (3.0333)+(0.0054)Thr+(0.0017) Orn+(0.0660)Phe+(−0.1787)Trp; 0.816, 0.837, 0.774, 0.772, 0.752, 0.803, 0.804, 0.783, (2.1541)+(0.0090) Gln+(−0.1616)His+(−0.0425)Tyr+(0.0965)Phe; 0.816, 0.836, 0.795, 0.785, 0.774, 0.817, 0.852, 0.807, (5.0005)+(−0.0095)Ala+(0.0053)Pro+(0.0631)Ile+(−0.1567)Trp; 0.816, 0.845, 0.805, 0.809, 0.815, 0.767, 0.799, 0.797, (3.5182)+(0.0091)Orn+(−0.0064)Lys+(0.0708) Phe+(−0.1665)Trp; 0.816, 0.834, 0.776, 0.759, 0.764, 0.814, 0.819, 0.789, (2.2648)+(0.0094) Gln+(−0.1690)His+(−0.0069)Lys+(0.0763)Phe; 0.816, 0.836, 0.801, 0.794, 0.832, 0.826, 0.738, 0.798, (6.9766)+(−0.1092)Cit+(−0.0036)Arg+(0.0554)Orn+(−0.1563)Trp; 0.816, 0.840, 0.799, 0.803, 0.810, 0.753, 0.799, 0.791, (3.2922)+(−0.0005)Gly+(0.0056)Orn+(0.0655)Phe+(−0.1733)Trp; 0.816, 0.841, 0.797, 0.788, 0.809, 0.828, 0.775, 0.800, (8.2720)+(−0.0875)His+(−0.0064)Arg+(0.0391)Orn+(−0.0980)Trp; 0.816, 0.844, 0.818, 0.829, 0.827, 0.774, 0.799, 0.807, (2.5685)+(0.0042)Gln+(−0.0228)Arg+(0.0772)Phe+(−0.1758) Trp; 0.816, 0.840, 0.772, 0.759, 0.781, 0.742, 0.809, 0.773, (2.8028)+(0.0026)Thr+(0.0397)Ile+(0.0449) Phe+(−0.1881)Trp; 0.816, 0.840, 0.771, 0.773, 0.763, 0.744, 0.805, 0.771, (3.2319)+(−0.0388)Tyr+(0.0434) Ile+(0.0670)Phe+(−0.1733)Trp; 0.816, 0.838, 0.776, 0.763, 0.783, 0.745, 0.821, 0.778, (2.9617)+(−0.0060) Orn+(0.0424)Ile+(0.0488)Phe+(−0.1866)Trp; 0.816, 0.832, 0.760, 0.737, 0.737, 0.824, 0.820, 0.780, (3.1450)+(0.0073)Gln+(−0.1412)His+(0.0960)Ile+(−0.0379)Leu; 0.816, 0.835, 0.799, 0.793, 0.804, 0.816, 0.794, 0.802, (8.3239)+(−0.0827)His+(0.0077)Pro+(0.0077)Tyr+(−0.1038)Trp; 0.816, 0.837, 0.814, 0.812, 0.806, 0.809, 0.840, 0.817, (4.2955)+(−0.0872)Asn+(0.0055)Gln+(0.0477)Ile+(−0.1600)Trp; 0.816, 0.835, 0.785, 0.781, 0.772, 0.858, 0.769, 0.795, (3.3460)+(0.0340)Ser+(−0.0879)Asn+(0.0084)Gln+(−0.1328) His; 0.816, 0.842, 0.800, 0.805, 0.809, 0.757, 0.795, 0.792, (3.2198)+(0.0062)Orn+(−0.0030)Leu+(0.0684) Phe+(−0.1712)Trp; 0.816, 0.842, 0.803, 0.808, 0.814, 0.755, 0.803, 0.795, (3.3373)+(−0.0002)Gly+(−0.0019)Leu+(0.0715)Phe+(−0.1717)Trp; 0.815, 0.845, 0.808, 0.813, 0.818, 0.766, 0.806, 0.801, (3.5543)+(0.0000)Gly+(−0.0050)Lys+(0.0755)Phe+(−0.1678)

Trp; 0.815, 0.842, 0.818, 0.822, 0.811, 0.798, 0.836, 0.817, (3.6653)+(−0.0064)Ala+(0.0046)Leu+(0.0799)Phe+(−0.1637)Trp; 0.815, 0.839, 0.808, 0.815, 0.819, 0.787, 0.786, 0.802, (4.7872)+(−0.0837)Cit+(−0.0245)Tyr+(0.1037)Phe+(−0.1626)Trp; 0.815, 0.836, 0.778, 0.772, 0.779, 0.791, 0.784, 0.782, (3.2510)+(0.0387)Ser+(−0.0084)Gly+(0.0052)Pro+(−0.1578)Trp; 0.815, 0.842, 0.824, 0.831, 0.817, 0.801, 0.836, 0.822, (3.8272)+(−0.0058)Ala+(−0.0023)Lys+(0.0855)Phe+(−0.1585)Trp; 0.815, 0.829, 0.732, 0.700, 0.731, 0.822, 0.751, 0.751, (2.0457)+(0.0320)Ser+(0.0054)Gln+(−0.1677)His+(0.0183)Leu; 0.815, 0.836, 0.802, 0.796, 0.775, 0.824, 0.856, 0.813, (3.8876)+(0.0031)Gln+(−0.0089)Ala+(0.0663)Ile+(−0.1635)Trp; 0.815, 0.844, 0.828, 0.834, 0.839, 0.790, 0.819, 0.820, (3.8949)+(0.0043)Tyr+(−0.2057)Met+(0.1101)Phe+(−0.1435)Trp; 0.815, 0.836, 0.790, 0.779, 0.770, 0.819, 0.839, 0.802, (4.7362)+(0.0087)Thr+(−0.0090)Ala+(0.0661)Ile+(−0.1638)Trp; 0.815, 0.837, 0.766, 0.760, 0.761, 0.805, 0.765, 0.773, (3.0161)+(0.0274)Ser+(−0.0229)Val+(0.0464)Leu+(−0.1591)Trp; 0.815, 0.834, 0.769, 0.740, 0.743, 0.835, 0.853, 0.793, (4.6064)+(−0.1341)His+(−0.0072)Ala+(0.0453)Ile+(0.0556)Phe; 0.815, 0.835, 0.771, 0.756, 0.780, 0.811, 0.762, 0.777, (3.6828)+(0.0072)Gly+(−0.1310)His+(−0.1994)Met+(0.1297)Phe; 0.815, 0.831, 0.764, 0.745, 0.723, 0.832, 0.849, 0.787, (6.4118)+(−0.0589)Asn+(−0.0765)His+(−0.0398)Val+(0.1396)Ile; 0.814, 0.838, 0.747, 0.729, 0.753, 0.843, 0.714, 0.760, (3.9919)+(0.0440)Ser+(−0.1143)His+(0.0126)Pro+(−0.1592)Met; 0.814, 0.837, 0.777, 0.744, 0.784, 0.810, 0.829, 0.792, (4.2846)+(−0.1217)His+(−0.2243)Met+(0.0477)Ile+(0.0942)Phe; 0.814, 0.834, 0.799, 0.794, 0.827, 0.826, 0.735, 0.796, (6.9713)+(−0.1105)Cit+(−0.0070)Tyr+(0.0559)Orn+(−0.1538)Trp; 0.814, 0.845, 0.808, 0.812, 0.818, 0.766, 0.806, 0.800, (3.5631)+(−0.0052)Lys+(0.0008)Leu+(0.0749)Phe+(−0.1683)Trp; 0.814, 0.838, 0.783, 0.773, 0.739, 0.849, 0.857, 0.804, (4.7993)+(−0.0029)Arg+(−0.0544)Val+(−0.2685)Met+(0.1899)Ile; 0.814, 0.840, 0.815, 0.830, 0.813, 0.771, 0.810, 0.806, (4.7289)+(−0.0585)Asn+(−0.0268)Tyr+(0.0925)Phe+(−0.1473)Trp; 0.814, 0.844, 0.819, 0.830, 0.826, 0.780, 0.802, 0.810, (4.0493)+(−0.0160)Arg+(−0.0065)Val+(0.0907)Phe+(−0.1591)Trp; 0.814, 0.838, 0.830, 0.862, 0.851, 0.855, 0.816, 0.846, (6.0237)+(−0.0754)Asn+(0.0086)Gln+(−0.0705)Cit+(−0.1410)Trp; 0.814, 0.830, 0.770, 0.756, 0.755, 0.809, 0.812, 0.783, (2.1781)+(0.0086)Gln+(−0.1681)His+(−0.0044)Val+(0.0785)Phe; 0.814, 0.832, 0.793, 0.787, 0.802, 0.822, 0.768, 0.795, (8.1194)+(0.0035)Gly+(−0.0936)His+(0.0088)Val+(−0.1049)Trp; 0.814, 0.839, 0.812, 0.827, 0.800, 0.782, 0.818, 0.807, (3.7956)+(−0.0049)Ala+(−0.0235)Tyr+(0.0945)Phe+(−0.1539)Trp; 0.814, 0.838, 0.786, 0.786, 0.773, 0.862, 0.756, 0.794, (3.0692)+(0.0317)Ser+(0.0076)Gln+(−0.1310)His+(−0.1234)Met; 0.814, 0.832, 0.791, 0.773, 0.800, 0.805, 0.807, 0.797, (8.0392)+(−0.0985)His+(0.0062)Lys+(0.0213)Leu+(−0.1151)Trp; 0.814, 0.836, 0.798, 0.795, 0.801, 0.814, 0.787, 0.800, (8.4970)+(−0.0796)His+(−0.0022)Arg+(0.0086)Pro+(−0.1009)Trp; 0.814, 0.832, 0.754, 0.733, 0.715, 0.825, 0.838, 0.778, (3.6783)+(0.0055)Gln+(−0.1227)His+(−0.0298)Val+(0.1135)Ile; 0.814, 0.839, 0.804, 0.800, 0.808, 0.819, 0.793, 0.805, (8.5953)+(−0.0732)His+(0.0099)Pro+(−0.0468)Met+(−0.0979)Trp; 0.813, 0.830, 0.774, 0.761, 0.708, 0.860, 0.885, 0.803, (3.6750)+(−0.0113)Ala+(−0.0708)Cit+(−0.0492)Val+(0.1781)Ile; 0.813, 0.833, 0.795, 0.795, 0.798, 0.818, 0.772, 0.796, (7.8532)+(0.0026)Gly+(−0.0911)His+(0.0109)Lys+(−0.1036)Trp; 0.813, 0.831, 0.767, 0.739, 0.756, 0.827, 0.822, 0.786, (3.3314)+(0.0090)Gln+(−0.1557)His+(−0.0081)Lys+(0.0483)Ile; 0.813, 0.835, 0.808, 0.799, 0.795, 0.824, 0.847, 0.816, (5.9042)+(−0.0054)Ala+(−0.1299)Met+(0.0744)Ile+(−0.1398)Trp; 0.813, 0.840, 0.755, 0.737, 0.764, 0.848, 0.715, 0.766, (4.2088)+(0.0378)Ser+(−0.1210)His+(−0.1223)Met+(0.0316)Orn; 0.813, 0.837, 0.790, 0.780, 0.791, 0.796, 0.805, 0.793, (5.7044)+(−0.0810)Asn+(0.0138)Thr+(0.0470)Ile+(−0.1606)Trp; 0.813, 0.832, 0.711, 0.674, 0.718, 0.798, 0.732, 0.730, (0.8705)+(0.0447)Ser+(−0.1603)His+(−0.0351)Cit+(0.0938)Phe; 0.813, 0.836, 0.777, 0.765, 0.784, 0.748, 0.816, 0.778, (2.9742)+(−0.0025)Pro+(0.0432)Ile+(0.0463)Phe+(−0.1850)Trp; 0.813, 0.834, 0.804, 0.798, 0.812, 0.829, 0.788, 0.807, (8.7544)+(−0.0673)His+(−0.0366)Cit+(0.0095)Pro+(−0.1075)Trp; 0.813, 0.832, 0.799, 0.782, 0.803, 0.822, 0.818, 0.807, (8.4947)+(−0.0914)His+(−0.0020)Ala+(0.0259)Leu+(−0.1094)Trp; 0.813, 0.838, 0.795, 0.812, 0.793, 0.748, 0.787, 0.785, (3.5466)+(−0.0339)Tyr+(−0.0009)Leu+(0.0906)Phe+(−0.1600)Trp; 0.813, 0.830, 0.767, 0.748, 0.755, 0.808, 0.813, 0.781, (2.0217)+(0.0088)Gln+(−0.1733)His+(−0.0004)Pro+(0.0707)Phe; 0.813, 0.828, 0.744, 0.723, 0.740, 0.831, 0.743, 0.759, (2.4500)+(0.0299)Ser+(0.0059)Gln+(−0.1606)His+(0.0051)Val; 0.812, 0.833, 0.808, 0.799, 0.789, 0.826, 0.856, 0.818, (5.9288)+(−0.0368)Asn+(−0.0072)Ala+(0.0657)Ile+(−0.1481)Trp; 0.812, 0.830, 0.767, 0.748, 0.755, 0.808, 0.813, 0.781, (2.0207)+(0.0088)Gln+(−0.1732)His+(−0.0003)Leu+(0.0705)Phe; 0.812, 0.831, 0.794, 0.775, 0.803, 0.815, 0.810, 0.801, (8.3222)+(0.0017)Asn+(−0.0946)His+(0.0241)Leu+(−0.1115)Trp; 0.812, 0.833, 0.737, 0.706, 0.710, 0.813, 0.823, 0.763, (4.9279)+(−0.1071)His+(−0.0356)Val+(0.0258)Orn+(0.1225)Ile; 0.812, 0.827, 0.735, 0.708, 0.701, 0.812, 0.821, 0.760, (5.0451)+(−0.1089)His+(0.0091)Thr+(−0.0341)Val+(0.1239)Ile; 0.812, 0.832, 0.802, 0.819, 0.815, 0.812, 0.723, 0.792, (6.4831)+(0.0235)Thr+(−0.1775)Met+(0.0040)Lys+(−0.1444)Trp; 0.812, 0.833, 0.781, 0.768, 0.773, 0.819, 0.804, 0.791, (1.9858)+(0.0116)Gln+(−0.1727)His+(−0.0231)Arg+(0.0777)Phe; 0.812, 0.832, 0.757, 0.736, 0.746, 0.800, 0.802, 0.771, (2.0544)+(0.0079)Gln+(−0.1767)His+(0.0067)Thr+(0.0696)Phe; 0.812, 0.838, 0.795, 0.812, 0.793, 0.746, 0.790, 0.785, (3.6285)+(−0.0004)Gly+(−0.0341)Tyr+(0.0896)Phe+(−0.1603)Trp; 0.812, 0.833, 0.795, 0.773, 0.806, 0.817, 0.815, 0.803, (8.2111)+(−0.0968)His+(0.0103)Tyr+(0.0231)Leu+(−0.1151)Trp; 0.812, 0.831, 0.798, 0.788, 0.807, 0.809, 0.796, 0.800, (8.1159)+(−0.0945)His+(0.0062)Val+(0.0090)Lys+(−0.1112)Trp; 0.812, 0.828, 0.758, 0.728, 0.735, 0.835, 0.830, 0.782, (5.5845)+(−0.1345)His+(0.0136)Thr+(−0.0070)Ala+(0.0568)Ile; 0.812, 0.826, 0.738, 0.719, 0.723, 0.844, 0.746, 0.758, (3.9273)+(0.0374)Ser+(−0.1280)His+(−0.0056)Ala+(0.0115)Pro; 0.812, 0.831, 0.743, 0.722, 0.742, 0.833, 0.736, 0.758, (2.8050)+(0.0276)Ser+(0.0050)Gln+(−0.1543)His+(0.0188)Orn; 0.812, 0.827, 0.761, 0.732, 0.749, 0.819, 0.819, 0.780, (3.0899)+(0.0084)Gln+(−0.1622)His+(−0.0030)Pro+(0.0468)Ile; 0.812, 0.833, 0.764, 0.772, 0.763, 0.795, 0.718, 0.762, (3.2489)+(0.0273)Ser+(0.0063)Pro+(−0.0169)Tyr+(−0.1497)Trp; 0.812, 0.829, 0.785, 0.781, 0.714, 0.862, 0.891, 0.812, (5.4739)+(−0.1006)Asn+(−0.0074)Ala+(−0.0541)Val+(0.1787)Ile; 0.812, 0.833, 0.767, 0.771, 0.768, 0.796, 0.735, 0.768, (2.7816)+(0.0302)Ser+(−

0.0057)Thr+(0.0057)Pro+(−0.1527)Trp; 0.812, 0.832, 0.796, 0.787, 0.775, 0.818, 0.850, 0.808, (4.9433)+(0.0006)Gly+(−0.0083)Ala+(0.0675)Ile+(−0.1568) Trp; 0.811, 0.829, 0.758, 0.740, 0.746, 0.805, 0.797, 0.772, (1.8310)+(0.0020)Gly+(0.0083)Gln+(−0.1741) His+(0.0728)Phe; 0.811, 0.842, 0.803, 0.808, 0.817, 0.758, 0.790, 0.793, (3.8711)+(−0.0184)Arg+(0.0037) Pro+(0.0761)Phe+(−0.1703)Trp; 0.811, 0.833, 0.807, 0.825, 0.815, 0.826, 0.728, 0.799, (6.8213)+(0.0251) Thr+(−0.0015)Ala+(−0.1577)Met+(−0.1396)Trp; 0.811, 0.839, 0.825, 0.834, 0.822, 0.799, 0.824, 0.820, (4.1970)+(−0.0054)Ala+(−0.0140)Arg+(0.0902)Phe+ (−0.1577)Trp; 0.811, 0.831, 0.808, 0.823, 0.821, 0.812, 0.736, 0.798, (7.0422)+(−0.0024)Gly+(0.0268)Thr+(−0.1690)Met+(−0.1424)Trp; 0.811, 0.828, 0.731, 0.695, 0.726, 0.835, 0.762, 0.755, (3.3756)+(0.0398)Ser+(−0.1462)His+(−0.0044)Ala+(0.0244)Leu; 0.811, 0.834, 0.807, 0.818, 0.825, 0.822, 0.731, 0.799, (6.5035)+(0.0244)Thr+(0.0176)Tyr+(−0.1936)Met+(−0.1464) Trp; 0.811, 0.829, 0.765, 0.758, 0.748, 0.848, 0.759, 0.778, (3.1230)+(0.0283)Ser+(0.0061)Gln+(−0.1446) His+(−0.0022)Ala; 0.811, 0.837, 0.789, 0.805, 0.788, 0.744, 0.777, 0.779, (3.4379)+(−0.0363)Tyr+(0.0096) Orn+(0.0843)Phe+(−0.1600)Trp; 0.811, 0.834, 0.770, 0.778, 0.777, 0.808, 0.705, 0.767, (3.5483)+(0.0320) Ser+(−0.0216)Arg+(0.0070)Pro+(−0.1506)Trp; 0.811, 0.836, 0.740, 0.708, 0.752, 0.829, 0.735, 0.756, (3.3118)+(0.0473)Ser+(−0.1330)His+(−0.1623)Met+(0.0304)Leu; 0.811, 0.832, 0.803, 0.804, 0.794, 0.827, 0.801, 0.806, (4.0489)+(0.0380)Ser+(−0.0076)Gly+(−0.0031)Ala+(−0.1436)Trp; 0.811, 0.832, 0.790, 0.772, 0.791, 0.815, 0.818, 0.799, (8.3663)+(−0.0902)His+(−0.0165)Val+(0.0504)Leu+(−0.1084)Trp; 0.811, 0.834, 0.818, 0.819, 0.823, 0.834, 0.795, 0.818, (7.7200)+(−0.0062)Ala+(−0.0702)Cit+(0.0142)Pro+(−0.1382)Trp; 0.811, 0.832, 0.761, 0.738, 0.752, 0.809, 0.805, 0.776, (2.0033)+(0.0083)Gln+(−0.1735)His+(0.0107)Orn+ (0.0661)Phe; 0.811, 0.833, 0.795, 0.785, 0.777, 0.815, 0.847, 0.806, (4.9222)+(−0.0084)Ala+(0.0064)Orn+ (0.0649)Ile+(−0.1571)Trp; 0.811, 0.833, 0.767, 0.770, 0.772, 0.800, 0.723, 0.766, (3.1908)+(0.0297)Ser+ (0.0056)Pro+(−0.0064)Lys+(−0.1489)Trp; 0.811, 0.838, 0.798, 0.814, 0.796, 0.752, 0.790, 0.788, (3.6783)+(−0.0324)Tyr+(−0.0026)Lys+(0.0918)Phe+ (−0.1582)Trp; 0.811, 0.830, 0.804, 0.803, 0.804, 0.819, 0.795, 0.805, (8.2595)+(−0.0867)His+(−0.0008)Ala+ (0.0113)Lys+(−0.1036)Trp; 0.810, 0.837, 0.803, 0.809, 0.819, 0.765, 0.778, 0.793, (3.8918)+(−0.0199)Arg+ (0.0130)Orn+(0.0718)Phe+(−0.1678)Trp; 0.810, 0.828, 0.770, 0.748, 0.761, 0.828, 0.807, 0.786, (3.1225)+(0.0109)Gln+(−0.1602)His+(−0.0209)Arg+ (0.0449)Ile; 0.810, 0.825, 0.752, 0.720, 0.743, 0.816, 0.808, 0.772, (3.0409)+(0.0078)Gln+(−0.1646)His+ (0.0044)Thr+(0.0422)Ile; 0.810, 0.831, 0.816, 0.824, 0.833, 0.826, 0.755, 0.810, (5.5175)+(0.0042)Gln+ (0.0100)Thr+(−0.0780)Cit+(−0.1625)Trp; 0.810, 0.835, 0.842, 0.856, 0.845, 0.850, 0.793, 0.836, (5.4438)+(0.0073)Gln+(−0.0645)Cit+(−0.0924)Met+ (−0.1392)Trp; 0.810, 0.834, 0.786, 0.783, 0.789, 0.796, 0.780, 0.787, (3.3162)+(0.0370)Ser+(−0.0084)Gly+ (0.0122)Orn+(−0.1560)Trp; 0.810, 0.834, 0.779, 0.758, 0.763, 0.833, 0.830, 0.796, (6.1820)+(−0.0886)His+(−0.1511)Met+(0.1324)Ile+(−0.0501)Leu; 0.810, 0.836, 0.783, 0.776, 0.793, 0.753, 0.805, 0.782, (3.6270)+(−0.0194)Arg+(0.0424)Ile+(0.0553)Phe+(−0.1799)Trp; 0.810, 0.834, 0.776, 0.770, 0.752, 0.800, 0.826, 0.787, (0.2209)+(−0.3247)Met+(0.1744)Ile+(−0.0961)Leu+ (0.1055)Phe; 0.810, 0.831, 0.743, 0.720, 0.742, 0.843, 0.734, 0.760, (4.0623)+(0.0328)Ser+(−0.1341)His+(−0.0031)Ala+(0.0278)Orn; 0.810, 0.829, 0.771, 0.766, 0.767, 0.851, 0.735, 0.780, (3.0439)+(0.0309)Ser+ (0.0082)Gln+(−0.1468)His+(−0.0224)Arg; 0.810, 0.834, 0.797, 0.811, 0.810, 0.816, 0.720, 0.789, (6.2620)+(0.0216)Thr+(−0.1736)Met+(0.0173)Orn+(−0.1415)Trp; 0.810, 0.826, 0.740, 0.720, 0.736, 0.828, 0.738, 0.756, (2.6042)+(0.0298)Ser+(0.0055)Gln+(−0.1538)His+(0.0053)Pro; 0.810, 0.825, 0.738, 0.713, 0.703, 0.815, 0.821, 0.763, (5.0639)+(0.0019)Gly+(−0.1025)His+(−0.0340)Val+(0.1261)Ile; 0.810, 0.831, 0.772, 0.762, 0.715, 0.823, 0.881, 0.795, (3.8224)+(−0.1505)Asn+(−0.0607)Val+(0.1632)Ile+(0.0631)Phe; 0.810, 0.829, 0.759, 0.749, 0.748, 0.843, 0.746, 0.771, (3.0972)+(0.0291)Ser+(0.0062)Gln+(−0.1468)His+(−0.0038)Lys; 0.810, 0.830, 0.739, 0.705, 0.744, 0.830, 0.751, 0.758, (3.9002)+(0.0395)Ser+(−0.0047)Gly+(−0.1396)His+(0.0244)Orn; 0.810, 0.829, 0.807, 0.806, 0.809, 0.815, 0.799, 0.808, (8.5292)+(−0.0228)Asn+(−0.0833)His+(0.0125)Lys+(−0.1041)Trp; 0.810, 0.826, 0.753, 0.742, 0.742, 0.836, 0.744, 0.766, (2.9040)+ (0.0286)Ser+(0.0060)Gln+(−0.1501)His+(−0.0005) Thr; 0.810, 0.832, 0.763, 0.767, 0.771, 0.786, 0.722, 0.761, (2.7135)+(0.0261)Ser+(0.0038)Pro+(0.0076) Orn+(−0.1585)Trp; 0.810, 0.830, 0.804, 0.808, 0.804, 0.833, 0.770, 0.804, (8.5238)+(0.0028)Gly+(−0.0797) His+(−0.0001)Ala+(−0.0940)Trp; 0.810, 0.833, 0.794, 0.776, 0.802, 0.812, 0.812, 0.801, (8.2462)+(−0.0954) His+(0.0024)Arg+(0.0242)Leu+(−0.1119)Trp; 0.810, 0.827, 0.806, 0.800, 0.810, 0.825, 0.801, 0.809, (8.7168)+(−0.0860)His+(−0.0014)Ala+(0.0087)Val+ (−0.1042)Trp; 0.810, 0.837, 0.806, 0.813, 0.822, 0.762, 0.785, 0.796, (3.7751)+(0.0009)Gly+(−0.0174)Arg+ (0.0801)Phe+(−0.1687)Trp; 0.810, 0.830, 0.791, 0.799, 0.782, 0.834, 0.755, 0.793, (3.4755)+(0.0260)Ser+(−0.0048)Ala+(0.0174)Orn+(−0.1451)Trp; 0.810, 0.830, 0.768, 0.773, 0.773, 0.795, 0.725, 0.766, (3.0252)+ (0.0269)Ser+(0.0053)Pro+(−0.0021)Val+(−0.1536) Trp; 0.809, 0.825, 0.752, 0.722, 0.742, 0.816, 0.807, 0.772, (2.9319)+(0.0012)Gly+(0.0080)Gln+(−0.1625) His+(0.0435)Ile; 0.809, 0.825, 0.744, 0.720, 0.708, 0.814, 0.832, 0.769, (5.3081)+(−0.0979)His+(−0.0325) Val+(0.1336)Ile+(−0.0085)Leu; 0.809, 0.830, 0.792, 0.801, 0.785, 0.835, 0.753, 0.794, (3.7787)+(0.0271) Ser+(0.0014)Thr+(−0.0038)Ala+(−0.1437)Trp; 0.809, 0.831, 0.732, 0.704, 0.743, 0.830, 0.711, 0.747, (4.0471)+(0.0341)Ser+(−0.1364)His+(0.0276)Orn+(−0.0051)Lys; 0.809, 0.830, 0.797, 0.795, 0.820, 0.812, 0.742, 0.792, (6.7657)+(0.0118)Thr+(−0.0771)Cit+ (0.0068)Pro+(−0.1612)Trp; 0.809, 0.829, 0.806, 0.812, 0.806, 0.834, 0.771, 0.806, (8.6863)+(−0.0109)Asn+ (0.0030)Gly+(−0.0772)His+(−0.0931)Trp; 0.809, 0.830, 0.796, 0.788, 0.775, 0.815, 0.849, 0.807, (5.1510)+(−0.0079)Ala+(−0.0053)Tyr+(0.0676)Ile+(−0.1546)Trp; 0.809, 0.839, 0.810, 0.817, 0.825, 0.763, 0.794, 0.799, (3.9502)+(−0.0169)Arg+(−0.0013)Leu+ (0.0804)Phe+(−0.1672)Trp; 0.809, 0.833, 0.801, 0.817, 0.816, 0.813, 0.717, 0.791, (6.6421)+(0.0247)Thr+ (0.0008)Val+(−0.1696)Met+(−0.1424)Trp; 0.809, 0.831, 0.804, 0.792, 0.814, 0.819, 0.801, 0.807, (8.4259)+(−0.0904)His+(0.0126)Tyr+(0.0071)Val+(−0.1097)Trp; 0.809, 0.832, 0.775, 0.782, 0.781, 0.810, 0.721, 0.774, (3.2415)+(0.0283)Ser+(0.0157)Orn+(−0.0073)Lys+(−0.1466)Trp; 0.809, 0.832, 0.762, 0.764, 0.770, 0.790, 0.723, 0.761, (3.0270)+(0.0281)Ser+(−0.0007)Gln+(0.0049)Pro+(−0.1559)Trp; 0.809, 0.832, 0.810, 0.810, 0.814, 0.822, 0.795, 0.810, (8.3905)+(−0.0822)His+(−0.0596)Met+(0.0146)Lys+(−0.1023)Trp; 0.809, 0.829, 0.731, 0.695, 0.741, 0.822, 0.739, 0.749, (3.8159)+(0.0451)Ser+(−0.0632)Asn+(−0.1372)His+(0.0209)Leu; 0.809, 0.827, 0.761, 0.743, 0.741, 0.813, 0.810, 0.777, (3.4909)+(0.0084)Gln+(−0.1515)His+(−0.0270)Tyr+(0.0495)Ile; 0.809, 0.831, 0.815, 0.813, 0.830, 0.816, 0.788, 0.812, (5.0136)+(0.0051)Gln+(−0.0817)Cit+(0.0146)Leu+(−0.1696)Trp; 0.809, 0.829, 0.744, 0.725, 0.725, 0.780, 0.806, 0.759, (4.6402)+(−0.1371)His+(−0.0491)Tyr+(0.0390)Ile+(0.0786)Phe; 0.808, 0.830, 0.732, 0.724, 0.724, 0.764, 0.744, 0.739, (4.3880)+(−0.1500)His+(0.0218)Thr+(−0.0566)Tyr+(0.1046)Phe; 0.808, 0.831, 0.802, 0.819, 0.820, 0.820, 0.704, 0.791, (7.1418)+(0.0288)Thr+(−0.0132)Arg+(−0.1612)Met+(−0.1394)Trp; 0.808, 0.830, 0.790, 0.789, 0.790, 0.803, 0.787, 0.792, (3.6192)+(0.0384)Ser+(−0.0082)Gly+(−0.0002)Thr+(−0.1522)Trp; 0.808, 0.830, 0.781, 0.779, 0.771, 0.822, 0.775, 0.787, (2.9611)+(0.0292)Ser+(−0.0056)Ala+(0.0171)Leu+(−0.1552)Trp; 0.808, 0.831, 0.746, 0.722, 0.755, 0.839, 0.723, 0.760, (4.4635)+(0.0392)Ser+(−0.0690)Asn+(−0.1235)His+(0.0287)Orn; 0.808, 0.825, 0.724, 0.682, 0.730, 0.815, 0.757, 0.746, (3.2667)+(0.0444)Ser+(−0.0040)Gly+(−0.1508)His+(0.0189)Leu; 0.808, 0.823, 0.717, 0.680, 0.717, 0.815, 0.746, 0.740, (3.3138)+(0.0383)Ser+(−0.1448)His+(−0.0176)Val+(0.0456)Leu; 0.808, 0.828, 0.802, 0.794, 0.811, 0.818, 0.793, 0.804, (8.5804)+(0.0012)Asn+(−0.0878)His+(0.0080)Val+(−0.1055)Trp; 0.808, 0.826, 0.720, 0.679, 0.731, 0.821, 0.730, 0.740, (3.4087)+(0.0421)Ser+(−0.1472)His+(−0.0090)Lys+(0.0248)Leu; 0.808, 0.831, 0.794, 0.803, 0.787, 0.839, 0.753, 0.796, (3.8930)+(0.0288)Ser+(−0.0034)Ala+(−0.0026)Lys+(−0.1398)Trp; 0.808, 0.827, 0.815, 0.815, 0.829, 0.818, 0.783, 0.811, (8.0818)+(−0.0400)Asn+(−0.0653)Cit+(0.0090)Pro+(−0.1401)Trp; 0.808, 0.831, 0.794, 0.784, 0.795, 0.796, 0.815, 0.797, (5.6821)+(0.0029)Pro+(−0.1724)Met+(0.0626)Ile+(−0.1434)Trp; 0.808, 0.833, 0.778, 0.768, 0.782, 0.788, 0.789, 0.782, (3.0340)+(0.0387)Ser+(−0.0081)Gly+(0.0093)Leu+(−0.1623)Trp; 0.808, 0.830, 0.793, 0.785, 0.822, 0.804, 0.749, 0.790, (6.4457)(0.0135)Thr+(−0.0795)Cit+(0.0150)Leu+(−0.1727)Trp; 0.808, 0.830, 0.802, 0.796, 0.808, 0.836, 0.780, 0.805, (8.1309)(0.0032)Gly+(−0.0876)His+(0.0203)Tyr+(−0.1020)Trp; 0.808, 0.829, 0.795, 0.809, 0.793, 0.837, 0.732, 0.793, (4.2202)+(0.0312)Ser+(−0.0028)Ala+(−0.0153)Arg+(−0.1382)Trp; 0.808, 0.827, 0.747, 0.723, 0.711, 0.817, 0.836, 0.772, (5.4084)+(−0.0995)His+(−0.0018)Pro+(−0.0348)Val+(0.1296)Ile; 0.808, 0.827, 0.710, 0.666, 0.721, 0.818, 0.724, 0.732, (2.9965)+(0.0366)Ser+(−0.1553)His+(0.0164)Orn+(0.0166)Leu; 0.808, 0.827, 0.754, 0.722, 0.747, 0.815, 0.812, 0.774, (3.0101)+(0.0079)Gln+(−0.1632)His+(0.0081)Orn+(0.0404)Ile; 0.808, 0.828, 0.837, 0.849, 0.840, 0.846, 0.794, 0.832, (5.5839)+(0.0060)Gln+(−0.0030)Ala+(−0.0710)Cit+(−0.1465)Trp; 0.808, 0.825, 0.756, 0.728, 0.734, 0.836, 0.818, 0.779, (5.3494)+(0.0041)Gly+(−0.1269)His+(−0.0066)Ala+(0.0608)Ile; 0.808, 0.828, 0.792, 0.782, 0.796, 0.798, 0.809, 0.796, (5.4986)+(−0.1707)Met+(0.0099)Orn+(0.0623)Ile+(−0.1436)Trp; 0.808, 0.831, 0.825, 0.841, 0.825, 0.824, 0.784, 0.819, (5.5542)+(−0.1088)Asn+(−0.0056)Gln+(0.0151)Thr+(−0.1462)Trp; 0.808, 0.831, 0.796, 0.806, 0.786, 0.836, 0.759, 0.797, (3.5343)+(0.0265)Ser+(0.0009) Gln+(−0.0039)Ala+(−0.1440)Trp; 0.808, 0.830, 0.793, 0.794, 0.792, 0.814, 0.781, 0.795, (3.9816)+(0.0406)Ser+(−0.0084)Gly+(−0.0052)Lys+(−0.1450)Trp; 0.808, 0.824, 0.742, 0.711, 0.728, 0.810, 0.801, 0.763, (5.1458)+(−0.1220)His+(0.0072)Thr+(0.1016)Ile+(−0.0415)Leu; 0.808, 0.832, 0.794, 0.797, 0.787, 0.849, 0.762, 0.799, (4.5995)+(0.0092)Gln+(−0.1364)His+(0.0221)Thr+(−0.1690)Met; 0.808, 0.831, 0.801, 0.791, 0.780, 0.823, 0.853, 0.812, (5.4072)+(−0.0079)Ala+(−0.0051)Lys+(0.0704)Ile+(−0.1512)Trp; 0.807, 0.835, 0.756, 0.749, 0.762, 0.850, 0.694, 0.764, (4.8062)+(0.0348)Ser+(−0.1177)His+(0.0181)Thr+(−0.1569)Met; 0.807, 0.832, 0.764, 0.762, 0.769, 0.797, 0.734, 0.766, (2.8281)+(0.0322)Ser+(−0.0098)Lys+(0.0160)Leu+(−0.1558)Trp; 0.807, 0.829, 0.797, 0.788, 0.799, 0.799, 0.817, 0.801, (5.8591)+(−0.0084)Asn+(−0.1562)Met+(0.0649)Ile+(−0.1427)Trp; 0.807, 0.831, 0.815, 0.821, 0.831, 0.843, 0.747, 0.811, (7.3461)+(0.0173)Thr+(−0.0036)Ala+(−0.0701)Cit+(−0.1494)Trp; 0.807, 0.828, 0.771, 0.751, 0.763, 0.816, 0.807, 0.784, (2.0475)+(0.0097)Gln+(−0.1673)His+(−0.0421)Cit+(0.0760)Phe; 0.807, 0.826, 0.746, 0.721, 0.709, 0.815, 0.835, 0.770, (5.4947)+(−0.0969)His+(−0.0349)Val+(−0.0026)Lys+(0.1294)Ile; 0.807, 0.824, 0.757, 0.746, 0.751, 0.842, 0.736, 0.769, (3.0133)+(0.0294)Ser+(0.0066)Gln+(−0.1431)His+(−0.0360)Cit; 0.807, 0.830, 0.814, 0.818, 0.826, 0.816, 0.776, 0.809, (5.2929)+(0.0050)Gln+(−0.0816)Cit+(0.0074)Pro+(−0.1613)Trp; 0.807, 0.825, 0.747, 0.729, 0.707, 0.815, 0.829, 0.770, (5.7567)+(−0.0932)His+(−0.0208)Tyr+(−0.0340)Val+(0.1310)Ile; 0.807, 0.830, 0.790, 0.788, 0.790, 0.802, 0.786, 0.792, (3.6027)+(0.0383)Ser+(−0.0082)Gly+(0.0002)Val+(−0.1527)Trp; 0.807, 0.829, 0.790, 0.782, 0.791, 0.799, 0.803, 0.794, (5.3784)+(0.0018)Gly+(−0.1712)Met+(0.0667)Ile+(−0.1429)Trp; 0.807, 0.826, 0.755, 0.740, 0.731, 0.809, 0.807, 0.772, (5.8998)+(−0.1026)His+(−0.0278)Tyr+(0.1161)Ile+(−0.0460)Leu; 0.807, 0.829, 0.772, 0.782, 0.774, 0.806, 0.714, 0.769, (3.2676)+(0.0258)Ser+(−0.0144)Tyr+(0.0142)Orn+(−0.1491)Trp; 0.807, 0.829, 0.776, 0.781, 0.779, 0.806, 0.736, 0.775, (2.8373)+(0.0286)Ser+(−0.0055)Thr+(0.0138)Orn+(−0.1513)Trp; 0.807, 0.831, 0.806, 0.810, 0.813, 0.840, 0.753, 0.804, (8.7794)+(0.0040)Gly+(−0.0687)His+(−0.0364)Cit+(−0.0982)Trp; 0.807, 0.831, 0.759, 0.757, 0.767, 0.783, 0.731, 0.759, (2.4883)+(0.0274)Ser+(0.0033)Pro+(0.0077)Leu+(−0.1642)Trp; 0.807, 0.829, 0.743, 0.709, 0.733, 0.816, 0.804, 0.766, (5.0254)+(−0.1197)His+(0.0212)Orn+(0.1025)Ile+(−0.0454)Leu; 0.807, 0.831, 0.775, 0.782, 0.781, 0.802, 0.724, 0.772, (3.0725)+(0.0254)Ser+(−0.0019)Val+(0.0126)Orn+(−0.1525)Trp; 0.807, 0.823, 0.760, 0.729, 0.755, 0.818, 0.812, 0.778, (3.0007)+(0.0094)Gln+(−0.1544)His+(−0.0459)Cit+(0.0473)Ile; 0.807, 0.827, 0.736, 0.712, 0.752, 0.833, 0.696, 0.748, (4.2235)+(0.0363)Ser+(−0.1345)His+(−0.0183)Arg+(0.0296)Orn; 0.807, 0.828, 0.739, 0.718, 0.744, 0.829, 0.724, 0.754, (4.3549)+(0.0427)Ser+(−0.0662)Asn+(−0.1212)His+(0.0078)Pro; 0.807, 0.833, 0.779, 0.788, 0.791, 0.817, 0.700, 0.774, (3.5973)+(0.0299)Ser+(−0.0224)Arg+(0.0192)Orn+(−0.1488)Trp; 0.806, 0.831, 0.792, 0.791, 0.791, 0.804, 0.788, 0.794, (3.4870)+(0.0377)Ser+(−0.0083)Gly+(0.0005)Gln+(−0.1533)Trp; 0.806, 0.827, 0.762, 0.725, 0.747, 0.836, 0.836, 0.786, (5.6514)+(−0.1284)His+(−0.0068)Ala+(0.0226)Orn+(0.0522)Ile; 0.806, 0.831, 0.799, 0.782, 0.808, 0.817, 0.812, 0.805, (8.5247)+(−0.0884)His+(−0.0400)Met+(0.0255)Leu+(−0.1078)Trp; 0.806, 0.828, 0.718, 0.684, 0.728, 0.822, 0.712, 0.737, (3.4414)+(0.0340)Ser+(−0.1439)His+

(0.0048)Pro+(0.0207)Orn; 0.806, 0.830, 0.802, 0.796, 0.807, 0.817, 0.798, 0.805, (8.0929)+(−0.0900)His+ (0.0105)Tyr+(0.0098)Lys+(−0.1081)Trp; 0.806, 0.827, 0.779, 0.787, 0.782, 0.813, 0.725, 0.777, (3.5121)+ (0.0289)Ser+(0.0004)Thr+(−0.0049)Lys+(−0.1460) Trp; 0.806, 0.825, 0.755, 0.748, 0.743, 0.837, 0.743, 0.768, (3.0494)+(0.0282)Ser+(0.0060)Gln+(−0.1469) His+(−0.0065)Tyr; 0.806, 0.823, 0.709, 0.666, 0.719, 0.813, 0.726, 0.731, (2.9629)+(0.0389)Ser+(−0.1532) His+(0.0033)Pro+(0.0174)Leu; 0.806, 0.830, 0.791, 0.794, 0.788, 0.807, 0.779, 0.792, (3.9719)+(0.0389) Ser+(−0.0084)Gly+(−0.0115)Tyr+(−0.1460)Trp; 0.806, 0.826, 0.804, 0.807, 0.827, 0.825, 0.733, 0.798, (6.9470)+(0.0003)Gly+(0.0144)Thr+(−0.0725)Cit+(− 0.1571)Trp; 0.806, 0.823, 0.733, 0.702, 0.735, 0.822, 0.749, 0.752, (3.8136)+(0.0430)Ser+(−0.0047)Gly+(− 0.1366)His+(0.0063)Pro; 0.806, 0.823, 0.746, 0.720, 0.715, 0.820, 0.827, 0.770, (5.6289)+(−0.0914)His+(− 0.0344)Cit+(−0.0350)Val+(0.1308)Ile; 0.806, 0.827, 0.778, 0.771, 0.777, 0.768, 0.809, 0.781, (3.5241)+ (0.0020)Gln+(−0.0020)Orn+(0.0489)Ile+(−0.1762) Trp; 0.806, 0.827, 0.797, 0.779, 0.813, 0.817, 0.800, 0.802, (8.6915)+(−0.0810)His+(−0.0365)Cit+(0.0254) Leu+(−0.1175)Trp; 0.806, 0.838, 0.809, 0.815, 0.825, 0.762, 0.794, 0.799, (3.9508)+(−0.0166)Arg+(− 0.0005)Lys+(0.0795)Phe+(−0.1678)Trp; 0.806, 0.828, 0.777, 0.779, 0.766, 0.773, 0.798, 0.779, (3.9166)+ (0.0024)Gln+(−0.0244)Tyr+(0.0522)Ile+(−0.1656) Trp; 0.806, 0.831, 0.769, 0.772, 0.777, 0.801, 0.720, 0.767, (3.0920)+(0.0268)Ser+(−0.0007)Gln+(0.0117) Orn+(−0.1544)Trp; 0.806, 0.835, 0.801, 0.816, 0.804, 0.760, 0.780, 0.790, (4.0243)+(−0.0135)Arg+(− 0.0287)Tyr+(0.0939)Phe+(−0.1580)Trp; 0.806, 0.830, 0.794, 0.802, 0.786, 0.835, 0.757, 0.795, (3.7298)+ (0.0278)Ser+(−0.0038)Ala+(0.0015)Tyr+(−0.1432) Trp; 0.806, 0.829, 0.802, 0.793, 0.811, 0.818, 0.796, 0.805, (8.5338)+(−0.0882)His+(0.0015)Arg+(0.0080) Val+(−0.1058)Trp; 0.806, 0.834, 0.742, 0.733, 0.714, 0.839, 0.754, 0.760, (−0.5532)+(0.0402)Ser+(−0.3095) Met+(0.1705)Ile+(−0.0749)Leu; 0.806, 0.828, 0.792, 0.782, 0.793, 0.793, 0.815, 0.796, (5.6139)+(−0.0593) Asn+(0.0086)Orn+(0.0471)Ile+(−0.1553)Trp; 0.806, 0.828, 0.723, 0.690, 0.734, 0.822, 0.715, 0.740, (3.5910)+(0.0339)Ser+(−0.1449)His+(0.0023)Val+ (0.0222)Orn; 0.806, 0.821, 0.738, 0.708, 0.741, 0.824, 0.750, 0.756, (3.8853)+(0.0430)Ser+(−0.0044)Gly+(− 0.1400)His+(0.0045)Val; 0.806, 0.827, 0.777, 0.788, 0.778, 0.810, 0.725, 0.775, (3.4438)+(0.0277)Ser+(− 0.0008)Thr+(−0.0079)Tyr+(−0.1476)Trp; 0.805, 0.828, 0.806, 0.810, 0.829, 0.830, 0.733, 0.800, (7.1581)+(0.0157)Thr+(−0.0719)Cit+(−0.0023)Lys+(− 0.1552)Trp; 0.805, 0.829, 0.800, 0.794, 0.784, 0.817, 0.842, 0.809, (5.5251)+(−0.0077)Ala+(−0.0104)Arg+ (0.0683)Ile+(−0.1526)Trp; 0.805, 0.828, 0.813, 0.814, 0.829, 0.818, 0.773, 0.809, (7.7121)+(−0.0607)Cit+ (0.0108)Pro+(−0.0833)Met+(−0.1355)Trp; 0.805, 0.829, 0.789, 0.796, 0.782, 0.831, 0.756, 0.791, (3.5070)+(0.0282)Ser+(−0.0043)Ala+(0.0031)Val+(− 0.1469)Trp; 0.805, 0.828, 0.794, 0.785, 0.795, 0.798, 0.814, 0.798, (5.6131)+(−0.1691)Met+(0.0017)Lys+ (0.0647)Ile+(−0.1449)Trp; 0.805, 0.829, 0.788, 0.788, 0.784, 0.793, 0.790, 0.789, (5.1604)+(−0.0270)Val+ (0.0218)Orn+(0.0479)Leu+(−0.1519)Trp; 0.805, 0.825, 0.811, 0.814, 0.811, 0.827, 0.789, 0.810, (8.9674)+(−0.0058)Asn+(−0.0747)His+(0.0000)Ala+ (−0.0944)Trp; 0.805, 0.827, 0.828, 0.838, 0.839, 0.831, 0.779, 0.822, (5.4327)+(0.0057)Gln+(−0.0742)Cit+(− 0.0010)Lys+(−0.1532)Trp; 0.805, 0.826, 0.801, 0.801, 0.828, 0.816, 0.734, 0.795, (6.8094)+(0.0138)Thr+(− 0.0759)Cit+(0.0033)Val+(−0.1631)Trp; 0.805, 0.828, 0.776, 0.783, 0.780, 0.810, 0.725, 0.774, (3.3635)+ (0.0296)Ser+(0.0018)Val+(−0.0057)Lys+(−0.1480) Trp; 0.805, 0.826, 0.798, 0.789, 0.819, 0.797, 0.779, 0.796, (6.7541)+(−0.0761)Cit+(0.0066)Pro+(0.0126) Leu+(−0.1622)Trp; 0.805, 0.828, 0.781, 0.790, 0.783, 0.815, 0.729, 0.779, (3.3702)+(0.0284)Ser+(0.0005) Gln+(−0.0051)Lys+(−0.1464)Trp; 0.805, 0.829, 0.766, 0.766, 0.771, 0.790, 0.741, 0.767, (2.5362)+(0.0301) Ser+(−0.0043)Thr+(0.0108)Leu+(−0.1599)Trp; 0.805, 0.830, 0.844, 0.863, 0.837, 0.842, 0.812, 0.838, (5.2885)+(−0.0564)Asn+(0.0076)Gln+(−0.0913)Met+ (−0.1317)Trp; 0.805, 0.830, 0.803, 0.808, 0.804, 0.832, 0.770, 0.803, (8.5141)+(0.0027)Gly+(−0.0799)His+ (0.0001)Arg+(−0.0941)Trp; 0.805, 0.826, 0.826, 0.835, 0.836, 0.830, 0.775, 0.819, (5.3574)+(0.0004)Gly+ (0.0055)Gln+(−0.0749)Cit+(−0.1543)Trp; 0.805, 0.829, 0.778, 0.755, 0.788, 0.807, 0.801, 0.788, (4.3758)+(−0.1254)His+(−0.1794)Met+(0.0247)Orn+ (0.1050)Phe; 0.805, 0.828, 0.728, 0.698, 0.737, 0.828, 0.717, 0.745, (3.7556)+(0.0336)Ser+(−0.1402)His+(− 0.0014)Thr+(0.0251)Orn; 0.805, 0.823, 0.712, 0.673, 0.722, 0.813, 0.724, 0.733, (3.1098)+(0.0383)Ser+(− 0.1539)His+(0.0014)Thr+(0.0196)Leu; 0.805, 0.822, 0.793, 0.778, 0.786, 0.835, 0.820, 0.805, (4.0394)+(− 0.0611)Asn+(0.0114)Gln+(−0.1504)His+(0.0132)Leu; 0.804, 0.824, 0.759, 0.732, 0.745, 0.817, 0.821, 0.779, (5.7670)+(−0.0218)Asn+(−0.1057)His+(0.1096)Ile+(− 0.0464)Leu; 0.804, 0.828, 0.782, 0.775, 0.781, 0.768, 0.813, 0.784, (3.6405)+(−0.0012)Gly+(0.0021)Gln+ (0.0476)Ile+(−0.1760)Trp; 0.804, 0.827, 0.778, 0.790, 0.790, 0.813, 0.696, 0.772, (3.9836)+(0.0292)Ser+ (0.0049)Thr+(−0.0204)Arg+(−0.1485)Trp; 0.804, 0.825, 0.737, 0.709, 0.742, 0.780, 0.769, 0.750, (4.6210)+(−0.1532)His+(0.0179)Thr+(−0.0086)Lys+ (0.0790)Phe; 0.804, 0.825, 0.806, 0.797, 0.823, 0.818, 0.789, 0.807, (8.9569)+(−0.0754)His+(−0.0377)Cit+ (0.0092)Val+(−0.1122)Trp; 0.804, 0.821, 0.739, 0.711, 0.723, 0.814, 0.790, 0.760, (4.8848)+(0.0031)Gly+(− 0.1178)His+(0.1065)Ile+(−0.0430)Leu; 0.804, 0.828, 0.775, 0.767, 0.775, 0.767, 0.803, 0.778, (3.5135)+ (0.0017)Gln+(0.0016)Thr+(0.0477)Ile+(−0.1771)Trp; 0.804, 0.831, 0.806, 0.811, 0.807, 0.834, 0.770, 0.806, (8.5901)+(0.0029)Gly+(−0.0776)His+(−0.0143)Met+ (−0.0927)Trp; 0.804, 0.826, 0.813, 0.807, 0.815, 0.836, 0.805, 0.816, (8.6540)+(−0.0811)His+(−0.0012)Ala+ (0.0209)Tyr+(−0.1020)Trp; 0.804, 0.822, 0.740, 0.717, 0.738, 0.838, 0.738, 0.758, (3.8950)+(0.0378)Ser+(− 0.1383)His+(−0.0034)Ala+(0.0075)Val; 0.804, 0.830, 0.800, 0.786, 0.805, 0.804, 0.823, 0.805, (5.5396)+ (0.0151)Tyr+(−0.1889)Met+(0.0648)Ile+(−0.1468) Trp; 0.804, 0.830, 0.763, 0.762, 0.772, 0.789, 0.729, 0.763, (2.5017)+(0.0268)Ser+(0.0069)Orn+(0.0083) Leu+(−0.1635)Trp; 0.804, 0.827, 0.764, 0.763, 0.757, 0.767, 0.777, 0.766, (4.5967)+(0.0074)Thr+(−0.0274) Tyr+(0.0525)Ile+(−0.1651)Trp; 0.804, 0.819, 0.718, 0.687, 0.725, 0.816, 0.715, 0.736, (3.4756)+(0.0371) Ser+(−0.1430)His+(0.0055)Pro+(0.0029)Val; 0.804, 0.822, 0.793, 0.790, 0.782, 0.842, 0.793, 0.801, (4.7632)+(−0.0783)Asn+(0.0102)Gln+(−0.1415)His+ (0.0133)Thr; 0.804, 0.828, 0.797, 0.784, 0.790, 0.841, 0.814, 0.807, (3.6372)+(0.0114)Gln+(−0.1481)His+(− 0.1400)Met+(0.0212)Leu; 0.804, 0.825, 0.746, 0.731, 0.748, 0.838, 0.715, 0.758, (4.9208)+(0.0385)Ser+(− 0.0688)Asn+(−0.1209)His+(0.0090)Thr; 0.804, 0.828, 0.778, 0.790, 0.777, 0.807, 0.725, 0.775, (3.3878)+(0.0269)Ser+(0.0003)Gln+(−0.0089)Tyr+(−0.1484)Trp; 0.804, 0.826, 0.803, 0.808, 0.825, 0.823, 0.729, 0.796, (7.0519)+(0.0152)Thr+(−0.0713)Cit+(−0.0043)Tyr+(−0.1554)Trp; 0.804, 0.826, 0.820, 0.825, 0.835, 0.822, 0.775, 0.814, (5.1891)+(0.0054)Gln+(−0.0796)Cit+(0.0041)Val+(−0.1625)Trp; 0.804, 0.825, 0.802, 0.813, 0.810, 0.803, 0.757, 0.796, (6.8961)+(−0.0843)Asn+(0.0163)Thr+(0.0043)Pro+(−0.1438)Trp; 0.804, 0.820, 0.736, 0.729, 0.646, 0.849, 0.860, 0.771, (0.3125)+(0.0208)Ser+(−0.0116)Ala+(−0.0520)Val+(0.1708)Ile; 0.804, 0.828, 0.779, 0.789, 0.781, 0.815, 0.721, 0.777, (3.6205)+(0.0289)Ser+(−0.0050)Tyr+(−0.0041)Lys+(−0.1440)Trp; 0.804, 0.827, 0.790, 0.781, 0.788, 0.792, 0.812, 0.793, (5.5169)+(−0.0584)Asn+(−0.0014)Gly+(0.0508)Ile+(−0.1551)Trp; 0.804, 0.826, 0.753, 0.763, 0.754, 0.782, 0.707, 0.751, (−2.7237)+(0.0542)Ser+(−0.0949)Asn+(−0.3071)Met+(0.1089)Phe; 0.803, 0.821, 0.767, 0.735, 0.745, 0.833, 0.848, 0.790, (5.8863)+(−0.1211)His+(−0.0075)Ala+(0.0039)Pro+(0.0547)Ile; 0.803, 0.819, 0.722, 0.695, 0.726, 0.820, 0.713, 0.738, (3.6668)+(0.0367)Ser+(−0.1378)His+(−0.0005)Thr+(0.0065)Pro; 0.803, 0.827, 0.775, 0.786, 0.775, 0.805, 0.723, 0.772, (3.3948)+(0.0274)Ser+(−0.0093)Tyr+(0.0008)Val+(−0.1492)Trp; 0.803, 0.827, 0.778, 0.786, 0.779, 0.805, 0.733, 0.776, (3.1455)+(0.0282)Ser+(0.0002)Gln+(−0.0025)Thr+(−0.1505)Trp; 0.803, 0.821, 0.718, 0.678, 0.719, 0.787, 0.774, 0.740, (3.3468)+(0.0050)Gly+(−0.1532)His+(0.0337)Ile+(0.0562)Phe; 0.803, 0.821, 0.731, 0.703, 0.739, 0.828, 0.717, 0.747, (3.8861)+(0.0385)Ser+(−0.1400)His+(0.0063)Val+(−0.0043)Lys; 0.803, 0.824, 0.792, 0.781, 0.784, 0.841, 0.800, 0.802, (4.3829)+(−0.0626)Asn+(0.0102)Gln+(−0.1414)His+(0.0227)Orn; 0.803, 0.821, 0.745, 0.724, 0.750, 0.832, 0.727, 0.758, (4.4239)+(0.0422)Ser+(−0.0562)Asn+(−0.1259)His+(0.0045)Val; 0.803, 0.827, 0.811, 0.805, 0.815, 0.830, 0.801, 0.813, (8.7447)+(−0.0101)Asn+(−0.0799)His+(0.0191)Tyr+(−0.1021)Trp; 0.803, 0.821, 0.721, 0.686, 0.734, 0.818, 0.715, 0.738, (3.5066)+(0.0420)Ser+(−0.1462)His+(−0.0141)Arg+(0.0198)Leu; 0.803, 0.824, 0.756, 0.730, 0.737, 0.819, 0.819, 0.776, (5.4911)+(−0.1122)His+(−0.0033)Pro+(0.1143)Ile+(−0.0465)Leu; 0.803, 0.821, 0.757, 0.739, 0.747, 0.843, 0.764, 0.773, (4.5186)+(0.0422)Ser+(−0.0047)Gly+(−0.1256)His+(−0.0019)Ala; 0.803, 0.825, 0.793, 0.784, 0.792, 0.792, 0.820, 0.797, (5.7215)+(−0.0545)Asn+(−0.0004)Pro+(0.0508)Ile+(−0.1555)Trp; 0.803, 0.822, 0.748, 0.727, 0.715, 0.817, 0.825, 0.771, (5.9235)+(−0.0906)His+(−0.0137)Arg+(−0.0375)Val+(0.1359)Ile; 0.803, 0.828, 0.817, 0.834, 0.812, 0.812, 0.787, 0.811, (4.7049)+(0.0058)Gln+(0.0089)Pro+(−0.1649)Met+(−0.1355)Trp; 0.803, 0.826, 0.788, 0.794, 0.808, 0.796, 0.729, 0.782, (5.9811)+(0.0259)Thr+(−0.2020)Met+(0.0171)Leu+(−0.1511)Trp; 0.803, 0.827, 0.777, 0.784, 0.779, 0.804, 0.732, 0.775, (3.1557)+(0.0285)Ser+(−0.0025)Thr+(0.0004)Val+(−0.1509)Trp; 0.803, 0.827, 0.806, 0.799, 0.813, 0.821, 0.796, 0.807, (8.7196)+(−0.0843)His+(0.0083)Val+(−0.0221)Met+(−0.1036)Trp; 0.803, 0.821, 0.743, 0.719, 0.741, 0.828, 0.750, 0.759, (4.2903)+(0.0407)Ser+(−0.0049)Gly+(−0.1344)His+(0.0042)Thr; 0.803, 0.827, 0.806, 0.804, 0.815, 0.823, 0.782, 0.806, (8.5235)+(−0.0772)His+(−0.0297)Cit+(0.0107)Lys+(−0.1074)Trp; 0.803, 0.822, 0.759, 0.747, 0.755, 0.845, 0.735, 0.770, (4.9822)+(0.0408)Ser+(−0.0558)Asn+(−0.1136)His+(−0.0013)Ala; 0.803, 0.829, 0.829, 0.842, 0.828, 0.825, 0.802, 0.824, (5.1398)+(−0.0902)Asn+(0.0057)Gln+(0.0178)Orn+(−0.1401)Trp; 0.803, 0.825, 0.727, 0.692, 0.753, 0.833, 0.691, 0.742, (3.9437)+(0.0338)Ser+(−0.1318)His+(−0.0643)Cit+(0.0430)Orn; 0.803, 0.824, 0.796, 0.795, 0.816, 0.811, 0.743, 0.791, (6.7942)+(0.0025)Gly+(−0.0756)Cit+(0.0086)Pro+(−0.1510)Trp; 0.803, 0.828, 0.788, 0.803, 0.794, 0.818, 0.712, 0.782, (3.4831)+(0.0292)Ser+(0.0017)Gln+(−0.0197)Arg+(−0.1474)Trp; 0.803, 0.825, 0.801, 0.801, 0.806, 0.810, 0.784, 0.800, (8.4039)+(−0.0867)His+(−0.0069)Arg+(0.0126)Lys+(−0.1045)Trp; 0.803, 0.824, 0.761, 0.744, 0.758, 0.838, 0.758, 0.774, (4.9336)+(0.0467)Ser+(−0.0558)Asn+(−0.0042)Gly+(−0.1154)His; 0.803, 0.822, 0.726, 0.700, 0.730, 0.823, 0.715, 0.742, (3.8546)+(0.0374)Ser+(−0.1345)His+(0.0068)Pro+(−0.0033)Lys; 0.803, 0.827, 0.829, 0.843, 0.824, 0.819, 0.809, 0.824, (5.1932)+(−0.0885)Asn+(0.0062)Gln+(0.0050)Pro+(−0.1413)Trp; 0.803, 0.829, 0.730, 0.709, 0.737, 0.826, 0.706, 0.744, (4.0882)+(0.0323)Ser+(−0.1352)His+(−0.0147)Tyr+(0.0285)Orn; 0.803, 0.830, 0.746, 0.733, 0.737, 0.785, 0.773, 0.757, (4.5795)+(−0.1375)His+(−0.0471)Tyr+(0.0290)Orn+(0.0905)Phe; 0.803, 0.829, 0.796, 0.800, 0.799, 0.815, 0.765, 0.795, (4.3066)+(0.0418)Ser+(−0.0080)Gly+(−0.0169)Arg+(−0.1455)Trp; 0.803, 0.826, 0.811, 0.814, 0.811, 0.827, 0.792, 0.811, (8.9100)+(−0.0074)Asn+(−0.0751)His+(0.0019)Arg+(−0.0948)Trp; 0.803, 0.824, 0.745, 0.716, 0.753, 0.780, 0.779, 0.757, (4.9500)+(−0.0613)Asn+(−0.1456)His+(0.0202)Thr+(0.0768)Phe; 0.803, 0.820, 0.727, 0.702, 0.718, 0.788, 0.769, 0.744, (5.7341)+(−0.1368)His+(0.0165)Thr+(−0.0366)Tyr+(0.0524)Ile; 0.802, 0.824, 0.815, 0.811, 0.825, 0.817, 0.802, 0.814, (7.2581)+(−0.0042)Ala+(−0.0693)Cit+(0.0214)Leu+(−0.1523)Trp; 0.802, 0.820, 0.750, 0.729, 0.746, 0.834, 0.755, 0.766, (4.4427)+(0.0428)Ser+(−0.0049)Gly+(−0.1283)His+(−0.0020)Lys; 0.802, 0.829, 0.748, 0.729, 0.757, 0.836, 0.716, 0.760, (3.9412)+(0.0435)Ser+(−0.1262)His+(0.0089)Val+(−0.1253)Met; 0.802, 0.827, 0.790, 0.791, 0.784, 0.786, 0.804, 0.791, (5.4591)+(0.0052)Pro+(−0.0246)Val+(0.0457)Leu+(−0.1523)Trp; 0.802, 0.825, 0.780, 0.791, 0.789, 0.813, 0.705, 0.775, (3.7700)+(0.0314)Ser+(−0.0181)Arg+(0.0012)Val+(−0.1470)Trp; 0.802, 0.824, 0.809, 0.824, 0.817, 0.815, 0.749, 0.801, (7.3471)+(−0.0828)Asn+(0.0189)Thr+(−0.0027)Val+(−0.1379)Trp; 0.802, 0.823, 0.803, 0.800, 0.823, 0.805, 0.766, 0.799, (7.0482)+(−0.0731)Cit+(0.0079)Pro+(0.0020)Val+(−0.1536)Trp; 0.802, 0.820, 0.820, 0.824, 0.832, 0.825, 0.783, 0.816, (7.5701)+(−0.0033)Ala+(−0.0679)Cit+(0.0067)Val+(−0.1453)Trp; 0.802, 0.829, 0.789, 0.783, 0.785, 0.786, 0.813, 0.792, (3.8693)+(0.0029)Gln+(−0.0101)Lys+(0.0551)Ile+(−0.1666)Trp; 0.802, 0.827, 0.793, 0.786, 0.786, 0.844, 0.789, 0.801, (4.1831)+(0.0096)Gln+(−0.1379)His+(−0.1094)Met+(0.0258)Orn; 0.802, 0.829, 0.760, 0.758, 0.768, 0.787, 0.730, 0.761, (2.7470)+(0.0287)Ser+(−0.0007)Gln+(0.0103)Leu+(−0.1621)Trp; 0.802, 0.826, 0.772, 0.760, 0.776, 0.766, 0.802, 0.776, (4.2587)+(−0.0011)Gly+(0.0044)Thr+(0.0478)Ile+(−0.1749)Trp; 0.802, 0.825, 0.810, 0.813, 0.812, 0.826, 0.787, 0.810, (8.9054)+(−0.0749)His+(0.0001)Ala+(−0.0091)Met+(−0.0942)Trp; 0.802, 0.823, 0.816, 0.830, 0.816, 0.830, 0.767, 0.811, (7.4091)+(−0.0752)Asn+(0.0199)Thr+(−0.0033)Ala+(−0.1380)Trp; 0.802, 0.822, 0.782, 0.772, 0.768, 0.840, 0.796, 0.794, (4.2396)+(0.0081)Gln+(−0.1461)His+(−0.0034)Ala+(0.0246)Orn; 0.802, 0.819, 0.743, 0.728, 0.736, 0.842, 0.724, 0.757, (4.3920)+(0.0337)Ser+(−0.1305)His+

(0.0049)Thr+(−0.0022)Ala; 0.802, 0.827, 0.795, 0.786, 0.797, 0.800, 0.813, 0.799, (5.7694)+(−0.0019)Arg+(−0.1610)Met+(0.0656)Ile+(−0.1431)Trp; 0.802, 0.826, 0.764, 0.756, 0.764, 0.852, 0.722, 0.773, (4.9352)+(0.0419)Ser+(−0.0371)Asn+(−0.1085)His+(−0.0702) Met; 0.802, 0.825, 0.770, 0.758, 0.773, 0.765, 0.797, 0.773, (4.1099)+(0.0037)Thr+(−0.0011)Orn+(0.0487)Ile+(−0.1747)Trp; 0.802, 0.823, 0.818, 0.829, 0.831, 0.837, 0.751, 0.812, (8.0816)+(−0.0409)Asn+(0.0034)Gly+(−0.0628)Cit+(−0.1315)Trp; 0.802, 0.826, 0.810, 0.812, 0.810, 0.827, 0.789, 0.810, (8.8185)+(−0.0766)His+(−0.0001)Ala+(0.0012)Arg+(−0.0950)Trp; 0.802, 0.823, 0.769, 0.766, 0.764, 0.767, 0.790, 0.772, (4.7063)+(−0.0235)Tyr+(0.0060)Orn+(0.0517)Ile+(−0.1608)Trp; 0.802, 0.826, 0.783, 0.784, 0.779, 0.791, 0.779, 0.783, (5.2381)+(0.0101)Thr+(−0.0254)Val+(0.0483)Leu+(−0.1597)Trp; 0.802, 0.828, 0.770, 0.773, 0.783, 0.799, 0.712, 0.767, (3.2251)+(0.0323)Ser+(−0.0195)Arg+(0.0120)Leu+(−0.1570)Trp; 0.802, 0.829, 0.763, 0.739, 0.753, 0.818, 0.808, 0.780, (4.5620)+(−0.1380)His+(−0.0050)Ala+(0.0252)Orn+(0.0724)Phe; 0.802, 0.826, 0.805, 0.815, 0.815, 0.806, 0.754, 0.798, (6.7049)+(−0.0856)Asn+(0.0148)Thr+(0.0168)Orn+(−0.1426)Trp; 0.802, 0.822, 0.722, 0.676, 0.726, 0.779, 0.793, 0.743, (3.8819)+(−0.1579)His+(0.0122)Thr+(0.0301)Ile+(0.0507)Phe; 0.802, 0.821, 0.771, 0.739, 0.751, 0.837, 0.848, 0.794, (6.1476)+(−0.0081)Asn+(−0.1200)His+(−0.0064)Ala+(0.0579)Ile; 0.802, 0.822, 0.800, 0.810, 0.787, 0.815, 0.792, 0.801, (5.6100)+(−0.0071)Ala+(0.0093)Pro+(0.0187)Orn+(−0.1406)Trp; 0.802, 0.820, 0.811, 0.812, 0.792, 0.854, 0.820, 0.819, (4.7431)+(−0.0558)Asn+(0.0112)Gln+(−0.1340)His+(−0.0018)Ala; 0.802, 0.829, 0.763, 0.766, 0.768, 0.786, 0.728, 0.762, (2.8994)+(0.0282)Ser+(−0.0145)Tyr+(0.0120)Leu+(−0.1575)Trp; 0.802, 0.822, 0.775, 0.762, 0.778, 0.766, 0.807, 0.778, (4.3096)+(−0.0005)Gly+(0.0016)Orn+(0.0487)Ile+(−0.1714)Trp; 0.802, 0.821, 0.715, 0.681, 0.721, 0.809, 0.723, 0.733, (3.4061)+(0.0390)Ser+(−0.1472)His+(−0.0156)Tyr+(0.0220) Leu; 0.802, 0.827, 0.780, 0.774, 0.778, 0.771, 0.809, 0.783, (3.5339)+(0.0020)Gln+(−0.0025)Pro+(0.0511)Ile+(−0.1754)Trp; 0.801, 0.827, 0.827, 0.836, 0.837, 0.830, 0.778, 0.820, (5.3899)+(0.0055)Gln+(−0.0743)Cit+(−0.0001)Tyr+(−0.1543)Trp; 0.801, 0.827, 0.793, 0.783, 0.792, 0.794, 0.821, 0.798, (5.7796)+(−0.0505)Asn+(−0.0023)Lys+(0.0519)Ile+(−0.1540)Trp; 0.801, 0.825, 0.789, 0.785, 0.783, 0.789, 0.813, 0.793, (5.9106)+(−0.0486)Asn+(−0.0142)Tyr+(0.0530)Ile+(−0.1505)Trp; 0.801, 0.827, 0.828, 0.838, 0.839, 0.830, 0.775, 0.820, (5.4297)+(0.0059)Gln+(−0.0715)Cit+(−0.0043)Arg+(−0.1532)Trp; 0.801, 0.826, 0.782, 0.794, 0.790, 0.816, 0.706, 0.777, (3.8862)+(0.0312)Ser+(−0.0178)Arg+(0.0001)Lys+(−0.1449)Trp; 0.801, 0.820, 0.801, 0.797, 0.789, 0.842, 0.809, 0.809, (4.4220)+(−0.0579)Asn+(0.0113)Gln+(−0.1416)His+(0.0018)Val; 0.801, 0.828, 0.774, 0.782, 0.778, 0.801, 0.726, 0.772, (3.2066)+(0.0272)Ser+(−0.0000)Gln+(−0.0000)Val+(−0.1524)Trp; 0.801, 0.820, 0.786, 0.770, 0.769, 0.840, 0.823, 0.801, (3.8574)+(0.0094)Gln+(−0.1553)His+(−0.0041)Ala+(0.0170)Leu; 0.801, 0.826, 0.805, 0.809, 0.829, 0.826, 0.727, 0.798, (7.1633)+(0.0164)Thr+(−0.0679)Cit+(−0.0064)Arg+(−0.1564)Trp; 0.801, 0.821, 0.807, 0.811, 0.790, 0.851, 0.801, 0.813, (4.3833)+(0.0108)Gln+(−0.1339)His+(−0.0005)Ala+(−0.0924) Met; 0.801, 0.829, 0.710, 0.690, 0.711, 0.769, 0.716, 0.722, (−5.2379)+(0.0523)Ser+(−0.4475)Met+(0.0549)Ile+(0.0871)Phe; 0.801, 0.821, 0.770, 0.739, 0.748, 0.838, 0.846, 0.793, (6.0890)+(−0.1204)His+(−0.0065)Ala+(−0.0017)Lys+(0.0592)Ile; 0.801, 0.825, 0.811, 0.815, 0.811, 0.828, 0.789, 0.811, (8.9760)+(−0.0046)Asn+(−0.0741)His+(−0.0051)Met+(−0.0940) Trp; 0.801, 0.818, 0.765, 0.762, 0.694, 0.839, 0.868, 0.791, (3.7346)+(−0.0093)Ala+(−0.0220)Arg+(−0.0546)Val+(0.1810)Ile; 0.801, 0.821, 0.732, 0.692, 0.733, 0.803, 0.788, 0.754, (5.5649)+(−0.1403)His+(0.0148)Thr+(−0.0077)Lys+(0.0482)Ile; 0.801, 0.819, 0.722, 0.704, 0.721, 0.818, 0.704, 0.737, (3.9411)+(0.0364)Ser+(−0.1312)His+(0.0082)Pro+(−0.0163) Tyr; 0.801, 0.824, 0.846, 0.863, 0.832, 0.848, 0.826, 0.842, (5.4530)+(−0.0767)Asn+(0.0068)Gln+(−0.0027)Ala+(−0.1339)Trp; 0.801, 0.829, 0.772, 0.758, 0.775, 0.781, 0.794, 0.777, (4.6947)+(0.0083)Thr+(−0.0107)Lys+(0.0549)Ile+(−0.1663)Trp; 0.801, 0.825, 0.804, 0.798, 0.814, 0.807, 0.798, 0.804, (6.9437)+(−0.0646)Cit+(−0.0165)Val+(0.0426)Leu+(−0.1550)Trp; 0.801, 0.822, 0.750, 0.723, 0.734, 0.813, 0.813, 0.771, (5.3817)+(−0.1127)His+(−0.0004)Lys+(0.1081)Ile+(−0.0452)Leu; 0.801, 0.826, 0.782, 0.795, 0.790, 0.816, 0.705, 0.777, (3.9043)+(0.0312)Ser+(−0.0177)Arg+(−0.0006)Tyr+(−0.1445)Trp; 0.801, 0.826, 0.759, 0.752, 0.759, 0.849, 0.716, 0.769, (4.6196)+(0.0395)Ser+(−0.1138)His+(0.0001)Ala+(−0.0979)Met; 0.801, 0.820, 0.754, 0.740, 0.737, 0.817, 0.783, 0.769, (4.1104)+(0.0049)Gly+(−0.1412)His+(−0.0044)Ala+(0.0875) Phe; 0.801, 0.823, 0.803, 0.801, 0.822, 0.807, 0.765, 0.799, (6.9920)+(−0.0715)Cit+(0.0083)Pro+(0.0016)Lys+(−0.1523)Trp; 0.801, 0.819, 0.768, 0.743, 0.744, 0.830, 0.838, 0.789, (6.2948)+(−0.1179)His+(−0.0058)Ala+(−0.0165)Tyr+(0.0607)Ile; 0.801, 0.819, 0.725, 0.698, 0.732, 0.822, 0.714, 0.741, (3.7173)+(0.0363)Ser+(−0.1437)His+(0.0018)Thr+(0.0049)Val; 0.800, 0.825, 0.806, 0.812, 0.814, 0.799, 0.777, 0.800, (6.4936)+(−0.0657)Asn+(0.0044)Pro+(0.0208)Orn+(−0.1371)Trp; 0.800, 0.823, 0.794, 0.790, 0.817, 0.800, 0.753, 0.790, (6.4992)+(0.0029)Gly+(−0.0769)Cit+(0.0171)Leu+(−0.1611)Trp; 0.800, 0.820, 0.737, 0.713, 0.734, 0.784, 0.772, 0.751, (4.2970)+(−0.1503)His+(0.0150)Thr+(−0.0069)Val+(0.0842)Phe; 0.800, 0.817, 0.732, 0.693, 0.731, 0.801, 0.790, 0.753, (5.2730)+(−0.1464)His+(0.0129)Thr+(−0.0033)Pro+(0.0479)Ile; 0.800, 0.818, 0.774, 0.755, 0.767, 0.826, 0.802, 0.788, (3.7650)+(0.0097)Gln+(−0.1592)His+(−0.0050)Lys+(0.0153)Leu; 0.800, 0.819, 0.772, 0.757, 0.769, 0.827, 0.780, 0.783, (4.0868)+(0.0083)Gln+(−0.1509)His+(0.0232)Orn+(−0.0035)Lys; 0.800, 0.817, 0.715, 0.676, 0.731, 0.812, 0.716, 0.734, (3.3301)+(0.0402)Ser+(−0.1449)His+(−0.0325)Cit+(0.0202)Leu; 0.800, 0.817, 0.803, 0.801, 0.788, 0.847, 0.807, 0.811, (4.5374)+(−0.0599)Asn+(0.0007)Gly+(0.0111)Gln+(−0.1377)His; 0.800, 0.822, 0.809, 0.820, 0.819, 0.805, 0.761, 0.801, (7.2315)+(−0.0803)Asn+(−0.0011)Gly+(0.0186)Thr+(−0.1434)Trp; 0.800, 0.827, 0.790, 0.788, 0.790, 0.785, 0.796, 0.790, (3.7945)+(0.0039)Gln+(−0.0212)Arg+(0.0512)Ile+(−0.1710)Trp; 0.800, 0.820, 0.804, 0.808, 0.790, 0.849, 0.794, 0.810, (4.3284)+(0.0003)Gly+(0.0108)Gln+(−0.1346)His+(−0.0964) Met; 0.800, 0.825, 0.783, 0.762, 0.789, 0.796, 0.814, 0.790, (4.4203)+(−0.1277)His+(−0.1970)Met+(0.0074)Lys+(0.1142)Phe; 0.800, 0.819, 0.737, 0.699, 0.737, 0.800, 0.793, 0.757, (5.7928)+(−0.0411)Asn+(−0.1372)His+(0.0163)Thr+(0.0433)Ile; 0.800, 0.823, 0.813, 0.815, 0.799, 0.852, 0.808, 0.819, (4.5541)+(−0.0365)Asn+(0.0117)Gln+(−0.1310)His+(−0.0710) Met; 0.800, 0.822, 0.795, 0.792, 0.783, 0.839, 0.794, 0.802, (4.0639)+(0.0109)Gln+(−0.1343)His+(0.0083)Pro+(−0.1328)Met; 0.800, 0.823, 0.768, 0.755, 0.763, 0.849, 0.754, 0.780, (4.7071)+(0.0455)Ser+(−0.0045)Gly+(−0.1119)His+(−0.0945)Met; 0.800, 0.822, 0.801, 0.806, 0.788, 0.808, 0.811, 0.803, (5.7028)+(−0.0073)Ala+(0.0096)Pro+(0.0114)Leu+(−0.1467)Trp; 0.800, 0.821, 0.818, 0.828, 0.808, 0.822, 0.807, 0.816, (7.1980)+(−0.0466)Asn+(−0.0054)Ala+(0.0110)Pro+(−0.1281)Trp; 0.800, 0.825, 0.741, 0.725, 0.715, 0.828, 0.777, 0.761, (−1.7307)+(0.0453)Ser+(−0.0075)Ala+(−0.3100)Met+(0.0798)Ile; 0.800, 0.823, 0.752, 0.723, 0.753, 0.814, 0.780, 0.768, (5.5659)+(0.0057)Gly+(−0.1171)His+(−0.1599)Met+(0.0673)Ile; 0.800, 0.825, 0.840, 0.857, 0.833, 0.833, 0.813, 0.834, (5.3972)+(−0.0844)Asn+(0.0067)Gln+(−0.0016)Val+(−0.1355)Trp; 0.800, 0.825, 0.777, 0.755, 0.785, 0.791, 0.807, 0.785, (4.5021)+(−0.1195)His+(0.0062)Pro+(−0.1985)Met+(0.1122)Phe; 0.800, 0.822, 0.781, 0.754, 0.767, 0.833, 0.843, 0.799, (6.5161)+(−0.1062)His+(−0.0050)Ala+(−0.1211)Met+(0.0688)Ile; 0.800, 0.825, 0.801, 0.808, 0.791, 0.799, 0.808, 0.802, (4.6487)+(0.0026)Gln+(−0.0227)Val+(0.0443)Leu+(−0.1564)Trp; 0.800, 0.825, 0.816, 0.809, 0.823, 0.840, 0.804, 0.819, (8.7198)+(−0.0769)His+(0.0277)Tyr+(−0.0504)Met+(−0.1018)Trp; 0.800, 0.824, 0.804, 0.802, 0.823, 0.808, 0.766, 0.800, (7.1151)+(−0.0715)Cit+(0.0006)Arg+(0.0084)Pro+(−0.1503)Trp; 0.800, 0.823, 0.816, 0.828, 0.821, 0.817, 0.776, 0.810, (6.9239)+(−0.0647)Asn+(−0.0045)Val+(0.0289)Orn+(−0.1262)Trp 0.902, 0.923, 0.809, 0.790, 0.778, 0.870, 0.878, 0.829, (−1.3217)+(0.0545)Ser+(−0.0544)Val+(−0.3973)Met+(0.1922)Ile+(0.1506)Phe+(−0.1179)Trp; 0.900, 0.919, 0.800, 0.780, 0.815, 0.860, 0.777, 0.808, (1.1114)+(0.0530)Ser+(−0.1384)His+(0.0420)Thr+(−0.3641)Met+(0.1993)Phe+(−0.1237)Trp; 0.899, 0.917, 0.812, 0.798, 0.789, 0.854, 0.864, 0.826, (2.2454)+(0.0452)Thr+(−0.0612)Val+(−0.4741)Met+(0.2021)Ile+(0.1569)Phe+(−0.1267)Trp; 0.894, 0.918, 0.783, 0.749, 0.760, 0.870, 0.859, 0.810, (−1.8219)+(0.0622)Ser+(−0.1003)His+(−0.0447)Val+(−0.4105)Met+(0.1701)Ile+(0.1621)Phe; 0.891, 0.913, 0.825, 0.813, 0.822, 0.870, 0.830, 0.834, (−0.7646)+(0.0539)Ser+(0.0080)Gln+(−0.1367)His+(−0.2716)Met+(0.1766)Phe+(−0.1028)Trp; 0.891, 0.910, 0.793, 0.765, 0.776, 0.856, 0.858, 0.814, (2.3264)+(−0.0966)His+(0.0489)Thr+(−0.0552)Val+(−0.4896)Met+(0.1897)Ile+(0.1580)Phe; 0.890, 0.916, 0.807, 0.794, 0.791, 0.854, 0.841, 0.820, (−1.8334)+(0.0536)Ser+(−0.3463)Met+(0.1735)Ile+(−0.0820)Leu+(0.1380)Phe+(−0.1330)Trp; 0.890, 0.912, 0.785, 0.765, 0.749, 0.870, 0.849, 0.808, (−3.2110)+(0.0409)Ser+(0.0284)Thr+(−0.0697)Val+(−0.5814)Met+(0.2181)Ile+(0.1512)Phe; 0.890, 0.914, 0.791, 0.754, 0.794, 0.854, 0.836, 0.810, (−0.4856)+(0.0659)Ser+(−0.1214)His+(−0.2902)Met+(0.0720)Ile+(0.1503)Phe+(−0.1121)Trp; 0.889, 0.910, 0.831, 0.819, 0.840, 0.854, 0.829, 0.835, (2.1791)+(0.0103)Gln+(−0.1446)His+(0.0467)Thr+(−0.3603)Met+(0.1795)Phe+(−0.1251)Trp; 0.888, 0.909, 0.797, 0.783, 0.752, 0.872, 0.876, 0.821, (−2.0528)+(0.0623)Ser+(−0.1191)Asn+(−0.0671)Val+(−0.3897)Met+(0.2086)Ile+(0.1559)Phe; 0.887, 0.911, 0.794, 0.768, 0.802, 0.853, 0.801, 0.806, (0.2218)+(0.0663)Ser+(−0.1176)His+(0.0128)Pro+(−0.2882)Met+(0.1713)Phe+(−0.1063)Trp; 0.885, 0.906, 0.770, 0.736, 0.762, 0.850, 0.821, 0.792, (−2.1269)+(0.0641)Ser+(−0.1326)His+(−0.3520)Met+(0.1518)Ile+(−0.0632)Leu+(0.1622)Phe; 0.885, 0.908, 0.812, 0.789, 0.821, 0.865, 0.815, 0.822, (0.6585)+(0.0637)Ser+(−0.1191)His+(0.0234)Tyr+(−0.2771)Met+(0.1715)Phe+(−0.1085)Trp; 0.884, 0.906, 0.805, 0.777, 0.785, 0.883, 0.862, 0.827, (2.1234)+(0.0509)Ser+(0.0590)Tyr+(−0.0488)Val+(−0.3619)Met+(0.1995)Ile+(−0.1244)Trp; 0.884, 0.905, 0.810, 0.795, 0.815, 0.858, 0.807, 0.819, (1.0354)+(0.0642)Ser+(−0.0298)Asn+(−0.1127)His+(−0.2223)Met+(0.1737)Phe+(−0.1009)Trp; 0.884, 0.909, 0.795, 0.777, 0.745, 0.877, 0.887, 0.821, (−3.0328)+(0.0510)Ser+(−0.0050)Ala+(−0.0625)Val+(−0.4487)Met+(0.2107)Ile+(0.1401)Phe; 0.883, 0.907, 0.791, 0.769, 0.747, 0.865, 0.888, 0.817, (−3.0576)+(0.0592)Ser+(−0.0056)Gly+(−0.0640)Val+(−0.4783)Met+(0.2055)Ile+(0.1405)Phe; 0.882, 0.903, 0.805, 0.787, 0.810, 0.855, 0.804, 0.814, (0.7088)+(0.0622)Ser+(−0.1177)His+(0.0009)Ala+(−0.2474)Met+(0.1748)Phe+(−0.1026)Trp; 0.882, 0.906, 0.804, 0.785, 0.812, 0.858, 0.803, 0.814, (0.7718)+(0.0609)Ser+(−0.1195)His+(−0.2422)Met+(0.0111)Orn+(0.1700)Phe+(−0.1017)Trp; 0.882, 0.905, 0.799, 0.771, 0.809, 0.852, 0.813, 0.811, (0.5016)+(0.0636)Ser+(−0.1239)His+(−0.2582)Met+(0.0196)Leu+(0.1610)Phe+(−0.1091)Trp; 0.881, 0.904, 0.802, 0.772, 0.819, 0.829, 0.825, 0.811, (4.6013)+(−0.1241)His+(0.0491)Thr+(−0.3361)Met+(0.0575)Ile+(0.1484)Phe+(−0.1339)Trp; 0.881, 0.904, 0.805, 0.787, 0.811, 0.852, 0.806, 0.814, (0.5622)+(0.0605)Ser+(−0.1208)His+(−0.2627)Met+(0.0083)Lys+(0.1749)Phe+(−0.1088)Trp; 0.881, 0.906, 0.790, 0.769, 0.755, 0.871, 0.860, 0.814, (−2.7772)+(0.0534)Ser+(−0.0583)Cit+(−0.0611)Val+(−0.4725)Met+(0.2025)Ile+(0.1483)Phe; 0.881, 0.903, 0.805, 0.784, 0.812, 0.856, 0.807, 0.815, (0.7259)+(0.0625)Ser+(−0.1217)His+(0.0048)Val+(−0.2448)Met+(0.1692)Phe+(−0.1064)Trp; 0.881, 0.902, 0.798, 0.784, 0.760, 0.859, 0.869, 0.818, (1.4747)+(−0.0872)Asn+(0.0451)Thr+(−0.0745)Val+(−0.4746)Met+(0.2248)Ile+(0.1468)Phe; 0.880, 0.904, 0.810, 0.792, 0.812, 0.857, 0.817, 0.819, (0.8210)+(0.0648)Ser+(−0.0022)Gly+(−0.1140)His+(−0.2398)Met+(0.1738)Phe+(−0.1039)Trp; 0.880, 0.905, 0.809, 0.792, 0.817, 0.858, 0.800, 0.817, (0.8548)+(0.0627)Ser+(−0.1030)His+(−0.0434)Cit+(−0.2268)Met+(0.1810)Phe+(−0.1120)Trp; 0.880, 0.902, 0.804, 0.783, 0.783, 0.880, 0.849, 0.824, (3.5594)+(0.0437)Ser+(−0.0504)Cit+(−0.0373)Val+(−0.2208)Met+(0.1758)Ile+(−0.1170)Trp; 0.880, 0.901, 0.798, 0.783, 0.774, 0.878, 0.833, 0.817, (3.5083)+(0.0341)Ser+(0.0217)Thr+(−0.0447)Val+(−0.3282)Met+(0.1883)Ile+(−0.1110)Trp; 0.880, 0.900, 0.831, 0.825, 0.800, 0.853, 0.898, 0.844, (1.6131)+(0.0057)Gln+(−0.0525)Val+(−0.3431)Met+(0.1808)Ile+(0.1304)Phe+(−0.1173)Trp; 0.880, 0.904, 0.789, 0.773, 0.750, 0.855, 0.866, 0.811, (1.3300)+(0.0530)Ser+(−0.1787)Asn+(−0.0502)Val+(0.1586)Ile+(0.1013)Phe+(−0.1205)Trp; 0.879, 0.903, 0.784, 0.768, 0.742, 0.863, 0.861, 0.808, (−3.3275)+(0.0510)Ser+(−0.0566)Val+(−0.4745)Met+(0.2287)Ile+(−0.0295)Leu+(0.1461)Phe; 0.879, 0.906, 0.789, 0.765, 0.751, 0.871, 0.874, 0.815, (−3.4771)+(0.0531)Ser+(0.0228)Tyr+(−0.0672)Val+(−0.5232)Met+(0.2117)Ile+(0.1378)Phe; 0.878, 0.903, 0.801, 0.777, 0.813, 0.835, 0.817, 0.811, (−1.3020)+(0.0581)Ser+(−0.0917)Cit+(−0.3118)Met+(0.0708)Ile+(0.1355)Phe+(−0.1702)Trp; 0.878, 0.905, 0.782, 0.763, 0.741, 0.862, 0.860, 0.807, (−3.2369)+(0.0521)Ser+(0.0053)Pro+(−0.0643)Val+(−0.4981)Met+(0.1980)Ile+(0.1419)Phe; 0.878, 0.904, 0.807, 0.792, 0.812, 0.857, 0.802, 0.816, (0.8772)+(0.0632)Ser+(−0.1150)His+(−0.0075)Arg+(−0.2326)Met+(0.1756)Phe+(−0.1014)Trp; 0.878, 0.898, 0.758, 0.725, 0.747, 0.823, 0.821, 0.779, (1.1231)+(0.0472)Ser+(−0.1274)His+(0.1065)Ile+(−0.0390)Leu+(0.1044)Phe+(−0.1281)Trp; 0.877, 0.903, 0.807, 0.797, 0.795, 0.855, 0.824, 0.818, (1.0488)+(0.0524)Ser+(−0.1170)Asn+(0.0077)Gln+(−0.1332)His+(0.1277)Phe+(−0.1078)Trp; 0.877, 0.900, 0.754, 0.707, 0.768, 0.840, 0.783, 0.775, (−1.3972)+(0.0567)Ser+(−0.1699)His+(0.0295)Thr+(−0.4330)Met+(0.0672)Ile+(0.1506)Phe; 0.877, 0.904, 0.782, 0.761, 0.740, 0.865, 0.866, 0.808, (−2.9436)+(0.0528)Ser+(−0.0012)Gln+(−0.0642)Val+(−0.4767)Met+(0.2056)Ile+(0.1425)Phe; 0.877, 0.900, 0.812, 0.798, 0.791, 0.876, 0.848, 0.828, (6.5712)+(0.0336)Thr+(−0.0519)Cit+(−0.0438)Val+(−0.2732)Met+(0.1832)Ile+(−0.1144)Trp; 0.877, 0.903, 0.819, 0.801, 0.795, 0.849, 0.894, 0.835, (4.9139)+(−0.0543)His+(−0.0452)Val+(−0.2526)Met+(0.1687)Ile+(0.1312)Phe+(−0.0958)Trp; 0.877, 0.900, 0.797, 0.784, 0.755, 0.863, 0.875, 0.819, (0.3843)+(0.0393)Thr+(−0.0042)Ala+(−0.0697)Val+(−0.5055)Met+(0.2222)Ile+(0.1346)Phe; 0.877, 0.899, 0.803, 0.787, 0.768, 0.879, 0.865, 0.824, (3.2446)+(0.0417)Ser+(−0.0046)Ala+(−0.0407)Val+(−0.2260)Met+(0.1885)Ile+(−0.1079)Trp; 0.877, 0.896, 0.806, 0.783, 0.828, 0.827, 0.804, 0.811, (5.1385)+(−0.1262)His+(0.0512)Thr+(−0.3199)Met+(0.0154)Leu+(0.1582)Phe+(−0.1315)Trp; 0.877, 0.895, 0.811, 0.802, 0.778, 0.873, 0.862, 0.828, (6.3171)+(0.0318)Thr+(−0.0048)Ala+(−0.0466)Val+(−0.2706)Met+(0.1948)Ile+(−0.1108)Trp; 0.877, 0.901, 0.770, 0.737, 0.753, 0.844, 0.841, 0.794, (1.5645)+(0.0502)Ser+(−0.1331)His+(−0.0071)Ala+(0.0682)Ile+(0.1022)Phe+(−0.1303)Trp; 0.877, 0.904, 0.787, 0.767, 0.744, 0.867, 0.870, 0.812, (−3.2265)+(0.0513)Ser+(−0.0640)Val+(−0.4840)Met+(−0.0021)Orn+(0.2050)Ile+(0.1430)Phe; 0.876, 0.899, 0.796, 0.776, 0.772, 0.871, 0.847, 0.817, (3.1391)+(0.0431)Ser+(0.0063)Pro+(−0.0420)Val+(−0.2707)Met+(0.1750)Ile+(−0.1119)Trp; 0.876, 0.896, 0.800, 0.782, 0.782, 0.859, 0.843, 0.817, (7.1237)+(−0.0566)His+(0.0346)Thr+(−0.0375)Val+(−0.2613)Met+(0.1722)Ile+(−0.0947)Trp; 0.876, 0.900, 0.789, 0.772, 0.802, 0.820, 0.788, 0.796, (−1.7780)+(0.0469)Ser+(0.0220)Thr+(−0.4185)Met+(0.0601)Ile+(0.1200)Phe+(−0.1623)Trp; 0.876, 0.900, 0.814, 0.814, 0.828, 0.840, 0.768, 0.812, (0.3731)+(0.0463)Ser+(−0.0799)Asn+(0.0272)Thr+(−0.3209)Met+(0.1461)Phe+(−0.1531)Trp; 0.876, 0.898, 0.813, 0.799, 0.830, 0.833, 0.801, 0.816, (5.1380)+(−0.1164)His+(0.0508)Thr+(−0.0016)Val+(−0.3109)Met+(0.1713)Phe+(−0.1240)Trp; 0.876, 0.898, 0.781, 0.748, 0.787, 0.859, 0.796, 0.798, (4.0210)+(0.0445)Ser+(−0.1021)His+(0.0220)Thr+(−0.2402)Met+(0.0941)Ile+(−0.1075)Trp; 0.876, 0.898, 0.804, 0.786, 0.774, 0.882, 0.856, 0.824, (3.7945)+(0.0469)Ser+(−0.0611)Asn+(−0.0421)Val+(−0.2051)Met+(0.1806)Ile+(−0.1024)Trp; 0.876, 0.899, 0.803, 0.783, 0.772, 0.871, 0.868, 0.824, (3.1847)+(0.0513)Ser+(−0.0059)Gly+(−0.0407)Val+(−0.2496)Met+(0.1795)Ile+(−0.1110)Trp; 0.876, 0.898, 0.815, 0.806, 0.785, 0.847, 0.882, 0.830, (3.0411)+(0.0040)Gly+(−0.0542)Val+(−0.3097)Met+(0.1869)Ile+(0.1305)Phe+(−0.1123)Trp; 0.876, 0.899, 0.777, 0.739, 0.777, 0.852, 0.825, 0.798, (−3.0222)+(0.0578)Ser+(0.0068)Gln+(−0.1683)His+(−0.3616)Met+(0.0626)Ile+(0.1415)Phe; 0.876, 0.900, 0.792, 0.772, 0.765, 0.863, 0.851, 0.813, (6.6553)+(0.0436)Thr+(−0.0620)Cit+(−0.0694)Val+(−0.5305)Met+(0.2201)Ile+(0.1426)Phe; 0.875, 0.898, 0.808, 0.802, 0.833, 0.838, 0.750, 0.806, (0.0690)+(0.0437)Ser+(0.0320)Thr+(−0.0895)Cit+(−0.3650)Met+(0.1686)Phe+(−0.1704)Trp; 0.875, 0.898, 0.810, 0.795, 0.828, 0.831, 0.799, 0.813, (5.0416)+(0.0077)Asn+(−0.1194)His+(0.0503)Thr+(−0.3161)Met+(0.1699)Phe+(−0.1255)Trp; 0.875, 0.899, 0.825, 0.817, 0.787, 0.854, 0.906, 0.841, (3.9291)+(−0.0044)Ala+(−0.0534)Val+(−0.2665)Met+(0.1920)Ile+(0.1248)Phe+(−0.1088)Trp; 0.875, 0.897, 0.794, 0.778, 0.763, 0.875, 0.845, 0.815, (4.6063)+(0.0465)Ser+(−0.1092)Asn+(−0.0635)Cit+(−0.0374)Val+(0.1596)Ile+(−0.1266)Trp; 0.875, 0.899, 0.781, 0.761, 0.783, 0.844, 0.786, 0.793, (2.7059)+(0.0543)Ser+(−0.1114)Asn+(−0.1258)His+(0.0185)Thr+(0.1304)Phe+(−0.1179)Trp; 0.875, 0.903, 0.785, 0.768, 0.746, 0.863, 0.855, 0.808, (−3.1220)+(0.0548)Ser+(−0.0162)Arg+(−0.0640)Val+(−0.4578)Met+(0.2053)Ile+(0.1464)Phe; 0.875, 0.898, 0.806, 0.793, 0.824, 0.832, 0.786, 0.809, (4.7360)+(0.0034)Gly+(−0.1236)His+(0.0487)Thr+(−0.3151)Met+(0.1724)Phe+(−0.1208)Trp; 0.875, 0.904, 0.786, 0.767, 0.743, 0.868, 0.870, 0.812, (−3.2133)+(0.0512)Ser+(−0.0641)Val+(−0.4828)Met+(−0.0003)Lys+(0.2046)Ile+(0.1423)Phe; 0.875, 0.895, 0.792, 0.776, 0.753, 0.867, 0.864, 0.815, (3.8125)+(0.0350)Ser+(−0.0086)Ala+(−0.0759)Cit+(−0.0342)Val+(0.1732)Ile+(−0.1444)Trp; 0.875, 0.898, 0.808, 0.792, 0.825, 0.827, 0.799, 0.811, (5.0167)+(−0.1163)His+(0.0493)Thr+(0.0042)Pro+(−0.3173)Met+(0.1656)Phe+(−0.1257)Trp; 0.874, 0.892, 0.811, 0.795, 0.789, 0.870, 0.856, 0.827, (5.8798)+(0.0306)Thr+(0.0275)Tyr+(−0.0494)Val+(−0.3312)Met+(0.1907)Ile+(−0.1191)Trp; 0.874, 0.898, 0.811, 0.797, 0.829, 0.831, 0.799, 0.814, (5.1472)+(−0.1179)His+(0.0507)Thr+(−0.0017)Tyr+(−0.3085)Met+(0.1695)Phe+(−0.1249)Trp; 0.874, 0.898, 0.788, 0.761, 0.770, 0.865, 0.842, 0.810, (3.8623)+(0.0473)Ser+(−0.0629)His+(−0.0301)Val+(−0.2091)Met+(0.1648)Ile+(−0.0919)Trp; 0.874, 0.898, 0.792, 0.790, 0.806, 0.814, 0.751, 0.790, (−1.0344)+(0.0456)Ser+(0.0230)Thr+(0.0098)Pro+(−0.4138)Met+(0.1413)Phe+(−0.1577)Trp; 0.874, 0.895, 0.788, 0.774, 0.751, 0.854, 0.859, 0.809, (0.0531)+(0.0005)Gly+(0.0394)Thr+(−0.0716)Val+(−0.5394)Met+(0.2193)Ile+(0.1383)Phe; 0.874, 0.897, 0.812, 0.798, 0.830, 0.831, 0.801, 0.815, (5.1552)+(−0.1177)His+(0.0509)Thr+(−0.3113)Met+(−0.0016)Orn+(0.1700)Phe+(−0.1256)Trp; 0.874, 0.896, 0.754, 0.722, 0.735, 0.823, 0.828, 0.777, (1.3999)+(0.0456)Ser+(−0.1187)His+(−0.0254)Val+(0.1124)Ile+(0.1002)Phe+(−0.1271)Trp; 0.874, 0.895, 0.768, 0.727, 0.765, 0.852, 0.820, 0.791, (−1.5196)+(0.0660)Ser+(−0.1481)His+(−0.0042)Ala+(−0.3256)Met+(0.0732)Ile+(0.1382)Phe; 0.873, 0.897, 0.812, 0.814, 0.827, 0.835, 0.756, 0.808, (−0.1619)+(0.0395)Ser+(0.0286)Thr+(−0.0081)Val+(−0.3801)Met+(0.1583)Phe+(−0.1520)Trp; 0.873, 0.895, 0.802, 0.787, 0.773, 0.876, 0.850, 0.821, (3.6154)+(0.0371)Ser+(−0.0090)Ala+(−0.0871)Cit+(0.1770)Ile+(−0.0599)Leu+(−0.1475)Trp; 0.873, 0.897, 0.812, 0.798, 0.829, 0.832, 0.800, 0.815, (5.1575)+(−0.1177)His+(0.0505)Thr+(−0.0002)Ala+(−0.3093)Met+(0.1691)Phe+(−0.1253)Trp; 0.873, 0.896, 0.799, 0.783, 0.771, 0.872, 0.851, 0.819, (3.0224)+(0.0410)Ser+(−0.0428)Val+(−0.2747)Met+(0.0061)Lys+(0.1815)Ile+(−0.1138)Trp; 0.873, 0.897, 0.810, 0.795, 0.829, 0.825, 0.801, 0.812, (4.9661)+(−0.1202)His+(0.0488)Thr+(−0.3182)Met+(0.0049)Lys+(0.1679)Phe+(−0.1273)Trp; 0.873, 0.896, 0.821, 0.812, 0.790, 0.844, 0.896, 0.836, (3.8662)+(−0.0081)Asn+(−0.0538)Val+(−0.2881)Met+(0.1849)Ile+(0.1257)Phe+(−0.1096)Trp; 0.873, 0.897, 0.811, 0.799, 0.833, 0.830, 0.787, 0.812, (5.5816)+(−0.1144)His+(0.0550)Thr+(−0.0157)Arg+ (−0.3019)Met+(0.1705)Phe+(−0.1270)Trp; 0.873, 0.896, 0.801, 0.784, 0.773, 0.874, 0.851, 0.821, (2.9282)+(0.0409)Ser+(0.0009)Gln+(−0.0410)Val+(− 0.2589)Met+(0.1794)Ile+(−0.1121)Trp; 0.873, 0.898, 0.818, 0.808, 0.788, 0.842, 0.891, 0.832, (3.7193)+ (0.0050)Pro+(−0.0540)Val+(−0.3080)Met+(0.1806) Ile+(0.1269)Phe+(−0.1125)Trp; 0.873, 0.900, 0.837, 0.818, 0.833, 0.859, 0.882, 0.848, (2.0349)+(0.0121) Gln+(−0.1284)His+(−0.2378)Met+(0.0584)Ile+ (0.1200)Phe+(−0.1165)Trp; 0.873, 0.894, 0.796, 0.777, 0.771, 0.871, 0.843, 0.816, (3.1019)+(0.0405)Ser+(− 0.0430)Val+(−0.2624)Met+(0.0147)Orn+(0.1798)Ile+ (−0.1110)Trp; 0.873, 0.898, 0.769, 0.735, 0.765, 0.837, 0.822, 0.790, (1.7038)+(0.0588)Ser+(−0.0844)Asn+(− 0.1247)His+(0.0537)Ile+(0.1038)Phe+(−0.1227)Trp; 0.872, 0.895, 0.789, 0.774, 0.751, 0.853, 0.860, 0.809, (0.1187)+(0.0392)Thr+(−0.0702)Val+(−0.5356)Met+ (0.2227)Ile+(−0.0048)Leu+(0.1384)Phe; 0.872, 0.897, 0.808, 0.807, 0.808, 0.826, 0.795, 0.809, (−0.3872)+ (0.0586)Ser+(−0.0695)Asn+(0.0110)Pro+(−0.2845) Met+(0.1316)Phe+(−0.1409)Trp; 0.872, 0.897, 0.818, 0.807, 0.789, 0.844, 0.891, 0.833, (3.6639)+(−0.0543) Val+(−0.2976)Met+(0.0093)Orn+(0.1841)Ile+(0.1213) Phe+(−0.1100)Trp; 0.872, 0.892, 0.805, 0.794, 0.778, 0.865, 0.849, 0.821, (6.2184)+(−0.0009)Gly+(0.0321) Thr+(−0.0472)Val+(−0.2963)Met+(0.1870)Ile+(− 0.1125)Trp; 0.872, 0.896, 0.789, 0.773, 0.751, 0.854, 0.860, 0.810, (0.1211)+(0.0396)Thr+(0.0010)Pro+(− 0.0716)Val+(−0.5408)Met+(0.2183)Ile+(0.1378)Phe; 0.872, 0.898, 0.791, 0.775, 0.753, 0.853, 0.864, 0.811, (0.1174)+(0.0429)Thr+(−0.0717)Val+(−0.5487)Met+ (−0.0139)Orn+(0.2238)Ile+(0.1444)Phe; 0.872, 0.895, 0.804, 0.803, 0.823, 0.830, 0.751, 0.802, (−0.3855)+ (0.0418)Ser+(0.0273)Thr+(−0.3721)Met+(−0.0047) Lys+(0.1470)Phe+(−0.1560)Trp; 0.872, 0.896, 0.792, 0.778, 0.754, 0.855, 0.861, 0.812, (−0.4936)+(0.0017) Gln+(0.0386)Thr+(−0.0713)Val+(−0.5505)Met+ (0.2181)Ile+(0.1387)Phe; 0.872, 0.892, 0.810, 0.801, 0.783, 0.867, 0.850, 0.825, (5.1257)+(0.0031)Gln+ (0.0295)Thr+(−0.0462)Val+(−0.3115)Met+(0.1835) Ile+(−0.1169)Trp; 0.872, 0.897, 0.784, 0.770, 0.755, 0.853, 0.836, 0.803, (0.6618)+(0.0508)Thr+(−0.0287) Arg+(−0.0751)Val+(−0.5262)Met+(0.2298)Ile+ (0.1475)Phe; 0.872, 0.893, 0.823, 0.823, 0.831, 0.842, 0.795, 0.823, (0.7735)+(0.0580)Ser+(−0.0672)Asn+(− 0.0788)Cit+(−0.2115)Met+(0.1522)Phe+(−0.1461) Trp; 0.872, 0.895, 0.804, 0.805, 0.831, 0.829, 0.726, 0.798, (−0.0447)+(0.0437)Ser+(0.0341)Thr+(−0.0257) Arg+(−0.3805)Met+(0.1530)Phe+(−0.1579)Trp; 0.871, 0.893, 0.767, 0.741, 0.747, 0.824, 0.833, 0.787, (0.6532)+(0.0399)Ser+(−0.1010)Cit+(−0.0387)Val+ (0.1447)Ile+(0.0903)Phe+(−0.1830)Trp; 0.871, 0.895, 0.801, 0.789, 0.816, 0.826, 0.782, 0.803, (−0.4540)+ (0.0581)Ser+(−0.0898)Cit+(0.0143)Pro+(−0.3145) Met+(0.1525)Phe+(−0.1610)Trp; 0.871, 0.894, 0.798, 0.781, 0.770, 0.870, 0.848, 0.817, (3.1438)+(0.0420) Ser+(−0.0384)Val+(−0.2517)Met+(0.1878)Ile+(− 0.0099)Leu+(−0.1101)Trp; 0.871, 0.895, 0.820, 0.810, 0.790, 0.843, 0.890, 0.833, (3.6738)+(−0.0474)Val+(− 0.2911)Met+(0.1986)Ile+(−0.0204)Leu+(0.1266)Phe+ (−0.1089)Trp; 0.871, 0.897, 0.818, 0.811, 0.786, 0.839, 0.890, 0.832, (3.2462)+(−0.0581)Val+(−0.3358)Met+ (0.0125)Lys+(0.1891)Ile+(0.1268)Phe+(−0.1163)Trp; 0.871, 0.895, 0.762, 0.726, 0.756, 0.827, 0.820, 0.782, (0.8269)+(0.0429)Ser+(0.0039)Gln+(−0.1493)His+ (0.0532)Ile+(0.0925)Phe+(−0.1345)Trp; 0.871, 0.897, 0.801, 0.802, 0.797, 0.825, 0.786, 0.803, (−0.8865)+ (0.0535)Ser+(0.0137)Pro+(−0.0091)Val+(−0.3360) Met+(0.1445)Phe+(−0.1393)Trp; 0.871, 0.892, 0.810, 0.800, 0.783, 0.867, 0.851, 0.825, (6.8120)+(−0.0424) Asn+(0.0335)Thr+(−0.0480)Val+(−0.2646)Met+ (0.1872)Ile+(−0.1073)Trp; 0.871, 0.895, 0.795, 0.779, 0.786, 0.855, 0.811, 0.808, (2.4257)+(0.0586)Ser+(− 0.0850)Asn+(−0.1155)His+(−0.0026)Ala+(0.1346) Phe+(−0.1062)Trp; 0.871, 0.888, 0.811, 0.791, 0.810, 0.856, 0.834, 0.823, (5.0596)+(0.0087)Gln+(−0.1134) His+(0.0284)Thr+(−0.2241)Met+(0.0791)Ile+(− 0.1159)Trp; 0.871, 0.897, 0.815, 0.798, 0.841, 0.833, 0.792, 0.816, (5.2824)+(−0.1036)His+(0.0517)Thr+(− 0.0508)Cit+(−0.2946)Met+(0.1765)Phe+(−0.1356) Trp; 0.871, 0.895, 0.756, 0.716, 0.752, 0.827, 0.816, 0.778, (1.5449)+(0.0511)Ser+(−0.1339)His+(−0.0108) Lys+(0.0614) Ile+(0.1007)Phe+(−0.1260)Trp; 0.871, 0.897, 0.797, 0.789, 0.772, 0.840, 0.837, 0.810, (0.8635)+(0.0485)Ser+(−0.1466)Asn+(0.1404)Ile+(− 0.0731)Leu+(0.0917)Phe+(−0.1395)Trp; 0.871, 0.900, 0.825, 0.810, 0.799, 0.852, 0.900, 0.840, (3.6620)+ (0.0189)Tyr+(−0.0547)Val+(−0.3223)Met+(0.1869) Ile+(0.1221)Phe+(−0.1142)Trp; 0.871, 0.898, 0.802, 0.787, 0.804, 0.828, 0.819, 0.810, (−1.1859)+(0.0587) Ser+(−0.0576)Asn+(−0.2971)Met+(0.0598)Ile+ (0.1109)Phe+(−0.1476)Trp; 0.871, 0.896, 0.787, 0.774, 0.749, 0.851, 0.858, 0.808, (0.1420)+(0.0403)Thr+(− 0.0082)Tyr+(−0.0709)Val+(−0.5292)Met+(0.2182)Ile+ (0.1402)Phe; 0.870, 0.895, 0.784, 0.741, 0.795, 0.857, 0.820, 0.803, (2.8514)+(0.0578)Ser+(−0.0991)His+ (0.0424)Tyr+(−0.2438)Met+(0.0940)Ile+(−0.1184) Trp; 0.870, 0.894, 0.804, 0.802, 0.796, 0.833, 0.806, 0.809, (−0.9039)+(0.0533)Ser+(−0.0048)Ala+(0.0145) Pro+(−0.3144)Met+(0.1326)Phe+(−0.1433)Trp; 0.870, 0.894, 0.786, 0.758, 0.779, 0.860, 0.821, 0.805, (3.6476)+(0.0495)Ser+(−0.0805)His+(−0.1772)Met+ (0.1341)Ile+(−0.0304)Leu+(−0.1014)Trp; 0.870, 0.890, 0.805, 0.795, 0.779, 0.864, 0.844, 0.821, (5.9503)+(0.0300)Thr+(−0.0479)Val+(−0.3079)Met+ (0.0045)Lys+(0.1867)Ile+(−0.1141)Trp; 0.870, 0.896, 0.756, 0.713, 0.762, 0.830, 0.803, 0.777, (0.9717)+ (0.0559)Ser+(−0.1185)His+(−0.0763)Cit+(0.0654)Ile+ (0.1134)Phe+(−0.1581)Trp; 0.870, 0.897, 0.813, 0.806, 0.811, 0.826, 0.828, 0.818, (2.2784)+(0.0315)Thr+(− 0.3586)Met+(0.1475)Ile+(−0.0720)Leu+(0.1298)Phe+ (−0.1440)Trp; 0.870, 0.892, 0.804, 0.793, 0.779, 0.863, 0.847, 0.820, (6.0995)+(0.0325)Thr+(−0.0501)Val+(− 0.3037)Met+(0.1815)Ile+(0.0092)Leu+(−0.1132)Trp; 0.870, 0.895, 0.816, 0.810, 0.829, 0.822, 0.798, 0.815, (−0.0766)+(0.0525)Ser+(−0.0089)Gly+(0.0286)Thr+ (−0.3786)Met+(0.1447)Phe+(−0.1642)Trp; 0.870, 0.895, 0.772, 0.751, 0.758, 0.841, 0.807, 0.789, (1.9594)+(0.0504)Ser+(−0.1286)His+(−0.0061)Ala+ (0.0101)Pro+(0.1227)Phe+(−0.1212)Trp; 0.870, 0.894, 0.797, 0.771, 0.790, 0.864, 0.830, 0.814, (2.4540)+ (0.0435)Ser+(0.0062)Gln+(−0.1068)His+(−0.1908) Met+(0.0901)Ile+(−0.1059)Trp; 0.870, 0.891, 0.803, 0.793, 0.777, 0.863, 0.843, 0.819, (6.1040)+(0.0310) Thr+(0.0023)Pro+(−0.0473)Val+(−0.3002)Met+ (0.1846)Ile+(−0.1123)Trp; 0.870, 0.896, 0.802, 0.784, 0.795, 0.839, 0.834, 0.813, (−1.5943)+(0.0537)Ser+(− 0.0051)Ala+(−0.3108)Met+(0.0703)Ile+(0.1090)Phe+ (−0.1489)Trp; 0.869, 0.897, 0.803, 0.784, 0.797, 0.875, 0.813, 0.817, (3.1790)+(0.0447)Ser+(−0.0674)Cit+(− 0.1848)Met+(0.1607)Ile+(−0.0544)Leu+(−0.1324)Trp; 0.869, 0.893, 0.826, 0.817, 0.824, 0.840, 0.846, 0.832, (4.0806)+(−0.0912)Asn+(0.0098)Gln+(−0.1333)His+
(0.0236)Thr+(0.1047)Phe+(−0.1234)Trp; 0.869, 0.894,
0.829, 0.834, 0.826, 0.850, 0.808, 0.830, (0.3755)+
(0.0547)Asn+(−0.0756)Ser+(−0.0061)Val+(−0.2286)
Met+(0.1454)Phe+(−0.1318)Trp; 0.869, 0.893, 0.790,
0.777, 0.776, 0.846, 0.816, 0.804, (1.2461)+(0.0423)
Ser+(0.0050)Gln+(−0.1418)His+(−0.0035)Ala+
(0.1239)Phe+(−0.1183)Trp; 0.869, 0.895, 0.780, 0.759,
0.780, 0.836, 0.796, 0.793, (2.1699)+(0.0590)Ser+(−
0.0907)Asn+(−0.1184)His+(0.0057)Pro+(0.1246)Phe+
(−0.1119)Trp; 0.869, 0.896, 0.821, 0.811, 0.790, 0.844,
0.894, 0.835, (3.8316)+(−0.0033)Arg+(−0.0537)Val+
(−0.2892)Met+(0.1854)Ile+(0.1263)Phe+(−0.1106)
Trp; 0.869, 0.896, 0.788, 0.772, 0.751, 0.855, 0.859,
0.809, (0.2904)+(0.0414)Thr+(−0.0711)Val+(−0.5313)
Met+(−0.0041)Lys+(0.2202)Ile+(0.1389)Phe; 0.869,
0.892, 0.750, 0.709, 0.750, 0.818, 0.807, 0.771,
(1.4934)+(0.0466)Ser+(−0.1422)His+(0.0045)Thr+
(0.0540)Ile+(0.0946)Phe+(−0.1361)Trp; 0.869, 0.893,
0.800, 0.783, 0.789, 0.871, 0.815, 0.815, (4.1082)+
(0.0451)Ser+(−0.0842)Asn+(−0.0783)Cit+(0.1465)
Ile+(−0.0537)Leu+(−0.1444)Trp; 0.869, 0.890, 0.770,
0.742, 0.747, 0.875, 0.816, 0.795, (3.1785)+(0.0381)
Ser+(−0.0850)His+(0.0248)Thr+(−0.0407)Val+(−
0.3478)Met+(0.1847)Ile; 0.869, 0.894, 0.805, 0.805,
0.823, 0.824, 0.753, 0.801, (−0.7569)+(0.0403)Ser+
(0.0008)Gln+(0.0252)Thr+(−0.3816)Met+(0.1444)
Phe+(−0.1594)Trp; 0.869, 0.894, 0.780, 0.761, 0.787,
0.844, 0.769, 0.790, (−1.5917)+(0.0454)Ser+(0.0066)
Gln+(−0.1764)His+(0.0279)Thr+(−0.3912)Met+
(0.1740)Phe; 0.869, 0.895, 0.809, 0.809, 0.822, 0.835,
0.763, 0.808, (−0.3426)+(0.0405)Ser+(0.0264)Thr+(−
0.0022)Ala+(−0.3665)Met+(0.1466)Phe+(−0.1574)
Trp; 0.869, 0.894, 0.805, 0.804, 0.823, 0.823, 0.754,
0.801, (−0.4795)+(0.0413)Ser+(0.0282)Thr+(−0.3834)
Met+(−0.0111)Orn+(0.1519)Phe+(−0.1603)Trp; 0.869,
0.895, 0.787, 0.769, 0.786, 0.842, 0.800, 0.799,
(2.3090)+(0.0582)Ser+(−0.0870)Asn+(−0.1185)His+
(0.0006)Val+(0.1287)Phe+(−0.1090)Trp; 0.869, 0.893,
0.817, 0.800, 0.786, 0.865, 0.892, 0.836, (0.5258)+
(0.0100)Gln+(−0.0985)His+(−0.0458)Val+(−0.3722)
Met+(0.1631)Ile+(0.1351)Phe; 0.869, 0.890, 0.824,
0.829, 0.825, 0.843, 0.795, 0.823, (0.2250)+(0.0564)
Ser+(−0.0653)Asn+(−0.0101)Arg+(−0.2300)Met+
(0.1366)Phe+(−0.1375)Trp; 0.869, 0.901, 0.824, 0.809,
0.797, 0.854, 0.898, 0.840, (4.1844)+(−0.0609)Cit+(−
0.0510)Val+(−0.2579)Met+(0.1827)Ile+(0.1353)Phe+
(−0.1182)Trp; 0.868, 0.895, 0.788, 0.771, 0.791, 0.812,
0.809, 0.796, (−1.9994)+(0.0558)Ser+(0.0057)Pro+(−
0.3633)Met+(0.0566)Ile+(0.1109)Phe+(−0.1533)Trp;
0.868, 0.892, 0.754, 0.707, 0.765, 0.838, 0.798, 0.777,
(−1.9080)+(0.0670)Ser+(−0.1511)His+(0.0053)Pro+(−
0.3599)Met+(0.0585)Ile+(0.1410)Phe; 0.868, 0.895,
0.796, 0.780, 0.770, 0.872, 0.842, 0.816, (3.3463)+
(0.0444)Ser+(−0.0119)Arg+(−0.0417)Val+(−0.2311)
Met+(0.1832)Ile+(−0.1109)Trp; 0.868, 0.891, 0.829,
0.827, 0.827, 0.837, 0.833, 0.831, (0.3991)+(0.0648)
Ser+(−0.0667)Asn+(−0.0068)Gly+(−0.2386)Met+
(0.1341)Phe+(−0.1412)Trp; 0.868, 0.896, 0.801, 0.781,
0.802, 0.817, 0.839, 0.810, (−1.5767)+(0.0643)Ser+(−
0.0067)Gly+(−0.3335)Met+(0.0613)Ile+(0.1087)Phe+
(−0.1557)Trp; 0.868, 0.894, 0.811, 0.799, 0.833, 0.844,
0.772, 0.812, (0.0980)+(0.0504)Ser+(−0.1092)Cit+(−
0.2618)Met+(0.0359)Orn+(0.1442)Phe+(−0.1602)Trp;
0.868, 0.889, 0.789, 0.764, 0.779, 0.848, 0.835, 0.806,
(3.2684)+(0.0388)Ser+(−0.0118)Ala+(−0.1003)Cit+
(0.0118)Pro+(0.0864)Ile+(−0.1745)Trp; 0.868, 0.896,
0.785, 0.765, 0.784, 0.845, 0.800, 0.798, (2.3402)+
(0.0569)Ser+(−0.0913)Asn+(−0.1196)His+(0.0126)
Orn+(0.1246)Phe+(−0.1080)Trp; 0.868, 0.891, 0.801,
0.792, 0.776, 0.865, 0.833, 0.817, (6.7713)+(0.0382)
Thr+(−0.0212)Arg+(−0.0496)Val+(−0.2765)Met+
(0.1948)Ile+(−0.1122)Trp; 0.868, 0.891, 0.826, 0.830,
0.822, 0.846, 0.808, 0.826, (0.2060)+(0.0545)Ser+(−
0.0705)Asn+(−0.0012)Ala+(−0.2287)Met+(0.1360)
Phe+(−0.1381)Trp; 0.868, 0.892, 0.782, 0.772, 0.729,
0.838, 0.877, 0.804, (0.9936)+(0.0306)Ser+(−0.0102)
Ala+(−0.0445)Val+(0.1636)Ile+(0.0800)Phe+(−
0.1555)Trp; 0.868, 0.892, 0.777, 0.753, 0.782, 0.842,
0.783, 0.790, (−2.4869)+(0.0571)Ser+(0.0073)Gln+(−
0.1658)His+(0.0106)Pro+(−0.3511)Met+(0.1619)Phe;
0.868, 0.890, 0.802, 0.791, 0.778, 0.860, 0.842, 0.818,
(5.9836)+(0.0294)Thr+(−0.0480)Val+(−0.2963)Met+
(0.0107)Orn+(0.1855)Ile+(−0.1124)Trp; 0.868, 0.895,
0.805, 0.799, 0.804, 0.815, 0.815, 0.808, (−0.8311)+
(0.0652)Ser+(−0.0078)Gly+(0.0120)Pro+(−0.3325)
Met+(0.1286)Phe+(−0.1503)Trp; 0.868, 0.891, 0.779,
0.744, 0.782, 0.851, 0.813, 0.797, (3.4931)+(0.0524)
Ser+(−0.0928)His+(0.0053)Pro+(−0.1883)Met+
(0.0860)Ile+(−0.1064)Trp; 0.868, 0.895, 0.832, 0.839,
0.828, 0.844, 0.815, 0.831, (−0.6892)+(0.0513)Ser+(−
0.0838)Asn+(0.0039)Gln+(−0.2447)Met+(0.1330)
Phe+(−0.1425)Trp; 0.868, 0.890, 0.796, 0.783, 0.745,
0.879, 0.874, 0.820, (4.2472)+(0.0428)Ser+(−0.1132)
Asn+(−0.0063)Ala+(−0.0417)Val+(0.1750)Ile+(−
0.1087)Trp; 0.868, 0.891, 0.761, 0.716, 0.775, 0.842,
0.796, 0.782, (−1.6262)+(0.0675)Ser+(−0.1412)His+(−
0.0439)Cit+(−0.3459)Met+(0.0672)Ile+(0.1438)Phe;
0.868, 0.892, 0.767, 0.744, 0.769, 0.829, 0.778, 0.780,
(2.2937)+(0.0451)Ser+(−0.1366)His+(0.0115)Thr+(−
0.0066)Lys+(0.1247)Phe+(−0.1208)Trp; 0.868, 0.894,
0.774, 0.754, 0.767, 0.840, 0.795, 0.789, (2.2525)+
(0.0447)Ser+(−0.1350)His+(0.0112)Thr+(−0.0038)
Ala+(0.1265)Phe+(−0.1230)Trp; 0.867, 0.891, 0.757,
0.715, 0.756, 0.819, 0.825, 0.779, (1.5060)+(0.0542)
Ser+(−0.0038)Gly+(−0.1366)His+(0.0553)Ile+
(0.0939)Phe+(−0.1360)Trp; 0.867, 0.893, 0.780, 0.755,
0.782, 0.838, 0.802, 0.794, (2.2478)+(0.0581)Ser+(−
0.0838)Asn+(−0.1233)His+(0.0115)Leu+(0.1186)
Phe+(−0.1141)Trp; 0.867, 0.889, 0.777, 0.753, 0.774,
0.841, 0.804, 0.793, (2.0388)+(0.0493)Ser+(−0.1334)
His+(−0.0039)Ala+(0.0052)Val+(0.1209)Phe+(−
0.1200)Trp; 0.867, 0.891, 0.753, 0.722, 0.772, 0.831,
0.741, 0.767, (−0.8189)+(0.0563)Ser+(−0.1611)His+
(0.0269)Thr+(0.0098)Pro+(−0.4047)Met+(0.1707)
Phe; 0.867, 0.895, 0.803, 0.802, 0.823, 0.824, 0.751,
0.800, (−0.5658)+(0.0414)Ser+(0.0253)Thr+(0.0018)
Tyr+(−0.3805)Met+(0.1444)Phe+(−0.1591)Trp; 0.867,
0.895, 0.792, 0.772, 0.789, 0.843, 0.814, 0.804,
(2.4275)+(0.0621)Ser+(−0.0859)Asn+(−0.0031)Gly+
(−0.1151)His+(0.1283)Phe+(−0.1105)Trp; 0.867,
0.891, 0.752, 0.712, 0.751, 0.820, 0.811, 0.774,
(1.4074)+(0.0485)Ser+(−0.1393)His+(−0.0010)Pro+
(0.0563)Ile+(0.0949)Phe+(−0.1333)Trp; 0.867, 0.893,
0.794, 0.778, 0.794, 0.817, 0.820, 0.802, (−1.9288)+
(0.0564)Ser+(−0.3435)Met+(−0.0160)Orn+(0.0684)
Ile+(0.1169)Phe+(−0.1541)Trp; 0.867, 0.896, 0.793,
0.775, 0.794, 0.850, 0.794, 0.803, (2.3480)+(0.0613)
Ser+(−0.0851)Asn+(−0.1000)His+(−0.0562)Cit+
(0.1417)Phe+(−0.1226)Trp; 0.867, 0.891, 0.770, 0.749,
0.760, 0.826, 0.805, 0.785, (−0.0684)+(0.0424)Ser+(−
0.1171)Cit+(0.1614)Ile+(−0.0751)Leu+(0.1005)Phe+
(−0.1877)Trp; 0.867, 0.890, 0.821, 0.824, 0.821, 0.837,
0.803, 0.821, (0.0351)+(0.0542)Ser+(−0.0729)Asn+(−

0.2437)Met+(0.0031)Lys+(0.1343)Phe+(−0.1420)Trp; 0.867, 0.891, 0.758, 0.713, 0.766, 0.840, 0.801, 0.780, (−1.6511)+(0.0665)Ser+(−0.0078)Asn+(−0.1508)His+ (−0.3388)Met+(0.0649)Ile+(0.1399)Phe; 0.867, 0.888, 0.790, 0.757, 0.799, 0.838, 0.824, 0.804, (0.1367)+ (0.0102)Gln+(−0.1786)His+(0.0394)Thr+(−0.4136) Met+(0.0524)Ile+(0.1319)Phe; 0.867, 0.892, 0.801, 0.786, 0.785, 0.856, 0.836, 0.816, (2.6511)+(0.0525) Ser+(−0.0066)Gly+(−0.2160)Met+(0.1593)Ile+(− 0.0571)Leu+(−0.1317)Trp; 0.867, 0.892, 0.774, 0.753, 0.772, 0.828, 0.794, 0.787, (1.3292)+(0.0396)Ser+ (0.0043)Gln+(−0.1484)His+(0.0066)Thr+(0.1172) Phe+(−0.1250)Trp; 0.867, 0.893, 0.800, 0.798, 0.806, 0.823, 0.774, 0.800, (−0.8880)+(0.0556)Ser+(−0.0141) Arg+(0.0115)Pro+(−0.3189)Met+(0.1333)Phe+(− 0.1456)Trp; 0.867, 0.891, 0.758, 0.711, 0.766, 0.840, 0.804, 0.780, (−1.7131)+(0.0671)Ser+(−0.0009)Gly+ (−0.1512)His+(−0.3443)Met+(0.0654)Ile+(0.1392) Phe; 0.866, 0.893, 0.787, 0.769, 0.784, 0.842, 0.800, 0.799, (2.2796)+(0.0581)Ser+(−0.0901)Asn+(− 0.1183)His+(0.0017)Lys+(0.1287)Phe+(−0.1095)Trp; 0.866, 0.889, 0.761, 0.734, 0.766, 0.822, 0.778, 0.775, (2.0257)+(0.0449)Ser+(−0.1406)His+(0.0087)Thr+ (0.0023)Val+(0.1167)Phe+(−0.1265)Trp; 0.866, 0.893, 0.758, 0.714, 0.766, 0.840, 0.800, 0.780, (−1.6271)+ (0.0678)Ser+(−0.1484)His+(−0.3320)Met+(−0.0062) Lys+(0.0684)Ile+(0.1411)Phe; 0.866, 0.890, 0.787, 0.757, 0.780, 0.862, 0.828, 0.807, (3.6922)+(0.0512) Ser+(−0.0915)His+(−0.0033)Ala+(−0.1574)Met+ (0.0972)Ile+(−0.1026)Trp; 0.866, 0.891, 0.795, 0.792, 0.797, 0.815, 0.784, 0.797, (−1.2230)+(0.0532)Ser+ (0.0113)Pro+(−0.3405)Met+(0.0012)Lys+(0.1306) Phe+(−0.1485)Trp; 0.866, 0.892, 0.777, 0.753, 0.772, 0.841, 0.806, 0.793, (2.0937)+(0.0472)Ser+(−0.1310) His+(−0.0036)Ala+(0.0119)Orn+(0.1224)Phe+(− 0.1156)Trp; 0.866, 0.894, 0.840, 0.838, 0.836, 0.858, 0.841, 0.843, (2.0299)+(0.0044)Gly+(0.0119)Gln+(− 0.1319)His+(−0.2072)Met+(0.1476)Phe+(−0.1045) Trp; 0.866, 0.892, 0.784, 0.767, 0.776, 0.836, 0.805, 0.796, (1.2252)+(0.0426)Ser+(0.0051)Gln+(−0.1436) His+(−0.0054)Lys+(0.1216)Phe+(−0.1167)Trp; 0.866, 0.890, 0.785, 0.751, 0.791, 0.860, 0.806, 0.802, (3.7885)+(0.0526)Ser+(−0.0815)His+(−0.0435)Cit+(− 0.1576)Met+(0.0935)Ile+(−0.1113)Trp; 0.866, 0.892, 0.791, 0.775, 0.793, 0.844, 0.791, 0.801, (2.4370)+ (0.0597)Ser+(−0.0754)Asn+(−0.1162)His+(−0.0134) Arg+(0.1334)Phe+(−0.1076)Trp; 0.866, 0.888, 0.801, 0.785, 0.785, 0.825, 0.862, 0.814, (3.1208)+(0.0076) Gln+(−0.1219)His+(0.0989)Ile+(−0.0386)Leu+ (0.0840)Phe+(−0.1265)Trp; 0.866, 0.894, 0.793, 0.776, 0.795, 0.823, 0.813, 0.802, (−1.7476)+(0.0555)Ser+(− 0.3303)Met+(−0.0055)Lys+(0.0653)Ile+(0.1103)Phe+ (−0.1483)Trp; 0.866, 0.895, 0.757, 0.721, 0.760, 0.828, 0.798, 0.777, (1.4925)+(0.0554)Ser+(−0.1343)His+(− 0.0241)Arg+(0.0596)Ile+(0.1037)Phe+(−0.1320)Trp; 0.866, 0.891, 0.795, 0.773, 0.814, 0.856, 0.771, 0.803, (3.0257)+(0.0414)Ser+(0.0176)Thr+(−0.0784)Cit+(− 0.2548)Met+(0.0840)Ile+(−0.1531)Trp; 0.866, 0.890, 0.776, 0.753, 0.775, 0.830, 0.802, 0.790, (1.0534)+ (0.0417)Ser+(0.0049)Gln+(−0.1499)His+(0.0040)Val+ (0.1119)Phe+(−0.1245)Trp; 0.866, 0.889, 0.817, 0.800, 0.799, 0.851, 0.876, 0.832, (3.5835)+(0.0088)Gln+(− 0.1319)His+(−0.0062)Ala+(0.0581)Ile+(0.0803)Phe+ (−0.1303)Trp; 0.866, 0.889, 0.771, 0.744, 0.770, 0.828, 0.806, 0.787, (1.0660)+(0.0421)Ser+(−0.0048)Gln+(− 0.1523)His+(0.0147)Leu+(0.1045)Phe+(−0.1284)Trp; 0.866, 0.890, 0.825, 0.825, 0.832, 0.841, 0.795, 0.823, (−0.8342)+(0.0482)Ser+(0.0037)Gln+(−0.0860)Cit+(− 0.2778)Met+(0.1531)Phe+(−0.1566)Trp; 0.866, 0.895, 0.843, 0.838, 0.841, 0.846, 0.859, 0.846, (2.3031)+ (0.0124)Gln+(−0.1264)His+(0.0070)Pro+(−0.2170) Met+(0.1381)Phe+(−0.1083)Trp; 0.866, 0.889, 0.804, 0.792, 0.779, 0.871, 0.839, 0.821, (2.8020)+(0.0416) Ser+(−0.0058)Ala+(−0.1867)Met+(0.1731)Ile+(− 0.0597)Leu+(−0.1252)Trp; 0.865, 0.888, 0.784, 0.750, 0.784, 0.855, 0.826, 0.804, (3.5909)+(0.0564)Ser+(− 0.0033)Gly+(−0.0910)His+(−0.1714)Met+(0.0910) Ile+(−0.1063)Trp; 0.865, 0.893, 0.794, 0.779, 0.798, 0.821, 0.808, 0.802, (−1.6680)+(0.0575)Ser+(−0.0151) Arg+(−0.3253)Met+(0.0635)Ile+(0.1129)Phe+(− 0.1509)Trp; 0.865, 0.889, 0.781, 0.747, 0.782, 0.854, 0.815, 0.800, (3.5323)+(0.0511)Ser+(−0.0958)His+(− 0.1835)Met+(0.0037)Lys+(0.0906)Ile+(−0.1071)Trp; 0.865, 0.892, 0.798, 0.797, 0.799, 0.816, 0.787, 0.800, (−1.4158)+(0.0521)Ser+(0.0010)Gln+(0.0110)Pro+(− 0.3405)Met+(0.1305)Phe+(−0.1484)Trp; 0.865, 0.895, 0.769, 0.749, 0.778, 0.834, 0.754, 0.779, (2.5338)+ (0.0471)Ser+(−0.1358)His+(0.0176)Thr+(−0.0274) Arg+(0.1296)Phe+(−0.1266)Trp; 0.865, 0.891, 0.804, 0.790, 0.766, 0.843, 0.894, 0.823, (5.5204)+(−0.0756) His+(−0.0068)Ala+(−0.0341)Val+(0.1401)Ile+ (0.0910)Phe+(−0.1166)Trp; 0.865, 0.891, 0.757, 0.713, 0.765, 0.840, 0.801, 0.779, (−1.7494)+(0.0664)Ser+(− 0.1512)His+(−0.3463)Met+(−0.0033)Orn+(0.0665) Ile+(0.1411)Phe; 0.865, 0.890, 0.773, 0.745, 0.768, 0.840, 0.810, 0.791, (2.0372)+(0.0496)Ser+(−0.1359) His+(−0.0044)Ala+(0.0178)Leu+(0.1135)Phe+(− 0.1237)Trp; 0.865, 0.895, 0.795, 0.773, 0.801, 0.823, 0.819, 0.804, (−2.0581)+(0.0556)Ser+(0.0151)Tyr+(− 0.3670)Met+(0.0633)Ile+(0.1059)Phe+(−0.1563)Trp; 0.865, 0.890, 0.758, 0.731, 0.762, 0.823, 0.776, 0.773, (1.9326)+(0.0456)Ser+(−0.1383)His+(0.0072)Thr+ (0.0036)Pro+(0.1169)Phe+(−0.1262)Trp; 0.865, 0.889, 0.791, 0.769, 0.797, 0.826, 0.809, 0.800, (1.3487)+ (0.0550)Ser+(−0.1235)Asn+(−0.1030)Cit+(0.0544) Ile+(0.0926)Phe+(−0.1805)Trp; 0.865, 0.890, 0.771, 0.750, 0.766, 0.827, 0.797, 0.785, (1.0884)+(0.0423) Ser+(0.0045)Gln+(−0.1457)His+(0.0039)Pro+(0.1143) Phe+(−0.1238)Trp; 0.865, 0.889, 0.809, 0.788, 0.838, 0.817, 0.799, 0.811, (2.9169)+(0.0417)Thr+(−0.0943) Cit+(−0.3517)Met+(0.0567)Ile+(0.1356)Phe+(− 0.1834)Trp; 0.865, 0.888, 0.796, 0.781, 0.791, 0.853, 0.804, 0.807, (−1.7952)+(0.0557)Ser+(−0.0577)Asn+ (0.0089)Gln+(−0.1605)His+(−0.2676)Met+(0.1623) Phe; 0.865, 0.892, 0.786, 0.774, 0.779, 0.837, 0.793, 0.796, (2.2847)+(0.0586)Ser+(−0.0854)Asn+(− 0.1150)His+(−0.0190)Tyr+(0.1393)Phe+(−0.1025)Trp; 0.865, 0.890, 0.780, 0.759, 0.773, 0.846, 0.801, 0.795, (2.1048)+(0.0494)Ser+(−0.1277)His+(−0.0031)Ala+ (−0.0024)Lys+(0.1286)Phe+(−0.1141)Trp; 0.865, 0.889, 0.769, 0.742, 0.772, 0.821, 0.799, 0.783, (2.2494)+(0.0499)Ser+(−0.0043)Gly+(−0.1359)His+ (0.0106)Thr+(0.1185)Phe+(−0.1282)Trp; 0.865, 0.888, 0.805, 0.784, 0.803, 0.866, 0.823, 0.819, (2.9717)+ (0.0465)Ser+(−0.0060)Ala+(−0.0755)Cit+(−0.1622) Met+(0.0960)Ile+(−0.1444)Trp; 0.865, 0.892, 0.852, 0.849, 0.848, 0.857, 0.864, 0.854, (2.5117)+(−0.0105) Asn+(0.0128)Gln+(−0.1258)His+(−0.1885)Met+ (0.1391)Phe+(−0.1051)Trp; 0.865, 0.893, 0.799, 0.796, 0.819, 0.820, 0.753, 0.797, (−0.7088)+(0.0421)Ser+ (0.0252)Thr+(−0.3842)Met+(0.0058)Leu+(0.1397) Phe+(−0.1608)Trp; 0.865, 0.890, 0.751, 0.711, 0.748, 0.819, 0.812, 0.772, (1.3571)+(0.0491)Ser+(−0.1387) His+(−0.0035)Orn+(0.0561)Ile+(0.0958)Phe+(−

0.1340)Trp; 0.865, 0.893, 0.845, 0.835, 0.844, 0.857, 0.867, 0.851, (2.3748)+(0.0127)Gln+(−0.1335)His+(−0.2057)Met+(0.0145)Leu+(0.1299)Phe+(−0.1120)Trp; 0.865, 0.891, 0.757, 0.714, 0.767, 0.837, 0.791, 0.777, (−1.6794)+(0.0690)Ser+(−0.1484)His+(−0.0117)Arg+(−0.3335)Met+(0.0656)Ile+(0.1416)Phe; 0.865, 0.894, 0.794, 0.782, 0.792, 0.842, 0.796, 0.803, (0.9549)+(0.0446)Ser+(0.0073)Gln+(−0.1453)His+(−0.0274)Arg+(0.1274)Phe+(−0.1172)Trp; 0.865, 0.889, 0.821, 0.817, 0.829, 0.835, 0.806, 0.821, (0.1829)+(0.0577)Ser+(−0.0039)Gly+(−0.0750)Cit+(−0.2586)Met+(0.1518)Phe+(−0.1545)Trp; 0.865, 0.891, 0.821, 0.824, 0.823, 0.839, 0.799, 0.821, (0.0942)+(0.0544)Ser+(−0.0720)Asn+(−0.2377)Met+(0.0051)Orn+(0.1323)Phe+(−0.1393)Trp; 0.865, 0.890, 0.786, 0.766, 0.781, 0.828, 0.823, 0.799, (1.2183)+(0.0475)Ser+(−0.0045)Gly+(0.0052)Gln+(−0.1433)His+(0.1159)Phe+(−0.1227)Trp; 0.865, 0.888, 0.781, 0.751, 0.782, 0.830, 0.823, 0.796, (2.7991)+(−0.1308)His+(0.0387)Thr+(−0.3675)Met+(0.1279)Ile+(−0.0562)Leu+(0.1397)Phe; 0.864, 0.889, 0.804, 0.791, 0.823, 0.839, 0.772, 0.806, (2.3497)+(0.0518)Ser+(−0.1359)Asn+(−0.1254)Cit+(0.0433)Orn+(0.1044)Phe+(−0.1673)Trp; 0.864, 0.890, 0.779, 0.745, 0.783, 0.851, 0.810, 0.797, (3.5422)+(0.0504)Ser+(−0.0975)His+(−0.1768)Met+(0.0137)Orn+(0.0882)Ile+(−0.1053)Trp; 0.864, 0.892, 0.797, 0.793, 0.802, 0.817, 0.786, 0.799, (−1.2270)+(0.0537)Ser+(0.0110)Pro+(0.0054)Tyr+(−0.3440)Met+(0.1298)Phe+(−0.1487)Trp; 0.864, 0.888, 0.782, 0.749, 0.774, 0.863, 0.827, 0.803, (4.2658)+(0.0461)Ser+(−0.0854)His+(−0.0063)Ala+(−0.0595)Cit+(0.0951)Ile+(−0.1256)Trp; 0.864, 0.891, 0.751, 0.719, 0.744, 0.816, 0.806, 0.771, (1.3876)+(0.0483)Ser+(−0.1346)His+(−0.0247)Tyr+(0.0557)Ile+(0.1074)Phe+(−0.1254)Trp; 0.864, 0.887, 0.791, 0.766, 0.788, 0.822, 0.842, 0.804, (3.4080)+(0.0072)Gln+(−0.1453)His+(0.0132)Thr+(0.0462)Ile+(0.0770)Phe+(−0.1387)Trp; 0.864, 0.888, 0.815, 0.812, 0.826, 0.838, 0.783, 0.815, (0.0448)+(0.0526)Ser+(−0.0812)Cit+(−0.2603)Met+(−0.0002)Lys+(0.1539)Phe+(−0.1533)Trp; 0.864, 0.884, 0.775, 0.750, 0.743, 0.856, 0.847, 0.799, (4.2402)+(0.0376)Ser+(−0.0802)His+(−0.0058)Ala+(−0.0245)Val+(0.1442)Ile+(−0.1113)Trp; 0.864, 0.889, 0.782, 0.750, 0.782, 0.854, 0.815, 0.800, (3.6743)+(0.0522)Ser+(−0.0094)Asn+(−0.0924)His+(−0.1661)Met+(0.0914)Ile+(−0.1051)Trp; 0.864, 0.888, 0.820, 0.803, 0.812, 0.838, 0.866, 0.830, (5.0566)+(−0.0729)His+(−0.1924)Met+(0.1327)Ile+(−0.0570)Leu+(0.1232)Phe+(−0.1063)Trp; 0.864, 0.893, 0.793, 0.777, 0.794, 0.818, 0.815, 0.801, (−2.0466)+(0.0535)Ser+(0.0008)Gln+(−0.3468)Met+(0.0622)Ile+(0.1090)Phe+(−0.1534)Trp; 0.864, 0.889, 0.825, 0.825, 0.823, 0.829, 0.826, 0.826, (−0.1857)+(0.0596)Ser+(−0.0072)Gly+(−0.0043)Val+(−0.2817)Met+(0.1400)Phe+(−0.1423)Trp; 0.864, 0.886, 0.767, 0.739, 0.769, 0.847, 0.778, 0.784, (−0.8531)+(0.0651)Ser+(−0.1440)His+(−0.0039)Ala+(0.0146)Pro+(−0.3181)Met+(0.1608)Phe; 0.864, 0.886, 0.759, 0.730, 0.762, 0.822, 0.782, 0.774, (1.7703)+(0.0486)Ser+(−0.1357)His+(0.0044)Pro+(0.0018)Val+(0.1145)Phe+(−0.1240)Trp; 0.864, 0.889, 0.770, 0.736, 0.767, 0.851, 0.803, 0.790, (4.0197)+(0.0434)Ser+(−0.0798)His+(−0.0580)Cit+(0.1226)Ile+(−0.0301)Leu+(−0.1288)Trp; 0.864, 0.889, 0.817, 0.815, 0.826, 0.840, 0.788, 0.817, (0.1084)+(0.0522)Ser+(−0.0008)Ala+(−0.0807)Cit+(−0.2550)Met+(0.1540)Phe+(−0.1526)Trp; 0.864, 0.892, 0.824, 0.826, 0.825, 0.842, 0.805, 0.825, (0.0360)+(0.0550)Ser+(−0.0689)Asn+(0.0075)Tyr+(−0.2492)Met+(0.1334)Phe+(−0.1414)Trp; 0.864, 0.892, 0.849, 0.846, 0.846, 0.856, 0.861, 0.852, (2.4120)+(0.0126)Gln+(−0.1277)His+(0.0002)Ala+(−0.1968)Met+(0.1405)Phe+(−0.1055)Trp; 0.864, 0.890, 0.764, 0.737, 0.783, 0.837, 0.741, 0.775, (0.0799)+(0.0530)Ser+(−0.1604)His+(0.0323)Thr+(−0.3660)Met+(−0.0063)Lys+(0.1763)Phe; 0.864, 0.889, 0.797, 0.776, 0.791, 0.861, 0.822, 0.812, (1.8167)+(0.0463)Ser+(0.0346)Tyr+(−0.2758)Met+(0.1638)Ile+(−0.0597)Leu+(−0.1427)Trp; 0.864, 0.888, 0.810, 0.801, 0.823, 0.832, 0.789, 0.811, (−0.1720)+(0.0535)Ser+(−0.0842)Cit+(−0.2714)Met+(0.0110)Leu+(0.1461)Phe+(−0.1599)Trp; 0.864, 0.891, 0.795, 0.792, 0.798, 0.815, 0.785, 0.797, (−1.1994)+(0.0534)Ser+(0.0111)Pro+(−0.3373)Met+(0.0010)Leu+(0.1301)Phe+(−0.1479)Trp; 0.864, 0.888, 0.754, 0.718, 0.762, 0.820, 0.782, 0.771, (2.0064)+(0.0451)Ser+(−0.1450)His+(0.0090)Thr+(0.0141)Leu+(0.1073)Phe+(−0.1317)Trp; 0.864, 0.887, 0.794, 0.769, 0.784, 0.857, 0.832, 0.811, (3.2807)+(0.0414)Ser+(−0.0853)Asn+(0.0072)Gln+(−0.1132)His+(0.0727)Ile+(−0.1148)Trp; 0.864, 0.889, 0.820, 0.803, 0.810, 0.841, 0.872, 0.831, (3.5412)+(−0.0498)Asn+(0.0104)Gln+(−0.1311)His+(0.0461)Ile+(0.0770)Phe+(−0.1270)Trp; 0.864, 0.888, 0.815, 0.812, 0.826, 0.837, 0.784, 0.815, (0.0255)+(0.0526)Ser+(−0.0815)Cit+(0.0003)Val+(−0.2612)Met+(0.1534)Phe+(−0.1539)Trp; 0.864, 0.887, 0.774, 0.750, 0.746, 0.858, 0.838, 0.798, (4.6036)+(0.0464)Ser+(−0.0829)Asn+(−0.0690)His+(−0.0291)Val+(0.1429)Ile+(−0.1011)Trp; 0.864, 0.883, 0.785, 0.761, 0.768, 0.854, 0.836, 0.805, (3.3127)+(0.0353)Ser+(0.0049)Gln+(−0.1169)His+(−0.0056)Ala+(0.0838)Ile+(−0.1203)Trp; 0.864, 0.892, 0.844, 0.840, 0.841, 0.848, 0.860, 0.847, (2.0904)+(0.0121)Gln+(−0.1342)His+(−0.2275)Met+(0.0111)Lys+(0.1425)Phe+(−0.1118)Trp; 0.863, 0.886, 0.784, 0.757, 0.779, 0.815, 0.841, 0.798, (4.9673)+(−0.1107)His+(0.0156)Thr+(0.0966)Ile+(−0.0378)Leu+(0.0869)Phe+(−0.1312)Trp; 0.863, 0.885, 0.792, 0.775, 0.767, 0.827, 0.866, 0.809, (3.5146)+(0.0063)Gln+(−0.1107)His+(−0.0256)Val+(0.1070)Ile+(0.0825)Phe+(−0.1245)Trp; 0.863, 0.891, 0.757, 0.712, 0.764, 0.839, 0.801, 0.779, (−1.6709)+(0.0656)Ser+(−0.1514)His+(−0.0041)Tyr+(−0.3390)Met+(0.0655)Ile+(0.1408)Phe; 0.863, 0.892, 0.849, 0.844, 0.846, 0.853, 0.863, 0.851, (2.4047)+(0.0126)Gln+(−0.1304)His+(0.0029)Val+(−0.1969)Met+(0.1366)Phe+(−0.1080)Trp; 0.863, 0.887, 0.774, 0.747, 0.757, 0.817, 0.850, 0.793, (4.8935)+(−0.1028)His+(0.0174)Thr+(−0.0298)Val+(0.1160)Ile+(0.0854)Phe+(−0.1281)Trp; 0.863, 0.885, 0.780, 0.755, 0.759, 0.856, 0.837, 0.802, (4.1227)+(0.0399)Ser+(−0.0899)His+(−0.0061)Ala+(0.1284)Ile+(−0.0302)Leu+(−0.1135)Trp; 0.863, 0.884, 0.765, 0.734, 0.751, 0.845, 0.817, 0.787, (4.2121)+(0.0410)Ser+(−0.0738)His+(−0.0527)Cit+(−0.0233)Val+(0.1356)Ile+(−0.1258)Trp; 0.863, 0.885, 0.780, 0.748, 0.781, 0.850, 0.814, 0.798, (3.0084)+(0.0371)Ser+(0.0059)Gln+(−0.1080)His+(−0.0611)Cit+(0.0802)Ile+(−0.1360)Trp; 0.863, 0.882, 0.803, 0.790, 0.765, 0.863, 0.875, 0.823, (6.3790)+(0.0162)Thr+(−0.0087)Ala+(−0.0729)Cit+(−0.0371)Val+(0.1714)Ile+(−0.1424)Trp; 0.863, 0.885, 0.783, 0.768, 0.732, 0.889, 0.849, 0.810, (1.5650)+(0.0333)Ser+(0.0217)Thr+(−0.0059)Ala+(−0.0563)Val+(−0.3799)Met+(0.2184)Ile; 0.863, 0.887, 0.792, 0.775, 0.751, 0.867, 0.868, 0.815, (4.3520)+(0.0524)Ser+(−0.1265)Asn+(−0.0061)Gly+(−0.0420)Val+(0.1596)Ile+(−0.1160)Trp; 0.863, 0.889, 0.762, 0.736, 0.763, 0.826, 0.784, 0.777, (1.8943)+(0.0496)Ser+(−0.1317)
His+(0.0052)Pro+(−0.0045)Lys+(0.1201)Phe+(−
0.1193)Trp; 0.863, 0.888, 0.783, 0.760, 0.776, 0.840,
0.817, 0.798, (2.1571)+(0.0537)Ser+(−0.0036)Gly+(−
0.1260)His+(−0.0031)Ala+(0.1256)Phe+(−0.1177)
Trp; 0.863, 0.888, 0.800, 0.789, 0.766, 0.839, 0.874,
0.817, (4.9568)+(−0.1417)Asn+(0.0221)Thr+(−
0.0505)Val+(0.1538)Ile+(0.0842)Phe+(−0.1306)Trp;
0.863, 0.885, 0.774, 0.749, 0.760, 0.852, 0.812, 0.793,
(3.4650)+(0.0302)Ser+(−0.1034)Cit+(−0.0349)Val+
(0.0353)Orn+(0.1427)Ile+(−0.1640)Trp; 0.863, 0.895,
0.811, 0.805, 0.802, 0.845, 0.820, 0.818, (−0.5507)+
(0.0517)Ser+(−0.0339)Val+(−0.3204)Met+(0.0609)
Leu+(0.1370)Phe+(−0.1400)Trp; 0.863, 0.890, 0.768,
0.743, 0.769, 0.831, 0.788, 0.783, (2.0556)+(0.0477)
Ser+(−0.1327)His+(0.0113)Orn+(−0.0050)Lys+
(0.1201)Phe+(−0.1146)Trp; 0.863, 0.890, 0.818, 0.824,
0.818, 0.835, 0.792, 0.817, (−0.4446)+(0.0488)Ser+(−
0.0006)Ala+(−0.0046)Val+(−0.2805)Met+(0.1422)
Phe+(−0.1403)Trp; 0.863, 0.889, 0.813, 0.800, 0.787,
0.841, 0.879, 0.827, (5.5709)+(−0.0835)His+(−0.0070)
Ala+(0.1302)Ile+(−0.0527)Leu+(0.0937)Phe+(−
0.1185)Trp; 0.863, 0.888, 0.815, 0.812, 0.826, 0.838,
0.784, 0.815, (0.0233)+(0.0525)Ser+(−0.0816)Cit+
(0.0007)Arg+(−0.2617)Met+(0.1538)Phe+(−0.1536)
Trp; 0.863, 0.884, 0.771, 0.738, 0.757, 0.850, 0.829,
0.794, (4.0266)+(0.0428)Ser+(−0.1045)His+(−0.0070)
Ala+(0.0064)Pro+(0.0814)Ile+(−0.1189)Trp; 0.863,
0.889, 0.754, 0.719, 0.774, 0.833, 0.745, 0.768,
(−0.4550)+(0.0535)Ser+(−0.1693)His+(0.0310)Thr+
(−0.3949)Met+(0.0155)Leu+(0.1606)Phe; 0.863,
0.887, 0.792, 0.780, 0.780, 0.852, 0.806, 0.805,
(2.6565)+(0.0384)Ser+(0.0084)Thr+(−0.2437)Met+
(0.1554)Ile+(−0.0546)Leu+(−0.1348)Trp; 0.863,
0.889, 0.794, 0.766, 0.784, 0.839, 0.853, 0.811,
(5.7173)+(−0.1214)His+(0.0225)Thr+(−0.0070)Ala+
(0.0585)Ile+(0.0849)Phe+(−0.1386)Trp; 0.863, 0.888,
0.816, 0.821, 0.818, 0.829, 0.789, 0.814, (−0.5584)+
(0.0482)Ser+(−0.0058)Val+(−0.2932)Met+(0.0033)
Lys+(0.1427)Phe+(−0.1425)Trp; 0.863, 0.891, 0.818,
0.818, 0.819, 0.834, 0.803, 0.818, (−0.0585)+(0.0554)
Ser+(−0.0692)Asn+(−0.2448)Met+(0.0061)Leu+
(0.1296)Phe+(−0.1422)Trp; 0.863, 0.889, 0.801, 0.785,
0.773, 0.833, 0.879, 0.818, (5.7446)+(−0.0428)Asn+(−
0.0718)His+(−0.0356)Val+(0.1300)Ile+(0.0895)Phe+
(−0.1126)Trp; 0.863, 0.889, 0.768, 0.740, 0.773, 0.829,
0.786, 0.782, (2.0007)+(0.0496)Ser+(−0.1342)His+
(0.0043)Val+(−0.0052)Lys+(0.1190)Phe+(−0.1184)
Trp; 0.863, 0.891, 0.820, 0.814, 0.834, 0.843, 0.791,
0.821, (−0.0691)+(0.0532)Ser+(−0.0814)Cit+(0.0147)
Tyr+(−0.2826)Met+(0.1505)Phe+(−0.1569)Trp; 0.863,
0.890, 0.777, 0.758, 0.771, 0.830, 0.800, 0.790,
(1.1804)+(0.0412)Ser+(0.0046)Gln+(−0.1460)His+
(0.0048)Orn+(0.1157)Phe+(−0.1208)Trp; 0.863, 0.889,
0.767, 0.737, 0.767, 0.823, 0.801, 0.782, (1.9300)+
(0.0545)Ser+(−0.0042)Gly+(−0.1310)His+(0.0055)
Pro+(0.1147)Phe+(−0.1255)Trp; 0.862, 0.890, 0.815,
0.807, 0.827, 0.820, 0.808, 0.815, (3.0045)+(0.0478)
Thr+(−0.0476)Val+(−0.4018)Met+(0.0773)Leu+
(0.1444)Phe+(−0.1555)Trp; 0.862, 0.890, 0.762, 0.737,
0.765, 0.826, 0.778, 0.777, (2.0560)+(0.0441)Ser+(−
0.1392)His+(0.0082)Thr+(0.0052)Orn+(0.1178)Phe+
(−0.1241)Trp; 0.862, 0.883, 0.811, 0.795, 0.793, 0.852,
0.864, 0.826, (0.0062)+(0.0116)Gln+(−0.1305)His+(−
0.3134)Met+(0.1368)Ile+(−0.0627)Leu+(0.1303)Phe;
0.862, 0.886, 0.805, 0.785, 0.794, 0.865, 0.835, 0.820,
(3.9584)+(0.0461)Ser+(−0.0734)Asn+(−0.0072)Ala+
(−0.0832)Cit+(0.0874)Ile+(−0.1536)Trp; 0.862, 0.888,
0.783, 0.757, 0.787, 0.846, 0.800, 0.797, (−2.2507)+
(0.0539)Ser+(0.0077)Gln+(−0.1716)His+(−0.3210)
Met+(0.0132)Leu+(0.1530)Phe; 0.862, 0.890, 0.764,
0.741, 0.789, 0.840, 0.719, 0.772, (0.1342)+(0.0545)
Ser+(−0.1584)His+(0.0363)Thr+(−0.0227)Arg+(−
0.3686)Met+(0.1778)Phe; 0.862, 0.888, 0.830, 0.827,
0.820, 0.848, 0.843, 0.835, (3.3589)+(−0.0610)Asn+
(0.0034)Gly+(0.0107)Gln+(−0.1298)His+(0.1065)
Phe+(−0.1130)Trp; 0.862, 0.888, 0.818, 0.812, 0.768,
0.854, 0.911, 0.836, (5.0118)+(−0.0713)Asn+(−
0.0075)Ala+(−0.0478)Val+(0.1664)Ile+(0.0865)Phe+
(−0.1230)Trp; 0.862, 0.892, 0.796, 0.793, 0.800, 0.813,
0.786, 0.798, (−1.1707)+(0.0540)Ser+(0.0117)Pro+(−
0.3362)Met+(−0.0057)Orn+(0.1339)Phe+(−0.1477)
Trp; 0.862, 0.886, 0.807, 0.793, 0.808, 0.826, 0.829,
0.814, (3.7059)+(0.0079)Gln+(−0.1425)His+(0.0180)
Thr+(−0.0058)Lys+(0.1061)Phe+(−0.1258)Trp; 0.862,
0.886, 0.780, 0.762, 0.750, 0.889, 0.810, 0.803,
(2.0491)+(0.0334)Ser+(0.0249)Thr+(−0.0577)Cit+(−
0.0553)Val+(−0.4016)Met+(0.2076)Ile; 0.862, 0.885,
0.806, 0.784, 0.798, 0.831, 0.861, 0.819, (3.3636)+
(0.0091)Gln+(−0.1363)His+(−0.0053)Lys+(0.0507)
Ile+(0.0776)Phe+(−0.1297)Trp; 0.862, 0.894, 0.855,
0.850, 0.855, 0.863, 0.864, 0.858, (2.2508)+(0.0135)
Gln+(−0.1156)His+(−0.0544)Cit+(−0.1821)Met+
(0.1518)Phe+(−0.1151)Trp; 0.862, 0.891, 0.821, 0.823,
0.824, 0.837, 0.797, 0.820, (−0.5815)+(0.0496)Ser+
(0.0134)Tyr+(−0.0052)Val+(−0.3040)Met+(0.1399)
Phe+(−0.1435)Trp; 0.862, 0.888, 0.759, 0.742, 0.756,
0.819, 0.766, 0.771, (2.0936)+(0.0434)Ser+(−0.1355)
His+(0.0137)Thr+(−0.0302)Tyr+(0.1349)Phe+(−
0.1183)Trp; 0.862, 0.888, 0.793, 0.771, 0.806, 0.843,
0.788, 0.802, (2.7887)+(0.0484)Ser+(−0.0749)Cit+
(0.0067)Pro+(−0.2175)Met+(0.0776)Ile+(−0.1531)
Trp; 0.862, 0.891, 0.767, 0.740, 0.779, 0.836, 0.761,
0.779, (2.1649)+(0.0468)Ser+(−0.1226)His+(0.0155)
Thr+(−0.0671)Cit+(0.1359)Phe+(−0.1458)Trp; 0.862,
0.886, 0.788, 0.770, 0.790, 0.845, 0.792, 0.799,
(−2.0421)+(0.0523)Ser+(0.0078)Gln+(−0.1671)His+
(0.0005)Ala+(−0.3088)Met+(0.1634)Phe; 0.862,
0.890, 0.801, 0.769, 0.822, 0.853, 0.805, 0.812,
(2.0511)+(0.0517)Ser+(−0.0769)Cit+(0.0386)Tyr+(−
0.2669)Met+(0.0863)Ile+(−0.1620)Trp; 0.862, 0.887,
0.789, 0.772, 0.790, 0.846, 0.794, 0.800, (−1.9995)+
(0.0523)Ser+(0.0078)Gln+(−0.1667)His+(0.0002)Val+
(−0.3055)Met+(0.1631)Phe; 0.862, 0.883, 0.796,
0.774, 0.786, 0.859, 0.831, 0.813, (3.7707)+(0.0409)
Ser+(−0.0083)Ala+(−0.0902)Cit+(−0.0127)Lys+
(0.1006)Ile+(−0.1581)Trp; 0.862, 0.887, 0.815, 0.817,
0.817, 0.830, 0.794, 0.815, (−0.6094)+(0.0489)Ser+(−
0.0013)Ala+(−0.2831)Met+(0.0010)Lys+(0.1348)
Phe+(−0.1453)Trp; 0.862, 0.892, 0.846, 0.841, 0.843,
0.853, 0.858, 0.849, (2.4961)+(0.0121)Gln+(−0.1282)
His+(−0.1947)Met+(0.0089)Orn+(0.1359)Phe+(−
0.1050)Trp; 0.862, 0.890, 0.788, 0.769, 0.787, 0.844,
0.801, 0.800, (0.8908)+(0.0444)Ser+(0.0059)Gln+(−
0.1300)His+(−0.0634)Cit+(0.1329)Phe+(−0.1355)Trp;
0.862, 0.888, 0.825, 0.825, 0.824, 0.823, 0.829, 0.825,
(−0.8441)+(0.0579)Ser+(−0.0075)Gly+(0.0021)Gln+
(−0.2941)Met+(0.1310)Phe+(−0.1491)Trp; 0.862,
0.883, 0.790, 0.770, 0.758, 0.870, 0.852, 0.813,
(5.9999)+(−0.0698)His+(0.0356)Thr+(−0.0035)Ala+
(−0.0449)Val+(−0.3132)Met+(0.1885)Ile; 0.862,
0.887, 0.799, 0.785, 0.784, 0.859, 0.819, 0.812,
(3.0000)+(0.0447)Ser+(−0.0404)Asn+(−0.1829)Met+
(0.1554)Ile+(−0.0555)Leu+(−0.1287)Trp; 0.862, 0.886, 0.776, 0.745, 0.788, 0.818, 0.801, 0.788, (0.9605)+(0.0456)Ser+(−0.1169)Cit+(−0.0220)Lys+ (0.0716)Ile+(0.0939)Phe+(−0.1893)Trp; 0.862, 0.884, 0.800, 0.780, 0.799, 0.849, 0.822, 0.812, (7.2924)+(− 0.0813)His+(0.0306)Thr+(−0.1943)Met+(0.1154)Ile+ (−0.0277)Leu+(−0.1092)Trp; 0.862, 0.886, 0.759, 0.733, 0.776, 0.830, 0.741, 0.770, (−0.2427)+(0.0522) Ser+(−0.1627)His+(0.0303)Thr+(0.0004)Ala+(− 0.3769)Met+(0.1726)Phe; 0.862, 0.889, 0.819, 0.825, 0.821, 0.839, 0.782, 0.817, (−0.2673)+(0.0512)Ser+(− 0.0124)Arg+(−0.0045)Val+(−0.2696)Met+(0.1437) Phe+(−0.1386)Trp; 0.862, 0.886, 0.766, 0.753, 0.735, 0.815, 0.828, 0.783, (0.7726)+(0.0391)Ser+(−0.0385) Arg+(−0.0478)Val+(0.1588)Ile+(0.0886)Phe+(− 0.1566)Trp; 0.862, 0.887, 0.764, 0.738, 0.781, 0.835, 0.745, 0.775, (0.0802)+(0.0548)Ser+(−0.0357)Asn+(− 0.1569)His+(0.0307)Thr+(−0.3490)Met+(0.1712)Phe; 0.862, 0.884, 0.803, 0.786, 0.804, 0.822, 0.828, 0.810, (3.5153)+(0.0077)Gln+(−0.1456)His+(0.0155)Thr+ (0.0015)Val+(0.0996)Phe+(−0.1295)Trp; 0.862, 0.887, 0.823, 0.822, 0.825, 0.827, 0.816, 0.822, (−0.1067)+ (0.0621)Ser+(−0.0071)Gly+(−0.0122)Arg+(−0.2722) Met+(0.1352)Phe+(−0.1448)Trp; 0.862, 0.885, 0.836, 0.831, 0.828, 0.845, 0.858, 0.841, (3.6527)+(−0.0537) Asn+(0.0112)Gln+(−0.1292)His+(0.0009)Val+ (0.1007)Phe+(−0.1149)Trp; 0.861, 0.887, 0.831, 0.830, 0.814, 0.835, 0.867, 0.837, (1.0670)+(0.0065)Gln+(− 0.2951)Met+(0.1623)Ile+(−0.0802)Leu+(0.1153)Phe+ (−0.1345)Trp; 0.861, 0.888, 0.763, 0.739, 0.778, 0.834, 0.743, 0.773, (−0.1525)+(0.0517)Ser+(−0.1593)His+ (0.0310)Thr+(−0.0027)Val+(−0.3728)Met+(0.1768) Phe; 0.861, 0.885, 0.755, 0.720, 0.761, 0.819, 0.788, 0.772, (1.7702)+(0.0487)Ser+(−0.1391)His+(0.0033) Pro+(0.0126)Leu+(0.1067)Phe+(−0.1278)Trp; 0.861, 0.888, 0.794, 0.790, 0.750, 0.844, 0.861, 0.811, (0.5930)+(0.0316)Ser+(−0.0111)Ala+(0.1686)Ile+(− 0.0786)Leu+(0.0776)Phe+(−0.1552)Trp; 0.861, 0.888, 0.759, 0.732, 0.761, 0.823, 0.781, 0.774, (1.8109)+ (0.0475)Ser+(−0.1354)His+(0.0044)Pro+(0.0067) Orn+(0.1142)Phe+(−0.1223)Trp; 0.861, 0.883, 0.803, 0.793, 0.769, 0.875, 0.851, 0.822, (3.7243)+(0.0406) Ser+(−0.0863)Asn+(−0.0075)Ala+(0.1609)Ile+(− 0.0610)Leu+(−0.1278)Trp; 0.861, 0.885, 0.781, 0.746, 0.788, 0.819, 0.831, 0.796, (5.6127)+(−0.1249)His+ (0.0234)Thr+(−0.0084)Lys+(0.0507)Ile+(0.0838)Phe+ (−0.1363)Trp; 0.861, 0.888, 0.765, 0.738, 0.767, 0.827, 0.787, 0.780, (1.9034)+(0.0471)Ser+(−0.1367)His+ (0.0023)Val+(0.0076)Orn+(0.1144)Phe+(−0.1210)Trp; 0.861, 0.887, 0.817, 0.821, 0.821, 0.834, 0.785, 0.815, (−0.3576)+(0.0514)Ser+(−0.0011)Ala+(−0.0127)Arg+ (−0.2661)Met+(0.1371)Phe+(−0.1421)Trp; 0.861, 0.887, 0.790, 0.773, 0.790, 0.847, 0.794, 0.801, (−1.9425)+(0.0526)Ser+(0.0078)Gln+(−0.1659)His+ (−0.3016)Met+(−0.0014)Lys+(0.1638)Phe; 0.861, 0.887, 0.762, 0.736, 0.778, 0.831, 0.749, 0.774, (−0.1607)+(0.0541)Ser+(−0.0016)Gly+(−0.1607)His+ (0.0306)Thr+(−0.3737)Met+(0.1711)Phe; 0.861, 0.890, 0.821, 0.829, 0.820, 0.833, 0.795, 0.819, (−0.9262)+(0.0466)Ser+(0.0019)Gln+(−0.0051)Val+ (−0.2928)Met+(0.1412)Phe+(−0.1425)Trp; 0.861, 0.886, 0.781, 0.762, 0.729, 0.883, 0.865, 0.810, (1.2558)+(0.0430)Ser+(−0.0082)Ala+(0.0112)Pro+(− 0.0516)Val+(−0.3203)Met+(0.1956)Ile; 0.861, 0.885, 0.786, 0.766, 0.773, 0.815, 0.842, 0.799, (4.5917)+ (0.0039)Gly+(−0.1006)His+(0.1083)Ile+(−0.0446) Leu+(0.0899)Phe+(−0.1218)Trp; 0.861, 0.889, 0.816, 0.821, 0.816, 0.834, 0.788, 0.815, (−0.4831)+(0.0483) Ser+(−0.0057)Val+(−0.2859)Met+(0.0059)Orn+ (0.1402)Phe+(−0.1397)Trp; 0.861, 0.886, 0.821, 0.819, 0.822, 0.824, 0.825, 0.822, (−0.3110)+(0.0599)Ser+(− 0.0072)Gly+(−0.0006)Ala+(−0.2816)Met+(0.1334) Phe+(−0.1465)Trp; 0.861, 0.885, 0.829, 0.818, 0.801, 0.875, 0.883, 0.844, (4.9134)+(0.0066)Gln+(−0.0570) Cit+(−0.0378)Val+(−0.1870)Met+(0.1670)Ile+(− 0.1228)Trp; 0.861, 0.888, 0.778, 0.766, 0.770, 0.824, 0.792, 0.788, (1.0973)+(0.0421)Ser+(0.0047)Gln+(− 0.1408)His+(−0.0206)Tyr+(0.1286)Phe+(−0.1143)Trp; 0.861, 0.886, 0.820, 0.818, 0.821, 0.820, 0.824, 0.821, (−0.3653)+(0.0601)Ser+(−0.0073)Gly+(−0.2865)Met+ (0.0003)Lys+(0.1330)Phe+(−0.1474)Trp; 0.861, 0.892, 0.852, 0.845, 0.851, 0.860, 0.867, 0.856, (2.3965)+ (0.0128)Gln+(−0.1297)His+(0.0154)Tyr+(−0.2172) Met+(0.1374)Phe+(−0.1094)Trp; 0.861, 0.888, 0.786, 0.766, 0.788, 0.847, 0.792, 0.798, (−1.9641)+(0.0520) Ser+(0.0075)Gln+(−0.1672)His+(−0.3047)Met+ (0.0067)Orn+(0.1609)Phe; 0.861, 0.887, 0.806, 0.787, 0.814, 0.856, 0.802, 0.815, (1.9876)+(0.0429)Ser+ (0.0035)Gln+(−0.0768)Cit+(−0.2133)Met+(0.0837) Ile+(−0.1550)Trp; 0.861, 0.881, 0.801, 0.788, 0.762, 0.889, 0.857, 0.824, (4.9664)+(0.0347)Thr+(−0.0063) Ala+(−0.0603)Cit+(−0.0556)Val+(−0.3403)Met+ (0.2140)Ile; 0.861, 0.885, 0.796, 0.773, 0.789, 0.830, 0.846, 0.810, (3.0453)+(0.0025)Gly+(0.0081)Gln+(− 0.1407) His+(0.0485)Ile+(0.0773)Phe+(−0.1323)Trp; 0.861, 0.889, 0.812, 0.804, 0.815, 0.832, 0.812, 0.816, (3.7194)+(0.0101)Gln+(−0.1474)His+(0.0244)Thr+(− 0.0319)Arg+(0.1114)Phe+(−0.1300)Trp; 0.861, 0.883, 0.801, 0.778, 0.799, 0.853, 0.830, 0.815, (7.6696)+(− 0.0927)His+(0.0342)Thr+(−0.0038)Ala+(−0.1808) Met+(0.0834)Ile+(−0.1139)Trp; 0.861, 0.886, 0.765, 0.731, 0.769, 0.821, 0.808, 0.782, (1.9837)+(0.0533) Ser+(−0.0035)Gly+(−0.1361)His+(0.0137)Leu+ (0.1076)Phe+(−0.1275)Trp; 0.861, 0.886, 0.834, 0.828, 0.826, 0.843, 0.855, 0.838, (3.6642)+(−0.0551)Asn+ (0.0110)Gln+(−0.1281)His+(0.0027)Pro+(0.0996) Phe+(−0.1155)Trp; 0.861, 0.882, 0.800, 0.774, 0.814, 0.848, 0.806, 0.811, (7.6639)+(−0.0823)His+(0.0350) Thr+(−0.0445)Cit+(−0.1880)Met+(0.0786)Ile+(− 0.1186)Trp; 0.861, 0.886, 0.801, 0.781, 0.810, 0.852, 0.796, 0.810, (3.3523)+(0.0502)Ser+(−0.0450)Asn+(− 0.0708)Cit+(−0.1609)Met+(0.0818)Ile+(−0.1466)Trp; 0.861, 0.885, 0.812, 0.796, 0.813, 0.860, 0.819, 0.822, (2.9654)+(0.0423)Ser+(−0.1216)Asn+(0.0056)Gln+(− 0.0904)Cit+(0.0693)Ile+(−0.1676)Trp; 0.861, 0.884, 0.795, 0.777, 0.749, 0.895, 0.865, 0.821, (1.8695)+ (0.0424)Ser+(−0.0068)Ala+(−0.0549)Cit+(−0.0477) Val+(−0.2786)Met+(0.2022)Ile; 0.861, 0.888, 0.820, 0.823, 0.820, 0.831, 0.801, 0.819, (−0.9915)+(0.0469) Ser+(0.0018)Gln+(−0.0014)Ala+(−0.2873)Met+ (0.1338)Phe+(−0.1463)Trp; 0.861, 0.886, 0.763, 0.728, 0.769, 0.830, 0.792, 0.780, (2.0265)+(0.0506)Ser+(− 0.1363)His+(−0.0081)Lys+(0.0182)Leu+(0.1113)Phe+ (−0.1214)Trp; 0.860, 0.884, 0.762, 0.733, 0.773, 0.834, 0.764, 0.776, (−0.8079)+(0.0664)Ser+(−0.0270)Asn+ (−0.1442)His+(0.0113)Pro+(−0.3100)Met+(0.1605) Phe; 0.860, 0.887, 0.761, 0.735, 0.785, 0.837, 0.727, 0.771, (−0.0384)+(0.0535)Ser+(−0.1543)His+(0.0332) Thr+(−0.0431)Cit+(−0.3756)Met+(0.1756)Phe; 0.860, 0.887, 0.815, 0.819, 0.818, 0.824, 0.793, 0.814, (−1.1092)+(0.0473)Ser+(0.0017)Gln+(−0.2979)Met+ (0.0003)Lys+(0.1331)Phe+(−0.1479)Trp; 0.860, 0.885, 0.782, 0.756, 0.755, 0.875, 0.839, 0.806, (1.9431)+ (0.0414)Ser+(0.0045)Gln+(−0.0927)His+(−0.0346) Val+(−0.2781)Met+(0.1652)Ile; 0.860, 0.886, 0.768, 0.733, 0.770, 0.850, 0.797, 0.788, (−0.7431)+(0.0624)
Ser+(−0.1369)His+(−0.0242)Val+(−0.3243)Met+
(0.0509)Leu+(0.1568)Phe; 0.860, 0.886, 0.819, 0.816,
0.777, 0.848, 0.896, 0.834, (3.8148)+(−0.1186)Asn+
(0.0045)Gln+(−0.0464)Val+(0.1461)Ile+(0.0803)Phe+
(−0.1314)Trp; 0.860, 0.882, 0.755, 0.719, 0.768, 0.833,
0.766, 0.772, (−1.1575)+(0.0653)Ser+(−0.1512)His+
(0.0106)Pro+(−0.3368)Met+(0.0083)Leu+(0.1545)
Phe; 0.860, 0.886, 0.792, 0.774, 0.789, 0.846, 0.806,
0.804, (−1.9746)+(0.0548)Ser+(−0.0022)Gly+(0.0081)
Gln+(−0.1654)His+(−0.3030)Met+(0.1611)Phe; 0.860,
0.890, 0.785, 0.767, 0.782, 0.847, 0.792, 0.797,
(2.2499)+(0.0526)Ser+(−0.1244)His+(−0.0028)Ala+
(−0.0188)Arg+(0.1339)Phe+(−0.1135)Trp; 0.860,
0.890, 0.812, 0.798, 0.770, 0.852, 0.907, 0.832,
(4.5275)+(−0.0096)Ala+(−0.0840)Cit+(−0.0421)Val+
(0.1697)Ile+(0.0958)Phe+(−0.1450)Trp; 0.860, 0.886,
0.760, 0.734, 0.776, 0.832, 0.742, 0.771, (−0.2070)+
(0.0521)Ser+(−0.1622)His+(0.0301)Thr+(−0.3736)
Met+(0.0006)Orn+(0.1722)Phe; 0.860, 0.885, 0.801,
0.785, 0.788, 0.816, 0.861, 0.812, (5.4173)+(−0.0157)
Asn+(−0.0885)His+(0.1108)Ile+(−0.0481)Leu+
(0.0886)Phe+(−0.1203)Trp; 0.860, 0.885, 0.793, 0.775,
0.796, 0.853, 0.792, 0.804, (−2.0167)+(0.0523)Ser+
(0.0086)Gln+(−0.1570)His+(−0.0401)Cit+(−0.3072)
Met+(0.1663)Phe; 0.860, 0.883, 0.818, 0.805, 0.793,
0.863, 0.874, 0.834, (5.1525)+(0.0085)Gln+(−0.0724)
His+(−0.0293)Val+(−0.1741)Met+(0.1488)Ile+(−
0.0978)Trp; 0.860, 0.887, 0.779, 0.749, 0.779, 0.852,
0.809, 0.797, (3.6799)+(0.0529)Ser+(−0.0928)His+(−
0.0064)Arg+(−0.1640)Met+(0.0925)Ile+(−0.1051)Trp;
0.860, 0.886, 0.792, 0.780, 0.778, 0.853, 0.810, 0.805,
(2.4785)+(0.0425)Ser+(0.0032)Pro+(−0.2281)Met+
(0.1543)Ile+(−0.0565)Leu+(−0.1313)Trp; 0.860,
0.885, 0.777, 0.748, 0.768, 0.850, 0.819, 0.796,
(4.2991)+(0.0463)Ser+(−0.0587)Asn+(−0.0873)His+
(0.1133)Ile+(−0.0278)Leu+(−0.1114)Trp; 0.860,
0.887, 0.819, 0.817, 0.821, 0.822, 0.822, 0.820,
(−0.3656)+(0.0600)Ser+(−0.0075)Gly+(−0.2872)Met+
(0.0050)Orn+(0.1302)Phe+(−0.1473)Trp; 0.860,
0.883, 0.801, 0.787, 0.801, 0.823, 0.823, 0.809,
(3.4603)+(0.0007)Gly+(0.0075)Gln+(−0.1445)His+
(0.0153)Thr+(0.1026)Phe+(−0.1278)Trp; 0.860, 0.888,
0.821, 0.828, 0.824, 0.832, 0.788, 0.818, (−1.1021)+
(0.0489)Ser+(0.0025)Gln+(−0.0147)Arg+(−0.2826)
Met+(0.1350)Phe+(−0.1456)Trp; 0.860, 0.888, 0.764,
0.724, 0.775, 0.849, 0.786, 0.784, (4.0850)+(0.0427)
Ser+(−0.0961)His+(−0.0781)Cit+(0.0330)Orn+
(0.0735)Ile+(−0.1376)Trp; 0.860, 0.881, 0.781, 0.753,
0.765, 0.858, 0.831, 0.802, (4.3682)+(0.0479)Ser+(−
0.0470)Asn+(−0.0963)His+(−0.0050)Ala+(0.0853)
Ile+(−0.1108)Trp; 0.860, 0.881, 0.794, 0.773, 0.768,
0.871, 0.844, 0.814, (4.1728)+(0.0062)Gln+(−0.0912)
His+(0.0315)Thr+(−0.0414)Val+(−0.3471)Met+
(0.1758)Ile; 0.860, 0.884, 0.792, 0.780, 0.777, 0.854,
0.810, 0.805, (2.5110)+(0.0417)Ser+(−0.2194)Met+
(0.0019)Orn+(0.1590)Ile+(−0.0575)Leu+(−0.1314)
Trp; 0.860, 0.886, 0.772, 0.744, 0.774, 0.826, 0.805,
0.787, (2.0103)+(0.0533)Ser+(−0.0037)Gly+(−0.1325)
His+(0.0029)Val+(0.1158)Phe+(−0.1234)Trp; 0.860,
0.885, 0.789, 0.771, 0.759, 0.849, 0.858, 0.809,
(2.7917)+(0.0065)Gly+(−0.0787)His+(−0.0499)Val+
(−0.3366)Met+(0.1743)Ile+(0.1352)Phe; 0.860, 0.887,
0.771, 0.731, 0.753, 0.877, 0.841, 0.800, (1.9178)+
(0.0531)Ser+(−0.0836)His+(0.0452)Tyr+(−0.0437)
Val+(−0.3490)Met+(0.1874)Ile; 0.860, 0.890, 0.821,
0.820, 0.823, 0.839, 0.805, 0.822, (−0.6576)+(0.0498)
Ser+(−0.0017)Ala+(0.0141)Tyr+(−0.2981)Met+
(0.1323)Phe+(−0.1474)Trp; 0.860, 0.884, 0.768, 0.737,
0.748, 0.865, 0.823, 0.793, (2.7448)+(0.0448)Ser+(−
0.0850)His+(−0.0388)Val+(−0.2722)Met+(0.0225)
Orn+(0.1696)Ile; 0.860, 0.887, 0.815, 0.817, 0.817,
0.835, 0.794, 0.816, (−0.5789)+(0.0488)Ser+(−0.0014)
Ala+(−0.2804)Met+(0.0030)Orn+(0.1335)Phe+(−
0.1442)Trp; 0.860, 0.886, 0.803, 0.787, 0.778, 0.862,
0.859, 0.821, (7.4713)+(−0.0934)Asn+(0.0232)Thr+(−
0.0639)Cit+(−0.0405)Val+(0.1570)Ile+(−0.1314)Trp;
0.860, 0.883, 0.778, 0.757, 0.733, 0.882, 0.852, 0.806,
(1.5906)+(0.0437)Ser+(−0.0084)Gly+(0.0244)Thr+(−
0.0590)Val+(−0.4157)Met+(0.2146)Ile; 0.860, 0.888,
0.784, 0.763, 0.783, 0.850, 0.795, 0.798, (2.1035)+
(0.0517)Ser+(−0.1107)His+(−0.0031)Ala+(−0.0577)
Cit+(0.1403)Phe+(−0.1301)Trp; 0.860, 0.884, 0.798,
0.777, 0.801, 0.823, 0.829, 0.807, (3.5421)+(0.0077)
Gln+(−0.1497)His+(0.0157)Thr+(0.0118)Leu+
(0.0908)Phe+(−0.1341)Trp; 0.860, 0.883, 0.803, 0.788,
0.804, 0.823, 0.826, 0.810, (3.5356)+(0.0076)Gln+(−
0.1441)His+(0.0156)Thr+(0.0001)Pro+(0.1018)Phe+
(−0.1282)Trp; 0.860, 0.883, 0.795, 0.773, 0.805, 0.848,
0.792, 0.804, (2.9446)+(0.0478)Ser+(−0.0728)Cit+(−
0.1839)Met+(−0.0046)Lys+(0.0870)Ile+(−0.1486)Trp;
0.860, 0.883, 0.761, 0.733, 0.770, 0.835, 0.761, 0.775,
(−0.9537)+(0.0644)Ser+(−0.1432)His+(0.0125)Pro+(−
0.0041)Val+(−0.3310)Met+(0.1664)Phe; 0.860, 0.889,
0.819, 0.820, 0.828, 0.835, 0.784, 0.817, (−0.5539)+
(0.0526)Ser+(−0.0134)Arg+(0.0138)Tyr+(−0.2941)
Met+(0.1336)Phe+(−0.1464)Trp; 0.860, 0.887, 0.777,
0.751, 0.775, 0.830, 0.808, 0.791, (2.1684)+(0.0547)
Ser+(−0.0040)Gly+(−0.1270)His+(−0.0045)Lys+
(0.1231)Phe+(−0.1170)Trp; 0.859, 0.880, 0.764, 0.733,
0.744, 0.836, 0.837, 0.787, (4.1433)+(0.0453)Ser+(−
0.0053)Gly+(−0.0866)His+(−0.0250)Val+(0.1322)Ile+
(−0.1159)Trp; 0.859, 0.885, 0.778, 0.750, 0.746, 0.877,
0.846, 0.805, (2.7973)+(0.0464)Ser+(−0.0762)His+(−
0.0038)Ala+(−0.0362)Val+(−0.2446)Met+(0.1762)Ile;
0.859, 0.887, 0.808, 0.782, 0.802, 0.839, 0.865, 0.822,
(2.8036)+(0.0103)Gln+(−0.1235)His+(−0.0714)Cit+
(0.0564)Ile+(0.0901)Phe+(−0.1472)Trp; 0.859, 0.884,
0.793, 0.783, 0.750, 0.870, 0.855, 0.814, (3.7777)+
(0.0413)Ser+(−0.1453)Asn+(0.0022)Gln+(−0.0420)
Val+(0.1583)Ile+(−0.1132)Trp; 0.859, 0.886, 0.801,
0.804, 0.789, 0.819, 0.804, 0.804, (1.6061)+(0.0489)
Ser+(−0.1531)Asn+(0.0071)Pro+(−0.0111)Val+
(0.1069)Phe+(−0.1366)Trp; 0.859, 0.885, 0.812, 0.816,
0.819, 0.824, 0.775, 0.809, (−0.5539)+(0.0514)Ser+(−
0.0153)Arg+(−0.2837)Met+(0.0043)Lys+(0.1357)
Phe+(−0.1463)Trp; 0.859, 0.882, 0.788, 0.778, 0.796,
0.860, 0.743, 0.794, (5.9475)+(0.0386)Ser+(−0.0874)
His+(0.0182)Thr+(0.0133)Pro+(−0.1731)Met+(−
0.1011)Trp; 0.859, 0.885, 0.776, 0.742, 0.780, 0.851,
0.802, 0.794, (4.4375)+(0.0504)Ser+(−0.0491)Asn+(−
0.0844)His+(−0.0524)Cit+(0.0802)Ile+(−0.1253)Trp;
0.859, 0.886, 0.812, 0.796, 0.806, 0.832, 0.853, 0.822,
(3.2648)+(0.0113)Gln+(−0.1398)His+(−0.0221)Arg+
(0.0497)Ile+(0.0800)Phe+(−0.1301)Trp; 0.859, 0.885,
0.835, 0.830, 0.827, 0.843, 0.856, 0.839, (3.6299)+(−
0.0601)Asn+(0.0111)Gln+(−0.1293)His+(0.0036)Lys+
(0.1000)Phe+(−0.1157)Trp; 0.859, 0.879, 0.765, 0.739,
0.745, 0.840, 0.823, 0.787, (3.5328)+(0.0334)Ser+
(0.0030)Gln+(−0.1001)His+(−0.0214)Val+(0.1231)
Ile+(−0.1170)Trp; 0.859, 0.889, 0.766, 0.746, 0.756,
0.847, 0.783, 0.783, (−4.1346)+(0.0541)Ser+(−0.0945)
Cit+(−0.4161)Met+(0.2004)Ile+(−0.1008)Leu+
(0.1473)Phe; 0.859, 0.887, 0.810, 0.794, 0.815, 0.835, 0.823, 0.817, (3.4891)+(0.0084)Gln+(−0.1318)His+ (0.0202)Thr+(−0.0675)Cit+(0.1196)Phe+(−0.1424) Trp; 0.859, 0.881, 0.794, 0.789, 0.744, 0.829, 0.886, 0.812, (3.5371)+(0.0092)Thr+(−0.0098)Ala+(−0.0452) Val+(0.1621)Ile+(0.0747)Phe+(−0.1514)Trp; 0.859, 0.884, 0.758, 0.725, 0.758, 0.824, 0.796, 0.776, (1.9404)+(0.0483)Ser+(−0.1352)His+(−0.0130)Val+ (0.0344)Leu+(0.1087)Phe+(−0.1251)Trp; 0.859, 0.884, 0.798, 0.788, 0.781, 0.856, 0.817, 0.810, (2.0881)+(0.0390)Ser+(0.0021)Gln+(−0.2283)Met+ (0.1593)Ile+(−0.0579)Leu+(−0.1337)Trp; 0.859, 0.884, 0.784, 0.769, 0.746, 0.869, 0.844, 0.807, (4.1978)+(0.0422)Ser+(−0.1479)Asn+(−0.0449)Val+ (0.0207)Orn+(0.1609)Ile+(−0.1099)Trp; 0.859, 0.884, 0.762, 0.724, 0.768, 0.845, 0.788, 0.781, (4.1719)+ (0.0423)Ser+(−0.0982)His+(0.0077)Thr+(−0.0583) Cit+(0.0798)Ile+(−0.1361)Trp; 0.859, 0.886, 0.783, 0.761, 0.761, 0.820, 0.863, 0.801, (5.1584)+(−0.0895) His+(−0.0319)Val+(0.0150)Orn+(0.1199)Ile+(0.0791) Phe+(−0.1185)Trp; 0.859, 0.889, 0.771, 0.739, 0.788, 0.840, 0.767, 0.784, (1.9869)+(0.0485)Ser+(−0.1126) His+(−0.0888)Cit+(0.0354)Orn+(0.1271)Phe+(− 0.1413)Trp; 0.859, 0.883, 0.804, 0.787, 0.764, 0.853, 0.892, 0.824, (6.9809)+(−0.0104)Ala+(−0.0717)Cit+ (0.0114)Pro+(−0.0379)Val+(0.1679)Ile+(−0.1306)Trp; 0.859, 0.882, 0.797, 0.791, 0.745, 0.829, 0.898, 0.816, (3.8111)+(−0.0102)Ala+(0.0055)Pro+(−0.0452)Val+ (0.1593)Ile+(0.0760)Phe+(−0.1458)Trp; 0.859, 0.888, 0.822, 0.819, 0.823, 0.824, 0.826, 0.823, (−0.4105)+ (0.0603)Ser+(−0.0072)Gly+(0.0062)Tyr+(−0.2951) Met+(0.1317)Phe+(−0.1487)Trp; 0.859, 0.887, 0.811, 0.813, 0.815, 0.825, 0.786, 0.810, (−0.7233)+(0.0492) Ser+(−0.2923)Met+(0.0014)Orn+(0.0007)Lys+ (0.1335)Phe+(−0.1464)Trp; 0.859, 0.884, 0.832, 0.824, 0.827, 0.839, 0.860, 0.837, (3.6550)+(−0.0514)Asn+ (0.0112)Gln+(−0.1331)His+(0.0098)Leu+(0.0927) Phe+(−0.1193)Trp; 0.859, 0.883, 0.770, 0.748, 0.748, 0.845, 0.822, 0.791, (3.4473)+(0.0335)Ser+(−0.0793) Cit+(0.0027)Pro+(−0.0341)Val+(0.1459)Ile+(−0.1610) Trp; 0.859, 0.882, 0.771, 0.749, 0.749, 0.847, 0.819, 0.791, (3.5027)+(0.0324)Ser+(0.0016)Thr+(−0.0781) Cit+(−0.0341)Val+(0.1484)Ile+(−0.1603)Trp; 0.859, 0.878, 0.773, 0.742, 0.760, 0.851, 0.826, 0.795, (4.1357)+(0.0433)Ser+(−0.1020)His+(−0.0054)Ala+ (−0.0037)Lys+(0.0887)Ile+(−0.1147)Trp; 0.859, 0.884, 0.794, 0.783, 0.778, 0.853, 0.811, 0.806, (2.4701)+ (0.0409)Ser+(−0.2281)Met+(0.0037)Lys+(0.1613)Ile+ (−0.0597)Leu+(−0.1341)Trp; 0.859, 0.885, 0.805, 0.796, 0.768, 0.837, 0.883, 0.821, (4.9586)+(−0.1011) Asn+(−0.0489)Val+(0.0164)Orn+(0.1501)Ile+(0.0759) Phe+(−0.1251)Trp; 0.859, 0.890, 0.851, 0.849, 0.847, 0.857, 0.859, 0.853, (2.4884)+(0.0134)Gln+(−0.1272) His+(−0.0096)Arg+(−0.1820)Met+(0.1400)Phe+(− 0.1049)Trp; 0.859, 0.887, 0.815, 0.806, 0.806, 0.840, 0.840, 0.823, (3.7455)+(0.0077)Gln+(−0.1393)His+ (0.0177)Thr+(−0.0042)Ala+(0.1092)Phe+(−0.1273) Trp; 0.859, 0.881, 0.772, 0.751, 0.749, 0.848, 0.820, 0.792, (3.4953)+(0.0332)Ser+(−0.0001)Gln+(−0.0770) Cit+(−0.0340)Val+(0.1486)Ile+(−0.1590)Trp; 0.859, 0.884, 0.808, 0.815, 0.800, 0.830, 0.793, 0.810, (2.0010)+(0.0443)Ser+(−0.1634)Asn+(0.0114)Thr+(− 0.0105)Val+(0.1101)Phe+(−0.1396)Trp; 0.859, 0.890, 0.814, 0.800, 0.785, 0.844, 0.889, 0.830, (5.4054)+(− 0.0748)Asn+(−0.0738)Cit+(−0.0445)Val+(0.1518)Ile+ (0.0955)Phe+(−0.1352)Trp; 0.859, 0.887, 0.775, 0.759, 0.766, 0.834, 0.793, 0.788, (1.9978)+(0.0490)Ser+(− 0.1267)His+(−0.0024)Ala+(−0.0164)Tyr+(0.1340) Phe+(−0.1118)Trp; 0.859, 0.883, 0.772, 0.745, 0.762, 0.840, 0.816, 0.791, (3.2076)+(0.0334)Ser+(0.0043) Gln+(−0.1132)His+(0.1031)Ile+(−0.0222)Leu+(− 0.1212)Trp; 0.859, 0.881, 0.771, 0.741, 0.758, 0.853, 0.822, 0.793, (4.2345)+(0.0396)Ser+(−0.1084)His+ (0.0060)Thr+(−0.0058)Ala+(0.0855)Ile+(−0.1200) Trp; 0.859, 0.885, 0.794, 0.774, 0.784, 0.814, 0.855, 0.807, (5.1846)+(−0.0967)His+(0.0101)Orn+(0.1071) Ile+(−0.0462)Leu+(0.0834)Phe+(−0.1215)Trp; 0.859, 0.886, 0.833, 0.826, 0.827, 0.844, 0.852, 0.838, (3.7595)+(−0.0557)Asn+(0.0106)Gln+(−0.1287)His+ (0.0112)Orn+(0.0969)Phe+(−0.1137)Trp; 0.859, 0.883, 0.782, 0.769, 0.742, 0.867, 0.841, 0.805, (4.4002)+ (0.0404)Ser+(−0.1498)Asn+(0.0104)Thr+(−0.0441) Val+(0.1631)Ile+(−0.1147)Trp; 0.859, 0.884, 0.794, 0.772, 0.811, 0.848, 0.775, 0.802, (4.1272)+(0.0454) Ser+(−0.1034)Asn+(−0.1118)Cit+(0.0376)Orn+ (0.0583)Ile+(−0.1654)Trp; 0.859, 0.881, 0.781, 0.757, 0.758, 0.861, 0.837, 0.803, (5.9442)+(−0.0778)His+ (0.0386)Thr+(−0.0513)Val+(−0.3448)Met+(0.1714) Ile+(0.0201)Leu; 0.859, 0.888, 0.766, 0.742, 0.773, 0.829, 0.768, 0.778, (1.9726)+(0.0533)Ser+(−0.1283) His+(−0.0216)Arg+(0.0063)Pro+(0.1242)Phe+(− 0.1204)Trp; 0.859, 0.889, 0.819, 0.820, 0.823, 0.829, 0.799, 0.818, (−1.2157)+(0.0480)Ser+(0.0018)Gln+ (0.0117)Tyr+(−0.3145)Met+(0.1306)Phe+(−0.1505) Trp; 0.859, 0.885, 0.765, 0.745, 0.765, 0.822, 0.779, 0.778, (1.8458)+(0.0487)Ser+(−0.1322)His+(−0.0232) Tyr+(0.0039)Val+(0.1276)Phe+(−0.1152)Trp; 0.859, 0.881, 0.795, 0.777, 0.782, 0.812, 0.858, 0.807, (5.0847)+(−0.0951)His+(0.0029)Lys+(0.1103)Ile+(− 0.0482)Leu+(0.0862)Phe+(−0.1240)Trp; 0.859, 0.882, 0.758, 0.728, 0.770, 0.833, 0.759, 0.773, (−1.0184)+ (0.0648)Ser+(−0.1479)His+(0.0115)Pro+(−0.3292) Met+(−0.0006)Lys+(0.1612)Phe; 0.859, 0.882, 0.759, 0.730, 0.775, 0.833, 0.750, 0.772, (−0.9528)+(0.0674) Ser+(−0.1444)His+(−0.0126)Arg+(0.0117)Pro+(− 0.3182)Met+(0.1629)Phe; 0.859, 0.881, 0.822, 0.819, 0.851, 0.817, 0.771, 0.815, (4.4312)+(−0.0401)Asn+ (0.0450)Thr+(−0.0848)Cit+(−0.2949)Met+(0.1500) Phe+(−0.1699)Trp; 0.859, 0.887, 0.812, 0.816, 0.819, 0.828, 0.775, 0.810, (−0.4575)+(0.0515)Ser+(−0.0143) Arg+(−0.2747)Met+(0.0065)Orn+(0.1333)Phe+(− 0.1429)Trp; 0.859, 0.882, 0.772, 0.740, 0.759, 0.851, 0.826, 0.794, (4.0935)+(0.0410)Ser+(−0.1085)His+(− 0.0058)Ala+(0.0133)Orn+(0.0829)Ile+(−0.1178)Trp; 0.858, 0.884, 0.767, 0.736, 0.744, 0.866, 0.824, 0.793, (2.7211)+(0.0481)Ser+(−0.0802)His+(0.0060)Pro+(− 0.0377)Val+(−0.2811)Met+(0.1655)Ile; 0.858, 0.883, 0.802, 0.787, 0.803, 0.823, 0.826, 0.810, (3.5610)+ (0.0075)Gln+(−0.1442)His+(0.0151)Thr+(0.0041) Orn+(0.1001)Phe+(−0.1278)Trp; 0.858, 0.886, 0.822, 0.833, 0.805, 0.836, 0.819, 0.823, (1.1269)+(0.0450) Ser+(−0.1567)Asn+(0.0028)Gln+(−0.0087)Val+ (0.1067)Phe+(−0.1387)Trp; 0.858, 0.883, 0.780, 0.759, 0.756, 0.820, 0.856, 0.798, (4.6904)+(0.0032)Gly+(− 0.0903)His+(−0.0305)Val+(0.1205)Ile+(0.0878)Phe+ (−0.1214)Trp; 0.858, 0.882, 0.760, 0.729, 0.770, 0.833, 0.770, 0.775, (−1.0042)+(0.0667)Ser+(−0.0015)Gly+ (−0.1469)His+(0.0116)Pro+(−0.3300)Met+(0.1598) Phe; 0.858, 0.885, 0.805, 0.783, 0.796, 0.832, 0.860, 0.818, (3.3138)+(0.0088)Gln+(−0.1394)His+(−0.0026) Pro+(0.0506)Ile+(0.0762)Phe+(−0.1317)Trp; 0.858, 0.882, 0.794, 0.769, 0.795, 0.858, 0.811, 0.809, (3.4091)+(0.0350)Ser+(−0.0097)Ala+(−0.1213)Cit+ (0.0372)Orn+(0.0802)Ile+(−0.1733)Trp; 0.858, 0.881, 0.792, 0.769, 0.782, 0.853, 0.829, 0.808, (3.3014)+

(0.0355)Ser+(0.0039)Thr+(−0.0091)Ala+(−0.0932)
Cit+(0.0905)Ile+(−0.1728)Trp; 0.858, 0.886, 0.830,
0.830, 0.854, 0.824, 0.783, 0.823, (1.7119)+(0.0057)
Gln+(0.0396)Thr+(−0.0908)Cit+(−0.3538)Met+
(0.1541)Phe+(−0.1751)Trp; 0.858, 0.886, 0.814, 0.822,
0.801, 0.835, 0.803, 0.815, (1.7293)+(0.0469)Ser+(−
0.1517)Asn+(−0.0104)Val+(0.0135)Orn+(0.1053)
Phe+(−0.1335)Trp; 0.858, 0.887, 0.787, 0.754, 0.795,
0.819, 0.836, 0.801, (5.8869)+(−0.0436)Asn+(−
0.1203)His+(0.0249)Thr+(0.0446)Ile+(0.0818)Phe+(−
0.1364)Trp; 0.858, 0.883, 0.821, 0.823, 0.819, 0.837,
0.806, 0.821, (1.1634)+(0.0490)Ser+(−0.1473)Asn+
(0.0049)Gln+(−0.0981)Cit+(0.1122)Phe+(−0.1619)
Trp; 0.858, 0.879, 0.777, 0.744, 0.763, 0.850, 0.838,
0.799, (4.1338)+(0.0488)Ser+(−0.0041)Gly+(−0.1029)
His+(−0.0056)Ala+(0.0859)Ile+(−0.1178)Trp; 0.858,
0.887, 0.759, 0.725, 0.764, 0.824, 0.790, 0.776,
(1.8774)+(0.0476)Ser+(−0.1400)His+(0.0057)Orn+
(0.0135)Leu+(0.1064)Phe+(−0.1258)Trp; 0.858,
0.885, 0.801, 0.794, 0.816, 0.828, 0.766, 0.801,
(2.5408)+(0.0494)Ser+(−0.1515)Asn+(0.0174)Thr+(−
0.1014)Cit+(0.1158)Phe+(−0.1720)Trp; 0.858, 0.881,
0.757, 0.726, 0.741, 0.837, 0.817, 0.780, (4.0332)+
(0.0356)Ser+(−0.0943)His+(−0.0245)Val+(0.0141)
Orn+(0.1279)Ile+(−0.1150)Trp; 0.858, 0.888, 0.773,
0.745, 0.774, 0.826, 0.806, 0.787, (2.0801)+(0.0519)
Ser+(−0.0039)Gly+(−0.1317)His+(0.0098)Orn+
(0.1155)Phe+(−0.1208)Trp; 0.858, 0.882, 0.780, 0.769,
0.710, 0.874, 0.886, 0.810, (0.1991)+(0.0549)Ser+(−
0.2232)Asn+(−0.0085)Ala+(−0.0624)Val+(0.1893)
Ile+(0.0999)Phe; 0.858, 0.885, 0.760, 0.737, 0.774,
0.830, 0.740, 0.770, (−0.1019)+(0.0513)Ser+(−0.1609)
His+(0.0309)Thr+(−0.0093)Tyr+(−0.3611)Met+
(0.1744)Phe; 0.858, 0.884, 0.802, 0.780, 0.796, 0.827,
0.859, 0.815, (3.2868)+(0.0087)Gln+(−0.1390)His+(−
0.0004)Orn+(0.0480)Ile+(0.0751)Phe+(−0.1325)Trp;
0.858, 0.885, 0.772, 0.750, 0.781, 0.831, 0.774, 0.784,
(2.0954)+(0.0526)Ser+(−0.1302)His+(−0.0198)Arg+
(0.0030)Val+(0.1249)Phe+(−0.1188)Trp; 0.858, 0.885,
0.843, 0.841, 0.829, 0.856, 0.866, 0.848, (3.7749)+(−
0.0504)Asn+(0.0112)Gln+(−0.1257)His+(−0.0027)
Ala+(0.1070)Phe+(−0.1122)Trp; 0.858, 0.885, 0.790,
0.763, 0.742, 0.896, 0.881, 0.821, (0.2928)+(0.0471)
Ser+(−0.0070)Ala+(0.0456)Tyr+(−0.0580)Val+(−
0.3851)Met+(0.2220)Ile; 0.858, 0.885, 0.802, 0.786,
0.810, 0.820, 0.816, 0.808, (6.3084)+(−0.0575)Asn+(−
0.1123)His+(0.0289)Thr+(−0.0029)Val+(0.1099)Phe+
(−0.1220)Trp; 0.858, 0.881, 0.799, 0.778, 0.787, 0.856,
0.841, 0.815, (2.7303)+(0.0338)Ser+(0.0023)Gln+(−
0.0092)Ala+(−0.0946)Cit+(0.0912)Ile+(−0.1746)Trp;
0.858, 0.882, 0.791, 0.771, 0.792, 0.835, 0.812, 0.802,
(2.3447)+(0.0508)Ser+(−0.0079)Gly+(0.0168)Thr+(−
0.2813)Met+(0.0775)Ile+(−0.1542)Trp; 0.858, 0.881,
0.786, 0.764, 0.765, 0.867, 0.832, 0.807, (6.1882)+(−
0.0663)His+(0.0373)Thr+(−0.0377)Cit+(−0.0453)
Val+(−0.3291)Met+(0.1859)Ile; 0.858, 0.884, 0.794,
0.782, 0.794, 0.851, 0.784, 0.803, (−2.1711)+(0.0546)
Ser+(0.0094)Gln+(−0.1644)His+(−0.0194)Arg+(−
0.2873)Met+(0.1659)Phe; 0.858, 0.887, 0.756, 0.736,
0.754, 0.817, 0.773, 0.770, (1.7109)+(0.0490)Ser+(−
0.1289)His+(0.0066)Pro+(−0.0274)Tyr+(0.1291)Phe+
(−0.1155)Trp; 0.858, 0.882, 0.777, 0.744, 0.792, 0.831,
0.793, 0.790, (3.3872)+(−0.1359)His+(0.0539)Thr+(−
0.0391)Val+(−0.4050)Met+(0.0707)Leu+(0.1467)Phe;
0.858, 0.882, 0.761, 0.730, 0.779, 0.831, 0.755, 0.774,
(−0.8821)+(0.0657)Ser+(−0.1387)His+(−0.0348)Cit+
(0.0119)Pro+(−0.3330)Met+(0.1633)Phe; 0.858,
0.882, 0.756, 0.724, 0.769, 0.833, 0.758, 0.771,
(−1.0576)+(0.0639)Ser+(−0.1496)His+(0.0110)Pro+(−
0.3284)Met+(0.0068)Orn+(0.1583)Phe; 0.858, 0.887,
0.789, 0.772, 0.790, 0.846, 0.794, 0.800, (−1.9957)+
(0.0523)Ser+(0.0078)Gln+(−0.1665)His+(0.0004)
Tyr+(−0.3058)Met+(0.1634)Phe; 0.858, 0.879, 0.784,
0.759, 0.760, 0.867, 0.841, 0.807, (5.7978)+(−0.0747)
His+(0.0355)Thr+(0.0131)Tyr+(−0.0469)Val+(−
0.3490)Met+(0.1867)Ile; 0.858, 0.876, 0.789, 0.773,
0.755, 0.847, 0.859, 0.809, (7.1391)+(−0.0731)His+
(0.0176)Thr+(−0.0063)Ala+(−0.0295)Val+(0.1474)
Ile+(−0.1169)Trp; 0.858, 0.881, 0.779, 0.756, 0.783,
0.848, 0.781, 0.792, (3.1826)+(0.0321)Ser+(−0.1094)
Cit+(0.0282)Orn+(0.1406)Ile+(−0.0556)Leu+(−
0.1687)Trp; 0.858, 0.880, 0.794, 0.768, 0.803, 0.836,
0.816, 0.806, (7.2919)+(−0.0981)His+(0.0332)Thr+(−
0.2096)Met+(0.0048)Lys+(0.0759)Ile+(−0.1158)Trp;
0.858, 0.880, 0.783, 0.762, 0.757, 0.862, 0.838, 0.805,
(5.7417)+(−0.0770)His+(0.0341)Thr+(−0.0463)Val+
(−0.3435)Met+(0.0058)Lys+(0.1844)Ile; 0.858, 0.880,
0.780, 0.755, 0.757, 0.861, 0.833, 0.801, (5.7754)+(−
0.0777)His+(0.0329)Thr+(−0.0460)Val+(−0.3260)
Met+(0.0177)Orn+(0.1805)Ile; 0.858, 0.883, 0.788,
0.767, 0.765, 0.820, 0.871, 0.806, (5.2198)+(−0.0850)
His+(−0.0319)Val+(−0.0003)Lys+(0.1232)Ile+
(0.0852)Phe+(−0.1200)Trp; 0.858, 0.884, 0.793, 0.769,
0.813, 0.851, 0.774, 0.802, (2.8545)+(0.0447)Ser+(−
0.0956)Cit+(−0.1973)Met+(0.0293)Orn+(0.0742)Ile+
(−0.1540)Trp; 0.858, 0.879, 0.791, 0.765, 0.798, 0.837,
0.813, 0.803, (7.2501)+(0.0128)Asn+(−0.0974)His+
(0.0336)Thr+(−0.2084)Met+(0.0789)Ile+(−0.1143)
Trp; 0.858, 0.882, 0.763, 0.725, 0.770, 0.842, 0.794,
0.783, (3.9857)+(0.0454)Ser+(−0.0939)His+(−0.0561)
Cit+(0.0028)Pro+(0.0782)Ile+(−0.1350)Trp; 0.858,
0.882, 0.779, 0.756, 0.776, 0.843, 0.804, 0.795,
(3.1184)+(0.0379)Ser+(0.0073)Gln+(−0.1247)His+(−
0.0249)Arg+(0.0781)Ile+(−0.1227)Trp; 0.858, 0.888,
0.815, 0.814, 0.821, 0.828, 0.794, 0.814, (−0.8209)+
(0.0499)Ser+(0.0115)Tyr+(−0.3091)Met+(0.0009)
Lys+(0.1317)Phe+(−0.1493)Trp; 0.858, 0.887, 0.816,
0.810, 0.818, 0.819, 0.822, 0.817, (−0.5151)+(0.0608)
Ser+(−0.0072)Gly+(−0.2926)Met+(0.0065)Leu+
(0.1272)Phe+(−0.1500)Trp; 0.858, 0.883, 0.826, 0.812,
0.800, 0.872, 0.883, 0.842, (4.5502)+(0.0053)Gln+
(0.0357)Tyr+(−0.0447)Val+(−0.2783)Met+(0.1768)
Ile+(−0.1210)Trp; 0.858, 0.880, 0.810, 0.804, 0.840,
0.807, 0.767, 0.805, (3.6186)+(0.0419)Thr+(−0.0877)
Cit+(0.0071)Pro+(−0.3424)Met+(0.1493)Phe+(−
0.1742)Trp; 0.858, 0.888, 0.815, 0.820, 0.818, 0.825,
0.793, 0.814, (−1.1037)+(0.0473)Ser+(0.0017)Gln+(−
0.2972)Met+(0.0000)Orn+(0.1332)Phe+(−0.1477)Trp;
0.858, 0.883, 0.768, 0.734, 0.768, 0.844, 0.803, 0.787,
(4.5473)+(0.0450)Ser+(−0.0670)Asn+(−0.1043)His+
(0.0095)Thr+(0.0738)Ile+(−0.1181)Trp; 0.858, 0.879,
0.793, 0.768, 0.801, 0.837, 0.814, 0.805, (7.4240)+(−
0.0952)His+(0.0340)Thr+(0.0004)Pro+(−0.1990)Met+
(0.0772)Ile+(−0.1145)Trp; 0.857, 0.889, 0.774, 0.752,
0.780, 0.836, 0.772, 0.785, (2.1904)+(0.0506)Ser+(−
0.1292)His+(−0.0216)Arg+(0.0140)Orn+(0.1236)
Phe+(−0.1160)Trp; 0.857, 0.880, 0.784, 0.771, 0.732,
0.853, 0.879, 0.809, (3.3990)+(0.0388)Ser+(−0.0071)
Gly+(−0.0086)Ala+(−0.0400)Val+(0.1706)Ile+(−
0.1366)Trp; 0.857, 0.881, 0.801, 0.797, 0.749, 0.832,
0.900, 0.819, (3.4636)+(0.0010)Gln+(−0.0092)Ala+(−
0.0446)Val+(0.1614)Ile+(0.0758)Phe+(−0.1471)Trp;
0.857, 0.879, 0.789, 0.764, 0.798, 0.838, 0.803, 0.801,
(7.1295)+(0.0025)Gly+(−0.0978)His+(0.0321)Thr+(−

0.1996)Met+(0.0796)Ile+(−0.1122)Trp; 0.857, 0.883, 0.808, 0.801, 0.768, 0.836, 0.887, 0.823, (4.7636)+(−0.0874)Asn+(−0.0411)Val+(0.1640)Ile+(−0.0203)Leu+(0.0837)Phe+(−0.1269)Trp; 0.857, 0.883, 0.761, 0.741, 0.729, 0.813, 0.842, 0.781, (0.7744)+(0.0334)Ser+(−0.0419)Val+(−0.0160)Lys+(0.1465)Ile+(0.0818)Phe+(−0.1550)Trp; 0.857, 0.882, 0.775, 0.753, 0.753, 0.854, 0.824, 0.796, (3.8270)+(0.0354)Ser+(−0.0752)Cit+(−0.0321)Val+(−0.0096)Lys+(0.1521)Ile+(−0.1491)Trp; 0.857, 0.882, 0.816, 0.816, 0.812, 0.844, 0.804, 0.819, (2.2265)+(0.0523)Ser+(−0.1184)Asn+(−0.0039)Ala+(−0.0884)Cit+(0.1228)Phe+(−0.1529)Trp; 0.857, 0.879, 0.752, 0.719, 0.720, 0.846, 0.838, 0.781, (0.7137)+(0.0607)Ser+(−0.1708)Asn+(−0.1013)His+(−0.0429)Val+(0.1346)Ile+(0.1114)Phe; 0.857, 0.882, 0.757, 0.729, 0.766, 0.830, 0.759, 0.771, (−0.9490)+(0.0641)Ser+(−0.1465)His+(0.0119)Pro+(−0.0092)Tyr+(−0.3185)Met+(0.1624)Phe; 0.857, 0.883, 0.790, 0.769, 0.799, 0.846, 0.783, 0.800, (4.1808)+(0.0442)Ser+(−0.1059)Asn+(0.0093)Thr+(−0.0875)Cit+(0.0684)Ile+(−0.1677)Trp; 0.857, 0.884, 0.788, 0.769, 0.764, 0.819, 0.868, 0.805, (5.1163)+(−0.0837)His+(−0.0281)Val+(0.1318)Ile+(−0.0133)Leu+(0.0867)Phe+(−0.1192)Trp; 0.857, 0.880, 0.783, 0.762, 0.756, 0.863, 0.839, 0.805, (6.1606)+(−0.0168)Asn+(−0.0706)His+(0.0363)Thr+(−0.0465)Val+(−0.3175)Met+(0.1856)Ile; 0.857, 0.881, 0.771, 0.736, 0.779, 0.815, 0.818, 0.787, (4.9239)+(0.0027)Gly+(−0.1303)His+(0.0180)Thr+(0.0479)Ile+(0.0802)Phe+(−0.1368)Trp; 0.857, 0.889, 0.846, 0.840, 0.841, 0.860, 0.862, 0.851, (3.4876)+(−0.0572)Asn+(0.0125)Gln+(−0.1139)His+(−0.0612)Cit+(0.1171)Phe+(−0.1225)Trp; 0.857, 0.884, 0.795, 0.778, 0.804, 0.821, 0.801, 0.801, (5.8565)+(−0.0585)Asn+(0.0032)Gly+(−0.1181)His+(0.0265)Thr+(0.1083)Phe+(−0.1214)Trp; 0.857, 0.883, 0.778, 0.763, 0.736, 0.884, 0.830, 0.803, (2.7414)+(0.0389)Ser+(−0.0969)Asn+(0.0240)Thr+(−0.0603)Val+(−0.3280)Met+(0.2153)Ile; 0.857, 0.882, 0.778, 0.766, 0.723, 0.855, 0.867, 0.803, (3.2069)+(0.0283)Ser+(−0.0104)Ala+(0.0069)Pro+(−0.0402)Val+(0.1646)Ile+(−0.1373)Trp; 0.857, 0.880, 0.796, 0.768, 0.807, 0.843, 0.818, 0.809, (7.3406)+(−0.0961)His+(0.0337)Thr+(0.0129)Tyr+(−0.2127)Met+(0.0765)Ile+(−0.1184)Trp; 0.857, 0.886, 0.774, 0.754, 0.779, 0.833, 0.774, 0.785, (2.1157)+(0.0523)Ser+(−0.1275)His+(−0.0199)Arg+(0.0004)Lys+(0.1290)Phe+(−0.1164)Trp; 0.857, 0.884, 0.801, 0.781, 0.811, 0.821, 0.818, 0.808, (6.2824)+(−0.0524)Asn+(−0.1152)His+(0.0282)Thr+(−0.0006)Lys+(0.1057)Phe+(−0.1248)Trp; 0.857, 0.881, 0.772, 0.751, 0.749, 0.848, 0.821, 0.792, (3.4759)+(0.0332)Ser+(−0.0772)Cit+(0.0003)Tyr+(−0.0340)Val+(0.1485)Ile+(−0.1592)Trp; 0.857, 0.887, 0.765, 0.747, 0.763, 0.822, 0.778, 0.778, (1.9053)+(0.0468)Ser+(−0.1308)His+(−0.0243)Tyr+(0.0121)Orn+(0.1283)Phe+(−0.1112)Trp; 0.857, 0.885, 0.802, 0.796, 0.762, 0.833, 0.877, 0.817, (4.3870)+(−0.1004)Asn+(0.0033)Gly+(−0.0478)Val+(0.1518)Ile+(0.0869)Phe+(−0.1288)Trp; 0.857, 0.884, 0.784, 0.770, 0.743, 0.865, 0.848, 0.806, (4.1413)+(0.0437)Ser+(−0.1340)Asn+(0.0021)Pro+(−0.0426)Val+(0.1583)Ile+(−0.1127)Trp; 0.857, 0.882, 0.789, 0.767, 0.797, 0.843, 0.791, 0.800, (3.9350)+(0.0469)Ser+(−0.0943)Asn+(−0.0846)Cit+(0.0036)Pro+(0.0660)Ile+(−0.1658)Trp; 0.857, 0.882, 0.801, 0.797, 0.750, 0.834, 0.894, 0.819, (3.7620)+(−0.0091)Ala+(−0.0360)Val+(0.1824)Ile+(−0.0292)Leu+(0.0780)Phe+(−0.1401)Trp; 0.857, 0.884, 0.772, 0.765, 0.756, 0.821, 0.789, 0.783, (0.2021)+(0.0422)Ser+(−0.0438)Arg+(0.1730)Ile+(−0.0896)Leu+(0.0885)Phe+(−0.1572)Trp; 0.857, 0.881, 0.768, 0.734, 0.760, 0.837, 0.826, 0.789, (3.9746)+(0.0466)Ser+(−0.0047)Gly+(−0.0970)His+(0.1116)Ile+(−0.0274)Leu+(−0.1202)Trp; 0.857, 0.880, 0.814, 0.806, 0.762, 0.863, 0.907, 0.835, (0.1328)+(0.0046)Gln+(−0.0048)Ala+(−0.0622)Val+(−0.3959)Met+(0.2046)Ile+(0.1205)Phe; 0.857, 0.884, 0.804, 0.785, 0.763, 0.858, 0.899, 0.826, (3.6725)+(−0.0654)His+(−0.0034)Ala+(−0.0511)Val+(−0.2948)Met+(0.1801)Ile+(0.1262)Phe; 0.857, 0.882, 0.772, 0.737, 0.760, 0.853, 0.830, 0.795, (3.8712)+(0.0437)Ser+(−0.1100)His+(−0.0066)Ala+(0.0186)Tyr+(0.0867)Ile+(−0.1250)Trp; 0.857, 0.877, 0.801, 0.777, 0.800, 0.843, 0.836, 0.814, (4.9636)+(0.0085)Gln+(−0.1090)His+(0.0125)Thr+(−0.0585)Cit+(0.0712)Ile+(−0.1405)Trp; 0.857, 0.880, 0.816, 0.807, 0.850, 0.822, 0.763, 0.811, (3.6803)+(0.0385)Thr+(−0.1040)Cit+(−0.3120)Met+(0.0256)Orn+(0.1429)Phe+(−0.1738)Trp; 0.857, 0.879, 0.779, 0.757, 0.754, 0.860, 0.830, 0.800, (5.7873)+(0.0016)Gly+(−0.0757)His+(0.0348)Thr+(−0.0451)Val+(−0.3314)Met+(0.1843)Ile; 0.857, 0.886, 0.767, 0.740, 0.775, 0.830, 0.778, 0.781, (2.0467)+(0.0529)Ser+(−0.1333)His+(−0.0192)Arg+(0.0132)Leu+(0.1173)Phe+(−0.1228)Trp; 0.857, 0.880, 0.803, 0.783, 0.775, 0.862, 0.870, 0.822, (6.4478)+(−0.0085)Ala+(−0.0948)Cit+(−0.0384)Val+(0.0473)Orn+(0.1643)Ile+(−0.1330)Trp; 0.857, 0.881, 0.806, 0.783, 0.793, 0.861, 0.852, 0.822, (6.6761)+(−0.0728)Cit+(−0.0424)Val+(−0.1513)Met+(0.0443)Orn+(0.1652)Ile+(−0.1168)Trp; 0.857, 0.881, 0.799, 0.794, 0.746, 0.832, 0.898, 0.817, (3.6635)+(0.0007)Gly+(−0.0091)Ala+(−0.0450)Val+(0.1628)Ile+(0.0774)Phe+(−0.1455)Trp; 0.857, 0.884, 0.801, 0.781, 0.811, 0.820, 0.818, 0.807, (6.2569)+(−0.0529)Asn+(−0.1152)His+(0.0279)Thr+(0.0004)Pro+(0.1049)Phe+(−0.1251)Trp; 0.857, 0.882, 0.799, 0.776, 0.806, 0.845, 0.810, 0.809, (2.8223)+(0.0528)Ser+(−0.0039)Gly+(−0.0663)Cit+(−0.2004)Met+(0.0832)Ile+(−0.1501)Trp; 0.857, 0.886, 0.793, 0.777, 0.767, 0.820, 0.869, 0.808, (5.6452)+(−0.0777)His+(−0.0150)Arg+(−0.0351)Val+(0.1316)Ile+(0.0910)Phe+(−0.1172)Trp; 0.857, 0.886, 0.794, 0.768, 0.775, 0.828, 0.876, 0.812, (5.3532)+(−0.0676)His+(−0.0594)Cit+(−0.0326)Val+(0.1297)Ile+(0.0961)Phe+(−0.1296)Trp; 0.857, 0.884, 0.795, 0.770, 0.808, 0.817, 0.818, 0.803, (6.2262)+(−0.0489)Asn+(−0.1202)His+(0.0278)Thr+(0.0088)Leu+(0.0971)Phe+(−0.1297)Trp; 0.857, 0.882, 0.785, 0.772, 0.744, 0.867, 0.847, 0.808, (4.1303)+(0.0431)Ser+(−0.1296)Asn+(−0.0397)Val+(0.1666)Ile+(−0.0085)Leu+(−0.1123)Trp; 0.857, 0.881, 0.761, 0.728, 0.755, 0.839, 0.807, 0.782, (3.8922)+(0.0384)Ser+(−0.1040)His+(0.0102)Orn+(0.1068)Ile+(−0.0253)Leu+(−0.1193)Trp; 0.856, 0.884, 0.788, 0.765, 0.778, 0.833, 0.840, 0.804, (0.6766)+(0.0408)Ser+(−0.0107)Ala+(−0.1105)Cit+(0.0798)Ile+(0.0882)Phe+(−0.1919)Trp; 0.856, 0.885, 0.760, 0.733, 0.761, 0.818, 0.786, 0.774, (1.8354)+(0.0488)Ser+(−0.1349)His+(−0.0216)Tyr+(0.0142)Leu+(0.1197)Phe+(−0.1191)Trp; 0.856, 0.878, 0.824, 0.817, 0.783, 0.870, 0.891, 0.840, (5.1343)+(0.0050)Gln+(−0.0049)Ala+(−0.0415)Val+(−0.1882)Met+(0.1790)Ile+(−0.1117)Trp; 0.856, 0.878, 0.778, 0.747, 0.803, 0.839, 0.764, 0.788, (3.7507)+(0.0373)Ser+(−0.1239)Cit+(0.0421)Orn+(−0.0189)Lys+(0.0727)Ile+(−0.1728)Trp; 0.856, 0.880, 0.791, 0.776, 0.781, 0.852, 0.804, 0.803, (2.2258)+(0.0394)Ser+(0.0140)Thr+(−0.0054)Ala+(−0.2470)Met+(0.0873)Ile+(−0.1465)Trp;

0.856, 0.885, 0.813, 0.821, 0.799, 0.833, 0.806, 0.815, (1.6629)+(0.0475)Ser+(−0.1468)Asn+(−0.0089)Val+ (0.0011)Lys+(0.1087)Phe+(−0.1371)Trp; 0.856, 0.885, 0.806, 0.805, 0.811, 0.823, 0.787, 0.807, (−0.8499)+ (0.0504)Ser+(−0.2959)Met+(−0.0007)Lys+(0.0073) Leu+(0.1282)Phe+(−0.1483)Trp; 0.856, 0.879, 0.793, 0.772, 0.783, 0.851, 0.826, 0.808, (3.2776)+(0.0381) Ser+(−0.0086)Ala+(−0.0874)Cit+(−0.0043)Arg+ (0.0909)Ile+(−0.1688)Trp; 0.856, 0.880, 0.791, 0.764, 0.801, 0.838, 0.812, 0.803, (7.3219)+(−0.0985)His+ (0.0324)Thr+(−0.1947)Met+(0.0117)Orn+(0.0744) Ile+(−0.1145)Trp; 0.856, 0.886, 0.810, 0.809, 0.812, 0.829, 0.798, 0.812, (−0.7356)+(0.0499)Ser+(−0.0018) Ala+(−0.2854)Met+(0.0083)Leu+(0.1280)Phe+(− 0.1473)Trp; 0.856, 0.883, 0.773, 0.753, 0.751, 0.850, 0.819, 0.793, (3.4505)+(0.0332)Ser+(−0.0782)Cit+(− 0.0264)Val+(0.1665)Ile+(−0.0245)Leu+(−0.1555)Trp; 0.856, 0.877, 0.804, 0.786, 0.788, 0.849, 0.852, 0.819, (5.4168)+(0.0075)Gln+(−0.1189)His+(0.0131)Thr+(− 0.0058)Ala+(0.0745)Ile+(−0.1286)Trp; 0.856, 0.880, 0.820, 0.808, 0.804, 0.859, 0.857, 0.832, (4.7648)+ (0.0098)Gln+(−0.0894)His+(−0.1441)Met+(0.1225) Ile+(−0.0340)Leu+(−0.1067)Trp; 0.856, 0.884, 0.805, 0.803, 0.763, 0.827, 0.883, 0.819, (4.8478)+(−0.0820) Asn+(−0.0258)Tyr+(−0.0468)Val+(0.1512)Ile+ (0.0955)Phe+(−0.1221)Trp; 0.856, 0.882, 0.795, 0.772, 0.806, 0.848, 0.791, 0.804, (2.7543)+(0.0470)Ser+(− 0.0723)Cit+(0.0006)Arg+(−0.2001)Met+(0.0844)Ile+ (−0.1507)Trp; 0.856, 0.878, 0.809, 0.795, 0.777, 0.857, 0.877, 0.827, (6.4757)+(−0.0051)Ala+(−0.0454)Val+ (−0.1711)Met+(0.0267)Orn+(0.1819)Ile+(−0.1052) Trp; 0.856, 0.885, 0.798, 0.777, 0.810, 0.817, 0.814, 0.804, (6.1891)+(−0.0531)Asn+(−0.1168)His+ (0.0261)Thr+(0.0121)Orn+(0.1002)Phe+(−0.1242) Trp; 0.856, 0.882, 0.778, 0.750, 0.800, 0.850, 0.753, 0.788, (5.1770)+(0.0417)Ser+(−0.1148)His+(0.0263) Thr+(−0.2043)Met+(0.0405)Leu+(−0.1112)Trp; 0.856, 0.879, 0.823, 0.803, 0.809, 0.867, 0.872, 0.838, (5.0639)+(0.0103)Gln+(−0.0961)His+(−0.0061)Ala+ (−0.0619)Cit+(0.0861)Ile+(−0.1309)Trp; 0.856, 0.875, 0.791, 0.773, 0.763, 0.839, 0.864, 0.810, (7.1204)+(− 0.0664)His+(−0.0059)Ala+(−0.0319)Val+(0.0265) Orn+(0.1457)Ile+(−0.1069)Trp; 0.856, 0.885, 0.840, 0.838, 0.833, 0.848, 0.851, 0.843, (3.6081)+(−0.0403) Asn+(0.0126)Gln+(−0.1304)His+(−0.0168)Arg+ (0.1065)Phe+(−0.1131)Trp; 0.856, 0.878, 0.816, 0.807, 0.773, 0.865, 0.896, 0.835, (5.1604)+(0.0048)Gln+(− 0.0086)Ala+(−0.0750)Cit+(−0.0346)Val+(0.1676)Ile+ (−0.1413)Trp; 0.856, 0.880, 0.773, 0.743, 0.767, 0.839, 0.816, 0.791, (3.2328)+(0.0357)Ser+(0.0051)Gln+(− 0.1207)His+(−0.0065)Lys+(0.0770)Ile+(−0.1201)Trp; 0.856, 0.880, 0.781, 0.759, 0.756, 0.862, 0.834, 0.803, (5.9125)+(−0.0736)His+(0.0356)Thr+(0.0014)Pro+(− 0.0457)Val+(−0.3334)Met+(0.1831)Ile; 0.856, 0.884, 0.801, 0.778, 0.805, 0.831, 0.829, 0.811, (4.7474)+ (0.0071)Gly+(−0.1069)His+(−0.1966)Met+(0.0607) Ile+(0.1169)Phe+(−0.1116)Trp; 0.856, 0.883, 0.785, 0.772, 0.743, 0.866, 0.849, 0.808, (4.1340)+(0.0434) Ser+(−0.1353)Asn+(−0.0427)Val+(0.0017)Lys+ (0.1604)Ile+(−0.1133)Trp; 0.856, 0.882, 0.827, 0.807, 0.822, 0.863, 0.862, 0.839, (4.6608)+(0.0116)Gln+(− 0.0963)His+(−0.0517)Cit+(−0.1174)Met+(0.0803)Ile+ (−0.1208)Trp; 0.856, 0.881, 0.796, 0.775, 0.782, 0.840, 0.852, 0.812, (5.3343)+(0.0049)Gly+(−0.1109)His+(− 0.0061)Ala+(0.0605)Ile+(0.0859)Phe+(−0.1248)Trp; 0.856, 0.880, 0.794, 0.771, 0.783, 0.852, 0.838, 0.811, (3.2650)+(0.0401)Ser+(−0.0022)Gly+(−0.0087)Ala+ (−0.0876)Cit+(0.0897)Ile+(−0.1696)Trp; 0.856, 0.882, 0.774, 0.744, 0.752, 0.875, 0.826, 0.799, (3.0243)+ (0.0470)Ser+(−0.0741)His+(−0.0308)Cit+(−0.0364) Val+(−0.2578)Met+(0.1705)Ile; 0.856, 0.885, 0.762, 0.733, 0.772, 0.828, 0.771, 0.776, (1.7543)+(0.0531) Ser+(−0.1148)His+(−0.0636)Cit+(0.0072)Pro+ (0.1291)Phe+(−0.1408)Trp; 0.856, 0.884, 0.774, 0.756, 0.768, 0.821, 0.801, 0.786, (2.0152)+(0.0549)Ser+(− 0.0046)Gly+(−0.1238)His+(−0.0259)Tyr+(0.1331) Phe+(−0.1130)Trp; 0.856, 0.881, 0.799, 0.793, 0.747, 0.832, 0.897, 0.817, (3.7760)+(−0.0091)Ala+(−0.0452) Val+(0.0050)Orn+(0.1621)Ile+(0.0740)Phe+(−0.1441) Trp; 0.856, 0.879, 0.799, 0.780, 0.786, 0.847, 0.842, 0.814, (2.0914)+(0.0538)Ser+(−0.0059)Gly+(−0.0046) Ala+(−0.2051)Met+(0.0860)Ile+(−0.1425)Trp; 0.856, 0.879, 0.788, 0.775, 0.789, 0.841, 0.784, 0.797, (2.7283)+(0.0430)Ser+(−0.0549)Asn+(0.0145)Thr+(− 0.2288)Met+(0.0760)Ile+(−0.1481)Trp; 0.856, 0.885, 0.821, 0.830, 0.799, 0.845, 0.823, 0.824, (1.7674)+ (0.0475)Ser+(−0.1363)Asn+(−0.0036)Ala+(−0.0064) Val+(0.1117)Phe+(−0.1349)Trp; 0.856, 0.879, 0.806, 0.792, 0.802, 0.828, 0.834, 0.814, (3.1345)+(0.0025) Gly+(0.0090)Gln+(−0.1445)His+(0.0123)Leu+ (0.0927)Phe+(−0.1262)Trp; 0.856, 0.877, 0.745, 0.716, 0.703, 0.850, 0.831, 0.775, (0.0706)+(0.0436)Ser+(− 0.1415)His+(−0.0088)Ala+(0.1230)Ile+(−0.0521) Leu+(0.0896)Phe; 0.856, 0.879, 0.778, 0.747, 0.772, 0.838, 0.832, 0.797, (3.1580)+(0.0415)Ser+(−0.0051) Gly+(0.0052)Gln+(−0.1231)His+(0.0717)Ile+(− 0.1257)Trp; 0.856, 0.884, 0.763, 0.729, 0.776, 0.828, 0.779, 0.778, (1.7795)+(0.0530)Ser+(−0.1211)His+(− 0.0622)Cit+(0.0171)Leu+(0.1217)Phe+(−0.1439)Trp; 0.856, 0.879, 0.743, 0.719, 0.714, 0.794, 0.826, 0.764, (1.3803)+(0.0352)Ser+(−0.0044)Gln+(−0.0459)Val+ (0.1483)Ile+(0.0765)Phe+(−0.1594)Trp; 0.856, 0.882, 0.823, 0.804, 0.792, 0.870, 0.903, 0.842, (6.5043)+(− 0.0055)Ala+(0.0372)Tyr+(−0.0454)Val+(−0.2031) Met+(0.1890)Ile+(−0.1131)Trp; 0.856, 0.882, 0.794, 0.770, 0.765, 0.849, 0.880, 0.816, (3.5114)+(−0.0722) His+(−0.0522)Val+(−0.3129)Met+(0.0187)Orn+ (0.1728)Ile+(0.1204)Phe; 0.856, 0.881, 0.784, 0.763, 0.765, 0.820, 0.852, 0.800, (3.7440)+(0.0126)Thr+(− 0.0913)Cit+(−0.0404)Val+(0.1414)Ile+(0.0809)Phe+ (−0.1701)Trp; 0.856, 0.878, 0.783, 0.766, 0.774, 0.849, 0.799, 0.797, (2.8688)+(0.0318)Ser+(0.0016)Gln+(− 0.0906)Cit+(0.1499)Ile+(−0.0571)Leu+(−0.1684)Trp; 0.856, 0.879, 0.815, 0.807, 0.776, 0.858, 0.888, 0.832, (6.4428)+(−0.0046)Ala+(−0.0458)Val+(−0.1913)Met+ (0.0107)Lys+(0.1853)Ile+(−0.1101)Trp; 0.856, 0.878, 0.758, 0.728, 0.739, 0.837, 0.817, 0.780, (4.0982)+ (0.0361)Ser+(−0.0922)His+(0.0030)Thr+(−0.0238) Val+(0.1297)Ile+(−0.1164)Trp; 0.856, 0.881, 0.790, 0.774, 0.775, 0.849, 0.823, 0.805, (1.9503)+(0.0458) Ser+(−0.0069)Ala+(0.0090)Pro+(−0.2221)Met+ (0.0800)Ile+(−0.1397)Trp; 0.856, 0.878, 0.798, 0.780, 0.793, 0.838, 0.830, 0.810, (2.5591)+(0.0577)Ser+(− 0.0439)Asn+(−0.0062)Gly+(−0.1939)Met+(0.0758) Ile+(−0.1442)Trp; 0.856, 0.879, 0.773, 0.744, 0.763, 0.851, 0.813, 0.793, (4.2656)+(0.0462)Ser+(−0.1014) His+(−0.0051)Ala+(−0.0140)Arg+(0.0888)Ile+(− 0.1155)Trp; 0.856, 0.877, 0.762, 0.731, 0.754, 0.837, 0.807, 0.782, (3.8951)+(0.0396)Ser+(−0.1008)His+ (0.0001)Thr+(0.1096)Ile+(−0.0253)Leu+(−0.1192) Trp; 0.856, 0.882, 0.758, 0.753, 0.720, 0.795, 0.826, 0.774, (0.8295)+(0.0278)Ser+(−0.0375)Tyr+(−0.0425) Val+(0.1385)Ile+(0.0928)Phe+(−0.1572)Trp; 0.856, 0.889, 0.815, 0.814, 0.821, 0.831, 0.794, 0.815, (−0.7940)+(0.0500)Ser+(0.0114)Tyr+(−0.3066)Met+
(0.0006)Orn+(0.1316)Phe+(−0.1485)Trp; 0.856,
0.881, 0.792, 0.772, 0.798, 0.846, 0.794, 0.802,
(4.0859)+(0.0467)Ser+(−0.0769)Asn+(−0.0827)Cit+
(−0.0075)Lys+(0.0758)Ile+(−0.1591)Trp; 0.856,
0.879, 0.784, 0.774, 0.738, 0.861, 0.848, 0.805,
(3.6551)+(0.0350)Ser+(−0.0075)Ala+(−0.0251)Arg+
(−0.0414)Val+(0.1787)Ile+(−0.1286)Trp; 0.856, 0.882,
0.795, 0.786, 0.775, 0.814, 0.850, 0.806, (5.1871)+(−
0.0876)His+(−0.0315)Tyr+(0.1181)Ile+(−0.0512)Leu+
(0.1044)Phe+(−0.1116)Trp; 0.856, 0.884, 0.775, 0.751,
0.782, 0.839, 0.780, 0.788, (2.0499)+(0.0524)Ser+(−
0.1119)His+(−0.0586)Cit+(−0.0040)Lys+(0.1377)
Phe+(−0.1299)Trp; 0.856, 0.886, 0.809, 0.810, 0.816,
0.825, 0.779, 0.807, (−0.6155)+(0.0525)Ser+(−0.0127)
Arg+(−0.2811)Met+(0.0065)Leu+(0.1309)Phe+(−
0.1462)Trp; 0.856, 0.884, 0.823, 0.817, 0.809, 0.841,
0.856, 0.831, (3.6143)+(0.0093)Gln+(−0.1316)His+(−
0.0050)Ala+(0.0067)Pro+(0.1038)Phe+(−0.1201)Trp;
0.856, 0.878, 0.800, 0.783, 0.778, 0.852, 0.851, 0.816,
(7.3588)+(−0.0833)His+(0.0168)Thr+(−0.0065)Ala+
(0.1221)Ile+(−0.0334)Leu+(−0.1208)Trp; 0.856,
0.882, 0.819, 0.806, 0.784, 0.864, 0.894, 0.837,
(7.3498)+(−0.0056)Ala+(−0.0495)Cit+(−0.0397)Val+
(−0.1089)Met+(0.1812)Ile+(−0.1101)Trp; 0.855,
0.880, 0.821, 0.816, 0.775, 0.864, 0.898, 0.838,
(0.4087)+(−0.0716)Asn+(0.0071)Gln+(−0.0643)Val+
(−0.3819)Met+(0.1986)Ile+(0.1252)Phe; 0.855, 0.883,
0.769, 0.741, 0.780, 0.832, 0.775, 0.782, (1.8219)+
(0.0526)Ser+(−0.1188)His+(−0.0627)Cit+(0.0059)
Val+(0.1282)Phe+(−0.1407)Trp; 0.855, 0.878, 0.827,
0.821, 0.793, 0.869, 0.883, 0.842, (5.3025)+(−0.0454)
Asn+(0.0064)Gln+(−0.0421)Val+(−0.1900)Met+
(0.1688)Ile+(−0.1083)Trp; 0.855, 0.886, 0.769, 0.752,
0.765, 0.826, 0.780, 0.781, (1.9243)+(0.0490)Ser+(−
0.1276)His+(−0.0206)Tyr+(−0.0020)Lys+(0.1333)
Phe+(−0.1110)Trp; 0.855, 0.879, 0.815, 0.805, 0.821,
0.850, 0.807, 0.821, (5.6439)+(0.0093)Gln+(−0.1254)
His+(0.0305)Thr+(−0.1946)Met+(0.0326)Leu+(−
0.1145)Trp; 0.855, 0.878, 0.757, 0.726, 0.738, 0.837,
0.819, 0.780, (4.0188)+(0.0376)Ser+(−0.0908)His+
(0.0013)Pro+(−0.0239)Val+(0.1290)Ile+(−0.1157)Trp;
0.855, 0.886, 0.810, 0.795, 0.812, 0.837, 0.828, 0.818,
(6.4436)+(−0.0505)Asn+(−0.1115)His+(0.0295)Thr+
(−0.0038)Ala+(0.1120)Phe+(−0.1234)Trp; 0.855,
0.883, 0.778, 0.746, 0.791, 0.812, 0.813, 0.790,
(5.9215)+(−0.1251)His+(0.0277)Thr+(−0.0217)Arg+
(0.0469)Ile+(0.0846)Phe+(−0.1407)Trp; 0.855, 0.881,
0.766, 0.731, 0.771, 0.844, 0.793, 0.785, (4.1834)+
(0.0460)Ser+(−0.0893)His+(−0.0549)Cit+(−0.0055)
Lys+(0.0852)Ile+(−0.1289)Trp; 0.855, 0.882, 0.799,
0.781, 0.785, 0.818, 0.861, 0.811, (5.2599)+(−0.0929)
His+(−0.0029)Pro+(0.1150)Ile+(−0.0482)Leu+
(0.0885)Phe+(−0.1211)Trp; 0.855, 0.880, 0.801, 0.791,
0.750, 0.859, 0.889, 0.822, (1.2298)+(0.0042)Gly+(−
0.0052)Ala+(−0.0626)Val+(−0.3692)Met+(0.2074)
Ile+(0.1218)Phe; 0.855, 0.883, 0.776, 0.754, 0.750,
0.845, 0.839, 0.797, (3.5460)+(0.0381)Ser+(−0.0037)
Gly+(−0.0711)Cit+(−0.0342)Val+(0.1476)Ile+(−
0.1579)Trp; 0.855, 0.877, 0.770, 0.739, 0.765, 0.841,
0.812, 0.789, (3.1552)+(0.0344)Ser+(0.0047)Gln+(−
0.1249)His+(0.0007)Thr+(0.0726)Ile+(−0.1247)Trp;
0.855, 0.882, 0.789, 0.775, 0.759, 0.816, 0.866, 0.804,
(5.2210)+(−0.0814)His+(−0.0232)Tyr+(−0.0318)Val+
(0.1246)Ile+(0.0969)Phe+(−0.1136)Trp; 0.855, 0.881,
0.812, 0.799, 0.776, 0.855, 0.892, 0.831, (6.9104)+(−
0.0067)Ala+(0.0094)Pro+(−0.0436)Val+(−0.1653)

Met+(0.1780)Ile+(−0.1044)Trp; 0.855, 0.882, 0.798,
0.780, 0.765, 0.845, 0.883, 0.818, (3.5141)+(−0.0672)
His+(−0.0463)Val+(−0.3125)Met+(0.1883)Ile+(−
0.0183)Leu+(0.1296)Phe; 0.855, 0.880, 0.785, 0.757,
0.799, 0.813, 0.811, 0.795, (5.8701)+(−0.1288)His+
(0.0256)Thr+(−0.0067)Lys+(0.0138)Leu+(0.0961)
Phe+(−0.1322)Trp; 0.855, 0.880, 0.773, 0.738, 0.772,
0.841, 0.819, 0.793, (4.3307)+(0.0531)Ser+(−0.0523)
Asn+(−0.0036)Gly+(−0.0985)His+(0.0745)Ile+(−
0.1171)Trp; 0.855, 0.880, 0.770, 0.735, 0.771, 0.844,
0.807, 0.789, (4.2739)+(0.0470)Ser+(−0.0602)Asn+(−
0.1036)His+(0.0144)Orn+(0.0717)Ile+(−0.1155)Trp;
0.855, 0.879, 0.764, 0.731, 0.773, 0.838, 0.778, 0.780,
(−0.5779)+(0.0619)Ser+(−0.1518)His+(−0.0011)Ala+
(−0.2920)Met+(0.0147)Leu+(0.1510)Phe; 0.855,
0.882, 0.782, 0.743, 0.797, 0.821, 0.824, 0.796,
(5.3148)+(−0.1087)His+(0.0240)Thr+(−0.0680)Cit+
(0.0508)Ile+(0.0941)Phe+(−0.1555)Trp; 0.855, 0.879,
0.757, 0.723, 0.763, 0.834, 0.778, 0.774, (4.4331)+
(0.0423)Ser+(−0.1122)His+(0.0102)Thr+(−0.0204)
Arg+(0.0780)Ile+(−0.1249)Trp; 0.855, 0.876, 0.815,
0.804, 0.788, 0.858, 0.868, 0.829, (5.2356)+(0.0080)
Gln+(−0.0952)His+(−0.0058)Ala+(0.1213)Ile+(−
0.0333)Leu+(−0.1176)Trp; 0.855, 0.879, 0.769, 0.757,
0.737, 0.877, 0.790, 0.790, (1.9998)+(0.0356)Ser+
(0.0306)Thr+(−0.0255)Arg+(−0.0597)Val+(−0.4011)
Met+(0.2161)Ile; 0.855, 0.878, 0.799, 0.787, 0.804,
0.834, 0.799, 0.806, (0.7808)+(0.0102)Gln+(−0.1689)
His+(0.0388)Thr+(−0.0046)Val+(−0.3628)Met+
(0.1593)Phe; 0.855, 0.878, 0.818, 0.811, 0.785, 0.858,
0.874, 0.832, (4.8797)+(0.0043)Gln+(−0.0442)Val+(−
0.2432)Met+(0.0085)Lys+(0.1728)Ile+(−0.1172)Trp;
0.855, 0.883, 0.786, 0.768, 0.746, 0.869, 0.853, 0.809,
(3.9761)+(0.0447)Ser+(−0.1394)Asn+(0.0119)Tyr+(−
0.0437)Val+(0.1622)Ile+(−0.1163)Trp; 0.855, 0.883,
0.790, 0.769, 0.765, 0.823, 0.871, 0.807, (5.2332)+(−
0.0853)His+(−0.0011)Pro+(−0.0319)Val+(0.1242)Ile+
(0.0855)Phe+(−0.1197)Trp; 0.855, 0.882, 0.808, 0.808,
0.785, 0.839, 0.829, 0.815, (1.5564)+(0.0484)Ser+(−
0.1360)Asn+(−0.0077)Ala+(0.0102)Pro+(0.0983)
Phe+(−0.1441)Trp; 0.855, 0.884, 0.785, 0.773, 0.748,
0.868, 0.837, 0.807, (4.3237)+(0.0457)Ser+(−0.1095)
Asn+(−0.0179)Arg+(−0.0435)Val+(0.1672)Ile+(−
0.1115)Trp; 0.855, 0.883, 0.791, 0.783, 0.778, 0.857,
0.796, 0.803, (2.8173)+(0.0457)Ser+(−0.0176)Arg+(−
0.1902)Met+(0.1690)Ile+(−0.0630)Leu+(−0.1267)Trp;
0.855, 0.886, 0.810, 0.811, 0.814, 0.821, 0.792, 0.810,
(−1.2236)+(0.0483)Ser+(0.0016)Gln+(−0.3036)Met+
(0.0065)Leu+(0.1275)Phe+(−0.1502)Trp; 0.855,
0.881, 0.820, 0.819, 0.848, 0.818, 0.764, 0.812,
(3.8129)+(0.0442)Thr+(−0.0807)Cit+(−0.0050)Val+(−
0.3265)Met+(0.1586)Phe+(−0.1672)Trp; 0.855, 0.879,
0.758, 0.742, 0.723, 0.802, 0.844, 0.778, (0.5017)+
(0.0316)Ser+(−0.0077)Thr+(−0.0434)Val+(0.1411)
Ile+(0.0731)Phe+(−0.1641)Trp; 0.855, 0.880, 0.827,
0.820, 0.817, 0.844, 0.858, 0.835, (3.5149)+(0.0098)
Gln+(−0.1369)His+(−0.0037)Ala+(0.0040)Val+
(0.1017)Phe+(−0.1208)Trp; 0.855, 0.878, 0.823, 0.804,
0.817, 0.859, 0.860, 0.835, (5.0640)+(−0.0436)Asn+
(0.0116)Gln+(−0.0984)His+(−0.0571)Cit+(0.0713)
Ile+(−0.1302)Trp; 0.855, 0.883, 0.802, 0.794, 0.753,
0.835, 0.902, 0.821, (4.0093)+(−0.0088)Ala+(−0.0445)
Val+(−0.0049)Lys+(0.1644)Ile+(0.0800)Phe+(−
0.1407)Trp; 0.855, 0.877, 0.827, 0.819, 0.797, 0.873,
0.877, 0.842, (4.6565)+(0.0062)Gln+(−0.0089)Ala+(−
0.0866)Cit+(0.1725)Ile+(−0.0623)Leu+(−0.1483)Trp;
0.855, 0.881, 0.776, 0.741, 0.784, 0.812, 0.827, 0.791, (5.3197)+(−0.1285)His+(0.0196)Thr+(0.0042)Orn+
(0.0462)Ile+(0.0771)Phe+(−0.1387)Trp; 0.855, 0.879,
0.817, 0.814, 0.850, 0.811, 0.758, 0.808, (3.9325)+
(0.0454)Thr+(−0.0808)Cit+(−0.0080)Arg+(−0.3232)
Met+(0.1527)Phe+(−0.1731)Trp; 0.855, 0.879, 0.769,
0.758, 0.743, 0.805, 0.829, 0.784, (−0.2442)+(0.0377)
Ser+(−0.0166)Thr+(0.1512)Ile+(−0.0784)Leu+
(0.0729)Phe+(−0.1578)Trp; 0.855, 0.880, 0.823, 0.819,
0.810, 0.845, 0.844, 0.829, (3.3207)+(0.0022)Gly+
(0.0092)Gln+(−0.1349)His+(−0.0032)Ala+(0.1096)
Phe+(−0.1176)Trp; 0.855, 0.878, 0.824, 0.809, 0.810,
0.860, 0.865, 0.836, (4.9673)+(0.0103)Gln+(−0.1050)
His+(−0.0033)Ala+(−0.1136)Met+(0.0793)Ile+(−
0.1121)Trp; 0.855, 0.879, 0.807, 0.790, 0.784, 0.847,
0.870, 0.823, (7.2186)+(−0.0504)His+(−0.0386)Val+(−
0.1835)Met+(0.0134)Lys+(0.1640)Ile+(−0.0984)Trp;
0.855, 0.885, 0.806, 0.786, 0.825, 0.833, 0.804, 0.812,
(6.5516)+(−0.0549)Asn+(−0.0993)His+(0.0328)Thr+
(−0.0646)Cit+(0.1207)Phe+(−0.1407)Trp; 0.855,
0.883, 0.800, 0.784, 0.788, 0.817, 0.855, 0.811,
(5.5847)+(−0.0858)His+(−0.0133)Arg+(0.1182)Ile+(−
0.0526)Leu+(0.0921)Phe+(−0.1201)Trp; 0.855, 0.879,
0.816, 0.802, 0.813, 0.829, 0.847, 0.823, (3.4306)+
(0.0097)Gln+(−0.1416)His+(−0.0027)Lys+(0.0128)
Leu+(0.0912)Phe+(−0.1247)Trp; 0.855, 0.883, 0.814,
0.801, 0.812, 0.862, 0.813, 0.822, (6.3627)+(0.0245)
Thr+(−0.0673)Cit+(−0.1927)Met+(0.1422)Ile+(−
0.0505)Leu+(−0.1364)Trp; 0.855, 0.881, 0.820, 0.826,
0.809, 0.839, 0.811, 0.821, (1.7532)+(0.0487)Ser+(−
0.1173)Asn+(−0.0044)Ala+(−0.0151)Arg+(0.1064)
Phe+(−0.1423)Trp; 0.855, 0.882, 0.773, 0.745, 0.746,
0.871, 0.833, 0.799, (3.1843)+(0.0489)Ser+(−0.0393)
Asn+(−0.0731)His+(−0.0391)Val+(−0.2312)Met+
(0.1739)Ile; 0.855, 0.884, 0.799, 0.788, 0.772, 0.846,
0.852, 0.815, (0.9819)+(0.0487)Ser+(−0.1272)Asn+(−
0.0085)Ala+(0.0581)Ile+(0.0769)Phe+(−0.1534)Trp;
0.855, 0.881, 0.792, 0.765, 0.785, 0.854, 0.834, 0.810,
(2.9927)+(0.0378)Ser+(−0.0097)Ala+(−0.0947)Cit+
(0.0140)Tyr+(0.0921)Ile+(−0.1770)Trp; 0.855, 0.874,
0.795, 0.781, 0.761, 0.883, 0.844, 0.817, (5.7111)+(−
0.0568)Asn+(0.0367)Thr+(−0.0517)Cit+(−0.0591)
Val+(−0.3285)Met+(0.2073)Ile; 0.855, 0.882, 0.773,
0.754, 0.751, 0.851, 0.814, 0.793, (3.7051)+(0.0364)
Ser+(−0.0624)Cit+(−0.0166)Arg+(−0.0361)Val+
(0.1562)Ile+(−0.1510)Trp; 0.855, 0.881, 0.799, 0.772,
0.795, 0.856, 0.837, 0.815, (1.1291)+(0.0496)Ser+(−
0.0066)Ala+(0.0410)Tyr+(−0.2683)Met+(0.0909)Ile+
(−0.1529)Trp; 0.855, 0.876, 0.781, 0.772, 0.727, 0.856,
0.865, 0.805, (3.2418)+(0.0284)Ser+(−0.0009)Thr+(−
0.0087)Ala+(−0.0394)Val+(0.1687)Ile+(−0.1366)Trp;
0.855, 0.880, 0.769, 0.735, 0.768, 0.842, 0.807, 0.788,
(4.2456)+(0.0481)Ser+(−0.0554)Asn+(−0.1007)His+
(0.0016)Pro+(0.0735)Ile+(−0.1161)Trp; 0.855, 0.877,
0.798, 0.781, 0.786, 0.853, 0.826, 0.811, (2.4964)+
(0.0477)Ser+(−0.0444)Asn+(−0.0048)Ala+(−0.1692)
Met+(0.0848)Ile+(−0.1380)Trp; 0.855, 0.882, 0.802,
0.779, 0.794, 0.829, 0.857, 0.815, (5.2018)+(−0.0695)
His+(−0.0686)Cit+(0.1252)Ile+(−0.0543)Leu+
(0.1034)Phe+(−0.1345)Trp; 0.855, 0.880, 0.809, 0.809,
0.812, 0.830, 0.791, 0.810, (2.1574)+(0.0532)Ser+(−
0.1274)Asn+(−0.0886)Cit+(−0.0030)Val+(0.1198)
Phe+(−0.1542)Trp; 0.855, 0.873, 0.805, 0.793, 0.772,
0.854, 0.872, 0.823, (5.5172)+(0.0066)Gln+(−0.0844)
His+(−0.0057)Ala+(−0.0246)Val+(0.1345)Ile+(−
0.1134)Trp; 0.855, 0.884, 0.808, 0.800, 0.770, 0.835,
0.891, 0.824, (4.8756)+(−0.0904)Asn+(−0.0002)Pro+
(−0.0475)Val+(0.1509)Ile+(0.0828)Phe+(−0.1287)Trp;
0.855, 0.881, 0.774, 0.752, 0.736, 0.883, 0.831, 0.801,
(0.7960)+(0.0372)Ser+(0.0189)Thr+(0.0306)Tyr+(−
0.0627)Val+(−0.4608)Met+(0.2203)Ile; 0.855, 0.880,
0.790, 0.776, 0.734, 0.892, 0.869, 0.818, (2.2893)+
(0.0469)Ser+(−0.0795)Asn+(−0.0053)Ala+(−0.0530)
Val+(−0.2301)Met+(0.2058)Ile; 0.855, 0.878, 0.809,
0.791, 0.801, 0.846, 0.844, 0.820, (5.5425)+(−0.0677)
Asn+(0.0093)Gln+(−0.1178)His+(0.0165)Thr+
(0.0616)Ile+(−0.1255)Trp; 0.855, 0.883, 0.809, 0.803,
0.771, 0.832, 0.889, 0.824, (5.0451)+(−0.0712)Asn+(−
0.0140)Arg+(−0.0484)Val+(0.1545)Ile+(0.0859)Phe+
(−0.1280)Trp; 0.855, 0.879, 0.798, 0.780, 0.779, 0.853,
0.844, 0.814, (3.6531)+(0.0499)Ser+(−0.1008)Asn+(−
0.0063)Gly+(0.1375)Ile+(−0.0565)Leu+(−0.1380)Trp;
0.855, 0.879, 0.763, 0.730, 0.756, 0.838, 0.808, 0.783,
(3.9448)+(0.0402)Ser+(−0.0994)His+(−0.0023)Lys+
(0.1095)Ile+(−0.0241)Leu+(−0.1175)Trp; 0.854,
0.881, 0.798, 0.776, 0.782, 0.847, 0.857, 0.815,
(7.2230)+(−0.0517)His+(−0.0377)Val+(−0.1522)Met+
(0.0301)Orn+(0.1593)Ile+(−0.0934)Trp; 0.854, 0.880,
0.772, 0.742, 0.747, 0.870, 0.831, 0.797, (2.7568)+
(0.0453)Ser+(−0.0828)His+(−0.0387)Val+(−0.2825)
Met+(0.0056)Lys+(0.1733)Ile; 0.854, 0.878, 0.757,
0.724, 0.741, 0.838, 0.819, 0.780, (3.8920)+(0.0384)
Ser+(−0.0941)His+(0.0108)Tyr+(−0.0244)Val+
(0.1304)Ile+(−0.1195)Trp; 0.854, 0.884, 0.795, 0.787,
0.797, 0.808, 0.800, 0.798, (6.2704)+(−0.0546)Asn+(−
0.1134)His+(0.0331)Thr+(−0.0359)Tyr+(0.1238)Phe+
(−0.1154)Trp; 0.854, 0.879, 0.828, 0.821, 0.791, 0.876,
0.886, 0.844, (5.6074)+(−0.0967)Asn+(0.0077)Gln+(−
0.0706)Cit+(−0.0363)Val+(0.1494)Ile+(−0.1313)Trp;
0.854, 0.885, 0.823, 0.814, 0.813, 0.835, 0.857, 0.830,
(3.8946)+(−0.0770)Cit+(−0.1943)Met+(0.1597)Ile+(−
0.0756)Leu+(0.1272)Phe+(−0.1367)Trp; 0.854, 0.882,
0.780, 0.758, 0.775, 0.856, 0.795, 0.796, (3.5062)+
(0.0364)Ser+(−0.0858)Cit+(−0.0076)Lys+(0.1478)
Ile+(−0.0513)Leu+(−0.1583)Trp; 0.854, 0.878, 0.794,
0.780, 0.757, 0.852, 0.867, 0.814, (3.0594)+(0.0402)
Ser+(−0.0070)Gly+(−0.0092)Ala+(0.1667)Ile+(−
0.0651)Leu+(−0.1445)Trp; 0.854, 0.880, 0.770, 0.740,
0.746, 0.867, 0.828, 0.795, (2.8134)+(0.0467)Ser+(−
0.0808)His+(−0.0372)Val+(−0.2643)Met+(0.1712)
Ile+(0.0006)Leu; 0.854, 0.877, 0.812, 0.802, 0.784,
0.855, 0.864, 0.826, (5.0964)+(0.0038)Gln+(−0.0440)
Val+(−0.2255)Met+(0.0185)Orn+(0.1708)Ile+(−
0.1119)Trp; 0.854, 0.881, 0.819, 0.815, 0.850, 0.819,
0.764, 0.812, (3.9846)+(0.0449)Thr+(−0.0867)Cit+(−
0.3160)Met+(−0.0047)Lys+(0.1543)Phe+(−0.1716)
Trp; 0.854, 0.878, 0.814, 0.807, 0.846, 0.807, 0.767,
0.807, (3.6467)+(0.0431)Thr+(−0.0870)Cit+(−0.3295)
Met+(0.0063)Leu+(0.1473)Phe+(−0.1770)Trp; 0.854,
0.876, 0.781, 0.771, 0.727, 0.856, 0.863, 0.804,
(3.2400)+(0.0268)Ser+(−0.0090)Ala+(−0.0403)Val+
(0.0081)Orn+(0.1674)Ile+(−0.1374)Trp; 0.854, 0.878,
0.792, 0.774, 0.799, 0.826, 0.797, 0.799, (0.5273)+
(0.0104)Gln+(−0.1731)His+(0.0375)Thr+(0.0039)
Pro+(−0.3739)Met+(0.1493)Phe; 0.854, 0.886, 0.835,
0.835, 0.823, 0.841, 0.858, 0.839, (3.6089)+(−0.0519)
Asn+(0.0112)Gln+(−0.1258)His+(−0.0137)Tyr+
(0.1092)Phe+(−0.1092)Trp; 0.854, 0.883, 0.808, 0.800,
0.769, 0.832, 0.890, 0.823, (4.8623)+(−0.0953)Asn+(−
0.0479)Val+(0.0022)Lys+(0.1502)Ile+(0.0818)Phe+(−
0.1291)Trp; 0.854, 0.880, 0.796, 0.776, 0.764, 0.844,
0.884, 0.817, (3.5104)+(0.0069)Asn+(−0.0702)His+(−
0.0513)Val+(−0.3217)Met+(0.1759)Ile+(0.1274)Phe;
0.854, 0.878, 0.769, 0.737, 0.766, 0.838, 0.812, 0.788,
(3.0663)+(0.0349)Ser+(0.0048)Gln+(−0.1268)His+

(0.0055)Tyr+(0.0721)Ile+(−0.1268)Trp; 0.854, 0.881, 0.763, 0.722, 0.769, 0.844, 0.797, 0.783, (3.8897)+(0.0460)Ser+(−0.0970)His+(−0.0561)Cit+(0.0104) Tyr+(0.0803)Ile+(−0.1378)Trp; 0.854, 0.881, 0.774, 0.743, 0.746, 0.868, 0.848, 0.801, (2.8344)+(0.0527) Ser+(−0.0044)Gly+(−0.0777)His+(−0.0378)Val+(−0.2593)Met+(0.1720)Ile; 0.854, 0.876, 0.779, 0.753, 0.764, 0.841, 0.835, 0.798, (7.0336)+(−0.0666)His+ (0.0181)Thr+(−0.0496)Cit+(−0.0280)Val+(0.1359) Ile+(−0.1266)Trp; 0.854, 0.880, 0.819, 0.820, 0.805, 0.828, 0.836, 0.823, (2.1097)+(0.0568)Ser+(−0.1416) Asn+(−0.0066)Gly+(−0.0083)Val+(0.1046)Phe+(−0.1378)Trp; 0.854, 0.879, 0.811, 0.810, 0.843, 0.812, 0.744, 0.802, (3.2839)+(0.0028)Gly+(0.0419)Thr+(−0.0899)Cit+(−0.3318)Met+(0.1551)Phe+(−0.1709) Trp; 0.854, 0.879, 0.810, 0.805, 0.814, 0.825, 0.804, 0.812, (2.2035)+(0.0559)Ser+(−0.1231)Asn+(−0.0026)Gly+(−0.0873)Cit+(0.1136)Phe+(−0.1602)Trp; 0.854, 0.872, 0.796, 0.787, 0.759, 0.883, 0.837, 0.817, (3.5246)+(0.0033)Gln+(0.0323)Thr+(−0.0613)Cit+(−0.0570)Val+(−0.3960)Met+(0.2045)Ile; 0.854, 0.878, 0.779, 0.759, 0.771, 0.849, 0.798, 0.794, (3.1498)+ (0.0370)Ser+(−0.0052)Thr+(−0.0840)Cit+(0.1532) Ile+(−0.0582)Leu+(−0.1608)Trp; 0.854, 0.877, 0.802, 0.792, 0.761, 0.860, 0.872, 0.821, (6.3027)+(0.0040) Gly+(−0.0080)Ala+(−0.0714)Cit+(−0.0361)Val+ (0.1725)Ile+(−0.1320)Trp; 0.854, 0.877, 0.776, 0.764, 0.724, 0.854, 0.861, 0.800, (3.5806)+(0.0305)Ser+(−0.0016)Gln+(−0.0085)Ala+(−0.0399)Val+(0.1710)Ile+ (−0.1342)Trp; 0.854, 0.878, 0.790, 0.775, 0.797, 0.831, 0.783, 0.796, (0.4304)+(0.0032)Gly+(0.0098)Gln+(−0.1764)His+(0.0370)Thr+(−0.3675)Met+(0.1564)Phe; 0.854, 0.883, 0.771, 0.748, 0.768, 0.798, 0.817, 0.783, (5.2891)+(−0.1260)His+(0.0248)Thr+(−0.0400)Tyr+ (0.0493)Ile+(0.0993)Phe+(−0.1294)Trp; 0.854, 0.884, 0.798, 0.780, 0.796, 0.826, 0.826, 0.807, (5.7900)+(−0.1179)His+(0.0228)Thr+(−0.0054)Ala+(0.0051)Pro+ (0.1075)Phe+(−0.1266)Trp; 0.854, 0.880, 0.817, 0.807, 0.813, 0.830, 0.843, 0.823, (3.3573)+(0.0096)Gln+(−0.1396)His+(0.0026)Val+(−0.0007)Lys+(0.0979)Phe+ (−0.1217)Trp; 0.854, 0.877, 0.758, 0.727, 0.739, 0.837, 0.820, 0.781, (4.0501)+(0.0376)Ser+(−0.0909)His+(−0.0244)Val+(0.1289)Ile+(0.0021)Leu+(−0.1154)Trp; 0.854, 0.882, 0.782, 0.753, 0.755, 0.888, 0.842, 0.809, (0.8795)+(0.0469)Ser+(−0.0482)Cit+(0.0380)Tyr+(−0.0563)Val+(−0.3958)Met+(0.2067)Ile; 0.854, 0.877, 0.770, 0.740, 0.765, 0.839, 0.812, 0.789, (3.1302)+ (0.0347)Ser+(0.0047)Gln+(−0.1247)His+(0.0001) Pro+(0.0726)Ile+(−0.1245)Trp; 0.854, 0.878, 0.769, 0.736, 0.767, 0.844, 0.807, 0.789, (4.2704)+(0.0480) Ser+(−0.0532)Asn+(−0.1003)His+(−0.0008)Lys+ (0.0761)Ile+(−0.1150)Trp; 0.854, 0.880, 0.779, 0.745, 0.784, 0.818, 0.829, 0.794, (5.4488)+(−0.1299)His+ (0.0219)Thr+(−0.0048)Pro+(0.0520)Ile+(0.0813)Phe+ (−0.1392)Trp; 0.854, 0.879, 0.765, 0.734, 0.775, 0.834, 0.776, 0.780, (−0.4167)+(0.0638)Ser+(−0.0260)Asn+ (−0.1484)His+(−0.2780)Met+(0.0126)Leu+(0.1517) Phe; 0.854, 0.886, 0.775, 0.760, 0.775, 0.830, 0.773, 0.784, (2.0891)+(0.0525)Ser+(−0.1244)His+(−0.0188) Arg+(−0.0188)Tyr+(0.1388)Phe+(−0.1100)Trp; 0.854, 0.879, 0.810, 0.800, 0.806, 0.829, 0.832, 0.817, (3.1127)+(0.0023)Gly+(0.0090)Gln+(−0.1418)His+ (0.0027)Val+(0.0998)Phe+(−0.1223)Trp; 0.854, 0.878, 0.759, 0.728, 0.741, 0.839, 0.820, 0.782, (4.1188)+ (0.0381)Ser+(−0.0880)His+(−0.0235)Val+(−0.0032) Lys+(0.1320)Ile+(−0.1129)Trp; 0.854, 0.880, 0.808, 0.805, 0.812, 0.829, 0.788, 0.809, (2.1909)+(0.0530) Ser+(−0.1186)Asn+(−0.0917)Cit+(−0.0036)Lys+ (0.1178)Phe+(−0.1570)Trp; 0.854, 0.878, 0.802, 0.781, 0.785, 0.860, 0.849, 0.819, (7.3654)+(−0.0740)Asn+(−0.0876)Cit+(−0.0417)Val+(0.0526)Orn+(0.1510)Ile+ (−0.1240)Trp; 0.854, 0.882, 0.822, 0.813, 0.794, 0.854, 0.882, 0.836, (4.3913)+(−0.0099)Ala+(−0.0973)Cit+ (0.1736)Ile+(−0.0766)Leu+(0.1048)Phe+(−0.1499) Trp; 0.854, 0.878, 0.782, 0.773, 0.730, 0.854, 0.861, 0.805, (3.2733)+(0.0279)Ser+(−0.0088)Ala+(−0.0324) Val+(0.1850)Ile+(−0.0231)Leu+(−0.1348)Trp; 0.854, 0.876, 0.810, 0.792, 0.798, 0.851, 0.852, 0.823, (4.7756)+(0.0091)Gln+(−0.0874)His+(−0.0596)Cit+ (0.1172)Ile+(−0.0321)Leu+(−0.1301)Trp; 0.854, 0.879, 0.767, 0.738, 0.776, 0.839, 0.772, 0.781, (−0.4046)+(0.0589)Ser+(−0.1495)His+(−0.0005)Ala+ (−0.2769)Met+(0.0136)Orn+(0.1572)Phe; 0.854, 0.886, 0.810, 0.806, 0.818, 0.825, 0.792, 0.810, (−0.9777)+(0.0509)Ser+(0.0119)Tyr+(−0.3152)Met+ (0.0071)Leu+(0.1255)Phe+(−0.1515)Trp; 0.854, 0.876, 0.803, 0.793, 0.826, 0.857, 0.743, 0.805, (5.6485)+(0.0423)Ser+(−0.1097)Asn+(−0.1136)Cit+ (0.0082)Pro+(0.0503)Orn+(−0.1503)Trp; 0.854, 0.878, 0.787, 0.765, 0.772, 0.829, 0.846, 0.803, (4.0067)+(−0.1092)Cit+(−0.0406)Val+(0.0366)Orn+(0.1365)Ile+ (0.0731)Phe+(−0.1600)Trp; 0.854, 0.882, 0.825, 0.833, 0.804, 0.846, 0.833, 0.829, (1.0716)+(0.0443)Ser+(−0.1424)Asn+(0.0028)Gln+(−0.0048)Ala+(0.0997) Phe+(−0.1450)Trp; 0.854, 0.880, 0.815, 0.804, 0.810, 0.826, 0.843, 0.821, (3.3393)+(0.0094)Gln+(−0.1392) His+(0.0021)Pro+(0.0018)Val+(0.0967)Phe+(−0.1227)Trp; 0.854, 0.876, 0.804, 0.802, 0.800, 0.859, 0.779, 0.810, (4.1504)+(0.0367)Ser+(0.0071)Gln+(−0.1000)His+(0.0135)Pro+(−0.1443)Met+(−0.0962) Trp; 0.854, 0.881, 0.830, 0.826, 0.806, 0.847, 0.876, 0.839, (3.7761)+(−0.0059)Ala+(−0.2055)Met+ (0.1677)Ile+(−0.0784)Leu+(0.1105)Phe+(−0.1244) Trp; 0.854, 0.884, 0.772, 0.754, 0.776, 0.828, 0.771, 0.782, (1.8983)+(0.0519)Ser+(−0.1109)His+(−0.0572) Cit+(−0.0201)Tyr+(0.1453)Phe+(−0.1271)Trp; 0.854, 0.886, 0.778, 0.756, 0.783, 0.831, 0.793, 0.790, (2.2574)+(0.0563)Ser+(−0.0032)Gly+(−0.1245)His+ (−0.0189)Arg+(0.1274)Phe+(−0.1176)Trp; 0.854, 0.872, 0.797, 0.782, 0.795, 0.833, 0.817, 0.807, (5.3433)+(0.0099)Gln+(−0.1289)His+(0.0182)Thr+(−0.0274)Arg+(0.0676)Ile+(−0.1315)Trp; 0.854, 0.881, 0.808, 0.823, 0.789, 0.825, 0.796, 0.808, (1.6311)+ (0.0486)Ser+(−0.1366)Asn+(−0.0289)Tyr+(−0.0076) Val+(0.1228)Phe+(−0.1297)Trp; 0.854, 0.877, 0.803, 0.795, 0.755, 0.866, 0.878, 0.824, (7.0970)+(−0.0928) Asn+(0.0211)Thr+(−0.0069)Ala+(−0.0445)Val+ (0.1731)Ile+(−0.1189)Trp; 0.854, 0.877, 0.762, 0.731, 0.754, 0.837, 0.807, 0.782, (3.8953)+(0.0396)Ser+(−0.1007)His+(−0.0001)Pro+(0.1099)Ile+(−0.0254) Leu+(−0.1191)Trp; 0.854, 0.885, 0.806, 0.805, 0.811, 0.821, 0.787, 0.806, (−0.8636)+(0.0503)Ser+(−0.2974) Met+(−0.0002)Orn+(0.0070)Leu+(0.1283)Phe+(−0.1487)Trp; 0.854, 0.882, 0.801, 0.783, 0.817, 0.822, 0.796, 0.805, (6.6511)+(−0.0395)Asn+(−0.1151)His+ (0.0328)Thr+(−0.0187)Arg+(0.1099)Phe+(−0.1273) Trp; 0.854, 0.881, 0.788, 0.764, 0.801, 0.814, 0.805, 0.796, (5.6640)+(−0.1249)His+(0.0223)Thr+(0.0131) Orn+(−0.0041)Lys+(0.1008)Phe+(−0.1252)Trp; 0.854, 0.878, 0.802, 0.777, 0.796, 0.856, 0.839, 0.817, (7.7943)+(−0.0821)His+(0.0234)Thr+(−0.0068)Ala+ (−0.0585)Cit+(0.0820)Ile+(−0.1340)Trp; 0.854, 0.878, 0.792, 0.768, 0.801, 0.838, 0.803, 0.802, (7.7380)+(−0.0941)His+(0.0366)Thr+(−0.0091)Arg+(−0.1902)

Met+(0.0774)Ile+(−0.1153)Trp; 0.853, 0.882, 0.818, 0.801, 0.794, 0.858, 0.882, 0.834, (5.9749)+(0.0333) Tyr+(−0.0488)Val+(−0.2732)Met+(0.0116)Lys+ (0.1822)Ile+(−0.1203)Trp; 0.853, 0.882, 0.797, 0.791, 0.793, 0.810, 0.815, 0.802, (3.5467)+(0.0072)Gln+(− 0.1396)His+(0.0200)Thr+(−0.0305)Tyr+(0.1177)Phe+ (−0.1204)Trp; 0.853, 0.883, 0.816, 0.826, 0.808, 0.833, 0.793, 0.815, (1.8139)+(0.0494)Ser+(−0.1292)Asn+(− 0.0154)Arg+(−0.0079)Val+(0.1126)Phe+(−0.1365) Trp; 0.853, 0.883, 0.794, 0.779, 0.795, 0.826, 0.812, 0.803, (5.5145)+(0.0020)Gly+(−0.1222)His+(0.0231) Thr+(−0.0040)Ala+(0.1120)Phe+(−0.1244)Trp; 0.853, 0.881, 0.766, 0.739, 0.761, 0.838, 0.795, 0.783, (4.1722)+(0.0450)Ser+(−0.0902)His+(−0.0209)Arg+ (0.1274)Ile+(−0.0344)Leu+(−0.1159)Trp; 0.853, 0.877, 0.758, 0.718, 0.761, 0.834, 0.799, 0.778, (3.9897)+(0.0416)Ser+(−0.1114)His+(0.0129)Orn+(− 0.0060)Lys+(0.0761)Ile+(−0.1189)Trp; 0.853, 0.881, 0.795, 0.788, 0.804, 0.820, 0.779, 0.798, (2.0211)+ (0.0545)Ser+(−0.1287)Asn+(−0.0977)Cit+(0.0075) Pro+(0.1091)Phe+(−0.1667)Trp; 0.853, 0.879, 0.769, 0.733, 0.769, 0.844, 0.809, 0.789, (4.1621)+(0.0487) Ser+(−0.0572)Asn+(−0.1030)His+(0.0091)Tyr+ (0.0745)Ile+(−0.1192)Trp; 0.853, 0.878, 0.762, 0.728, 0.755, 0.837, 0.808, 0.782, (3.8342)+(0.0399)Ser+(− 0.1024)His+(0.0045)Tyr+(0.1091)Ile+(−0.0253)Leu+ (−0.1211)Trp; 0.853, 0.879, 0.787, 0.765, 0.798, 0.809, 0.808, 0.795, (5.5664)+(−0.1241)His+(0.0224)Thr+ (0.0008)Pro+(−0.0007)Val+(0.1037)Phe+(−0.1276) Trp; 0.853, 0.879, 0.796, 0.772, 0.802, 0.844, 0.810, 0.807, (1.7687)+(0.0515)Ser+(−0.0472)Asn+(0.0304) Tyr+(−0.2456)Met+(0.0769)Ile+(−0.1522)Trp; 0.853, 0.877, 0.794, 0.775, 0.804, 0.859, 0.775, 0.803, (5.2235)+(0.0478)Ser+(−0.0871)His+(0.0129)Pro+ (0.0338)Tyr+(−0.1721)Met+(−0.1070)Trp; 0.853, 0.880, 0.767, 0.739, 0.775, 0.838, 0.770, 0.781, (−0.4033)+(0.0585)Ser+(−0.1475)His+(−0.0025)Val+ (−0.2779)Met+(0.0150)Orn+(0.1602)Phe; 0.853, 0.876, 0.817, 0.810, 0.784, 0.859, 0.873, 0.831, (4.9305)+(0.0008)Gly+(0.0047)Gln+(−0.0419)Val+(− 0.2217)Met+(0.1715)Ile+(−0.1131)Trp; 0.853, 0.879, 0.826, 0.822, 0.813, 0.843, 0.855, 0.833, (3.5052)+ (0.0095)Gln+(−0.1340)His+(−0.0033)Ala+(0.0012) Lys+(0.1067)Phe+(−0.1183)Trp; 0.853, 0.880, 0.799, 0.781, 0.800, 0.829, 0.823, 0.808, (5.8222)+(−0.1210) His+(0.0244)Thr+(−0.0042)Ala+(0.0013)Val+ (0.1088)Phe+(−0.1273)Trp; 0.853, 0.880, 0.805, 0.792, 0.780, 0.858, 0.851, 0.820, (6.5462)+(0.0047)Gly+(− 0.0529)Cit+(−0.0398)Val+(−0.1568)Met+(0.1732)Ile+ (−0.1147)Trp; 0.853, 0.879, 0.791, 0.773, 0.735, 0.884, 0.887, 0.820, (1.3510)+(0.0500)Ser+(−0.0061)Gly+(− 0.0057)Ala+(−0.0518)Val+(−0.2988)Met+(0.2055)Ile; 0.853, 0.877, 0.786, 0.773, 0.791, 0.849, 0.766, 0.794, (5.1177)+(0.0440)Ser+(−0.0892)His+(0.0149)Pro+(− 0.1640)Met+(0.0121)Lys+(−0.1050)Trp; 0.853, 0.879, 0.791, 0.769, 0.801, 0.829, 0.802, 0.800, (0.5373)+ (0.0105)Gln+(−0.1793)His+(0.0393)Thr+(−0.3774) Met+(0.0103)Leu+(0.1432)Phe; 0.853, 0.881, 0.827, 0.839, 0.841, 0.808, 0.781, 0.817, (1.6661)+(0.0043) Gln+(0.0376)Thr+(−0.0102)Val+(−0.3675)Met+ (0.1471)Phe+(−0.1541)Trp; 0.853, 0.879, 0.806, 0.803, 0.811, 0.826, 0.788, 0.807, (2.1018)+(0.0529)Ser+(− 0.1251)Asn+(−0.0917)Cit+(0.0000)Arg+(0.1151)Phe+ (−0.1595)Trp; 0.853, 0.883, 0.801, 0.784, 0.801, 0.830, 0.821, 0.809, (5.9036)+(−0.1190)His+(0.0256)Thr+(− 0.0040)Ala+(−0.0026)Lys+(0.1123)Phe+(−0.1250) Trp; 0.853, 0.880, 0.789, 0.766, 0.801, 0.814, 0.807, 0.797, (5.7142)+(−0.1235)His+(0.0240)Thr+(0.0000) Val+(−0.0033)Lys+(0.1058)Phe+(−0.1265)Trp; 0.853, 0.880, 0.783, 0.761, 0.793, 0.810, 0.798, 0.791, (5.2625)+(0.0022)Gly+(−0.1268)His+(0.0212)Thr+(− 0.0001)Val+(0.1054)Phe+(−0.1261)Trp; 0.853, 0.878, 0.789, 0.769, 0.786, 0.830, 0.821, 0.801, (1.9274)+ (0.0568)Ser+(−0.0069)Gly+(0.0056)Pro+(−0.2481) Met+(0.0714)Ile+(−0.1480)Trp; 0.853, 0.880, 0.760, 0.724, 0.774, 0.836, 0.772, 0.776, (−0.6754)+(0.0610) Ser+(−0.1541)His+(−0.2962)Met+(0.0094)Orn+ (0.0121)Leu+(0.1492)Phe; 0.853, 0.881, 0.810, 0.817, 0.826, 0.795, 0.769, 0.802, (3.0139)+(0.0392)Thr+ (0.0082)Pro+(−0.0122)Val+(−0.3683)Met+(0.1471) Phe+(−0.1488)Trp; 0.853, 0.881, 0.783, 0.761, 0.775, 0.848, 0.811, 0.799, (3.2888)+(0.0391)Ser+(−0.0034) Gly+(−0.0827)Cit+(0.1481)Ile+(−0.0565)Leu+(− 0.1646)Trp; 0.853, 0.884, 0.802, 0.784, 0.791, 0.826, 0.857, 0.814, (3.2800)+(0.0086)Gln+(−0.1346)His+(− 0.0222)Tyr+(0.0491)Ile+(0.0865)Phe+(−0.1254)Trp; 0.853, 0.878, 0.782, 0.770, 0.732, 0.856, 0.861, 0.805, (3.4668)+(0.0310)Ser+(−0.0084)Ala+(−0.0380)Val+(− 0.0084)Lys+(0.1711)Ile+(−0.1294)Trp; 0.853, 0.879, 0.765, 0.732, 0.784, 0.847, 0.752, 0.779, (−0.2887)+ (0.0592)Ser+(−0.1395)His+(−0.0565)Cit+(−0.2795) Met+(0.0290)Orn+(0.1555)Phe; 0.853, 0.878, 0.796, 0.781, 0.802, 0.831, 0.797, 0.803, (0.8290)+(0.0106) Gln+(−0.1733)His+(0.0397)Thr+(−0.3593)Met+(− 0.0039)Lys+(0.1535)Phe; 0.853, 0.878, 0.817, 0.810, 0.785, 0.857, 0.874, 0.831, (5.0230)+(0.0048)Gln+ (0.0038)Pro+(−0.0421)Val+(−0.2294)Met+(0.1676) Ile+(−0.1133)Trp; 0.853, 0.873, 0.810, 0.799, 0.783, 0.854, 0.867, 0.825, (5.6444)+(−0.0643)Asn+(0.0086) Gln+(−0.0820)His+(−0.0264)Val+(0.1260)Ile+(− 0.1061)Trp; 0.853, 0.879, 0.778, 0.760, 0.771, 0.849, 0.792, 0.793, (3.2943)+(0.0343)Ser+(−0.0864)Cit+(− 0.0040)Tyr+(0.1496)Ile+(−0.0564)Leu+(−0.1629)Trp; 0.853, 0.875, 0.756, 0.720, 0.757, 0.834, 0.794, 0.776, (4.1211)+(0.0405)Ser+(−0.1107)His+(0.0050)Thr+(− 0.0057)Lys+(0.0783)Ile+(−0.1207)Trp; 0.853, 0.877, 0.785, 0.762, 0.764, 0.843, 0.847, 0.804, (7.6402)+(− 0.0653)Asn+(−0.0666)His+(0.0222)Thr+(−0.0329) Val+(0.1409)Ile+(−0.1100)Trp; 0.853, 0.874, 0.810, 0.793, 0.794, 0.848, 0.862, 0.825, (5.2139)+(0.0088) Gln+(−0.1137)His+(−0.0061)Ala+(0.0042)Pro+ (0.0710)Ile+(−0.1230)Trp; 0.853, 0.880, 0.803, 0.807, 0.803, 0.823, 0.779, 0.803, (2.0225)+(0.0538)Ser+(− 0.1193)Asn+(−0.0886)Cit+(−0.0255)Tyr+(0.1286) Phe+(−0.1510)Trp; 0.853, 0.880, 0.809, 0.796, 0.780, 0.852, 0.871, 0.825, (6.2637)+(0.0054)Pro+(−0.0470) Val+(−0.2383)Met+(0.0121)Lys+(0.1731)Ile+(− 0.1140)Trp; 0.853, 0.881, 0.824, 0.814, 0.813, 0.843, 0.861, 0.833, (3.5808)+(0.0097)Gln+(−0.1388)His+(− 0.0040)Ala+(0.0143)Leu+(0.0950)Phe+(−0.1241)Trp; 0.853, 0.876, 0.763, 0.725, 0.763, 0.830, 0.815, 0.783, (4.0817)+(0.0495)Ser+(−0.0044)Gly+(−0.1050)His+ (−0.0055)Lys+(0.0785)Ile+(−0.1200)Trp; 0.853, 0.880, 0.789, 0.766, 0.801, 0.813, 0.807, 0.797, (5.6983)+(−0.1233)His+(0.0237)Thr+(0.0006)Pro+(− 0.0033)Lys+(0.1052)Phe+(−0.1267)Trp; 0.853, 0.876, 0.780, 0.770, 0.726, 0.854, 0.866, 0.804, (3.0792)+ (0.0284)Ser+(−0.0093)Ala+(0.0087)Tyr+(−0.0403) Val+(0.1701)Ile+(−0.1406)Trp; 0.853, 0.879, 0.825, 0.801, 0.823, 0.858, 0.865, 0.837, (4.4850)+(0.0111) Gln+(−0.1120)His+(0.0277)Tyr+(−0.1733)Met+ (0.0738)Ile+(−0.1210)Trp; 0.853, 0.881, 0.766, 0.728, 0.771, 0.842, 0.799, 0.785, (4.0528)+(0.0475)Ser+(− 0.0017)Gly+(−0.0939)His+(−0.0516)Cit+(0.0804)Ile+

(−0.1322)Trp; 0.853, 0.879, 0.812, 0.797, 0.809, 0.826, 0.847, 0.820, (3.3749)+(0.0094)Gln+(−0.1422)His+ (0.0012)Pro+(0.0110)Leu+(0.0897)Phe+(−0.1262)Trp; 0.853, 0.884, 0.807, 0.802, 0.757, 0.837, 0.901, 0.824, (4.3817)+(−0.0082)Ala+(−0.0196)Arg+(−0.0475)Val+ (0.1702)Ile+(0.0862)Phe+(−0.1360)Trp; 0.853, 0.878, 0.775, 0.747, 0.788, 0.808, 0.798, 0.785, (5.2334)+ (0.0025)Gly+(−0.1326)His+(0.0211)Thr+(0.0116) Leu+(0.0948)Phe+(−0.1319)Trp; 0.853, 0.877, 0.768, 0.738, 0.768, 0.843, 0.796, 0.786, (4.3687)+(0.0496) Ser+(−0.0418)Asn+(−0.0997)His+(−0.0116)Arg+ (0.0778)Ile+(−0.1155)Trp; 0.853, 0.878, 0.766, 0.736, 0.776, 0.838, 0.768, 0.780, (−0.3931)+(0.0595)Ser+(− 0.1494)His+(−0.2757)Met+(0.0139)Orn+(−0.0018) Lys+(0.1576)Phe; 0.853, 0.878, 0.765, 0.734, 0.788, 0.805, 0.769, 0.774, (0.7248)+(0.0373)Ser+(−0.1351) Cit+(0.0265)Orn+(0.0486)Ile+(0.0698)Phe+(−0.2088) Trp; 0.853, 0.880, 0.814, 0.805, 0.809, 0.827, 0.842, 0.820, (3.3601)+(0.0093)Gln+(−0.1373)His+(0.0025) Pro+(−0.0002)Lys+(0.0993)Phe+(−0.1211)Trp; 0.853, 0.877, 0.760, 0.721, 0.761, 0.830, 0.812, 0.781, (4.0858)+(0.0458)Ser+(−0.0044)Gly+(−0.1125)His+ (0.0049)Thr+(0.0735)Ile+(−0.1262)Trp; 0.853, 0.878, 0.770, 0.739, 0.765, 0.838, 0.810, 0.788, (3.1649)+ (0.0344)Ser+(0.0045)Gln+(−0.1254)His+(0.0044) Orn+(0.0715)Ile+(−0.1246)Trp; 0.853, 0.879, 0.804, 0.799, 0.810, 0.825, 0.789, 0.806, (2.0574)+(0.0529) Ser+(−0.1248)Asn+(−0.0928)Cit+(0.0040)Leu+ (0.1114)Phe+(−0.1627)Trp; 0.853, 0.881, 0.817, 0.824, 0.798, 0.842, 0.821, 0.821, (1.6512)+(0.0472)Ser+(− 0.1285)Asn+(−0.0046)Ala+(−0.0016)Lys+(0.1025) Phe+(−0.1417)Trp; 0.853, 0.878, 0.827, 0.834, 0.844, 0.811, 0.782, 0.818, (3.9635)+(−0.0513)Asn+(0.0425) Thr+(−0.0111)Val+(−0.3070)Met+(0.1482)Phe+(− 0.1449)Trp; 0.853, 0.880, 0.778, 0.758, 0.771, 0.848, 0.792, 0.792, (3.2032)+(0.0345)Ser+(−0.0879)Cit+ (0.0005)Pro+(0.1488)Ile+(−0.0565)Leu+(−0.1656) Trp; 0.853, 0.879, 0.779, 0.762, 0.775, 0.853, 0.782, 0.793, (3.4244)+(0.0382)Ser+(−0.0733)Cit+(−0.0168) Arg+(0.1589)Ile+(−0.0613)Leu+(−0.1577)Trp; 0.853, 0.878, 0.783, 0.766, 0.760, 0.822, 0.849, 0.799, (3.3342)+(0.0045)Gly+(−0.0908)Cit+(−0.0399)Val+ (0.1444)Ile+(0.0863)Phe+(−0.1639)Trp; 0.853, 0.880, 0.798, 0.797, 0.743, 0.830, 0.893, 0.816, (3.8580)+(− 0.0082)Ala+(−0.0189)Tyr+(−0.0445)Val+(0.1615)Ile+ (0.0863)Phe+(−0.1394)Trp; 0.853, 0.880, 0.764, 0.731, 0.779, 0.839, 0.768, 0.779, (−0.5166)+(0.0631)Ser+(− 0.1441)His+(−0.0353)Cit+(−0.2997)Met+(0.0146) Leu+(0.1543)Phe; 0.853, 0.879, 0.800, 0.783, 0.812, 0.837, 0.791, 0.806, (0.7194)+(0.0112)Gln+(−0.1660) His+(0.0394)Thr+(−0.0460)Cit+(−0.3655)Met+ (0.1558)Phe; 0.853, 0.876, 0.804, 0.796, 0.761, 0.850, 0.883, 0.822, (−0.2433)+(0.0023)Gly+(0.0041)Gln+(− 0.0636)Val+(−0.4370)Met+(0.1997)Ile+(0.1242)Phe; 0.853, 0.880, 0.764, 0.728, 0.771, 0.842, 0.788, 0.782, (4.1408)+(0.0468)Ser+(−0.0937)His+(−0.0484)Cit+(− 0.0076)Arg+(0.0823)Ile+(−0.1306)Trp; 0.853, 0.879, 0.814, 0.798, 0.806, 0.852, 0.844, 0.825, (4.5941)+ (0.0028)Gly+(0.0100)Gln+(−0.1091)His+(−0.1396) Met+(0.0768)Ile+(−0.1114)Trp; 0.853, 0.877, 0.784, 0.767, 0.731, 0.885, 0.864, 0.812, (1.2558)+(0.0413) Ser+(−0.0001)Gln+(−0.0059)Ala+(−0.0515)Val+(− 0.3037)Met+(0.2054)Ile; 0.853, 0.877, 0.759, 0.723, 0.765, 0.835, 0.785, 0.777, (4.1643)+(0.0446)Ser+(− 0.1109)His+(−0.0183)Arg+(0.0158)Orn+(0.0754)Ile+ (−0.1217)Trp; 0.852, 0.878, 0.762, 0.729, 0.773, 0.833, 0.778, 0.778, (−0.6323)+(0.0632)Ser+(−0.0009)Gly+ (−0.1518)His+(−0.2972)Met+(0.0136)Leu+(0.1509) Phe; 0.852, 0.879, 0.761, 0.728, 0.774, 0.835, 0.771, 0.777, (−0.5887)+(0.0630)Ser+(−0.1515)His+(− 0.2914)Met+(−0.0030)Lys+(0.0148)Leu+(0.1517)Phe; 0.852, 0.878, 0.768, 0.752, 0.730, 0.872, 0.816, 0.793, (1.3742)+(0.0335)Ser+(0.0207)Thr+(0.0039)Pro+(− 0.0585)Val+(−0.4193)Met+(0.2064)Ile; 0.852, 0.877, 0.811, 0.801, 0.773, 0.860, 0.879, 0.828, (6.4716)+ (0.0025)Gly+(−0.0048)Ala+(−0.0429)Val+(−0.1624) Met+(0.1843)Ile+(−0.1053)Trp; 0.852, 0.878, 0.781, 0.763, 0.732, 0.883, 0.859, 0.809, (1.1897)+(0.0392) Ser+(−0.0061)Ala+(−0.0532)Val+(−0.3108)Met+ (0.0163)Orn+(0.2038)Ile; 0.852, 0.877, 0.785, 0.763, 0.794, 0.838, 0.789, 0.796, (1.3956)+(0.0438)Ser+ (0.0107)Thr+(0.0265)Tyr+(−0.3095)Met+(0.0781)Ile+ (−0.1584)Trp; 0.852, 0.877, 0.808, 0.787, 0.788, 0.854, 0.871, 0.825, (6.0830)+(0.0274)Tyr+(−0.0477)Val+(− 0.2427)Met+(0.0224)Orn+(0.1787)Ile+(−0.1119)Trp; 0.852, 0.883, 0.799, 0.796, 0.779, 0.833, 0.826, 0.808, (1.7192)+(0.0501)Ser+(−0.1603)Asn+(−0.0338)Val+ (0.0531)Leu+(0.1032)Phe+(−0.1381)Trp; 0.852, 0.874, 0.741, 0.706, 0.723, 0.831, 0.803, 0.766, (0.2788)+(0.0567)Ser+(−0.1190)Asn+(−0.1350)His+ (0.1092)Ile+(−0.0537)Leu+(0.1080)Phe; 0.852, 0.880, 0.797, 0.779, 0.761, 0.844, 0.886, 0.817, (3.1454)+(− 0.0745)His+(−0.0547)Val+(−0.3500)Met+(0.0122) Lys+(0.1769)Ile+(0.1281)Phe; 0.852, 0.877, 0.804, 0.776, 0.810, 0.847, 0.832, 0.816, (4.9631)+(0.0087) Gln+(−0.1038)His+(−0.0743)Cit+(0.0301)Orn+ (0.0646)Ile+(−0.1374)Trp; 0.852, 0.876, 0.805, 0.792, 0.780, 0.848, 0.862, 0.820, (6.0536)+(−0.0476)Val+(− 0.2262)Met+(0.0210)Orn+(0.0084)Lys+(0.1759)Ile+ (−0.1117)Trp; 0.852, 0.875, 0.794, 0.777, 0.758, 0.843, 0.877, 0.814, (7.3653)+(−0.0580)His+(−0.0071)Ala+ (0.0066)Pro+(−0.0320)Val+(0.1483)Ile+(−0.1074)Trp; 0.852, 0.879, 0.763, 0.745, 0.725, 0.803, 0.859, 0.783, (0.9591)+(0.0391)Ser+(−0.0079)Gly+(−0.0443)Val+ (0.1422)Ile+(0.0645)Phe+(−0.1623)Trp; 0.852, 0.879, 0.810, 0.791, 0.788, 0.860, 0.870, 0.827, (5.7756)+ (0.0039)Gly+(0.0383)Tyr+(−0.0467)Val+(−0.2569) Met+(0.1836)Ile+(−0.1143)Trp; 0.852, 0.881, 0.824, 0.817, 0.814, 0.843, 0.851, 0.831, (3.6460)+(0.0090) Gln+(−0.1340)His+(−0.0036)Ala+(0.0128)Orn+ (0.1016)Phe+(−0.1170)Trp; 0.852, 0.879, 0.791, 0.783, 0.760, 0.859, 0.824, 0.807, (3.3329)+(0.0378)Ser+(− 0.0079)Ala+(−0.0279)Arg+(0.1839)Ile+(−0.0729) Leu+(−0.1355)Trp; 0.852, 0.872, 0.808, 0.791, 0.792, 0.853, 0.855, 0.823, (5.0919)+(0.0015)Gly+(0.0086) Gln+(−0.1152)His+(−0.0052)Ala+(0.0749)Ile+(− 0.1217)Trp; 0.852, 0.872, 0.794, 0.776, 0.783, 0.834, 0.835, 0.807, (4.9946)+(0.0071)Gln+(−0.1122)His+ (0.0082)Thr+(0.0973)Ile+(−0.0242)Leu+(−0.1247) Trp; 0.852, 0.880, 0.785, 0.770, 0.793, 0.854, 0.757, 0.793, (5.2454)+(0.0427)Ser+(−0.0893)His+(0.0128) Pro+(−0.1353)Met+(0.0258)Orn+(−0.0967)Trp; 0.852, 0.876, 0.778, 0.763, 0.781, 0.830, 0.772, 0.787, (1.9164)+(0.0412)Ser+(0.0121)Thr+(0.0039)Pro+(− 0.2827)Met+(0.0736)Ile+(−0.1507)Trp; 0.852, 0.881, 0.814, 0.818, 0.799, 0.842, 0.813, 0.818, (1.9232)+ (0.0435)Ser+(−0.1443)Asn+(0.0099)Thr+(−0.0054) Ala+(0.1007)Phe+(−0.1471)Trp; 0.852, 0.878, 0.800, 0.784, 0.806, 0.834, 0.804, 0.807, (0.8099)+(−0.0227) Asn+(0.0109)Gln+(−0.1714)His+(0.0386)Thr+(− 0.3481)Met+(0.1501)Phe; 0.852, 0.880, 0.795, 0.774, 0.763, 0.843, 0.882, 0.816, (3.5896)+(−0.0679)His+ (0.0029)Pro+(−0.0520)Val+(−0.3232)Met+(0.1738) Ile+(0.1267)Phe; 0.852, 0.879, 0.808, 0.799, 0.804, 0.826, 0.829, 0.814, (3.1456)+(0.0021)Gly+(0.0088) Gln+(−0.1388)His+(0.0023)Pro+(0.1017)Phe+(−0.1212)Trp; 0.852, 0.878, 0.811, 0.796, 0.809, 0.828, 0.842, 0.819, (3.4528)+(0.0091)Gln+(−0.1427)His+(0.0078)Orn+(0.0107)Leu+(0.0876)Phe+(−0.1253) Trp; 0.852, 0.879, 0.777, 0.748, 0.784, 0.813, 0.816, 0.790, (5.6002)+(−0.1272)His+(0.0250)Thr+(−0.0200) Val+(0.0420)Leu+(0.0955)Phe+(−0.1319)Trp; 0.852, 0.874, 0.820, 0.806, 0.804, 0.859, 0.866, 0.834, (5.3744)+(−0.0314)Asn+(0.0100)Gln+(−0.1099)His+(−0.0046)Ala+(0.0719)Ile+(−0.1187)Trp; 0.852, 0.879, 0.819, 0.803, 0.810, 0.853, 0.856, 0.831, (4.7484)+(0.0105)Gln+(−0.1072)His+(0.0028)Pro+(−0.1402) Met+(0.0718)Ile+(−0.1131)Trp; 0.852, 0.884, 0.775, 0.753, 0.784, 0.837, 0.773, 0.787, (2.0608)+(0.0535) Ser+(−0.1137)His+(−0.0506)Cit+(−0.0114)Arg+(0.1377)Phe+(−0.1297)Trp; 0.852, 0.882, 0.813, 0.820, 0.804, 0.822, 0.808, 0.813, (0.9136)+(0.0449)Ser+(−0.1460)Asn+(0.0028)Gln+(−0.0037)Lys+(0.0930) Phe+(−0.1491)Trp; 0.852, 0.878, 0.811, 0.804, 0.806, 0.829, 0.831, 0.817, (3.1491)+(0.0022)Gly+(0.0089) Gln+(−0.1389)His+(0.0001)Lys+(0.1040)Phe+(−0.1199)Trp; 0.852, 0.877, 0.755, 0.741, 0.719, 0.803, 0.833, 0.774, (0.4912)+(0.0276)Ser+(−0.0361)Val+(0.1617)Ile+(−0.0281)Leu+(0.0717)Phe+(−0.1623) Trp; 0.852, 0.873, 0.801, 0.782, 0.781, 0.848, 0.857, 0.817, (5.1363)+(0.0079)Gln+(−0.0813)His+(−0.0542) Cit+(−0.0222)Val+(0.1252)Ile+(−0.1256)Trp; 0.852, 0.877, 0.797, 0.782, 0.770, 0.825, 0.871, 0.812, (3.2245)+(0.0026)Gln+(−0.0878)Cit+(−0.0389)Val+(0.1398)Ile+(0.0798)Phe+(−0.1658)Trp; 0.852, 0.877, 0.762, 0.766, 0.734, 0.788, 0.792, 0.770, (0.3870)+(0.0286)Ser+(−0.0492)Tyr+(0.1432)Ile+(−0.0761) Leu+(0.0967)Phe+(−0.1513)Trp; 0.852, 0.875, 0.815, 0.803, 0.798, 0.850, 0.854, 0.826, (5.2074)+(−0.0474) Asn+(0.0096)Gln+(−0.0978)His+(0.1047)Ile+(−0.0303)Leu+(−0.1153)Trp; 0.852, 0.877, 0.796, 0.769, 0.800, 0.836, 0.832, 0.809, (1.3947)+(0.0575)Ser+(−0.0061)Gly+(0.0278)Tyr+(−0.2791)Met+(0.0783)Ile+(−0.1559)Trp; 0.852, 0.873, 0.790, 0.766, 0.779, 0.842, 0.841, 0.807, (7.4444)+(−0.1007)His+(0.0196)Thr+(−0.0064)Ala+(0.0028)Pro+(0.0730)Ile+(−0.1269)Trp; 0.852, 0.876, 0.784, 0.754, 0.776, 0.843, 0.835, 0.802, (6.9960)+(−0.0578)His+(−0.0728)Cit+(−0.0310)Val+(0.0466)Orn+(0.1347)Ile+(−0.1209)Trp; 0.852, 0.878, 0.797, 0.782, 0.803, 0.831, 0.800, 0.804, (0.6370)+(0.0106)Gln+(−0.1744)His+(0.0392)Thr+(−0.3678) Met+(−0.0054)Orn+(0.1546)Phe; 0.852, 0.879, 0.791, 0.771, 0.797, 0.844, 0.793, 0.801, (3.9162)+(0.0465) Ser+(−0.0915)Asn+(−0.0822)Cit+(−0.0002)Arg+(0.0699)Ile+(−0.1634)Trp; 0.852, 0.877, 0.798, 0.788, 0.809, 0.833, 0.774, 0.801, (0.6978)+(0.0125)Gln+(−0.1732)His+(0.0460)Thr+(−0.0267)Arg+(−0.3707) Met+(0.1570)Phe; 0.852, 0.877, 0.779, 0.764, 0.783, 0.832, 0.775, 0.788, (2.0330)+(0.0403)Ser+(0.0138) Thr+(−0.2739)Met+(−0.0048)Orn+(0.0800)Ile+(−0.1513)Trp; 0.852, 0.876, 0.792, 0.776, 0.778, 0.850, 0.821, 0.806, (2.0378)+(0.0455)Ser+(−0.0051)Ala+(−0.1965)Met+(−0.0034)Lys+(0.0891)Ile+(−0.1389)Trp; 0.852, 0.880, 0.791, 0.770, 0.798, 0.845, 0.796, 0.802, (3.8552)+(0.0468)Ser+(−0.0941)Asn+(−0.0835)Cit+(0.0047)Tyr+(0.0695)Ile+(−0.1656)Trp; 0.852, 0.876, 0.818, 0.814, 0.783, 0.860, 0.873, 0.833, (4.9377)+(0.0050)Gln+(−0.0373)Val+(−0.2160)Met+(0.1805) Ile+(−0.0146)Leu+(−0.1124)Trp; 0.852, 0.879, 0.819, 0.804, 0.835, 0.849, 0.801, 0.823, (4.3746)+(0.0057) Gln+(0.0253)Thr+(−0.0817)Cit+(−0.2352)Met+(0.0731)Ile+(−0.1647)Trp; 0.852, 0.880, 0.785, 0.764, 0.795, 0.812, 0.797, 0.792, (5.3883)+(0.0021)Gly+(−0.1257)His+(0.0224)Thr+(−0.0028)Lys+(0.1072)Phe+(−0.1249)Trp; 0.852, 0.881, 0.775, 0.748, 0.758, 0.865, 0.815, 0.796, (1.2623)+(0.0412)Ser+(0.0060)Gln+(−0.1237)His+(−0.2381)Met+(0.1300)Ile+(−0.0348)Leu; 0.852, 0.879, 0.767, 0.736, 0.776, 0.838, 0.777, 0.782, (−0.4055)+(0.0610)Ser+(−0.0015)Gly+(−0.1489)His+(−0.2792)Met+(0.0138)Orn+(0.1556)Phe; 0.852, 0.879, 0.823, 0.821, 0.845, 0.823, 0.778, 0.817, (3.9070)+(0.0434)Thr+(−0.0031)Ala+(−0.0843)Cit+(−0.3053)Met+(0.1543)Phe+(−0.1708)Trp; 0.852, 0.876, 0.806, 0.797, 0.775, 0.849, 0.862, 0.821, (5.9610)+(0.0023)Gly+(−0.0463)Val+(−0.2302)Met+(0.0112) Lys+(0.1788)Ile+(−0.1132)Trp; 0.852, 0.876, 0.761, 0.722, 0.761, 0.829, 0.813, 0.781, (3.9413)+(0.0479) Ser+(−0.0042)Gly+(−0.1096)His+(0.0012)Pro+(0.0732)Ile+(−0.1246)Trp; 0.852, 0.881, 0.797, 0.777, 0.774, 0.827, 0.875, 0.813, (4.4418)+(−0.0828)Cit+(−0.0391)Val+(−0.0083)Lys+(0.1468)Ile+(0.0897)Phe+(−0.1526)Trp; 0.852, 0.876, 0.787, 0.773, 0.785, 0.835, 0.795, 0.797, (2.3472)+(0.0493)Ser+(−0.0490)Asn+(0.0049)Pro+(−0.2083)Met+(0.0706)Ile+(−0.1424) Trp; 0.852, 0.875, 0.815, 0.803, 0.773, 0.864, 0.896, 0.834, (7.5019)+(−0.0309)Asn+(−0.0069)Ala+(−0.0582)Cit+(−0.0383)Val+(0.1722)Ile+(−0.1194)Trp; 0.852, 0.879, 0.823, 0.807, 0.814, 0.856, 0.860, 0.834, (4.8460)+(−0.0099)Asn+(0.0108)Gln+(−0.1066)His+(−0.1262)Met+(0.0737)Ile+(−0.1124)Trp; 0.852, 0.879, 0.808, 0.797, 0.805, 0.831, 0.829, 0.815, (3.2440)+(0.0020)Gly+(0.0085)Gln+(−0.1395)His+(0.0098)Orn+(0.0992)Phe+(−0.1195)Trp; 0.852, 0.873, 0.789, 0.763, 0.782, 0.839, 0.835, 0.805, (7.3684)+(−0.1059)His+(0.0183)Thr+(−0.0060)Ala+(0.0163)Orn+(0.0713)Ile+(−0.1264)Trp; 0.852, 0.876, 0.768, 0.743, 0.775, 0.835, 0.770, 0.781, (−0.3541)+(0.0601)Ser+(−0.1466)His+(0.0001)Ala+(−0.0006)Val+(−0.2801) Met+(0.1633)Phe; 0.852, 0.875, 0.800, 0.778, 0.799, 0.847, 0.829, 0.813, (4.5386)+(0.0039)Gly+(0.0092) Gln+(−0.1055)His+(−0.0620)Cit+(0.0754)Ile+(−0.1355)Trp; 0.852, 0.879, 0.783, 0.756, 0.743, 0.891, 0.856, 0.812, (1.5799)+(0.0508)Ser+(−0.0815)Asn+(0.0362)Tyr+(−0.0607)Val+(−0.3299)Met+(0.2119) Ile; 0.852, 0.875, 0.791, 0.772, 0.787, 0.833, 0.822, 0.803, (2.0568)+(0.0559)Ser+(−0.0066)Gly+(−0.2220) Met+(−0.0032)Lys+(0.0794)Ile+(−0.1451)Trp; 0.852, 0.875, 0.754, 0.718, 0.756, 0.830, 0.793, 0.774, (3.9426)+(0.0401)Ser+(−0.1143)His+(0.0033)Thr+(0.0002)Pro+(0.0746)Ile+(−0.1241)Trp; 0.852, 0.876, 0.816, 0.807, 0.783, 0.855, 0.877, 0.831, (6.7732)+(−0.0293)Asn+(−0.0472)Val+(−0.2023)Met+(0.0130) Lys+(0.1772)Ile+(−0.1096)Trp; 0.852, 0.873, 0.806, 0.792, 0.781, 0.850, 0.861, 0.821, (6.7859)+(−0.0303) Asn+(−0.0466)Val+(−0.1775)Met+(0.0287)Orn+(0.1739)Ile+(−0.1025)Trp; 0.852, 0.871, 0.800, 0.786, 0.764, 0.849, 0.878, 0.819, (7.6985)+(−0.0179)Asn+(−0.0532)His+(−0.0053)Ala+(−0.0328)Val+(0.1541)Ile+(−0.1033)Trp; 0.852, 0.879, 0.768, 0.741, 0.778, 0.838, 0.770, 0.782, (−0.1745)+(0.0615)Ser+(−0.0340)Asn+(−0.1450)His+(−0.2560)Met+(0.0135)Orn+(0.1559) Phe; 0.852, 0.877, 0.793, 0.781, 0.797, 0.827, 0.793, 0.799, (0.7834)+(0.0101)Gln+(−0.1708)His+(0.0391) Thr+(−0.0172)Tyr+(−0.3430)Met+(0.1564)Phe; 0.852, 0.878, 0.771, 0.748, 0.777, 0.838, 0.775, 0.784, (−0.0644)+(0.0625)Ser+(−0.0332)Asn+(−0.1421)His+(−0.0003)Ala+(−0.2542)Met+(0.1614)Phe; 0.852, 0.874, 0.798, 0.787, 0.750, 0.885, 0.865, 0.822, (5.2881)+(−0.0564)Asn+(0.0341)Thr+(−0.0049)Ala+(−0.0600)Val+(−0.3106)Met+(0.2147)Ile; 0.852, 0.880, 0.773, 0.759, 0.750, 0.796, 0.841, 0.786, (0.4540)+(0.0398)Ser+(−0.0085)Gly+(0.1380)Ile+(−0.0723)Leu+(0.0645)Phe+(−0.1674)Trp; 0.852, 0.879, 0.814, 0.802, 0.812, 0.831, 0.840, 0.821, (3.4315)+(0.0090)Gln+(−0.1396)His+(0.0015)Val+(0.0094)Orn+(0.0948)Phe+(−0.1210)Trp; 0.852, 0.879, 0.813, 0.802, 0.773, 0.861, 0.893, 0.832, (−0.4061)+(0.0067)Gln+(−0.0587)Cit+(−0.0616)Val+(−0.4239)Met+(0.1981)Ile+(0.1297)Phe; 0.852, 0.873, 0.788, 0.766, 0.768, 0.835, 0.850, 0.805, (7.3995)+(−0.0418)Asn+(−0.0643)His+(−0.0341)Val+(0.0297)Orn+(0.1378)Ile+(−0.1024)Trp; 0.852, 0.879, 0.793, 0.787, 0.760, 0.816, 0.864, 0.807, (4.2104)+(−0.0802)Cit+(−0.0345)Tyr+(−0.0405)Val+(0.1468)Ile+(0.1029)Phe+(−0.1473)Trp; 0.852, 0.878, 0.811, 0.798, 0.802, 0.831, 0.852, 0.821, (3.5271)+(0.0091)Gln+(−0.1383)His+(−0.0119)Val+(0.0302)Leu+(0.0917)Phe+(−0.1247)Trp; 0.852, 0.882, 0.818, 0.828, 0.813, 0.824, 0.795, 0.815, (0.9168)+(0.0459)Ser+(−0.1370)Asn+(0.0035)Gln+(−0.0190)Arg+(0.0965)Phe+(−0.1512)Trp; 0.852, 0.873, 0.806, 0.805, 0.798, 0.855, 0.792, 0.812, (4.6410)+(0.0370)Ser+(−0.0852)Asn+(0.0080)Gln+(−0.1015)His+(0.0097)Pro+(−0.0994)Trp; 0.852, 0.875, 0.800, 0.793, 0.778, 0.852, 0.828, 0.813, (2.9510)+(0.0376)Ser+(−0.1224)Asn+(0.0031)Gln+(0.1383)Ile+(−0.0580)Leu+(−0.1368)Trp; 0.852, 0.883, 0.798, 0.779, 0.800, 0.829, 0.820, 0.807, (5.7516)+(−0.1216)His+(0.0224)Thr+(−0.0042)Ala+(0.0134)Orn+(0.1049)Phe+(−0.1251)Trp; 0.851, 0.878, 0.787, 0.770, 0.815, 0.826, 0.745, 0.789, (2.0021)+(0.0389)Ser+(−0.1405)Cit+(0.0490)Orn+(−0.0184)Lys+(0.1042)Phe+(−0.1758)Trp; 0.851, 0.879, 0.762, 0.735, 0.745, 0.845, 0.810, 0.784, (4.4039)+(0.0428)Ser+(−0.0811)His+(−0.0219)Arg+(−0.0271)Val+(0.1440)Ile+(−0.1118)Trp; 0.851, 0.877, 0.772, 0.751, 0.777, 0.839, 0.773, 0.785, (−0.0102)+(0.0625)Ser+(−0.0367)Asn+(−0.1396)His+(−0.0020)Val+(−0.2513)Met+(0.1643)Phe; 0.851, 0.881, 0.811, 0.794, 0.789, 0.852, 0.873, 0.827, (7.1486)+(−0.0460)Cit+(0.0055)Pro+(−0.0406)Val+(−0.1585)Met+(0.1664)Ile+(−0.1138)Trp; 0.851, 0.875, 0.796, 0.787, 0.752, 0.847, 0.871, 0.814, (1.9807)+(−0.0542)Asn+(0.0051)Gly+(−0.0650)Val+(−0.3525)Met+(0.2017)Ile+(0.1246)Phe; 0.851, 0.876, 0.779, 0.764, 0.781, 0.835, 0.772, 0.788, (2.1648)+(0.0408)Ser+(0.0145)Thr+(−0.2629)Met+(−0.0055)Lys+(0.0807)Ile+(−0.1477)Trp; 0.851, 0.888, 0.783, 0.773, 0.738, 0.854, 0.849, 0.804, (−4.0834)+(0.0480)Ser+(−0.0079)Ala+(−0.3698)Met+(0.1997)Ile+(−0.0977)Leu+(0.1268)Phe; 0.851, 0.877, 0.809, 0.794, 0.779, 0.854, 0.883, 0.827, (7.6850)+(−0.0422)His+(−0.0038)Ala+(−0.0359)Val+(−0.1162)Met+(0.1687)Ile+(−0.0943)Trp; 0.851, 0.879, 0.780, 0.750, 0.795, 0.808, 0.808, 0.790, (5.5569)+(−0.1309)His+(0.0213)Thr+(0.0102)Orn+(0.0100)Leu+(0.0898)Phe+(−0.1327)Trp; 0.851, 0.870, 0.791, 0.770, 0.787, 0.829, 0.827, 0.803, (5.0167)+(0.0004)Gly+(0.0074)Gln+(−0.1265)His+(0.0106)Thr+(0.0640)Ile+(−0.1293)Trp; 0.851, 0.879, 0.780, 0.755, 0.756, 0.885, 0.818, 0.803, (1.6919)+(0.0391)Ser+(−0.0696)Cit+(−0.0527)Val+(−0.3268)Met+(0.0328)Orn+(0.1885)Ile; 0.851, 0.879, 0.794, 0.772, 0.798, 0.842, 0.807, 0.805, (3.9604)+(0.0498)Ser+(−0.0904)Asn+(−0.0025)Gly+(−0.0784)Cit+(0.0687)Ile+(−0.1634)Trp; 0.851, 0.874, 0.814, 0.809, 0.792, 0.858, 0.842, 0.825, (6.0479)+(0.0216)Thr+(−0.0062)Ala+(−0.1864)Met+(0.1574)Ile+(−0.0579)Leu+(−0.1307)Trp; 0.851, 0.877, 0.830, 0.823, 0.817, 0.866, 0.850, 0.839, (4.2629)+(0.0076)Gln+(−0.0721)Cit+(−0.1497)Met+(0.1562)Ile+(−0.0593)Leu+(−0.1396)Trp; 0.851, 0.878, 0.796, 0.779, 0.803, 0.830, 0.799, 0.803, (0.6681)+(0.0104)Gln+(−0.1742)His+(0.0382)Thr+(−0.0001)Ala+(−0.3632)Met+(0.1519)Phe; 0.851, 0.871, 0.793, 0.783, 0.744, 0.878, 0.862, 0.817, (4.2961)+(−0.0004)Gly+(0.0317)Thr+(−0.0054)Ala+(−0.0588)Val+(−0.3584)Met+(0.2143)Ile; 0.851, 0.883, 0.766, 0.753, 0.748, 0.803, 0.811, 0.778, (0.3092)+(0.0331)Ser+(−0.0136)Lys+(0.1358)Ile+(−0.0650)Leu+(0.0741)Phe+(−0.1596)Trp; 0.851, 0.880, 0.783, 0.766, 0.757, 0.830, 0.848, 0.800, (0.4951)+(0.0384)Ser+(−0.0098)Ala+(−0.0168)Lys+(0.0710)Ile+(0.0694)Phe+(−0.1642)Trp; 0.851, 0.882, 0.795, 0.771, 0.796, 0.831, 0.827, 0.806, (5.8685)+(−0.1258)His+(0.0249)Thr+(−0.0048)Ala+(0.0143)Leu+(0.0990)Phe+(−0.1330)Trp; 0.851, 0.877, 0.765, 0.748, 0.727, 0.874, 0.813, 0.791, (1.7317)+(0.0344)Ser+(−0.0013)Gln+(0.0219)Thr+(−0.0587)Val+(−0.4059)Met+(0.2130)Ile; 0.851, 0.877, 0.817, 0.803, 0.820, 0.857, 0.818, 0.825, (6.5034)+(0.0293)Thr+(−0.0066)Ala+(−0.0787)Cit+(−0.1750)Met+(0.0828)Ile+(−0.1511)Trp; 0.851, 0.877, 0.799, 0.782, 0.792, 0.836, 0.831, 0.810, (1.4012)+(0.0531)Ser+(−0.0070)Gly+(0.0024)Gln+(−0.2424)Met+(0.0768)Ile+(−0.1501)Trp; 0.851, 0.880, 0.799, 0.801, 0.796, 0.817, 0.788, 0.800, (1.7343)+(0.0447)Ser+(−0.1437)Asn+(0.0082)Thr+(−0.0051)Lys+(0.0941)Phe+(−0.1497)Trp; 0.851, 0.875, 0.806, 0.796, 0.764, 0.851, 0.889, 0.825, (−0.0565)+(0.0044)Gln+(−0.0639)Val+(−0.4315)Met+(0.0049)Orn+(0.1988)Ile+(0.1210)Phe; 0.851, 0.880, 0.815, 0.804, 0.813, 0.833, 0.839, 0.822, (3.4671)+(0.0089)Gln+(−0.1378)His+(0.0107)Orn+(−0.0008)Lys+(0.0970)Phe+(−0.1189)Trp; 0.851, 0.879, 0.786, 0.763, 0.798, 0.812, 0.805, 0.795, (5.5054)+(−0.1253)His+(0.0208)Thr+(−0.0013)Val+(0.0127)Orn+(0.0999)Phe+(−0.1259)Trp; 0.851, 0.878, 0.782, 0.754, 0.797, 0.808, 0.810, 0.792, (5.6269)+(−0.1303)His+(0.0232)Thr+(−0.0007)Pro+(0.0113)Leu+(0.0938)Phe+(−0.1337)Trp; 0.851, 0.877, 0.761, 0.721, 0.763, 0.833, 0.814, 0.783, (3.9640)+(0.0465)Ser+(−0.0041)Gly+(−0.1125)His+(0.0105)Orn+(0.0717)Ile+(−0.1244)Trp; 0.851, 0.875, 0.815, 0.805, 0.776, 0.858, 0.890, 0.832, (6.9793)+(−0.0083)Asn+(−0.0047)Ala+(−0.0430)Val+(−0.1454)Met+(0.1826)Ile+(−0.1040)Trp; 0.851, 0.873, 0.816, 0.821, 0.808, 0.868, 0.786, 0.821, (5.4461)+(0.0299)Ser+(−0.0887)Asn+(0.0080)Gln+(−0.1021)His+(0.0132)Thr+(−0.1009)Trp; 0.851, 0.873, 0.791, 0.781, 0.794, 0.854, 0.768, 0.799, (5.8291)+(0.0466)Ser+(−0.0335)Asn+(−0.0781)His+(0.0141)Pro+(−0.1006)Met+(−0.0962)Trp; 0.851, 0.871, 0.783, 0.764, 0.762, 0.831, 0.841, 0.799, (5.3017)+(0.0054)Gln+(−0.0992)His+(0.0106)Thr+(−0.0234)Val+(0.1197)Ile+(−0.1201)Trp; 0.851, 0.881, 0.821, 0.818, 0.814, 0.841, 0.826, 0.825, (3.0865)+(0.0029)Gly+(0.0112)Gln+(−0.1395)His+(−0.0212)Arg+(0.1112)Phe+(−0.1170)Trp; 0.851, 0.881, 0.824, 0.820, 0.820, 0.834, 0.838, 0.828, (3.3690)+(0.0116)Gln+(−0.1376)His+(−0.0211)Arg+(0.0036)Pro+(0.1040)Phe+(−0.1189)Trp; 0.851, 0.876, 0.758, 0.723, 0.763, 0.832, 0.786, 0.776, (4.1042)+(0.0462)Ser+(−0.1074)His+(−0.0167)Arg+(0.0022)Pro+(0.0766)Ile+(−0.1218)Trp; 0.851, 0.873, 0.791, 0.768, 0.780, 0.843, 0.839, 0.808, (7.5912)+(−0.1003)His+(0.0213)Thr+(−0.0058)Ala+(−0.0026)Lys+(0.0766)Ile+(−0.1258)Trp; 0.851, 0.875, 0.805, 0.795, 0.762, 0.849, 0.887, 0.823, (−0.0824)+(0.0046)Gln+(0.0022)Pro+(−0.0636)Val+ (−0.4385)Met+(0.1972)Ile+(0.1225)Phe; 0.851, 0.880, 0.782, 0.760, 0.792, 0.810, 0.798, 0.790, (5.2454)+ (0.0022)Gly+(−0.1267)His+(0.0209)Thr+(0.0006) Pro+(0.1046)Phe+(−0.1263)Trp; 0.851, 0.874, 0.805, 0.799, 0.760, 0.848, 0.885, 0.823, (−0.2290)+(0.0047) Gln+(−0.0552)Val+(−0.4250)Met+(0.2188)Ile+(− 0.0279)Leu+(0.1251)Phe; 0.851, 0.876, 0.780, 0.766, 0.789, 0.836, 0.757, 0.787, (2.4262)+(0.0414)Ser+ (0.0179)Thr+(−0.0170)Arg+(−0.2644)Met+(0.0788) Ile+(−0.1496)Trp; 0.851, 0.873, 0.813, 0.793, 0.798, 0.854, 0.867, 0.828, (5.1283)+(0.0090)Gln+(−0.1180) His+(−0.0058)Ala+(0.0126)Tyr+(0.0737)Ile+(− 0.1270)Trp; 0.851, 0.877, 0.755, 0.738, 0.720, 0.799, 0.837, 0.774, (0.5779)+(0.0291)Ser+(−0.0439)Val+(− 0.0092)Orn+(0.1428)Ile+(0.0747)Phe+(−0.1692)Trp; 0.851, 0.873, 0.813, 0.796, 0.797, 0.853, 0.861, 0.827, (5.2317)+(0.0090)Gln+(−0.1137)His+(−0.0051)Ala+ (−0.0012)Lys+(0.0748)Ile+(−0.1214)Trp; 0.851, 0.880, 0.781, 0.757, 0.792, 0.811, 0.797, 0.789, (5.2102)+(0.0021)Gly+(−0.1283)His+(0.0194)Thr+ (0.0117)Orn+(0.1001)Phe+(−0.1254)Trp; 0.851, 0.874, 0.809, 0.805, 0.794, 0.817, 0.846, 0.816, (4.3123)+(− 0.0885)Asn+(0.0106)Thr+(0.1282)Ile+(−0.0692)Leu+ (0.0732)Phe+(−0.1469)Trp; 0.851, 0.876, 0.792, 0.766, 0.792, 0.845, 0.823, 0.806, (7.1411)+(−0.0729)His+ (0.0167)Thr+(−0.0534)Cit+(0.1111)Ile+(−0.0310) Leu+(−0.1311)Trp; 0.851, 0.875, 0.742, 0.710, 0.695, 0.849, 0.849, 0.776, (0.4469)+(0.0407)Ser+(−0.1301) His+(−0.0082)Ala+(−0.0306)Val+(0.1215)Ile+ (0.0814)Phe; 0.851, 0.880, 0.810, 0.785, 0.794, 0.855, 0.878, 0.828, (7.3511)+(−0.0459)His+(0.0320)Tyr+(− 0.0383)Val+(−0.1833)Met+(0.1663)Ile+(−0.1019)Trp; 0.851, 0.877, 0.769, 0.742, 0.776, 0.835, 0.775, 0.782, (−0.3309)+(0.0615)Ser+(−0.0011)Gly+(−0.1463)His+ (0.0000)Ala+(−0.2791)Met+(0.1613)Phe; 0.851, 0.880, 0.814, 0.795, 0.790, 0.853, 0.883, 0.830, (6.3936)+(0.0032)Pro+(0.0306)Tyr+(−0.0459)Val+(− 0.2384)Met+(0.1768)Ile+(−0.1129)Trp; 0.851, 0.881, 0.784, 0.771, 0.775, 0.818, 0.813, 0.794, (0.9148)+ (0.0494)Ser+(−0.1255)Asn+(−0.0095)Lys+(0.0479) Ile+(0.0732)Phe+(−0.1565)Trp; 0.851, 0.878, 0.780, 0.769, 0.784, 0.796, 0.791, 0.785, (5.5484)+(−0.1228) His+(0.0272)Thr+(−0.0349)Tyr+(0.0006)Val+(0.1206) Phe+(−0.1197)Trp; 0.851, 0.872, 0.794, 0.773, 0.789, 0.830, 0.831, 0.806, (5.2285)+(0.0077)Gln+(−0.1239) His+(0.0126)Thr+(−0.0055)Lys+(0.0669)Ile+(− 0.1273)Trp; 0.851, 0.880, 0.786, 0.768, 0.748, 0.886, 0.839, 0.810, (2.7468)+(0.0476)Ser+(−0.0793)Asn+(− 0.0445)Cit+(−0.0519)Val+(−0.2464)Met+(0.1946)Ile; 0.851, 0.875, 0.833, 0.828, 0.814, 0.868, 0.860, 0.843, (4.8479)+(−0.0763)Asn+(0.0085)Gln+(−0.0834)Cit+ (0.1455)Ile+(−0.0584)Leu+(−0.1487)Trp; 0.851, 0.871, 0.791, 0.778, 0.754, 0.844, 0.864, 0.810, (7.0906)+(0.0024)Gly+(−0.0624)His+(−0.0056)Ala+ (−0.0304)Val+(0.1505)Ile+(−0.1068)Trp; 0.851, 0.878, 0.814, 0.813, 0.845, 0.807, 0.759, 0.806, (3.7261)+ (0.0437)Thr+(−0.0850)Cit+(−0.0065)Tyr+(−0.3192) Met+(0.1540)Phe+(−0.1719)Trp; 0.851, 0.878, 0.761, 0.729, 0.772, 0.832, 0.772, 0.776, (−0.6177)+(0.0618) Ser+(−0.1521)His+(−0.0036)Tyr+(−0.2930)Met+ (0.0137)Leu+(0.1524)Phe; 0.851, 0.876, 0.756, 0.717, 0.759, 0.833, 0.794, 0.776, (3.9180)+(0.0395)Ser+(− 0.1163)His+(0.0021)Thr+(0.0094)Orn+(0.0725)Ile+(− 0.1240)Trp; 0.851, 0.875, 0.768, 0.737, 0.782, 0.797, 0.800, 0.779, (0.6560)+(0.0427)Ser+(−0.0028)Gly+(− 0.1095)Cit+(0.0543)Ile+(0.0736)Phe+(−0.2055)Trp; 0.851, 0.874, 0.805, 0.796, 0.761, 0.857, 0.883, 0.824, (6.8920)+(−0.0692)Asn+(−0.0067)Ala+(−0.0450)Val+ (0.0271)Orn+(0.1680)Ile+(−0.1099)Trp; 0.851, 0.874, 0.814, 0.805, 0.776, 0.856, 0.886, 0.831, (6.8277)+(− 0.0049)Ala+(−0.0383)Val+(−0.1479)Met+(0.1921) Ile+(−0.0143)Leu+(−0.1044)Trp; 0.851, 0.878, 0.764, 0.734, 0.777, 0.834, 0.766, 0.778, (−0.5475)+(0.0641) Ser+(−0.1493)His+(−0.0106)Arg+(−0.2849)Met+ (0.0127)Leu+(0.1540)Phe; 0.851, 0.876, 0.809, 0.799, 0.758, 0.859, 0.907, 0.831, (2.5979)+(−0.0349)Asn+(− 0.0047)Ala+(−0.0632)Val+(−0.3179)Met+(0.2059) Ile+(0.1191)Phe; 0.851, 0.874, 0.812, 0.791, 0.808, 0.847, 0.852, 0.825, (4.9215)+(0.0105)Gln+(−0.1017) His+(−0.0587)Cit+(−0.0051)Lys+(0.0764)Ile+(− 0.1325)Trp; 0.851, 0.871, 0.788, 0.765, 0.775, 0.841, 0.833, 0.804, (7.2283)+(0.0018)Gly+(−0.1031)His+ (0.0189)Thr+(−0.0058)Ala+(0.0762)Ile+(−0.1254) Trp; 0.851, 0.878, 0.817, 0.799, 0.811, 0.854, 0.852, 0.829, (4.8284)+(0.0100)Gln+(−0.1091)His+(−0.1330) Met+(0.0094)Orn+(0.0716)Ile+(−0.1126)Trp; 0.851, 0.882, 0.807, 0.813, 0.800, 0.812, 0.800, 0.806, (1.0933)+(0.0426)Ser+(−0.1601)Asn+(0.0025)Gln+ (−0.0055)Thr+(0.0897)Phe+(−0.1540)Trp; 0.851, 0.882, 0.799, 0.786, 0.816, 0.783, 0.806, 0.798, (2.3486)+ (0.0402)Thr+(−0.3781)Met+(−0.0258)Orn+(0.0577) Ile+(0.1213)Phe+(−0.1712)Trp; 0.851, 0.877, 0.817, 0.798, 0.794, 0.858, 0.885, 0.834, (6.5750)+(−0.0108) Asn+(0.0321)Tyr+(−0.0457)Val+(−0.2222)Met+ (0.1791)Ile+(−0.1118)Trp; 0.851, 0.870, 0.788, 0.775, 0.755, 0.878, 0.824, 0.808, (4.4898)+(0.0015)Gly+ (0.0335)Thr+(−0.0572)Cit+(−0.0577)Val+(−0.3796) Met+(0.2061)Ile; 0.851, 0.874, 0.809, 0.790, 0.795, 0.852, 0.858, 0.824, (5.2890)+(0.0084)Gln+(−0.1162) His+(−0.0054)Ala+(0.0119)Orn+(0.0709)Ile+(− 0.1221)Trp; 0.851, 0.874, 0.795, 0.772, 0.785, 0.845, 0.842, 0.811, (7.7870)+(−0.0216)Asn+(−0.0979)His+ (0.0227)Thr+(−0.0056)Ala+(0.0738)Ile+(−0.1252) Trp; 0.851, 0.877, 0.820, 0.803, 0.812, 0.850, 0.858, 0.831, (4.6917)+(0.0103)Gln+(−0.1097)His+(−0.1439) Met+(0.0044)Lys+(0.0727)Ile+(−0.1143)Trp; 0.851, 0.875, 0.757, 0.720, 0.758, 0.833, 0.797, 0.777, (3.9599)+(0.0428)Ser+(−0.1086)His+(0.0008)Pro+(− 0.0047)Lys+(0.0779)Ile+(−0.1196)Trp; 0.851, 0.870, 0.795, 0.780, 0.759, 0.845, 0.872, 0.814, (7.2563)+(− 0.0621)His+(−0.0057)Ala+(−0.0315)Val+(0.0041) Lys+(0.1498)Ile+(−0.1093)Trp; 0.851, 0.876, 0.758, 0.742, 0.724, 0.803, 0.838, 0.777, (0.6936)+(0.0274) Ser+(−0.0029)Pro+(−0.0442)Val+(0.1442)Ile+ (0.0707)Phe+(−0.1660)Trp; 0.851, 0.878, 0.824, 0.825, 0.800, 0.831, 0.864, 0.830, (3.0094)+(−0.0979)Asn+ (0.0053)Gln+(0.1337)Ile+(−0.0717)Leu+(0.0707) Phe+(−0.1472)Trp; 0.851, 0.878, 0.778, 0.766, 0.783, 0.798, 0.786, 0.783, (5.4138)+(0.0009)Gly+(−0.1233) His+(0.0265)Thr+(−0.0335)Tyr+(0.1213)Phe+(− 0.1187)Trp; 0.851, 0.880, 0.827, 0.823, 0.822, 0.837, 0.839, 0.830, (3.3666)+(0.0118)Gln+(−0.1392)His+(− 0.0201)Arg+(0.0018)Val+(0.1041)Phe+(−0.1185)Trp; 0.851, 0.876, 0.792, 0.776, 0.779, 0.849, 0.819, 0.806, (1.9068)+(0.0444)Ser+(−0.0052)Ala+(−0.2068)Met+ (0.0033)Orn+(0.0860)Ile+(−0.1415)Trp; 0.850, 0.873, 0.804, 0.788, 0.770, 0.854, 0.881, 0.823, (7.7361)+(− 0.0414)His+(−0.0062)Ala+(−0.0480)Cit+(−0.0317) Val+(0.1599)Ile+(−0.1121)Trp; 0.850, 0.879, 0.769, 0.740, 0.745, 0.869, 0.821, 0.794, (2.9195)+(0.0484) Ser+(−0.0788)His+(−0.0086)Arg+(−0.0371)Val+(− 0.2499)Met+(0.1714)Ile; 0.850, 0.877, 0.772, 0.748, 0.779, 0.836, 0.778, 0.785, (−0.0697)+(0.0637)Ser+(−

0.0323)Asn+(−0.0009)Gly+(−0.1417)His+(−0.2560) Met+(0.1605)Phe; 0.850, 0.883, 0.806, 0.800, 0.817, 0.798, 0.805, 0.805, (0.9631)+(0.0040)Gln+(0.0320) Thr+(−0.3834)Met+(0.0497)Ile+(0.1063)Phe+(− 0.1683)Trp; 0.850, 0.880, 0.825, 0.822, 0.790, 0.851, 0.886, 0.837, (4.5654)+(−0.0476)Asn+(−0.0086)Ala+ (0.1569)Ile+(−0.0762)Leu+(0.0802)Phe+(−0.1352) Trp; 0.850, 0.879, 0.813, 0.801, 0.784, 0.855, 0.872, 0.828, (6.7508)+(−0.0406)Cit+(−0.0431)Val+(− 0.1861)Met+(0.0096)Lys+(0.1734)Ile+(−0.1157)Trp; 0.850, 0.876, 0.767, 0.742, 0.776, 0.835, 0.770, 0.781, (−0.3597)+(0.0602)Ser+(−0.1472)His+(−0.0000)Ala+ (−0.2799)Met+(−0.0001)Lys+(0.1624)Phe; 0.850, 0.883, 0.833, 0.841, 0.847, 0.812, 0.799, 0.825, (1.8994)+(−0.0663)Asn+(0.0060)Gln+(0.0361)Thr+(− 0.3192)Met+(0.1275)Phe+(−0.1595)Trp; 0.850, 0.878, 0.802, 0.790, 0.752, 0.855, 0.900, 0.824, (1.7946)+(− 0.0050)Ala+(−0.0633)Val+(−0.3537)Met+(0.0134) Orn+(0.2046)Ile+(0.1127)Phe; 0.850, 0.874, 0.762, 0.732, 0.780, 0.799, 0.781, 0.773, (0.5142)+(0.0392) Ser+(−0.1143)Cit+(0.0007)Pro+(0.0547)Ile+(0.0743) Phe+(−0.2063)Trp; 0.850, 0.874, 0.810, 0.803, 0.809, 0.857, 0.800, 0.817, (4.2182)+(0.0364)Ser+(−0.0703) Asn+(0.0087)Gln+(−0.1175)His+(0.0116)Val+(− 0.1084)Trp; 0.850, 0.871, 0.818, 0.813, 0.834, 0.874, 0.755, 0.819, (6.1616)+(0.0395)Ser+(−0.0954)Asn+(− 0.0032)Ala+(−0.1138)Cit+(0.0591)Orn+(−0.1351)Trp; 0.850, 0.880, 0.812, 0.799, 0.810, 0.828, 0.839, 0.819, (3.4320)+(0.0088)Gln+(−0.1381)His+(0.0019)Pro+ (0.0094)Orn+(0.0952)Phe+(−0.1206)Trp; 0.850, 0.879, 0.805, 0.781, 0.793, 0.836, 0.874, 0.821, (6.0874)+(−0.1021)His+(−0.0069)Ala+(0.0039)Pro+ (0.0559)Ile+(0.0809)Phe+(−0.1266)Trp; 0.850, 0.878, 0.771, 0.742, 0.748, 0.866, 0.824, 0.795, (2.5498)+ (0.0480)Ser+(−0.1025)His+(−0.0053)Ala+(−0.1954) Met+(0.1464)Ile+(−0.0392)Leu; 0.850, 0.876, 0.800, 0.791, 0.793, 0.843, 0.812, 0.810, (1.7097)+(0.0452) Ser+(−0.0637)Asn+(0.0036)Gln+(−0.1980)Met+ (0.0746)Ile+(−0.1454)Trp; 0.850, 0.881, 0.815, 0.820, 0.797, 0.843, 0.820, 0.820, (1.6419)+(0.0464)Ser+(− 0.1343)Asn+(−0.0050)Ala+(0.0087)Orn+(0.0974) Phe+(−0.1419)Trp; 0.850, 0.876, 0.797, 0.783, 0.782, 0.851, 0.826, 0.810, (1.5211)+(0.0425)Ser+(0.0017) Gln+(−0.0051)Ala+(−0.2131)Met+(0.0864)Ile+(− 0.1435)Trp; 0.850, 0.874, 0.808, 0.796, 0.767, 0.858, 0.889, 0.827, (6.9248)+(−0.0077)Ala+(−0.0627)Cit+(− 0.0369)Val+(−0.0010)Lys+(0.1719)Ile+(−0.1278)Trp; 0.850, 0.875, 0.810, 0.802, 0.778, 0.851, 0.868, 0.825, (6.2270)+(−0.0411)Val+(−0.2202)Met+(0.0122)Lys+ (0.1894)Ile+(−0.0176)Leu+(−0.1124)Trp; 0.850, 0.882, 0.773, 0.747, 0.780, 0.831, 0.783, 0.785, (1.9568)+(0.0529)Ser+(−0.0010)Gly+(−0.1138)His+ (−0.0566)Cit+(0.1339)Phe+(−0.1335)Trp; 0.850, 0.877, 0.801, 0.785, 0.801, 0.851, 0.810, 0.812, (3.8707)+(0.0396)Ser+(−0.0791)Asn+(0.0083)Gln+(− 0.1211)His+(0.0297)Leu+(−0.1099)Trp; 0.850, 0.881, 0.797, 0.777, 0.764, 0.844, 0.886, 0.818, (3.5827)+(− 0.0688)His+(0.0008)Arg+(−0.0516)Val+(−0.3172) Met+(0.1761)Ile+(0.1272)Phe; 0.850, 0.875, 0.789, 0.781, 0.750, 0.851, 0.845, 0.807, (2.8899)+(0.0293) Ser+(−0.0103)Ala+(0.0045)Pro+(0.1609)Ile+(− 0.0645)Leu+(−0.1448)Trp; 0.850, 0.875, 0.785, 0.761, 0.795, 0.840, 0.790, 0.796, (3.0176)+(0.0360)Ser+ (0.0025)Gln+(−0.0959)Cit+(−0.0156)Lys+(0.0809) Ile+(−0.1757)Trp; 0.850, 0.875, 0.802, 0.786, 0.779, 0.845, 0.860, 0.817, (6.3016)+(0.0027)Pro+(−0.0458) Val+(−0.2084)Met+(0.0239)Orn+(0.1721)Ile+(− 0.1069)Trp; 0.850, 0.873, 0.801, 0.787, 0.777, 0.846, 0.855, 0.816, (6.1184)+(0.0013)Gly+(−0.0457)Val+(− 0.2062)Met+(0.0239)Orn+(0.1752)Ile+(−0.1070)Trp; 0.850, 0.872, 0.796, 0.787, 0.746, 0.883, 0.865, 0.820, (3.6212)+(0.0018)Gln+(0.0301)Thr+(−0.0055)Ala+(− 0.0584)Val+(−0.3671)Met+(0.2129)Ile; 0.850, 0.879, 0.803, 0.778, 0.795, 0.837, 0.866, 0.819, (6.1174)+(− 0.1072)His+(−0.0061)Ala+(0.0146)Orn+(0.0557)Ile+ (0.0767)Phe+(−0.1253)Trp; 0.850, 0.877, 0.769, 0.754, 0.729, 0.873, 0.817, 0.793, (1.3818)+(0.0327)Ser+ (0.0218)Thr+(−0.0595)Val+(−0.4144)Met+(0.2093) Ile+(0.0035)Leu; 0.850, 0.876, 0.762, 0.723, 0.763, 0.830, 0.813, 0.782, (3.9286)+(0.0478)Ser+(−0.0040) Gly+(−0.1103)His+(0.0022)Tyr+(0.0745)Ile+(− 0.1248)Trp; 0.850, 0.880, 0.786, 0.762, 0.798, 0.810, 0.806, 0.794, (5.5158)+(−0.1263)His+(0.0207)Thr+ (0.0001)Pro+(0.0121)Orn+(0.0982)Phe+(−0.1272)Trp; 0.850, 0.874, 0.804, 0.795, 0.752, 0.854, 0.899, 0.825, (1.8321)+(−0.0050)Ala+(−0.0540)Val+(−0.3433)Met+ (0.2247)Ile+(−0.0278)Leu+(0.1202)Phe; 0.850, 0.874, 0.762, 0.731, 0.779, 0.798, 0.782, 0.773, (0.5921)+ (0.0397)Ser+(−0.0004)Gln+(−0.1134)Cit+(0.0555) Ile+(0.0750)Phe+(−0.2054)Trp; 0.850, 0.883, 0.807, 0.789, 0.817, 0.844, 0.810, 0.815, (6.1079)+(−0.1038) His+(0.0297)Thr+(−0.0048)Ala+(−0.0672)Cit+ (0.1290)Phe+(−0.1420)Trp; 0.850, 0.878, 0.817, 0.812, 0.806, 0.826, 0.842, 0.822, (3.3097)+(0.0096)Gln+(− 0.1366)His+(−0.0178)Tyr+(0.0030)Val+(0.1061)Phe+ (−0.1166)Trp; 0.850, 0.877, 0.766, 0.739, 0.780, 0.838, 0.757, 0.778, (−0.3211)+(0.0614)Ser+(−0.1466)His+(− 0.0132)Arg+(−0.2654)Met+(0.0151)Orn+(0.1580) Phe; 0.850, 0.875, 0.770, 0.744, 0.782, 0.840, 0.765, 0.783, (−0.2172)+(0.0610)Ser+(−0.1396)His+(− 0.0335)Cit+(0.0008)Val+(−0.2806)Met+(0.1639)Phe; 0.850, 0.878, 0.778, 0.767, 0.781, 0.794, 0.789, 0.783, (5.4813)+(−0.1216)His+(0.0264)Thr+(0.0025)Pro+(− 0.0364)Tyr+(0.1195)Phe+(−0.1192)Trp; 0.850, 0.876, 0.800, 0.787, 0.749, 0.854, 0.900, 0.823, (2.0275)+(− 0.0066)Ala+(0.0082)Pro+(−0.0625)Val+(−0.3621) Met+(0.2006)Ile+(0.1164)Phe; 0.850, 0.877, 0.769, 0.743, 0.776, 0.836, 0.775, 0.783, (−0.3105)+(0.0614) Ser+(−0.0011)Gly+(−0.1455)His+(−0.0006)Val+(− 0.2782)Met+(0.1622)Phe; 0.850, 0.875, 0.791, 0.779, 0.743, 0.878, 0.859, 0.815, (4.3085)+(0.0306)Thr+(− 0.0068)Ala+(0.0070)Pro+(−0.0583)Val+(−0.3630) Met+(0.2072)Ile; 0.850, 0.875, 0.787, 0.761, 0.776, 0.848, 0.836, 0.805, (6.3778)+(−0.0987)Cit+(−0.0364) Val+(0.0503)Orn+(−0.0094)Lys+(0.1464)Ile+(− 0.1393)Trp; 0.850, 0.879, 0.814, 0.809, 0.802, 0.824, 0.845, 0.820, (2.8738)+(0.0030)Gly+(−0.2531)Met+ (0.1595)Ile+(−0.0782)Leu+(0.1134)Phe+(−0.1275) Trp; 0.850, 0.877, 0.778, 0.759, 0.753, 0.860, 0.819, 0.798, (6.4120)+(−0.0704)His+(0.0411)Thr+(−0.0162) Arg+(−0.0475)Val+(−0.3216)Met+(0.1891)Ile; 0.850, 0.878, 0.770, 0.747, 0.776, 0.835, 0.773, 0.783, (−0.1149)+(0.0624)Ser+(−0.0332)Asn+(−0.1426)His+ (−0.2580)Met+(0.0006)Lys+(0.1612)Phe; 0.850, 0.872, 0.787, 0.769, 0.761, 0.879, 0.826, 0.808, (4.4153)+(0.0298)Thr+(−0.0688)Cit+(−0.0586)Val+(− 0.3688)Met+(0.0270)Orn+(0.1998)Ile; 0.850, 0.875, 0.792, 0.771, 0.790, 0.832, 0.822, 0.804, (1.9264)+ (0.0551)Ser+(−0.0067)Gly+(−0.2333)Met+(0.0043) Orn+(0.0761)Ile+(−0.1477)Trp; 0.850, 0.875, 0.764, 0.747, 0.769, 0.794, 0.781, 0.773, (0.5898)+(0.0399) Ser+(−0.1090)Cit+(−0.0378)Tyr+(0.0560)Ile+(0.0965) Phe+(−0.1921)Trp; 0.850, 0.878, 0.813, 0.805, 0.804, 0.825, 0.845, 0.820, (3.3598)+(0.0095)Gln+(−0.1390)

His+(−0.0173)Tyr+(0.0118)Leu+(0.0994)Phe+(−0.1202)Trp; 0.850, 0.878, 0.775, 0.758, 0.780, 0.798, 0.793, 0.782, (5.5806)+(−0.1281)His+(0.0275)Thr+(−0.0357)Tyr+(0.0117)Leu+(0.1114)Phe+(−0.1251)Trp; 0.850, 0.876, 0.772, 0.746, 0.782, 0.841, 0.767, 0.784, (−0.1681)+(0.0608)Ser+(−0.1383)His+(−0.0003)Ala+(−0.0331)Cit+(−0.2776)Met+(0.1649)Phe; 0.850, 0.872, 0.803, 0.784, 0.786, 0.843, 0.856, 0.818, (7.3380)+(−0.0745)His+(−0.0060)Ala+(0.0228)Orn+(0.1261)Ile+(−0.0410)Leu+(−0.1111)Trp; 0.850, 0.879, 0.774, 0.751, 0.783, 0.842, 0.766, 0.786, (0.0909)+(0.0635)Ser+(−0.0347)Asn+(−0.1337)His+(−0.0335)Cit+(−0.2541)Met+(0.1641)Phe; 0.850, 0.875, 0.756, 0.742, 0.739, 0.794, 0.799, 0.768, (0.6559)+(0.0315)Ser+(−0.0025)Gln+(0.1380)Ile+(−0.0724)Leu+(0.0689)Phe+(−0.1646)Trp; 0.850, 0.881, 0.820, 0.803, 0.820, 0.844, 0.851, 0.829, (3.1785)+(0.0107)Gln+(−0.1293)His+(−0.0615)Cit+(0.0136)Leu+(0.1038)Phe+(−0.1364)Trp; 0.850, 0.879, 0.782, 0.771, 0.786, 0.802, 0.791, 0.787, (5.6383)+(−0.1212)His+(0.0284)Thr+(−0.0344)Tyr+(−0.0026)Lys+(0.1229)Phe+(−0.1182)Trp; 0.850, 0.877, 0.793, 0.778, 0.768, 0.825, 0.862, 0.808, (3.9218)+(−0.0869)Cit+(−0.0291)Val+(0.1697)Ile+(−0.0375)Leu+(0.0891)Phe+(−0.1540)Trp; 0.850, 0.874, 0.790, 0.779, 0.769, 0.847, 0.820, 0.804, (3.4041)+(0.0414)Ser+(−0.1018)Asn+(−0.0021)Thr+(0.1405)Ile+(−0.0582)Leu+(−0.1342)Trp; 0.850, 0.875, 0.758, 0.724, 0.762, 0.833, 0.787, 0.777, (4.1380)+(0.0463)Ser+(−0.1065)His+(−0.0153)Arg+(−0.0013)Lys+(0.0801)Ile+(−0.1198)Trp; 0.850, 0.874, 0.754, 0.716, 0.757, 0.831, 0.794, 0.775, (3.9002)+(0.0404)Ser+(−0.1150)His+(0.0029)Thr+(0.0029)Tyr+(0.0746)Ile+(−0.1252)Trp; 0.850, 0.877, 0.815, 0.797, 0.791, 0.854, 0.883, 0.831, (6.3750)+(0.0315)Tyr+(−0.0433)Val+(−0.2292)Met+(0.1845)Ile+(−0.0076)Leu+(−0.1126)Trp; 0.850, 0.881, 0.803, 0.807, 0.795, 0.809, 0.805, 0.804, (0.8832)+(0.0451)Ser+(−0.1548)Asn+(0.0024)Gln+(0.0036)Pro+(0.0876)Phe+(−0.1530)Trp; 0.850, 0.878, 0.801, 0.794, 0.797, 0.805, 0.826, 0.806, (1.8218)+(0.0566)Ser+(−0.1413)Asn+(−0.0068)Gly+(0.0043)Pro+(0.0850)Phe+(−0.1528)Trp; 0.850, 0.872, 0.809, 0.793, 0.800, 0.847, 0.845, 0.821, (5.0483)+(−0.0464)Asn+(0.0024)Gly+(0.0099)Gln+(−0.1159)His+(0.0642)Ile+(−0.1189)Trp; 0.850, 0.880, 0.797, 0.777, 0.765, 0.845, 0.885, 0.818, (3.6045)+(−0.0686)His+(0.0002)Tyr+(−0.0517)Val+(−0.3159)Met+(0.1762)Ile+(0.1272)Phe; 0.850, 0.880, 0.798, 0.776, 0.766, 0.850, 0.886, 0.820, (3.7214)+(−0.0626)His+(−0.0301)Cit+(−0.0519)Val+(−0.3057)Met+(0.1774)Ile+(0.1294)Phe; 0.850, 0.875, 0.790, 0.779, 0.772, 0.846, 0.817, 0.803, (3.4481)+(0.0402)Ser+(−0.1079)Asn+(0.0045)Orn+(0.1376)Ile+(−0.0576)Leu+(−0.1349)Trp; 0.850, 0.874, 0.810, 0.798, 0.771, 0.860, 0.886, 0.829, (6.8927)+(−0.0077)Ala+(−0.0638)Cit+(−0.0293)Val+(0.1878)Ile+(−0.0244)Leu+(−0.1256)Trp; 0.850, 0.870, 0.792, 0.772, 0.788, 0.831, 0.829, 0.805, (5.0990)+(0.0075)Gln+(−0.1265)His+(0.0115)Thr+(−0.0022)Pro+(0.0664)Ile+(−0.1293)Trp; 0.850, 0.880, 0.824, 0.816, 0.820, 0.838, 0.844, 0.829, (3.3774)+(0.0117)Gln+(−0.1420)His+(−0.0196)Arg+(0.0102)Leu+(0.0969)Phe+(−0.1221)Trp; 0.850, 0.874, 0.790, 0.775, 0.786, 0.841, 0.798, 0.800, (2.3839)+(0.0486)Ser+(−0.0469)Asn+(−0.1917)Met+(−0.0011)Lys+(0.0769)Ile+(−0.1418)Trp; 0.850, 0.881, 0.824, 0.801, 0.820, 0.846, 0.874, 0.835, (6.0142)+(−0.0922)His+(−0.0039)Ala+(−0.1520)Met+(0.0621)Ile+(0.1084)Phe+(−0.1168)Trp; 0.850, 0.876, 0.819, 0.813, 0.806, 0.822, 0.857, 0.824, (3.3309)+(0.0043)Asn+(−0.2450)Met+(0.1582)Ile+(−0.0778)Leu+(0.1110)Phe+(−0.1284)Trp; 0.850, 0.878, 0.794, 0.795, 0.791, 0.806, 0.791, 0.795, (1.4981)+(0.0456)Ser+(−0.1511)Asn+(0.0046)Thr+(0.0034)Pro+(0.0884)Phe+(−0.1531)Trp; 0.850, 0.877, 0.784, 0.769, 0.730, 0.884, 0.863, 0.811, (1.2949)+(0.0405)Ser+(−0.0060)Ala+(−0.0475)Val+(−0.2975)Met+(0.2168)Ile+(−0.0147)Leu; 0.850, 0.874, 0.789, 0.779, 0.786, 0.856, 0.772, 0.798, (5.6071)+(0.0445)Ser+(−0.0808)His+(−0.0024)Ala+(0.0162)Pro+(−0.1163)Met+(−0.0943)Trp; 0.850, 0.878, 0.821, 0.820, 0.804, 0.838, 0.845, 0.827, (1.9949)+(0.0555)Ser+(−0.1290)Asn+(−0.0062)Gly+(−0.0044)Ala+(0.0984)Phe+(−0.1436)Trp; 0.850, 0.878, 0.806, 0.778, 0.812, 0.823, 0.855, 0.817, (5.1465)+(0.0400)Asn+(−0.1038)His+(−0.2076)Met+(0.0608)Ile+(0.1128)Phe+(−0.1189)Trp; 0.850, 0.874, 0.809, 0.786, 0.806, 0.843, 0.849, 0.821, (4.7956)+(0.0100)Gln+(−0.1052)His+(−0.0566)Cit+(0.0011)Pro+(0.0713)Ile+(−0.1355)Trp; 0.850, 0.871, 0.788, 0.774, 0.755, 0.877, 0.829, 0.809, (4.6427)+(0.0342)Thr+(−0.0547)Cit+(0.0022)Pro+(−0.0580)Val+(−0.3831)Met+(0.2037)Ile

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A method of evaluating pancreatic cancer, comprising:
obtaining amino acid concentration data on a concentration value of an amino acid in blood collected from a subject to be evaluated;
evaluating a state of pancreatic cancer in the subject by calculating a value of a formula using (i) the obtained amino acid concentration data of the subject and (ii) the formula previously established for evaluating the state of pancreatic cancer, including an explanatory variable to be substituted with the concentration value of the amino acid, wherein the amino acid concentration data includes the concentration values of at least two amino acids of Asn, His, Thr, Ala, Cit, Arg, Tyr, Val, Met, Lys, Trp, Gly, Pro, Orn, Ile, Leu, Phe, Ser, and Gln, and the formula includes at least two explanatory variables to be substituted with the concentration values of at least two amino acids of Asn, His, Thr, Ala, Cit, Arg, Tyr, Val, Met, Lys, Trp, Gly, Pro, Orn, Ile, Leu, Phe, Ser, and Gln, wherein said evaluating comprises assigning the subject based on a relationship between the calculated value of the formula with respect to one or more thresholds to (a) a pancreatic cancer category for subjects affected with pancreatic cancer; (b) a healthy category for healthy subjects; and (c) an other cancer category for subjects affected with a cancer other than pancreatic cancer; and
administering to the subject assigned to the pancreatic cancer category at least one of gemcitabine, erlotinib, and TS-1.

2. The method of evaluating pancreatic cancer according to claim 1, wherein the formula is any one of a logistic regression equation, a fractional expression, a linear discriminant, a multiple regression equation, a formula prepared by a support vector machine, a formula prepared by a Mahalanobis' generalized distance method, a formula prepared by canonical discriminant analysis, and a formula prepared by a decision tree.

3. The method according to claim 1, wherein said administering comprises administering to the subject assigned to the pancreatic cancer category a combination of gemcitabine, erlotinib, and TS-1.

* * * * *